US011141433B2

(12) United States Patent
Wickham et al.

(10) Patent No.: US 11,141,433 B2
(45) Date of Patent: Oct. 12, 2021

(54) THERAPEUTIC CELL SYSTEMS AND METHODS FOR TREATING CANCER AND INFECTIOUS DISEASES

(71) Applicant: Rubius Therapeutics, Inc., Cambridge, MA (US)

(72) Inventors: Thomas Joseph Wickham, Groton, MA (US); Sivan Elloul, Newton, MA (US)

(73) Assignee: Rubius Therapeutics, Inc., Cambridge, MA (US)

( * ) Notice: Subject to any disclaimer, the term of this patent is extended or adjusted under 35 U.S.C. 154(b) by 360 days.

(21) Appl. No.: 16/297,540

(22) Filed: Mar. 8, 2019

(65) Prior Publication Data

US 2019/0298769 A1 Oct. 3, 2019

Related U.S. Application Data

(60) Provisional application No. 62/640,530, filed on Mar. 8, 2018, provisional application No. 62/660,657, filed on Apr. 20, 2018, provisional application No. 62/680,490, filed on Jun. 4, 2018, provisional application No. 62/692,487, filed on Jun. 29, 2018, provisional application No. 62/732,050, filed on Sep. 17, 2018, provisional application No. 62/757,717, filed on Nov. 8, 2018.

(51) Int. Cl.

| | |
|---|---|
| ***A61K 35/17*** | (2015.01) |
| ***A61P 35/00*** | (2006.01) |
| ***A61K 35/18*** | (2015.01) |
| ***A61K 38/17*** | (2006.01) |
| ***A61K 38/19*** | (2006.01) |
| ***A61K 38/20*** | (2006.01) |
| ***A61K 38/30*** | (2006.01) |
| ***C12N 5/078*** | (2010.01) |
| ***C12N 5/0783*** | (2010.01) |
| ***C12N 15/86*** | (2006.01) |
| ***A61K 39/00*** | (2006.01) |
| ***C07K 14/705*** | (2006.01) |
| ***A61K 39/395*** | (2006.01) |
| *A61K 47/68* | (2017.01) |

(52) U.S. Cl.

CPC .............. *A61K 35/17* (2013.01); *A61K 35/18* (2013.01); *A61K 38/1774* (2013.01); *A61K 38/191* (2013.01); *A61K 38/208* (2013.01); *A61K 38/2086* (2013.01); *A61K 38/30* (2013.01); *A61K 39/0011* (2013.01); *A61K 39/3955* (2013.01); *A61P 35/00* (2018.01); *C07K 14/705* (2013.01); *C12N 5/0641* (2013.01); *C12N 5/0646* (2013.01); *C12N 15/86* (2013.01); *A61K 39/39533* (2013.01); *A61K 47/6811* (2017.08); *C07K 2319/00* (2013.01); *C12N 2510/00* (2013.01)

(58) Field of Classification Search

CPC ...................................................... A61K 35/17

See application file for complete search history.

(56) References Cited

U.S. PATENT DOCUMENTS

| | | | | |
|---|---|---|---|---|
| 4,327,710 | A | 5/1982 | DeLoach et al. | |
| 4,935,223 | A | 6/1990 | Phillips | |
| 5,753,221 | A | 5/1998 | Magnani et al. | |
| 6,139,836 | A | 10/2000 | Magnani et al. | |
| 6,495,351 | B2 | 12/2002 | McHale | |
| 9,574,178 | B2 | 2/2017 | Mitchell et al. | |
| 2006/0188490 | A1 * | 8/2006 | Hoerr ...................... | A61K 39/00 424/93.21 |
| 2007/0243137 | A1 | 10/2007 | Hainfeld | |
| 2010/0040546 | A1 | 2/2010 | Hyde et al. | |

FOREIGN PATENT DOCUMENTS

| | | |
|---|---|---|
| WO | WO 2005/035584 | 4/2005 |
| WO | WO 2012/032433 | 3/2012 |
| WO | WO 2014/183066 | 11/2014 |
| WO | WO 2014/183071 | 11/2014 |
| WO | WO 2015/073587 | 5/2015 |
| WO | WO 2015/153102 | 10/2015 |
| WO | WO 2017/123646 | 7/2017 |
| WO | WO 2017/123650 | 7/2017 |
| WO | WO 2018/009838 | 1/2018 |
| WO | WO 2018/102740 | 6/2018 |
| WO | WO 2018/151829 | 8/2018 |
| WO | WO 2019/036855 | 2/2019 |

(Continued)

OTHER PUBLICATIONS

Cheuk et al. (Cancer Gene Therapy (2004) 11, 215-226) (Year: 2004).*

Mill et al. (Cell Reports 17, 1-10; Sep. 27, 2016) (Year: 2016).*

C. Bagnis (Hematology Education: the education program for the annual congress of the European Hematology Association. 2012; 6:405-410). (Year: 2012).*

(Continued)

*Primary Examiner* — Scott Long

(74) *Attorney, Agent, or Firm* — Fish & Richardson P.C.

(57) ABSTRACT

The present disclosure relates to erythroid cells that have been engineered to include, e.g., at the surface of the cell, one or more exogenous stimulatory polypeptides, wherein the exogenous stimulatory polypeptides presented are sufficient to stimulate an immune killer cell. The engineered enucleated cells of the present disclosure are useful in methods of activating NK cells and/or CD8+T-cells in a subject in need thereof, such as subjects having cancer or an infectious disease, and in particular cancers or infectious diseases characterized by downregulation of MHC Class I presentation.

30 Claims, 57 Drawing Sheets

Specification includes a Sequence Listing.

(56) References Cited

FOREIGN PATENT DOCUMENTS

WO WO 2019/173798 9/2019

OTHER PUBLICATIONS

Kim et al. (Oncotarget. Mar. 29, 2016;7(13):16130-45. doi: 10.18632/oncotarget.7470.) (Year: 2016).*
Sutherland et al. (Blood. 2006;108:1313-1319). (Year: 2006).*
Alderson et al., "Molecular and Biological Characterization of Human 4-IBB and Its Ligand," *Eur. J. Immunol.* 24(9):2219-2227, 1994.
Alter et al., "CD107 a as a functional marker for the identification of natural killer cell activity," *J. Immunol. Methods* 294(1-2):15-22, 2004.
Altschul et al., "Gapped BLAST and PSI-BLAST: A New Generation of Protein Database Search Programs," *Nucleic Acids Res.* 25(17):3389-3402, 1997.
Appay et al., "Memory $CD8^+$T Cells Vary in Differentiation Phenotype in Different Persistent Virus Infections," *Nature Med.* 8(4):379-385, 2002.
Bar-Zvi et al., "Assembled Clathrin in Erythrocytes," *J. Biol. Chem.* 262:17719-17723, 1987.
Bettinger et al., "Peptide-mediated RNA Delivery: A Novel Approach for Enhanced Transfection of Primary and Post-Mitotic Cells," *Nucleic Acids Res.* 29(18):3882-3891, 2001.
Bierhuizen et al., "Efficient Detection and Selection of Immature Rhesus Monkey and Human CD34+ Hematopoietic Cells Expressing the Enhanced Green Fluorescent Protein (EGFP)," *Leukemia* 13(4):605-613, 1999.
Brown et al., "Neo-antigens Predicted by Tumor Genome Meta-Analysis Correlate With Increased Patient Survival," *Genome Res.* 24(5):743-50, 2014.
Brun et al., "A New Method for Isolation of Reticulocytes: Positive Selection of Human Reticulocytes by Immunomagnetic Separation," *Blood* 76(11):2397-2403, 1990.
Carlens et al., "A New Method for In Vitro Expansion of Cytotoxic Human CD3-$CD56^+$Natural Killer Cells," *Hum. Immunol.* 62(10):1092-1098, 2001.
Chang et al., "Stem Cell-Derived Erythroid Cells Mediate Long-Term Systemic Protein Delivery," *Nat. Biotechnol.* 24(8):1017-21, 2006.
Claverie et al., "Information enhancement methods for large scale sequence analysis," *Comput. Chem.* 17(2):191-201, 1993.
Corpet, "Multiple Sequence Alignment With Hierarchical Clustering," *Nucleic Acids Res.* 16(22):10881-90, 1988.
European Office Action in European Appln. No. 19713277.2, dated Oct. 15, 2020, 5 pages.
Fibach et al., "Proliferation and Maturation of Human Erythroid Progenitors in Liquid Culture," *Blood* 73(1):100-3, 1989.
Fiercebiotech.com, [online], "Flagship-backed Rubius raises $120M to take off-the-shelf red blood cell cancer therapeutics into the clinic," dated Jun. 21, 2017, retrieved on Jul. 6, 2020, retrieved from URL<https://www.fiercebiotech.com/biotech/flagship-backed-rubius-raises-120m-to-take-off-shelf-red-blood-cell-cancer-therapeutics>, 4 pages.
Flynn et al., "Methotrexate-loaded, Photosensitized Erythrocytes: A Photo-Activatable carrier/delivery System for Use in Cancer Therapy," *Cancer Lett.* 82(2):225-229, 1994.
Genbank Accession No. NP 001129240.1, "poliovirus receptor isoform beta precursor [*Homo sapiens*]," Mar. 1, 2018, 3 pages.
Genbank Accession No. CAG33293.1, "CD48 [*Homo sapiens*]," Oct. 16, 2008, 2 pages.
Genbank Accession No. NP_003802.1, "tumor necrosis factor ligand superfamily member 9 [*Homo sapiens*]," Jan. 22, 2018, 3 pages.
Giarratana et al., "Proof of Principle for Transfusion of in Vitro-Generated Red Blood Cells," *Blood* 118(19):5071-9, 2011.
Goodman et al., "The Isolation of Reticulocyte-Free Human Red Blood Cells," *Exp. Biol. Med.* 232(11):1470-1476, 2007.
Goodman, "Grading and Staging Systems for Inflammation and Fibrosis in Chronic Liver Diseases," *J. Hepatol.* 47(4):598-607, 2007.
Harding et al., "A Beta-Lactamase With Reduced Immunogenicity for the Targeted Delivery of Chemotherapeutics Using Antibody-Directed Enzyme Prodrug Therapy," *Mol. Cancer Ther.* 4(11):1791-800, 2005.
Haworth et al., "Going Back to Class I: MHC and Immunotherapies for Childhood Cancer," *Pediatric Blood Cancer* 62(4):571-576, 2015.
Henikoff et al., "Amino Acid Substitution Matrices From Protein Blocks," *Proc. Natl. Acad. Sci. U.S.A.* 89:10915-9, 1989.
Higgins et al., "CLUSTAL: A Package for Performing Multiple Sequence Alignment on a Microcomputer," *Gene* 73:237-244, 1988.
Higgins et al., "Fast and Sensitive Multiple Sequence Alignments on a Microcomputer," *Comput. Appl. Biosci.* 5(2):151-3, 1989.
Hirose et al., "Immortalization of Erythroblasts by c-MYC and BCL-XL Enables Large-Scale Erythrocyte Production From Human Pluripotent Stem Cells," *Stem Cell Reports* 1(6):499-508, 2013.
Hossle et al., "Gene Therapy of Hematopoietic Stem Cells: Strategies for Improvement," *News Physiol. Sci.* 17:87-92, 2002.
Huang et al., "Extensive Ex Vivo Expansion of Functional Human Erythroid Precursors Established From Umbilical Cord Blood Cells by Defined Factors," *Mol. Ther.* 22(2):451-63, 2014.
Huang et al., "Parallelization of a Local Similarity Algorithm," *Comp. Appl. Biosci.* 8(2):155-65, 1992.
Ishak et al., "Histological grading and staging of chronic hepatitis," *J. Hepatol.* 22(6):696-9, 1995.
Junghans, "The Challenges of Solid Tumor for Designer CAR-T Therapies: A 25-year Perspective," *Cancer Gene Therapy* 24(3):89-99, 2017.
Karlin et al., "Applications and Statistics for Multiple High-Scoring Segments in Molecular Sequences," *Proc. Natl. Acad. Sci. U.S.A.* 90(12):5873-7, 1993.
Katzung & Trevor's Pharmacology Examination & Board Review, 11th ed., Chapter 2, 11 pages, 2013.
Keller et al., "Transgene Expression, but Not Gene Delivery, is Improved by Adhesion-Assisted Lipofection of Hematopoietic Cells," *Gene Therapy* 6(5):931-938, 1999.
Klinmnan et al., "ELISPOT Assay to Detect Cytokine-Secreting Murine and Human Cells," *Current Protocols in Immunology*, pp. 6.19.1-6.19.8, 1994.
Kubo et al., "Primary Tumors Limit Metastasis Formation Through Induction of IL15-Mediated Cross-Talk Between Patrolling Monocytes and NK Cells," *Cancer Immunol. Res.* 5(9):812-20, 2017.
Kurita et al., "Establishment of Immortalized Human Erythroid Progenitor Cell Lines Able to Produce Enucleated Red Blood Cells," *PLOS One*, 8:e59890, 15 pages, 2013.
Levine et al., "Antiviral Effect and Ex Vivo $CD4^+$T Cell Proliferation in HIV-positive Patients as a Result of CD28 Costimulation," *Science* 272(5270):1939-1943, 1996.
Levine et al., "Effects of CD28 Costimulation on Long-Term Proliferation of $CD4^+$T Cells in the Absence of Exogenous Feeder Cells," *J. Immunol.* 159(12):5921-5930, 1997.
Lienert et al., "Synthetic biology in mammalian cells: next generation research tools and therapeutics," *Nature Rev. Mol. Cell Biol.* 15(2):95-107, 2014.
Liu et al., "Systematic Comparison of 2A Peptides for Cloning Multi-Genes in a Polycistronic Vector," *Sci. Rep.* 7(1):2193, 9 pages, 2017.
Lortat-Jacob et al., "Structural Diversity of Heparan Sulfate Binding Domains in Chemokines," *Proc. Natl. Acad. Sci. U.S.A.* 99(3):1229-1234, 2002.
Lutolf et al., "Synthesis and Physicochemical Characterization of End-Linked Poly(ethylene Glycol)-Co-Peptide Hydrogels Formed by Michael-type Addition," *Biomacromolecules* 4(3):713-22, 2003.
Malik et al., "An In Vitro Model of Human Red Blood Cell Production From Hematopoietic Progenitor Cells," *Blood* 91(8):2664-2671, 1998.
Medicalnewstoday.com, [online], "What are lymphocytes and what are healthy levels to have?" Jan. 13, 2020, retrieved on Jul. 6, 2020, retrieved from URL<https://www.medicalnewstoday.com/articles/320987>, 16 pages.

(56) References Cited

OTHER PUBLICATIONS

Myers et al., "Optimal Alignments in Linear Space," *Comp. Appl. Biol. Sci.* 4(1):11-17, 1988.
Needleman et al., "A General Method Applicable to the Search for Similarities in the Amino Acid Sequence of Two Proteins," *J. Mol. Biol.* 48(3):443-53, 1970.
Neildez-Nguyen et al., "Human Erythroid Cells Produced Ex Vivo at Large Scale Differentiate Into Red Blood Cells In Vivo," *Nature Biotech.* 20(5):467-472, 2002.
Neves et al., "Imaging Cell Surface Glycosylation In Vivo Using 'Double Click' Chemistry," *Bioconjugate Chem.* 24(6):934-41, 2013.
Niu et al., "Cytokine-mediated Disruption of Lymphocyte Trafficking, Hemopoiesis, and Induction of Lymphopenia, Anemia, and Thrombocytopenia in anti-CD137-treated Mice," *J. Immunol.* 178(7):4194-4213, 2007.
Noble el al.. "Reticulocytes. I. Isolation and in Vitro Maturation of Synchronized Populations," *Blood* 74(1):475-481, 1989.
Oldak et al., "Optimisation of Transfection Conditions of $CD34^+$ Hematopoietic Cells Derived From Human Umbilical Cord Blood," *Acta Biochim. Polonica* 49(3):625-632, 2002.
Osten et al., "Viral Vectors: A Wide Range of Choices and High Levels of Service," *HEP* 178:177-202, 2007.
Overwijk et al., "B16 as a Mouse Model for Human Melanoma," *Current Protocols tn Immunology*, Chapter 20:Unit 20.1, 29 pages, 2001.
Papapetrou et al., "Genetic Modification of Hematopoietic Stem Cells With Nonviral Systems: Past Progress and Future Prospects," *Gene Therapy* 1:S118-S130, 2005.
Paszko et al., "Immunoliposomes," *Curr. Med. Chem.* 19(31):5239-77, 2012.
PCT International Preliminary Report on Patentability in International Patent Appln. No. PCT/US2019/021490, dated Sep. 8, 2020, 10 pages.
PCT International Search Report and Written Opinion in International Patent Appln. No. PCT/US2019/021490, dated Jun. 24, 2019, 13 pages.
Pearson et al., "Improved Tools for Biological Sequence Comparison," *Proc. Natl. Acad. Sci. U.S.A.* 85(8):2444-8, 1988.
Pearson et al., "Using the FASTA Program to Search Protein and DNA Sequence Databases," *Methods Mol. Biol.* 24:307-331, 1994.
Robinson et al., "Optimizing the Stability of Single-Chain Proteins by Linker Length and Composition Mutagenesis," *Proc. Natl. Acad. Sci. U.S.A.* 95(11):5929-34, 1998.
Rooney et al., "Molecular and Genetic Properties of Tumors Associated With Local Immune Cytolytic Activity," *Cell* 160(1-2):48-61, 2015.
Rutledge et al., "Tumor-infiltrating Lymphocytes in Glioblastoma Are Associated With Specific Genomic Alterations and Related to Transcriptional Ciass," *Clin. Cancer Res.* 19(18):4951-60, 2013.
Sallusto et al., "Two Subsets of Memory T Lymphocytes With Distinct Homing Potentials and Effector Functions," *Nature* 401:708-712, 1999.
Schmiedel et al., "The RNA Binding Protein IMP3 Facilitates Tumor Immune Escape by Downregulating the Stress-Induced Ligands ULPB2 and MICB," *Elife* 5:e13426, 18 pages, 2016.
Selby et al., "Preclinical Development of Ipilimumab and Nivolumab Combination Immunotherapy: Mouse Tumor Models, In Vitro Functional Studies, and Cynomolgus Macaque Toxicology," *PLoS One* 11(9):e0161779, 19 pages, 2016.
Sharma et al., "The Future of Immune Checkpoint Therapy," *Science* 348:56-61, 2015.
Shin et al., "Low Molecular Weight Polyethylenimine for Efficient Transfection of Human Hematopoietic and Umbilical Cord Blood-Derived $CD34^+$Cells," *Biochim. Biophys. Acta* 1725(3):377-384, 2005.
Smith et al., "Comparison of Biosequences," *Adv. Appl. Math.* 2:482-89, 1981.
Sticker et al., "Human Population-Based Identification of $CD4^+$T-cell Peptide Epitope Determinants," *J. Immunol. Methods* 281(1-2):95-108, 2003.
Sun et al., "Surface-Engineering of Red Blood Cells as Artificial Antigen Presenting Cells Promising for Cancer Immunotherapy," *Adv. Sci. News* 13:1701864, 8 pages, 2017.
Swee et al., "Sortase-mediated Modification of αDEC205 Affords Optimization of Antigen Presentation and Immunization Against a Set of Viral Epitopes," *Proc. Natl. Acad. Sci. U.S.A.* 111(4):1428-33, 2013.
Tao et al., "Enhanced Green Fluorescent Protein Is a Nearly Ideal Long-Term Expression Tracer for Hematopoietic Stem Cells, Whereas DsRed-express Fluorescent Protein Is Not," *Stem Cells* 25:670-678, 2007.
Tendeloo et al., "Highly Efficient Gene Delivery by mRNA Electroporation in Human Hematopoietic Cells: Superiority to Lipofection and Passive Pulsing of mRNA and to Electroporation of Plasmid cDNA for Tumor Antigen Loading of Dendritic Cells," *Blood* 98(1):49-56, 2001.
Tortorella et al., "Viral Subversion of the Immune System," *Ann. Rev. Immunol.* 18:861-926, 2000.
Ulbrich et al., "Targeted Drug Delivery With Polymere and Magnetic Nanoparticles: Covalent and Noncovalent Approaches, Release Control, and Clinical Studies," *Chem. Rev.* 116(9):5338-431, 2016.
Van Den Berg et al., "Method of Isolating Erythrocytes Influences Their Measured Polyamine Content," *Clin. Chem.* 33(6):1081-1082, 1987.
Van Schravendijk et al., "Normal Human Erythrocytes Express CD36, an Adhesion Molecule of Monocytes, Platelets, and Endothelial Cells," *Blood* 80(8):2105-14, 1992.
Vanderbyl et al., "Transgene Expression After Stable Transfer of a Mammalian Artificial Chromosome Into Human Hematopoietic Cells," *Exp. Hematol.* 33(12):1470-1476, 2005.
Verma et al., "Gene Transfer Into Human Umbilical Cord Blood-Derived $CD34^+$Cells by Particle-Mediated Gene Transfer," *Gene Therapy* 5:692-699, 1998.
Von Andrian et al., "Homing and Cellular Traffic in Lymph Nodes," *Nat. Rev. Immunol.* 3:867-878, 2003.
Wang et al., "Platelet Generation In Vivo and In Vitro," *Springerplus* 5(1):787, 10 pages, 2016.
Wei et al., "The Sushi Domain of Soluble IL-15 Receptor Alpha Is Essential for Binding IL-15 and Inhibiting Inflammatory and Allogenic Responses In Vitro and In Vivo," *J. Immunol.* 167(1):277-282, 2001.
Wooten et al., "Statistics of local complexity in amino acid sequences and sequence databases," *Comput. Chem.* 17:149-163, 1993.
Xu et al., "Clinical Manifestations and Arsenic Methylation After a Rare Subacute Arsenic Poisoning Accident," *Toxicol. Sci.* 103(2):278-284, 2008.
Zakeri et al., "Peptide Tag Forming a Rapid Covalent Bond to a Protein, Through Engineering a Bacterial Adhesin," *Proc. Natl. Acad. Sci. U.S.A.* 109:E690-E697, 2012.
Zakeri et al., "Spontaneous Intermolecular Amide Bond Formation Between Side Chains for Irreversible Peptide Targeting," *JACS*, 132:4526-7, 2010.
Zhang et al., "Development and Characterization of a Reliable Mouse Model of Colorectal Cancer Metastasis to the Liver," *Clin. Exp. Metastasis* 30(7):903-18, 2013.

* cited by examiner

SEQUENCE LISTING

<160> NUMBER OF SEQ ID NOS: 83

<210> SEQ ID NO 1
<211> LENGTH: 304
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 1

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Gly Gly Gly Gly Ser Gly Gly Gly Gly
        115                 120                 125

Ser Ile Thr Cys Pro Pro Pro Met Ser Val Glu His Ala Asp Ile Trp
    130                 135                 140

Val Lys Ser Tyr Ser Leu Tyr Ser Arg Glu Arg Tyr Ile Cys Asn Ser
145                 150                 155                 160

Gly Phe Lys Arg Lys Ala Gly Thr Ser Ser Leu Thr Glu Cys Val Leu
                165                 170                 175

-continued

Asn Lys Ala Thr Asn Val Ala His Trp Thr Thr Pro Ser Leu Lys Cys
180 185 190

Ile Arg Asp Pro Ala Leu Val His Gln Arg Pro Ala Pro Pro Ser Thr
195 200 205

Val Thr Thr Ala Gly Val Thr Pro Gln Pro Glu Ser Leu Ser Pro Ser
210 215 220

Gly Lys Glu Pro Ala Ala Ser Ser Pro Ser Ser Asn Asn Thr Ala Ala
225 230 235 240

Thr Thr Ala Ala Ile Val Pro Gly Ser Gln Leu Met Pro Ser Lys Ser
245 250 255

Pro Ser Thr Gly Thr Thr Glu Ile Ser Ser His Glu Ser Ser His Gly
260 265 270

Thr Pro Ser Gln Thr Thr Ala Lys Asn Trp Glu Leu Thr Ala Ser Ala
275 280 285

Ser His Gln Pro Pro Gly Val Tyr Pro Gln Gly His Ser Asp Thr Thr
290 295 300

<210> SEQ ID NO 2
<211> LENGTH: 207
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2

Asn Trp Val Asn Val Ile Ser Asp Leu Lys Lys Ile Glu Asp Leu Ile
1 5 10 15

Gln Ser Met His Ile Asp Ala Thr Leu Tyr Thr Glu Ser Asp Val His
20 25 30

Pro Ser Cys Lys Val Thr Ala Met Lys Cys Phe Leu Leu Glu Leu Gln
35 40 45

Val Ile Ser Leu Glu Ser Gly Asp Ala Ser Ile His Asp Thr Val Glu
50 55 60

Asn Leu Ile Ile Leu Ala Asn Asn Ser Leu Ser Ser Asn Gly Asn Val
65 70 75 80

Thr Glu Ser Gly Cys Lys Glu Cys Glu Glu Leu Glu Glu Lys Asn Ile
85 90 95

Lys Glu Phe Leu Gln Ser Phe Val His Ile Val Gln Met Phe Ile Asn
100 105 110

Thr Ser Gly Gly Gly Gly Ser Gly Gly Gly Gly Ser Gly Gly Gly Gly
115 120 125

Ser Ile Thr Cys Pro Pro Pro Met Ser Val Glu His Ala Asp Ile Trp
130 135 140

Val Lys Ser Tyr Ser Leu Tyr Ser Arg Glu Arg Tyr Ile Cys Asn Ser
145 150 155 160

Gly Phe Lys Arg Lys Ala Gly Thr Ser Ser Leu Thr Glu Cys Val Leu
165 170 175

Asn Lys Ala Thr Asn Val Ala His Trp Thr Thr Pro Ser Leu Lys Cys
180 185 190

Ile Arg Asp Pro Ala Leu Val His Gln Arg Pro Ala Pro Pro Ser
195 200 205

<210> SEQ ID NO 3
<211> LENGTH: 162
<212> TYPE: PRT
<213> ORGANISM: Homo sapiens

<400> SEQUENCE: 3

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser
```

<210> SEQ ID NO 4
<211> LENGTH: 114
<212> TYPE: PRT
<213> ORGANISM: Homo sapiens

<400> SEQUENCE: 4

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 5
<211> LENGTH: 267
<212> TYPE: PRT
<213> ORGANISM: Homo sapiens

<400> SEQUENCE: 5

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30
```

```
Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265


<210> SEQ ID NO 6
<211> LENGTH: 237
<212> TYPE: PRT
<213> ORGANISM: Homo sapiens

<400> SEQUENCE: 6

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
```

```
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr Val
                165                 170                 175

Ala Ile Ser Thr Ser Thr Val Leu Leu Cys Gly Leu Ser Ala Val Ser
            180                 185                 190

Leu Leu Ala Cys Tyr Leu Lys Ser Arg Gln Thr Pro Pro Leu Ala Ser
        195                 200                 205

Val Glu Met Glu Ala Met Glu Ala Leu Pro Val Thr Trp Gly Thr Ser
    210                 215                 220

Ser Arg Asp Glu Asp Leu Glu Asn Cys Ser His His Leu
225                 230                 235


<210> SEQ ID NO 7
<211> LENGTH: 205
<212> TYPE: PRT
<213> ORGANISM: Homo sapiens

<400> SEQUENCE: 7

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr
        195                 200                 205


<210> SEQ ID NO 8
<211> LENGTH: 175
<212> TYPE: PRT
<213> ORGANISM: Homo sapiens

<400> SEQUENCE: 8

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
```

-continued

```
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr
                165                 170                 175


<210> SEQ ID NO 9
<211> LENGTH: 65
<212> TYPE: PRT
<213> ORGANISM: Homo sapiens

<400> SEQUENCE: 9

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65


<210> SEQ ID NO 10
<211> LENGTH: 78
<212> TYPE: PRT
<213> ORGANISM: Homo sapiens

<400> SEQUENCE: 10

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser
65                  70                  75


<210> SEQ ID NO 11
<211> LENGTH: 5
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 11

Gly Gly Gly Gly Ser
1 5

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Gly Gly Gly Gly Ser Gly Gly Gly Gly Ser Gly Gly Gly Gly Ser
1 5 10 15

<210> SEQ ID NO 13
<211> LENGTH: 342
<212> TYPE: DNA
<213> ORGANISM: Homo sapiens

<400> SEQUENCE: 13
aactgggtga acgttattag tgaccttaaa aagatcgaag atttgataca gtcaatgcac 60
atagacgcga cgctttatac agaatctgat gtacatcctt catgcaaggt tactgctatg 120
aagtgttttc ttctcgaact ccaagtaata agtcttgaga gcggagatgc gagcattcat 180
gacaccgttg agaatcttat tatattggct aacaactctc tgtccagcaa tggtaatgtg 240
acagaaagcg ggtgtaagga gtgcgaggaa ctcgaggaga agaacatcaa agagttcttg 300
cagtctttcg tccatattgt ccagatgttc ataaatacta gc 342

<210> SEQ ID NO 14
<211> LENGTH: 342
<212> TYPE: DNA
<213> ORGANISM: Homo sapiens

<400> SEQUENCE: 14
aactgggtaa acgtcataag cgacctcaaa aagatcgagg accttataca gtctatgcac 60
atagatgcga cactttacac ggaatcagac gtgcacccgt cctgcaaagt cacagccatg 120
aagtgctttc ttctcgaact gcaggtaatt tctctcgaat caggtgacgc atctatccac 180
gacacagttg aaaatcttat tatcctggct aataactccc ttagctcaaa cggcaatgtc 240
accgagagtg gatgtaaaga atgtgaggaa cttgaagaga aaaacataaa ggaattcttg 300
cagagtttcg ttcatattgt gcaaatgttc atcaatacta gt 342

<210> SEQ ID NO 15
<211> LENGTH: 525
<212> TYPE: DNA
<213> ORGANISM: Homo sapiens

<400> SEQUENCE: 15
atcacatgcc caccgcccat gtctgttgaa cacgcagaca tttgggttaa aagttactca 60
ctttactcac gcgagagata tatatgcaac agcggcttca agcgcaaagc aggcactagt 120
agtcttacag agtgcgtgct caataaagct acaaatgtag ctcattggac tactcctagt 180
ctcaaatgca ttcgggaccc cgcgcttgtg caccagagac ctgcgccgcc gtccacagtg 240

```
acgacagctg gtgtaacccc ccaacctgaa tcccttagtc cgtctggtaa agaaccggcg    300

gcgtcttcac cttccagcaa taatactgcg gcgacaacag ccgcgatagt tcctggatcc    360

caactcatgc cgtcaaagtc tccttcaacg ggaacgacag agatctcttc acatgaaagt    420

tctcatggaa caccgagcca aactacggca aagaactggg aactgactgc ctcagcaagc    480

caccagccgc caggggtgta cccgcaaggg cactcagata ctact                    525


<210> SEQ ID NO 16
<211> LENGTH: 234
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

atcacctgcc cgcctcccat gagcgtggaa cacgcggaca tttgggttaa gagctacagt     60

ctttacagcc gggagcgcta tatctgcaac tcagggttta agcggaaagc agggacatca    120

agtttgacag aatgtgtgtt gaacaaggct acaaatgttg ctcactggac cacgccatct    180

ttgaagtgta tccgagatcc cgcgcttgtc catcagcgcc cagcgcctcc ctcc          234


<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

gggggaggtg gctctggtgg aggcgggagt ggcgggggcg gctca                     45


<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

ggcgggggg gaagcggtgg tggagggagc gggggtggtg gatcc                      45


<210> SEQ ID NO 19
<211> LENGTH: 912
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

aactgggtga acgttattag tgaccttaaa aagatcgaag atttgataca gtcaatgcac     60

atagacgcga cgctttatac agaatctgat gtacatcctt catgcaaggt tactgctatg    120

aagtgttttc ttctcgaact ccaagtaata agtcttgaga gcggagatgc gagcattcat    180

gacaccgttg agaatcttat tatattggct aacaactctc tgtccagcaa tggtaatgtg    240

acagaaagcg ggtgtaagga gtgcgaggaa ctcgaggaga agaacatcaa agagttcttg    300

cagtctttcg tccatattgt ccagatgttc ataaatacta gcgggggagg tggctctggt    360
```

-continued

```
ggaggcggga gtggcggggg cggctcaatc acatgcccac cgcccatgtc tgttgaacac    420

gcagacattt gggttaaaag ttactcactt tactcacgcg agagatatat atgcaacagc    480

ggcttcaagc gcaaagcagg cactagtagt cttacagagt gcgtgctcaa taaagctaca    540

aatgtagctc attggactac tcctagtctc aaatgcattc gggaccccgc gcttgtgcac    600

cagagacctg cgccgccgtc cacagtgacg acagctggtg taacccccca acctgaatcc    660

cttagtccgt ctggtaaaga accggcggcg tcttcacctt ccagcaataa tactgcggcg    720

acaacagccg cgatagttcc tggatcccaa ctcatgccgt caaagtctcc ttcaacggga    780

acgacagaga tctcttcaca tgaaagttct catggaacac cgagccaaac tacggcaaag    840

aactgggaac tgactgcctc agcaagccac cagccgccag ggtgtaccc gcaagggcac     900

tcagatacta ct                                                         912
```

<210> SEQ ID NO 20
<211> LENGTH: 621
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
aactgggtaa acgtcataag cgacctcaaa aagatcgagg accttataca gtctatgcac     60

atagatgcga cactttacac ggaatcagac gtgcacccgt cctgcaaagt cacagccatg    120

aagtgctttc ttctcgaact gcaggtaatt tctctcgaat caggtgacgc atctatccac    180

gacacagttg aaaatcttat tatcctggct aataactccc ttagctcaaa cggcaatgtc    240

accgagagtg gatgtaaaga atgtgaggaa cttgaagaga aaaacataaa ggaattcttg    300

cagagtttcg ttcatattgt gcaaatgttc atcaatacta gtggcggggg gggaagcggt    360

ggtggaggga gcgggggtgg tggatccatc acctgccccgc ctcccatgag cgtggaacac    420

gcggacattt gggttaagag ctacagtctt tacagccggg agcgctatat ctgcaactca    480

gggtttaagc ggaaagcagg gacatcaagt ttgacagaat gtgtgttgaa caaggctaca    540

aatgttgctc actggaccac gccatctttg aagtgtatcc gagatcccgc gcttgtccat    600

cagcgcccag cgcctccctc c                                               621
```

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

```
Met Tyr Gly Lys Ile Ile Phe Val Leu Leu Leu Ser Glu Ile Val Ser
1               5                   10                  15

Ile Ser Ala
```

<210> SEQ ID NO 22
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22

```
atgtatggaa aaataatctt tgtattacta ttgtcagaaa ttgtgagcat atcagca        57


<210> SEQ ID NO 23
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Ser Gly Gly Ser Gly Gly Tyr Pro Tyr Asp Val Pro Asp Tyr
1               5                   10                  15

Ala Gly Gly Gly Ser Gly Gly Gly Ser
            20                  25


<210> SEQ ID NO 24
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24

ggaggatctg gcgggtctgg aggctacccc tatgacgtgc ccgactatgc cggcggaggg     60

tctggaggcg gttcc                                                      75


<210> SEQ ID NO 25
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Leu Ser Thr Thr Glu Val Ala Met His Thr Ser Thr Ser Ser Ser Val
1               5                   10                  15

Thr Lys Ser Tyr Ile Ser Ser Gln Thr Asn Asp Thr His Lys Arg Asp
            20                  25                  30

Thr Tyr Ala Ala Thr Pro Arg Ala His Glu Val Ser Glu Ile Ser Val
        35                  40                  45

Arg Thr Val Tyr Pro Pro Glu Glu Glu Thr Gly Glu Arg Val Gln Leu
    50                  55                  60

Ala His His Phe Ser Glu Pro Glu Ile Thr Leu Ile Ile Phe Gly Val
65                  70                  75                  80

Met Ala Gly Val Ile Gly Thr Ile Leu Leu Ile Ser Tyr Gly Ile Arg
                85                  90                  95

Arg Leu Ile Lys Lys Ser Pro Ser Asp Val Lys Pro Leu Pro Ser Pro
            100                 105                 110

Asp Thr Asp Val Pro Leu Ser Ser Val Glu Ile Glu Asn Pro Glu Thr
        115                 120                 125

Ser Asp Gln
    130


<210> SEQ ID NO 26
<211> LENGTH: 393
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 26
ttaagtacca ctgaggtggc aatgcacact tcaacctctt cttcagtcac aaagagttac 60
atctcatcac agacaaatga tacgcacaaa cgggacacat atgcagccac tcctagagct 120
catgaagttt cagaaatttc tgttagaact gtttaccctc cagaagagga aaccggagaa 180
agggtacaac ttgcccatca tttctctgaa ccagagataa cactcattat ttttggggtg 240
atggctggtg ttattggaac gatcctctta atttcttacg gtattcgccg actgataaag 300
aaaagcccat ctgatgtaaa acctctcccc tcacctgaca cagacgtgcc tttaagttct 360
gttgaaatag aaaatccaga gacaagtgat caa 393

<210> SEQ ID NO 27
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Met Tyr Gly Lys Ile Ile Phe Val Leu Leu Leu Ser Glu Ile Val Ser
1               5                   10                  15

Ile Ser Ala Asn Trp Val Asn Val Ile Ser Asp Leu Lys Lys Ile Glu
            20                  25                  30

Asp Leu Ile Gln Ser Met His Ile Asp Ala Thr Leu Tyr Thr Glu Ser
        35                  40                  45

Asp Val His Pro Ser Cys Lys Val Thr Ala Met Lys Cys Phe Leu Leu
    50                  55                  60

Glu Leu Gln Val Ile Ser Leu Glu Ser Gly Asp Ala Ser Ile His Asp
65                  70                  75                  80

Thr Val Glu Asn Leu Ile Ile Leu Ala Asn Asn Ser Leu Ser Ser Asn
                85                  90                  95

Gly Asn Val Thr Glu Ser Gly Cys Lys Glu Cys Glu Glu Leu Glu Glu
            100                 105                 110

Lys Asn Ile Lys Glu Phe Leu Gln Ser Phe Val His Ile Val Gln Met
        115                 120                 125

Phe Ile Asn Thr Ser Gly Gly Ser Gly Gly Ser Gly Gly Tyr Pro Tyr
    130                 135                 140

Asp Val Pro Asp Tyr Ala Gly Gly Gly Ser Gly Gly Gly Ser Leu Ser
145                 150                 155                 160

Thr Thr Glu Val Ala Met His Thr Ser Thr Ser Ser Ser Val Thr Lys
                165                 170                 175

Ser Tyr Ile Ser Ser Gln Thr Asn Asp Thr His Lys Arg Asp Thr Tyr
            180                 185                 190

Ala Ala Thr Pro Arg Ala His Glu Val Ser Glu Ile Ser Val Arg Thr
        195                 200                 205

Val Tyr Pro Pro Glu Glu Glu Thr Gly Glu Arg Val Gln Leu Ala His
    210                 215                 220

His Phe Ser Glu Pro Glu Ile Thr Leu Ile Ile Phe Gly Val Met Ala
225                 230                 235                 240

Gly Val Ile Gly Thr Ile Leu Leu Ile Ser Tyr Gly Ile Arg Arg Leu
                245                 250                 255

Ile Lys Lys Ser Pro Ser Asp Val Lys Pro Leu Pro Ser Pro Asp Thr
```

260 265 270

Asp Val Pro Leu Ser Ser Val Glu Ile Glu Asn Pro Glu Thr Ser Asp
275 280 285

Gln

<210> SEQ ID NO 28
<211> LENGTH: 867
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28
atgtatggaa aaataatctt tgtattacta ttgtcagaaa ttgtgagcat atcagcaaac 60
tgggtaaatg tgatttcaga cctgaaaaaa atcgaagacc ttattcaatc catgcacatc 120
gacgcgacac tttatactga atcagacgta cacccgtcct gtaaggttac tgcgatgaag 180
tgctttctgt tggaattgca agtgatctcc ctcgaatcag gggatgcatc cattcatgat 240
accgtcgaga atttgatcat tctggcaaat aactccctca gtagtaacgg gaatgtgacc 300
gagtctgggt gtaaggagtg cgaagagttg gaggaaaaga atatcaaaga attccttcag 360
tcctttgttc acatcgtgca aatgtttatt aatacatctg gaggatctgg cgggtctgga 420
ggctacccct atgacgtgcc cgactatgcc ggcggagggt ctggaggcgg ttccttaagt 480
accactgagg tggcaatgca cacttcaacc tcttcttcag tcacaaagag ttacatctca 540
tcacagacaa atgatacgca caaacgggac acatatgcag ccactcctag agctcatgaa 600
gtttcagaaa tttctgttag aactgtttac cctccagaag aggaaaccgg agaaagggta 660
caacttgccc atcatttctc tgaaccagag ataacactca ttatttttgg ggtgatggct 720
ggtgttattg gaacgatcct cttaatttct tacggtattc gccgactgat aaagaaaagc 780
ccatctgatg taaaacctct cccctcacct gacacagacg tgcctttaag ttctgttgaa 840
atagaaaatc cagagacaag tgatcaa 867

<210> SEQ ID NO 29
<211> LENGTH: 479
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Met Tyr Gly Lys Ile Ile Phe Val Leu Leu Leu Ser Glu Ile Val Ser
1 5 10 15

Ile Ser Ala Asn Trp Val Asn Val Ile Ser Asp Leu Lys Lys Ile Glu
20 25 30

Asp Leu Ile Gln Ser Met His Ile Asp Ala Thr Leu Tyr Thr Glu Ser
35 40 45

Asp Val His Pro Ser Cys Lys Val Thr Ala Met Lys Cys Phe Leu Leu
50 55 60

Glu Leu Gln Val Ile Ser Leu Glu Ser Gly Asp Ala Ser Ile His Asp
65 70 75 80

Thr Val Glu Asn Leu Ile Ile Leu Ala Asn Asn Ser Leu Ser Ser Asn
85 90 95

Gly Asn Val Thr Glu Ser Gly Cys Lys Glu Cys Glu Glu Leu Glu Glu
100 105 110

-continued

```
Lys Asn Ile Lys Glu Phe Leu Gln Ser Phe Val His Ile Val Gln Met
        115                 120                 125

Phe Ile Asn Thr Ser Gly Gly Gly Gly Ser Gly Gly Gly Gly Ser Gly
    130                 135                 140

Gly Gly Gly Ser Ile Thr Cys Pro Pro Pro Met Ser Val Glu His Ala
145                 150                 155                 160

Asp Ile Trp Val Lys Ser Tyr Ser Leu Tyr Ser Arg Glu Arg Tyr Ile
                165                 170                 175

Cys Asn Ser Gly Phe Lys Arg Lys Ala Gly Thr Ser Ser Leu Thr Glu
            180                 185                 190

Cys Val Leu Asn Lys Ala Thr Asn Val Ala His Trp Thr Thr Pro Ser
        195                 200                 205

Leu Lys Cys Ile Arg Asp Pro Ala Leu Val His Gln Arg Pro Ala Pro
    210                 215                 220

Pro Ser Thr Val Thr Thr Ala Gly Val Thr Pro Gln Pro Glu Ser Leu
225                 230                 235                 240

Ser Pro Ser Gly Lys Glu Pro Ala Ala Ser Ser Pro Ser Ser Asn Asn
                245                 250                 255

Thr Ala Ala Thr Thr Ala Ala Ile Val Pro Gly Ser Gln Leu Met Pro
            260                 265                 270

Ser Lys Ser Pro Ser Thr Gly Thr Thr Glu Ile Ser Ser His Glu Ser
        275                 280                 285

Ser His Gly Thr Pro Ser Gln Thr Thr Ala Lys Asn Trp Glu Leu Thr
    290                 295                 300

Ala Ser Ala Ser His Gln Pro Pro Gly Val Tyr Pro Gln Gly His Ser
305                 310                 315                 320

Asp Thr Thr Gly Gly Ser Gly Gly Ser Gly Gly Tyr Pro Tyr Asp Val
                325                 330                 335

Pro Asp Tyr Ala Gly Gly Gly Ser Gly Gly Gly Ser Leu Ser Thr Thr
            340                 345                 350

Glu Val Ala Met His Thr Ser Thr Ser Ser Ser Val Thr Lys Ser Tyr
        355                 360                 365

Ile Ser Ser Gln Thr Asn Asp Thr His Lys Arg Asp Thr Tyr Ala Ala
    370                 375                 380

Thr Pro Arg Ala His Glu Val Ser Glu Ile Ser Val Arg Thr Val Tyr
385                 390                 395                 400

Pro Pro Glu Glu Glu Thr Gly Glu Arg Val Gln Leu Ala His His Phe
                405                 410                 415

Ser Glu Pro Glu Ile Thr Leu Ile Ile Phe Gly Val Met Ala Gly Val
            420                 425                 430

Ile Gly Thr Ile Leu Leu Ile Ser Tyr Gly Ile Arg Arg Leu Ile Lys
        435                 440                 445

Lys Ser Pro Ser Asp Val Lys Pro Leu Pro Ser Pro Asp Thr Asp Val
    450                 455                 460

Pro Leu Ser Ser Val Glu Ile Glu Asn Pro Glu Thr Ser Asp Gln
465                 470                 475
```

```
<210> SEQ ID NO 30
<211> LENGTH: 1437
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 30
atgtatggaa aaataatctt tgtattacta ttgtcagaaa ttgtgagcat atcagcaaac 60
tgggtgaacg ttattagtga ccttaaaaag atcgaagatt tgatacagtc aatgcacata 120
gacgcgacgc tttatacaga atctgatgta catccttcat gcaaggttac tgctatgaag 180
tgttttcttc tcgaactcca agtaataagt cttgagagcg gagatgcgag cattcatgac 240
accgttgaga atcttattat attggctaac aactctctgt ccagcaatgg taatgtgaca 300
gaaagcgggt gtaaggagtg cgaggaactc gaggagaaga acatcaaaga gttcttgcag 360
tctttcgtcc atattgtcca gatgttcata aatactagcg ggggaggtgg ctctggtgga 420
ggcgggagtg gcgggggcgg ctcaatcaca tgcccaccgc ccatgtctgt tgaacacgca 480
gacatttggg ttaaaagtta ctcactttac tcacgcgaga gatatatatg caacagcggc 540
ttcaagcgca aagcaggcac tagtagtctt acagagtgcg tgctcaataa agctacaaat 600
gtagctcatt ggactactcc tagtctcaaa tgcattcggg accccgcgct tgtgcaccag 660
agacctgcgc cgccgtccac agtgacgaca gctggtgtaa ccccccaacc tgaatccctt 720
agtccgtctg gtaaagaacc ggcggcgtct tcaccttcca gcaataatac tgcggcgaca 780
acagccgcga tagttcctgg atcccaactc atgccgtcaa agtctccttc aacgggaacg 840
acagagatct cttcacatga aagttctcat ggaacaccga gccaaactac ggcaaagaac 900
tgggaactga ctgcctcagc aagccaccag ccgccagggg tgtacccgca agggcactca 960
gatactactg gaggatctgg cgggtctgga ggctacccct atgacgtgcc cgactatgcc 1020
ggcggagggt ctggaggcgg ttccttaagt accactgagg tggcaatgca cacttcaacc 1080
tcttcttcag tcacaaagag ttacatctca tcacagacaa atgatacgca caaacgggac 1140
acatatgcag ccactcctag agctcatgaa gtttcagaaa tttctgttag aactgtttac 1200
cctccagaag aggaaaccgg agaaagggta caacttgccc atcatttctc tgaaccagag 1260
ataacactca ttatttttgg ggtgatggct ggtgttattg gaacgatcct cttaatttct 1320
tacggtattc gccgactgat aaagaaaagc ccatctgatg taaaacctct cccctcacct 1380
gacacagacg tgcctttaag ttctgttgaa atagaaaatc cagagacaag tgatcaa 1437

<210> SEQ ID NO 31
<211> LENGTH: 382
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Met Tyr Gly Lys Ile Ile Phe Val Leu Leu Leu Ser Glu Ile Val Ser
1 5 10 15

Ile Ser Ala Asn Trp Val Asn Val Ile Ser Asp Leu Lys Lys Ile Glu
20 25 30

Asp Leu Ile Gln Ser Met His Ile Asp Ala Thr Leu Tyr Thr Glu Ser
35 40 45

Asp Val His Pro Ser Cys Lys Val Thr Ala Met Lys Cys Phe Leu Leu
50 55 60

Glu Leu Gln Val Ile Ser Leu Glu Ser Gly Asp Ala Ser Ile His Asp
65 70 75 80

Thr Val Glu Asn Leu Ile Ile Leu Ala Asn Asn Ser Leu Ser Ser Asn
85 90 95

-continued

```
Gly Asn Val Thr Glu Ser Gly Cys Lys Glu Cys Glu Glu Leu Glu Glu
            100                 105                 110

Lys Asn Ile Lys Glu Phe Leu Gln Ser Phe Val His Ile Val Gln Met
        115                 120                 125

Phe Ile Asn Thr Ser Gly Gly Gly Gly Ser Gly Gly Gly Gly Ser Gly
    130                 135                 140

Gly Gly Gly Ser Ile Thr Cys Pro Pro Pro Met Ser Val Glu His Ala
145                 150                 155                 160

Asp Ile Trp Val Lys Ser Tyr Ser Leu Tyr Ser Arg Glu Arg Tyr Ile
                165                 170                 175

Cys Asn Ser Gly Phe Lys Arg Lys Ala Gly Thr Ser Ser Leu Thr Glu
            180                 185                 190

Cys Val Leu Asn Lys Ala Thr Asn Val Ala His Trp Thr Thr Pro Ser
        195                 200                 205

Leu Lys Cys Ile Arg Asp Pro Ala Leu Val His Gln Arg Pro Ala Pro
    210                 215                 220

Pro Ser Gly Gly Ser Gly Gly Ser Gly Gly Tyr Pro Tyr Asp Val Pro
225                 230                 235                 240

Asp Tyr Ala Gly Gly Gly Ser Gly Gly Gly Ser Leu Ser Thr Thr Glu
                245                 250                 255

Val Ala Met His Thr Ser Thr Ser Ser Ser Val Thr Lys Ser Tyr Ile
            260                 265                 270

Ser Ser Gln Thr Asn Asp Thr His Lys Arg Asp Thr Tyr Ala Ala Thr
        275                 280                 285

Pro Arg Ala His Glu Val Ser Glu Ile Ser Val Arg Thr Val Tyr Pro
    290                 295                 300

Pro Glu Glu Glu Thr Gly Glu Arg Val Gln Leu Ala His His Phe Ser
305                 310                 315                 320

Glu Pro Glu Ile Thr Leu Ile Ile Phe Gly Val Met Ala Gly Val Ile
                325                 330                 335

Gly Thr Ile Leu Leu Ile Ser Tyr Gly Ile Arg Arg Leu Ile Lys Lys
            340                 345                 350

Ser Pro Ser Asp Val Lys Pro Leu Pro Ser Pro Asp Thr Asp Val Pro
        355                 360                 365

Leu Ser Ser Val Glu Ile Glu Asn Pro Glu Thr Ser Asp Gln
    370                 375                 380
```

<210> SEQ ID NO 32
<211> LENGTH: 1146
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
atgtatggaa aaataatctt tgtattacta ttgtcagaaa ttgtgagcat atcagcaaac      60

tgggtaaacg tcataagcga cctcaaaaag atcgaggacc ttatacagtc tatgcacata     120

gatgcgacac tttacacgga atcagacgtg caccccgtcct gcaaagtcac agccatgaag    180

tgctttcttc tcgaactgca ggtaatttct ctcgaatcag gtgacgcatc tatccacgac     240

acagttgaaa atcttattat cctggctaat aactccctta gctcaaacgg caatgtcacc     300

gagagtggat gtaaagaatg tgaggaactt gaagagaaaa acataaagga attcttgcag     360

agtttcgttc atattgtgca aatgttcatc aatactagtg gcgggggggg aagcggtggt     420
```

ggagggagcg ggggtggtgg atccatcacc tgcccgcctc ccatgagcgt ggaacacgcg 480
gacatttggg ttaagagcta cagtctttac agccgggagc gctatatctg caactcaggg 540
tttaagcgga aagcagggac atcaagtttg acagaatgtg tgttgaacaa ggctacaaat 600
gttgctcact ggaccacgcc atcttttgaag tgtatccgag atcccgcgct tgtccatcag 660
cgcccagcgc ctccctccgg aggatctggc gggtctggag gctaccccta tgacgtgccc 720
gactatgccg gcggagggtc tggaggcggt tccttaagta ccactgaggt ggcaatgcac 780
acttcaacct cttcttcagt cacaaagagt tacatctcat cacagacaaa tgatacgcac 840
aaacgggaca catatgcagc cactcctaga gctcatgaag tttcagaaat ttctgttaga 900
actgtttacc ctccagaaga ggaaaccgga gaaagggtac aacttgccca tcatttctct 960
gaaccagaga taacactcat tatttttggg gtgatggctg gtgttattgg aacgatcctc 1020
ttaatttctt acggtattcg ccgactgata aagaaaagcc catctgatgt aaaacctctc 1080
ccctcacctg acacagacgt gcctttaagt tctgttgaaa tagaaaatcc agagacaagt 1140
gatcaa 1146

<210> SEQ ID NO 33
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Gly Gly Ser Gly Gly Ser Gly Gly Gly Gly Gly Ser Gly Gly Gly Ser
1 5 10 15

Gly Gly Gly Ser Gly Gly Gly Ser
20

<210> SEQ ID NO 34
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
ggaggatctg gcgggtctgg aggcggcggc ggcagcggcg gcggcagcgg cggagggtct 60
ggaggcggtt cc 72

<210> SEQ ID NO 35
<211> LENGTH: 288
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

Met Tyr Gly Lys Ile Ile Phe Val Leu Leu Leu Ser Glu Ile Val Ser
1 5 10 15

Ile Ser Ala Asn Trp Val Asn Val Ile Ser Asp Leu Lys Lys Ile Glu
20 25 30

Asp Leu Ile Gln Ser Met His Ile Asp Ala Thr Leu Tyr Thr Glu Ser
35 40 45

Asp Val His Pro Ser Cys Lys Val Thr Ala Met Lys Cys Phe Leu Leu

```
    50                  55                  60

Glu Leu Gln Val Ile Ser Leu Glu Ser Gly Asp Ala Ser Ile His Asp
65                  70                  75                  80

Thr Val Glu Asn Leu Ile Ile Leu Ala Asn Asn Ser Leu Ser Ser Asn
                85                  90                  95

Gly Asn Val Thr Glu Ser Gly Cys Lys Glu Cys Glu Glu Leu Glu Glu
            100                 105                 110

Lys Asn Ile Lys Glu Phe Leu Gln Ser Phe Val His Ile Val Gln Met
        115                 120                 125

Phe Ile Asn Thr Ser Gly Gly Ser Gly Gly Ser Gly Gly Gly Gly Gly
    130                 135                 140

Ser Gly Gly Gly Ser Gly Gly Gly Ser Gly Gly Gly Ser Leu Ser Thr
145                 150                 155                 160

Thr Glu Val Ala Met His Thr Ser Thr Ser Ser Ser Val Thr Lys Ser
                165                 170                 175

Tyr Ile Ser Ser Gln Thr Asn Asp Thr His Lys Arg Asp Thr Tyr Ala
            180                 185                 190

Ala Thr Pro Arg Ala His Glu Val Ser Glu Ile Ser Val Arg Thr Val
        195                 200                 205

Tyr Pro Pro Glu Glu Glu Thr Gly Glu Arg Val Gln Leu Ala His His
    210                 215                 220

Phe Ser Glu Pro Glu Ile Thr Leu Ile Ile Phe Gly Val Met Ala Gly
225                 230                 235                 240

Val Ile Gly Thr Ile Leu Leu Ile Ser Tyr Gly Ile Arg Arg Leu Ile
                245                 250                 255

Lys Lys Ser Pro Ser Asp Val Lys Pro Leu Pro Ser Pro Asp Thr Asp
            260                 265                 270

Val Pro Leu Ser Ser Val Glu Ile Glu Asn Pro Glu Thr Ser Asp Gln
        275                 280                 285
```

<210> SEQ ID NO 36
<211> LENGTH: 864
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
atgtatggaa aaataatctt tgtattacta ttgtcagaaa ttgtgagcat atcagcaaac     60

tgggtaaatg tgatttcaga cctgaaaaaa atcgaagacc ttattcaatc catgcacatc    120

gacgcgacac tttatactga atcagacgta cacccgtcct gtaaggttac tgcgatgaag    180

tgctttctgt tggaattgca agtgatctcc ctcgaatcag gggatgcatc cattcatgat    240

accgtcgaga atttgatcat tctggcaaat aactccctca gtagtaacgg gaatgtgacc    300

gagtctgggt gtaaggagtg cgaagagttg gaggaaaaga atatcaaaga attccttcag    360

tcctttgttc acatcgtgca aatgtttatt aatacatctg gaggatctgg cgggtctgga    420

ggcggcggcg gcagcggcgg cggcagcggc ggagggtctg gaggcggttc cttaagtacc    480

actgaggtgg caatgcacac ttcaacctct tcttcagtca caaagagtta catctcatca    540

cagacaaatg atacgcacaa acgggacaca tatgcagcca ctcctagagc tcatgaagtt    600

tcagaaattt ctgttagaac tgtttaccct ccagaagagg aaaccggaga aagggtacaa    660

cttgcccatc atttctctga accagagata acactcatta tttttggggt gatggctggt    720
```

```
gttattggaa cgatcctctt aatttcttac ggtattcgcc gactgataaa gaaaagccca    780

tctgatgtaa aacctctccc ctcacctgac acagacgtgc ctttaagttc tgttgaaata    840

gaaaatccag agacaagtga tcaa                                           864


<210> SEQ ID NO 37
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Tyr Gly Lys Ile Ile Phe Val Leu Leu Leu Ser Glu Ile Val Ser
1               5                   10                  15

Ile Ser Ala Asn Trp Val Asn Val Ile Ser Asp Leu Lys Lys Ile Glu
            20                  25                  30

Asp Leu Ile Gln Ser Met His Ile Asp Ala Thr Leu Tyr Thr Glu Ser
        35                  40                  45

Asp Val His Pro Ser Cys Lys Val Thr Ala Met Lys Cys Phe Leu Leu
    50                  55                  60

Glu Leu Gln Val Ile Ser Leu Glu Ser Gly Asp Ala Ser Ile His Asp
65                  70                  75                  80

Thr Val Glu Asn Leu Ile Ile Leu Ala Asn Asn Ser Leu Ser Ser Asn
                85                  90                  95

Gly Asn Val Thr Glu Ser Gly Cys Lys Glu Cys Glu Glu Leu Glu Glu
            100                 105                 110

Lys Asn Ile Lys Glu Phe Leu Gln Ser Phe Val His Ile Val Gln Met
        115                 120                 125

Phe Ile Asn Thr Ser Gly Gly Gly Gly Ser Gly Gly Gly Gly Ser Gly
    130                 135                 140

Gly Gly Gly Ser Ile Thr Cys Pro Pro Pro Met Ser Val Glu His Ala
145                 150                 155                 160

Asp Ile Trp Val Lys Ser Tyr Ser Leu Tyr Ser Arg Glu Arg Tyr Ile
                165                 170                 175

Cys Asn Ser Gly Phe Lys Arg Lys Ala Gly Thr Ser Ser Leu Thr Glu
            180                 185                 190

Cys Val Leu Asn Lys Ala Thr Asn Val Ala His Trp Thr Thr Pro Ser
        195                 200                 205

Leu Lys Cys Ile Arg Asp Pro Ala Leu Val His Gln Arg Pro Ala Pro
    210                 215                 220

Pro Ser Thr Val Thr Thr Ala Gly Val Thr Pro Gln Pro Glu Ser Leu
225                 230                 235                 240

Ser Pro Ser Gly Lys Glu Pro Ala Ala Ser Ser Pro Ser Ser Asn Asn
                245                 250                 255

Thr Ala Ala Thr Thr Ala Ala Ile Val Pro Gly Ser Gln Leu Met Pro
            260                 265                 270

Ser Lys Ser Pro Ser Thr Gly Thr Thr Glu Ile Ser Ser His Glu Ser
        275                 280                 285

Ser His Gly Thr Pro Ser Gln Thr Thr Ala Lys Asn Trp Glu Leu Thr
    290                 295                 300

Ala Ser Ala Ser His Gln Pro Pro Gly Val Tyr Pro Gln Gly His Ser
305                 310                 315                 320

Asp Thr Thr Gly Gly Ser Gly Gly Ser Gly Gly Gly Gly Ser Gly
                325                 330                 335
```

```
Gly Gly Ser Gly Gly Gly Ser Gly Gly Gly Ser Leu Ser Thr Thr Glu
            340                 345                 350

Val Ala Met His Thr Ser Thr Ser Ser Ser Val Thr Lys Ser Tyr Ile
        355                 360                 365

Ser Ser Gln Thr Asn Asp Thr His Lys Arg Asp Thr Tyr Ala Ala Thr
    370                 375                 380

Pro Arg Ala His Glu Val Ser Glu Ile Ser Val Arg Thr Val Tyr Pro
385                 390                 395                 400

Pro Glu Glu Glu Thr Gly Glu Arg Val Gln Leu Ala His His Phe Ser
                405                 410                 415

Glu Pro Glu Ile Thr Leu Ile Ile Phe Gly Val Met Ala Gly Val Ile
            420                 425                 430

Gly Thr Ile Leu Leu Ile Ser Tyr Gly Ile Arg Arg Leu Ile Lys Lys
        435                 440                 445

Ser Pro Ser Asp Val Lys Pro Leu Pro Ser Pro Asp Thr Asp Val Pro
    450                 455                 460

Leu Ser Ser Val Glu Ile Glu Asn Pro Glu Thr Ser Asp Gln
465                 470                 475
```

<210> SEQ ID NO 38
<211> LENGTH: 1434
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 38

```
atgtatggaa aaataatctt tgtattacta ttgtcagaaa ttgtgagcat atcagcaaac     60

tgggtgaacg ttattagtga ccttaaaaag atcgaagatt tgatacagtc aatgcacata    120

gacgcgacgc tttatacaga atctgatgta catccttcat gcaaggttac tgctatgaag    180

tgttttcttc tcgaactcca agtaataagt cttgagagcg gagatgcgag cattcatgac    240

accgttgaga atcttattat attggctaac aactctctgt ccagcaatgg taatgtgaca    300

gaaagcgggt gtaaggagtg cgaggaactc gaggagaaga acatcaaaga gttcttgcag    360

tctttcgtcc atattgtcca gatgttcata aatactagcg ggggaggtgg ctctggtgga    420

ggcgggagtg gcgggggcgg ctcaatcaca tgcccaccgc ccatgtctgt tgaacacgca    480

gacatttggg ttaaaagtta ctcactttac tcacgcgaga gatatatatg caacagcggc    540

ttcaagcgca aagcaggcac tagtagtctt acagagtgcg tgctcaataa agctacaaat    600

gtagctcatt ggactactcc tagtctcaaa tgcattcggg accccgcgct tgtgcaccag    660

agacctgcgc cgccgtccac agtgacgaca gctggtgtaa ccccccaacc tgaatccctt    720

agtccgtctg gtaaagaacc ggcggcgtct tcaccttcca gcaataatac tgcggcgaca    780

acagccgcga tagttcctgg atcccaactc atgccgtcaa agtctccttc aacgggaacg    840

acagagatct cttcacatga aagttctcat ggaacaccga gccaaactac ggcaaagaac    900

tgggaactga ctgcctcagc aagccaccag ccgccagggg tgtacccgca agggcactca    960

gatactactg gaggatctgg cgggtctgga ggcggcggcg gcagcggcgg cggcagcggc   1020

ggagggtctg gaggcggttc cttaagtacc actgaggtgg caatgcacac ttcaacctct   1080

tcttcagtca caaagagtta catctcatca cagacaaatg atacgcacaa acgggacaca   1140

tatgcagcca ctcctagagc tcatgaagtt tcagaaattt ctgttagaac tgtttaccct   1200
```

-continued

```
ccagaagagg aaaccggaga aagggtacaa cttgcccatc atttctctga accagagata   1260

acactcatta tttttggggt gatggctggt gttattggaa cgatcctctt aatttcttac   1320

ggtattcgcc gactgataaa gaaaagccca tctgatgtaa aacctctccc ctcacctgac   1380

acagacgtgc ctttaagttc tgttgaaata gaaaatccag agacaagtga tcaa         1434


<210> SEQ ID NO 39
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Gly Ser Gly Gly Ser Gly Gly Gly Pro Glu Asp Glu Pro Gly Ser
1               5                   10                  15

Gly Ser Gly Gly Gly Ser Gly Gly Gly Ser
            20                  25


<210> SEQ ID NO 40
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

ggaggatctg gcgggtctgg aggcggcccc gaggacgagc ccggcagcgg cagcggcgga     60

gggtctggag gcggttcc                                                   78


<210> SEQ ID NO 41
<211> LENGTH: 205
<212> TYPE: PRT
<213> ORGANISM: Homo sapiens

<400> SEQUENCE: 41

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30

Ala Gly Leu Leu Asp Leu Arg Gln Gly Met Phe Ala Gln Leu Val Ala
        35                  40                  45

Gln Asn Val Leu Leu Ile Asp Gly Pro Leu Ser Trp Tyr Ser Asp Pro
    50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
            100                 105                 110

Ser Leu Ala Leu His Leu Gln Pro Leu Arg Ser Ala Ala Gly Ala Ala
        115                 120                 125

Ala Leu Ala Leu Thr Val Asp Leu Pro Pro Ala Ser Ser Glu Ala Arg
    130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
```

```
                165                 170                 175

Trp Gln Leu Thr Gln Gly Ala Thr Val Leu Gly Leu Phe Arg Val Thr
            180                 185                 190

Pro Glu Ile Pro Ala Gly Leu Pro Ser Pro Arg Ser Glu
        195                 200                 205
```

<210> SEQ ID NO 42
<211> LENGTH: 615
<212> TYPE: DNA
<213> ORGANISM: Homo sapiens

<400> SEQUENCE: 42

```
gcctgcccct gggccgtgtc cggggctcgc gcctcgcccg gctccgcggc cagcccgaga     60

ctccgcgagg gtcccgagct ttcgcccgac gatcccgccg gcctcttgga cctgcggcag    120

ggcatgtttg cgcagctggt ggcccaaaat gttctgctga tcgatgggcc cctgagctgg    180

tacagtgacc caggcctggc aggcgtgtcc ctgacggggg gcctgagcta caaagaggac    240

acgaaggagc tggtggtggc caaggctgga gtctactatg tcttctttca actagagctg    300

cggcgcgtgg tggccggcga gggctcaggc tccgtttcac ttgcgctgca cctgcagcca    360

ctgcgctctg ctgctggggc cgccgccctg gctttgaccg tggacctgcc acccgcctcc    420

tccgaggctc ggaactcggc cttcggtttc cagggccgct tgctgcacct gagtgccggc    480

cagcgcctgg gcgtccatct tcacactgag gccagggcac gccatgcctg gcagcttacc    540

cagggcgcca cagtcttggg actcttccgg gtgacccccg aaatcccagc cggactccct    600

tcaccgaggt cggaa                                                     615
```

<210> SEQ ID NO 43
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Met Tyr Gly Lys Ile Ile Phe Val Leu Leu Leu Ser Glu Ile Val Ser
1               5                   10                  15

Ile Ser Ala Ala Cys Pro Trp Ala Val Ser Gly Ala Arg Ala Ser Pro
            20                  25                  30

Gly Ser Ala Ala Ser Pro Arg Leu Arg Glu Gly Pro Glu Leu Ser Pro
        35                  40                  45

Asp Asp Pro Ala Gly Leu Leu Asp Leu Arg Gln Gly Met Phe Ala Gln
    50                  55                  60

Leu Val Ala Gln Asn Val Leu Leu Ile Asp Gly Pro Leu Ser Trp Tyr
65                  70                  75                  80

Ser Asp Pro Gly Leu Ala Gly Val Ser Leu Thr Gly Gly Leu Ser Tyr
                85                  90                  95

Lys Glu Asp Thr Lys Glu Leu Val Val Ala Lys Ala Gly Val Tyr Tyr
            100                 105                 110

Val Phe Phe Gln Leu Glu Leu Arg Arg Val Val Ala Gly Glu Gly Ser
        115                 120                 125

Gly Ser Val Ser Leu Ala Leu His Leu Gln Pro Leu Arg Ser Ala Ala
    130                 135                 140

Gly Ala Ala Ala Leu Ala Leu Thr Val Asp Leu Pro Pro Ala Ser Ser
145                 150                 155                 160
```

```
Glu Ala Arg Asn Ser Ala Phe Gly Phe Gln Gly Arg Leu Leu His Leu
                165                 170                 175

Ser Ala Gly Gln Arg Leu Gly Val His Leu His Thr Glu Ala Arg Ala
            180                 185                 190

Arg His Ala Trp Gln Leu Thr Gln Gly Ala Thr Val Leu Gly Leu Phe
        195                 200                 205

Arg Val Thr Pro Glu Ile Pro Ala Gly Leu Pro Ser Pro Arg Ser Glu
    210                 215                 220

Gly Gly Ser Gly Gly Ser Gly Gly Gly Pro Glu Asp Glu Pro Gly Ser
225                 230                 235                 240

Gly Ser Gly Gly Gly Ser Gly Gly Gly Ser Leu Ser Thr Thr Glu Val
                245                 250                 255

Ala Met His Thr Ser Thr Ser Ser Ser Val Thr Lys Ser Tyr Ile Ser
            260                 265                 270

Ser Gln Thr Asn Asp Thr His Lys Arg Asp Thr Tyr Ala Ala Thr Pro
        275                 280                 285

Arg Ala His Glu Val Ser Glu Ile Ser Val Arg Thr Val Tyr Pro Pro
    290                 295                 300

Glu Glu Glu Thr Gly Glu Arg Val Gln Leu Ala His His Phe Ser Glu
305                 310                 315                 320

Pro Glu Ile Thr Leu Ile Ile Phe Gly Val Met Ala Gly Val Ile Gly
                325                 330                 335

Thr Ile Leu Leu Ile Ser Tyr Gly Ile Arg Arg Leu Ile Lys Lys Ser
            340                 345                 350

Pro Ser Asp Val Lys Pro Leu Pro Ser Pro Asp Thr Asp Val Pro Leu
        355                 360                 365

Ser Ser Val Glu Ile Glu Asn Pro Glu Thr Ser Asp Gln
    370                 375                 380
```

<210> SEQ ID NO 44
<211> LENGTH: 1143
<212> TYPE: DNA
<213> ORGANISM: Homo sapiens

<400> SEQUENCE: 44

```
atgtatggaa aaataatctt tgtattacta ttgtcagaaa ttgtgagcat atcagcagcc      60

tgcccctggg ccgtgtccgg ggctcgcgcc tcgcccggct ccgcggccag cccgagactc     120

cgcgagggtc ccgagctttc gcccgacgat cccgccggcc tcttggacct gcggcagggc     180

atgtttgcgc agctggtggc ccaaaatgtt ctgctgatcg atgggcccct gagctggtac     240

agtgacccag gcctggcagg cgtgtccctg acggggggcc tgagctacaa agaggacacg     300

aaggagctgg tggtggccaa ggctggagtc tactatgtct tctttcaact agagctgcgg     360

cgcgtggtgg ccggcgaggg ctcaggctcc gtttcacttg cgctgcacct gcagccactg     420

cgctctgctg ctggggccgc cgccctggct ttgaccgtgg acctgccacc cgcctcctcc     480

gaggctcgga actcggcctt cggtttccag ggccgcttgc tgcacctgag tgccggccag     540

cgcctgggcg tccatcttca cactgaggcc agggcacgcc atgcctggca gcttacccag     600

ggcgccacag tcttgggact cttccgggtg acccccgaaa tcccagccgg actcccttca     660

ccgaggtcgg aaggaggatc tggcgggtct ggaggcggcc ccgaggacga gcccggcagc     720

ggcagcggcg gagggtctgg aggcggttcc ttaagtacca ctgaggtggc aatgcacact     780

tcaacctctt cttcagtcac aaagagttac atctcatcac agacaaatga tacgcacaaa     840

cgggacacat atgcagccac tcctagagct catgaagttt cagaaatttc tgttagaact     900
```

```
gtttaccctc cagaagagga aaccggagaa agggtacaac ttgcccatca tttctctgaa     960

ccagagataa cactcattat ttttggggtg atggctggtg ttattggaac gatcctctta    1020

atttcttacg gtattcgccg actgataaag aaaagcccat ctgatgtaaa acctctcccc    1080

tcacctgaca cagacgtgcc tttaagttct gttgaaatag aaaatccaga gacaagtgat    1140

caa                                                                  1143


<210> SEQ ID NO 45
<211> LENGTH: 306
<212> TYPE: PRT
<213> ORGANISM: Homo sapiens

<400> SEQUENCE: 45

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305
```

<210> SEQ ID NO 46
<211> LENGTH: 918
<212> TYPE: DNA
<213> ORGANISM: Homo sapiens

<400> SEQUENCE: 46
atctgggagc tgaagaagga cgtgtacgtg gtggagctgg actggtatcc tgatgcccca 60
ggcgagatgg tggtgctgac ctgcgacaca cctgaggagg atggcatcac ctggacactg 120
gatcagagca gcgaggtgct gggctccggc aagaccctga caatccaggt gaaggagttc 180
ggcgacgccg gccagtacac atgtcacaag ggaggagagg tgctgagcca ctccctgctg 240
ctgctgcaca agaaggagga cggcatctgg tctacagaca tcctgaagga tcagaaggag 300
cccaagaaca agaccttcct gcggtgcgag gccaagaatt atagcggccg gttcacctgt 360
tggtggctga ccacaatctc taccgacctg accttcagcg tgaagtctag ccggggctcc 420
tctgaccctc agggagtgac atgcggagca gccaccctgt ccgccgagcg ggtgagaggc 480
gataacaagg agtacgagta tagcgtggag tgccaggagg actccgcctg tccagcagca 540
gaggagagcc tgccaatcga agtgatggtg gatgccgtgc acaagctgaa gtacgagaat 600
tatacaagct ccttctttat cagggacatc atcaagcccg atccccctaa gaacctgcag 660
ctgaagcccc tgaagaacag ccggcaggtg gaggtgtctt gggagtaccc cgacacctgg 720
agcacacctc actcctattt ctctctgacc ttttgcgtgc aggtgcaggg caagtccaag 780
agggagaaga aggaccgcgt gttcaccgat aagacatctg ccaccgtgat ctgtcggaag 840
aacgcctcta tcagcgtgcg ggcccaggat agatactatt ctagctcctg gagcgagtgg 900
gcctccgtgc catgttct 918

<210> SEQ ID NO 47
<211> LENGTH: 197
<212> TYPE: PRT
<213> ORGANISM: Homo sapiens

<400> SEQUENCE: 47

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu

```
                165                 170                 175

Leu His Ala Phe Arg Ile Arg Ala Val Thr Ile Asp Arg Val Met Ser
            180                 185                 190

Tyr Leu Asn Ala Ser
        195


<210> SEQ ID NO 48
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

cggaatctgc cagtggcaac cccagacccc ggaatgttcc catgcctgca ccactctcag      60

aacctgctga gggccgtgag caatatgctg cagaaggccc gccagacact ggagttttac     120

ccttgtacca gcgaggagat cgaccacgag gacatcacaa aggataagac ctccacagtg     180

gaggcctgcc tgccactgga gctgaccaag aacgagagct gtctgaacag ccgggagacc     240

agcttcatca ccaacggcag ctgcctggcc tccagaaaga catcttttat gatggccctg     300

tgcctgtcta gcatctacga ggacctgaag atgtatcagg tggagttcaa gaccatgaac     360

gccaagctgc tgatggaccc caagaggcag attttcctgg accagaatat gctggccgtg     420

atcgacgagc tgatgcaggc cctgaacttt aattccgaga cagtgcctca gaagtcctct     480

ctggaggagc cagatttcta caagaccaag atcaagctgt gcatcctgct gcacgccttc     540

cggatcagag ccgtgaccat cgaccgcgtg atgagctatc tgaatgcctc c              591


<210> SEQ ID NO 49
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Gln Pro Gln Glu Ser His Val His Tyr Ser Arg Trp Glu Asp Gly
1               5                   10                  15

Ser Arg Asp Gly Val Ser Leu Gly Ala Val Ser Ser Thr Glu Glu Ala
            20                  25                  30

Ser Arg Cys Arg Arg Ile Ser Gln Arg Leu Cys Thr Gly Lys Leu Gly
        35                  40                  45

Ile Ala Met Lys Val Leu Gly Gly Val Ala Leu Phe Trp Ile Ile Phe
    50                  55                  60

Ile Leu Gly Tyr Leu Thr Gly Tyr Tyr Val His Lys Cys Lys
65                  70                  75


<210> SEQ ID NO 50
<211> LENGTH: 234
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

atgcaaccgc aagagagtca cgtacattat tcaagatggg aagatggaag tcgggacggt      60

gtgtctctcg gcgctgttag ttcaacggag gaagcgtctc gctgtcgccg gataagtcaa     120
```

```
cgcctttgta cgggaaaact gggtatagct atgaaggtcc tcggcggggt ggcgttgttt    180

tggattatct ttatacttgg gtatctgacc ggttactatg ttcacaagtg taaa          234


<210> SEQ ID NO 51
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Gly Ser Gly Gly Ser Gly Gly Gly Gly Gly Ser Gly Gly Gly Ser
1               5                   10                  15

Gly Gly Gly Ser Gly Gly Gly Ser
            20


<210> SEQ ID NO 52
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52

ggaggatctg gcgggtctgg aggcggcggc ggcagcggcg gcggcagcgg cggagggtct     60

ggaggcggtt cc                                                          72


<210> SEQ ID NO 53
<211> LENGTH: 692
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Tyr Gly Lys Ile Ile Phe Val Leu Leu Leu Ser Glu Ile Val Ser
1               5                   10                  15

Ile Ser Ala Ile Trp Glu Leu Lys Lys Asp Val Tyr Val Val Glu Leu
            20                  25                  30

Asp Trp Tyr Pro Asp Ala Pro Gly Glu Met Val Val Leu Thr Cys Asp
        35                  40                  45

Thr Pro Glu Glu Asp Gly Ile Thr Trp Thr Leu Asp Gln Ser Ser Glu
    50                  55                  60

Val Leu Gly Ser Gly Lys Thr Leu Thr Ile Gln Val Lys Glu Phe Gly
65                  70                  75                  80

Asp Ala Gly Gln Tyr Thr Cys His Lys Gly Gly Glu Val Leu Ser His
                85                  90                  95

Ser Leu Leu Leu Leu His Lys Lys Glu Asp Gly Ile Trp Ser Thr Asp
            100                 105                 110

Ile Leu Lys Asp Gln Lys Glu Pro Lys Asn Lys Thr Phe Leu Arg Cys
        115                 120                 125

Glu Ala Lys Asn Tyr Ser Gly Arg Phe Thr Cys Trp Trp Leu Thr Thr
    130                 135                 140

Ile Ser Thr Asp Leu Thr Phe Ser Val Lys Ser Ser Arg Gly Ser Ser
145                 150                 155                 160

Asp Pro Gln Gly Val Thr Cys Gly Ala Ala Thr Leu Ser Ala Glu Arg
```

-continued

```
                165                 170                 175

Val Arg Gly Asp Asn Lys Glu Tyr Glu Tyr Ser Val Glu Cys Gln Glu
            180                 185                 190

Asp Ser Ala Cys Pro Ala Ala Glu Glu Ser Leu Pro Ile Glu Val Met
        195                 200                 205

Val Asp Ala Val His Lys Leu Lys Tyr Glu Asn Tyr Thr Ser Ser Phe
    210                 215                 220

Phe Ile Arg Asp Ile Ile Lys Pro Asp Pro Pro Lys Asn Leu Gln Leu
225                 230                 235                 240

Lys Pro Leu Lys Asn Ser Arg Gln Val Glu Val Ser Trp Glu Tyr Pro
                245                 250                 255

Asp Thr Trp Ser Thr Pro His Ser Tyr Phe Ser Leu Thr Phe Cys Val
            260                 265                 270

Gln Val Gln Gly Lys Ser Lys Arg Glu Lys Lys Asp Arg Val Phe Thr
        275                 280                 285

Asp Lys Thr Ser Ala Thr Val Ile Cys Arg Lys Asn Ala Ser Ile Ser
    290                 295                 300

Val Arg Ala Gln Asp Arg Tyr Tyr Ser Ser Ser Trp Ser Glu Trp Ala
305                 310                 315                 320

Ser Val Pro Cys Ser Gly Gly Gly Gly Ser Gly Gly Gly Gly Ser Gly
                325                 330                 335

Gly Gly Gly Ser Arg Asn Leu Pro Val Ala Thr Pro Asp Pro Gly Met
            340                 345                 350

Phe Pro Cys Leu His His Ser Gln Asn Leu Leu Arg Ala Val Ser Asn
        355                 360                 365

Met Leu Gln Lys Ala Arg Gln Thr Leu Glu Phe Tyr Pro Cys Thr Ser
    370                 375                 380

Glu Glu Ile Asp His Glu Asp Ile Thr Lys Asp Lys Thr Ser Thr Val
385                 390                 395                 400

Glu Ala Cys Leu Pro Leu Glu Leu Thr Lys Asn Glu Ser Cys Leu Asn
                405                 410                 415

Ser Arg Glu Thr Ser Phe Ile Thr Asn Gly Ser Cys Leu Ala Ser Arg
            420                 425                 430

Lys Thr Ser Phe Met Met Ala Leu Cys Leu Ser Ser Ile Tyr Glu Asp
        435                 440                 445

Leu Lys Met Tyr Gln Val Glu Phe Lys Thr Met Asn Ala Lys Leu Leu
    450                 455                 460

Met Asp Pro Lys Arg Gln Ile Phe Leu Asp Gln Asn Met Leu Ala Val
465                 470                 475                 480

Ile Asp Glu Leu Met Gln Ala Leu Asn Phe Asn Ser Glu Thr Val Pro
                485                 490                 495

Gln Lys Ser Ser Leu Glu Glu Pro Asp Phe Tyr Lys Thr Lys Ile Lys
            500                 505                 510

Leu Cys Ile Leu Leu His Ala Phe Arg Ile Arg Ala Val Thr Ile Asp
        515                 520                 525

Arg Val Met Ser Tyr Leu Asn Ala Ser Gly Gly Ser Gly Gly Ser Gly
    530                 535                 540

Gly Gly Gly Gly Ser Gly Gly Gly Ser Gly Gly Gly Ser Gly Gly Gly
545                 550                 555                 560

Ser Leu Ser Thr Thr Glu Val Ala Met His Thr Ser Thr Ser Ser Ser
                565                 570                 575

Val Thr Lys Ser Tyr Ile Ser Ser Gln Thr Asn Asp Thr His Lys Arg
            580                 585                 590
```

```
Asp Thr Tyr Ala Ala Thr Pro Arg Ala His Glu Val Ser Glu Ile Ser
        595                 600                 605

Val Arg Thr Val Tyr Pro Pro Glu Glu Glu Thr Gly Glu Arg Val Gln
    610                 615                 620

Leu Ala His His Phe Ser Glu Pro Glu Ile Thr Leu Ile Ile Phe Gly
625                 630                 635                 640

Val Met Ala Gly Val Ile Gly Thr Ile Leu Leu Ile Ser Tyr Gly Ile
                645                 650                 655

Arg Arg Leu Ile Lys Lys Ser Pro Ser Asp Val Lys Pro Leu Pro Ser
            660                 665                 670

Pro Asp Thr Asp Val Pro Leu Ser Ser Val Glu Ile Glu Asn Pro Glu
        675                 680                 685

Thr Ser Asp Gln
    690
```

<210> SEQ ID NO 54
<211> LENGTH: 2076
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
atgtatggaa aaataatctt tgtattacta ttgtcagaaa ttgtgagcat atcagcaatc     60

tgggagctga agaaggacgt gtacgtggtg gagctggact ggtatcctga tgccccaggc    120

gagatggtgg tgctgacctg cgacacacct gaggaggatg gcatcacctg gacactggat    180

cagagcagcg aggtgctggg ctccggcaag accctgacaa tccaggtgaa ggagttcggc    240

gacgccggcc agtacacatg tcacaaggga ggagaggtgc tgagccactc cctgctgctg    300

ctgcacaaga aggaggacgg catctggtct acagacatcc tgaaggatca gaaggagccc    360

aagaacaaga ccttcctgcg gtgcgaggcc aagaattata gcggccggtt cacctgttgg    420

tggctgacca caatctctac cgacctgacc ttcagcgtga agtctagccg gggctcctct    480

gaccctcagg gagtgacatg cggagcagcc accctgtccg ccgagcgggt gagaggcgat    540

aacaaggagt acgagtatag cgtggagtgc caggaggact ccgcctgtcc agcagcagag    600

gagagcctgc caatcgaagt gatggtggat gccgtgcaca agctgaagta cgagaattat    660

acaagctcct tctttatcag ggacatcatc aagcccgatc cccctaagaa cctgcagctg    720

aagcccctga agaacagccg gcaggtggag gtgtcttggg agtaccccga cacctggagc    780

acacctcact cctatttctc tctgaccttt tgcgtgcagg tgcagggcaa gtccaagagg    840

gagaagaagg accgcgtgtt caccgataag acatctgcca ccgtgatctg tcggaagaac    900

gcctctatca gcgtgcgggc ccaggataga tactattcta gctcctggag cgagtgggcc    960

tccgtgccat gttctggagg aggaggcagc ggcggaggag gctccggcgg cggcggcagc   1020

cggaatctgc cagtggcaac cccagacccc ggaatgttcc catgcctgca ccactctcag   1080

aacctgctga gggccgtgag caatatgctg cagaaggccc gccagacact ggagttttac   1140

ccttgtacca gcgaggagat cgaccacgag gacatcacaa aggataagac ctccacagtg   1200

gaggcctgcc tgccactgga gctgaccaag aacgagagct gtctgaacag ccgggagacc   1260

agcttcatca ccaacggcag ctgcctggcc tccagaaaga catcttttat gatggccctg   1320

tgcctgtcta gcatctacga ggacctgaag atgtatcagg tggagttcaa gaccatgaac   1380
```

gccaagctgc tgatggaccc caagaggcag attttcctgg accagaatat gctggccgtg 1440
atcgacgagc tgatgcaggc cctgaacttt aattccgaga cagtgcctca gaagtcctct 1500
ctggaggagc cagatttcta caagaccaag atcaagctgt gcatcctgct gcacgccttc 1560
cggatcagag ccgtgaccat cgaccgcgtg atgagctatc tgaatgcctc cggaggatct 1620
ggcgggtctg gaggcggcgg cggcagcggc ggcggcagcg gcggagggtc tggaggcggt 1680
tccttaagta ccactgaggt ggcaatgcac acttcaacct cttcttcagt cacaaagagt 1740
tacatctcat cacagacaaa tgatacgcac aaacgggaca catatgcagc cactcctaga 1800
gctcatgaag tttcagaaat ttctgttaga actgtttacc ctccagaaga ggaaaccgga 1860
gaaagggtac aacttgccca tcatttctct gaaccagaga taacactcat tatttttggg 1920
gtgatggctg gtgttattgg aacgatcctc ttaatttctt acggtattcg ccgactgata 1980
aagaaaagcc catctgatgt aaaacctctc ccctcacctg acacagacgt gcctttaagt 2040
tctgttgaaa tagaaaatcc agagacaagt gatcaa 2076

<210> SEQ ID NO 55
<211> LENGTH: 611
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

Met Gln Pro Gln Glu Ser His Val His Tyr Ser Arg Trp Glu Asp Gly
1 5 10 15

Ser Arg Asp Gly Val Ser Leu Gly Ala Val Ser Ser Thr Glu Glu Ala
20 25 30

Ser Arg Cys Arg Arg Ile Ser Gln Arg Leu Cys Thr Gly Lys Leu Gly
35 40 45

Ile Ala Met Lys Val Leu Gly Gly Val Ala Leu Phe Trp Ile Ile Phe
50 55 60

Ile Leu Gly Tyr Leu Thr Gly Tyr Tyr Val His Lys Cys Lys Gly Gly
65 70 75 80

Gly Gly Ser Gly Gly Gly Gly Ser Gly Gly Gly Gly Ser Ile Trp Glu
85 90 95

Leu Lys Lys Asp Val Tyr Val Val Glu Leu Asp Trp Tyr Pro Asp Ala
100 105 110

Pro Gly Glu Met Val Val Leu Thr Cys Asp Thr Pro Glu Glu Asp Gly
115 120 125

Ile Thr Trp Thr Leu Asp Gln Ser Ser Glu Val Leu Gly Ser Gly Lys
130 135 140

Thr Leu Thr Ile Gln Val Lys Glu Phe Gly Asp Ala Gly Gln Tyr Thr
145 150 155 160

Cys His Lys Gly Gly Glu Val Leu Ser His Ser Leu Leu Leu Leu His
165 170 175

Lys Lys Glu Asp Gly Ile Trp Ser Thr Asp Ile Leu Lys Asp Gln Lys
180 185 190

Glu Pro Lys Asn Lys Thr Phe Leu Arg Cys Glu Ala Lys Asn Tyr Ser
195 200 205

Gly Arg Phe Thr Cys Trp Trp Leu Thr Thr Ile Ser Thr Asp Leu Thr
210 215 220

Phe Ser Val Lys Ser Ser Arg Gly Ser Ser Asp Pro Gln Gly Val Thr
225 230 235 240

```
Cys Gly Ala Ala Thr Leu Ser Ala Glu Arg Val Arg Gly Asp Asn Lys
                245                 250                 255

Glu Tyr Glu Tyr Ser Val Glu Cys Gln Glu Asp Ser Ala Cys Pro Ala
            260                 265                 270

Ala Glu Glu Ser Leu Pro Ile Glu Val Met Val Asp Ala Val His Lys
        275                 280                 285

Leu Lys Tyr Glu Asn Tyr Thr Ser Ser Phe Phe Ile Arg Asp Ile Ile
    290                 295                 300

Lys Pro Asp Pro Pro Lys Asn Leu Gln Leu Lys Pro Leu Lys Asn Ser
305                 310                 315                 320

Arg Gln Val Glu Val Ser Trp Glu Tyr Pro Asp Thr Trp Ser Thr Pro
                325                 330                 335

His Ser Tyr Phe Ser Leu Thr Phe Cys Val Gln Val Gln Gly Lys Ser
            340                 345                 350

Lys Arg Glu Lys Lys Asp Arg Val Phe Thr Asp Lys Thr Ser Ala Thr
        355                 360                 365

Val Ile Cys Arg Lys Asn Ala Ser Ile Ser Val Arg Ala Gln Asp Arg
    370                 375                 380

Tyr Tyr Ser Ser Ser Trp Ser Glu Trp Ala Ser Val Pro Cys Ser Gly
385                 390                 395                 400

Gly Gly Gly Ser Gly Gly Gly Gly Ser Gly Gly Gly Gly Ser Arg Asn
                405                 410                 415

Leu Pro Val Ala Thr Pro Asp Pro Gly Met Phe Pro Cys Leu His His
            420                 425                 430

Ser Gln Asn Leu Leu Arg Ala Val Ser Asn Met Leu Gln Lys Ala Arg
        435                 440                 445

Gln Thr Leu Glu Phe Tyr Pro Cys Thr Ser Glu Glu Ile Asp His Glu
    450                 455                 460

Asp Ile Thr Lys Asp Lys Thr Ser Thr Val Glu Ala Cys Leu Pro Leu
465                 470                 475                 480

Glu Leu Thr Lys Asn Glu Ser Cys Leu Asn Ser Arg Glu Thr Ser Phe
                485                 490                 495

Ile Thr Asn Gly Ser Cys Leu Ala Ser Arg Lys Thr Ser Phe Met Met
            500                 505                 510

Ala Leu Cys Leu Ser Ser Ile Tyr Glu Asp Leu Lys Met Tyr Gln Val
        515                 520                 525

Glu Phe Lys Thr Met Asn Ala Lys Leu Leu Met Asp Pro Lys Arg Gln
    530                 535                 540

Ile Phe Leu Asp Gln Asn Met Leu Ala Val Ile Asp Glu Leu Met Gln
545                 550                 555                 560

Ala Leu Asn Phe Asn Ser Glu Thr Val Pro Gln Lys Ser Ser Leu Glu
                565                 570                 575

Glu Pro Asp Phe Tyr Lys Thr Lys Ile Lys Leu Cys Ile Leu Leu His
            580                 585                 590

Ala Phe Arg Ile Arg Ala Val Thr Ile Asp Arg Val Met Ser Tyr Leu
        595                 600                 605

Asn Ala Ser
    610
```

<210> SEQ ID NO 56
<211> LENGTH: 1833
<212> TYPE: DNA
<213> ORGANISM: Artificial Sequence
<220> FEATURE:

-continued

<223> OTHER INFORMATION: Description of Artificial Sequence: Synthetic polynucleotide

<400> SEQUENCE: 56

```
atgcaaccgc aagagagtca cgtacattat tcaagatggg aagatggaag tcgggacggt     60
gtgtctctcg gcgctgttag ttcaacggag gaagcgtctc gctgtcgccg gataagtcaa    120
cgcctttgta cgggaaaact gggtatagct atgaaggtcc tcggcggggt ggcgttgttt    180
tggattatct ttatacttgg gtatctgacc ggttactatg ttcacaagtg taaaggaggt    240
ggaggatcag gtggaggtgg ttcaggtgga ggaggtagca tctgggagct gaagaaggac    300
gtgtacgtgg tggagctgga ctggtatcct gatgccccag gcgagatggt ggtgctgacc    360
tgcgacacac ctgaggagga tggcatcacc tggacactgg atcagagcag cgaggtgctg    420
ggctccggca agaccctgac aatccaggtg aaggagttcg gcgacgccgg ccagtacaca    480
tgtcacaagg gaggagaggt gctgagccac tccctgctgc tgctgcacaa gaaggaggac    540
ggcatctggt ctacagacat cctgaaggat cagaaggagc ccaagaacaa gaccttcctg    600
cggtgcgagg ccaagaatta tagcggccgg ttcacctgtt ggtggctgac cacaatctct    660
accgacctga ccttcagcgt gaagtctagc cggggctcct ctgaccctca gggagtgaca    720
tgcggagcag ccaccctgtc cgccgagcgg gtgagaggcg ataacaagga gtacgagtat    780
agcgtggagt gccaggagga ctccgcctgt ccagcagcag aggagagcct gccaatcgaa    840
gtgatggtgg atgccgtgca caagctgaag tacgagaatt atacaagctc cttctttatc    900
agggacatca tcaagcccga tcccccctaag aacctgcagc tgaagcccct gaagaacagc    960
cggcaggtgg aggtgtcttg ggagtacccc gacacctgga gcacacctca ctcctatttc   1020
tctctgacct tttgcgtgca ggtgcagggc aagtccaaga gggagaagaa ggaccgcgtg   1080
ttcaccgata agacatctgc caccgtgatc tgtcggaaga acgcctctat cagcgtgcgg   1140
gcccaggata gatactattc tagctcctgg agcgagtggg cctccgtgcc atgttctgga   1200
ggaggaggca gcggcggagg aggctccggc ggcggcggca gccggaatct gccagtggca   1260
accccagacc ccggaatgtt cccatgcctg caccactctc agaacctgct gagggccgtg   1320
agcaatatgc tgcagaaggc ccgccagaca ctggagtttt acccttgtac cagcgaggag   1380
atcgaccacg aggacatcac aaaggataag acctccacag tggaggcctg cctgccactg   1440
gagctgacca agaacgagag ctgtctgaac agccgggaga ccagcttcat caccaacggc   1500
agctgcctgg cctccagaaa gacatctttt atgatggccc tgtgcctgtc tagcatctac   1560
gaggacctga agatgtatca ggtggagttc aagaccatga acgccaagct gctgatggac   1620
cccaagaggc agattttcct ggaccagaat atgctggccg tgatcgacga gctgatgcag   1680
gccctgaact ttaattccga gacagtgcct cagaagtcct ctctggagga gccagatttc   1740
tacaagacca agatcaagct gtgcatcctg ctgcacgcct tccggatcag agccgtgacc   1800
atcgaccgcg tgatgagcta tctgaatgcc tcc                                1833
```

<210> SEQ ID NO 57
<211> LENGTH: 518
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

Ile Trp Glu Leu Lys Lys Asp Val Tyr Val Val Glu Leu Asp Trp Tyr

-continued

```
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Gly Gly Gly Gly Ser Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
    370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430
```

```
Tyr Gln Val Glu Phe Lys Thr Met Asn Ala Lys Leu Leu Met Asp Pro
        435                 440                 445

Lys Arg Gln Ile Phe Leu Asp Gln Asn Met Leu Ala Val Ile Asp Glu
    450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser
        515
```

<210> SEQ ID NO 58
<211> LENGTH: 1554
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
atctgggagc tgaagaagga cgtgtacgtg gtggagctgg actggtatcc tgatgcccca     60

ggcgagatgg tggtgctgac ctgcgacaca cctgaggagg atggcatcac ctggacactg    120

gatcagagca gcgaggtgct gggctccggc aagaccctga caatccaggt gaaggagttc    180

ggcgacgccg gccagtacac atgtcacaag ggaggagagg tgctgagcca ctccctgctg    240

ctgctgcaca agaaggagga cggcatctgg tctacagaca tcctgaagga tcagaaggag    300

cccaagaaca agaccttcct gcggtgcgag gccaagaatt atagcggccg gttcacctgt    360

tggtggctga ccacaatctc taccgacctg accttcagcg tgaagtctag ccggggctcc    420

tctgaccctc agggagtgac atgcggagca gccaccctgt ccgccgagcg ggtgagaggc    480

gataacaagg agtacgagta tagcgtggag tgccaggagg actccgcctg tccagcagca    540

gaggagagcc tgccaatcga agtgatggtg gatgccgtgc acaagctgaa gtacgagaat    600

tatacaagct ccttctttat cagggacatc atcaagcccg atccccctaa gaacctgcag    660

ctgaagcccc tgaagaacag ccggcaggtg gaggtgtctt gggagtaccc cgacacctgg    720

agcacacctc actcctattt ctctctgacc ttttgcgtgc aggtgcaggg caagtccaag    780

agggagaaga aggaccgcgt gttcaccgat aagacatctg ccaccgtgat ctgtcggaag    840

aacgcctcta tcagcgtgcg ggcccaggat agatactatt ctagctcctg gagcgagtgg    900

gcctccgtgc catgttctgg aggaggaggc agcggcggag gaggctccgg cggcggcggc    960

agccggaatc tgccagtggc aaccccagac cccggaatgt tcccatgcct gcaccactct   1020

cagaacctgc tgagggccgt gagcaatatg ctgcagaagg cccgccagac actggagttt   1080

taccettgta ccagcgagga gatcgaccac gaggacatca caaaggataa gacctccaca   1140

gtggaggcct gcctgccact ggagctgacc aagaacgaga gctgtctgaa cagccgggag   1200

accagcttca tcaccaacgg cagctgcctg gcctccagaa agacatcttt tatgatggcc   1260

ctgtgcctgt ctagcatcta cgaggacctg aagatgtatc aggtggagtt caagaccatg   1320

aacgccaagc tgctgatgga ccccaagagg cagattttcc tggaccagaa tatgctggcc   1380

gtgatcgacg agctgatgca ggccctgaac tttaattccg agacagtgcc tcagaagtcc   1440

tctctggagg agccagattt ctacaagacc aagatcaagc tgtgcatcct gctgcacgcc   1500
```

ttccggatca gagccgtgac catcgaccgc gtgatgagct atctgaatgc ctcc 1554

<210> SEQ ID NO 59
<211> LENGTH: 238
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 59

```
Met Gly Trp Ser Cys Ile Ile Leu Phe Leu Val Ala Thr Ala Thr Gly
1               5                   10                  15

Val His Ser His His His His His His Glu Asn Leu Tyr Phe Gln Gly
            20                  25                  30

Arg Thr Glu Pro Arg Pro Ala Leu Thr Ile Thr Thr Ser Pro Asn Leu
        35                  40                  45

Gly Thr Arg Glu Asn Asn Ala Asp Gln Val Thr Pro Val Ser His Ile
    50                  55                  60

Gly Cys Pro Asn Thr Thr Gln Gln Gly Ser Pro Val Phe Ala Lys Leu
65                  70                  75                  80

Leu Ala Lys Asn Gln Ala Ser Leu Cys Asn Thr Thr Leu Asn Trp His
                85                  90                  95

Ser Gln Asp Gly Ala Gly Ser Ser Tyr Leu Ser Gln Gly Leu Arg Tyr
            100                 105                 110

Glu Glu Asp Lys Lys Glu Leu Val Val Asp Ser Pro Gly Leu Tyr Tyr
        115                 120                 125

Val Phe Leu Glu Leu Lys Leu Ser Pro Thr Phe Thr Asn Thr Gly His
    130                 135                 140

Lys Val Gln Gly Trp Val Ser Leu Val Leu Gln Ala Lys Pro Gln Val
145                 150                 155                 160

Asp Asp Phe Asp Asn Leu Ala Leu Thr Val Glu Leu Phe Pro Cys Ser
                165                 170                 175

Met Glu Asn Lys Leu Val Asp Arg Ser Trp Ser Gln Leu Leu Leu Leu
            180                 185                 190

Lys Ala Gly His Arg Leu Ser Val Gly Leu Arg Ala Tyr Leu His Gly
        195                 200                 205

Ala Gln Asp Ala Tyr Arg Asp Trp Glu Leu Ser Tyr Pro Asn Thr Thr
    210                 215                 220

Ser Phe Gly Leu Phe Leu Val Lys Pro Asp Asn Pro Trp Glu
225                 230                 235
```

<210> SEQ ID NO 60
<211> LENGTH: 475
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 60

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45
```

-continued

```
Pro Ser Val Phe Ile Phe Pro Pro Lys Ile Lys Asp Val Leu Met Ile
    50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Glu Asn Leu Tyr Phe Gln Gly Gly Ile Thr Cys Pro Pro Pro
            260                 265                 270

Met Ser Val Glu His Ala Asp Ile Trp Val Lys Ser Tyr Ser Leu Tyr
        275                 280                 285

Ser Arg Glu Arg Tyr Ile Cys Asn Ser Gly Phe Lys Arg Lys Ala Gly
    290                 295                 300

Thr Ser Ser Leu Thr Glu Cys Val Leu Asn Lys Ala Thr Asn Val Ala
305                 310                 315                 320

His Trp Thr Thr Pro Ser Leu Lys Cys Ile Arg Asp Pro Gly Ser Gly
                325                 330                 335

Ser Gly Ser Gly Ser Gly Ser Glu Asp Glu Asp Glu Asp Glu Asp Gly
            340                 345                 350

Ser Gly Ser Gly Ser Gly Ser Gly Ser Asn Trp Val Asn Val Ile Ser
        355                 360                 365

Asp Leu Lys Lys Ile Glu Asp Leu Ile Gln Ser Met His Ile Asp Ala
    370                 375                 380

Thr Leu Tyr Thr Glu Ser Asp Val His Pro Ser Cys Lys Val Thr Ala
385                 390                 395                 400

Met Lys Cys Phe Leu Leu Glu Leu Gln Val Ile Ser Leu Glu Ser Gly
                405                 410                 415

Asp Ala Ser Ile His Asp Thr Val Glu Asn Leu Ile Ile Leu Ala Asn
            420                 425                 430

Asn Ser Leu Ser Ser Asn Gly Asn Val Thr Glu Ser Gly Cys Lys Glu
        435                 440                 445

Cys Glu Glu Leu Glu Glu Lys Asn Ile Lys Glu Phe Leu Gln Ser Phe
    450                 455                 460

Val His Ile Val Gln Met Phe Ile Asn Thr Ser
```

465 470 475

<210> SEQ ID NO 61
<211> LENGTH: 794
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 61

Met Arg Val Pro Ala Gln Leu Leu Gly Leu Leu Leu Leu Trp Leu Pro
1 5 10 15

Gly Ala Arg Cys Glu Pro Arg Val Pro Ile Thr Gln Asn Pro Cys Pro
20 25 30

Pro Leu Lys Glu Cys Pro Pro Cys Ala Ala Pro Asp Leu Leu Gly Gly
35 40 45

Pro Ser Val Phe Ile Phe Pro Pro Lys Ile Lys Asp Val Leu Met Ile
50 55 60

Ser Leu Ser Pro Met Val Thr Cys Val Val Val Ala Val Ser Glu Asp
65 70 75 80

Asp Pro Asp Val Gln Ile Ser Trp Phe Val Asn Asn Val Glu Val His
85 90 95

Thr Ala Gln Thr Gln Thr His Arg Glu Asp Tyr Asn Ser Thr Leu Arg
100 105 110

Val Val Ser Ala Leu Pro Ile Gln His Gln Asp Trp Met Ser Gly Lys
115 120 125

Glu Phe Lys Cys Lys Val Asn Asn Arg Ala Leu Pro Ser Pro Ile Glu
130 135 140

Lys Thr Ile Ser Lys Pro Arg Gly Pro Val Arg Ala Pro Gln Val Tyr
145 150 155 160

Val Leu Pro Pro Pro Ala Glu Glu Met Thr Lys Lys Glu Phe Ser Leu
165 170 175

Thr Cys Met Ile Thr Gly Phe Leu Pro Ala Glu Ile Ala Val Asp Trp
180 185 190

Thr Ser Asn Gly Arg Thr Glu Gln Asn Tyr Lys Asn Thr Ala Thr Val
195 200 205

Leu Asp Ser Asp Gly Ser Tyr Phe Met Tyr Ser Lys Leu Arg Val Gln
210 215 220

Lys Ser Thr Trp Glu Arg Gly Ser Leu Phe Ala Cys Ser Val Val His
225 230 235 240

Glu Gly Leu His Asn His Leu Thr Thr Lys Thr Ile Ser Arg Ser Leu
245 250 255

Gly Lys Gly Gly Gly Gly Ser Gly Gly Gly Gly Ser Gly Gly Gly Gly
260 265 270

Ser Met Trp Glu Leu Glu Lys Asp Val Tyr Val Val Glu Val Asp Trp
275 280 285

Thr Pro Asp Ala Pro Gly Glu Thr Val Asn Leu Thr Cys Asp Thr Pro
290 295 300

Glu Glu Asp Asp Ile Thr Trp Thr Ser Asp Gln Arg His Gly Val Ile
305 310 315 320

Gly Ser Gly Lys Thr Leu Thr Ile Thr Val Lys Glu Phe Leu Asp Ala
325 330 335

Gly Gln Tyr Thr Cys His Lys Gly Gly Glu Thr Leu Ser His Ser His
340 345 350

-continued

```
Leu Leu Leu His Lys Lys Glu Asn Gly Ile Trp Ser Thr Glu Ile Leu
        355                 360                 365

Lys Asn Phe Lys Asn Lys Thr Phe Leu Lys Cys Glu Ala Pro Asn Tyr
    370                 375                 380

Ser Gly Arg Phe Thr Cys Ser Trp Leu Val Gln Arg Asn Met Asp Leu
385                 390                 395                 400

Lys Phe Asn Ile Lys Ser Ser Ser Ser Ser Pro Asp Ser Arg Ala Val
                405                 410                 415

Thr Cys Gly Met Ala Ser Leu Ser Ala Glu Lys Val Thr Leu Asp Gln
            420                 425                 430

Arg Asp Tyr Glu Lys Tyr Ser Val Ser Cys Gln Glu Asp Val Thr Cys
        435                 440                 445

Pro Thr Ala Glu Glu Thr Leu Pro Ile Glu Leu Ala Leu Glu Ala Arg
    450                 455                 460

Gln Gln Asn Lys Tyr Glu Asn Tyr Ser Thr Ser Phe Phe Ile Arg Asp
465                 470                 475                 480

Ile Ile Lys Pro Asp Pro Pro Lys Asn Leu Gln Met Lys Pro Leu Lys
                485                 490                 495

Asn Ser Gln Val Glu Val Ser Trp Glu Tyr Pro Asp Ser Trp Ser Thr
            500                 505                 510

Pro His Ser Tyr Phe Ser Leu Lys Phe Phe Val Arg Ile Gln Arg Lys
        515                 520                 525

Lys Glu Lys Met Lys Glu Thr Glu Glu Gly Cys Asn Gln Lys Gly Ala
    530                 535                 540

Phe Leu Val Glu Lys Thr Ser Thr Glu Val Gln Cys Lys Gly Gly Asn
545                 550                 555                 560

Val Cys Val Gln Ala Gln Asp Arg Tyr Tyr Asn Ser Ser Cys Ser Lys
                565                 570                 575

Trp Ala Cys Val Pro Cys Arg Val Arg Ser Gly Gly Gly Gly Ser Gly
            580                 585                 590

Gly Gly Gly Ser Gly Gly Gly Gly Ser Arg Val Ile Pro Val Ser Gly
        595                 600                 605

Pro Ala Arg Cys Leu Ser Gln Ser Arg Asn Leu Leu Lys Thr Thr Asp
    610                 615                 620

Asp Met Val Lys Thr Ala Arg Glu Lys Leu Lys His Tyr Ser Cys Thr
625                 630                 635                 640

Ala Glu Asp Ile Asp His Glu Asp Ile Thr Arg Asp Gln Thr Ser Thr
                645                 650                 655

Leu Lys Thr Cys Leu Pro Leu Glu Leu His Lys Asn Glu Ser Cys Leu
            660                 665                 670

Ala Thr Arg Glu Thr Ser Ser Thr Thr Arg Gly Ser Cys Leu Pro Pro
        675                 680                 685

Gln Lys Thr Ser Leu Met Met Thr Leu Cys Leu Gly Ser Ile Tyr Glu
    690                 695                 700

Asp Leu Lys Met Tyr Gln Thr Glu Phe Gln Ala Ile Asn Ala Ala Leu
705                 710                 715                 720

Gln Asn His Asn His Gln Gln Ile Ile Leu Asp Lys Gly Met Leu Val
                725                 730                 735

Ala Ile Asp Glu Leu Met Gln Ser Leu Asn His Asn Gly Glu Thr Leu
            740                 745                 750

Arg Gln Lys Pro Pro Val Gly Glu Ala Asp Pro Tyr Arg Val Lys Met
        755                 760                 765

Lys Leu Cys Ile Leu Leu His Ala Phe Ser Thr Arg Val Val Thr Ile
```

770 775 780

Asn Arg Val Met Gly Tyr Leu Ser Ser Ala
785 790

<210> SEQ ID NO 62
<211> LENGTH: 1015
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

Met Tyr Gly Lys Ile Ile Phe Val Leu Leu Leu Ser Glu Ile Val Ser
1 5 10 15

Ile Ser Ala Ala Cys Pro Trp Ala Val Ser Gly Ala Arg Ala Ser Pro
20 25 30

Gly Ser Ala Ala Ser Pro Arg Leu Arg Glu Gly Pro Glu Leu Ser Pro
35 40 45

Asp Asp Pro Ala Gly Leu Leu Asp Leu Arg Gln Gly Met Phe Ala Gln
50 55 60

Leu Val Ala Gln Asn Val Leu Leu Ile Asp Gly Pro Leu Ser Trp Tyr
65 70 75 80

Ser Asp Pro Gly Leu Ala Gly Val Ser Leu Thr Gly Gly Leu Ser Tyr
85 90 95

Lys Glu Asp Thr Lys Glu Leu Val Val Ala Lys Ala Gly Val Tyr Tyr
100 105 110

Val Phe Phe Gln Leu Glu Leu Arg Arg Val Val Ala Gly Glu Gly Ser
115 120 125

Gly Ser Val Ser Leu Ala Leu His Leu Gln Pro Leu Arg Ser Ala Ala
130 135 140

Gly Ala Ala Ala Leu Ala Leu Thr Val Asp Leu Pro Pro Ala Ser Ser
145 150 155 160

Glu Ala Arg Asn Ser Ala Phe Gly Phe Gln Gly Arg Leu Leu His Leu
165 170 175

Ser Ala Gly Gln Arg Leu Gly Val His Leu His Thr Glu Ala Arg Ala
180 185 190

Arg His Ala Trp Gln Leu Thr Gln Gly Ala Thr Val Leu Gly Leu Phe
195 200 205

Arg Val Thr Pro Glu Ile Pro Ala Gly Leu Pro Ser Pro Arg Ser Glu
210 215 220

Gly Gly Ser Gly Gly Ser Gly Gly Gly Pro Glu Asp Glu Pro Gly Ser
225 230 235 240

Gly Ser Gly Gly Gly Ser Gly Gly Gly Ser Leu Ser Thr Thr Glu Val
245 250 255

Ala Met His Thr Ser Thr Ser Ser Ser Val Thr Lys Ser Tyr Ile Ser
260 265 270

Ser Gln Thr Asn Asp Thr His Lys Arg Asp Thr Tyr Ala Ala Thr Pro
275 280 285

Arg Ala His Glu Val Ser Glu Ile Ser Val Arg Thr Val Tyr Pro Pro
290 295 300

Glu Glu Glu Thr Gly Glu Arg Val Gln Leu Ala His His Phe Ser Glu
305 310 315 320

Pro Glu Ile Thr Leu Ile Ile Phe Gly Val Met Ala Gly Val Ile Gly
325 330 335

-continued

```
Thr Ile Leu Leu Ile Ser Tyr Gly Ile Arg Arg Leu Ile Lys Lys Ser
            340                 345                 350

Pro Ser Asp Val Lys Pro Leu Pro Ser Pro Asp Thr Asp Val Pro Leu
        355                 360                 365

Ser Ser Val Glu Ile Glu Asn Pro Glu Thr Ser Asp Gln Ala Ala Ala
    370                 375                 380

Glu Gly Arg Gly Ser Leu Leu Thr Cys Gly Asp Val Glu Glu Asn Pro
385                 390                 395                 400

Gly Pro Ser Gly Met Gln Pro Gln Glu Ser His Val His Tyr Ser Arg
                405                 410                 415

Trp Glu Asp Gly Ser Arg Asp Gly Val Ser Leu Gly Ala Val Ser Ser
            420                 425                 430

Thr Glu Glu Ala Ser Arg Cys Arg Arg Ile Ser Gln Arg Leu Cys Thr
        435                 440                 445

Gly Lys Leu Gly Ile Ala Met Lys Val Leu Gly Gly Val Ala Leu Phe
    450                 455                 460

Trp Ile Ile Phe Ile Leu Gly Tyr Leu Thr Gly Tyr Tyr Val His Lys
465                 470                 475                 480

Cys Lys Gly Gly Gly Gly Ser Gly Gly Gly Gly Ser Gly Gly Gly Gly
                485                 490                 495

Ser Ile Trp Glu Leu Lys Lys Asp Val Tyr Val Val Glu Leu Asp Trp
            500                 505                 510

Tyr Pro Asp Ala Pro Gly Glu Met Val Val Leu Thr Cys Asp Thr Pro
        515                 520                 525

Glu Glu Asp Gly Ile Thr Trp Thr Leu Asp Gln Ser Ser Glu Val Leu
    530                 535                 540

Gly Ser Gly Lys Thr Leu Thr Ile Gln Val Lys Glu Phe Gly Asp Ala
545                 550                 555                 560

Gly Gln Tyr Thr Cys His Lys Gly Gly Glu Val Leu Ser His Ser Leu
                565                 570                 575

Leu Leu Leu His Lys Lys Glu Asp Gly Ile Trp Ser Thr Asp Ile Leu
            580                 585                 590

Lys Asp Gln Lys Glu Pro Lys Asn Lys Thr Phe Leu Arg Cys Glu Ala
        595                 600                 605

Lys Asn Tyr Ser Gly Arg Phe Thr Cys Trp Trp Leu Thr Thr Ile Ser
    610                 615                 620

Thr Asp Leu Thr Phe Ser Val Lys Ser Ser Arg Gly Ser Ser Asp Pro
625                 630                 635                 640

Gln Gly Val Thr Cys Gly Ala Ala Thr Leu Ser Ala Glu Arg Val Arg
                645                 650                 655

Gly Asp Asn Lys Glu Tyr Glu Tyr Ser Val Glu Cys Gln Glu Asp Ser
            660                 665                 670

Ala Cys Pro Ala Ala Glu Glu Ser Leu Pro Ile Glu Val Met Val Asp
        675                 680                 685

Ala Val His Lys Leu Lys Tyr Glu Asn Tyr Thr Ser Ser Phe Phe Ile
    690                 695                 700

Arg Asp Ile Ile Lys Pro Asp Pro Pro Lys Asn Leu Gln Leu Lys Pro
705                 710                 715                 720

Leu Lys Asn Ser Arg Gln Val Glu Val Ser Trp Glu Tyr Pro Asp Thr
                725                 730                 735

Trp Ser Thr Pro His Ser Tyr Phe Ser Leu Thr Phe Cys Val Gln Val
            740                 745                 750

Gln Gly Lys Ser Lys Arg Glu Lys Lys Asp Arg Val Phe Thr Asp Lys
```

```
        755                 760                 765

Thr Ser Ala Thr Val Ile Cys Arg Lys Asn Ala Ser Ile Ser Val Arg
    770                 775                 780

Ala Gln Asp Arg Tyr Tyr Ser Ser Ser Trp Ser Glu Trp Ala Ser Val
785                 790                 795                 800

Pro Cys Ser Gly Gly Gly Gly Ser Gly Gly Gly Gly Ser Gly Gly Gly
                805                 810                 815

Gly Ser Arg Asn Leu Pro Val Ala Thr Pro Asp Pro Gly Met Phe Pro
            820                 825                 830

Cys Leu His His Ser Gln Asn Leu Leu Arg Ala Val Ser Asn Met Leu
        835                 840                 845

Gln Lys Ala Arg Gln Thr Leu Glu Phe Tyr Pro Cys Thr Ser Glu Glu
    850                 855                 860

Ile Asp His Glu Asp Ile Thr Lys Asp Lys Thr Ser Thr Val Glu Ala
865                 870                 875                 880

Cys Leu Pro Leu Glu Leu Thr Lys Asn Glu Ser Cys Leu Asn Ser Arg
                885                 890                 895

Glu Thr Ser Phe Ile Thr Asn Gly Ser Cys Leu Ala Ser Arg Lys Thr
            900                 905                 910

Ser Phe Met Met Ala Leu Cys Leu Ser Ser Ile Tyr Glu Asp Leu Lys
        915                 920                 925

Met Tyr Gln Val Glu Phe Lys Thr Met Asn Ala Lys Leu Leu Met Asp
    930                 935                 940

Pro Lys Arg Gln Ile Phe Leu Asp Gln Asn Met Leu Ala Val Ile Asp
945                 950                 955                 960

Glu Leu Met Gln Ala Leu Asn Phe Asn Ser Glu Thr Val Pro Gln Lys
                965                 970                 975

Ser Ser Leu Glu Glu Pro Asp Phe Tyr Lys Thr Lys Ile Lys Leu Cys
            980                 985                 990

Ile Leu Leu His Ala Phe Arg Ile  Arg Ala Val Thr Ile  Asp Arg Val
        995                 1000                1005

Met Ser  Tyr Leu Asn Ala Ser
    1010                1015
```

<210> SEQ ID NO 63
<211> LENGTH: 3048
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

```
atgtatggaa aaataatctt tgtattacta ttgtcagaaa ttgtgagcat atcagcagcc     60

tgcccctggg ccgtgtccgg ggctcgcgcc tcgcccggct ccgcggccag cccgagactc    120

cgcgagggtc ccgagctttc gcccgacgat cccgccggcc tcttggacct gcggcagggc    180

atgtttgcgc agctggtggc ccaaaatgtt ctgctgatcg atgggcccct gagctggtac    240

agtgacccag gcctggcagg cgtgtccctg acgggggggcc tgagctacaa agaggacacg    300

aaggagctgg tggtggccaa ggctggagtc tactatgtct tctttcaact agagctgcgg    360

cgcgtggtgg ccggcgaggg ctcaggctcc gtttcacttg cgctgcacct gcagccactg    420

cgctctgctg ctggggccgc cgccctggct ttgaccgtgg acctgccacc cgcctcctcc    480

gaggctcgga actcggcctt cggtttccag ggccgcttgc tgcacctgag tgccggccag    540
```

-continued

```
cgcctgggcg tccatcttca cactgaggcc agggcacgcc atgcctggca gcttacccag    600
ggcgccacag tcttgggact cttccgggtg acccccgaaa tcccagccgg actcccttca    660
ccgaggtcgg aaggaggatc tggcgggtct ggaggcggcc ccgaggacga gcccggcagc    720
ggcagcggcg gagggtctgg aggcggttcc ttaagtacca ctgaggtggc aatgcacact    780
tcaacctctt cttcagtcac aaagagttac atctcatcac agacaaatga tacgcacaaa    840
cgggacacat atgcagccac tcctagagct catgaagttt cagaaatttc tgttagaact    900
gtttaccctc cagaagagga aaccggagaa agggtacaac ttgcccatca tttctctgaa    960
ccagagataa cactcattat ttttggggtg atggctggtg ttattggaac gatcctctta   1020
atttcttacg gtattcgccg actgataaag aaaagcccat ctgatgtaaa acctctcccc   1080
tcacctgaca cagacgtgcc tttaagttct gttgaaatag aaaatccaga gacaagtgat   1140
caagcggccg ctgagggcag aggaagtctt ctaacatgcg gtgacgtgga ggagaatccc   1200
ggcccttccg gaatgcaacc gcaagagagt cacgtacatt attcaagatg ggaagatgga   1260
agtcgggacg gtgtgtctct cggcgctgtt agttcaacgg aggaagcgtc tcgctgtcgc   1320
cggataagtc aacgcctttg tacgggaaaa ctgggtatag ctatgaaggt cctcggcggg   1380
gtggcgttgt tttggattat ctttatactt gggtatctga ccggttacta tgttcacaag   1440
tgtaaaggag gtggaggatc aggtggaggt ggttcaggtg gaggaggtag catctgggag   1500
ctgaagaagg acgtgtacgt ggtggagctg gactggtatc ctgatgcccc aggcgagatg   1560
gtggtgctga cctgcgacac acctgaggag gatggcatca cctggacact ggatcagagc   1620
agcgaggtgc tgggctccgg caagaccctg acaatccagg tgaaggagtt cggcgacgcc   1680
ggccagtaca catgtcacaa gggaggagag gtgctgagcc actccctgct gctgctgcac   1740
aagaaggagg acggcatctg gtctacagac atcctgaagg atcagaagga gcccaagaac   1800
aagaccttcc tgcggtgcga ggccaagaat tatagcggcc ggttcacctg ttggtggctg   1860
accacaatct ctaccgacct gaccttcagc gtgaagtcta gccggggctc ctctgaccct   1920
cagggagtga catgcggagc agccaccctg tccgccgagc gggtgagagg cgataacaag   1980
gagtacgagt atagcgtgga gtgccaggag gactccgcct gtccagcagc agaggagagc   2040
ctgccaatcg aagtgatggt ggatgccgtg cacaagctga agtacgagaa ttatacaagc   2100
tccttcttta tcagggacat catcaagccc gatcccccta agaacctgca gctgaagccc   2160
ctgaagaaca gccggcaggt ggaggtgtct tgggagtacc ccgacacctg gagcacacct   2220
cactcctatt tctctctgac cttttgcgtg caggtgcagg gcaagtccaa gagggagaag   2280
aaggaccgcg tgttcaccga taagacatct gccaccgtga tctgtcggaa gaacgcctct   2340
atcagcgtgc gggcccagga tagatactat tctagctcct ggagcgagtg ggcctccgtg   2400
ccatgttctg gaggaggagg cagcggcgga ggaggctccg gcggcggcgg cagccggaat   2460
ctgccagtgg caaccccaga ccccggaatg ttcccatgcc tgcaccactc tcagaacctg   2520
ctgagggccg tgagcaatat gctgcagaag gcccgccaga cactggagtt ttacccttgt   2580
accagcgagg agatcgacca cgaggacatc acaaaggata agacctccac agtggaggcc   2640
tgcctgccac tggagctgac caagaacgag agctgtctga acagccggga gaccagcttc   2700
atcaccaacg gcagctgcct ggcctccaga aagacatctt ttatgatggc cctgtgcctg   2760
tctagcatct acgaggacct gaagatgtat caggtggagt tcaagaccat gaacgccaag   2820
ctgctgatgg accccaagag gcagattttc ctggaccaga atatgctggc cgtgatcgac   2880
gagctgatgc aggccctgaa ctttaattcc gagacagtgc ctcagaagtc ctctctggag   2940
```

gagccagatt tctacaagac caagatcaag ctgtgcatcc tgctgcacgc cttccggatc 3000
agagccgtga ccatcgaccg cgtgatgagc tatctgaatg cctcctag 3048

<210> SEQ ID NO 64
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Ala Ala Ala Glu Gly Arg Gly Ser Leu Leu Thr Cys Gly Asp Val Glu
1 5 10 15

Glu Asn Pro Gly Pro Ser Gly
20

<210> SEQ ID NO 65
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 65
gcggccgctg agggcagagg aagtcttcta acatgcggtg acgtggagga gaatcccggc 60
ccttccgga 69

<210> SEQ ID NO 66
<211> LENGTH: 150
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

Met Tyr Gly Lys Ile Ile Phe Val Leu Leu Leu Ser Ala Ile Val Ser
1 5 10 15

Ile Ser Ala Leu Ser Thr Thr Glu Val Ala Met His Thr Ser Thr Ser
20 25 30

Ser Ser Val Thr Lys Ser Tyr Ile Ser Ser Gln Thr Asn Asp Thr His
35 40 45

Lys Arg Asp Thr Tyr Ala Ala Thr Pro Arg Ala His Glu Val Ser Glu
50 55 60

Ile Ser Val Arg Thr Val Tyr Pro Pro Glu Glu Glu Thr Gly Glu Arg
65 70 75 80

Val Gln Leu Ala His His Phe Ser Glu Pro Glu Ile Thr Leu Ile Ile
85 90 95

Phe Gly Val Met Ala Gly Val Ile Gly Thr Ile Leu Leu Ile Ser Tyr
100 105 110

Gly Ile Arg Arg Leu Ile Lys Lys Ser Pro Ser Asp Val Lys Pro Leu
115 120 125

Pro Ser Pro Asp Thr Asp Val Pro Leu Ser Ser Val Glu Ile Glu Asn
130 135 140

Pro Glu Thr Ser Asp Gln
145 150

```
<210> SEQ ID NO 67
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ser Gly Ser Gly Ser Gly Ser Gly Ser Glu Asp Glu Asp Glu Asp
1               5                   10                  15

Glu Asp Gly Ser Gly Ser Gly Ser Gly Ser Gly Ser
            20                  25


<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Gly Gly Gly Ser Gly Gly Gly Gly Ser Gly Gly Gly Gly Ser Gly
1               5                   10                  15

Gly Gly Gly Ser
            20


<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Ser Gly Ser Gly Ser Gly Ser Glu Asp Gly Ser Gly Ser Gly Ser
1               5                   10                  15

Gly Ser


<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Ser Gly Ser Gly Ser Gly Ser Gly Ser Gly Ser Gly Ser Gly Ser
1               5                   10                  15

Gly Ser


<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Cys Gly Gly Ser Gly Gly Gly Gly Ser Gly Gly Gly Gly Ser
1               5                   10                  15
```

<210> SEQ ID NO 72
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

```
Ser Gly Arg Gly Gly Gly Gly Ser Gly Gly Gly Gly Ser Gly Gly Gly
1               5                   10                  15

Gly Ser Gly Gly Gly Gly Ser Ser Pro Ala
            20                  25
```

<210> SEQ ID NO 73
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

```
Gly Gly Gly Gly Ser Gly Gly Gly Gly Ser Gly Gly Gly Gly Ser Gly
1               5                   10                  15

Gly Gly Gly Ser Gly Gly Gly Gly
            20
```

<210> SEQ ID NO 74
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Ser Gly Arg Gly Ala Ser Ser Gly Ser Ser Gly Ser Gly Ser Gln Lys
1               5                   10                  15

Lys Pro Arg Tyr Glu Ile Arg Trp Lys Val Val Val Ile Ser Ala Ile
            20                  25                  30

Leu Ala Leu Val Val Leu Thr Val Ile Ser Leu Ile Ile Leu Ile Met
        35                  40                  45

Leu Trp Gly Ser Gly Met Gln Ser Pro Ala
    50                  55
```

<210> SEQ ID NO 75
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly-Gly-Gly-
      Gly-Ser" repeating units

<400> SEQUENCE: 75

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30
```

```
Gly Gly Ser Gly Gly Gly Gly Ser Gly Gly Gly Gly Ser Gly Gly Gly
        35                  40                  45

Gly Ser
    50


<210> SEQ ID NO 76
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Met Gly Trp Ser Cys Ile Ile Leu Phe Leu Val Ala Thr Ala Thr Gly
1               5                   10                  15

Val His Ser


<210> SEQ ID NO 77
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Met Arg Val Pro Ala Gln Leu Leu Gly Leu Leu Leu Leu Trp Leu Pro
1               5                   10                  15

Gly Ala Arg Cys
            20


<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Tyr Pro Tyr Asp Val Pro Asp Tyr Ala
1               5


<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu Gln Lys Leu Ile Ser Glu Glu Asp Leu
1               5                   10


<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asp Tyr Lys Asp Asp Asp Asp Lys
```

-continued

```
1               5


<210> SEQ ID NO 81
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81

gagggcagag gaagtcttct aacatgcggt gacgtggagg sgsstcccgg ccct          54


<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 82

Leu Pro Xaa Thr Gly
1               5


<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 83

Leu Pro Xaa Thr Ala
1               5
```

THERAPEUTIC CELL SYSTEMS AND METHODS FOR TREATING CANCER AND INFECTIOUS DISEASES

RELATED APPLICATIONS

This application claims priority to U.S. Provisional Patent Application No. 62/640,530, filed on Mar. 8, 2018, U.S. Provisional Patent Application No. 62/660,657, filed on Apr. 20, 2018, U.S. Provisional Patent Application No. 62/680,490, filed on Jun. 4, 2018, U.S. Provisional Patent Application No. 62/692,487, filed on Jun. 29, 2018, U.S. Provisional Patent Application No. 62/732,050, filed on Sep. 17, 2018, and U.S. Provisional Patent Application No. 62/757,717, filed on Nov. 8, 2018, the entire contents of each of which are incorporated herein by reference for all purposes.

SEQUENCE LISTING

The instant application contains a Sequence Listing which has been submitted electronically in ASCII format and is hereby incorporated by reference in its entirety. Said ASCII copy, created on Mar. 5, 2019, is named 129267-00207_SL.txt and is 127,920 bytes in size.

BACKGROUND

CD8+ T cells and NK cells are cytotoxic effector cells of the immune system. While CD8+ T cells and NK cells have different mechanisms of target recognition and signaling cascades, both are types of killer cells that share the similar goal of killing infected and transformed cells. Several strategies have been used to stimulate CD8+ T cell and NK cell responses to tumors. CD8+ T cells play a critical role in current cancer immunotherapies. Cytokine therapy is used in the treatment of some human cancers, where treatment with cytokines such as interleukins (e.g. IL-2, IL-12. IL-15, IL-18 and IL-21) or TNFα enhances local CD8+ T cell and NK cell activity (e.g. differentiation and activation). The effect of IL-2 administration on activation and expansion of NK cells in cancer patients has been assessed in several trials, with mixed outcomes depending on the type of tumor and the conditions used for IL-2 administration. Further, such therapies involving administration of cytokines are associated with potential toxicities.

Studies have shown a positive correlation between the amount of CD8+ tumor infiltrating lymphocytes and progression-free survival with immunotherapy (see, e.g. Sharma et al., Science 2015, 348: 56-61). CAR-T cells utilize the cytotoxicity of CD8+ T cells to eradicate cancer. However, one of the challenges of CAR-T therapy is that CAR-T cells are not tumor specific. There has been a significant concern for safety of CAR-T targeting, particularly in solid tumors (Junghans, Cancer Gene Therapy (2017) 24, 89-99).

Currently, some of the most promising approaches for targeting NK cells involves adoptive cell transfer, including the use of autologous NK cells, allogeneic NK cells, NK cell lines and CAR NK cells. However, these approaches are associated with significant drawbacks, such as low efficacy, the requirement for substantial depletion of T cells to avoid GVHD (for allogeneic cells), low persistence in subjects, and difficulties in expanding and/or manufacturing large numbers of cells.

Thus, there remains a need in the art for alternative ways to exploit immune killer cells (e.g. NK cells and CD8+T-cells) for therapeutic purposes.

SUMMARY OF THE INVENTION

The present disclosure relates to erythroid cells (e.g. engineered erythroid cells) that are engineered to stimulate immune killer cells (e.g. NK cells and/or CD8+T-cells). In particular, the present invention provides erythroid cells that have been engineered to stimulate immune killer cells (e.g. NK cells and/or CD8+T-cells) by the expression on the cell surface of the erythroid cell of one or more exogenous stimulatory polypeptides sufficient to activate and/or expand the NK cells and/or CD8+T-cells, such as, for example, IL-12, IL-15/IL-15RA, 4-1BBL or combinations thereof. The engineered erythroid cells can be nucleated, e.g., erythroid precursor cells (e.g., erythrocyte precursor cells), or can be enucleated erythroid cells, e.g., reticulocytes or erythrocytes. The invention further provides uses for these engineered erythroid cells in activating NK cells and/or CD8+ T-cells in a subject in need thereof, such as subjects having cancer or subjects having an infectious disease.

The engineered erythroid cells provided herein provide the significant advantage over current immune killer cell targeting technologies of being naturally immuno-privileged and directly mediating stimulation of the immune killer cells in vivo, thus avoiding the disadvantages associated with adoptive cell transfer of immune killer cells. Engineered erythroid cells of the present invention can be engineered to stimulate both NK cells and CD8+ cells simultaneously when exposed to these cell populations in vivo. In particular, it is a finding of the present invention, that engineered erythroid cells comprising IL-12, IL-15/IL-15RA, 4-1BBL or combinations thereof, drive a potent activation of primary CD4+, CD8+, NK and NKT cells, and induce NK cell cytotoxicity. The in vivo stimulation of both NK cells and CD8+ T-cells represents an important innovation over existing therapies, where stimulation occurs ex vivo, and is typically restricted to stimulation of one population of immune cells (e.g. NK cells or CD8+ T-cells) at a time.

The engineered erythroid cells provide the additional advantages of presenting, e.g. comprising on the cell surface, multiple different stimulatory molecules on a single erythroid cell, and in significantly high numbers, as well as delivering and maintaining the stimulatory signals via the erythroid cells directly throughout the circulatory system and with a long circulation half-life, thus providing a safer and more effective method for stimulating immune killer cells. In particular embodiments, the stimulatory molecules on the engineered erythroid cells of the present invention work together synergistically to activate immune killer cells, as described herein. The erythroid cells engineered to stimulate an immune cell, as described herein, are used in some embodiments, to treat cancer, including metastatic cancer. It is a finding of the present invention that engineered erythroid cells comprising IL-12, IL-15/IL-15RA, 4-1BBL and combinations thereof, can effectively slow tumor growth and reduce tumor burden in vivo.

Accordingly, in a first aspect, the disclosure provides an enucleated cell engineered to stimulate an immune killer cell, wherein the enucleated cell comprises at least a first exogenous stimulatory polypeptide and a second exogenous stimulatory polypeptide, wherein the exogenous stimulatory polypeptides are sufficient to stimulate the immune killer cell. In some embodiments, the immune killer cell is a natural killer (NK) cell. In some embodiments, the immune killer cell is a CD8+ T-cell. In some embodiments, the enucleated cell comprises at least a first exogenous stimulatory polypeptide, a second exogenous stimulatory polypeptide and a third exogenous stimulatory polypeptide. In some embodiments, at least one of the exogenous stimulatory polypeptides comprises a polypeptide selected from the group consisting of: IL-1, IL-2, IL-12, IL-15, IL-15/IL-15RA fusion, IL-18, IL-21, interferon alpha (IFN$\alpha$), 4-1BBL, Poliovirus Receptor (PVR/CD155), CD48, human leukocyte antigen (HLA)-A, HLA-C, HLA-G, heparan sulfate (HS), HLA-E, CpG, Immunoglobulin G (IgG), MHC class I chain-related proteins (MIC), B7-H6, NkP44L, Nectin2, NK-T-B antigen (NTBA), activation-induced C-type lectin (AICL), and insulin-like growth factor 1 (IGF-1). In some embodiments, at least one of the exogenous stimulatory polypeptides comprises IL-15/IL-15RA fusion. In some embodiments, at least one of the exogenous stimulatory polypeptides comprises IL-12. In some embodiments, at least one of the exogenous stimulatory polypeptides comprises 4-1BBL. In some embodiments, the MIC protein is selected from the group consisting of: MHC class I chain-related protein A (MICA), MHC class I chain-related protein B (MICB) and UL16 binding proteins (ULBP). In some embodiments, at least one of the exogenous stimulatory polypeptides comprises a polypeptide selected from the group consisting of: IL-15/IL-15RA fusion, MICA, MICB, and insulin-like growth factor 1 (IGF-1). In some embodiments, the first exogenous stimulatory polypeptide comprises IL-15/IL-15RA and the second exogenous stimulatory polypeptide comprises a polypeptide selected from the group consisting of: IL-1, IL-2, IL-12, IL-18, IL-21, 4-1BBL, IFN$\alpha$, MICA, MICB, PVR and CD48. In some embodiments, the first exogenous stimulatory polypeptide comprises IL-15/IL-15RA and the second exogenous stimulatory polypeptide comprises 4-1BBL. In some embodiments, the first exogenous stimulatory polypeptide comprises IL-15/IL-15RA and the second exogenous stimulatory polypeptide comprises IL-12. In some embodiments, the first exogenous stimulatory polypeptide comprises IL-12 and the second exogenous stimulatory polypeptide comprises 4-1BBL. In some embodiments, the first exogenous stimulatory polypeptide and the second exogenous stimulatory polypeptide are selected from the group consisting of: IL-18 and IL-12, IL-18 and IL-21, IL-12 and 4-1BBL, IL-12 and IL-15/IL-15RA fusion, and 4-1BBL and IL-15/IL-15RA fusion. In some embodiments, the first exogenous stimulatory polypeptide comprises IL-12, the second exogenous polypeptide comprises IL-18 and the third exogenous stimulatory polypeptide comprises IL15/IL-15RA fusion. In some embodiments, the first exogenous stimulatory polypeptide comprises IL-12, the second exogenous polypeptide comprises IL-18 and the third exogenous stimulatory polypeptide comprises IL-15. In some embodiments, at least one exogenous polypeptide is present at a copy number of greater than $10^4$, $10^5$, or $10^6$. In some embodiments, the first exogenous stimulatory polypeptide is present at a copy number of no more than 10%, 20%, 30%, 40%, 50%, 60%, 70%, 80%, or 90% greater, or no more than 2, 5, 10, 20, 50, 100, 200, 500, or 1000 times greater than the copy number of the second exogenous stimulatory polypeptide. In some embodiments, the second exogenous stimulatory polypeptide is present at a copy number of no more than 10%, 20%, 30%, 40%, 50%, 60%, 70%, 80%, or 90% greater, or no more than 2, 5, 10, 20, 50, 100, 200, 500, or 1000 times greater than the copy number of the first exogenous stimulatory polypeptide. In some embodiments, the first exogenous stimulatory polypeptide and the second exogenous stimulatory polypeptide have an abundance ratio of about 1:1, from about 2:1 to 1:2, from about 5:1 to 1:5, from about 10:1 to 1:10, from about 20:1 to 1:20, from about 50:1 to 1:50, or from about 100:1 to 1:100 by weight or by copy number. In some embodiments, the first and the second exogenous stimulatory polypeptides are present as a fusion polypeptide. In some embodiments, the first, the second and the third exogenous stimulatory polypeptides are present as a fusion polypeptide. In some embodiments of any of the aspects and embodiments herein, at least one or more exogenous stimulatory polypeptides are present at the surface of the engineered enucleated cell. In some embodiments of any of the aspects and embodiments herein, at least one or more exogenous stimulatory polypeptides further comprise a transmembrane domain. In some embodiments, the transmembrane domain comprises glycophorin A (GPA) or a transmembrane portion thereof. In some embodiments, the transmembrane domain comprises small integral membrane protein 1 (SMIM1), or a transmembrane portion thereof. In some embodiments of any of the aspects and embodiments herein, the enucleated cell is capable of activating an NK cell. In some embodiments of any of the aspects and embodiments herein, the enucleated cell is capable of expanding an NK cell. In some embodiments, the NK cell is a memory-like NK cell. In some embodiments of any of the aspects and embodiments herein, the enucleated cell is capable of activating a CD8+ T-cell. In some embodiments of any of the aspects and embodiments herein, the enucleated cell is capable of expanding a CD8+ T-cell. In some embodiments, the CD8+ T-cell is a memory T-cell. In some embodiments of any of the aspects and embodiments herein, the enucleated cell is an erythroid cell. In some embodiments, the erythroid cell is a reticulocyte. In some embodiments, the erythroid cell is an erythrocyte.

In another aspect, the disclosure provides an engineered enucleated cell comprising a first exogenous stimulatory polypeptide, wherein the first exogenous stimulatory polypeptide comprises an interleukin-15 (IL-15) polypeptide, or a fragment thereof, and an extracellular portion of an interleukin-15 receptor alpha (IL-15RA) polypeptide, or a fragment thereof. In some embodiments, the IL-15 polypeptide and the extracellular portion of an IL-15RA polypeptide are present as a complex. In some embodiments, the first exogenous stimulatory polypeptide comprises a fusion polypeptide. In some embodiments, the IL-15 polypeptide, or a fragment thereof, is linked to the extracellular portion of the IL-15RA polypeptide, or a fragment thereof, by a linker. In some embodiments, the linker comprises GGGGS (SEQ ID NO: 11). In some embodiments, the linker comprises a $(GGGGS)_3$ linker (SEQ ID NO: 12). In some embodiments, the fusion polypeptide comprises an amino acid sequence that is at least 95% identical to SEQ ID NO: 1. In some embodiments, the fusion polypeptide comprises an amino acid sequence that is at least 95% identical to SEQ ID NO: 29 or SEQ ID NO: 37. In some embodiments, the first exogenous stimulatory polypeptide comprises an IL-15 polypeptide, or a fragment thereof, and an IL-15 receptor alpha sushi-binding domain. In some embodiments, the IL-15 polypeptide, or a fragment thereof, and the IL-15 receptor alpha sushi-binding domain are present as a complex. In some embodiments, the IL-15 polypeptide, or a fragment thereof, and the IL-15 receptor alpha sushi-binding domain are present as a fusion polypeptide. In some embodiments, the IL-15 polypeptide, or a fragment thereof, is linked to the IL-15 receptor alpha sushi-binding domain by a linker. In some embodiments, the linker comprises GGGGS (SEQ ID NO: 11). In some embodiments, the linker comprises a $(GGGGS)_3$ linker (SEQ ID NO: 12). In some embodiments, the fusion polypeptide comprises an amino acid sequence that is at least 95% identical to SEQ ID NO: 2. In some embodiments, the fusion polypeptide comprises an amino acid sequence that is at least 95% identical to SEQ ID NO: 31. In some embodiments, the engineered enucleated cell further comprises a second exogenous stimulatory polypeptide. In some embodiments, the second exogenous stimulatory polypeptide comprises 4-1BBL. In some embodiments, the second exogenous stimulatory polypeptide comprises an amino acid sequence that is at least 95% identical to SEQ ID NO: 41. In some embodiments, the second exogenous stimulatory polypeptide comprises an amino acid sequence that is at least 95% identical to SEQ ID NO: 43. In some embodiments, the second exogenous stimulatory polypeptide comprises IL-12. In some embodiments, the second exogenous stimulatory polypeptide comprises a fusion polypeptide comprising the p40 and p35 subunits of IL-12. In some embodiments, the second exogenous stimulatory polypeptide comprises an amino acid sequence that is at least 95% identical to SEQ ID NO: 37. In some embodiments, the second exogenous stimulatory polypeptide comprises an amino acid sequence that is at least 95% identical to SEQ ID NO: 55. In some embodiments of the aspects and embodiments herein, the engineered enucleated cell further comprises one or more exogenous stimulatory polypeptides selected from the group consisting of IL-1, IL-2, IL-12, IL-18, IL-21, interferon alpha (IFNα), Poliovirus Receptor (PVR/CD155), CD48, human leukocyte antigen (HLA)-A, HLA-C, HLA-G, heparin sulfate (HS), HLA-E, CpG, Immunoglobulin G (IgG), UL16 binding proteins (ULBP), MHC class I chain-related proteins (MIC), B7-H6, NkP44L, Nectin2, NK-T-B antigen (NTBA), activation-induced C-type lectin (AICL) and insulin-like growth factor 1 (IGF-1). In some embodiments, the MIC protein is MHC class I chain-related protein A (MICA) or MHC class I chain-related protein B (MICB). In some embodiments of the aspects and embodiments herein, one or more of the exogenous stimulatory polypeptides are present at the surface of the engineered enucleated cell. In some embodiments of the aspects and embodiments herein, the exogenous stimulatory polypeptides are sufficient to stimulate an immune killer cell. In some embodiments of the aspects and embodiments herein, the first exogenous stimulatory polypeptide is present at a copy number of greater than $10^4$, $10^5$, or $10^6$. In some embodiments of the aspects and embodiments herein, the first exogenous stimulatory polypeptide is present at a copy number of no more than 10%, 20%, 30%, 40%, 50%, 60%, 70%, 80%, or 90% greater, or no more than 2, 5, 10, 20, 50, 100, 200, 500, or 1000 times greater than the copy number of the second exogenous stimulatory polypeptide. In some embodiments of the aspects and embodiments therein, the second exogenous stimulatory polypeptide is present at a copy number of noe more than 10%, 20%, 30%, 40%, 50%, 60%, 70%<80%, or 90% greater, no more than 2, 5, 10, 20, 50, 100, 200, 500, or 1000 times greater than the copy number of the first exogenous stimulatory polypeptide. In some embodiments of the aspects and embodiments herein, the first exogenous stimulatory polypeptide and the second exogenous stimulatory polypeptide have an abundance ratio of about 1:1, from about 2:1 to 1:2, from about 5:1 to 1:5, from about 10:1 to 1:10, from about 20:1 to 1:20, from, about 50:1 to 1:50, of from about 100:1 to 1:100 by weight or by copy number. In some embodiments, the engineered enucleated cell further comprises a second exogenous polypeptide and a third exogenous stimulatory polypeptide. In some embodiments of the aspects and embodiments herein, the engineered enucleated cell comprises two exogenous stimulatory polypeptides and the two exogenous stimulatory polypeptides are present as a fusion polypeptide. In some embodiments of the aspects and embodiments herein, the engineered enucleated cell comprises three exogenous stimulatory polypeptides and the three exogenous stimulatory polypeptides are present as a fusion polypeptide. In some embodiments of the aspects and embodiments herein, one or more of the exogenous stimulatory polypeptides further comprise a transmembrane domain. In some embodiments, the transmembrane domain comprises glycophorin A (GPA) or a transmembrane portion thereof. In some embodiments, the transmembrane domain comprises small integral membrane protein 1 (SMIM1), or a transmembrane portion thereof In some embodiments of the aspects and embodiments herein, the engineered enucleated cell is capable of stimulating an immune cell. In some embodiments, the immune cell is a killer immune cell. In some embodiments, the killer immune cell is a natural killer (NK) cell. In some embodiments, the NK cell is a memory-like NK cell. In some embodiments, the killer immune cell is a CD8+T-cell. In some embodiments, the CD8+T-cell is a memory T cell. In some embodiments, stimulating the immune cell comprises expanding the immune cell. In some embodiments of the aspects and embodiments herein, the engineered enucleated cell is an erythroid cell. In some embodiments, the erythroid cell is a reticulocyte. In some embodiments, the erythroid cell is an erythrocyte.

In another aspect, the disclosure provides an engineered enucleated cell comprising at least a first exogenous stimulatory polypeptide comprising a polypeptide selected from the group consisting of: MHC class I chain-related protein A (MICA), MHC class I chain-related protein B (MICB), and insulin-like growth factor 1 (IGF-1). In some embodiments, the enucleated cell further comprises a second exogenous polypeptide. In some embodiments, the second exogenous stimulatory polypeptide comprises a polypeptide selected from the group consisting of IL-1, IL-2, IL-12, IL-15, IL-15/IL-15RA fusion, IL-18, IL-21, interferon alpha (IFNα), 4-1BBL, Poliovirus Receptor (PVR/CD155), CD48, HLA-A, HLA-C, HLA-G, heparan sulfate (HS), HLA-E, CpG, IgG, UL16 binding proteins (ULBP), MHC class I chain-related polypeptide (MIC), B7-H6, NkP44L, Nectin2, NK-T-B antigen (NTBA), activation-induced C-type lectin (AICL) and insulin-like growth factor 1 (IGF-1). In some embodiments of the aspects and embodiments herein, one or more of the exogenous stimulatory polypeptides are present at the surface of the engineered enucleated cell. In some embodiments of the aspects and embodiments herein, the exogenous stimulatory polypeptides are sufficient to stimulate an immune killer cell. In some embodiments, the exogenous stimulatory polypeptide is present at a copy number of greater than $10^4$, $10^5$, or $10^6$. In some embodiments, the first exogenous stimulatory polypeptide is present at a copy number of no more than 10%, 20%, 30%, 40%, 50%, 60%, 70%, 80%, or 90% greater, or no more than 2, 5, 10, 20, 50, 100, 200, 500, or 1000 times greater than the copy number of the second exogenous stimulatory polypeptide. In some embodiments, the second exogenous stimulatory polypeptide is present at a copy number of no more than 10%, 20%, 30%, 40%, 50%, 60%, 70%, 80%, or 90% greater, or no more than 2, 5, 10, 20, 50, 100, 200, 500, or 1000 times greater than the copy number of the first exogenous stimulatory polypeptide. In some embodiments, the first exogenous stimulatory polypeptide and the second exogenous stimulatory polypeptide have an abundance ratio of about 1:1, from about 2:1 to 1:2, from about 5:1 to 1:5, from about 10:1 to 1:10, from about 20:1 to 1:20, from about 50:1 to 1:50, or from about 100:1 to 1:100 by weight or by copy number. In some embodiments, the enucleated cell further comprises a third exogenous stimulatory polypeptide. In some embodiments of the aspects and embodiments herein, the engineered enucleated cell comprises two exogenous stimulatory polypeptides and the two exogenous stimulatory polypeptides are present as a fusion polypeptide. In some embodiments of the aspects and embodiments herein, the engineered enucleated cell comprises three exogenous stimulatory polypeptides and the three exogenous stimulatory polypeptides are present as a fusion polypeptide. In some embodiments of the aspects and embodiments herein, one or more of the exogenous stimulatory polypeptides comprises a transmembrane domain. In some embodiments, the transmembrane domain comprises glycophorin A (GPA) or a transmembrane portion thereof. In some embodiments, the transmembrane domain comprises small integral membrane protein 1 (SMIM1), or a transmembrane portion thereof. In some embodiments of the aspects and embodiments herein, the engineered enucleated cell is capable of stimulating an immune cell. In some embodiments, the immune cell is a killer immune cell. In some embodiments, the killer immune cell is a natural killer (NK) cell. In some embodiments, the NK cell is a memory-like NK cell. In some embodiments, the killer immune cell is a CD8+ T-cell. In some embodiments, the CD8+ T-cell is a memory T cell. In some embodiments, stimulating the immune cell comprises activating the immune cell. In some embodiments, stimulating the immune cell comprises expanding the immune cell.

In another aspect, the disclosure provides a method of stimulating an immune killer cell, comprising contacting the immune killer cell with the engineered enucleated cell of any one of the aspects and embodiments herein, in an amount effective to stimulate the immune killer cell. In some embodiments, the immune killer cell is an NK cell. In some embodiments, the immune killer cell is a CD8+ T-cell. In some embodiments, the stimulating comprises activating the NK cell. In some embodiments, the stimulating comprises expanding the NK cell. In some embodiments, the stimulating comprises activating the CD8+ T-cell. In some embodiments, the stimulating comprises expanding the CD8+ T-cell. In some embodiments, the CD8+ T-cell is a memory T-cell. In some embodiments of the aspects and embodiments herein, the contacting is performed in vivo. In some embodiments of the aspects and embodiments herein, the contacting is performed ex vivo. In some embodiments of the aspects and embodiments herein, the contacting is performed in vitro. In some embodiments, the method further comprises administering the engineered enucleated cell to a subject in need of immune killer cell activation. In some embodiments, the subject has cancer. In some embodiments, the cancer is characterized by low MHC class I presentation. In some embodiments, the cancer comprises a PD-1-responsive tumor. In some embodiments, the cancer comprises tumors with a high mutational burden. In some embodiments, the subject is being treated with a chemotherapeutic agent that decreases MHC class I presentation. In some embodiments, the cancer is selected from lung cancer, hepatocellular cancer, melanoma, and lymphoma. In some embodiments, the cancer comprises lymphoma, and the lymphoma comprises Hodgkin's lymphoma or non-Hodgkin's lymphoma. In some embodiments, the subject has an infectious disease. In some embodiments, the infectious diseases is caused by a viral infection. In some embodiments, the viral infection is characterized by low MHC class I presentation. In some embodiments, the viral infection is caused by a virus selected from the group consisting of: adenovirus, Epstein barr virus (EBV), hepatitis B virus (HBV), tuberculosis, human immunodeficiency virus (HIV), herpes simplex virus (HSV), papilloma virus, and cytomegalovirus.

In another aspect, the disclosure provides a method of treating a cancer in a subject, comprising administering to the subject the engineered enucleated cell of any of the aspects and embodiments herein, in an amount effective to treat the cancer in the subject. In some embodiments, the cancer comprises low MHC class I presentation. In some embodiments, the cancer comprises a PD-1 responsive tumor. In some embodiments, the cancer comprises a tumor with a high mutational burden. In some embodiments, the cancer is selected from lung cancer, hepatocellular cancer, melanoma, and lymphoma. In some embodiments, the cancer comprises lymphoma, and the lymphoma is selected from Hodgkin's Lymphoma or non-Hodgkin's lymphoma.

In another aspect, the disclosure provides a method of treating an infectious disease in a subject, comprising administering to the subject the engineered enucleated cell of any of the aspects and embodiments herein, in an amount effective to treat the infectious disease in the subject. In some embodiments, the infectious diseases is caused by a viral infection. In some embodiments, the viral infection is characterized by down-regulation of MHC I presentation. In some embodiments, the viral infection is caused by a virus selected from adenovirus, Epstein barr virus (EBV), hepatitis B virus (HBV), tuberculosis, human immunodeficiency virus (HIV), herpes simplex virus (HSV), papilloma virus and cytomegalovirus.

In another aspect, the disclosure provides an enucleated erythroid cell engineered to stimulate an immune cell, wherein the immune cell is a killer cell, comprising two or more exogenous stimulatory polypeptides at the surface of the engineered enucleated cell, wherein the two or more exogenous stimulatory polypeptides are sufficient to stimulate the immune cell, produced by a process comprising introducing two or more exogenous nucleic acids, each encoding one of the exogenous stimulatory polypeptides, into a nucleated erythroid cell; and culturing the nucleated erythroid cell under conditions suitable for enucleation of the nucleated erythroid cell and for production of the two or more exogenous stimulatory polypeptides.

In another aspect, the disclosure provides an engineered enucleated erythroid cell, comprising a first exogenous stimulatory polypeptide, wherein the first exogenous stimulatory polypeptide comprises an IL-15 polypeptide, or a fragment thereof, linked to the extracellular portion of an IL-15RA polypeptide, or a fragment thereof, by a linker to form an IL-15/IL-15RA fusion, produced by a process comprising introducing an exogenous nucleic acid encoding the IL-15/IL-15RA fusion into a nucleated erythroid cell; and culturing the nucleated erythroid cell under conditions suitable for enucleation of the nucleated erythroid cell and for production of the IL-15/IL-15RA fusion.

In another aspect, the disclosure provides an engineered enucleated erythroid cell, comprising a first exogenous stimulatory polypeptide, wherein the first exogenous stimulatory polypeptide comprises an IL-15 polypeptide, or a fragment thereof, linked to the extracellular portion of an IL-15RA polypeptide, or a fragment thereof, by a linker to form an IL-15/IL-15RA fusion; and a second exogenous stimulatory polypeptide, wherein the second exogenous stimulatory polypeptide comprises 4-1BBL, or a fragment thereof, wherein the cell is produced by a process comprising i. introducing a first exogenous nucleic acid encoding the first exogenous stimulatory polypeptide into a nucleated erythroid cell; ii. introducing a second exogenous nucleic acid encoding the second exogenous stimulatory polypeptide into the nucleated erythroid cell; and iii. culturing the nucleated erythroid cell under conditions suitable for enucleation of the nucleated erythroid cell and for production of the first exogenous stimulatory polypeptide and the second exogenous stimulatory polypeptide.

In another aspect, the disclosure provides an engineered enucleated erythroid cell, comprising i. a first exogenous stimulatory polypeptide, wherein the first exogenous stimulatory polypeptide comprises an IL-15 polypeptide, or a fragment thereof, linked to the extracellular portion of an IL-15RA polypeptide, or a fragment thereof, by a linker to form an IL-15/IL-15RA fusion; and ii. a second exogenous stimulatory polypeptide, wherein the second exogenous stimulatory polypeptide comprises IL-12, or a fragment thereof, wherein the cell is produced by a process comprising i. introducing a first exogenous nucleic acid encoding the first exogenous stimulatory polypeptide into a nucleated erythroid cell; ii. introducing a second exogenous nucleic acid encoding the second exogenous stimulatory polypeptide into the nucleated erythroid cell; and iii. culturing the nucleated erythroid cell under conditions suitable for enucleation of the nucleated erythroid cell and for production of the first exogenous stimulatory polypeptide and the second exogenous stimulatory polypeptide.

In another aspect, the disclosure provides an engineered enucleated erythroid cell, comprising i. a first exogenous stimulatory polypeptide, wherein the first exogenous stimulatory polypeptide comprises 4-1BBL, or a fragment thereof; and ii. a second exogenous stimulatory polypeptide, wherein the second exogenous stimulatory polypeptide comprises IL-12, or a fragment thereof, wherein the cell is produced by a process comprising i. introducing a first exogenous nucleic acid encoding the first exogenous stimulatory polypeptide into a nucleated erythroid cell; ii. introducing a second exogenous nucleic acid encoding the second exogenous stimulatory polypeptide into the nucleated erythroid cell; and iii. culturing the nucleated erythroid cell under conditions suitable for enucleation of the nucleated erythroid cell and for production of the first exogenous stimulatory polypeptide and the second exogenous stimulatory polypeptide. In some embodiments of the above aspects and embodiments, the introducing step comprises transfecting the nucleated cell with a single lentiviral vector comprising both the first exogenous nucleic acid and the second exogenous nucleic acid. In some embodiments of the above aspects and embodiments, the introducing step comprises transfecting the nucleated erythroid cell with both a first lentiviral vector comprising the first exogenous nucleic acid and a second lentiviral vector comprising the second exogenous nucleic acid.

In another aspect, the disclosure provides an engineered enucleated erythroid cell, comprising at least one exogenous stimulatory polypeptide selected from the group consisting of: IL-15/IL-15RA fusion, MHC class I chain-related protein A (MICA), MHC class I chain-related protein B (MICB) and insulin-like growth factor 1 (IGF-1), at the surface of the engineered enucleated cell, produced by a process comprising introducing an exogenous nucleic acid encoding the at least one exogenous stimulatory polypeptide into a nucleated erythroid cell; and culturing the nucleated erythroid cell under conditions suitable for enucleation of the nucleated erythroid cell and for production of the at least one exogenous stimulatory polypeptide. In some embodiments of the above aspects and embodiments, the exogenous nucleic acid comprises DNA. In some embodiments of the above aspects and embodiments, the exogenous nucleic acid comprises RNA. In some embodiments of the above aspects and embodiments, the introducing step comprises viral transduction. In some embodiments of the above aspects and embodiments, the introducing step comprises electroporation. In some embodiments of the above aspects and embodiments, the introducing step comprises utilizing one or more of: liposome mediated transfer, adenovirus, adeno-associated virus, herpes virus, a retroviral based vector, lipofection, and a lentiviral vector. In some embodiments of the above aspects and embodiments, the introducing step comprises introducing the exogenous nucleic acid by transfection of a lentiviral vector. In some embodiments of the above aspects and embodiments, the lentiviral vector comprises a promoter selected from the group consisting of: beta-globin promoter, murine stem cell virus (MSCV) promoter, Gibbon ape leukemia virus (GALV) promoter, human elongation factor 1alpha (EF1alpha) promoter, CAG CMV immediate early enhancer and the chicken beta-actin (CAG), and human phosphoglycerate kinase 1 (PGK) promoter.

BRIEF DESCRIPTION OF THE DRAWINGS

In FIG. 2A 40,000 purified NK cells from one donor were plated in duplicate and cultured for 7 days with a titration of: engineered erythroid cells (900,000, 300,000, 100,000), rhIL-2 (1000, 100, 10 U/mL), rhIL-15 (10, 1, 0.1 ng/mL). NK cells cultured without engineered erythroid cells (no RBC) and PBMCs cultured with erythroid cells which express on their surface just the HA epitope tag were used as negative controls. Analysis was carried out on day 7. In FIG. 2B NK cells were cultured with 900,000 engineered erythrocytes, and the copy number that was expressed on these cells was used to calculate the total IL-15 copy number that was presented to the cells (shown on the X axis). In FIG. 2C NK cells were cultured with 300,000 engineered erythrocytes, and the copy number that was expressed on these cells was used to calculate the total IL-15 copy number that was presented to the cells (shown on the X axis).

In FIG. 2D 100,000 PBMCs from two donors (plated in duplicate) were cultured with 900,000, 300,000 or 100,000 engineered erythroid cells. PBMCs cultured without engineered erythroid cells (no RBC) and PBMCs cultured with erythroid cells which express on their surface just the HA epitope tag were used as negative controls. Flow cytometry analysis was carried out on day 7, applying a gate on live/dead, CD56+CD3− cells. In FIG. 2E PBMCs were cultured with 900,000 engineered erythrocytes, and the copy number that was expressed on these cells was used to calculate the total IL-15 copy number that was presented to the cells (shown on the X axis). In FIG. 2F PBMCs cells were cultured with 300,000 engineered erythrocytes, and the copy number that was expressed on these cells was used to calculate the total IL-15 copy number that was presented to the cells (shown on the X axis).

DETAILED DESCRIPTION

Figure 1A:
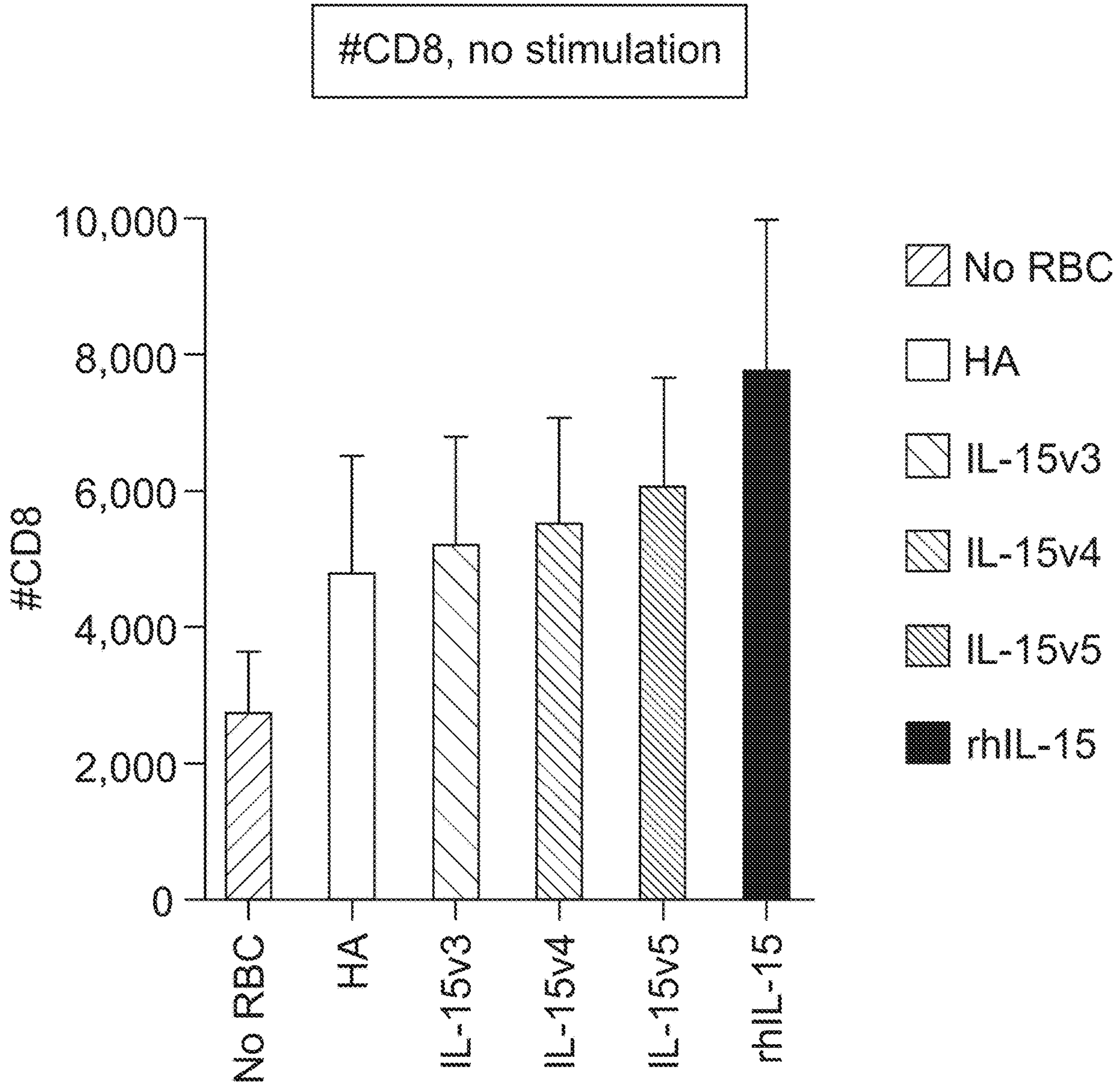
FIG. 1A is a graph showing that erythroid cells, engineered to express IL-15 variants v3, v4 and v5, when cultured with peripheral blood mononuclear cells (PBMCs) and unstimulated, induce an increase in total number of CD8+ cells. 100,000 PBMCs from 3 donors were cultured with 300,000 engineered erythroid cells. PBMCs cultured without engineered erythroid cells (no RBC) and PBMCs cultured with erythroid cells which express on their surface just the HA epitope tag were used as negative controls. PBMCs cultured with recombinant human IL-15 (rh IL-15) were used as a comparison to soluble IL-15. The total number of CD8+ cells was counted on day 5. The results shown in FIG. 1A are representative of 4 independent experiments with 2-3 PBMC donors each (total of 6 different PBMC donors tested).

The present disclosure is based on the development of erythroid cells that have been engineered to stimulate immune killer cells (e.g. stimulate the expansion, activation and/or cytotoxic activity of NK cells and/or $CD8^+$T-cells) by the expression on the cell surface of the erythroid cell of one or more exogenous stimulatory polypeptides, such as stimulatory cytokines, sufficient to activate and/or expand the NK cells and/or $CD8^+$T-cells. In some embodiments, the present invention provides engineered erythroid cells comprising IL-12, IL-15/IL-15RA, 4-1BBL, or combinations thereof, e.g., 4-1BBL and IL-15/IL-15RA, 4-1BBL and IL-12, or IL-12 and IL-15/IL-15RA, which have been found to drive potent activation of CD4+, CD8+ and NK cells, and to induce NK cell cytotoxicity. According to embodiments of the present disclosure, the engineered erythroid cells are nucleated cells, or are enucleated cells. The engineered erythroid cells provided herein provide the significant advantage over current immune killer cell targeting technologies of being naturally immuno-privileged and directly mediating stimulation of the immune killer cells (e.g. NK cells and/or $CD8^+$T-cells) in vivo, thus avoiding the disadvantages associated with adoptive cell transfer of immune killer cells. The engineered erythroid cells provide the additional advantages of being able to present, e.g. comprise on the cell surface, several different stimulatory molecules on a single enucleated cell, and in significantly high numbers, e.g., 4-1BBL and IL-12, 4-1BBL and IL-15/IL-15RA, or IL-12 and IL-15/IL-15RA, as well as delivering and maintaining the stimulatory signals via the erythroid cells directly throughout the circulatory system and with a long circulation half-life, thus providing a safer and more effective method for stimulating immune killer cells.

Many modifications and other embodiments of the inventions set forth herein will easily come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Definitions

As used in this specification and the appended claims, the singular forms “a”, “an” and “the” include plural references unless the content clearly dictates otherwise.

The use of the alternative (e.g., “or”) should be understood to mean either one, both, or any combination thereof of the alternatives.

As used herein, the term “about,” when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, any concentration range, percentage range, ratio range, or integer range is to be understood to include the value of any integer within the recited range and, when appropriate, fractions thereof (such as one tenth and one hundredth of an integer), unless otherwise indicated.

As used herein, “comprise,” “comprising,” and “comprises” and “comprised of” are meant to be synonymous with “include”, “including”, “includes” or “contain”, “containing”, “contains” and are inclusive or open-ended terms that specifies the presence of what follows e.g. component and do not exclude or preclude the presence of additional, non-recited components, features, element, members, steps, known in the art or disclosed therein.

As used herein, the terms “such as”, “for example” and the like are intended to refer to exemplary embodiments and not to limit the scope of the present disclosure.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, preferred materials and methods are described herein.

As used herein, the terms "activating CD8+ T cells" or "CD8+ T cell activation" refer to a process (e.g., a signaling event) causing or resulting in one or more cellular responses of a CD8+ T cell (CTL), selected from: proliferation, differentiation, cytokine secretion, cytotoxic effector molecule release, cytotoxic activity, and expression of activation markers. As used herein, an "activated CD8+ T cell" refers to a CD8+ T cell that has received an activating signal, and thus demonstrates one or more cellular responses, selected from proliferation, differentiation, cytokine secretion, cytotoxic effector molecule release, cytotoxic activity, and expression of activation markers. Suitable assays to measure CD8+ T cell activation are known in the art and are described herein.

As used herein, the terms "expanding a CD8+ T cell" or "CD8+ T cell expansion" refer to a process wherein a CD8+ T cell undergoes a series of cell divisions and thereby expands in cell number. The term "expanded CD8+ T cells" relates to CD8+ T cells obtained through CD8+ T cell expansion. Suitable assays to measure T cell expansion are known in the art and are described herein.

As used herein, the term "activating an NK cell" or "NK cell activation" refers to a process (e.g., a signaling event) causing or resulting in an NK cell being capable of killing cells with deficiencies in MHC class I expression. As used herein, an "activated NK cell" refers to an NK cell that has received an activating signal, and is thus capable of killing cells with deficiencies in MHC class I expression. Suitable assays to measure NK cell activation are known in the art and are described herein.

As used herein, the terms "expanding an NK cell" or "NK cell expansion" refer to a process wherein an NK cell undergoes a series of cell divisions and thereby expands in cell number. The term "expanded NK cells" relates to NK cells obtained through NK cell expansion. Suitable assays to measure NK cell expansion are known in the art and are described herein.

As used herein, "administration," "administering" and variants thereof refers to introducing a composition or agent into a subject and includes concurrent and sequential introduction of a composition or agent. "Administration" can refer, e.g., to therapeutic, pharmacokinetic, diagnostic, research, placebo, and experimental methods. "Administration" also encompasses in vitro and ex vivo treatments. The introduction of a composition or agent into a subject is by any suitable route, including orally, pulmonarily, intranasally, parenterally (intravenously, intramuscularly, intraperitoneally, or subcutaneously), rectally, intralymphatically, or topically. Administration includes self-administration and the administration by another. Administration can be carried out by any suitable route. A suitable route of administration allows the composition or the agent to perform its intended function. For example, if a suitable route is intravenous, the composition is administered by introducing the composition or agent into a vein of the subject.

As used herein, the term "antibody" is used in the broadest sense and encompasses various antibody structures, including but not limited to monoclonal antibodies, polyclonal antibodies, and antibody fragments so long as they exhibit the desired antigen-binding activity.

As used herein, the term "cancer" refers to diseases in which abnormal cells divide without control. In some embodiments, cancer is able to invade other tissues. There are more than 100 different types of cancer. Most cancers are named for the organ or type of cell in which they start—for example, cancer that begins in the colon is called colon cancer; cancer that begins in melanocytes of the skin is called melanoma. Cancer types can be grouped into broader categories. The main categories of cancer include: carcinoma (meaning a cancer that begins in the skin or in tissues that line or cover internal organs, and its subtypes, including adenocarcinoma, basal cell carcinoma, squamous cell carcinoma, and transitional cell carcinoma); sarcoma (meaning a cancer that begins in bone, cartilage, fat, muscle, blood vessels, or other connective or supportive tissue); leukemia (meaning a cancer that starts in blood-forming tissue (e.g., bone marrow) and causes large numbers of abnormal blood cells to be produced and enter the blood; lymphoma and myeloma (meaning cancers that begin in the cells of the immune system); and central nervous system (CNS) cancers (meaning cancers that begin in the tissues of the brain and spinal cord). The term "myelodysplastic syndrome" refers to a type of cancer in which the bone marrow does not make enough healthy blood cells (white blood cells, red blood cells, and platelets) and there are abnormal cells in the blood and/or bone marrow. Myelodysplastic syndrome may become acute myeloid leukemia (AML). In certain embodiments, the cancer is selected from cancers including, but not limited to, ACUTE lymphoblastic leukemia (ALL), ACUTE myeloid leukemia (AML), anal cancer, bile duct cancer, bladder cancer, bone cancer, bowel cancer, brain tumour, breast cancer, cancer of unknown primary, cancer spread to bone, cancer spread to brain, cancer spread to liver, cancer spread to lung, carcinoid, cervical cancer, choriocarcinoma, chronic lymphocytic leukemia (CLL), chronic myeloid leukemia (CML), colon cancer, colorectal cancer, endometrial cancer, eye cancer, gallbladder cancer, gastric cancer, gestational trophoblastic tumour (GTT), hairy cell leukemia, head and neck cancer, Hodgkin lymphoma, kidney cancer, laryngeal cancer, leukemia, liver cancer, lung cancer, lymphoma, melanoma skin cancer, mesothelioma, men's cancer, molar pregnancy, mouth and oropharyngeal cancer, myeloma, nasal and sinus cancers, nasopharyngeal cancer, non hodgkin lymphoma (NHL), oesophageal cancer, ovarian cancer, pancreatic cancer, penile cancer, prostate cancer, rare cancers, rectal cancer, salivary gland cancer, secondary cancers, skin cancer (non melanoma), soft tissue sarcoma, stomach cancer, testicular cancer, thyroid cancer, unknown primary cancer, uterine cancer, vaginal cancer, and vulval cancer.

As used herein, the term "click reaction" refers to a range of reactions used to covalently link a first and a second moiety, for convenient production of linked products. It typically has one or more of the following characteristics: it is fast, is specific, is high-yield, is efficient, is spontaneous, does not significantly alter biocompatibility of the linked entities, has a high reaction rate, produces a stable product, favors production of a single reaction product, has high atom economy, is chemoselective, is modular, is stereoselective, is insensitive to oxygen, is insensitive to water, is high purity, generates only inoffensive or relatively non-toxic by-products that can be removed by nonchromatographic methods (e.g., crystallization or distillation), needs no solvent or can be performed in a solvent that is benign or physiologically compatible, e.g., water, stable under physiological conditions. Examples include an alkyne/azide reaction, a diene/dienophile reaction, or a thiol/alkene reaction.

Other reactions can be used. In some embodiments, the click reaction is fast, specific, and high-yield.

As used herein, the term "click handle" refers to a chemical moiety that is capable of reacting with a second click handle in a click reaction to produce a click signature. In embodiments, a click handle is comprised by a coupling reagent, and the coupling reagent may further comprise a substrate reactive moiety.

As used herein, the term "cytokine" refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Cytokines can act both locally and distantly from a site of release. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of other cytokines. Non limiting examples of cytokines include e.g., IL-1, IL-2, IL-3, IL-4, IL-5, IL-6, IL-7, IL-8, IL-9, IL-10, IL-11, IL-12/IL-23 P40, IL13, IL-15, IL-15/IL-15-RA, IL-17, IL-18, IL-21, IL-23, TGF-β, IFNγ, GM-CSF, Groα, MCP-1 and TNF-α.

As used herein, the term "endogenous" is meant to refer to a native form of compound (e.g., a small molecule) or process. For example, in some embodiments, the term "endogenous" refers to the native form of a nucleic acid or polypeptide in its natural location in the organism or in the genome of an organism.

As used herein, the term "an engineered cell" is meant to refer to a genetically-modified cell or progeny thereof. In some embodiments, an engineered cell (e.g. an engineered enucleated cell) can be produced using coupling reagents to link an exogenous polypeptide to the surface of the cell (e.g. using click chemistry).

As used herein, the term "enucleated" refers to a cell, e.g., a reticulocyte or mature red blood cell (erythrocyte) that lacks a nucleus. In an embodiment an enucleated cell is a cell that has lost its nucleus through differentiation from a precursor cell, e.g., a hematopoietic stem cell (e.g., a CD34+ cell), a common myeloid progenitor (CMP), a megakaryocyte erythrocyte progenitor cell (MEP), a burst-forming unit erythrocyte (BFU-E), a colony-forming unit erythrocyte (CFU-E), a pro-erythroblast, an early basophilic erythroblast, a late basophilic erythroblast, a polychromatic erythroblast, or an orthochromatic erythroblast, or an induced pluripotent cell, into a reticulocyte or mature red blood cell. In an embodiment an enucleated cell is a cell that has lost its nucleus through in vitro differentiation from a precursor cell, e.g., a hematopoietic stem cell (e.g., a CD34+ cell), a common myeloid progenitor (CMP), a megakaryocyte erythrocyte progenitor cell (MEP), a burst-forming unit erythrocyte (BFU-E), a colony-forming unit erythrocyte (CFU-E), a pro-erythroblast, an early basophilic erythroblast, a late basophilic erythroblast, a polychromatic erythroblast, or an orthochromatic erythroblast, or an induced pluripotent cell into a reticulocyte or mature red blood cell. In an embodiment an enucleated cell lacks DNA. In an embodiment an enucleated cell is incapable of expressing a polypeptide, e.g., incapable of transcribing and/or translating DNA into protein, e.g., lacks the cellular machinery necessary to transcribe and/or translate DNA into protein. In some embodiments, an enucleated cell is an erythrocyte, a reticulocyte, or a platelet.

In some embodiments, the enucleated cells are not platelets, and therefore are "platelet free enucleated" cells ("PFE" cells). It should be understood that platelets do not have nuclei, and in this particular embodiment, platelets are not intended to be encompassed.

As used herein, "erythroid cell" includes a nucleated red blood cell, a red blood cell precursor, an enucleated mature red blood cell, and a reticulocyte. As used herein, an erythroid cell can includes an erythroid precursor cell, a cell capable of differentiating into a reticulocyte or erythrocyte. For example, erythroid precursor cells include any of a cord blood stem cell, a CD34+ cell, a hematopoietic stem cell (HSC), a spleen colony forming (CFU-S) cell, a common myeloid progenitor (CMP) cell, a blastocyte colony-forming cell, a burst forming unit-erythroid (BFU-E), a megakaryocyte-erythroid progenitor (MEP) cell, an erythroid colony-forming unit (CFU-E), a reticulocyte, an erythrocyte, an induced pluripotent stem cell (iPSC), a mesenchymal stem cell (MSC), a polychromatic normoblast, an orthochromatic normoblast. A preparation of erythroid cells can include any of these cells or a combination thereof. In some embodiments, the erythroid precursor cells are immortal or immortalized cells. For example, immortalized erythroblast cells can be generated by retroviral transduction of CD34+ hematopoietic progenitor cells to express Oct4, Sox2, Klf4, cMyc, and suppress TP53 (e.g., as described in Huang et al., (2014) Mol. Ther. 22(2): 451-63, the entire contents of which are incorporated by reference herein). In addition, the cells may be intended for autologous use or provide a source for allogeneic transfusion. In some embodiments, erythroid cells are cultured. In an embodiment an erythroid cell is an enucleated red blood cell.

As used herein, the term "exogenous," when used in the context of nucleic acid, includes a transgene and recombinant nucleic acids.

As used herein, the term "exogenous nucleic acid" refers to a nucleic acid (e.g., a gene) which is not native to a cell, but which is introduced into the cell or a progenitor of the cell. An exogenous nucleic acid may include a region or open reading frame (e.g., a gene) that is homologous to, or identical to, an endogenous nucleic acid native to the cell. In some embodiments, the exogenous nucleic acid comprises RNA. In some embodiments, the exogenous nucleic acid comprises DNA. In some embodiments, the exogenous nucleic acid is integrated into the genome of the cell. In some embodiments, the exogenous nucleic acid is processed by the cellular machinery to produce an exogenous polypeptide. In some embodiments, the exogenous nucleic acid is not retained by the cell or by a cell that is the progeny of the cell into which the exogenous nucleic acid was introduced.

As used herein, the term "exogenous polypeptide" refers to a polypeptide that is not produced by a wild-type cell of that type or is present at a lower level in a wild-type cell than in a cell containing the exogenous polypeptide. In some embodiments, an exogenous polypeptide refers to a polypeptide that is introduced into or onto a cell, or is caused to be expressed by the cell by introducing an exogenous nucleic acid encoding the exogenous polypeptide into the cell or into a progenitor of the cell. In some embodiments, an exogenous polypeptide is a polypeptide encoded by an exogenous nucleic acid that was introduced into the cell, or a progenitor of the cell, which nucleic acid is optionally not retained by the cell. In some embodiments, an exogenous polypeptide is a polypeptide conjugated to the surface of the cell by chemical or enzymatic means.

As used herein, the term "exogenous stimulatory polypeptide" includes a polypeptide comprised by (e.g., intracellularly or at the cell surface) an engineered erythroid cell that specifically binds a cognate polypeptide (e.g., receptor) on an immune cell, such as an immune killer cell (e.g. an NK cell or a CD8+ T cell), thereby providing a signal which mediates stimulation of the immune cell, such as the proliferation, activation, expansion and the like of the immune cell. In some embodiments, one or more exogenous stimulatory polypeptides are sufficient to stimulate an immune killer cell ex vivo or in vivo. Exemplary exogenous stimulatory polypeptides are described in more detail below.

As used herein, the term "express" or "expression" refers to the process to produce a polypeptide, including transcription and translation. Expression may be, e.g., increased by a number of approaches, including: increasing the number of genes encoding the polypeptide, increasing the transcription of the gene (such as by placing the gene under the control of a constitutive promoter), increasing the translation of the gene, knocking out of a competitive gene, or a combination of these and/or other approaches.

As used herein, the terms "first", "second" and "third", etc. with respect to exogenous stimulatory polypeptides are used for convenience of distinguishing when there is more than one type of exogenous stimulatory polypeptide. Use of these terms is not intended to confer a specific order or orientation of the exogenous stimulatory polypeptides unless explicitly so stated.

As used herein, the term "fragment" refers to sequences of at least 6 (contiguous) nucleic acids or at least 4 (contiguous) amino acids, a length sufficient to allow for specific hybridization in the case of nucleic acids or for specific recognition of an epitope in the case of amino acids, and are at most some portion less than a full length sequence. Fragments may be derived from any contiguous portion of a nucleic acid or amino acid sequence of choice.

As used herein, the term "gene" is used broadly to refer to any segment of nucleic acid associated with expression of a given RNA or protein. Thus, genes include regions encoding expressed RNAs (which typically include polypeptide coding sequences) and, often, the regulatory sequences required for their expression. Genes can be obtained from a variety of sources, including cloning from a source of interest or synthesizing from known or predicted sequence information, and may include sequences designed to have specifically desired parameters.

As used herein the term "extracelluar portion of IL-15RA" refers to the portion of the IL-15RA polypeptide that is amino-terminal to the transmembrane domain of IL-15RA and is found on the outer surface of the cell. The extracellular portion of IL-15RA may include the IL-15RA signal peptide. In certain embodiments, the extracelluar portion of IL-15RA consists of the amino acid sequence of SEQ ID NO: 7 or SEQ ID NO: 8.

As used herein the term "Sushi domain of IL-15RA" refers to an approximately 60 aa residue region at the amino-terminus of the mature IL-15RA polypeptide comprising four cysteine residues. The first cysteine residue forms a disulfide bond with the third cysteine, and the second cysteine forms a disulfide bridge with the fourth cysteine. The Sushi domain of IL-15RA is involved in the binding of IL-15. In certain embodiments, the Sushi domain of IL-15RA consists of the amino acid sequence of SEQ ID NO: 9.

As used herein, the term "low MHC I presentation" refers to a decreased level (e.g. by down-regulation of expression) of MHC I molecules at the surface of cells (e.g. tumor cells).

As used herein the term "nucleic acid molecule" refers to a single or double-stranded polymer of deoxyribonucleotide or ribonucleotide bases. It includes chromosomal DNA and self-replicating plasmids, vectors, mRNA, tRNA, siRNA, etc. which may be recombinant and from which exogenous polypeptides may be expressed when the nucleic acid is introduced into a cell.

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity." (a) The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence. (b) The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches. Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, *CABIOS* 5:151-153 (1989); Corpet, et al., Nucleic Acids Research 16:10881-90 (1988); Huang, et al., Computer Applications in the *Biosciences,* 8:155-65 (1992), and Pearson, et al., *Methods in Molecular Biology,* 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995). Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) *Proc. Natl. Acad. Sci. USA* 89:10915). In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, *Comput. Chem.,* 17:149-163 (1993)) and XNU (Claverie and States, *Comput. Chem.,* 17:191-201 (1993)) low-complexity filters may be employed alone or in combination. (c) The term "sequence identity" or "identity" in the context of two nucleic acid or polypeptide sequences is used herein to refer to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4:11-17 (1988) e.g., as implemented in the program PC/GENE (Intelligenetics, Mountain View, Calif., USA). (d) The term "percentage of sequence identity" is used herein mean the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. (e) The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid. Mutations may also be made to the nucleotide sequences of the present proteins by reference to the genetic code, including taking into account codon degeneracy.

As used herein, the term "pharmaceutically acceptable carrier" includes any of the standard pharmaceutical carriers, such as a phosphate buffered saline solution, water, emulsions such as an oil/water or water/oil, and various types of wetting agents. The term also encompasses any of the agents approved by a regulatory agency of the US Federal government or listed in the US Pharmacopeia for use in animals, including humans, as well as any carrier or diluent that does not cause significant irritation to a subject and does not abrogate the biological activity and properties of the administered agent.

As used herein, the terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" also are inclusive of modifications including, but not limited to, glycosylation, lipid attachment, sulfation, gamma-carboxylation of glutamic acid residues, hydroxylation, and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well. According to some embodiments, the peptide is of any length or size.

As used herein, polypeptides referred to herein as "recombinant" refer to polypeptides which have been produced by recombinant DNA methodology, including those that are generated by procedures which rely upon a method of artificial recombination, such as the polymerase chain reaction (PCR) and/or cloning into a vector using restriction enzymes.

As used herein, the term "stimulate an immune cell" or "stimulating an immune cell" refers to a process (e.g., involving a signaling event or stimulus) causing or resulting in a cellular response, such as activation and/or expansion, of an immune cell, e.g. a killer immune cell (e.g. an NK cell and/or a CD8+ T cell). In some embodiments, stimulating an immune cell (e.g., an NK cell and/or a CD8+ T cell) refers to providing a stimulus or signal (e.g., a stimulating polypeptide) that results in the activation and/or expansion of the immune cell.

As used herein, the term "sufficient to stimulate an immune cell" refers to an amount or level of a signaling event or stimulus, e.g. of exogenous stimulatory polypeptide, that promotes a cellular response of an immune cell.

As used herein, the terms "subject," "individual," "host," and "patient," are used interchangeably herein and refer to any mammalian subject for whom diagnosis, treatment, or therapy is desired, particularly humans. The methods described herein are applicable to both human therapy and veterinary applications. In some embodiments, the subject is a mammal, and in particular embodiments the subject is a human.

As used herein, the phrase "subject in need" refers to a subject that (i) will be administered an engineered erythroid cell (or pharmaceutical composition comprising an engineered erythroid cell) according to the described invention, (ii) is receiving an engineered erythroid cell (or pharmaceutical composition comprising an engineered erythroid cell) according to the described invention; or (iii) has received an engineered erythroid cell (or pharmaceutical composition comprising an engineered erythroid cell) according to the described invention, unless the context and usage of the phrase indicates otherwise As used herein, the term "suppress," "decrease," "interfere," "inhibit" and/or "reduce" (and like terms) generally refers to the act of reducing, either directly or indirectly, a concentration, level, function, activity, or behavior relative to the natural, expected, or average, or relative to a control condition.

As used herein, the terms "suppressing immune cells" or "inhibiting immune cells" refer to a process (e.g., a signaling event) causing or resulting in the inhibition or suppression of one or more cellular responses or activities of an immune cell, selected from: proliferation, differentiation, cytokine secretion, cytotoxic effector molecule release, cytotoxic activity, and expression of activation markers, or resulting in anergizing of an immune cell or induction of apoptosis of an immune cell. Suitable assays to measure immune cell inhibition or suppression are known in the art and are described herein.

As used herein, the terms "therapeutic amount", "therapeutically effective amount", an "amount effective", or "pharmaceutically effective amount" of an active agent (e.g. an engineered erythroid cell as described herein) are used interchangeably to refer to an amount that is sufficient to provide the intended benefit of treatment. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods. Additionally, the terms "therapeutic amount", "therapeutically effective amounts" and "pharmaceutically effective amounts" include prophylactic or preventative amounts of the compositions of the described invention. In prophylactic or preventative applications of the described invention, pharmaceutical compositions or medicaments are administered to a patient susceptible to, or otherwise at risk of, a disease, disorder or condition in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition. It is generally preferred that a maximum dose be used, that is, the highest safe dose according to some medical judgment. The terms "dose" and "dosage" are used interchangeably herein.

As used herein the term "therapeutic effect" refers to a consequence of treatment, the results of which are judged to be desirable and beneficial. A therapeutic effect can include, directly or indirectly, the arrest, reduction, or elimination of a disease manifestation. A therapeutic effect can also include, directly or indirectly, the arrest reduction or elimination of the progression of a disease manifestation.

For any therapeutic agent described herein the therapeutically effective amount may be initially determined from preliminary in vitro studies and/or animal models. A therapeutically effective dose may also be determined from human data. The applied dose may be adjusted based on the relative bioavailability and potency of the administered agent. Adjusting the dose to achieve maximal efficacy based on the methods described above and other well-known methods is within the capabilities of the ordinarily skilled artisan. General principles for determining therapeutic effectiveness, which may be found in Chapter 1 of Goodman and Gilman's The Pharmacological Basis of Therapeutics, 10th Edition, McGraw-Hill (New York) (2001), incorporated herein by reference, are summarized below.

Pharmacokinetic principles provide a basis for modifying a dosage regimen to obtain a desired degree of therapeutic efficacy with a minimum of unacceptable adverse effects. In situations where the drug's plasma concentration can be measured and related to the therapeutic window, additional guidance for dosage modification can be obtained.

Drug products are considered to be pharmaceutical equivalents if they contain the same active ingredients and are identical in strength or concentration, dosage form, and route of administration. Two pharmaceutically equivalent drug products are considered to be bioequivalent when the rates and extents of bioavailability of the active ingredient in the two products are not significantly different under suitable test conditions.

As used herein, the terms "treat," "treating," and/or "treatment" include abrogating, substantially inhibiting, slowing or reversing the progression of a condition, substantially ameliorating clinical symptoms of a condition, or substantially preventing the appearance of clinical symptoms of a condition, obtaining beneficial or desired clinical results. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

Beneficial or desired clinical results, such as pharmacologic and/or physiologic effects include, but are not limited to, preventing the disease, disorder or condition from occurring in a subject that may be predisposed to the disease, disorder or condition but does not yet experience or exhibit symptoms of the disease (prophylactic treatment), alleviation of symptoms of the disease, disorder or condition, diminishment of extent of the disease, disorder or condition, stabilization (i.e., not worsening) of the disease, disorder or condition, preventing spread of the disease, disorder or condition, delaying or slowing of the disease, disorder or condition progression, amelioration or palliation of the disease, disorder or condition, and combinations thereof, as well as prolonging survival as compared to expected survival if not receiving treatment.

As used herein, the term "variant" refers to a polypeptide which differs from the original protein by one or more amino acid substitutions, deletions, insertions, or other modifications. These modifications do not significantly change the biological activity of the original protein. In many cases, a variant retains at least 10%, 20%, 30%, 40%, 50%, 60%, 70%, 80%, 90%, 95%, or 100% of the biological activity of original protein. The biological activity of a variant can also be higher than that of the original protein. A variant can be naturally-occurring, such as by allelic variation or polymorphism, or be deliberately engineered.

The amino acid sequence of a variant is substantially identical to that of the original protein. In many embodiments, a variant shares at least 50%, 60%, 70%, 75%, 80%, 85%, 90%, 91%, 92%, 93%, 94%, 95%, 96%, 97%, 98%, or 99%, or more global sequence identity or similarity with the original protein. Sequence identity or similarity can be determined using various methods known in the art, such as Basic Local Alignment Tool (BLAST), dot matrix analysis, or the dynamic programming method. In one example, the sequence identity or similarity is determined by using the Genetics Computer Group (GCG) programs GAP (Needleman-Wunsch algorithm) The amino acid sequences of a variant and the original protein can be substantially identical in one or more regions, but divergent in other regions. A variant may include a fragment (e.g., a biologically active fragment of a polypeptide). In some embodiments, a fragment may lack up to about 1, 2, 3, 4, 5, 10, 20, 30, 40, 50, or 100 amino acid residues on the N-terminus, C-terminus, or both ends (each independently) of a polypeptide, as compared to the full-length polypeptide.

I. Engineered Erythroid Cells

The present disclosure features erythroid cells and enucleated cells that are engineered to stimulate an immune cell. In some embodiments an enucleated cell is a erythroid cell, for example, that has lost its nucleus through differentiation from an erythroid precursor cell. It will be understood, however, that not all enucleated cells are erythroid cells and, accordingly, enucleated cells encompassed herein can also include, e.g., platelets. In some embodiments, enucleated cells are not platelets and are therefore platelet free enucleated cells. In certain aspects of the disclosure, the erythroid cell is a reticulocyte or an erythrocyte (red blood cell (RBC)). Erythrocytes offer a number of advantages over other cells, including being non-autologous due to lack of major histocompatibility complex (MHC), having longer circulation time, and being amenable to production in large numbers. In certain aspects of the disclosure, the engineered erythroid cells are nucleated.

The engineered erythroid cells provided herein provide a significant advantage over current immune killer cell targeting technologies of being naturally immuno-privileged and directly mediating stimulation of the immune killer cells in vivo, thus avoiding the disadvantages associated with adoptive cell transfer of immune killer cells. Engineered erythroid cells of the present invention can be engineered to stimulate both NK cells and CD8+ cells simultaneously when exposed to these cell populations in vivo. In particular, it is a finding of the present invention, that engineered erythroid cells comprising IL-12, IL-15/IL-15RA, 4-1BBL or combinations thereof, e.g., 4-1BBL and IL-15/IL-15RA, 4-1BBL and IL-12, or IL-12 and IL-15/IL-15RA, drive a potent activation of primary CD4+, CD8+, NK and NKT cells, and induce NK cell cytotoxicity.

In some aspects, the present disclosure provides an erythroid cell engineered to stimulate an immune cell, wherein the immune cell is an immune killer cell, comprising a plurality of exogenous stimulatory polypeptides sufficient to stimulate the immune killer cell. Immune killer cells include natural killer (NK) cells and CD8+ T-cells.

In some aspects, the present disclosure provides an engineered erythroid cell comprising a first exogenous stimulatory polypeptide, wherein the first exogenous stimulatory polypeptide comprises an interleukin-15 (IL-15) polypeptide, or a fragment thereof, and an extracellular portion of an interleukin-15 receptor alpha (IL-15RA) polypeptide, or a fragment thereof. In some embodiments, the genetically engineered erythroid cell is capable of stimulating immune cells, including immune killer cells. In some embodiments, the present disclosure provides an engineered erythroid cell comprising a first exogenous stimulatory polypeptide, wherein the first exogenous stimulatory polypeptide comprises an interleukin-15 (IL-15) polypeptide, or a fragment thereof, and an extracellular portion of an interleukin-15 receptor alpha (IL-15RA) polypeptide, or a fragment thereof, and a second exogenous stimulatory polypeptide, wherein the second exogenous stimulatory polypeptide comprises 4-1BBL, or a fragment thereof.

In some aspects, the present disclosure provides an engineered erythroid cell comprising a first exogenous stimulatory polypeptide, wherein the first exogenous stimulatory polypeptide comprises an interleukin-15 (IL-15) polypeptide, or a fragment thereof, and an extracellular portion of an interleukin-15 receptor alpha (IL-15RA) polypeptide, or a fragment thereof, and a second exogenous stimulatory polypeptide, wherein the second exogenous stimulatory polypeptide comprises an interleukin (IL-12) polypeptide, or a fragment thereof.

In some aspects, the present disclosure provides an engineered erythroid cell comprising a first exogenous stimulatory polypeptide, wherein the first exogenous stimulatory polypeptide comprises an interleukin-12 (IL-12) polypeptide, or a fragment thereof, and a second exogenous stimulatory polypeptide, wherein the second exogenous stimulatory polypeptide comprises a 4-1BBL polypeptide, or a fragment thereof.

In some aspects, the present disclosure provides an engineered erythroid cell comprising at least one exogenous stimulatory polypeptide selected from the group consisting of MHC class I chain-related protein A (MICA), MHC class I chain-related protein B (MICB), and insulin-like growth factor 1 (IGF-1).

The engineered erythroid cells provide the additional advantages of presenting, e.g. comprising on the cell surface, multiple different stimulatory molecules on a single erythroid cell, and in significantly high numbers, as well as delivering and maintaining the stimulatory signals via the erythroid cells directly throughout the circulatory system and with a long circulation half-life, thus providing a safer and more effective method for stimulating immune killer cells.

Engineered Erythroid Cells Comprising Exogenous Stimulatory Polypeptides

An exogenous stimulatory polypeptide of the present invention is a polypeptide that, alone or in combination with other exogenous stimulatory polypeptides, mediates stimulation of an immune killer cell (e.g. an NK cell and/or a CD8+ T-cell). It is a feature of the present invention that, in some embodiments, the exogenous stimulatory polypeptides comprised by the erythroid cell are capable of stimulating more than one type of immune killer cell, e.g. the engineered erythroid cells comprising exogenous stimulatory polypeptides of the present invention are capable of stimulating both an NK cell and a CD8+ Tcell.

In some embodiments, stimulating an immune killer cell refers to expansion of the immune killer cell. In some embodiments, stimulating an immune killer cells refers to activation of the immune killer cell. In some embodiments, stimulating an immune killer cells refers to an increase in cytoxicity of the immune killer cell. In certain embodiments, stimulating the immune killer cell refers to a combination of one or more of expansion, activation and/or increased cytoxicity of the immune killer cell. In particular embodiments, the one or more exogenous stimulatory polypeptides expressed on the cell surface of the engineered erythroid cells are sufficient to activate and/or expand immune killer cells (e.g. NK cells and/or $CD8^+$ T-cells) ex vivo. In particular embodiments, the one or more exogenous stimulatory polypeptides expressed on the cell surface of the engineered erythroid cells are sufficient to activate and/or expand immune killer cells (e.g. NK cells and/or $CD8^+$ T-cells) in vivo. Assays to detect if the exogenous stimulatory polypeptides are sufficient to stimulate an immune killer cell are described herein. The disclosure thus provides, in one aspect, an erythroid cell engineered to stimulate an immune cell, wherein the immune cell is an immune killer cell, comprising a plurality of exogenous stimulatory polypeptides sufficient to stimulate the immune killer cell. In some embodiments, the plurality of exogenous stimulatory polypeptides are selected from cytokines, Human Leukocyte Antigens (HLA), MHC class I chain-related proteins (MIC), proteins of the Immunoglobulin Superfamily (IgSF), NK cell cytotoxicity triggering receptor ligands, and insulin like growth factors. In some embodiments, the exogenous stimulatory polypeptide is shown in Table 1.

TABLE 1

Exogenous Stimulatory Polypeptides

| Category | Examples |
|---|---|
| Cytokines | interleukin-1 (IL-1), interleukin-2 (IL-2), interleukin-12 (IL-12), interleukin-15 (IL-15), IL-15/IL-15RA fusion, interleukin-18 (IL-18), interleukin-21 (IL-21) and interferon alpha (IFNα) |
| Human Leukocyte Antigen (HLA) Proteins | HLA-A, HLA-C, HLA-E, HLA-G |
| MHC class I chain-related proteins (MIC) | MICA, MICB, ULBP |
| Immunoglobulin Superfamily (IgSF) | PVR/CD155 (e.g., Accession Number NP_001129240.1), CD48 (e.g., Accession Number CAG33293.1), Nectin2 , NK-T-B antigen. |
| NK Cytotoxicity Triggering Receptor Ligands | NKp44 ligands, NKp30 ligands, NKp46 ligands |
| Insulin like Growth Factors | IGF-1 |
| Others | 4-1BBL (e.g., Accession Number NP_003802.1), HS/HSPG, AICL, CpG |

Unless otherwise specified, the sequence accession numbers specified herein, including in any Table herein, refer to the database entries current as of Mar. 8, 2019. When one gene or protein references a plurality of sequence accession numbers, all of the sequence variants are encompassed.

Cytokines

In some embodiments, the invention provides an erythroid cell engineered to stimulate an immune cell, wherein the immune cell is an immune killer cell, comprising a plurality of exogenous stimulatory polypeptides sufficient to stimulate the immune killer cell, including one or more cytokines. Thus, the disclosure encompasses a cytokine, including a full-length, fragment, homologue, variant or mutant of the cytokine. A cytokine includes a protein that is capable of affecting the biological function of another cell. A biological function affected by a cytokine can include, but is not limited to, cell growth, cell differentiation or cell death. Preferably, a cytokine of the present disclosure is capable of binding to a specific receptor on the surface of a cell, thereby stimulating an immune killer cell (e.g. an NK cell and/or a CD8+T-cell).

A preferred cytokine includes, among others, an interleukin, an interferon, an immunoglobulin superfamily molecule, a tumor necrosis factor family molecule and/or a chemokine. A more preferred cytokine of the disclosure includes interleukin-1 (IL-1), interleukin-2 (IL-2), interleukin-12 (IL-12), interleukin-15 (IL-15), IL-15/IL-15RA fusion, interleukin-18 (IL-18), interleukin-21 (IL-21) and interferon alpha (IFNα). In some embodiments, a particularly preferred cytokine of the disclosure is IL-15/IL-15RA fusion. In some embodiments, a particularly preferred cytokine of the disclosure is IL-12. One skilled in the art would appreciate, once armed with the teachings provided herein, that the invention encompasses a cytokine, such as are well-known in the art, as well as any discovered in the future.

In some embodiments, an erythroid cell engineered to stimulate an immune cell comprises one or more (e.g., 2, 3, 4, 5, or more) cytokines, or variants or fragments thereof.

Human Leukocyte Antigen (HLA) Proteins

In some embodiments, the invention provides an erythroid cell engineered to stimulate an immune cell, wherein the immune cell is an immune killer cell, comprising a plurality of exogenous stimulatory polypeptides sufficient to stimulate the immune killer cell, including one or more human leukocyte antigen proteins. Thus, the disclosure encompasses an HLA protein, including a full-length, fragment, homologue, variant or mutant of the HLA protein. The HLA gene family provides instructions for making a group of related proteins known as the human leukocyte antigen (HLA) complex. HLA is the human version of the major histocompatibility complex (MHC), a gene family that occurs in many species. In humans, the MHC complex consists of more than 200 genes located close together on chromosome 6. Genes in this complex are categorized into three basic groups: class I, class II, and class III. Humans have three main MHC class I genes, known as HLA-A, HLA-B, and HLA-C. The proteins produced from these genes are present on the surface of almost all cells. HLA genes have many possible variations, and some HLA genes have hundreds of identified versions (alleles), each of which is given a particular number (such as HLA-B27). Closely related alleles are categorized together; for example, at least 40 very similar alleles are subtypes of HLA-B27.

In some embodiments, the HLA protein is human leukocyte antigen (HLA)-A. In some embodiments, the HLA protein is human leukocyte antigen (HLA)-C. In some embodiments, the HLA protein is human leukocyte antigen (HLA)-E. In some embodiments, the HLA protein is human leukocyte antigen (HLA)-G.

In some embodiments, an erythroid cell engineered to stimulate an immune cell comprises one or more (e.g., 2, 3, 4, 5, or more) HLA proteins, or variants or fragments thereof.

MHC Class I Chain-Related Proteins (MIC)

In some embodiments, the disclosure encompasses an erythroid cell engineered to stimulate an immune cell, wherein the immune cell is an immune killer cell, comprising a plurality of exogenous stimulatory polypeptides sufficient to stimulate the immune killer cell, including one or more Major Histocompatibility complex (MHC) class I chain related (MIC) proteins. Thus, the disclosure encompasses a MIC protein, including a full-length, fragment, homologue, variant or mutant of the MIC protein. MIC proteins show homology with classical human leukocyte antigen (HLA) molecules, but they do not combine with beta2 microglobulin, do not bind peptide and are not expressed on normal circulating lymphocytes. MIC proteins engage the activating natural killer cell receptor NKG2D.

The UL16-binding proteins (ULBPs) are a novel family of MHC class I-related molecules (MICs) that were identified based on their ability to bind to the human cytomegalovirus (HCMV) glycoprotein UL16. UL16 also binds to a member of another family of MHC class I-like molecules, MICB. The ULBPs and MICs are ligands for NKG2D/DAP10, an activating receptor expressed by natural killer (NK) cells and other immune effector cells, and this interaction can be blocked by UL16. Engagement of NKG2D/DAP10 by ULBPs or MICs expressed on a target cell can overcome an inhibitory signal generated by NK-cell recognition of MHC class I molecules and trigger NK cytotoxicity. ULBPs elicit their effects on NK cells by activating the janus kinase 2, signal transducer and activator of transcription 5, extracellular-signal-regulated kinase mitogen-activated protein kinase and Akt/protein kinase B signal transduction pathways. Although ULBPs alone activate multiple signaling pathways and induce modest cytokine production, ULBPs synergize strongly with interleukin-12 for production of interferon-gamma by NK cells.

In some embodiments, the MIC protein is a MHC class I chain-related protein A (MICA). In some embodiments, the MIC protein is a MHC class I chain-related protein B (MICB). In some embodiments, the MIC protein is UL16 binding proteins (ULBP).

In some embodiments, an erythroid cell engineered to stimulate an immune cell comprises one or more (e.g., 2, 3, 4, 5, or more) MIC proteins, or variants or fragments thereof.

Immunoglobulin Superfamily (IgSF)

In some embodiments, the disclosure encompasses an erythroid cell engineered to stimulate an immune cell, wherein the immune cell is an immune killer cell, comprising a plurality of exogenous stimulatory polypeptides sufficient to stimulate the immune killer cell, including one or more IgS family proteins. Thus, the disclosure encompasses a member of the IgSF superfamily, including a full-length, fragment, homologue, variant or mutant of the IgSF superfamily member. The immunoglobulin superfamily (IgSF) is a class of proteins that are associated with the adhesion, binding and recognition processes of cells. Molecules are categorized as members of this superfamily based on shared structural features with immunoglobulins); they all possess a domain known as an immunoglobulin domain or fold. Members of the IgSF include cell surface antigen receptors, co-receptors and co-stimulatory molecules of the immune system, molecules involved in antigen presentation to lymphocytes, cell adhesion molecules, certain cytokine receptors and intracellular muscle proteins. Members of the IgSF can be classified as follows: antigen receptors (e.g. antibodies or immunoglobulins: IgA, IgD, IgE, IgG, IgM); antigen presenting molecules (e.g. MHC class I, MHC class II); co-receptors (e.g. CD4, CD8); co-stimulatory or inhibitory molecules (e.g. CD28, CD80, CD86); receptors on Natural killer cells (e.g. killer-cell immunoglobulin-like receptors (KIR)); receptors on leukocytes (e.g., leukocyte immunoglobulin-like receptors (LILR)); IGSF CAMs (e.g., NCAMs, ICAM-1); cytokine receptors; growth factor receptors; receptor tyrosine kinases/phosphatases; IgG binding receptors.

Poliovirus Receptor (PVR/CD155) is a transmembrane glycoprotein belonging to the immunoglobulin superfamily. PVR/CD155 mediates NK cell adhesion and triggers NK cell effector functions. PVR/CD155 binds two different NK cell receptors: CD96 and CD226. These interactions accumulate at the cell-cell contact site, leading to the formation of a mature immunological synapse between NK cell and target cell. This may trigger adhesion and secretion of lytic granules and IFN-gamma (IFNγ) and activate cytoxicity of activated NK cells, and may also promote NK cell-target cell modular exchange, and PVR transfer to the NK cell.

Poliovirus receptor-related 2 (PVRL2), also known as Nectin-2, is a single-pass type I membrane glycoprotein with two Ig-like C2-type domains and an Ig-like V-type domain. This protein is one of the plasma membrane components of adherens junctions.

CD48 antigen (Cluster of Differentiation 48), also known as B-lymphocyte activation marker (BLAST-1) or signaling lymphocytic activation molecule 2 (SLAMF2), is a protein that in humans is encoded by the CD48 gene. CD48 is a member of the CD2 subfamily of the IgSF, which includes SLAM (signaling lymphocyte activation molecules) proteins, such as CD84, CD150, CD229 and CD244. CD48 is found on the surface of lymphocytes and other immune cells, dendritic cells and endothelial cells, and participates in activation and differentiation pathways in these cells.

NK-T-B antigen (NTBA) is a surface molecule expressed on NK, T, and B cells. In human NK cells, NTBA has been shown to act primarily as a coreceptor since it could trigger cytolytic activity only in cells expressing high surface densities of natural cytotoxicity receptors (NCR). Molecular cloning revealed that NTBA is a member of the Ig superfamily characterized by structural features that allowed its assignment to the CD2 family.

In some embodiments, the IgSF protein is IgG. In some embodiments, the IgSF protein is PVR/CD155. In some embodiments, the IgSF protein is CD48. In some embodiments, the IgSF protein is Nectin2. In some embodiments, the IgSF protein is NK-T-B antigen.

In some embodiments, an erythroid cell engineered to stimulate an immune cell comprises one or more (e.g., 2, 3, 4, 5, or more) IgSF proteins, or variants or fragments thereof.

Heparan Sulfate/Heparan Sulfate Proteoglycan

In some embodiments, the invention provides an erythroid cell engineered to stimulate an immune cell, wherein the immune cell is an immune killer cell, comprising a plurality of exogenous stimulatory polypeptides sufficient to stimulate the immune killer cell, including one or more heparan sulfate/heparin sulfate proteoglycans. Heparan sulfate (HS) is a linear polysaccharide found in all animal tissues. It occurs as a proteoglycan (HSPG) in which two or three HS chains are attached in close proximity to cell surface or extracellular matrix proteins. Heparan sulfate proteoglycans (HSPGs) are glycoproteins ubiquitously distributed on the cell surface and in the extracellular matrix. Their heparan sulfate moieties often represent alternative attachment points for extracellular proteins that target specific receptors. Thus, HSPGs modulate ligand-receptor encounters and participate in numerous biological processes.

Molecular and cell-based studies indicate that heparan sulfate binds in vitro to several major molecules including L-selectin, chemokines, and integrins involved in lymphocyte homing. Most chemokines, including the secondary lymphoid chemokine CCL21 (also called SLC), which is indispensable for lymphocyte homing, bind in vitro to heparan sulfate or its highly sulfated analog heparin (Lortat-Jacob et al., Proc. Natl. Acad. Sci. USA. 2002; 99: 1229-1234). Heparan sulfate-bound chemokines are recognized by chemokine receptors such as CCR6 and CCR7, thereby activating integrins leading to lymphocyte extravasation (von Andrian and Mempel, Nat. Rev. Immunol. 2003; 3: 867-878, the entire contents of which are incorporated by reference herein). Multiple lines of evidence indicate that heparan sulfate functions in transcytosis, presentation, and gradient formation of chemokines to promote lymphocyte migration.

In some embodiments, an erythroid cell engineered to stimulate an immune cell comprises one or more (e.g., 2, 3, 4, 5, or more) HS polysaccharides, or variants or fragments thereof.

Natural Killer Cytotoxicity Triggering Receptor Ligands

In some embodiments, the disclosure encompasses an erythroid cell engineered to stimulate an immune cell, wherein the immune cell is an immune killer cell, comprising a plurality of exogenous stimulatory polypeptides sufficient to stimulate the immune killer cell, including one or more natural killer cytotoxicity triggering receptor ligands. NK cells are equipped with activating receptors, including several natural cytotoxicity receptors (i.e., NCR1, NCR2, and NCR3, best known as NKp46, NKp44, and NKp30, respectively), which are directly involved in the killing of transformed cells. NKp44 it is not expressed by resting NK cells but only by their activated counterparts. The expression of ligands for activating NK receptors is currently considered as an indicator of a pathological scenario.

In some embodiments, an erythroid cell engineered to stimulate an immune cell comprises one or more (e.g., 2, 3, 4, 5, or more) NK cytotoxicity triggering receptor ligands, or variants or fragments thereof.

In some embodiments, an erythroid cell engineered to stimulate an immune cell comprises an exogenous stimulatory polypeptide that is selected from the group consisting of IL-1, IL-2, IL-12, IL-15, IL-15/IL-15RA fusion, IL-18, IL-21, interferon alpha (IFNα), 4-1BBL, Poliovirus Receptor (PVR/CD155), CD48, human leukocyte antigen (HLA)-A, HLA-C, HLA-G, heparan sulfate (HS), HLA-E, CpG, Immunoglobulin G (IgG), UL16 binding proteins (ULBP), MHC class I chain-related proteins (MIC), B7-H6, NkP44L, Nectin2, NK-T-B antigen (NTBA), activation-induced C-type lectin (AICL) and insulin-like growth factor 1 (IGF-1). In some embodiments, the MIC protein is MHC class I chain-related protein A (MICA) or MHC class I chain-related protein B (MICB).

In some embodiments, an erythroid cell engineered to stimulate an immune cell comprises an exogenous stimulatory polypeptide comprising or consisting of an IL-12 polypeptide, or a fragment thereof. In some embodiments, an erythroid cell engineered to stimulate an immune cell comprises an exogenous stimulatory polypeptide comprising or consisting of a 4-1BBL polypeptide, or a fragment thereof. In some embodiments, an erythroid cell engineered to stimulate an immune cell comprises an exogenous stimulatory polypeptide comprising or consisting of an IL-15 polypeptide, or a fragment thereof. In some embodiments, an erythroid cell engineered to stimulate an immune cell comprises an exogenous stimulatory polypeptide comprising or consisting of an IL-15/IL-15RA fusion polypeptide, or a fragment thereof.

In some embodiments, the erythroid cell engineered to stimulate an immune cell comprises an exogenous stimulatory polypeptide that is selected from the group consisting of IL-15/IL-15RA fusion, MHC class I chain-related protein A (MICA) or MHC class I chain-related protein B (MICB), and insulin-like growth factor 1 (IGF-1).

In certain embodiments, the erythroid cell engineered to stimulate an immune cell comprises at least two exogenous polypeptides. In some embodiments, the first exogenous stimulatory polypeptide comprises or consists of IL-15/IL-15RA and the second exogenous stimulatory polypeptide comprises or consists of a polypeptide selected from the group consisting of IL-1, IL-2, IL-12, IL-18, IL-21, interferon alpha (IFNα), MHC class I chain-related protein A (MICA) or MHC class I chain-related protein B (MICB), Poliovirus Receptor (PVR/CD155) and CD48. In some embodiments, the first exogenous polypeptide is IL-15/IL-15RA and the second exogenous polypeptide is IL-1. In some embodiments, the first exogenous polypeptide is IL-15/IL-15RA and the second exogenous polypeptide is IL-2. In some embodiments, the first exogenous polypeptide is IL-15/IL-15RA and the second exogenous polypeptide is IL-12. In some embodiments, the first exogenous polypeptide is IL-15/IL-15RA and the second exogenous polypeptide is IL-18. In some embodiments, the first exogenous polypeptide is IL-15/IL-15RA and the second exogenous polypeptide is IL-21. In some embodiments, the first exogenous polypeptide is IL-15/IL-15RA and the second exogenous polypeptide is IFNα. In some embodiments, the first exogenous polypeptide is IL-15/IL-15RA and the second exogenous polypeptide is MICA. In some embodiments, the first exogenous polypeptide is IL-15/IL-15RA and the second exogenous polypeptide is MICB. In some embodiments, the first exogenous polypeptide is IL-15/IL-15RA and the second exogenous polypeptide is PVR. In some embodiments, the first exogenous polypeptide is IL-15/IL-15RA and the second exogenous polypeptide is CD48.

In certain embodiments, the first exogenous stimulatory polypeptide and the second exogenous stimulatory polypeptide are selected from the group consisting of 4-1BBL and IL-15/IL-15R, 4-1BBL and IL-12, and IL_12 and IL-15/IL-15RA. In some embodiments, the first exogenous polypeptide is 4-1BBL and the second exogenous polypeptide is IL-15/IL-15RA. In some embodiments, the first exogenous polypeptide is 4-1BBL and the second exogenous polypeptide is IL-12. In some embodiments, the first exogenous polypeptide is IL-12 and the second exogenous polypeptide is IL-15/IL-15RA.

In certain embodiments, the first exogenous stimulatory polypeptide and the second exogenous stimulatory polypeptide are selected from the group consisting of IL-18 and IL-12, and IL-18 and IL-21. In some embodiments, the first exogenous polypeptide is IL-18 and the second exogenous polypeptide is IL-12. In some embodiments, the first exogenous polypeptide is IL-18 and the second exogenous polypeptide is IL-21.

In certain embodiments, the erythroid cell engineered to stimulate an immune cell comprises at least three exogenous polypeptides. In some embodiments, the first exogenous stimulatory polypeptide is IL-12, the second exogenous polypeptide is IL-18 and the third exogenous stimulatory polypeptide is IL-15/IL-15RA fusion. In further embodiments, an erythroid cell engineered to stimulate an immune cell comprises a first exogenous stimulatory polypeptide that is IL-12, a second exogenous polypeptide that is IL-18 and a third exogenous stimulatory polypeptide that is IL-15/IL-15RA fusion, wherein the erythroid cell is capable of stimulating a memory-like NK cell. In some embodiments, the first exogenous stimulatory polypeptide is IL-12, the second exogenous polypeptide is IL-18 and the third exogenous stimulatory polypeptide is IL-15. In further embodiments, an erythroid cell engineered to stimulate an immune cell comprises a first exogenous stimulatory polypeptide that is IL-12, a second exogenous polypeptide that is IL-18 and a third exogenous stimulatory polypeptide that is IL-15, wherein the erythroid cell is capable of stimulating a memory-like NK cell.

The disclosure provides, in another aspect, an engineered erythroid cell comprising at least one exogenous stimulatory polypeptide selected from the group consisting of MHC class I chain-related protein A (MICA), MHC class I chain-related protein B (MICB) and insulin-like growth factor 1 (IGF-1). In some embodiments, the engineered erythroid cell comprises at least one exogenous stimulatory polypeptide selected from the group consisting of MICA, MICB and IGF-1, and further comprises an exogenous stimulatory polypeptide selected from the group consisting of: IL-1, IL-2, IL-12, IL-15, IL-15/IL-15RA fusion, IL-18, IL-21, interferon alpha (IFNα), 4-1BBL, Poliovirus Receptor (PVR/CD155), CD48, HLA-A, HLA-C, HLA-G, heparan sulfate (HS), HLA-E, CpG, IgG, UL16 binding proteins (ULBP), MHC class I chain-related (MIC), B7-H6, NkP44L, Nectin2, NK-T-B antigen (NTBA), activation-induced C-type lectin (AICL) and insulin-like growth factor 1 (IGF-1).

In certain embodiments, the erythroid cell engineered to stimulate an immune cell comprises at least one exogenous stimulatory polypeptide, wherein the exogenous stimulatory polypeptide is IL-12. In some embodiments, the erythroid cell engineered to stimulate an immune cell comprises a first exogenous stimulatory polypeptide, wherein the first exogenous stimulatory polypeptide is IL-12, and a second exogenous stimulatory polypeptide. In some embodiments, the first exogenous stimulatory polypeptide is IL-12 and the second exogenous stimulatory polypeptide is an IL-15 polypeptide. In some embodiments, the first exogenous stimulatory polypeptide is IL-12 and the second exogenous stimulatory polypeptide is IL-15/IL-15RA. In some embodiments, the first exogenous stimulatory polypeptide is IL-12 and the second exogenous stimulatory polypeptide is 4-1BBL. In some embodiments, the IL-12 is an IL-12 p40/IL-12 p35 fusion polypeptide.

In embodiments, an engineered erythroid cell described herein comprises three or more, e.g., at least 4, 5, 6, 7, 8, 9, 10, 11, 12, 13, 14, 15, 16, 17, 18, 19, 20, 50, 100, 200, 500, or 1000 exogenous stimulatory polypeptides. In embodiments, a population of engineered erythroid cells described herein comprises three or more, e.g., at least 4, 5, 6, 7, 8, 9, 10, 11, 12, 13, 14, 15, 16, 17, 18, 19, 20, 50, 100, 200, 500, 1000, 2000, or 5000 exogenous stimulatory polypeptides, e.g., wherein different engineered erythroid cells in the population comprise different exogenous stimulatory polypeptides or wherein different engineered erythroid cells in the population comprise different pluralities of exogenous stimulatory polypeptides. In some embodiments, the engineered erythroid cell is an enucleated cell. In some embodiments, the engineered erythroid cell is a nucleated cell.

In some embodiments, the at least two exogenous stimulatory polypeptides are present as a fusion polypeptide. In another embodiment, the at least three exogenous stimulatory polypeptides are present as a fusion polypeptide.

Anchor/Transmembrane Domains

In certain embodiments, the exogenous stimulatory polypeptide is not released from the erythroid cell. In some embodiments, the exogenous stimulatory polypeptides are presented at the surface of the genetically engineered erythroid cell, i.e., the exogenous stimulatory polypeptide is attached to the erythroid cell membrane. In some embodiment, the exogenous stimulatory polypeptides further comprise a transmembrane domain that anchors the polypeptide to the erythroid cell membrane. In certain embodiments, the polypeptide sequence that anchors the exogenous stimulatory polypeptide to the erythroid cell membrane (e.g., a transmembrane domain) is heterologous to a polypeptide present in the exogenous stimulatory polypeptide. For example, in some embodiments, the polypeptide sequence that anchors the exogenous stimulatory polypeptide to the erythroid cell membrane is heterologous to the IL-15 polypeptide and/or the IL-15RA polypeptide, the 4-1BBL polypeptide or the IL-12 polypeptide.

In some embodiments, the transmembrane domain comprises or consists of a transmembrane domain of a type 1 membrane protein. In some embodiments, the type 1 membrane protein is selected from the group consisting of Glycophorin A (GPA); glycophorin B (GPB); Basigin (also known as CD147); CD44; CD58 (also known as LFA3); Intercellular Adhesion Molecule 4 (ICAM4); Basal Cell Adhesion Molecule (BCAM); CR1; CD99; Erythroblast Membrane Associated Protein (ERMAP); junctional adhesion molecule A (JAM-A); neuroplastin (NPTN); AMIGO2; and DS Cell Adhesion Molecule Like 1 (DSCAML1). In some embodiments, the transmembrane domain comprises or consists of a transmembrane domain of a type 2 membrane protein. In some embodiments, the type 2 membrane protein is selected from the group consisting of small integral membrane protein 1 (SMIM1), transferrin receptor (CD71); Fas ligand (FasL) transmembrane; and Kell. In some embodiments, the polypeptide sequence that anchors the exogenous stimulatory polypeptide to the erythroid cell membrane comprises, consists of, or is derived from (e.g., a fragment of) a GPI-linked membrane protein. In some embodiments, the GPI-linked membrane protein is selected from the group consisting of CD59; CD55; and Semaphorin 7A (SEMA7A).

In particular embodiments, the transmembrane domain comprises glycophorin A (GPA) or a transmembrane portion thereof. Without being bound by theory, in certain embodiments, GPA is preferred because it has a cytoplasmic domain that interacts with the reticulocyte cytoskeleton that has a role in retaining the GPA as the cell differentiates and matures. In some embodiments, the transmembrane domain comprises small integral membrane protein 1 (SMIM1) or a transmembrane portion thereof. In some embodiments, the anchor is selected from an amino acid sequence listed in Table 2.

TABLE 2

Anchor Sequences

| SEQ ID NO: | Sequence name | Sequence description | Amino acid sequence |
|---|---|---|---|
| 66 | GPA | Full length GPA | MYGKIIFVLLLSAIVSISALSTTEVAMHTSTSSSVTKSYISSQTNDTHKRDTYAATPRAHEVSEISVRTVYPPEEETGERVQLAHHFSEPEITLIIFGVMAGVIGTILLISYGIRRLIKKSPSDVKPLPSPDTDVPLSSVEIENPETSDQ |
| 25 | GPA | Fragment of GPA comprising a transmembrane domain | LSTTEVAMHTSTSSSVTKSYISSQTNDTHKRDTYAATPRAHEVSEISVRTVYPPEEETGERVQLAHHFSEPEITLIIFGVMAGVIGTILLISYGIRRLIKKSPSDVKPLPSPDTDVPLSSVEIENPETSDQ |
| 49 | SMIM1 | SMIM1 | MQPQESHVHYSRWEDGSRDGVSLGAVSSTEEASRCRRISQRLCTGKLGIAMKVLGGVALFWIIFILGYLTGYYVHKCK |

In some embodiments, one or more of the exogenous stimulatory polypeptide is a fusion protein, e.g., is a fusion with an endogenous red blood cell protein or fragment thereof, e.g., a transmembrane protein, e.g., GPA or a transmembrane fragment thereof. In some embodiments, one or more of the exogenous stimulatory polypeptide is fused with a domain that promotes dimerization or multimerization, e.g., with a second fusion exogenous stimulatory polypeptide, which optionally comprises a dimerization domain. In some embodiments, the dimerization domain comprises a portion of an antibody molecule, e.g., an Fc domain or CH3 domain. In some embodiments, the first and second dimerization domains comprise knob-in-hole mutations (e.g., a T366Y knob and a Y407T hole) to promote heterodimerization.

Linkers

The exogenous stimulatory polypeptides of the invention may comprise one or more linkers. For example, a linker may be disposed between two polypeptide sequences of the exogenous stimulatory polypeptide (e.g., between a cytokine polypeptide sequence and a transmembrane domain sequence, between two subunit sequences of an exogenous stimulatory polypeptide (e.g., between the p40 and p35 subunits of IL-12), or between two stimulatory polypeptides (e.g., IL-15 and IL-15RA)).

In some embodiments, the linker comprises or consists of 1, 2, 3, 4, 5, 6, 7, 8, 9, 10, 11, 12, 13, 14, 15, 16, 17, 18, 19, 20 or more amino acids in length. In some embodiments, the linker comprises or consists of between about 5 and about 25 amino acids in length, between about 5 and about 20 amino acids in length, between about 10 and about 25 amino acids in length, or between about 10 and about 20 amino acids in length. In some embodiments, the linker useful in the invention comprises or consists of 10, 11, 12, 13, 14, 15, 16, 17, 18, 19, or 20 amino acids in length. In a preferred embodiment, the linker is non-immunogenic.

In some embodiments, the linker is selected from an amino acid sequence presented in Table 3.

TABLE 3

Linker Sequences

| SEQ ID NO. | Sequence Description | Amino Acid Sequence |
|---|---|---|
| 11 | G4S linker | GGGGS |
| 12 | $(G4S)_3$ linker | GGGGSGGGGSGGGGS |
| 23 | Linker-HA-linker | GGSGGSGGYPYDVPDYAGGGSGGGS |

TABLE 3-continued

| Linker Sequences | | |
|---|---|---|
| SEQ ID NO. | Sequence Description | Amino Acid Sequence |
| 33 | Linker | GGSGGSGGGGGSGGGSGGGSGGGS |
| 39 | Linker | GGSGGSGGGPEDEPGSGSGGGSGGGS |
| 51 | Linker | GGSGGSGGGGGSGGGSGGGSGGGS |
| 67 | Linker | GSGSGSGSGSEDEDEDEDGSGSGSGSGS |
| 68 | Linker | GGGGSGGGGSGGGGSGGGGS |
| 69 | Linker | GSGSGSGSEDGSGSGSGS |
| 70 | Linker | GSGSGSGSGSGSGSGS |
| 71 | Linker | GCGGSGGGGSGGGGS |
| 33 | Linker | GGSGGSGGGGGSGGGSGGGSGGGS |
| 72 | Linker | SGRGGGGSGGGGSGGGGSGGGGSSPA |
| 73 | Linker | GGGGSGGGGSGGGGSGGGGSGGGG |
| 74 | Snorkel linker | SGRGASSGSSGSGSQKKPRYEIRWKVVVI SAILALVVLTVISLIILIMLWGSGMQSPA |

In some embodiments, the linker comprises the amino acid sequence $(GGGGS)_n$ (SEQ ID NO: 75), wherein n is 1, 2, 3, 4, 5, 6, 7, 8, 9 or 10. In some embodiments, the linker consists of the $(GGGGS)_n$ linker (SEQ ID NO: 75), wherein n is 1, 2, 3, 4, 5, 6, 7, 8, 9 or 10. In some embodiments, the linker comprises the amino acid sequence GGGGSGGGGSGGGGS (SEQ ID NO: 12). In some embodiments, the linker consists of the amino acid sequence of SEQ ID NO: 12. In some embodiments, the linker comprises the amino acid sequence SEQ ID NO: 23. In some embodiments, the linker consists of the amino acid sequence of SEQ ID NO: 23. In some embodiments, the linker comprises the amino acid sequence SEQ ID NO: 33. In some embodiments, the linker consists of the amino acid sequence of SEQ ID NO: 33. In some embodiments, the linker comprises the amino acid sequence SEQ ID NO: 39. In some embodiments, the linker consists of the amino acid sequence of SEQ ID NO: 39. In some embodiments, the linker comprises the amino acid sequence SEQ ID NO: 51. In some embodiments, the linker consists of the amino acid sequence of SEQ ID NO: 51.

Other suitable linkers, which are known to one skilled in the art, may be used, e.g., to link an exogenous stimulatory polypeptide to a transmembrane domain, to link two exogenous stimulatory polypeptides (e.g., IL-15 and IL-15RA) or to link subunits of an exogenous stimulatory polypeptide (e.g., p30 and p40 of IL12).

Leader Sequences

In some embodiments, the exogenous stimulatory polypeptide comprises a leader (signal) sequence. In some embodiments, the exogenous stimulatory polypeptide is a fusion polypeptide comprising a leader sequence. In some embodiments, the leader sequence is selected from the sequences set forth in Table 4.

TABLE 4

| Leader Sequences | | |
|---|---|---|
| SEQ ID NO. | Sequence Description | Amino Acid Sequence |
| 21 | GPA signal peptide | MYGKIIFVLLLSEIVSISA |
| 76 | Ig heavy chain V region 3 signal sequence | MGWSCIILFLVATATGVHS |
| 77 | light chain leader | MRVPAQLLGLLLLWLPGARC |

Engineered Erythroid Cells Comprising IL-15/IL-15RA

The disclosure provides, in another aspect, an engineered erythroid cell comprising a first exogenous stimulatory polypeptide, wherein the first exogenous stimulatory polypeptide comprises an interleukin-15 (IL-15) polypeptide, or a fragment thereof, and an extracellular portion of an interleukin-15 receptor alpha (IL-15RA) polypeptide, or a fragment thereof. In some embodiments, the engineered erythroid cell is an enucleated cell. In some embodiments, the engineered erythroid cell is a nucleated cell.

In some embodiments, the IL-15 polypeptide and the extracellular portion of an IL-15RA polypeptide are present as a complex. In another embodiment, the IL-15 polypeptide and the extracellular portion of an IL-15RA polypeptide are present as a fusion polypeptide. In some embodiments, the IL-15 polypeptide is linked to the extracellular portion of the IL-15RA polypeptide by a linker.

In certain embodiments, the invention provides an engineered erythroid cell comprising an exogenous stimulatory polypeptide comprising an interleukin-15 (IL-15) polypeptide, or a fragment thereof (e.g., an IL-15 receptor binding fragment). In some embodiments, the IL-15 polypeptide comprises the immature form of wild-type human IL-15 which includes the signal peptide (underlined):

(SEQ ID NO: 3)

MRISKPHLRSISIQCYLCLLLNSHFLTEAGIHVFILGCFSAGLPKTEANW

VNVISDLKKIEDLIQSMHIDATLYTESDVHPSCKVTAMKCFLLELQVISL

ESGDASIHDTVENLIILANNSLSSNGNVTESGCKECEELEEKNIKEFLQS

FVHIVQMFINTS.

In some embodiments, the IL-15 polypeptide comprises a variant of the immature form of wild-type human IL-15 having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 3. In a particular embodiment, the IL-15 polypeptide consists of the amino acid sequence of SEQ ID NO: 3.

In some embodiments, the IL-15 polypeptide comprises the mature form of wild-type human IL-15:

(SEQ ID NO: 4)
NWVNVISDLKKIEDLIQSMHIDATLYTESDVHPSCKVTAMKCFLLELQVI
SLESGDASIHDTVENLIILANNSLSSNGNVTESGCKECEELEEKNIKEFL
QSFVHIVQMFINTS.

In some embodiments, the IL-15 polypeptide comprises a variant of the mature form of wild-type human IL-15 having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 4. In a particular embodiment, the IL-15 polypeptide consists of the amino acid sequence of SEQ ID NO: 4.

In some embodiments, the fragment of the IL-15 polypeptide comprises at least 10, 20, 30, 40, 50, 60, 70, 80, 90, 100, 110, 120, 130, 140, 150 or 160 amino acids. In some embodiments, the fragment of the IL-15 polypeptide comprises fewer than 20, 30, 40, 50, 60, 70, 80, 90, 100, 110, 120, 130, 140, 150 or 160 amino acids. In some embodiments, fragments or variants of the IL-15 polypeptide retain at least 50%, 55%, 60%, 65%, 70%, 75%, 80%, 85%, 90%, 95%, 98% or 99% of the function of wild-type human IL-15 polypeptide to bind IL-15RA polypeptide, as measured by assays well known in the art, e.g., ELISA, Biacore, or co-immunoprecipitation. In some embodiments, fragments or variants of the IL-15 polypeptide retain at least 50%, 55%, 60%, 65%, 70%, 75%, 80%, 85%, 90%, 95%, 98% or 99% of the function of wild-type human IL-15 polypeptide to induce IL-15-mediated signal transduction, as measured by assays well-known in the art, e.g., electromobility shift assays, ELISAs and other immunoassays.

In some embodiments, the exogenous stimulatory polypeptide comprises an interleukin-15 receptor α (IL-15RA) polypeptide, or a fragment thereof. In some embodiments, the IL-15RA comprises the immature form of wild-type human IL-15RA which includes the signal peptide (underlined):

(SEQ ID NO: 5)
MAPRRARGCRTLGLPALLLLLLLRPPATRGITCPPPMSVEHADIWVKSYS
LYSRERYICNSGFKRKAGTSSLTECVLNKATNVAHWTTPSLKCIRDPALV
HQRPAPPSTVTTAGVTPQPESLSPSGKEPAASSPSSNNTAATTAAIVPGS
QLMPSKSPSTGTTEISSHESSHGTPSQTTAKNWELTASASHQPPGVYPQG
HSDTTVAISTSTVLLCGLSAVSLLACYLKSRQTPPLASVEMEAMEALPVT
WGTSSRDEDLENCSHHL.

In some embodiments, the IL-15RA polypeptide comprises a variant of the immature form of wild-type human IL-15RA having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 5. In a particular embodiment, the IL-15RA polypeptide consists of the amino acid sequence of SEQ ID NO: 5.

In some embodiments, the IL-15RA polypeptide comprises the mature form of wild-type human IL-15RA:

(SEQ ID NO: 6)
ITCPPPMSVEHADIWVKSYSLYSRERYICNSGFKRKAGTSSLTECVLNKA
TNVAHWTTPSLKCIRDPALVHQRPAPPSTVTTAGVTPQPESLSPSGKEPA
ASSPSSNNTAATTAAIVPGSQLMPSKSPSTGTTEISSHESSHGTPSQTTA
KNWELTASASHQPPGVYPQGHSDTTVAISTSTVLLCGLSAVSLLACYLKS
RQTPPLASVEMEAMEALPVTWGTSSRDEDLENCSHHL.

In some embodiments, the IL-15RA polypeptide comprises a variant of the mature form of wild-type human IL-15Ra having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 6. In a particular embodiment, the IL-15Ra polypeptide consists of the amino acid sequence of SEQ ID NO: 6.

In some embodiments, the IL-15Ra polypeptide comprises an extracellular portion of an IL-15Ra polypeptide. For example, the IL-15Ra polypeptide may lack the transmembrane domain of wild-type IL-15Ra, and optionally, the intracellular domain of wild-type IL-15Ra. In some embodiments, IL-15Ra polypeptide comprises the immature form of an extracellular wild-type human IL-15Ra which includes the signal peptide (underlined):

(SEQ ID NO: 7)
MAPRRARGCRTLGLPALLLLLLLRPPATRGITCPPPMSVEHADIWVKSYS
LYSRERYICNSGFKRKAGTSSLTECVLNKATNVAHWTTPSLKCIRDPALV
HQRPAPPSTVTTAGVTPQPESLSPSGKEPAASSPSSNNTAATTAAIVPGS
QLMPSKSPSTGTTEISSHESSHGTPSQTTAKNWELTASASHQPPGVYPQG
HSDTT.

In some embodiments, the IL-15Ra polypeptide comprises a variant of the immature form of an extracellular wild-type human IL-15Ra having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 7. In a particular embodiment, the IL-15Ra polypeptide consists of the amino acid sequence of SEQ ID NO: 7.

In some embodiments, the IL-15Ra polypeptide comprises the mature form of an extracellular wild-type human IL-15Ra:

(SEQ ID NO: 8)
ITCPPPMSVEHADIWVKSYSLYSRERYICNSGFKRKAGTSSLTECVLNKA
TNVAHWTTPSLKCIRDPALVHQRPAPPSTVTTAGVTPQPESLSPSGKEPA
ASSPSSNNTAATTAAIVPGSQLMPSKSPSTGTTEISSHESSHGTPSQTTA
KNWELTASASHQPPGVYPQGHSDTT.

In some embodiments, the IL-15Ra polypeptide comprises a variant of the mature form of an extracellular wild-type human IL-15Ra having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 8. In a particular embodiment, the IL-15RA polypeptide consists of the amino acid sequence of SEQ ID NO: 8.

IL-15 specifically binds to the IL-15RA polypeptide with high affinity via the "sushi domain" in exon 2 of the extracellular domain of the receptor (Wei et al., J Immunol. 2001; 167:277-282). In some embodiments, the IL-15Ra polypeptide comprises the sushi domain of wild-type human IL-15RA:

(SEQ ID NO: 9)
ITCPPPMSVEHADIWVKSYSLYSRERYICNSGFKRKAGTSSLTECVLNKA
TNVAHWTTPSLKCIR.

In some embodiments, the IL-15RA polypeptide comprises a variant of the sushi domain of wild-type human IL-15RA having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 8. In a particular embodiment, the IL-15Ra polypeptide consists of the amino acid sequence of SEQ ID NO: 8.

In some embodiments, the IL-15RA polypeptide comprises the sushi domain of wild-type human IL-15Ra or a variant thereof and at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 60, 70, 80, 90 or 100 additional amino acids of human IL-15RA. In a particular embodiment, the IL-15RA polypeptide comprises the sushi domain of wild-type human IL-15RA and 13 additional amino acids of human IL-15RA:

(SEQ ID NO: 10)
ITCPPPMSVEHADIWVKSYSLYSRERYICNSGFKRKAGTSSLTECVLNKA
TNVAHWTTPSLKCIRDPALVHQRPAPPS.

In some embodiments, the IL-15RA polypeptide comprises an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 10. In a particular embodiment, the IL-15RA polypeptide consists of the amino acid sequence of SEQ ID NO: 10.

In some embodiments, the fragment of the IL-15RA polypeptide comprises at least 10, 20, 30, 40, 50, 60, 70, 80, 90, 100, 110, 120, 130, 140, 150, 160, 170, 180, 190 or 200 amino acids. In some embodiments, the fragment of the IL-15RA polypeptide comprises at least 10, 20, 30, 40, 50, 60, 70, 80, 90, 100, 110, 120, 130, 140, 150, 160, 170, 180, 190 or 200 amino acids, and comprises the sushi domain. In some embodiments, the IL-15RA fragment or variant retains at least 50%, 55%, 60%, 65%, 70%, 75%, 80%, 85%, 90%, 95%, 98% or 99% of the function of a wildtype human IL-15RA polypeptide to bind an IL-15 polypeptide, as measured by assays well known in the art, e.g., ELISA, Biacore, co-immunoprecipitation. In another preferred embodiment, IL-15RA variants or fragments retain at least 50%, 55%, 60%, 65%, 70%, 75%, 80%, 85%, 90%, 95%, 98% or 99% of the function of a wild-type human IL-15RA polypeptide to induce IL-15-mediated signal transduction, as measured by assays well-known in the art, e.g., electromobility shift assays, ELISAs and other immunoassays.

In some embodiments, the exogenous stimulatory polypeptide comprises an IL-15 polypeptide or a fragment thereof and an IL-15RA polypeptide or a fragment thereof (e.g., an IL-15 binding fragment). Any of the IL-15 polypeptides described herein may be combined with any of the IL-15RA polypeptides described herein to form the exogenous stimulatory polypeptide. In some embodiments, the IL-15 polypeptide and the IL-15RA polypeptide are present as a complex. The components of an IL-15/IL-15RA complex may be directly fused, using either non-covalent bonds or covalent bonds (e.g., by combining amino acid sequences via peptide bonds). In a particular embodiment, the IL-15 polypeptide and the IL-15RA polypeptide are present as a fusion polypeptide.

In some embodiments, the exogenous stimulatory polypeptide comprises an IL-15RA polypeptide and a signal peptide. In some embodiments, the exogenous stimulatory polypeptide is a fusion polypeptide comprising an IL-15RA polypeptide and a signal peptide. In some embodiments, the exogenous stimulatory polypeptide comprises a signal peptide comprising or consisting of an amino acid sequence set forth in Table 4. In some embodiments, the exogenous stimulatory polypeptide comprises a signal peptide comprising or consisting of a GPA signal peptide. In some embodiments, the exogenous stimulatory polypeptide comprises a signal peptide comprising or consisting of the amino acid sequence of SEQ ID NO: 21. In some embodiments, the exogenous stimulatory polypeptide comprises a leader sequence comprising or consisting of the amino acid sequence of SEQ ID NO: 21, an IL-15 polypeptide, and an IL-15RA polypeptide. In some embodiments, the exogenous stimulatory polypeptide comprises a leader sequence comprising or consisting of the amino acid sequence of SEQ ID NO: 21, a mature human IL-15 polypeptide comprising or consisting of the amino acid sequence of SEQ ID NO: 4, and an IL-15RA polypeptide comprising or consisting of the amino acid sequence of SEQ ID NO: 8. In some embodiments, the mature human IL-15 polypeptide and the IL-15RA polypeptide are connected by a flexible linker comprising or consisting of the amino acid sequence of SEQ ID NO: 12.

The IL-15 and IL-15RA polypeptides may be combined using one or more linkers. Any of the linkers provided herein may be used. In some embodiments, the linker is a peptide that is 1, 2, 3, 4, 5, 6, 7, 8, 9, 10, 11, 12, 13, 14, 15, 16, 17, 18, 19, 20 or more amino acids long. In a specific embodiment, the linker is long enough to preserve the ability of IL-15 to bind to the IL-15RA. In other embodiments, the linker is long enough to preserve the ability of the IL-15/IL-15RA complex to bind to the βγ IL-15 receptor complex and to act as an agonist to mediate IL-15 signal transduction. In some embodiments, the linker comprises or consists of an amino acid sequence listed in Table 3. In some embodiments, the linker comprises the amino acid sequence $(GGGGS)_n$ (SEQ ID NO: 75), wherein n is 1, 2, 3, 4, 5, 6, 7, 8, 9 or 10. In some embodiments, the linker consists of the $(GGGGS)_n$ linker (SEQ ID NO: 75), wherein n is 1, 2, 3, 4, 5, 6, 7, 8, 9 or 10. In a particular embodiment, the linker comprises the amino acid sequence GGGGSGGGGSGGGGS (SEQ ID NO: 12). In a further particular embodiment, the linker consists of the amino acid sequence of SEQ ID NO: 12.

Other suitable linkers, which are known to one skilled in the art, may be used to link the IL-15 and IL-15RA polypeptides. In some embodiments, the linker useful in the invention is between 5 and 25 amino acids in length, 5-20 amino acids in length, 10-25 amino acids in length, or 10-20 amino acids in length. In some embodiments, the linker useful in the invention is 10, 11, 12, 13, 14, 15, 16, 17, 18, 19, or 20 amino acids in length. In a preferred embodiment, the linker is non-immunogenic.

In some embodiments, the exogenous stimulatory polypeptide comprises an IL-15 polypeptide and an extracellular region of the IL-15Ra polypeptide. For example, in some embodiments, the exogenous stimulatory polypeptide comprises the amino acid sequence of SEQ ID NO: 1, or an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 1. In a particular embodiment, the exogenous stimulatory polypeptide consists of the amino acid sequence of SEQ ID NO: 1.

In some embodiments, the exogenous stimulatory polypeptide comprises an IL-15 polypeptide and the sushi domain of the IL-15RA polypeptide. For example, in some embodiments, the exogenous stimulatory polypeptide comprises the amino acid sequence of SEQ ID NO: 2, or an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 2. In a particular embodiment, the exogenous stimulatory polypeptide consists of the amino acid sequence of SEQ ID NO: 2.

In certain embodiments, the IL-15 polypeptide, IL-15RA polypeptide, or IL-15/IL-15RA complex or fusion polypeptide are not released from the erythroid cell. For example, in some embodiments the IL-15 polypeptide, IL-15Ra polypeptide, or IL-15/IL-15RA complex or fusion polypeptide are attached to the erythroid cell membrane. In some embodiments, the exogenous stimulatory polypeptide further comprises a polypeptide sequence (e.g. a transmembrane region) that anchors the polypeptide to the erythroid cell membrane (referred to herein as an anchor or transmembrane domain). In certain embodiments, the polypeptide sequence that anchors the polypeptide to the erythroid cell membrane is heterologous to another polypeptide in the exogenous stimulatory polypeptide. For example, in some embodiments, the polypeptide sequence that anchors the polypeptide to the erythroid cell membrane is heterologous to the IL-15 polypeptide and/or the IL-15RA polypeptide. In certain embodiments, the polypeptide sequence that anchors the polypeptide to the erythroid cell membrane is a GPA sequence.

Other polypeptides useful for anchoring the exogenous polypeptide to the erythroid cell membrane are known to the skilled person and are contemplated for inclusion in the exogenous polypeptides comprising IL-15, IL-15RA, or IL-15/IL-15RA fusion. Non-limiting examples include small integral membrane protein 1 (SMIM1), transferrin receptor, Fas ligand (FasL), Kell and Band 3. Band 3 anion transport protein, truncated transferrin receptor and Fas Ligand (FasL) transmembrane domain.

In some embodiments, the anchor or transmembrane domain comprises or consists of a type 1 membrane protein or a transmembrane portion thereof. For example, in some embodiments, the anchor or transmembrane domain comprises a type 1 membrane protein or a transmembrane portion thereof selected from the group consisting of Glycophorin A (GPA); glycophorin B (GPB); Basigin (also known as CD147); CD44; CD58 (also known as LFA3); Intercellular Adhesion Molecule 4 (ICAM4); Basal Cell Adhesion Molecule (BCAM); CR1; CD99; Erythroblast Membrane Associated Protein (ERMAP); junctional adhesion molecule A (JAM-A); neuroplastin (NPTN); AMIGO2; and DS Cell Adhesion Molecule Like 1 (DSCAML1). In some embodiments, the anchor or transmembrane domain comprises or consists of a type 2 membrane protein or a transmembrane portion thereof. For example in some embodiments, the anchor or transmembrane domain comprises a type 2 membrane protein or a transmembrane portion thereof selected from the group consisting of small integral membrane protein 1 (SMIM1), transferrin receptor (CD71); Fas ligand (FasL) transmembrane; and Kell. In some embodiments, the anchor is a GPI-linked membrane protein. In some embodiments, the GPI-linked membrane protein anchor is selected from the group consisting of CD59; CD55; and Semaphorin 7A (SEMA7A).

In some embodiments, the anchor or transmembrane domain comprises or consists of small integral membrane protein 1 (SMIM1) or a transmembrane portion thereof. In some embodiments, the anchor or transmembrane domain comprises or consists of glycophorin A (GPA), or a fragment thereof (e.g., a transmembrane portion thereof). In some embodiments, the anchor or transmembrane domain comprises or consists of an amino acid sequence provided in Table 2.

In some embodiments, a linker is disposed between the anchor or transmembrane domain and an IL-15 polypeptide, an IL-15RA polypeptide, or an IL-15/IL-15RA polypeptide. Suitable linkers include, without limitation, any linker amino acid sequence provided in Table 3. In some embodiments, the linker between the anchor or transmembrane domain, e.g., GPA, and an IL-15 polypeptide, an IL-15RA polypeptide, or an IL-15/IL-15RA polypeptide comprises or consists of an HA linker. In some embodiments, the linker comprises or consists of the amino acid sequence of SEQ ID NO: 33.

In some embodiments, the exogenous stimulatory polypeptide comprises an anchor comprising the amino acid sequence of SEQ ID NO: 25, an interleukin-15 (IL-15) polypeptide, and an extracellular portion of an interleukin-15 receptor alpha (IL-15RA) polypeptide. In some embodiments, the exogenous stimulatory polypeptide comprises an anchor comprising or consisting of the amino acid sequence of SEQ ID NO: 25, mature human IL-15 comprising or consisting of the amino acid sequence of SEQ ID NO: 4, and mature human extracellular IL-15RA comprising or consisting of the amino acid sequence of SEQ ID NO: 8, whereby the mature human IL-15 amino acid sequence and the mature human extracellular IL-15 RA amino acid sequence are connected by a flexible linker comprising or consisting of the amino acid sequence of SEQ ID NO: 12.

In some embodiments, the exogenous stimulatory polypeptide comprises: a signal peptide (e.g., a GPA signal peptide) comprising or consisting of the amino acid sequence of SEQ ID NO: 21, a mature human IL-15 comprising or consisting of SEQ ID NO: 4, a flexible linker (e.g., connecting the mature human IL-15 and the mature human extracellular IL-15RA) comprising or consisting of the amino acid sequence of SEQ ID NO: 12, a mature human extracellular IL-15RA comprising or consisting of the amino acid sequence of SEQ ID NO: 8, a linker comprising or consisting of the amino acid sequence of SEQ ID NO: 33, and an anchor comprising or consisting of an amino acid sequence of SEQ ID NO: 25. In some embodiments, the exogenous stimulatory polypeptide comprises (e.g., from N-terminus to C-terminus): a mature human IL-15 comprising or consisting of SEQ ID NO: 4, a flexible linker (e.g., connecting the mature human IL-15 and the mature human extracellular IL-15RA) comprising or consisting of the amino acid sequence of SEQ ID NO: 12, a mature human extracellular IL-15RA comprising or consisting of the amino acid sequence of SEQ ID NO: 8, a linker comprising or consisting of the amino acid sequence of SEQ ID NO: 33, and an anchor comprising or consisting of an amino acid sequence of SEQ ID NO: 25. In some embodiments, the exogenous stimulatory polypeptide comprises or consists of SEQ ID NO: 37.

In a particular embodiment, the exogenous stimulatory polypeptide comprises the amino acid sequence of SEQ ID NO: 27 or an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 27. In some embodiments, the exogenous stimulatory polypeptide consists of the amino acid sequence of SEQ ID NO: 27.

In a particular embodiment, the exogenous stimulatory polypeptide comprises the amino acid sequence of SEQ ID NO: 29 or an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 29. In some embodiments, the exogenous stimulatory polypeptide consists of the amino acid sequence of SEQ ID NO: 29.

In a particular embodiment, the exogenous stimulatory polypeptide comprises the amino acid sequence of SEQ ID NO: 31 or an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 31. In some embodiments, the exogenous stimulatory polypeptide consists of the amino acid sequence of SEQ ID NO: 31.

In a particular embodiment, the exogenous stimulatory polypeptide comprises the amino acid sequence of SEQ ID NO: 35 or an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 35. In some embodiments, the exogenous stimulatory polypeptide consists of the amino acid sequence of SEQ ID NO: 35.

In a particular embodiment, the exogenous stimulatory polypeptide comprises the amino acid sequence of SEQ ID NO: 37 or an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 37. In some embodiments, the exogenous stimulatory polypeptide consists of the amino acid sequence of SEQ ID NO: 37.

IL-15/IL-15RA and 4-1BBL

The engineered erythroid cell may comprise a first exogenous stimulatory polypeptide comprising an IL-15 polypeptide and/or an IL-15RA polypeptide as described herein and one or more additional exogenous stimulatory polypeptides. For example, the engineered erythroid cell may further comprise a second exogenous stimulatory polypeptide comprising a 4-1BBL (4-1BB ligand) polypeptide. Thus, the invention also provides an engineered erythroid cell comprising a first exogenous stimulatory polypeptide, wherein the first exogenous stimulatory polypeptide comprises an interleukin-15 (IL-15) polypeptide, or a fragment thereof (e.g., an IL-15 receptor-binding fragment), and an extracellular portion of an interleukin-15 receptor alpha (IL-15RA) polypeptide, or a fragment thereof, and a second exogenous stimulatory polypeptide, wherein the second exogenous stimulatory polypeptide comprises 4-1BBL, or a stimulatory fragment thereof.

As used throughout herein, in one embodiment, an "IL-15 polypeptide fragment" or "IL-15 fragment" is an IL-15 fragment that binds to IL-15RA, i.e., an IL-15RA-binding fragment of IL-15. As used throughout herein, in one embodiment, an "IL-15 polypeptide fragment" or "IL-15 fragment" is an IL-15 fragment that retains a biological activity of IL-15.

As used throughout herein, in one embodiment, an "IL-15RA polypeptide fragment" or "IL-15RA fragment" is an IL-15RA fragment that binds to IL-15, i.e., an IL-15-binding fragment of IL-15RA. As used throughout herein, in one embodiment, an "IL-15RA polypeptide fragment" or "IL-15RA fragment" is an IL-15RA fragment that retains a biological activity of IL-15RA.

4-1BBL is the ligand for 4-1BB (also known as Tumor Necrosis Factor Ligand Superfamily, Member 9 (TNFSF9), or CD137), a member of a family of receptors found on the surfaces of cells of the immune system. See Alderson et al., 1994, Eur. J. Immunol. 24:2219-2227. 4-1BB binding to 4-1BBL has been shown to promote cell activation, survival, and differentiation in T cells, NK cells, and dendritic cells. The binding of 4-1BB to 4-1BB ligand (4-1BBL) has been documented to promote cell activation, survival, and differentiation, primarily through 4-1BB signaling activity in T cells, NK cells, and dendritic cells (DCs).

In certain embodiments, 4-1BBL is in its natural trimeric form. In further embodiments, the engineered erythroid cells described herein express 4-1BBL in its natural trimeric form, where the natural trimeric form is important for the efficacy and activity of the engineered erythroid cells. In some embodiments, the exogenous stimulatory polypeptide comprises or consists of human 4-1BBL, e.g., the extracellular portion of human 4-1BBL. In some embodiments, the 4 exogenous stimulatory polypeptide comprises SEQ ID NO:41. In some embodiments, the exogenous stimulatory polypeptide consists of SEQ ID NO:41.

In some embodiments, the exogenous stimulatory polypeptide comprises a 4-1BBL polypeptide and a leader (signal) sequence. In some embodiments, the exogenous stimulatory polypeptide is a fusion polypeptide comprising a 4-1BBL polypeptide and a leader sequence. In some embodiments, the leader sequence comprises or consists of an amino acid sequence set forth in Table 4. In some embodiments, the leader sequence comprises a GPA signal peptide. In some embodiments, the leader sequence comprises or consists of the amino acid sequence of SEQ ID NO: 21. In some embodiments, the exogenous stimulatory polypeptide comprises a 4-1BBL polypeptide and a leader sequence comprising or consisting of the amino acid sequence SEQ ID NO: 21. In some embodiments, the exogenous stimulatory polypeptide comprises a leader sequence comprising or consisting of the amino acid sequence of SEQ ID NO: 21, and a human extracellular 4-1BBL comprising or consisting of the amino acid sequence of SEQ ID NO: 41.

In some embodiments, the exogenous stimulatory polypeptide comprises a 4-1BBL polypeptide and is attached to the erythroid cell membrane. In some embodiments, the exogenous stimulatory polypeptide comprises a 4-1BBL polypeptide and an anchor or transmembrane domain that anchors the polypeptide to the erythroid cell membrane. In certain embodiments, the anchor or transmembrane domain is heterologous to the 4-1BBL polypeptide. In certain embodiments, the anchor or transmembrane domain comprises or consists of GPA or a transmembrane portion thereof. In certain embodiments, the anchor or transmembrane domain comprises or consists of SMIM1 or a transmembrane portion thereof. In some embodiments, the anchor or transmembrane domain comprises or consists of small integral membrane protein 1 (SMIM1), transferrin receptor, Fas ligand (FasL), Kell or Band 3, or a transmembrane portion (e.g., a transmembrane domain) thereof. The exogenous stimulatory polypeptide comprising a 4-1BBL polypeptide may comprise any of the anchor or transmembrane domains described herein. In some embodiments, the exogenous stimulatory polypeptide comprising a 4-1BBL polypeptide comprises an anchor or transmembrane domain set forth in Table 2.

In some embodiments, the exogenous stimulatory polypeptide comprises an anchor comprising or consisting of the amino acid sequence of SEQ ID NO: 25, and a 4-1BBL polypeptide. In some embodiments, the exogenous stimulatory polypeptide comprises an anchor comprising or consisting of the amino acid sequence of SEQ ID NO: 25, and a 4-1BBL polypeptide comprising or consisting of the amino acid sequence of SEQ ID NO: 41.

The exogenous stimulatory polypeptide comprising a 4-1BBL polypeptide may comprise one or more linkers. For instance, the exogenous stimulatory polypeptide may comprise any of the linkers provided herein (e.g., a linker comprising or consisting of an amino acid sequence provided in Table 3. In some embodiments, the exogenous stimulatory polypeptide comprises GPA (or a transmembrane portion thereof), a 4-1BBL polypeptide, and a linker disposed between the GPA (or the transmembrane portion thereof) and the 4-1BBL polypeptide. In some embodiments, the exogenous stimulatory polypeptide comprises a linker comprising or consisting of the amino acid sequence of SEQ ID NO: 39. In some embodiments, the exogenous stimulatory polypeptide comprises a linker which consists of the amino acid sequence of SEQ ID NO: 39.

In some embodiments, the exogenous stimulatory polypeptide comprises a signal peptide, a 4-1BBL polypeptide and an anchor. In some embodiments, the exogenous stimulatory polypeptide comprises a signal peptide, a 4-1BBL peptide, a linker, and an anchor. In some embodiments, the exogenous stimulatory polypeptide comprises (e.g., from N-terminus to C-terminus) a signal peptide comprising or consisting of the amino acid sequence of SEQ ID NO: 21, a 4-1BBL polypeptide comprising or consisting of the amino acid sequence of SEQ ID NO: 41, a linker comprising or consisting of the amino acid sequence of SEQ ID NO: 39 (e.g., disposed between the 4-1BBL polypeptide and the anchor, and an anchor comprising or consisting of the amino acid sequence of SEQ ID NO: 25. In some embodiments, the exogenous stimulatory polypeptide comprises a 4-1BBL peptide, a linker, and an anchor. In some embodiments, the exogenous stimulatory polypeptide comprises (e.g., from N-terminus to C-terminus) a 4-1BBL polypeptide comprising or consisting of the amino acid sequence of SEQ ID NO: 41, a linker comprising or consisting of the amino acid sequence of SEQ ID NO: 39 (e.g., disposed between the 4-1BBL polypeptide and the anchor, and an anchor comprising or consisting of the amino acid sequence of SEQ ID NO: 25. In some embodiments, the exogenous stimulatory polypeptide comprises or consists of the amino acid sequence of SEQ ID NO: 43.

In a particular embodiment, the exogenous stimulatory polypeptide comprises the amino acid sequence of SEQ ID NO: 43 or an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 43. In some embodiments, the exogenous stimulatory polypeptide consists of the amino acid sequence of SEQ ID NO: 43.

In certain embodiments, the combination of a first exogenous stimulatory polypeptide comprising IL-15/IL-15RA and a second exogenous stimulatory polypeptide comprising 4-1BBL induces a synergistic response (e.g., during immune killer cell activation). For example, exogenous stimulatory polypeptides, each comprising either IL-15/IL-15RA or 4-1BBL, when expressed on an erythroid cell, may act together to produce a more robust activation of immune killer cells (e.g. NK cells and/or CD8+ T-cells) as compared to the effects of either stimulatory polypeptide alone. Such synergistic activity is demonstrated in the Examples provided herein. Accordingly, In some embodiments, the invention provides an engineered erythroid cell comprising a first and a second exogenous stimulatory polypeptides, wherein the first exogenous stimulatory polypeptide comprises an IL-15 polypeptide, or fragment thereof, and an extracellular portion of IL-15RA, or a fragment thereof, wherein the second exogenous stimulatory polypeptide comprises 4-1BB, and wherein the first exogenous stimulatory polypeptide and second exogenous stimulatory polypeptide stimulate an immune killer cell with synergistic activity ex vivo or in vivo. In one embodiment, the IL-15 and IL-15RA are present as a fusion protein and, e.g., at the surface of the cell.

IL-15 Toxicity

In some aspects, the disclosure provides an engineered erythroid cell comprising a first exogenous stimulatory polypeptide comprising an IL-15 polypeptide, wherein the cell is capable of stimulating an immune killer cell, and wherein the cell has a higher therapeutic index (TI) as compared to an isolated IL-15 polypeptide upon administration to a subject. In some embodiments, the cell has an at least 5%, 10%, 15%, 20%, 30%, 40%, 50%, 60%, 70%, 80%, 90% higher therapeutic index as compared to an isolated IL-15 polypeptide upon administration to a subject. In some embodiments, the cell has an at least 1-fold, 2-fold, 3-fold, 4-fold, 5-fold, or 10-fold higher therapeutic index as compared to an isolated IL-15 polypeptide upon administration to a subject.

In some aspects, the disclosure provides an engineered erythroid cell comprising a first exogenous stimulatory polypeptide comprising an IL-15 polypeptide, wherein the cell exhibits less toxicity as compared to an isolated IL-15 polypeptide upon administration to a subject. In some embodiments, an isolated polypeptide, e.g., IL-12 polypeptide, IL-15 polypeptide, or 4-1BB agonist antibody, refers to a polypeptide that is recombinant. In some embodiments, an isolated polypeptide, e.g., IL-12 polypeptide, IL-15 polypeptide, or 4-1BB agonist polypeptide (such as a 4-1BB agonist antibody), refers to a polypeptide that is not comprised in a cell, in a cell membrane, on the cell surface, and/or conjugated to a cell.

In some embodiments, the cell exhibits less toxicity as compared to an equivalent amount of isolated IL-15 polypeptide. In some embodiments, the equivalent amount of isolated IL-15 polypeptide is an amount quantitatively or functionally equivalent to the amount of IL-15 polypeptide comprised in the cell. In some embodiments, the equivalent amount of an isolated IL-15 polypeptide is the quantitatively same amount (e.g., in copy number or molarity) as the amount of IL-15 polypeptide comprised in the engineered erythroid cell. In some embodiments, the equivalent amount of isolated IL-15 polypeptide is an amount of isolated IL-15 polypeptide having the same biological activity as the amount of IL-15 polypeptide comprised in the engineered erythroid cell. In some embodiments, the equivalent amount of isolated IL-15 polypeptide is an amount of isolated IL-15 polypeptide having the same biological activity as the engineered erythroid cell comprising the IL-15 polypeptide. In some embodiments, the equivalent amount of isolated IL-15 polypeptide is an amount of isolated IL-15 polypeptide having the same therapeutic potency as the amount of IL-15 polypeptide comprised in the engineered erythroid cell. In some embodiments, the equivalent amount of isolated IL-15 polypeptide is an amount of isolated IL-15 polypeptide having the same therapeutic potency as the engineered erythroid cell comprising the IL-15 polypeptide. In some embodiments, the first exogenous polypeptide comprises an IL-15 polypeptide, or a fragment thereof, and an extracellular portion of an IL-15RA polypeptide, or a fragment thereof.

In some embodiments, the first exogenous polypeptide comprises an IL-15 polypeptide, or a fragment thereof, and an extracellular portion of an IL-15RA polypeptide, or a fragment thereof. In some embodiments, the IL-15 polypeptide and the extracellular portion of an IL-15RA polypeptide are present as a complex. In some embodiments, the IL-15 polypeptide and the extracellular portion of an IL-15RA polypeptide are a fusion polypeptide. In some embodiments, the IL-15 polypeptide, or a fragment thereof, is linked to the extracellular portion of the IL-15RA polypeptide, or a fragment thereof, by a linker. In some embodiments, the linker comprises GGGGS (SEQ ID NO: 11). In some embodiments, the linker comprises a $(GGGGS)_3$ linker (SEQ ID NO: 12). In some embodiments, the fusion polypeptide comprises an amino acid sequence that is at least 95% identical to SEQ ID NO: 1.

In some embodiments, the first exogenous stimulatory polypeptide comprises an IL-15 polypeptide, or a fragment thereof, and a IL-15 receptor alpha sushi-binding domain. In some embodiments, the IL-15 polypeptide, or a fragment thereof, and the IL-15 receptor alpha sushi-binding domain are present as a complex. In some embodiments, the IL-15 polypeptide, or a fragment thereof, and the IL-15 receptor alpha sushi-binding domain are present as a fusion polypeptide. In some embodiments, the IL-15 polypeptide, or a fragment thereof, is linked to the IL-15 receptor alpha sushi-binding domain by a linker. In some embodiments, the linker comprises GGGGS (SEQ ID NO: 11), optionally wherein the linker comprises a $(GGGGS)_3$ linker (SEQ ID NO: 12). In some embodiments, the fusion polypeptide comprises an amino acid sequence that is at least 95% identical to SEQ ID NO: 2.

In some embodiments, the toxicity comprises liver toxicity. In some embodiments, the toxicity comprises blood toxicity. In some embodiments, the liver toxicity is measured by an indicator of liver toxicity selected from the group consisting of increased serum level of IFNg, increased serum level of ALT, increased level of infiltrating macrophages in the liver, increased level of infiltrating CD8+ T cells or CD8+/Eomes+/KLGR1+ T cells in the liver, increased liver weight, increased liver inflammation score, decreased neutrophil count, decreased lymphocyte count, decreased monocyte count, and decreased hemoglobin level. In some embodiments, the indicator of liver toxicity comprises increased serum level of interferon gamma (IFNg). In some embodiments, the indicator of liver toxicity comprises increased serum level of alanine transaminase (ALT). In some embodiments, the indicator of liver toxicity comprises increased level of infiltrating macrophages in the liver or spleen. In some embodiments, the indicator of liver toxicity comprises increased infiltration of CD8+ T cells or CD8+/Eomes+/KLGR1+ T cells in the liver. In some embodiments, the indicator of liver toxicity comprises increased liver inflammation score. Numerical scores can be used for providing a semi-quantitative assessment of histological features. Histological studies can help define the grading and staging to produce a numerical index of histological activity. Grading is used to describe the intensity of necroinflammatory activity. Staging is a measure of fibrosis and architectural alteration, i.e. structural progression of the disease.

In some embodiments, the liver inflammation score is an Ishak score. The Ishak score utilizes histological grading and staging to assign scores on a scale of 0-6 (7 stages) depending on the severity of the necroinflammatory features (periportal or periseptal interface hepatitis, confluent necrosis, focal (spotty) lytic necrosis, apoptosis and focal inflammation, and portal inflammation). A higher Ishak score implies a worse or more severe disease process or outcome, and can be used as a measure to define liver toxicity (see e.g., Ishak K et al., 1995; Goodman Z D et al., 2007 J Hepatol; 47(4):598-607, incorporated by reference in their entirety herein). In some embodiments, the indicator of liver toxicity is increased liver inflammation, as defined by the Ishak score.

In some embodiments, the liver toxicity is assessed using a mouse model for liver toxicity. In some embodiments, a mouse model of toxicity can be used to assess the potential toxicity of any of the engineered erythroid cells described herein (see for e.g., Niu et al J Immunology 2007 178:4194-4213, the entire contents of which is incorporated herein by reference). Briefly, liver toxicity can be determined by the development of immunological anomalies, which can include but are not limited to, elevated levels of the alanine transaminase (ALT) liver enzyme, liver infiltration of macrophages, liver infiltration of CD8+ T cells, lymphopenia, thrombocytopenia, anemia, lowered levels of hemoglobin, splenomegaly, lymphadenopathy, hepatomegaly, multifocal hepatitis, anemia, altered trafficking of B cells and CD8+ T cells, loss of NK cells, and a 10-fold increase in bone marrow (BM) cells bearing the phenotype of hemopoietic stem cells. Accordingly, in some embodiments, a mouse model is used to assess liver toxicity by determining one or more of the following in mice prior to administration of the engineered erythroid cells and at a time point(s) after administration of the engineered erythroid cells described herein: elevated levels of ALT liver enzyme liver infiltration of macrophages, liver infiltration of CD8+ T cells, lymphopenia, thrombocytopenia, anemia, lowered levels of hemoglobin, splenomegaly, lymphadenopathy, hepatomegaly, multifocal hepatitis, anemia, altered trafficking of B cells and CD8+ T cells, loss of NK cells, and a 10-fold increase in bone marrow (BM) cells bearing the phenotype of hemopoietic stem cells.

In some embodiments, the blood toxicity is measured by an indicator of blood toxicity selected from the group consisting of decreased neutrophil count, decreased lymphocyte count, decreased monocyte count, and decreased hemoglobin level. In some embodiments, the indicator of blood toxicity is measured in a whole blood sample. In some embodiments, the indicator of blood toxicity is measured in a serum sample. In some embodiments, the indicator of blood toxicity is measured in a plasma sample.

In some embodiments, the toxicity is measured by decreased body weight.

In some embodiments, a level of the indicator of toxicity measured in the subject after administration of the cell is compared to a level of the indicator of toxicity before administration. In some embodiments, a level of the indicator of toxicity measured in the subject after administration of the cell is compared to a threshold or control level of the indicator of toxicity.

Normal blood test results for typical liver function in humans include alanine transaminase (ALT) levels of about 7 to 55 units per liter of serum (see e.g., www.mayoclinic.org/tests-procedures/liver-function-tests/about/pac-20394595). When the liver is damaged, for e.g., due to toxicity, ALT is released into the bloodstream and its levels increase. In some embodiments, the indicator of liver toxicity is increased serum level of alanine transaminase (ALT). In some embodiments, the indicator of liver toxicity is serum level of ALT of greater than about 55 units per liter of blood in a human subject. In some embodiments, the indicator of liver toxicity is serum level of ALT of greater than about 75 units per liter of blood in a human subject. In some embodiments, the indicator of liver toxicity is serum level of ALT of greater than about 100 units per liter of blood in a human subject. In some embodiments, the indicator of liver toxicity is serum level of ALT of greater than about 250 units per liter of blood in a human subject. In some embodiments, the indicator of liver toxicity is serum level of ALT of greater than about 500 units per liter of blood in a human subject. In some embodiments, the indicator of liver toxicity is serum level of ALT of greater than about 750 units per liter of blood in a human subject. In some embodiments, the indicator of liver toxicity is serum level of ALT of greater than about 1000 units per liter of blood in a human subject.

Normal blood test results for typical liver function in humans include aspartate transaminase (AST) levels of about 8 to 48 units per liter of serum (see e.g., www.mayoclinic.org/tests-procedures/liver-function-tests/about/pac-20394595). Like ALT, AST is normally present in blood at low levels, and an increase in AST levels indicate liver damage. In some embodiments, the indicator of liver toxicity is serum level of AST of greater than about 48 units per liter of blood in a human subject. In some embodiments, the indicator of liver toxicity is serum level of AST of greater than about 60 units per liter of blood in a human subject. In some embodiments, the indicator of liver toxicity is serum level of AST of greater than about 75 units per liter of blood in a human subject. In some embodiments, the indicator of liver toxicity is serum level of AST of greater than about 100 units per liter of blood in a human subject. In some embodiments, the indicator of liver toxicity is serum level of AST of greater than about 250 units per liter of blood in a human subject. In some embodiments, the indicator of liver toxicity is serum level of AST of greater than about 500 units per liter of blood in a human subject. In some embodiments, the indicator of liver toxicity is serum level of AST of greater than about 750 units per liter of blood in a human subject. In some embodiments, the indicator of liver toxicity is serum level of AST of greater than about 800 units per liter of blood in a human subject. In some embodiments, the indicator of liver toxicity is serum level of AST of greater than about 1000 units per liter of blood in a human subject.

Normal blood test results for typical liver function in humans include alkaline phosphatase (ALP) levels of about 45 to 115 units per liter of serum (see e.g., www.mayoclinic.org/tests-procedures/liver-function-tests/about/pac-20394595). Higher-than-normal levels of ALP can indicate liver damage or disease. In some embodiments, the indicator of liver toxicity is increased serum level of alkaline phosphatase (ALP). In some embodiments, the indicator of liver toxicity is serum level of ALP of greater than about 115 units per liter of serum. In some embodiments, the indicator of liver toxicity is serum level of ALP of greater than about 150 units per liter of blood in a human subject. In some embodiments, the indicator of liver toxicity is serum level of ALP of greater than about 250 units per liter of blood in a human subject. In some embodiments, the indicator of liver toxicity is serum level of ALP of greater than about 500 units per liter of blood in a human subject. In some embodiments, the indicator of liver toxicity is serum level of ALP of greater than about 750 units per liter of blood in a human subject. In some embodiments, the indicator of liver toxicity is serum level of ALP of greater than about 1000 units per liter of blood in a human subject.

Normal blood test results in human adults include between 800 and 4,800 lymphocytes in 1 μL of blood (see e.g., www.medicalnewstoday.com/articles/320987.php). Lymphocytopenia is the condition of having an abnormally decreased lymphocyte count in the blood. Lymphocytopenia is a frequent result from administration of cytotoxic agents. In some embodiments, the indicator of blood toxicity is identified by a decreased lymphocyte count. In some embodiments, the indicator of blood toxicity is a decreased lymphocyte count of less than about 800 lymphocytes per microliter of blood. In some embodiments, the indicator of blood toxicity is a decreased lymphocyte count of less than about 600 lymphocytes per microliter of blood. In some embodiments, the indicator of blood toxicity is a decreased lymphocyte count of less than about 400 lymphocytes per microliter of blood. In some embodiments, the indicator of blood toxicity is a decreased lymphocyte count of less than about 200 lymphocytes per microliter of blood. In some embodiments, the indicator of blood toxicity is a decreased lymphocyte count of less than about 100 lymphocytes per microliter of blood.

Normal blood test results in human adults include between 3.9 and 5.65 million cells in 1 μL of blood (see e.g., www.mayoclinic.org/tests-procedures/complete-blood-count/about/pac-20384919). A decreased red blood cell count can occur when red blood cells are excessively damaged by certain chemicals or toxins. In some embodiments, the indicator of blood toxicity is identified by a decreased red blood cell count. In some embodiments, the indicator of blood toxicity is a decreased red blood cell count of less than about $3.9\times10^6$ red blood cells per microliter of blood. In some embodiments, the indicator of blood toxicity is a decreased red blood cell count of less than about $1\times10^6$ red blood cells per microliter of blood. In some embodiments, the indicator of blood toxicity is a decreased red blood cell count of less than about $3\times10^5$ red blood cells per microliter of blood. In some embodiments, the indicator of blood toxicity is a decreased red blood cell count of less than about $1\times10^5$ red blood cells per microliter of blood. In some embodiments, the indicator of blood toxicity is a decreased red blood cell count of less than about $3\times10^4$ red blood cells per microliter of blood. In some embodiments, the indicator of blood toxicity is a decreased red blood cell count of less than about $1\times10^4$ red blood cells per microliter of blood. In some embodiments, the indicator of blood toxicity is a decreased red blood cell count of less than about $3\times10^3$ red blood cells per microliter of blood. In some embodiments, the indicator of blood toxicity is a decreased red blood cell count of less than about $1\times10^3$ red blood cells per microliter of blood. In some embodiments, the indicator of blood toxicity is a decreased red blood cell count of less than about $3\times10^2$ red blood cells per microliter of blood. In some embodiments, the indicator of blood toxicity is a decreased red blood cell count of less than about $1\times10^2$ red blood cells per microliter of blood.

Normal blood test results in human adults include between 3,400 to 9,600 cells in 1 μL of blood (see e.g., www.mayoclinic.org/tests-procedures/complete-blood-count/about/pac-20384919). Leukopenia is a decrease in the white blood cell (leukocyte) counts in the blood, which can be induced by toxicity (see e.g., Xu et al., 2008, Toxicological Sciences. 103 (2): 278-284). In some embodiments, the indicator of blood toxicity is identified by a decreased white blood cell count. In some embodiments, the indicator of blood toxicity is a decreased white blood cell count of less than about 3,400 white blood cells per microliter of blood. In some embodiments, the indicator of blood toxicity is a decreased white blood cell count of less than about 3,000 white blood cells per microliter of blood. In some embodiments, the indicator of blood toxicity is a decreased white blood cell count of less than about 2,500 white blood cells per microliter of blood. In some embodiments, the indicator of blood toxicity is a decreased white blood cell count of less than about 2,000 white blood cells per microliter of blood. In some embodiments, the indicator of blood toxicity is a decreased white blood cell count of less than about 1,500 white blood cells per microliter of blood. In some embodiments, the indicator of blood toxicity is a decreased white blood cell count of less than about 1,000 white blood cells per microliter of blood. In some embodiments, the indicator of blood toxicity is a decreased white blood cell count of less than about 500 white blood cells per microliter of blood. In some embodiments, the indicator of blood toxicity is a decreased white blood cell count of less than about 100 white blood cells per microliter of blood.

Normal blood test results in human adults include between 116 and 166 grams per liter of blood (see e.g., www.mayoclinic.org/tests-procedures/complete-blood-count/about/pac-20384919). In some embodiments, the indicator of blood toxicity is identified by a decreased hemoglobin level. In some embodiments, the indicator of blood toxicity is a decreased hemoglobin level of less than about 116 grams per liter of blood. In some embodiments, the indicator of blood toxicity is a decreased hemoglobin level of less than about 110 grams per liter of blood. In some embodiments, the indicator of blood toxicity is a decreased hemoglobin level of less than about 100 grams per liter of blood. In some embodiments, the indicator of blood toxicity is a decreased hemoglobin level of less than about 90 grams per liter of blood. In some embodiments, the indicator of blood toxicity is a decreased hemoglobin level of less than about 80 grams per liter of blood. In some embodiments, the indicator of blood toxicity is a decreased hemoglobin level of less than about 70 grams per liter of blood. In some embodiments, the indicator of blood toxicity is a decreased hemoglobin level of less than about 60 grams per liter of blood. In some embodiments, the indicator of blood toxicity is a decreased hemoglobin level of less than about 50 grams per liter of blood. In some embodiments, the indicator of blood toxicity is a decreased hemoglobin level of less than about 40 grams per liter of blood. In some embodiments, the indicator of blood toxicity is a decreased hemoglobin level of less than about 30 grams per liter of blood. In some embodiments, the indicator of blood toxicity is a decreased hemoglobin level of less than about 20 grams per liter of blood. In some embodiments, the indicator of blood toxicity is a decreased hemoglobin level of less than about 10 grams per liter of blood.

In some embodiments, the cell exhibits at least 10%, at least 20%, at least 30%, at least 40%, at least 50%, at least 60%, at least 70%, at least 80%, at least 90%, at least 95% or at least 100% less toxicity upon administration to the subject than the isolated IL-15 polypeptide. In some embodiments, the cell exhibits at least 1.5-fold, at least 2-fold, at least 3-fold, at least 4-fold, at least 5-fold or at least 10-fold less toxicity upon administration to the subject than the isolated IL-15 polypeptide.

In some embodiments, the cell is capable of stimulating an immune killer cell in the subject.

4-1BBL Toxicity

In some aspects, the present disclosure provide an engineered erythroid cell comprising a first exogenous stimulatory polypeptide comprising a 4-1BBL polypeptide, wherein the cell is capable of stimulating an immune killer cell, and wherein the cell has a higher therapeutic index (TI) as compared to an isolated 4-1BBL agonist antibody upon administration to a subject. In some embodiments, the cell has an at least 5%, 10%, 15%, 20%, 30%, 40%, 50%, 60%, 70%, 80%, 90% or higher therapeutic index as compared to an isolated 4-1BBL agonist antibody upon administration to a subject. In some embodiments, the cell has an at least 1-fold, 2-fold, 3-fold, 4-fold, 5-fold, or 10-fold higher therapeutic index as compared to an isolated 4-1BBL agonist antibody upon administration to a subject.

In some aspects, the present disclosure provides an engineered erythroid cell comprising a first exogenous stimulatory polypeptide comprising a 4-1BBL polypeptide, wherein the cell is capable of stimulating an immune killer cell, and wherein the cell exhibits less toxicity as compared to an isolated 4-1BB agonist antibody upon administration to a subject. In some embodiments, an isolated polypeptide, e.g., IL-12 polypeptide, IL-15 polypeptide, or 4-1BB agonist antibody, refers to a polypeptide that is recombinant. In some embodiments, an isolated polypeptide, e.g., IL-12 polypeptide, IL-15 polypeptide, or 4-1BB agonist polypeptide (such as a 4-1BB agonist antibody), refers to a polypeptide that is not comprised in a cell, in a cell membrane, on the cell surface, and/or conjugated to a cell. In some embodiments, the cell exhibits less toxicity as compared to an equivalent amount of isolated 4-1BB agonist antibody. In some embodiments, the equivalent amount of isolated 4-1BB agonist antibody is an amount equivalent to the amount of 4-1BBL polypeptide comprised in the cell. In some embodiments, the equivalent amount of isolated 4-1BB agonist antibody is an amount of isolated 4-1BB agonist antibody equivalent (e.g., in copy number, weight or molarity) to the amount of 4-1BBL polypeptide comprised in the engineered erythroid cell. In some embodiments, the equivalent amount of isolated 4-1BB agonist antibody is an amount of isolated 4-1BB agonist antibody having the same agonist activity as the amount of 4-1BBL polypeptide comprised in the engineered erythroid cell. In some embodiments, the equivalent amount of isolated 4-1BB agonist antibody is an amount of isolated 4-1BB agonist antibody having the same agonist activity as the engineered erythroid cell comprising the 4-1BBL polypeptide. In some embodiments, the equivalent amount of isolated 4-1BB agonist antibody is an amount of isolated 4-1BB agonist antibody having the same biological effect as the amount of 4-1BBL polypeptide comprised in the engineered erythroid cell. In some embodiments, the equivalent amount of isolated 4-1BB agonist antibody is an amount of isolated 4-1BB agonist antibody having the same biological effect as the engineered erythroid cell comprising the 4-1BBL polypeptide. In some embodiments, the equivalent amount of isolated 4-1BB agonist antibody is an amount of isolated 4-1BB agonist antibody having the same therapeutic potency as the amount of 4-1BBL polypeptide comprised in the engineered erythroid cell. In some embodiments, the equivalent amount of isolated 4-1BB agonist antibody is an amount of isolated 4-1BB agonist antibody having the same therapeutic potency as the engineered erythroid cell comprising the 4-1BBL polypeptide.

In some embodiments, the 4-1BB agonist antibody is the antibody 3H3, or an antigen-binding fragment thereof, or the antibody utomilumab, or an antigen-binding fragment thereof.

In some embodiments, the toxicity comprises liver toxicity. In some embodiments, the toxicity comprises blood toxicity. In some embodiments, the liver toxicity is measured by an indicator of liver toxicity selected from the group consisting of increased serum level of IFNg, increased serum level of ALT, increased level of infiltrating macrophages in the liver, increased level of infiltrating CD8+ T cells or CD8+/Eomes+/KLGR1+ T cells in the liver, increased liver weight, increased liver inflammation score, decreased neutrophil count, decreased lymphocyte count, decreased monocyte count, and decreased hemoglobin level. In some embodiments, the indicator of liver toxicity comprises increased serum level of interferon gamma (IFNg). In some embodiments, the indicator of liver toxicity comprises increased serum level of alanine transaminase (ALT). In some embodiments, the indicator of liver toxicity comprises increased level of infiltrating macrophages in the liver or spleen. In some embodiments, the indicator of liver toxicity comprises increased infiltration of CD8+ T cells or CD8+/Eomes+/KLGR1+ T cells in the liver. In some embodiments, the indicator of liver toxicity comprises increased liver inflammation score.

In some embodiments, the liver inflammation score is an Ishak score, as described herein.

In some embodiments, the liver toxicity is assessed using a mouse model for liver toxicity, as described herein.

In some embodiments, the blood toxicity is measured by an indicator of blood toxicity selected from the group consisting of decreased neutrophil count, decreased lymphocyte count, decreased monocyte count, and decreased hemoglobin level. In some embodiments, the indicator of blood toxicity is measured in a whole blood sample. In some embodiments, the indicator of blood toxicity is measured in a serum sample. In some embodiments, the indicator of blood toxicity is measured in a plasma sample.

In some embodiments, the toxicity is measured by decreased body weight.

In some embodiments, a level of the indicator of toxicity measured in the subject after administration of the cell is compared to a level of the indicator of toxicity before administration. In some embodiments, a level of the indicator of toxicity measured in the subject after administration of the cell is compared to a threshold or control level of the indicator of toxicity. In some embodiments, the indicator of toxicity is determined by serum ALT levels, as described herein. In some embodiments, the indicator of liver toxicity is increased serum level of ALT, as described herein. In some embodiments, the indicator of toxicity is determined by serum AST levels, as described herein. In some embodiments, the indicator of liver toxicity is increased serum level of AST, as described herein. In some embodiments, the indicator of toxicity is determined by serum ALP levels, as described herein. In some embodiments, the indicator of liver toxicity is increased serum level of ALP, as described herein. In some embodiments, the indicator of toxicity is determined by lymphocyte count, as described herein. In some embodiments, the indicator of blood toxicity is identified by a decreased lymphocyte count. In some embodiments, the indicator of blood toxicity is identified by a red blood cell count, as described herein. In some embodiments, the indicator of blood toxicity is identified by a decreased red blood cell count, as described herein. In some embodiments, the indicator of blood toxicity is identified by a white blood cell count, as described herein. In some embodiments, the indicator of blood toxicity is identified by a decreased white blood cell count, as described herein. In some embodiments, the indicator of blood toxicity is identified by a hemoglobin level, as described herein. In some embodiments, the indicator of blood toxicity is identified by a decreased hemoglobin level.

In some embodiments, the cell exhibits at least 10%, at least 20%, at least 30%, at least 40%, at least 50%, at least 60%, at least 70%, at least 80%, at least 90%, at least 95% or at least 100% less toxicity upon administration to the subject than the isolated 4-1BB agonist antibody. In some embodiments, the cell exhibits at least 1.5-fold, at least 2-fold, at least 3-fold, at least 4-fold, at least 5-fold or at least 10-fold less toxicity upon administration to the subject than the isolated 4-1BB agonist antibody.

In some embodiments, the cell is capable of stimulating an immune killer cell in the subject.

IL-15 and 4-1BBL Toxicity

In some aspects, the disclosure provides an engineered erythroid cell comprising a first exogenous stimulatory polypeptide and a second exogenous stimulatory polypeptide, wherein the first exogenous stimulatory polypeptide comprises a 4-1BBL polypeptide and the second exogenous stimulatory polypeptide comprises an IL-15 polypeptide, wherein the cell is capable of stimulating an immune killer cell, and wherein the cell has a higher therapeutic index (TI) as compared to an isolated 4-1BBL agonist antibody, an isolated IL-15 polypeptide, or a combination thereof, upon administration to a subject. In some embodiments, the cell has an at least 5%, 10%, 15%, 20%, 30%, 40%, 50%, 60%, 70%, 80%, 90% higher therapeutic index as compared to an isolated 4-1BBL agonist antibody, an isolated IL-15 polypeptide, or a combination thereof, upon administration to a subject. In some embodiments, the cell has an at least 1-fold, 2-fold, 3-fold, 4-fold, 5-fold, or 10-fold higher therapeutic index as compared to an isolated 4-1BBL agonist antibody, an isolated IL-15 polypeptide, or a combination thereof, upon administration to a subject.

In some aspects, the disclosure provides an engineered erythroid cell comprising a first exogenous stimulatory polypeptide and second exogenous stimulatory polypeptide, wherein the first exogenous stimulatory polypeptide comprises a 4-1BBL polypeptide, and the second exogenous stimulatory polypeptide comprises an IL-15 polypeptide, wherein the cell exhibits less toxicity as compared to an isolated 4-1BB agonist polypeptide, an isolated IL-15 polypeptide, or a combination thereof, upon administration to a subject.

In some embodiments, the cell exhibits less toxicity as compared to an equivalent amount of an isolated 4-1BB agonist polypeptide, an equivalent amount of an isolated IL-15 polypeptide, or a combination thereof, upon administration to a subject. In some embodiments, the equivalent amount of isolated 4-1BB agonist antibody is an amount equivalent to the amount of 4-1BBL polypeptide comprised in the cell. In some embodiments, the equivalent amount of isolated 4-1BB agonist antibody is an amount of isolated 4-1BB agonist antibody equivalent (e.g., in copy number, weight or molarity) to the amount of 4-1BBL polypeptide comprised in the engineered erythroid cell. In some embodiments, the equivalent amount of isolated 4-1BB agonist antibody is an amount of isolated 4-1BB agonist antibody having the same agonist activity as the amount of 4-1BBL polypeptide comprised in the engineered erythroid cell. In some embodiments, the equivalent amount of isolated 4-1BB agonist antibody is an amount of isolated 4-1BB agonist antibody having the same biological effect as the amount of 4-1BBL polypeptide comprised in the engineered erythroid cell. In some embodiments, the equivalent amount of isolated 4-1BB agonist antibody is an amount of isolated 4-1BB agonist antibody having the same therapeutic potency as the amount of 4-1BBL polypeptide comprised in the engineered erythroid cell. In some embodiments, the 4-1BB agonist antibody is the antibody 3H3, or an antigen-binding fragment thereof, or the antibody utomilumab, or an antigen-binding fragment thereof. In some embodiments, the equivalent amount of isolated IL-15 polypeptide is an amount quantitatively or functionally equivalent to the amount of IL-15 polypeptide comprised in the cell. In some embodiments, the equivalent amount of an isolated IL-15 polypeptide is the quantitatively same amount (e.g., in copy number or molarity) as the amount of IL-15 polypeptide comprised in the engineered erythroid cell. In some embodiments, the equivalent amount of isolated IL-15 polypeptide is an amount of isolated IL-15 polypeptide having the same biological activity as the amount of IL-15 polypeptide comprised in the engineered erythroid cell. In some embodiments, the equivalent amount of isolated IL-15 polypeptide is an amount of isolated IL-15 polypeptide having the same therapeutic potency as the amount of IL-15 polypeptide comprised in the engineered erythroid cell.

In some embodiments, the second exogenous polypeptide comprises an IL-15 polypeptide, or a fragment thereof, and an extracellular portion of an IL-15RA polypeptide, or a fragment thereof.

In some embodiments, the first exogenous polypeptide comprises an IL-15 polypeptide, or a fragment thereof, and an extracellular portion of an IL-15RA polypeptide, or a fragment thereof. In some embodiments, the IL-15 polypeptide and the extracellular portion of an IL-15RA polypeptide are present as a complex. In some embodiments, the IL-15 polypeptide and the extracellular portion of an IL-15RA polypeptide are a fusion polypeptide. In some embodiments, the IL-15 polypeptide, or a fragment thereof, is linked to the extracellular portion of the IL-15RA polypeptide, or a fragment thereof, by a linker. In some embodiments, the linker comprises GGGGS (SEQ ID NO: 11). In some embodiments, the linker comprises a $(GGGGS)_3$ linker (SEQ ID NO: 12). In some embodiments, the fusion polypeptide comprises an amino acid sequence that is at least 95% identical to SEQ ID NO: 1.

In some embodiments, the first exogenous stimulatory polypeptide comprises an IL-15 polypeptide, or a fragment thereof, and a IL-15 receptor alpha sushi-binding domain. In some embodiments, the IL-15 polypeptide, or a fragment thereof, and the IL-15 receptor alpha sushi-binding domain are present as a complex. In some embodiments, the IL-15 polypeptide, or a fragment thereof, and the IL-15 receptor alpha sushi-binding domain are present as a fusion polypeptide. In some embodiments, the IL-15 polypeptide, or a fragment thereof, is linked to the IL-15 receptor alpha sushi-binding domain by a linker. In some embodiments, the linker comprises GGGGS (SEQ ID NO: 11), optionally wherein the linker comprises a $(GGGGS)_3$ linker (SEQ ID NO: 12). In some embodiments, the fusion polypeptide comprises an amino acid sequence that is at least 95% identical to SEQ ID NO: 2.

In some embodiments, the toxicity comprises liver toxicity. In some embodiments, the toxicity comprises blood toxicity. In some embodiments, the liver toxicity is measured by an indicator of liver toxicity selected from the group consisting of increased serum level of IFNg, increased serum level of ALT, increased level of infiltrating macrophages in the liver, increased level of infiltrating CD8+ T cells or CD8+/Eomes+/KLGR1+ T cells in the liver, increased liver weight, increased liver inflammation score, decreased neutrophil count, decreased lymphocyte count, decreased monocyte count, and decreased hemoglobin level. In some embodiments, the indicator of liver toxicity comprises increased serum level of interferon gamma (IFNg). In some embodiments, the indicator of liver toxicity comprises increased serum level of alanine transaminase (ALT). In some embodiments, the indicator of liver toxicity comprises increased level of infiltrating macrophages in the liver or spleen. In some embodiments, the indicator of liver toxicity comprises increased infiltration of CD8+ T cells or CD8+/Eomes+/KLGR1+ T cells in the liver. In some embodiments, the indicator of liver toxicity comprises increased liver inflammation score.

In some embodiments, the liver inflammation score is an Ishak score, as described herein.

In some embodiments, the liver toxicity is assessed using a mouse model for liver toxicity, as described herein.

In some embodiments, the blood toxicity is measured by an indicator of blood toxicity selected from the group consisting of decreased neutrophil count, decreased lymphocyte count, decreased monocyte count, and decreased hemoglobin level. In some embodiments, the indicator of blood toxicity is measured in a whole blood sample. In some embodiments, the indicator of blood toxicity is measured in a serum sample. In some embodiments, the indicator of blood toxicity is measured in a plasma sample.

In some embodiments, the toxicity is measured by decreased body weight.

In some embodiments, a level of the indicator of toxicity measured in the subject after administration of the cell is compared to a level of the indicator of toxicity before administration. In some embodiments, a level of the indicator of toxicity measured in the subject after administration of the cell is compared to a threshold or control level of the indicator of toxicity. In some embodiments, the indicator of toxicity is determined by serum ALT levels, as described herein. In some embodiments, the indicator of liver toxicity is increased serum level of ALT, as described herein. In some embodiments, the indicator of toxicity is determined by serum AST levels, as described herein. In some embodiments, the indicator of liver toxicity is increased serum level of AST, as described herein. In some embodiments, the indicator of toxicity is determined by serum ALP levels, as described herein. In some embodiments, the indicator of liver toxicity is increased serum level of ALP, as described herein. In some embodiments, the indicator of toxicity is determined by lymphocyte count, as described herein. In some embodiments, the indicator of blood toxicity is identified by a decreased lymphocyte count. In some embodiments, the indicator of blood toxicity is identified by a red blood cell count, as described herein. In some embodiments, the indicator of blood toxicity is identified by a decreased red blood cell count, as described herein. In some embodiments, the indicator of blood toxicity is identified by a white blood cell count, as described herein. In some embodiments, the indicator of blood toxicity is identified by a decreased white blood cell count, as described herein. In some embodiments, the indicator of blood toxicity is identified by a hemoglobin level, as described herein. In some embodiments, the indicator of blood toxicity is identified by a decreased hemoglobin level.

In some embodiments, the cell exhibits at least 10%, at least 20%, at least 30%, at least 40%, at least 50%, at least 60%, at least 70%, at least 80%, at least 90%, at least 95% or at least 100% less toxicity upon administration to the subject than the isolated 4-1BBL polypeptide and the isolated IL-15 polypeptide. In some embodiments, the cell exhibits at least 1.5-fold, at least 2-fold, at least 3-fold, at least 4-fold, at least 5-fold or at least 10-fold less toxicity upon administration to the subject than the isolated 4-1BBL polypeptide and the isolated IL-15 polypeptide.

In some embodiments, the cell is capable of stimulating an immune killer cell in the subject In certain embodiments, the engineered erythroid cell further comprises one or more exogenous stimulatory polypeptides selected from the group consisting of IL-1, IL-2, IL-12, IL-18, IL-21, interferon alpha (IFNα), Poliovirus Receptor (PVR/CD155), CD48, human leukocyte antigen (HLA)-A, HLA-C, HLA-G, heparan sulfate (HS), HLA-E, CpG, Immunoglobulin G (IgG), UL16 binding proteins (ULBP), MHC class I chain-related proteins (MIC), B7-H6, NkP44L, Nectin2, NK-T-B antigen (NTBA), activation-induced C-type lectin (AICL) and insulin-like growth factor 1 (IGF-1).

In certain embodiments, the exogenous stimulatory polypeptide does not comprise an antibody or antibody fragment, e.g. an Fc portion of an antibody.

Nucleic Acid Sequences

In certain embodiments, the invention provides an engineered erythroid cell (e.g. an engineered erythroid precursor cell) comprising a nucleic acid sequence encoding an exogenous stimulatory polypeptide as described herein. In certain embodiments, the invention provides an engineered erythroid cell prepared by using a nucleic acid sequence encoding an exogenous stimulatory polypeptide as described herein. For example, in some embodiments, the erythroid cell comprises a nucleic acid sequence encoding an exogenous stimulatory polypeptide comprising an IL-15 polypeptide, for example, a mature human IL-15. In some embodiments, the nucleic acid sequence encoding the IL-15 polypeptide comprises the nucleic acid sequence of SEQ ID NO: 13 or SEQ ID NO: 14. In some embodiments, the nucleic acid sequence encoding the IL-15 polypeptide comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 13. In some embodiments, the nucleic acid sequence encoding the exogenous stimulatory polypeptide comprising an IL-15 polypeptide comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 14. In some embodiments, the nucleic acid sequence encoding the exogenous stimulatory polypeptide comprising an IL-15 polypeptide consists of the nucleic acid sequence of SEQ ID NO: 13 or SEQ ID NO: 14.

In some embodiments, the engineered erythroid cell comprises a nucleic acid sequence encoding an exogenous stimulatory polypeptide comprising an IL-15RA polypeptide (for example, a mature extracellular human IL-15RA). In some embodiments, the nucleic acid sequence encoding the exogenous stimulatory polypeptide comprising an IL-15RA polypeptide comprises the nucleic acid sequence of SEQ ID NO: 15 or SEQ ID NO: 16. In some embodiments, the nucleic acid sequence encoding the exogenous stimulatory polypeptide comprising an IL-15Ra polypeptide comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 15. In some embodiments, the nucleic acid sequence encoding the exogenous stimulatory polypeptide comprising an IL-15RA polypeptide comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 16. In some embodiments, the nucleic acid sequence encoding the exogenous stimulatory polypeptide comprising an IL-15RA polypeptide consists of the nucleic acid sequence of SEQ ID NO: 15 or SEQ ID NO: 16.

In a particular embodiment, the nucleic acid sequence encoding an exogenous stimulatory polypeptide comprises the nucleic acid sequence of SEQ ID NO: 19 or SEQ ID NO: 20. In some embodiments, the nucleic acid sequence encoding an exogenous stimulatory polypeptide comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 19. In some embodiments, the nucleic acid sequence encoding an exogenous stimulatory polypeptide comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 20.

In some embodiments, the engineered erythroid cell comprises a nucleic acid sequence encoding a linker, e.g., a $(G_4S)_3$ linker (SEQ ID NO: 12). In some embodiments, the nucleic acid sequence encoding the linker comprises the nucleic acid sequence of SEQ ID NO: 17 or SEQ ID NO: 18. In some embodiments, the nucleic acid sequence encoding the linker comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 17. In some embodiments, the nucleic acid sequence encoding the linker comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 18.

In some embodiments, the engineered erythroid cell comprises a nucleic acid sequence encoding an exogenous stimulatory polypeptide comprising an IL-15 V3 construct. In some embodiments, the nucleic acid sequence encoding the exogenous stimulatory polypeptide comprising an IL-15 V3 construct comprises the nucleic acid sequence of SEQ ID NO: 28. In some embodiments, the nucleic acid sequence encoding the exogenous stimulatory polypeptide comprising an IL-15 V3 construct comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 28. In some embodiments, the nucleic acid sequence encoding the exogenous stimulatory polypeptide comprising an IL-15 V3 construct comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 28. In some embodiments, the nucleic acid sequence encoding the exogenous stimulatory polypeptide comprising an IL-15 V3 construct consists of the nucleic acid sequence of SEQ ID NO: 28.

In some embodiments, the engineered erythroid cell comprises a nucleic acid sequence encoding an exogenous stimulatory polypeptide comprising an IL-15/IL-15Ra V4 construct. In some embodiments, the nucleic acid sequence encoding the exogenous stimulatory polypeptide comprising an IL-15/IL-15Ra V4 construct comprises the nucleic acid sequence of SEQ ID NO: 30. In some embodiments, the nucleic acid sequence encoding the exogenous stimulatory polypeptide comprising an IL-15/IL-15Ra V4 construct comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 30. In some embodiments, the nucleic acid sequence encoding the exogenous stimulatory polypeptide comprising an IL-15/IL-15Ra V4 construct comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 30. In some embodiments, the nucleic acid sequence encoding the exogenous stimulatory polypeptide comprising an IL-15/IL-15Ra V4 construct consists of the nucleic acid sequence of SEQ ID NO: 30.

In some embodiments, the engineered erythroid cell comprises a nucleic acid sequence encoding an exogenous stimulatory polypeptide comprising an IL-15/IL-15Ra V5 construct. In some embodiments, the nucleic acid sequence encoding the exogenous stimulatory polypeptide comprising an IL-15/IL-15Ra V5 construct comprises the nucleic acid sequence of SEQ ID NO: 32. In some embodiments, the nucleic acid sequence encoding the exogenous stimulatory polypeptide comprising an IL-15/IL-15Ra V5 construct comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 32. In some embodiments, the nucleic acid sequence encoding the exogenous stimulatory polypeptide comprising an IL-15/IL-15Ra V5 construct comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 32. In some embodiments, the nucleic acid sequence encoding the exogenous stimulatory polypeptide comprising an IL-15/IL-15RaV5 construct consists of the nucleic acid sequence of SEQ ID NO: 32.

In some embodiments, the engineered erythroid cell comprises a nucleic acid sequence encoding an exogenous stimulatory polypeptide comprising an IL-15 V3.1 construct. In some embodiments, the nucleic acid sequence encoding the exogenous stimulatory polypeptide comprising an IL-15 V3.1 construct comprises the nucleic acid sequence of SEQ ID NO: 36. In some embodiments, the nucleic acid sequence encoding the exogenous stimulatory polypeptide comprising an IL-15 V3.1 construct comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 36. In some embodiments, the nucleic acid sequence encoding the exogenous stimulatory polypeptide comprising an IL-15 V3.1 construct comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 36. In some embodiments, the nucleic acid sequence encoding the exogenous stimulatory polypeptide comprising an IL-15 V3.1 construct consists of the nucleic acid sequence of SEQ ID NO: 36.

In some embodiments, the engineered erythroid cell comprises a nucleic acid sequence encoding an exogenous stimulatory polypeptide comprising an IL-15/IL-15Ra V4.1 construct. In some embodiments, the nucleic acid sequence encoding the exogenous stimulatory polypeptide comprising an IL-15/IL-15Ra V4.1 construct comprises the nucleic acid sequence of SEQ ID NO: 38. In some embodiments, the nucleic acid sequence encoding the IL-15/IL-15Ra V4.1 construct comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 38. In some embodiments, the nucleic acid sequence encoding the exogenous stimulatory polypeptide comprising an IL-15/IL-15Ra V4.1 construct comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 38. In some embodiments, the nucleic acid sequence encoding the exogenous stimulatory polypeptide comprising an IL-15/IL-15Ra V4.1 construct consists of the nucleic acid sequence of SEQ ID NO: 38.

In some embodiments, the engineered erythroid cell comprises a nucleic acid sequence encoding an exogenous stimulatory polypeptide comprising an 4-1BBL polypeptide, for example, a human 4-1BBL polypeptide. In some embodiments, the nucleic acid sequence encoding the exogenous stimulatory polypeptide comprising an 4-1BBL polypeptide comprises the nucleic acid sequence of SEQ ID NO: 42. In some embodiments, the nucleic acid sequence encoding the 4-1BBL polypeptide comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 42. In some embodiments, the nucleic acid sequence encoding the exogenous stimulatory polypeptide comprising an 4-1BBL polypeptide comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 42. In some embodiments, the nucleic acid sequence encoding the exogenous stimulatory polypeptide comprising an 4-1BBL polypeptide consists of the nucleic acid sequence of SEQ ID NO: 42.

In some embodiments, the engineered erythroid cell comprises a nucleic acid sequence encoding a exogenous stimulatory polypeptide comprising a 4-1BBL polypeptide. In some embodiments, the nucleic acid sequence encoding the exogenous stimulatory polypeptide comprising a 4-1BBL polypeptide comprises the nucleic acid sequence of SEQ ID NO: 44. In some embodiments, the nucleic acid sequence encoding the exogenous stimulatory polypeptide comprising an 4-1BBL polypeptide comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 44. In some embodiments, the nucleic acid sequence encoding the exogenous stimulatory polypeptide comprising an 4-1BBL polypeptide comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 44. In some embodiments, the nucleic acid sequence encoding the exogenous stimulatory polypeptide comprising an 4-1BBL polypeptide consists of the nucleic acid sequence of SEQ ID NO: 44.

In some embodiments, the nucleic acid sequence encoding the exogenous stimulatory polypeptide or a component thereof is codon optimized (e.g., codon optimized for expression in a human cell). For example, in some embodiments, the nucleic acid sequence encoding the IL-15 polypeptide, the IL-15RA polypeptide, the 4-1BBL polypeptide, and/or the linker is codon optimized. In other embodiments, the nucleic acid sequence encoding the exogenous stimulatory polypeptide or a component thereof is not codon optimized. For example, in some embodiments, the nucleic acid sequence encoding the IL-15 polypeptide, the IL-15RA polypeptide, the 4-1BBL polypeptide, and/or the linker is not codon optimized.

Engineered Erythroid Cells Comprising IL-12

The disclosure provides, in another aspect, an engineered erythroid cell comprising a first exogenous stimulatory polypeptide, wherein the first exogenous stimulatory polypeptide comprises an interleukin-12 polypeptide, or fragment thereof (e.g., an IL-12 receptor binding fragment). In some embodiments, the IL-12 polypeptide is a p40 (IL-12 p40) polypeptide, or a fragment thereof. In some embodiments, the IL-12 polypeptide is a p35 (IL-12 p35) polypeptide, or a fragment thereof. In some embodiments, the IL-12 polypeptide is a p40-p35 fusion polypeptide (IL-12 p40- p35) polypeptide, or a fragment thereof. In some embodiments, the engineered erythroid cell is an enucleated cell. In some embodiments, the engineered erythroid cell is a nucleated cell.

As used throughout herein, in one embodiment, an IL-12 fragment or IL-12 polypeptide fragment refers to an IL-12 fragment that binds to an IL-12 receptor, i.e., an IL-12 receptor-binding fragment of IL-12. As used throughout herein, in one embodiment, an IL-12 fragment or IL-12 polypeptide fragment refers to an IL-12 fragment that retains a biological activity of IL-12.

In certain embodiments, the invention provides an engineered erythroid cell comprising an exogenous stimulatory polypeptide comprising the IL-12 p40 polypeptide or a fragment thereof:

(SEQ ID NO: 45)
IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT
FCVQVQGKSKREKKDRVFTDKTSATVICRKNASISVRAQDRYYSSSWSEW
ASVPCS.

In some embodiments, the IL-12 polypeptide comprises a variant of the IL-12 p40 having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 45. In a particular embodiment, the IL-12 p40 polypeptide consists of the amino acid sequence of SEQ ID NO: 45.

The disclosure provides, in another aspect, an engineered erythroid cell comprising a first exogenous stimulatory polypeptide, wherein the first exogenous stimulatory polypeptide comprises an interleukin-12 p35 (IL-12 p35) polypeptide, or a fragment thereof. In some embodiments, the engineered erythroid cell is an enucleated cell. In some embodiments, the engineered erythroid cell is a nucleated cell.

In certain embodiments, the invention provides an engineered erythroid cell comprising an exogenous stimulatory polypeptide comprising the IL-12 p35 polypeptide or a fragment thereof:

(SEQ ID NO: 47)
RNLPVATPDPGMFPCLHHSQNLLRAVSNMLQKARQTLEFYPCTSEEIDHE
DITKDKTSTVEACLPLELTKNESCLNSRETSFITNGSCLASRKTSFMMAL
CLSSIYEDLKMYQVEEKTMNAKLLMDPKRQIELDQNMLAVIDELMQALNE
NSETVPQKSSLEEPDFYKTKIKLCILLHAFRIRAVTIDRVMSYLNAS.

In some embodiments, the IL-12 polypeptide comprises a variant of the IL-12 p35 having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 47. In a particular embodiment, the IL-12 p40 polypeptide consists of the amino acid sequence of SEQ ID NO: 47.

In some embodiments, the disclosure provides an engineered erythroid cell comprising a first exogenous stimulatory polypeptide, wherein the first exogenous stimulatory polypeptide comprises an interleukin-12 p40 (IL-12 p40) polypeptide, or a fragment thereof, and interleukin-12 p35 (IL-12 p35) polypeptide, or a fragment thereof. In some embodiments, the engineered erythroid cell is an enucleated cell. In some embodiments, the engineered erythroid cell is a nucleated cell.

In some embodiments, the IL-12 p40 polypeptide and the IL-12 p35 polypeptide are present as a complex. In another embodiment, the IL-12 p40 polypeptide and the IL-12 p35 polypeptide are present as a fusion polypeptide. In some embodiments, the IL-12 p40 polypeptide is linked to the IL-12 p35 polypeptide by a linker.

In some embodiments, the exogenous stimulatory polypeptide comprises a mature human IL-12p40 polypeptide comprising or consisting of the amino sequence of SEQ ID NO: 45, and a IL-12p35 polypeptide comprising or consisting of the amino acid sequence of SEQ ID NO: 47. In some embodiments, the mature human IL-12p40 polypeptide and the IL-12p35 polypeptide are connected by a linker (e.g., a flexible linker). Any of the linkers described herein may be used. In some embodiments, the linker comprises the amino acid sequence $(GGGGS)_n$ (SEQ ID NO: 75), wherein n is 1, 2, 3, 4, 5, 6, 7, 8, 9 or 10. In some embodiments, the linker consists of the $(GGGGS)_n$ linker (SEQ ID NO: 75), wherein n is 1, 2, 3, 4, 5, 6, 7, 8, 9 or 10. In some embodiments, the linker comprises an amino acid sequence set forth in Table 3. In a particular embodiment, the linker comprises the amino acid sequence GGGGSGGGGSGGGGS (SEQ ID NO: 12). In a further particular embodiment, the linker consists of the amino acid sequence of SEQ ID NO: 12. In some embodiments, the exogenous stimulatory polypeptide comprises mature human IL-12p40 (SEQ ID NO: 45) and IL-12p35 (SEQ ID NO: 47) connected by a flexible linker (SEQ ID NO: 12).

Other suitable linkers, which are known to one skilled in the art, may be used to link the IL-12 p40 and IL-12 p35 polypeptides. In some embodiments, the linker useful in the invention is between 5 and 25 amino acids in length, 5-20 amino acids in length, 10-25 amino acids in length, or 10-20 amino acids in length. In some embodiments, the linker useful in the invention is 10, 11, 12, 13, 14, 15, 16, 17, 18, 19, or 20 amino acids in length. In a preferred embodiment, the linker is non-immunogenic.

In certain embodiments, the invention provides an engineered erythroid cell comprising an exogenous stimulatory polypeptide comprising the IL-12 p40 polypeptide linked to the IL-12 p35 polypeptide by a linker, or a fragment thereof:

(SEQ ID NO: 57)
IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA

-continued

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVETDKTSATVICRKNASISVRAQDRYYSSSWSEW

ASVPCSGGGGSGGGGSGGGGSRNLPVATPDPGMFPCLHHSQNLLRAVSNM

LQKARQTLEFYPCTSEEIDHEDITKDKTSTVEACLPLELTKNESCLNSRE

TSFITNGSCLASRKTSFMMALCLSSIYEDLKMYQVEFKTMNAKLLMDPKR

QIFLDQNMLAVIDELMQALNFNSETVPQKSSLEEPDFYKTKIKLCILLHA

FRIRAVTIDRVMSYLNAS.

In some embodiments, the IL-12 polypeptide comprises a variant of the IL-12 p40/IL-12 p35 fusion having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 57. In a particular embodiment, the IL-12 p40 polypeptide consists of the amino acid sequence of SEQ ID NO: 57.

In some embodiments, the fragment of the IL-12 p40/IL-12 p35 fusion polypeptide comprises at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 or 510 amino acids. In some embodiments, the fragment of the IL-12 p40/IL-12 p35 fusion polypeptide comprises fewer than 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 or 510 amino acids. In some embodiments, fragments or variants of the IL-12 p40/IL-12 p35 fusion polypeptide retain at least 50%, 55%, 60%, 65%, 70%, 75%, 80%, 85%, 90%, 95%, 98% or 99% of the function of wild-type human IL-12 to bind IL-12 receptor, as measured by assays well known in the art, e.g., ELISA, Biacore, or co-immunoprecipitation. In some embodiments, fragments or variants of the IL-12 p40/IL-12 p35 fusion polypeptide retain at least 50%, 55%, 60%, 65%, 70%, 75%, 80%, 85%, 90%, 95%, 98% or 99% of the function of wild-type human IL-12 to induce IL-12-mediated signal transduction, as measured by assays well-known in the art, e.g., electromobility shift assays, ELISAs and other immunoassays.

In some embodiments, the exogenous stimulatory polypeptide comprises an IL-12 polypeptide and a signal peptide. In some embodiments, the exogenous stimulatory polypeptide is a fusion polypeptide comprising an IL-12 polypeptide and a signal peptide. In some embodiments, the exogenous stimulatory polypeptide comprises a signal peptide comprising or consisting of an amino acid sequence set forth in Table 4. In some embodiments, the exogenous stimulatory polypeptide comprises a signal peptide comprising or consisting of a GPA signal peptide. In some embodiments, the exogenous stimulatory polypeptide comprises a signal peptide comprising or consisting of the amino acid sequence of SEQ ID NO: 21. In some embodiments, the exogenous stimulatory polypeptide comprises a leader sequence comprising the amino acid sequence of SEQ ID NO: 21 and aninterleukin-12 (IL-12) polypeptide.

In some embodiments, the exogenous stimulatory polypeptide comprising an IL-12 p40/IL-12 p35 fusion polypeptide is attached to the erythroid cell membrane. In some embodiments, the exogenous stimulatory polypeptide comprises a an IL-12 p40/IL-12 p35 fusion polypeptide and an anchor or transmembrane domain that anchors the polypeptide to the erythroid cell membrane. In certain embodiments, the anchor or transmembrane domain is heterologous to the IL-12 p40/IL-12 p35 fusion polypeptide. In certain embodiments, the anchor or transmembrane domain comprises or consists of GPA or a transmembrane portion thereof. In certain embodiments, the anchor or transmembrane domain comprises or consists of SMIM1, or a transmembrane portion thereof. In some embodiments, the anchor or transmembrane domain comprises or consists of small integral membrane protein 1 (SMIM1), transferrin receptor, Fas ligand (FasL), Kell, or Band 3, or a transmembrane portion thereof (e.g., a transmembrane domain). The exogenous stimulatory polypeptide comprising an IL-12 p40/IL-12 p35 fusion polypeptide may comprising any of the anchor or transmembrane domains described herein.

In some embodiments, the exogenous stimulatory polypeptide comprising an IL-12 p40/IL-12 p35 fusion polypeptide comprises an anchor or transmembrane domain comprising an amino acid sequence as set forth in Table 2. In some embodiments, the exogenous stimulatory polypeptide comprises a mature human IL-12p40 polypeptide comprising or consisting of the amino acid sequence of SEQ ID NO: 45, a linker (e.g., a flexible linker comprising or consisting of the amino acid sequence of SEQ ID NO: 12), and an anchor sequence. In some embodiments, the exogenous stimulatory polypeptide comprises (e.g., from N-terminus to C-terminus), an anchor domain comprising or consisting of the amino acid sequence of SEQ ID NO: 49, a human IL-12 p40 polypeptide comprising or consisting of the amino acid sequence of SEQ ID NO: 45, and a human IL-12 p35 polypeptide comprising or consisting of an amino acid sequence of SEQ ID NO: 47. In some embodiments, the exogenous stimulatory polypeptide comprises (e.g., from N-terminus to C-terminus), an anchor domain comprising or consisting of the amino acid sequence of SEQ ID NO: 49, a linker (e.g., a flexible linker) comprising or consisting of an amino acid sequence of SEQ ID NO: 12, a human IL-12 p40 polypeptide comprising or consisting of the amino acid sequence of SEQ ID NO: 45, a linker (e.g., a flexible linker) comprising or consisting of an amino acid sequence of SEQ ID NO: 12, and a human IL-12 p35 polypeptide comprising or consisting of an amino acid sequence of SEQ ID NO: 47.

In some embodiments, the exogenous stimulatory polypeptide comprises an anchor comprising or consisting of the amino acid sequence of SEQ ID NO: 49 and an IL-12 polypeptide. In some embodiments, the exogenous stimulatory polypeptide comprises an anchor comprising or consisting of SEQ ID NO: 49 and a human IL-12 p40 polypeptide comprising or consisting of the amino acid sequence of SEQ ID NO: 45, and a human IL-12 p35 polypeptide comprising or consisting of the amino acid sequence of SEQ ID NO: 47. In some embodiments, the exogenous stimulatory polypeptide comprises (e.g., from N-terminus to C-terminus) an anchor comprising or consisting of the amino acid sequence of SEQ ID NO: 49, a human IL-12 p40 polypeptide comprising or consisting of the amino acid sequence of SEQ ID NO: 45, a linker (e.g., a flexible linker) comprising or consisting of the amino acid sequence of SEQ ID NO: 12, and a human IL-12 p35 polypeptide comprising or consisting of the amino acid sequence of SEQ ID NO: 47. In some embodiments, the exogenous stimulatory polypeptide comprises the amino acid sequence of SEQ ID NO: 55. In some embodiments, the exogenous stimulatory polypeptide consists of the amino acid sequence of SEQ ID NO: 55.

In some embodiments, an exogenous stimulatory polypeptide comprising an IL-12 polypeptide linked to an anchor comprising SMIM1 (or a SMIM1 transmembrane portion) exhibits increased cell surface expression relative to the cell surface expression of an exogenous stimulatory polypeptide comprising an IL-12 polypeptide linked to an anchor comprising GPA (or a GPA transmembrane portion (e.g., a GPA transmembrane domain)).

In a particular embodiment, the exogenous stimulatory polypeptide comprises the amino acid sequence of SEQ ID NO: 53 or an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 53. In some embodiments, the exogenous stimulatory polypeptide consists of the amino acid sequence of SEQ ID NO: 53.

In a particular embodiment, the exogenous stimulatory polypeptide comprises the amino acid sequence of SEQ ID NO: 55 or an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 55. In some embodiments, the exogenous stimulatory polypeptide consists of the amino acid sequence of SEQ ID NO: 55.

IL-12 and 4-1BBL

The engineered erythroid cell may comprise a first exogenous stimulatory polypeptide comprising the IL-12 p40/IL-12 p35 fusion polypeptide as described herein and one or more additional exogenous stimulatory polypeptides. For example, the engineered erythroid cell may further comprise a second exogenous stimulatory polypeptide comprising a 4-1BBL (4-1BB ligand) polypeptide. Thus, the invention also provides an engineered erythroid cell comprising a first exogenous stimulatory polypeptide, wherein the first exogenous stimulatory polypeptide comprises an interleukin-12 p40 (IL-12 p40) polypeptide, or a fragment thereof, and an interleukin-12 p35 (IL-12 p35) polypeptide, or a fragment thereof, (e.g., an IL-12 p40-p35 fusion polypeptide) and a second exogenous stimulatory polypeptide, wherein the second exogenous stimulatory polypeptide comprises 4-1BBL, or a stimulatory fragment thereof.

In certain embodiments, 4-1BBL is in its natural trimeric form. In further embodiments, the engineered erythroid cells described herein express 4-1BBL in its natural trimeric form, where the natural trimeric form is important for the efficacy and activity of the engineered erythroid cells. In some embodiments, the exogenous stimulatory polypeptide comprises human 4-1BBL, e.g., an extracellular portion of human 4-1BBL. In some embodiments, the exogenous stimulatory polypeptide comprises a 4-1BBL polypeptide comprising or consisting of the amino acid sequence of SEQ ID NO: 41. In some embodiments, the first exogenous stimulatory polypeptide comprises an interleukin-12 (IL-12) polypeptide, e.g., a human IL-12 p40 polypeptide comprising or consisting of SEQ ID NO: 45 and a human IL-12 p35 polypeptide comprising or consisting of SEQ ID NO: 47 (e.g., an IL-12 p40-p35 fusion polypeptide comprising the amino acid sequence of SEQ ID NO: 57).

In some embodiments, the first exogenous stimulatory polypeptide comprises (e.g., from N-terminus to C-terminus) an anchor (e.g., a SMIM1 anchor) comprising or consisting of the amino acid sequence of SEQ ID NO: 49, a human IL-12 p40 polypeptide comprising or consisting of the amino acid sequence of SEQ ID NO: 45, a linker comprising the amino acid sequence of SEQ ID NO: 12, and a human IL-12 p35 polypeptide comprising or consisting of the amino acid sequence of SEQ ID NO: 47. In some embodiments, the second exogenous stimulatory polypeptide comprises a human extracellular 4-1BBL polypeptide comprising or consisting of the amino acid sequence of SEQ ID NO: 41, a linker (e.g., a 4-1BBL linker) comprising or consisting of the amino acid sequence of SEQ ID NO: 39, and a GPA anchor comprising or consisting of the amino acid sequence of SEQ ID NO: 25). In some embodiments, the first exogenous stimulatory polypeptide comprises or consists of the amino acid sequence of SEQ ID NO: 55, and the second exogenous stimulatory polypeptide comprises or consists of the amino acid sequence of SEQ ID NO: 43.

In some embodiments, the first exogenous stimulatory polypeptide and the second exogenous stimulatory polypeptide are encoded by a single nucleic acid molecule, and initially expressed as a single fusion polypeptide, wherein a T2A skip peptide (e.g., SEQ ID NO: 64) is disposed between the first exogenous stimulatory polypeptide and the second exogenous stimulatory polypeptide. In some embodiments, the first exogenous stimulatory polypeptide comprising 4-1BBL polypeptide and the second exogenous stimulatory polypeptide comprising IL-12 polypeptide are encoded by a single nucleic acid molecule, and initially expressed as a single fusion polypeptide, wherein a T2A skip peptide (e.g., SEQ ID NO: 64) is disposed between the exogenous stimulatory polypeptide comprising a 4-1BBL polypeptide and the exogenous stimulatory polypeptide comprising an IL-12 polypeptide. Introduction of the 2A skip peptide or element (e.g., a T2A sequence) allows for post-translational cleavage into two separate exogenous stimulatory polypeptides (comprising either 4-1BBL or IL-12 polypeptides) (see, e.g., Liu et al. (2017) Sci. Rep. 7(1): 2193, incorporated in its entirety herein by reference). According to certain embodiments, following post-translational cleavage, the exogenous stimulatory polypeptide comprising a 4-1BBL polypeptide and the exogenous stimulatory polypeptide comprising an IL-12 polypeptide are anchored to the erythroid cell surface. Multiple 2A elements are known in the art and can be used as described herein, including T2A, P2A, E2A, and F2A (see, e.g., Liu et al. 2017).

In some embodiments, the engineered erythroid cell comprises a polypeptide which comprises a GPA signal peptide (SEQ ID NO: 21), a 4-1BBL polypeptide (SEQ ID NO: 41), a 4-1BBL linker (SEQ ID NO: 40), a GPA anchor (SEQ ID NO: 25), a T2A skip peptide (SEQ ID NO: 64), a SMIM1 anchor (SEQ ID NO: 49), a linker (SEQ ID NO: 12), an IL12 p40 polypeptide (SEQ ID NO: 45), a flexible linker (SEQ ID NO: 12), and an IL-12 p35 polypeptide (SEQ ID NO: 47).

In some embodiments, the polypeptide comprises SEQ ID NO: 62. In some embodiments, the polypeptide consists of SEQ ID NO: 62. In some embodiments, the engineered erythroid cell is prepared by using a nucleic acid that encodes a polypeptide which encodes, e.g., from 5' to 3', a GPA signal peptide (SEQ ID NO: 21), a 4-1BBL polypeptide (SEQ ID NO: 41), a 4-1BBL linker (SEQ ID NO: 40), a GPA anchor (SEQ ID NO: 25), a T2A skip peptide (SEQ ID NO: 64), a SMIM1 anchor (SEQ ID NO: 49), a linker (SEQ ID NO: 12), an IL12 p40 polypeptide (SEQ ID NO: 45), a flexible linker (SEQ ID NO: 12), and an IL-12 p35 polypeptide (SEQ ID NO: 47). In some embodiments, the nucleic acid encodes a polypeptide comprising SEQ ID NO: 62. In some embodiments, the nucleic acid comprises or consists of SEQ ID NO: 63.

In certain embodiments, the combination of a first exogenous stimulatory polypeptide comprising IL-12 and a second exogenous stimulatory polypeptide comprising 4-1BBL produces a synergistic response (e.g., during immune killer cell activation). For example, exogenous stimulatory polypeptides, each comprising either IL-12 or 4-1BBL, when expressed on an erythroid cell, may act together to produce a more robust activation of immune killer cells (e.g. NK cells and/or CD8+ T-cells) as compared to the effects of either stimulatory polypeptide alone. Such synergistic activity is demonstrated in the Examples provided herein. Accordingly, in some embodiments, the invention provides an engineered erythroid cell comprising a first and a second exogenous stimulatory polypeptides, wherein the first exogenous stimulatory polypeptide comprises an IL-12 polypeptide, or fragment thereof, and wherein the second exogenous stimulatory polypeptide comprises 4-1BBL, wherein the first exogenous stimulatory polypeptide and second exogenous stimulatory polypeptide stimulate an immune killer cell with synergistic activity ex vivo or in vivo. In one embodiment, the first exogenous stimulatory polypeptide comprises IL-12 p40/IL-12 p35 as a fusion protein and, e.g., at the surface of the cell.

In another embodiment, the engineered erythroid cell may comprise a first exogenous stimulatory polypeptide comprising the IL-12 p40/IL-12 p35 fusion polypeptide as described herein and one or more additional exogenous stimulatory polypeptides. For example, the engineered erythroid cell may further comprise a second exogenous stimulatory polypeptide from the group comprising the IL-15 polypeptide, or a fragment thereof, and an extracellular portion of IL-15RA, or a fragment thereof. Thus, the invention also provides an engineered erythroid cell comprising a first exogenous stimulatory polypeptide, wherein the first exogenous stimulatory polypeptide comprises an interleukin-12 p40 (IL-12 p40) polypeptide, or a fragment thereof, and an interleukin-12 p35 (IL-12 p35) polypeptide, or a fragment thereof, (e.g., an IL-12 p40-p35 fusion polypeptide) and a second exogenous stimulatory polypeptide, wherein the second exogenous stimulatory polypeptide comprises the IL-15 polypeptide, or a fragment thereof, and an extracellular portion of IL-15RA, or a fragment thereof (e.g., an IL-15/IL-15RA fusion polypeptide).

In certain embodiments, the combination of a first exogenous stimulatory polypeptide comprising IL-12 and a second exogenous stimulatory polypeptide comprising IL-15/IL-15RA produces a synergistic response (e.g., during immune killer cell activation). For example, exogenous stimulatory polypeptides, each comprising either IL-12 or IL-15/IL-15RA, when expressed on an erythroid cell, may act together to produce a more robust activation of immune killer cells (e.g. NK cells and/or CD8+ T-cells) as compared to the effects of either stimulatory polypeptide alone. Such synergistic activity is demonstrated in the Examples provided herein. Accordingly, in some embodiments, the invention provides an engineered erythroid cell comprising a first and a second exogenous stimulatory polypeptides, wherein the first exogenous stimulatory polypeptide comprises an IL-12 polypeptide, or fragment thereof, and wherein the second exogenous stimulatory polypeptide comprises IL-15/IL-15RA, wherein the first exogenous stimulatory polypeptide and second exogenous stimulatory polypeptide stimulate an immune killer cell with synergistic activity ex vivo or in vivo. In one embodiment, the first exogenous stimulatory polypeptide comprises IL-12 p40/IL-12 p35 as a fusion protein and, e.g., at the surface of the cell.

IL-12 Toxicity

In some aspects, the present disclosure provides an engineered erythroid cell comprising a first exogenous stimulatory polypeptide comprising an IL-12 polypeptide, wherein the cell is capable of stimulating an immune killer cell, and wherein the cell has a higher therapeutic index (TI) as compared to an isolated IL-12 polypeptide upon administration to a subject. In some embodiments, the cell has an at least 5%, 10%, 15%, 20%, 30%, 40%, 50%, 60%, 70%, 80%, 90% higher therapeutic index as compared to an isolated IL-12 polypeptide upon administration to a subject. In some embodiments, the cell has an at least 1-fold, 2-fold, 3-fold, 4-fold, 5-fold, or 10-fold higher therapeutic index as compared to an isolated IL-12 polypeptide upon administration to a subject.

In some aspects, the disclosure provides an engineered erythroid cell comprising a first exogenous stimulatory polypeptide comprising an IL-12 polypeptide, wherein the cell exhibits less toxicity as compared to an isolated IL-12 polypeptide upon administration to a subject.

In some embodiments, an isolated polypeptide, e.g., IL-12 polypeptide, IL-15 polypeptide, or 4-1BB agonist antibody, refers to a polypeptide that is recombinant. In some embodiments, an isolated polypeptide, e.g., IL-12 polypeptide, IL-15 polypeptide, or 4-1BB agonist polypeptide (such as a 4-1BB agonist antibody), refers to a polypeptide that is not comprised in a cell, in a cell membrane, on the cell surface, and/or conjugated to a cell.

In some embodiments, the cell exhibits less toxicity as compared to an equivalent amount of isolated IL-12 polypeptide. In some embodiments, the equivalent amount of isolated IL-12 polypeptide is an amount quantitatively or functionally equivalent to the amount of IL-12 polypeptide comprised in the cell. In some embodiments, the equivalent amount of an isolated IL-12 polypeptide is the quantitatively same amount (e.g., in copy number or molarity) as the amount of IL-12 polypeptide comprised in the engineered erythroid cell. In some embodiments, the equivalent amount of isolated IL-12 polypeptide is an amount of isolated IL-12 polypeptide having the same biological activity as the amount of IL-12 polypeptide comprised in the engineered erythroid cell. In some embodiments, the equivalent amount of isolated IL-12 polypeptide is an amount of isolated IL-12 polypeptide having the same biological activity as the engineered erythroid cell comprising the IL-12 polypeptide. In some embodiments, the equivalent amount of isolated IL-12 polypeptide is an amount of isolated IL-12 polypeptide having the same therapeutic potency as the amount of IL-12 polypeptide comprised in the engineered erythroid cell. In some embodiments, the equivalent amount of isolated IL-12 polypeptide is an amount of isolated IL-12 polypeptide having the same therapeutic potency as the engineered erythroid cell comprising the IL-12 polypeptide.

In some embodiments, the IL-12 polypeptide comprises a p40 polypeptide and p35 polypeptide.

In some embodiments, the toxicity comprises liver toxicity. In some embodiments, the toxicity comprises blood toxicity. In some embodiments, the liver toxicity is measured by an indicator of liver toxicity selected from the group consisting of increased serum level of IFNg, increased serum level of ALT, increased level of infiltrating macrophages in the liver, increased level of infiltrating CD8+ T cells or CD8+/Eomes+/KLGR1+ T cells in the liver, increased liver weight, increased liver inflammation score, decreased neutrophil count, decreased lymphocyte count, decreased monocyte count, and decreased hemoglobin level. In some embodiments, the indicator of liver toxicity comprises increased serum level of interferon gamma (IFNg). In some embodiments, the indicator of liver toxicity comprises increased serum level of alanine transaminase (ALT). In some embodiments, the indicator of liver toxicity comprises increased level of infiltrating macrophages in the liver or spleen. In some embodiments, the indicator of liver toxicity comprises increased infiltration of CD8+ T cells or CD8+/Eomes+/KLGR1+ T cells in the liver. In some embodiments, the indicator of liver toxicity comprises increased liver inflammation score.

In some embodiments, the liver inflammation score is an Ishak score, as described herein.

In some embodiments, the liver toxicity is assessed using a mouse model for liver toxicity, as described herein.

In some embodiments, the blood toxicity is measured by an indicator of blood toxicity selected from the group consisting of decreased neutrophil count, decreased lymphocyte count, decreased monocyte count, and decreased hemoglobin level. In some embodiments, the indicator of blood toxicity is measured in a whole blood sample. In some embodiments, the indicator of blood toxicity is measured in a serum sample. In some embodiments, the indicator of blood toxicity is measured in a plasma sample.

In some embodiments, the toxicity is measured by decreased body weight.

In some embodiments, a level of the indicator of toxicity measured in the subject after administration of the cell is compared to a level of the indicator of toxicity before administration. In some embodiments, a level of the indicator of toxicity measured in the subject after administration of the cell is compared to a threshold or control level of the indicator of toxicity. In some embodiments, the indicator of toxicity is determined by serum ALT levels, as described herein. In some embodiments, the indicator of liver toxicity is increased serum level of ALT, as described herein. In some embodiments, the indicator of toxicity is determined by serum AST levels, as described herein. In some embodiments, the indicator of liver toxicity is increased serum level of AST, as described herein. In some embodiments, the indicator of toxicity is determined by serum ALP levels, as described herein. In some embodiments, the indicator of liver toxicity is increased serum level of ALP, as described herein. In some embodiments, the indicator of toxicity is determined by lymphocyte count, as described herein. In some embodiments, the indicator of blood toxicity is identified by a decreased lymphocyte count. In some embodiments, the indicator of blood toxicity is identified by a red blood cell count, as described herein. In some embodiments, the indicator of blood toxicity is identified by a decreased red blood cell count, as described herein. In some embodiments, the indicator of blood toxicity is identified by a white blood cell count, as described herein. In some embodiments, the indicator of blood toxicity is identified by a decreased white blood cell count, as described herein. In some embodiments, the indicator of blood toxicity is identified by a hemoglobin level, as described herein. In some embodiments, the indicator of blood toxicity is identified by a decreased hemoglobin level.

In some embodiments, the cell exhibits at least 10%, at least 20%, at least 30%, at least 40%, at least 50%, at least 60%, at least 70%, at least 80%, at least 90%, at least 95% or at least 100% less toxicity upon administration to the subject than the isolated IL-12 polypeptide. In some embodiments, the cell exhibits at least 1.5-fold, at least 2-fold, at least 3-fold, at least 4-fold, at least 5-fold or at least 10-fold less toxicity upon administration to the subject than the isolated IL-12 polypeptide.

In some embodiments, the cell is capable of stimulating an immune killer cell in the subject.

IL-12 and 4-1BBL Toxicity

In some aspects, the disclosure provides an engineered erythroid cell comprising a first exogenous stimulatory polypeptide and a second exogenous stimulatory polypeptide, wherein the first exogenous stimulatory polypeptide comprises a 4-1BBL polypeptide and the second exogenous stimulatory polypeptide comprises an IL-12 polypeptide, wherein the cell is capable of stimulating an immune killer cell, and wherein the cell has a higher therapeutic index (TI) as compared to an isolated 4-1BBL agonist antibody, an isolated IL-12 polypeptide, or a combination thereof, upon administration to a subject. In some embodiments, the cell has an at least 5%, 10%, 15%, 20%, 30%, 40%, 50%, 60%, 70%, 80%, 90% higher therapeutic index as compared to an isolated 4-1BBL agonist antibody, an isolated IL-12 polypeptide, or a combination thereof, upon administration to a subject. In some embodiments, the cell has an at least 1-fold, 2-fold, 3-fold, 4-fold, 5-fold, or 10-fold higher therapeutic index as compared to an isolated 4-1BBL agonist antibody, an isolated IL-12 polypeptide, or a combination thereof, upon administration to a subject.

In some aspects, the disclosure provides an engineered erythroid cell comprising a first exogenous stimulatory polypeptide and second exogenous stimulatory polypeptide, wherein the first exogenous stimulatory polypeptide comprises a 4-1BBL polypeptide, and the second exogenous stimulatory polypeptide comprises an IL-12 polypeptide, wherein the cell exhibits less toxicity as compared to an isolated 4-1BB agonist polypeptide, an isolated IL-12 polypeptide, or a combination thereof, upon administration to a subject. In some embodiments, the cell exhibits less toxicity as compared to an equivalent amount of an isolated 4-1BB agonist polypeptide, an equivalent amount of an isolated IL-12 polypeptide, or a combination thereof, upon administration to a subject. In some embodiments, the equivalent amount of isolated 4-1BB agonist antibody is an amount equivalent to the amount of 4-1BBL polypeptide comprised in the cell. In some embodiments, the equivalent amount of isolated 4-1BB agonist antibody is an amount of isolated 4-1BB agonist antibody equivalent (e.g., in copy number, weight or molarity) to the amount of 4-1BBL polypeptide comprised in the engineered erythroid cell. In some embodiments, the equivalent amount of isolated 4-1BB agonist antibody is an amount of isolated 4-1BB agonist antibody having the same agonist activity as the amount of 4-1BBL polypeptide comprised in the engineered erythroid cell. In some embodiments, the equivalent amount of isolated 4-1BB agonist antibody is an amount of isolated 4-1BB agonist antibody having the same biological effect as the amount of 4-1BBL polypeptide comprised in the engineered erythroid cell. In some embodiments, the equivalent amount of isolated 4-1BB agonist antibody is an amount of isolated 4-1BB agonist antibody having the same therapeutic potency as the amount of 4-1BBL polypeptide comprised in the engineered erythroid cell.

In some embodiments, the 4-1BB agonist antibody is the antibody 3H3, or an antigen-binding fragment thereof, or the antibody utomilumab, or an antigen-binding fragment thereof.

In some embodiments, the equivalent amount of isolated IL-12 polypeptide is an amount quantitatively or functionally equivalent to the amount of IL-12 polypeptide comprised in the cell. In some embodiments, the equivalent amount of an isolated IL-12 polypeptide is the quantitatively same amount (e.g., in copy number or molarity) as the amount of IL-12 polypeptide comprised in the engineered erythroid cell. In some embodiments, the equivalent amount of isolated IL-12 polypeptide is an amount of isolated IL-12 polypeptide having the same biological activity as the amount of IL-12 polypeptide comprised in the engineered erythroid cell. In some embodiments, the equivalent amount of isolated IL-12 polypeptide is an amount of isolated IL-12 polypeptide having the same therapeutic potency as the amount of IL-12 polypeptide comprised in the engineered erythroid cell. In some embodiments, the IL-12 polypeptide comprises a p40 polypeptide and p35 polypeptide.

In some embodiments, the toxicity comprises liver toxicity. In some embodiments, the toxicity comprises blood toxicity. In some embodiments, the liver toxicity is measured by an indicator of liver toxicity selected from the group consisting of increased serum level of IFNg, increased serum level of ALT, increased level of infiltrating macrophages in the liver, increased level of infiltrating CD8+ T cells or CD8+/Eomes+/KLGR1+ T cells in the liver, increased liver weight, increased liver inflammation score, decreased neutrophil count, decreased lymphocyte count, decreased monocyte count, and decreased hemoglobin level. In some embodiments, the indicator of liver toxicity comprises increased serum level of interferon gamma (IFNg). In some embodiments, the indicator of liver toxicity comprises increased serum level of alanine transaminase (ALT). In some embodiments, the indicator of liver toxicity comprises increased level of infiltrating macrophages in the liver or spleen. In some embodiments, the indicator of liver toxicity comprises increased infiltration of CD8+ T cells or CD8+/Eomes+/KLGR1+ T cells in the liver. In some embodiments, the indicator of liver toxicity comprises increased liver inflammation score.

In some embodiments, the cell exhibits at least 10%, at least 20%, at least 30%, at least 40%, at least 50%, at least 60%, at least 70%, at least 80%, at least 90%, at least 95% or at least 100% less toxicity upon administration to the subject than the isolated 4-1BBL polypeptide and the isolated IL-12 polypeptide. In some embodiments, the cell exhibits at least 1.5-fold, at least 2-fold, at least 3-fold, at least 4-fold, at least 5-fold or at least 10-fold less toxicity upon administration to the subject than the isolated 4-1BBL polypeptide and the isolated IL-12 polypeptide.

In some embodiments, the cell is capable of stimulating an immune killer cell in the subject.

IL-12 and IL-15 Toxicity

In some aspects, the disclosure provides an engineered erythroid cell comprising a first exogenous stimulatory polypeptide and a second exogenous stimulatory polypeptide, wherein the first exogenous stimulatory polypeptide comprises a IL-12 polypeptide and the second exogenous stimulatory polypeptide comprises an IL-15 polypeptide, wherein the cell is capable of stimulating an immune killer cell, and wherein the cell has a higher therapeutic index (TI) as compared to an isolated IL-12 polypeptide, an isolated IL-15 polypeptide, or a combination thereof, upon administration to a subject. In some embodiments, the cell has an at least 5%, 10%, 15%, 20%, 30%, 40%, 50%, 60%, 70%, 80%, 90% higher therapeutic index as compared to an isolated IL-12 polypeptide, an isolated IL-15 polypeptide, or a combination thereof, upon administration to a subject. In some embodiments, the cell has an at least 1-fold, 2-fold, 3-fold, 4-fold, 5-fold, or 10-fold higher therapeutic index as compared to an isolated IL-12 polypeptide, an isolated IL-15 polypeptide, or a combination thereof, upon administration to a subject.

In some aspects, the disclosure provides an engineered erythroid cell comprising a first exogenous stimulatory polypeptide and second exogenous stimulatory polypeptide, wherein the first exogenous stimulatory polypeptide comprises a IL-12 polypeptide, and the second exogenous stimulatory polypeptide comprises an IL-15 polypeptide, wherein the cell exhibits less toxicity as compared to an isolated IL-12 polypeptide, an isolated IL-15 polypeptide, or a combination thereof, upon administration to a subject. In some embodiments, the cell exhibits less toxicity as compared to an equivalent amount of an isolated IL-12 polypeptide, an equivalent amount of an isolated IL-15 polypeptide, or a combination thereof, upon administration to a subject. In some embodiments, the equivalent amount of isolated IL-12 polypeptide is an amount quantitatively or functionally equivalent to the amount of IL-12 polypeptide comprised in the cell. In some embodiments, the equivalent amount of an isolated IL-12 polypeptide is the quantitatively same amount (e.g., in copy number or molarity) as the amount of IL-12 polypeptide comprised in the engineered erythroid cell. In some embodiments, the equivalent amount of isolated IL-12 polypeptide is an amount of isolated IL-12 polypeptide having the same biological activity as the amount of IL-12 polypeptide comprised in the engineered erythroid cell. In some embodiments, the equivalent amount of isolated IL-12 polypeptide is an amount of isolated IL-12 polypeptide having the same therapeutic potency as the amount of IL-12 polypeptide comprised in the engineered erythroid cell.

In some embodiments, the IL-12 polypeptide comprises a p40 polypeptide and p35 polypeptide.

In some embodiments, the equivalent amount of isolated IL-15 polypeptide is an amount quantitatively or functionally equivalent to the amount of IL-15 polypeptide comprised in the cell. In some embodiments, the equivalent amount of an isolated IL-15 polypeptide is the quantitatively same amount (e.g., in copy number or molarity) as the amount of IL-15 polypeptide comprised in the engineered erythroid cell. In some embodiments, the equivalent amount of isolated IL-15 polypeptide is an amount of isolated IL-15 polypeptide having the same biological activity as the amount of IL-15 polypeptide comprised in the engineered erythroid cell. In some embodiments, the equivalent amount of isolated IL-15 polypeptide is an amount of isolated IL-15 polypeptide having the same therapeutic potency as the amount of IL-15 polypeptide comprised in the engineered erythroid cell.

In some embodiments, the second exogenous polypeptide comprises an IL-15 polypeptide, or a fragment thereof, and an extracellular portion of an IL-15RA polypeptide, or a fragment thereof.

In some embodiments, the first exogenous polypeptide comprises an IL-15 polypeptide, or a fragment thereof, and an extracellular portion of an IL-15RA polypeptide, or a fragment thereof. In some embodiments, the IL-15 polypeptide and the extracellular portion of an IL-15RA polypeptide are present as a complex. In some embodiments, the IL-15 polypeptide and the extracellular portion of an IL-15RA polypeptide are a fusion polypeptide. In some embodiments, the IL-15 polypeptide, or a fragment thereof, is linked to the extracellular portion of the IL-15RA polypeptide, or a fragment thereof, by a linker. In some embodiments, the linker comprises GGGGS (SEQ ID NO: 11). In some embodiments, the linker comprises a $(GGGGS)_3$ linker (SEQ ID NO: 12). In some embodiments, the fusion polypeptide comprises an amino acid sequence that is at least 95% identical to SEQ ID NO. 1.

In some embodiments, the first exogenous stimulatory polypeptide comprises an IL-15 polypeptide, or a fragment thereof, and a IL-15 receptor alpha sushi-binding domain. In some embodiments, the IL-15 polypeptide, or a fragment thereof, and the IL-15 receptor alpha sushi-binding domain are present as a complex. In some embodiments, the IL-15 polypeptide, or a fragment thereof, and the IL-15 receptor alpha sushi-binding domain are present as a fusion polypeptide. In some embodiments, the IL-15 polypeptide, or a fragment thereof, is linked to the IL-15 receptor alpha sushi-binding domain by a linker. In some embodiments, the linker comprises GGGGS (SEQ ID NO: 11), optionally wherein the linker comprises a $(GGGGS)_3$ linker (SEQ ID NO: 12). In some embodiments, the fusion polypeptide comprises an amino acid sequence that is at least 95% identical to SEQ ID NO. 2.

In some embodiments, the toxicity comprises liver toxicity. In some embodiments, the toxicity comprises blood toxicity. In some embodiments, the liver toxicity is measured by an indicator of liver toxicity selected from the group consisting of increased serum level of IFNg, increased serum level of ALT, increased level of infiltrating macrophages in the liver, increased level of infiltrating CD8+ T cells or CD8+/Eomes+/KLGR1+ T cells in the liver, increased liver weight, increased liver inflammation score, decreased neutrophil count, decreased lymphocyte count, decreased monocyte count, and decreased hemoglobin level. In some embodiments, the indicator of liver toxicity comprises increased serum level of interferon gamma (IFNg). In some embodiments, the indicator of liver toxicity comprises increased serum level of alanine transaminase (ALT). In some embodiments, the indicator of liver toxicity comprises increased level of infiltrating macrophages in the liver or spleen. In some embodiments, the indicator of liver toxicity comprises increased infiltration of CD8+ T cells or CD8+/Eomes+/KLGR1+ T cells in the liver. In some embodiments, the indicator of liver toxicity comprises increased liver inflammation score.

In some embodiments, the liver inflammation score is an Ishak score, as described herein.

In some embodiments, the liver toxicity is assessed using a mouse model for liver toxicity, as described herein.

In some embodiments, the blood toxicity is measured by an indicator of blood toxicity selected from the group consisting of decreased neutrophil count, decreased lymphocyte count, decreased monocyte count, and decreased hemoglobin level. In some embodiments, the indicator of blood toxicity is measured in a whole blood sample. In some embodiments, the indicator of blood toxicity is measured in a serum sample. In some embodiments, the indicator of blood toxicity is measured in a plasma sample.

In some embodiments, the toxicity is measured by decreased body weight.

In some embodiments, a level of the indicator of toxicity measured in the subject after administration of the cell is compared to a level of the indicator of toxicity before administration. In some embodiments, a level of the indicator of toxicity measured in the subject after administration of the cell is compared to a threshold or control level of the indicator of toxicity. In some embodiments, the indicator of toxicity is determined by serum ALT levels, as described herein. In some embodiments, the indicator of liver toxicity is increased serum level of ALT, as described herein. In some embodiments, the indicator of toxicity is determined by serum AST levels, as described herein. In some embodiments, the indicator of liver toxicity is increased serum level of AST, as described herein. In some embodiments, the indicator of toxicity is determined by serum ALP levels, as described herein. In some embodiments, the indicator of liver toxicity is increased serum level of ALP, as described herein. In some embodiments, the indicator of toxicity is determined by lymphocyte count, as described herein. In some embodiments, the indicator of blood toxicity is identified by a decreased lymphocyte count. In some embodiments, the indicator of blood toxicity is identified by a red blood cell count, as described herein. In some embodiments, the indicator of blood toxicity is identified by a decreased red blood cell count, as described herein. In some embodiments, the indicator of blood toxicity is identified by a white blood cell count, as described herein. In some embodiments, the indicator of blood toxicity is identified by a decreased white blood cell count, as described herein. In some embodiments, the indicator of blood toxicity is identified by a hemoglobin level, as described herein. In some embodiments, the indicator of blood toxicity is identified by a decreased hemoglobin level.

In some embodiments, the cell exhibits at least 10%, at least 20%, at least 30%, at least 40%, at least 50%, at least 60%, at least 70%, at least 80%, at least 90%, at least 95% or at least 100% less toxicity upon administration to the subject than the isolated IL-12 polypeptide and the isolated IL-15 polypeptide. In some embodiments, the cell exhibits at least 1.5-fold, at least 2-fold, at least 3-fold, at least 4-fold, at least 5-fold or at least 10-fold less toxicity upon administration to the subject than the isolated IL-12 polypeptide and the isolated IL-15 polypeptide.

In some embodiments, the cell is capable of stimulating an immune killer cell in the subject.

Nucleic Acid Sequences Encoding IL-12 Polypeptides

In certain embodiments, the invention provides an engineered erythroid cell comprising a nucleic acid sequence encoding an exogenous stimulatory polypeptide comprising an IL-12 polypeptide as described herein. In certain embodiments, the invention provides an engineered erythroid cell prepared by using (e.g., introducing into an erythroid precursor cell) a nucleic acid sequence encoding an exogenous stimulatory polypeptide comprising IL-12 as described herein. For example, in some embodiments, the erythroid cell comprises a nucleic acid sequence encoding an exogenous stimulatory polypeptide comprising an IL-12 p40 polypeptide. In some embodiments, the nucleic acid sequence encoding the exogenous stimulatory polypeptide comprising an IL-12 p40 polypeptide comprises the nucleic acid sequence of SEQ ID NO: 46. In some embodiments, the nucleic acid sequence encoding the exogenous stimulatory polypeptide comprising an IL-12 p40 polypeptide comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 46. In some embodiments, the nucleic acid sequence encoding the exogenous stimulatory polypeptide comprising an IL-12 p40 polypeptide consists of the nucleic acid sequence of SEQ ID NO: 46.

In some embodiments, the engineered erythroid cell comprises a nucleic acid sequence encoding an exogenous stimulatory polypeptide comprising an IL-12 p35 polypeptide. In some embodiments, the nucleic acid sequence encoding the exogenous stimulatory polypeptide comprising an IL-12 p35 polypeptide comprises the nucleic acid sequence of SEQ ID NO: 48. In some embodiments, the nucleic acid sequence encoding the exogenous stimulatory polypeptide comprising an IL-12 p35 polypeptide comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 48. In some embodiments, the nucleic acid sequence encoding the exogenous stimulatory polypeptide comprising an IL-12 p35 polypeptide consists of the nucleic acid sequence of SEQ ID NO: 48.

In a particular embodiment, the nucleic acid sequence encoding an exogenous stimulatory polypeptide comprising an IL-12 polypeptide comprises the nucleic acid sequence of SEQ ID NO: 58. In some embodiments, the nucleic acid sequence encoding an exogenous stimulatory polypeptide comprising an IL-12 polypeptide comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 58.

In a particular embodiment, the nucleic acid sequence encodes an exogenous stimulatory polypeptide comprising an IL-12 V1 construct. In a particular embodiment, the nucleic acid sequence encoding an exogenous stimulatory polypeptide comprising an IL-12 V1 construct comprises the nucleic acid sequence of SEQ ID NO: 54. In some embodiments, the nucleic acid sequence encoding an exogenous stimulatory polypeptide comprising an IL-12 V1 construct comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 54.

In a particular embodiment, the nucleic acid sequence encodes an exogenous stimulatory polypeptide comprising an IL-12 V2 construct. In a particular embodiment, the nucleic acid sequence encoding an exogenous stimulatory polypeptide comprising an IL-12 V2 construct comprises the nucleic acid sequence of SEQ ID NO: 56. In some embodiments, the nucleic acid sequence encoding an exogenous stimulatory polypeptide comprising an IL-12 V2 construct comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 56.

In a particular embodiment, the nucleic acid sequence encodes a exogenous stimulatory polypeptide comprising a 4-1BBL-T2A-IL-12 construct. In a particular embodiment, the nucleic acid sequence encoding a exogenous stimulatory polypeptide comprising a 4-1BBL-T2A-IL-12 construct comprises the nucleic acid sequence of SEQ ID NO: 63. In some embodiments, the nucleic acid sequence encoding a exogenous stimulatory polypeptide comprising a 4-1BBL-T2A-IL-12 construct comprises a nucleic acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO: 63.

Various methods and software programs can be used to determine the homology between two or more peptides or nucleic acids, such as NCBI BLAST, Clustal W, MAFFT, Clustal Omega, AlignMe, Praline, or another suitable method or algorithm. In some embodiments, percent identity is calculated by FastDB based upon the following parameters: mismatch penalty of 1; gap penalty of 1; gap size penalty of 0.33; and joining penalty of 30.

An example of a useful algorithm is PILEUP. PILEUP creates a multiple sequence alignment from a group of related sequences using progressive, pairwise alignments. It can also plot a tree showing the clustering relationships used to create the alignment. Useful PILEUP parameters including a default gap weight of 3.00, a default gap length weight of 0.10, and weighted end gaps.

Another example of a useful algorithm is the BLAST algorithm. A useful example of a BLAST program is the WU-BLAST-2 program. WU-BLAST-2 uses several search parameters, most of which are set to the default values. The adjustable parameters are set with the following values: overlap span=1, overlap fraction=0.125, word threshold (T)=ll. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST. Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to about 22 bits.

An additional useful tool is Clustal, a series of commonly used computer programs for multiple sequence alignment. Recent versions of Clustal include ClustalW, ClustalX and Clustal Omega. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

Polypeptides and Nucleic Acids

In one aspect, the disclosure provides isolated exogenous stimulatory polypeptides described herein. In some embodiments, the exogenous stimulatory polypeptide comprises an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, or 100% sequence identity to the amino acid sequence of an exogenous stimulatory polypeptide described herein. In some embodiments, the polypeptide comprises a signal sequence. In some embodiments, the polypeptide lacks a signal sequence. In some embodiments, the exogenous stimulatory polypeptides are recombinantly produced. Methods for producing recombinant proteins are known in the art and described herein.

In another aspect, the disclosure provides nucleic acids (e.g., DNA or RNA (e.g., mRNA)) encoding an exogenous polypeptide described herein. In some embodiments, the nucleic acids are codon-optimized for expression in a desired cell type (e.g., a bacterial or mammalian cell).

Polypeptide Copy Number

It will be appreciated by one skilled in the art that use of recombinant DNA technologies can improve control of expression of transfected nucleic acid molecules by manipulating, for example, the number of copies of the nucleic acid molecules within the host cell.

As discussed herein, in one aspect, the disclosure features an erythroid cell engineered to stimulate an immune cell, wherein the immune cell is an immune killer cell, comprising a plurality of exogenous stimulatory polypeptides sufficient to stimulate the immune killer cell. In some embodiments, the engineered erythroid cell is an enucleated cell. In some embodiments, the engineered erythroid cell is a nucleated cell. In some embodiments, the erythroid cell comprises a first exogenous stimulatory polypeptide and a second exogenous polypeptide. In some embodiments, the erythroid cell comprises at least a first exogenous stimulatory polypeptide, a second exogenous polypeptide and a third exogenous stimulatory polypeptide. In some embodiments, at least one exogenous polypeptide is present at a copy number of greater than $10^4$, $10^5$, or $10^6$. In some embodiments, the first exogenous stimulatory polypeptide is present at a copy number of no more than 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% greater, or no more than 2, 5, 10, 20, 50, 100, 200, 500, or 1000 times greater than the copy number of the second exogenous stimulatory polypeptide. In some embodiments, the second exogenous stimulatory polypeptide is present at a copy number of no more than 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% greater, or no more than 2, 5, 10, 20, 50, 100, 200, 500, or 1000 times greater than the copy number of the first exogenous stimulatory polypeptide. In some embodiments, the first exogenous stimulatory polypeptide and the second exogenous stimulatory polypeptide have an abundance ratio of about 1:1, from about 2:1 to 1:2, from about 5:1 to 1:5, from about 10:1 to 1:10, from about 20:1 to 1:20, from about 50:1 to 1:50, or from about 100:1 to 1:100 by weight or by copy number. In some embodiments, the first exogenous polypeptide comprises between about 50,000 to about 600,000 copies of the first exogenous polypeptide, for example about 50,000, 60,000, 60,000, 80,000, 90,000, 100,000, 110,000, 120,000, 130,000, 140,000, 150,000, 155,000, 160,000, 165,000, 170,000, 175,000, 180,000, 185,000, 190,000, 195,000, 200,000, 205,000, 210,000, 215,000, 220,000, 225,000, 230,000, 235,000, 240,000, 245,000, 250,000, 255,000, 260,000, 265,000, 270,000, 275,000, 280,000, 285,000, 290,000, 295,000, 300,000, 305,000, 310,000, 315,000, 320,000, 325,000, 330,000, 335,000, 340,000, 345,000, 350,000, 355,000, 360,000, 365,000, 370,000, 375,000, 380,000, 385,000, 390,000, 395,000, 400,000, 450,000, 500,000, 550,000, 600,000 copies of the first polypeptide. In some embodiments, the engineered erythroid cell comprises between about 50,000-600,000, between about 100,000-600,000, between about 100,000-500,000, between about 100,000-400,000, between about 100,000-150,000, between about 150,000-300,000, or between 150,000-200,000 copies of the first exogenous polypeptide. In some embodiments, the engineered erythroid cell comprises at least about 75,000 copies of the first exogenous polypeptide. In some embodiments, the engineered erythroid cell comprises at least about 100,000 copies of the first exogenous polypeptide. In some embodiments, the engineered erythroid cell comprises at least about 125,000 copies of the first exogenous polypeptide. In some embodiments, the engineered erythroid cell comprises at least about 150,000 copies of the first exogenous polypeptide. In some embodiments, the engineered erythroid cell comprises at least about 175,000 copies of the first exogenous polypeptide. In some embodiments, the engineered erythroid cell comprises at least about 200,000 copies of the first exogenous polypeptide. In some embodiments, the engineered erythroid cell comprises at least about 250,000 copies of the first exogenous polypeptide. In some embodiments, the engineered erythroid cell comprises at least about 300,000 copies of the first exogenous polypeptide. In some embodiments, the engineered erythroid cell comprises at least about 400,000 copies of the first exogenous polypeptide. In some embodiments, the engineered erythroid cell comprises at least about 500,000 copies of the first exogenous polypeptide. In some embodiments, the second exogenous polypeptide comprises between about 50,000 to about 600,000 copies of the second exogenous polypeptide, for example about 50,000, 60,000, 60,000, 80,000, 90,000, 100,000, 110,000, 120,000, 130,000, 140, 000, 150,000, 155,000, 160,000, 165,000, 170,000, 175,000, 180,000, 185,000, 190,000, 195,000, 200,000, 205,000, 210, 000, 215,000, 220,000, 225,000, 230,000, 235,000, 240,000, 245,000, 250,000, 255,000, 260,000, 265,000, 270,000, 275, 000, 280,000, 285,000, 290,000, 295,000, 300,000, 305,000, 310,000, 315,000, 320,000, 325,000, 330,000, 335,000, 340, 000, 345,000, 350,000, 355,000, 360,000, 365,000, 370,000, 375,000, 380,000, 385,000, 390,000, 395,000, 400,000, 450, 000, 500,000, 550,000, 600,000 copies of the second polypeptide. In some embodiments, the engineered erythroid cell comprises between about 50,000-600,000, between about 100,000-600,000, between about 100,000-500,000, between about 100,000-400,000, between about 100,000-150,000, between about 150,000-300,000, or between 150,000-200, 000 copies of the second exogenous polypeptide. In some embodiments, the engineered erythroid cell comprises at least about 75,000 copies of the second exogenous polypeptide. In some embodiments, the engineered erythroid cell comprises at least about 100,000 copies of the second exogenous polypeptide. In some embodiments, the engineered erythroid cell comprises at least about 125,000 copies of the second exogenous polypeptide. In some embodiments, the engineered erythroid cell comprises at least about 150,000 copies of the second exogenous polypeptide. In some embodiments, the engineered erythroid cell comprises at least about 175,000 copies of the second exogenous polypeptide. In some embodiments, the engineered erythroid cell comprises at least about 200,000 copies of the second exogenous polypeptide. In some embodiments, the engineered erythroid cell comprises at least about 250,000 copies of the second exogenous polypeptide. In some embodiments, the engineered erythroid cell comprises at least about 300,000 copies of the second exogenous polypeptide. In some embodiments, the engineered erythroid cell comprises at least about 400,000 copies of the second exogenous polypeptide. In some embodiments, the engineered erythroid cell comprises at least about 500,000 copies of the second exogenous polypeptide. As described herein, in another aspect, the disclosure features an engineered erythroid cell comprising a first exogenous stimulatory polypeptide, wherein the first exogenous stimulatory polypeptide comprises an interleukin-15 (IL-15) polypeptide, or a fragment thereof, and an extracellular portion of an interleukin-15 receptor alpha (IL-15RA) polypeptide, or a fragment thereof. In some embodiments, the engineered erythroid cell is an enucleated cell. In another aspect, the disclosure features an engineered erythroid cell comprising a first exogenous stimulatory polypeptide, wherein the first exogenous stimulatory polypeptide comprises a 4-1BBL polypeptide, or a fragment thereof. In another aspect, the disclosure features an engineered erythroid cell comprising a first exogenous stimulatory polypeptide, wherein the first exogenous stimulatory polypeptide comprises an IL-12 polypeptide, or a fragment thereof.

In some embodiments of the above aspects, the engineered erythroid cell further comprises one or more additional exogenous stimulatory polypeptides (e.g., 4-1BBL and IL-15/IL-15RA, 4-1BBL and IL-12, or IL-12 and IL-15/IL-15RA).

In some embodiments of the above aspects, the engineered erythroid cell is a nucleated cell.

In some embodiments of the above aspects and embodiments, the first exogenous stimulatory polypeptide is present at a copy number of greater than $10^4$, $10^5$, or $10^6$. In some embodiments, the first exogenous stimulatory polypeptide is present at a copy number of no more than 10%, 20%, 30%, 40%, 50%, 60%, 70%, 80%, or 90% greater, or no more than 2, 5, 10, 20, 50, 100, 200, 500, or 1000 times greater than the copy number of the second exogenous stimulatory polypeptide. In some embodiments, the second exogenous stimulatory polypeptide is present at a copy number of no more than 10%, 20%, 30%, 40%, 50%, 60%, 70%, 80%, or 90% greater, or no more than 2, 5, 10, 20, 50, 100, 200, 500, or 1000 times greater than the copy number of the first exogenous stimulatory polypeptide. In some embodiments, the first exogenous stimulatory polypeptide and the second exogenous stimulatory polypeptide have an abundance ratio of about 1:1, from about 2:1 to 1:2, from about 5:1 to 1:5, from about 10:1 to 1:10, from about 20:1 to 1:20, from about 50:1 to 1:50, or from about 100:1 to 1:100 by weight or by copy number. In some embodiments, the first exogenous polypeptide comprises between about 50,000 to about 600, 000 copies of the first exogenous polypeptide, for example about 50,000, 60,000, 60,000, 80,000, 90,000, 100,000, 110,000, 120,000, 130,000, 140,000, 150,000, 155,000, 160, 000, 165,000, 170,000, 175,000, 180,000, 185,000, 190,000, 195,000, 200,000, 205,000, 210,000, 215,000, 220,000, 225, 000, 230,000, 235,000, 240,000, 245,000, 250,000, 255,000, 260,000, 265,000, 270,000, 275,000, 280,000, 285,000, 290, 000, 295,000, 300,000, 305,000, 310,000, 315,000, 320,000, 325,000, 330,000, 335,000, 340,000, 345,000, 350,000, 355, 000, 360,000, 365,000, 370,000, 375,000, 380,000, 385,000, 390,000, 395,000, 400,000, 450,000, 500,000, 550,000, 600, 000 copies of the first polypeptide. In some embodiments, the engineered erythroid cell comprises between about 50,000-600,000, between about 100,000-600,000, between about 100,000-500,000, between about 100,000-400,000, between about 150,000-300,000, between about 100,000-150,000, or between 150,000-200,000 copies of the first exogenous polypeptide. In some embodiments, the engineered erythroid cell comprises at least about 75,000 copies of the first exogenous polypeptide. In some embodiments, the engineered erythroid cell comprises at least about 100, 000 copies of the first exogenous polypeptide. In some embodiments, the engineered erythroid cell comprises at least about 125,000 copies of the first exogenous polypeptide. In some embodiments, the engineered erythroid cell comprises at least about 150,000 copies of the first exogenous polypeptide. In some embodiments, the engineered erythroid cell comprises at least about 175,000 copies of the first exogenous polypeptide. In some embodiments, the engineered erythroid cell comprises at least about 200,000 copies of the first exogenous polypeptide. In some embodiments, the engineered erythroid cell comprises at least about 250,000 copies of the first exogenous polypeptide. In some embodiments, the engineered erythroid cell comprises at least about 300,000 copies of the first exogenous polypeptide. In some embodiments, the engineered erythroid cell comprises at least about 400,000 copies of the first exogenous polypeptide. In some embodiments, the engineered erythroid cell comprises at least about 500,000 copies of the first exogenous polypeptide. In some embodiments, the second exogenous polypeptide comprises between about 50,000 to about 600,000 copies of the second exogenous polypeptide, for example about 50,000, 60,000, 60,000, 80,000, 90,000, 100,000, 110,000, 120,000, 130,000, 140,000, 150,000, 155,000, 160,000, 165,000, 170,000, 175,000, 180,000, 185,000, 190,000, 195,000, 200,000, 205,000, 210,000, 215,000, 220,000, 225,000, 230,000, 235,000, 240,000, 245,000, 250,000, 255,000, 260,000, 265,000, 270,000, 275,000, 280,000, 285,000, 290,000, 295,000, 300,000, 305,000, 310,000, 315,000, 320,000, 325,000, 330,000, 335,000, 340,000, 345,000, 350,000, 355,000, 360,000, 365,000, 370,000, 375,000, 380,000, 385,000, 390,000, 395,000, 400,000, 450,000, 500,000, 550,000, 600,000 copies of the second polypeptide. In some embodiments, the engineered erythroid cell comprises between about 50,000-600,000, between about 100,000-600,000, between about 100,000-500,000, between about 100,000-400,000, between about 150,000-300,000, between about 100,000-150,000, or between 150,000-200,000 copies of the second exogenous polypeptide. In some embodiments, the engineered erythroid cell comprises at least about 75,000 copies of the second exogenous polypeptide. In some embodiments, the engineered erythroid cell comprises at least about 100,000 copies of the second exogenous polypeptide. In some embodiments, the engineered erythroid cell comprises at least about 125,000 copies of the second exogenous polypeptide. In some embodiments, the engineered erythroid cell comprises at least about 150,000 copies of the second exogenous polypeptide. In some embodiments, the engineered erythroid cell comprises at least about 175,000 copies of the second exogenous polypeptide. In some embodiments, the engineered erythroid cell comprises at least about 200,000 copies of the second exogenous polypeptide. In some embodiments, the engineered erythroid cell comprises at least about 250,000 copies of the second exogenous polypeptide. In some embodiments, the engineered erythroid cell comprises at least about 300,000 copies of the second exogenous polypeptide. In some embodiments, the engineered erythroid cell comprises at least about 400,000 copies of the second exogenous polypeptide. In some embodiments, the engineered erythroid cell comprises at least about 500,000 copies of the second exogenous polypeptide.

As described herein, in another aspect, the disclosure features an engineered erythroid cell comprising at least one exogenous stimulatory polypeptide selected from the group consisting of MHC class I chain-related protein A (MICA), MHC class I chain-related protein B (MICB), and insulin-like growth factor 1 (IGF-1). In some embodiments, the erythroid cell comprises at least the first exogenous stimulatory polypeptide and a second exogenous polypeptide. In some embodiments, the exogenous polypeptide is present at a copy number of greater than $10^4$, $10^5$, or $10^6$. In some embodiments, the first exogenous stimulatory polypeptide is present at a copy number of no more than 10%, 20%, 30%, 40%, 50%, 60%, 70%, 80%, or 90% greater, or no more than 2, 5, 10, 20, 50, 100, 200, 500, or 1000 times greater than the copy number of the second exogenous stimulatory polypeptide. In some embodiments, the second exogenous stimulatory polypeptide is present at a copy number of no more than 10%, 20%, 30%, 40%, 50%, 60%, 70%, 80%, or 90% greater, or no more than 2, 5, 10, 20, 50, 100, 200, 500, or 1000 times greater than the copy number of the first exogenous stimulatory polypeptide. In some embodiments, the first exogenous stimulatory polypeptide and the second exogenous stimulatory polypeptide have an abundance ratio of about 1:1, from about 2:1 to 1:2, from about 5:1 to 1:5, from about 10:1 to 1:10, from about 20:1 to 1:20, from about 50:1 to 1:50, or from about 100:1 to 1:100 by weight or by copy number. In some embodiments, the first exogenous polypeptide comprises between about 50,000 to about 600,000 copies of the first exogenous polypeptide, for example about 50,000, 60,000, 60,000, 80,000, 90,000, 100,000, 110,000, 120,000, 130,000, 140,000, 150,000, 155,000, 160,000, 165,000, 170,000, 175,000, 180,000, 185,000, 190,000, 195,000, 200,000, 205,000, 210,000, 215,000, 220,000, 225,000, 230,000, 235,000, 240,000, 245,000, 250,000, 255,000, 260,000, 265,000, 270,000, 275,000, 280,000, 285,000, 290,000, 295,000, 300,000, 305,000, 310,000, 315,000, 320,000, 325,000, 330,000, 335,000, 340,000, 345,000, 350,000, 355,000, 360,000, 365,000, 370,000, 375,000, 380,000, 385,000, 390,000, 395,000, 400,000, 450,000, 500,000, 550,000, 600,000 copies of the first polypeptide. In some embodiments, the engineered erythroid cell comprises between about 50,000-600,000, between about 100,000-600,000, between about 100,000-500,000, between about 100,000-400,000, between about 150,000-300,000, between about 100,000-150,000, or between 150,000-200,000 copies of the first exogenous polypeptide. In some embodiments, the engineered erythroid cell comprises at least about 75,000 copies of the first exogenous polypeptide. In some embodiments, the engineered erythroid cell comprises at least about 100,000 copies of the first exogenous polypeptide. In some embodiments, the engineered erythroid cell comprises at least about 125,000 copies of the first exogenous polypeptide. In some embodiments, the engineered erythroid cell comprises at least about 150,000 copies of the first exogenous polypeptide. In some embodiments, the engineered erythroid cell comprises at least about 175,000 copies of the first exogenous polypeptide. In some embodiments, the engineered erythroid cell comprises at least about 200,000 copies of the first exogenous polypeptide. In some embodiments, the engineered erythroid cell comprises at least about 250,000 copies of the first exogenous polypeptide. In some embodiments, the engineered erythroid cell comprises at least about 300,000 copies of the first exogenous polypeptide. In some embodiments, the engineered erythroid cell comprises at least about 400,000 copies of the first exogenous polypeptide. In some embodiments, the engineered erythroid cell comprises at least about 500,000 copies of the first exogenous polypeptide. In some embodiments, the second exogenous polypeptide comprises between about 50,000 to about 600,000 copies of the second exogenous polypeptide, for example about 50,000, 60,000, 60,000, 80,000, 90,000, 100,000, 110,000, 120,000, 130,000, 140,000, 150,000, 155,000, 160,000, 165,000, 170,000, 175,000, 180,000, 185,000, 190,000, 195,000, 200,000, 205,000, 210,000, 215,000, 220,000, 225,000, 230,000, 235,000, 240,000, 245,000, 250,000, 255,000, 260,000, 265,000, 270,000, 275,000, 280,000, 285,000, 290,000, 295,000, 300,000, 305,000, 310,000, 315,000, 320,000, 325,000, 330,000, 335,000, 340,000, 345,000, 350,000, 355,000, 360,000, 365,000, 370,000, 375,000, 380,000, 385,000, 390,000, 395,000, 400,000, 450,000, 500,000, 550,000, 600,000 copies of the second polypeptide. In some embodiments, the engineered erythroid cell comprises between about 50,000-600,000, between about 100,000-600,000, between about 100,000-500,000, between about 100,000-400,000, between about 150,000-300,000, between about 100,000-150,000, or between 150,000-200,000 copies of the second exogenous polypeptide. In some embodiments, the engineered erythroid cell comprises at least about 75,000 copies of the second exogenous polypeptide. In some embodiments, the engineered erythroid cell comprises at least about 100,000 copies of the second exogenous polypeptide. In some embodiments, the engineered erythroid cell comprises at least about 125,000 copies of the second exogenous polypeptide. In some embodiments, the engineered erythroid cell comprises at least about 150,000 copies of the second exogenous polypeptide. In some embodiments, the engineered erythroid cell comprises at least about 175,000 copies of the second exogenous polypeptide. In some embodiments, the engineered erythroid cell comprises at least about 200,000 copies of the second exogenous polypeptide. In some embodiments, the engineered erythroid cell comprises at least about 250,000 copies of the second exogenous polypeptide. In some embodiments, the engineered erythroid cell comprises at least about 300,000 copies of the second exogenous polypeptide. In some embodiments, the engineered erythroid cell comprises at least about 400,000 copies of the second exogenous polypeptide. In some embodiments, the engineered erythroid cell comprises at least about 500,000 copies of the second exogenous polypeptide.

In Vivo Half-Life

In some embodiments, an exogenous polypeptide described herein, when included in or on an engineered erythroid cell or an enucleated cell and administered to a subject, exhibits a prolonged in vivo half-life as compared to a corresponding exogenous polypeptide that is administered by itself (i.e., not on or in a cell described herein). In some embodiments, the exogenous polypeptide has an in vivo half-life that is longer than the in vivo half-life of a corresponding exogenous polypeptide that is administered by itself, or the in vivo half-life of a corresponding pegylated version of the exogenous polypeptide that is administered by itself. In some embodiments, the exogenous polypeptide has an in vivo half-life of between about 24 hours and 240 days (e.g., 24 hours, 36 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32, days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 101 days, 102 days, 103 days, 104 days, 105 days, 106 days, 107 days, 108 days, 109 days, 110 days, 111 days, 112 days, 113 days, 114 days, 115 days, 116 days, 117 days, 118 days, 119 days, 120 days, 121 days, 122 days, 123 days, 124 days, 125 days, 126 days, 127 days, 128 days, 129 days, 130 days, 131 days, 132, days, 133 days, 134 days, 135 days, 136 days, 137 days, 138 days, 139 days, 140 days, 141 days, 142 days, 143 days, 144 days, 145 days, 146 days, 147 days, 148 days, 149 days, 150 days, 151 days, 152 days, 153 days, 154 days, 155 days, 156 days, 157 days, 158 days, 159 days, 160 days, 161 days, 162 days, 163 days, 164 days, 165 days, 166 days, 167 days, 168 days, 169 days, 170 days, 171 days, 172 days, 173 days, 174 days, 175 days, 176 days, 177 days, 178 days, 179 days, 180 days, 181 days, 182 days, 183 days, 184 days, 185 days, 186 days, 187 days, 188 days, 189 days, 190 days, 191 days, 192 days, 193 days, 194 days, 195 days, 196 days, 197 days, 198 days, 919 days, 200 days, 201 days, 202 days, 203 days, 204 days, 205 days, 206 days, 207 days, 208 days, 209 days, 210 days, 211 days, 212 days, 213 days, 214 days, 215 days, 216 days, 217 days, 218 days, 219 days, 220 days, 221 days, 222 days, 223 days, 224 days, 225 days, 226 days, 227 days, 228 days, 229 days, 230 days, 231 days, 232, days, 233 days, 234 days, 235 days, 236 days, 237 days, 238 days, 239 days, or 240 days. In some embodiments, the exogenous polypeptide has an in vivo half-life of greater than 1 day, 2 days, 3 days, 5 days, 10 days, 25 days, 50 days, 75 days, 100 days, 125 days, 150 days, 175 days, 200 days, 225 days, 235 days, or 250 days. In some embodiments, the exogenous polypeptide has an in vivo half-life of 1 week, 2 weeks, 3 weeks, 1 month, 2 months, 3 months, 4 months, 5 months, 6 months, 7 months, 8 months, 9 months, 10 months, 11 months, a year, or more.

In some embodiments, the enucleated cells (e.g., reticulocytes, erythrocytes, or platelets) of the present disclosure resides in circulation after administration to a subject for at least about 1 day to about 240 days (e.g., for at least about 1 day, 2 days, 3 days, 4 day, 5 days, 6 days, 7 days, 8 days, 9 days, 10 days, 11 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 101 days, 102 days, 103 days, 104 days, 105 days, 106 days, 107 days, 108 days, 109 days, 110 days, 111 days, 112 days, 113 days, 114 days, 115 days, 116 days, 117 days, 118 days, 119 days, 120 days, 121 days, 122 days, 123 days, 124 days, 125 days, 126 days, 127 days, 128 days, 129 days, 130 days, 131 days, 132 days, 133 days, 134 days, 135 days, 136 days, 137 days, 138 days, 139 days 140 days, 141 days, 142 days, 143 days, 144 days, 145 days, 146 days, 147 days, 148 days, 149 days, 150 days, 151 days, 152 days, 153 days, 154 days, 155 days, 156 days, 157 days, 158 days, 159 days, 160 days, 161 days, 162 days, 163 days, 164 days, 165 days, 166 days, 167 days, 168 days, 169 days, 170 days, 171 days, 172 days, 173 days, 174 days, 175 days, 176 days, 177 days, 178 days, 179 days, 180 days, 181 days, 182 days, 183 days, 184 days, 185 days, 186 days, 187 days, 188 days, 189 days, 190 days, 191 days, 192 days, 193 days, 194 days, 195 days, 196 days, 197 days, 198 days, 199 days, 200 days, 201 days, 202 days, 203 days, 204 days, 205 days, 206 days, 207 days, 208 days, 209 days, 210 days, 211 days, 212 days, 213 days, 214 days, 215 days, 216 days, 217 days, 218 days, 219 days, 220 days, 221 days, 222 days, 223 days, 224 days, 225 days, 226 days, 227 days, 228 days, 229 days, 230 days, 231 days, 232 days, 233 days, 234 days, 235 days, 236 days, 237 days, 238 days, 239 days, or 240 days.

Stimulation of Immune Killer Cells

As described herein, the present invention provides engineered erythroid cells that are capable of stimulating immune cells, including for example, cytolytic T cells (CD8+ cells), memory CD8+ T cells, T helper cells (CD4+ cells) and NK cells. In some embodiments, the engineered erythroid cell is an enucleated cell. In some embodiments, the engineered erythroid cell is a nucleated cell. The stimulation of the immune cells may enhance normal cellular functions, or initiate normal cell functions in an abnormal cell. In a preferred embodiments, the invention provides engineered erythroid cells that are capable of stimulating immune killer cells. Immune killer cells that may be stimulated include, for example, cytolytic T cells (CD8+ cells), memory CD8+ T cells, and NK cells. In some embodiments, the killer immune cells are Natural Killer (NK) cells. In some embodiments, the NK cells are memory-like NK cells. In some embodiments, the killer immune cells are CD8+ T-cells. In some embodiments, the CD8+ T-cells are memory T cells. Accordingly, the present invention also provides populations of cells resulting from stimulation with the engineered erythroid cells described herein.

It is a feature of the present invention that, in some embodiments, the engineered erythroid cells are capable of stimulating more than one type of immune killer cell at the same time, for example, more than one of cytolytic T cells (CD8+ cells), memory CD8+ T cells and NK cells. In some embodiments, the engineered erythroid cells are capable of stimulating both CD8+ T cells and NK cells. It is a finding of the present invention, that engineered erythroid cells comprising exogenous stimulatory polypeptides comprising either IL-12, IL-15/IL-15RA, 4-1BBL, or combinations thereof, e.g., 4-1BBL and IL-15/IL-15RA, 4-1BBL and IL-12, or IL-12 and IL-15/IL-15RA, induce a potent activation of primary CD4+, CD8+, NK and NKT cells, and induce NK cell cytotoxicity.

In some embodiments, stimulating the immune killer cells refers to expansion of the immune killer cell. In some embodiments, stimulating the immune killer cells refers to activation of the immune killer cell. In some embodiments, stimulating the immune killer cells refers to an increase in cytoxicity of the immune killer cell.

In certain embodiments, the engineered erythroid cells as described herein are sufficient to stimulate an immune killer cell ex vivo. In other embodiments, the engineered erythroid cells as described herein are sufficient to stimulate an immune killer cell in vivo.

NK Cell Activation and Expansion

In some embodiments, the engineered erythroid cells described herein are capable of activating NK cells.

In some embodiments, the engineered erythroid cells described herein are capable of expanding NK cells.

Degranulation/Cytotoxicity

The defining functional feature of NK cells remains their intrinsic ability to conduct "natural killing" of cellular targets without prior sensitization.

Accordingly, In some embodiments, the engineered erythroid cells described herein are capable of activating and expanding NK cells, such that the NK cells that are activated and expanded by the engineered erythroid cells described herein exhibit higher degranulation activity compared to control NK cells. For example, degranulation activity can be estimated through the determination of CD107a expression, for example by flow cytometry. CD107a surface expression correlates closely with degranulation and release of cytotoxic granules. Degranulation as measured by CD107a expression correlates to cytotoxic activity of an effector cell, such as an NK cell. The method of determining degranulation activity through the determination of CD107a expression is well known to a person skilled in the art. See, for example, Alter G, Malenfant J M, Altfeld M. CD107a as a functional marker for the identification of natural killer cell activity. J Immunol Methods. 2004; 294: 15-22, the entire contents of which are incorporated herein by reference.

In some embodiments the expanded and activated NK cells, obtained by using the engineered erythroid cells of the invention, have at least about 50%, about 60%, about 70%, about 80% or about 90% increased cytotoxicity, e.g. as measured by degranulation activity, compared to non expanded NK cells. In some embodiments the expanded and activated NK cells have at least about 100% increased cytotoxicity compared to non expanded NK cells. In some embodiments the expanded and activated NK cells have at least about 200% increased cytotoxicity compared to non expanded NK cells. In some embodiments the expanded and activated NK cells have at least about 300% increased cytotoxicity compared to non-ex vivo expanded NK cells. In some embodiments the expanded and activated NK cells have at least about 400% increased cytotoxicity compared to non-ex vivo expanded NK cells.

In some embodiments the expanded and activated NK cells, by using the engineered erythroid cells of the invention, have at least about 50%, about 60%, about 70%, about 80% or about 90% increased degranulation activity compared to non expanded NK cells. In some embodiments the expanded and activated NK cells have at least about 100% increased degranulation activity compared to non expanded NK cells. In some embodiments the expanded and activated NK cells have at least about 200% increased degranulation activity compared to non expanded NK cells. In some embodiments the expanded and activated NK cells have at least about 300% increased degranulation activity compared to non-ex vivo expanded NK cells. In some embodiments the expanded and activated NK cells have at least about 400% increased degranulation activity compared to non-ex vivo expanded NK cells.

Markers of NK Cell Maturation and Activation

Human NK cells are phenotypically characterized by the expression of CD56 and the absence of CD3 and can be further subdivided into a $CD56^{bright}$ population and a $CD56^{dim}$ population. The $CD56^{bright}$ population produces immunoregulatory cytokines, including interferon-γ (IFNγ), tumor necrosis factor-beta (TNF-β), tumor necrosis factor-α (TNF-α), granulocyte macrophage-colony stimulating factor (GMCSF), IL-10, and IL-13 (4). The $CD56^{dim}$ subset is the terminally differentiated successor of the $CD56^{bright}$ population and is primarily responsible for exerting cytolytic functions. However, $CD56^{dim}$ NK cells can produce cytokines, specifically IFNγ, after cell triggering via NKp46 of NKp30 activating receptors or after stimulation with combinations of IL-2, IL-12, and IL-15.

In some embodiments, various markers of NK cell maturation and/or activation can be detected using, e.g. flow cytometric methods. For example, a classical marker of NK cells, is the activating receptor FcγRIII, also called CD16.

The activation of NK cells leads to the release of cytotoxic granules containing perforin and various granzymes and to cytokine production, most prominently interferon-γ (IFNγ). In addition, the expression at the cell surface of death-inducing ligands belonging to the tumor necrosis factor (TNF) family, such as Fas ligand (FasL) and TNF-related apoptosis-inducing ligand (TRAIL), also drives the activation of the caspase enzymatic cascade through the binding to the death receptors (DRs), namely, Fas, DR4 (TRAIL-RI), and DR5 (TRAIL-RII), on target cells.

In some embodiments, the engineered erythroid cells described herein upregulate at least one NK cell activating receptor (e.g., an activating receptor listed in Table 5) by at least about 20%, about 30%, about 40%, about 50%, about 60%, about 70%, about 80%, about 90%, about 100%, about 150%, about 200%, about 300% or more. In some embodiments, the engineered erythroid cells described herein upregulate at least one NK cell activating receptor by at least about 75%. In some embodiments, the engineered erythroid cells described herein upregulate at least one NK cell activating receptor by at least about 100%. In some embodiments, the engineered erythroid cells described herein upregulate at least one NK cell activating receptor by at least about 200%.

According to another embodiment, the engineered erythroid cells described herein downregulate expression of at least one NK cell receptor, such as an inhibitory receptor or a chemokine receptor (e.g. CCR7). For example, certain NK cell inhibitory receptors are called KIRs (Killing Inhibitory Receptors or CD158). Non-limiting examples of inhibitory receptors are inhibitory killer immunoglobulin-like receptors (KIRs), GL183, KIR2DL 1, Lir-1, NKB1, and NKG2A.

In some embodiments, the engineered erythroid cells described herein downregulate at least one NK cell inhibitory receptor (e.g., an inhibitory receptor listed in Table 5) by at least about 20%, about 30%, about 40%, about 50%, about 60%, about 70%, about 80%, about 90%, about 100%, about 150%, about 200%, about 300% or more. In some embodiments, the engineered erythroid cells described herein downregulate at least one NK cell inhibitory receptor by at least about 75%. In some embodiments, the engineered erythroid cells described herein downregulate at least one NK cell inhibitory receptor by at least about 100%. In some embodiments, the engineered erythroid cells described herein downregulate at least one NK cell inhibitory receptor by at least about 200%.

The change in receptor expression can be calculated by mean fluorescence intensity (MFI) ratios:

$$MFI_{dayX}/MFI_{day0}$$

where x is the number of days of expansion of the NK cell.

When the MFI for day X samples is higher than for day 0, the MFI ratio will be higher than 1, which indicates the relative extent of upregulation in that receptor. Thus, a MFI ratio of e.g. 1.5 would mean a 50% upregulation of a specific receptor. The calculation of MFI ratios is well known to persons skilled in the art.

Various NK cell activating or inhibitory receptors are shown below in Table 5.

TABLE 5

| Receptor Family | Species | Activating/Inhibitory |
|---|---|---|
| CD16 | H | Act |
| KIR | H | Act/Inhib |
| KIR2DL1 | | Inhib |
| KIR2DL2/3 | | Inhib |
| KIR2DL4 | | Act |
| KIR2DL5 | | Inhib |
| KIR3DL1 | | Inhib |
| KIR3DL2 | | Inhib |
| KIR2DS1 | | Act |
| KIR2DS2 | | Act |
| KIR2DS3 | | Act |
| KIR2DS4 | | Act |
| KIR2DS5 | | Act |
| KIR3DS1 | | Act |
| CD94-NKG2 | H/M | Act/Inhib |
| NKG2A | | Inhib |
| NKG2C | | Act |
| NKG2E | | Act |
| NKG2D | H/M | Act |
| NCRs | H/M | Act |
| NKp30 | | Act |
| NKp44 | | Act |
| NKp46 | | Act |
| NKp80 | | Act |
| LILR | H/M | Inhib |
| 2B4 | H/M | Act/Inhib |

TABLE 5-continued

| Receptor Family | Species | Activating/Inhibitory |
|---|---|---|
| KLRG1 | H/M | Inhib |
| DNAM-1 | H/M | Act |

Abbreviations in Table 5: ACT, activation; BAT-3, HLA-B-associated transcript 3; H, human; HA, hemagglutinin; HLA, human leukocyte antigen; INHIB, inhibitory; KIR, killer immunoglobulin-like receptor; KLRG1, killer cell lectin-like receptor G1; LILR, leukocyte immunoglobulin-like receptor; M, mouse; MHC, major histocompatibility complex; MULT-1, mouse UL16-binding-like transcript-1; NCR, natural cytotoxicity receptor; NK, natural killer; PVR, polio virus receptor; RAE-1, retinoic acid early transcript-1.

CD8+ T Cell Activation and Expansion

In some embodiments, the engineered erythroid cells described herein are capable of activating CD8+ T-cells. In some embodiments, the engineered erythroid cells described herein are capable of expanding CD8+ T-cells. In some embodiments, the engineered erythroid cells described herein are capable of activating and expanding CD8+ T-cells. In some embodiments, the engineered erythroid cell is an enucleated cell. In some embodiments, the engineered erythroid cell is a nucleated cell.

T cell activation and expansion can be measured by various assays as described herein. For example, T cell activities that may be measured include the induction of proliferation of T cells, the induction of signaling in T cells, the induction of expression of activation markers in T cells, the induction of cytokine secretion by T cells, and the cytotoxic activity of T cells. For example, in certain embodiments, CD8+ T cell activation is measured by a proliferation assay.

Cytokine Secretion

The activation of CD8+ T-cells by an engineered erythroid cell of the invention may be assessed or measured by determining secretion of cytokines, such as gamma interferon (IFNγ), tumor necrosis factor alpha (TNFa), interleukin-12 (IL-12) or interleukin 2 (IL-2). In some embodiments, ELISA is used to determine cytokine secretion, for example secretion of gamma interferon (IFNγ), tumor necrosis factor alpha (TNFa), interleukin-12 (IL-12) or interleukin 2 (IL-2). The ELISPOT (enzyme-linked immunospot) technique may be used to detect T cells that secrete a given cytokine (e.g., gamma interferon (IFNγ)) in response to stimulation with the engineered erythroid cells described herein. T cells are cultured with engineered erythroid cells in wells which have been coated with anti-IFNγ antibodies. The secreted IFNγ is captured by the coated antibody and then revealed with a second antibody coupled to a chromogenic substrate. Thus, locally secreted cytokine molecules form spots, with each spot corresponding to one IFNγ-secreting cell. The number of spots allows one to determine the frequency of IFNγ-secreting cells in the analyzed sample. The ELISPOT assay has also been described for the detection of tumor necrosis factor alpha, interleukin-4 (IL-4), IL-5, IL-6, IL-10, IL-12, granulocyte-macrophage colony-stimulating factor, and granzyme B-secreting lymphocytes (Klinman D, Nutman T. Current protocols in immunology. New York, N.Y.: John Wiley & Sons, Inc.; 1994. pp. 6.19.1-6.19.8, incorporated by reference in its entirety herein).

Flow cytometric analyses of intracellular cytokines may be used to measure the cytokine content in culture supernatants, but provides no information on the number of T cells that actually secrete the cytokine. When T cells are treated with inhibitors of secretion such as monensin or brefeldin A, they accumulate cytokines within their cytoplasm upon activation (e.g. with an engineered erythroid cell of the present invention). After fixation and permeabilization of the lymphocytes, intracellular cytokines can be quantified by cytometry. This technique allows the determination of the cytokines produced, the type of cells that produce these cytokines, and the quantity of cytokine produced per cell.

Cytotoxicity

The activation of CD8+ T-cells by an engineered erythroid cell of the invention may be assessed by assaying the cytotoxic activity of the CD8+ T-cells.

The cytotoxic activity of T cells may be assessed by any suitable technique known to those of skill in the art. For example, a sample comprising T cells that have been exposed to the engineered erythroid cells according to the invention can be assayed for cytotoxic activity after an appropriate period of time, in a standard cytotoxic assay. Such assays may include, but are not limited to, the chromium release CTL assay and the Alamar Blue™ fluorescence assay known in the art.

Proliferation/Expansion

The ability of the engineered erythroid cells of the invention to expand T cells can be evaluated by using CFSE staining. Engineered erythroid cells are mixed with CD8+ T cells (e.g. from a subject suffering from a disease or disorder, such as cancer). To compare the initial rate of cell expansion, the cells are subject to CFSE staining to determine how well engineered erythroid cells induced the proliferation of T cells. CFSE staining provides a much more quantitative endpoint and allows simultaneous phenotyping of the expanded cells. Every day after stimulation, an aliquot of cells is removed from each culture and analyzed by flow cytometry. CFSE staining makes cells highly fluorescent. Upon cell division, the fluorescence is halved and thus the more times a cell divides the less fluorescent it becomes. The ability of engineered erythroid cells to induce T cell proliferation is quantitated by measuring the number of cells that divided once, twice, three times and so on. The engineered erythroid cells that induce the greatest number of cell divisions at a particular time point is deemed as the most potent expander.

To determine how well these engineered erythroid cells promote long-term growth of T cells, cell growth curves can be generated. These experiments are set up as the foregoing CFSE experiments, but no CFSE is used. Every 2-3 days of culture, T cells are removed from the respective cultures and counted using a Coulter counter which measures how many cells are present and the mean volume of the cells. The mean cell volume is the best predicator of when to restimulate the cells. In general, when T cells are properly stimulated they triple their cell volume. When this volume is reduced to more than about half of the initial blast, it may be necessary to restimulate the T cells to maintain a log linear expansion (Levine et al., 1996, Science 272:1939-1943; Levine et al., 1997, J. Immunol. 159:5921-5930). The time it takes each engineered erythroid cell to induce 20 population doublings is calculated. The relative differences of each engineered erythroid cell to induce this level of T cell expansion is an important criteria on which a particular engineered erythroid cell is assessed.

In addition, the phenotypes of the cells expanded by each engineered erythroid cell can be characterized to determine whether a particular subset is preferentially expanded. Prior to each restimulation, a phenotype analysis of the expanding T cell populations is performed to define the differentiation state of the expanded T cells using the CD27 and CD28 definitions proposed by Appay et al. (2002, Nature Med. 8, 379-385, incorporated by reference in its entirety herein) and CCR7 definitions proposed by Sallusto et al. (1999, Nature 401:708-712, incorporated by reference in its entirety herein). Perforin and Granzyme B intracellular staining can be used to perform a gross measure to estimate cytolytic potential.

Apoptosis Markers

In certain embodiments of the present invention, stimulation, activation, and expansion of T cells using the engineered erythroid cells as described herein enhances expression of certain key molecules in T cells that protect again apoptosis or otherwise prolong survival in vivo or in vitro. Apoptosis usually results from induction of a specific signal in the T cell. Thus, the engineered erythroid cells of the invention may provide for protecting a T cell from cell death resulting from stimulation of the T cell. Therefore, also included in the present invention is the enhanced T cell growth by protection from premature death or from absence or depletion of recognized T cell growth markers, such as Bcl-xL, growth factors, cytokines, or lymphokines normally necessary for T cell survival, as well as from Fas or Tumor Necrosis Factor Receptor (TNFR) cross-linking or by exposure to certain hormones or stress.

Tiling

According to certain embodiments, a first exogenous stimulatory polypeptide and a second exogenous stimulatory polypeptide have amino acid sequences which overlap. In certain embodiments, an engineered erythroid cell as described herein comprises a plurality of exogenous stimulatory polypeptides (e.g. one or more, two or more, three or more, etc). In certain embodiments, an engineered erythroid cell as described herein comprises a first exogenous stimulatory polypeptide and a second exogenous stimulatory polypeptide, and wherein the first exogenous stimulatory polypeptide and the second exogenous stimulatory polypeptide have amino acid sequences which overlap by at least 2 amino acids. According to certain embodiments, the overlap is between 2 amino acids and 23 amino acids, for example the overlap is 2, 3, 4, 5, 6, 7, 8, 9, 10, 11, 12, 13, 14, 15, 16, 17, 18, 19, 20, 21, 22 or 23 amino acids. According to one embodiment, the exogenous stimulatory polypeptide is between 8-10 amino acids in length, and the overlap is between 6-8 amino acids. According to another embodiment, the exogenous stimulatory polypeptide is between 14-20 amino acids in length, and the overlap is between 12-18 amino acids. Tiling polypeptides in this way provides broader recognition of antigen.

Methods for tiling polypeptides are known in the art, and are described, for example in Harding et al., which describes the development and testing of 15 mer polypeptides, overlapping by 12 amino acids, that were tested in a human CD4+ T-cell-based proliferative assay (Molecular Cancer Therapeutics, November 2005, Volume 4, Issue 11, incorporated by reference in its entirety herein). Sticker, et al. describes a human cell-based method to identify functional CD4(+) T-cell epitopes in any protein (J Immunol Methods. 2003 Oct. 1; 281(1-2):95-108, incorporated by reference in its entirety herein).

Modifications

One or more of the exogenous stimulatory proteins may have post-translational modifications characteristic of eukaryotic cells, e.g., mammalian cells, e.g., human cells. In some embodiments, one or more (e.g., 2, 3, 4, 5, 6, 7, 8, 9, 10, or more) of the exogenous stimulatory proteins are glycosylated, phosphorylated, or both. In vitro detection of glycoproteins can be accomplished on SDS-PAGE gels and Western Blots using a modification of Periodic acid-Schiff (PAS) methods. Cellular localization of glycoproteins can be accomplished utilizing lectin fluorescent conjugates known in the art. Phosphorylation may be assessed by Western blot using phospho-specific antibodies.

Post-translation modifications also include conjugation to a hydrophobic group (e.g., myristoylation, palmitoylation, isoprenylation, prenylation, or glypiation), conjugation to a cofactor (e.g., lipoylation, flavin moiety (e.g., FMN or FAD), heme C attachment, phosphopantetheinylation, or retinylidene Schiff base formation), diphthamide formation, ethanolamine phosphoglycerol attachment, hypusine formation, acylation (e.g. O-acylation, N-acylation, or S-acylation), formylation, acetylation, alkylation (e.g., methylation or ethylation), amidation, butyrylation, gamma-carboxylation, malonylation, hydroxylation, iodination, nucleotide addition such as ADP-ribosylation, oxidation, phosphate ester (O-linked) or phosphoramidate (N-linked) formation, (e.g., phosphorylation or adenylylation), propionylation, pyroglutamate formation, S-glutathionylation, S-nitrosylation, succinylation, sulfation, ISGylation, SUMOylation, ubiquitination, Neddylation, or a chemical modification of an amino acid (e.g., citrullination, deamidation, eliminylation, or carbamylation), formation of a disulfide bridge, racemization (e.g., of proline, serine, alanine, or methionine). In embodiments, glycosylation includes the addition of a glycosyl group to arginine, asparagine, cysteine, hydroxylysine, serine, threonine, tyrosine, or tryptophan, resulting in a glycoprotein. In embodiments, the glycosylation comprises, e.g., O-linked glycosylation or N-linked glycosylation.

In some embodiments of the above aspects and embodiments, the engineered erythroid cell is an enucleated cell. In some embodiments of the above aspects and embodiments, the engineered erythroid cell is a nucleated cell.

Populations of Engineered Erythroid Cells

In one aspect, the invention features cell populations comprising the engineered erythroid cells of the invention, e.g., a plurality or population of the engineered erythroid cells. In various embodiments, the engineered erythroid cell population comprises predominantly enucleated cells, predominantly nucleated cells, or a mixture of enucleated and nucleated cells. In such cell populations, the enucleated cells can comprise reticulocytes, erythrocytes, or a mixture of reticulocytes and erythrocytes. In some embodiments, the enucleated cells are reticulocytes. In some embodiments, the enucleated cells are erythrocytes.

In some embodiments, the engineered erythroid cell population consists essentially of enucleated cells. In some embodiments, the engineered erythroid cell population comprises predominantly or substantially enucleated cells. For example, in some embodiments, the population of engineered erythroid cells comprises at least about 80% or more enucleated cells. In some embodiments, the population provided herein comprises at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99, or about 100% enucleated cells. In some embodiments, the population provided herein comprises greater than about 80% enucleated cells. In some embodiments, the population of engineered erythroid cells comprises greater than about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% enucleated cells. In some embodiments, the population of engineered erythroid cells comprises between about 80% and about 100% enucleated cells, for example between about 80% and about 95%, about 80% and about 90%, about 80% and about 85%, about 85% and about 100%, about 85% and about 95%, about 85% and about 90%, about 90% and about 100%, about 90% and about 95%, or about 95% and about 100% of enucleated cells.

In some embodiments, the population of engineered erythroid cells comprises less than about 20% nucleated cells. For example, in embodiments, the population of engineered erythroid cells comprises less than about 1%, about 2%, about 3%, about 5%, about 6%, about 7%, about 8%, about 9%, about 10%, about 11%, about 12%, about 13%, about 14%, about 15%, about 16%, about 17%, about 18%, about 19%, or less than about 20% nucleated cells. In some embodiments, the population of engineered erythroid cells comprises less than about 1% nucleated cells. In some embodiments, the population of engineered erythroid cells comprises less than about 2% nucleated cells. In some embodiments, the population of engineered erythroid cells comprises less than about 3% nucleated cells. In some embodiments, the population of engineered erythroid cells comprises less than about 4% nucleated cells. In some embodiments, the population of engineered erythroid cells comprises less than about 5% nucleated cells. In some embodiments, the population of engineered erythroid cells comprises less than about 10% nucleated cells. In some embodiments, the population of engineered erythroid cells comprises less than about 15% nucleated cells. In some embodiments, the population of engineered erythroid cells comprises between 0% and 20% nucleated cells. In some embodiments, the populations of engineered erythroid cells comprise between about 0% and 20% nucleated cells, for example between about 0% and 19%, between about 0% and 15%, between about 0% and 10%, between about 0% and 5%, between about 0% and 4%, between about 0% and 3%, between about 0% and 2% nucleated cells, or between about 5% and 20%, between about 10% and 20%, or between about 15% and 20% nucleated cells.

In some embodiments, the disclosure features a population of the engineered erythroid cells of the invention, wherein the population of engineered erythroid cells comprises less than 20% nucleated cells and at least 80% enucleated cells, or comprises less than 15% nucleated cells and at least 85% nucleated cells, or comprises less than 10% nucleated cells and at least 90% enucleated cells, or comprises less than 5% nucleated cells and at least 95% enucleated cells. In some embodiments, the disclosure features populations of the engineered erythroid cells of the invention, wherein the population of engineered erythroid cells comprises about 0% nucleated cells and about 100% enucleated cells, about 1% nucleated cells and about 99% enucleated cells, about 2% nucleated cells and about 98% enucleated cells, about 3% nucleated cells and about 97% enucleated cells, about 4% nucleated cells and about 96% enucleated cells, about 5% nucleated cells and about 95% enucleated cells, about 6% nucleated cells and about 94% enucleated cells, about 7% nucleated cells and about 93% enucleated cells, about 8% nucleated cells and about 92% enucleated cells, about 9% nucleated cells and about 91% enucleated cells, about 10% nucleated cells and about 90% enucleated cells, about 11% nucleated cells and about 89% enucleated cells, about 12% nucleated cells and about 88% enucleated cells, about 13% nucleated cells and about 87% enucleated cells, about 14% nucleated cells and about 86% enucleated cells, about 85% nucleated cells and about 85% enucleated cells, about 16% nucleated cells and about 84% enucleated cells, about 17% nucleated cells and about 83% enucleated cells, about 18% nucleated cells and about 82% enucleated cells, about 19% nucleated cells and about 81% enucleated cells, or about 20% nucleated cells and about 80% enucleated cells.

In another embodiment, the engineered erythroid cell population comprises predominantly or substantially nucleated cells. In some embodiments, the engineered erythroid cell population consists essentially of nucleated cells. In various embodiments, the nucleated cells in the engineered erythroid cell population are erythrocyte (or fully mature red blood cell) precursor cells. In embodiments, the erythroid precursor cells are selected from the group consisting of pluripotent hematopoietic stem cells (HSCs), multipotent myeloid progenitor cells, CFU-S cells, BFU-E cells, CFU-E cells, pronormoblasts, basophilic normoblasts, polychromatophilic normoblasts and orthochromatophilic normoblasts.

In certain embodiments, the population of engineered erythroid cells comprises at least about 10%, at least about 20%, at least about 30%, at least about 40%, at least about 50%, at least about 60%, at least about 70%, at least about 75%, at least about 80%, at least about 85%, at least about 90%, at least about 95%, at least about 98%, at least about 99% or 100% nucleated cells.

It will be understood that during the preparation of the engineered erythroid cells of the invention, some fraction of cells may not become conjugated with an exogenous polypeptide or transduced to express an exogenous polypeptide. Accordingly, in some embodiments, a population of engineered erythroid cells provided herein comprises a mixture of engineered erythroid cells and unmodified erythroid cells, i.e., some fraction of cells in the population will not comprise, present, or express an exogenous polypeptide. For example, a population of engineered erythroid cells can comprise, in various embodiments, at least about 10%, 20%, 30%, 40%, 50%, 60%, 70%, 80%, 90%, 91%, 92%, 93%, 94%, 95%, 96%, 97%, 98% or 99% engineered erythroid cells, wherein the remaining erythroid cells in the population are not engineered. In embodiments, a single unit dose of engineered erythroid cells can comprise, in various embodiments, at least about 10%, 20%, 30%, 40%, 50%, 60%, 70%, 80%, 90%, 91%, 92%, 93%, 94%, 95%, 96%, 97%, 98% or 99% engineered erythroid cells, wherein the remaining erythroid cells in the dose are not engineered.

II. Methods of Making Engineered Erythroid Cells

Various methods of making engineered erythroid cells, e.g. enucleated cells, are contemplated by the present disclosure. In some embodiments, the engineered erythroid cell is an enucleated cell. In some embodiments, the engineered erythroid cell is a nucleated cell.

In one aspect, the present disclosure features an enucleated cell engineered to stimulate an immune cell, wherein the immune cell is a killer cell, comprising a plurality of exogenous stimulatory polypeptides at the surface of the engineered enucleated cell, wherein the plurality of exogenous stimulatory polypeptides are sufficient to stimulate the immune cell, produced by a process comprising introducing one or more exogenous nucleic acids, each encoding one or more of the plurality of exogenous stimulatory polypeptides into a nucleated erythroid cell; and culturing the nucleated erythroid cell under conditions suitable for enucleation of the nucleated erythroid cell and for production of one or more of the plurality of exogenous stimulatory polypeptides.

In another aspect, the disclosure features an engineered enucleated erythroid cell, comprising a first exogenous stimulatory polypeptide, wherein the first exogenous stimulatory polypeptide comprises IL-15/IL-15RA fusion, produced by a process comprising introducing an exogenous nucleic acid encoding the exogenous stimulatory polypeptide comprising an IL-15/IL-15RA fusion into a nucleated erythroid cell; and culturing the nucleated erythroid cell under conditions suitable for enucleation of the nucleated erythroid cell and for production of the exogenous stimulatory polypeptide comprising an IL-15/IL-15RA fusion.

In another aspect, the disclosure provides an engineered enucleated erythroid cell, comprising a first exogenous stimulatory polypeptide, wherein the first exogenous stimulatory polypeptide comprises a 4-1BBL polypeptide, produced by a process comprising introducing an exogenous nucleic acid encoding the exogenous stimulatory polypeptide comprising a 4-1BBL polypeptide into a nucleated erythroid cell; and culturing the nucleated erythroid cell under conditions suitable for enucleation of the nucleated erythroid cell and for production of the exogenous stimulatory polypeptide comprising a 4-1BBL polypeptide.

In another aspect, the disclosure features an engineered enucleated erythroid cell, comprising at least one exogenous stimulatory polypeptide comprising either IL-15/IL-15RA fusion, MHC class I chain-related protein A (MICA), insulin-like growth factor 1 (IGF-1), CD48, or CD155, at the surface of the engineered enucleated cell, produced by a process comprising introducing an exogenous nucleic acid encoding the at least one exogenous stimulatory polypeptide into a nucleated erythroid cell; and culturing the nucleated erythroid cell under conditions suitable for enucleation of the nucleated erythroid cell and for production of the at least one exogenous stimulatory polypeptide.

In another aspect, the disclosure features an engineered enucleated erythroid cell, comprising a first exogenous stimulatory polypeptide, wherein the first exogenous stimulatory polypeptide comprises IL-12 p40/IL-12 p35 fusion, produced by a process comprising introducing an exogenous nucleic acid encoding the exogenous stimulatory polypeptide comprising an IL-12 p40/IL-12 p35 fusion into a nucleated erythroid cell; and culturing the nucleated erythroid cell under conditions suitable for enucleation of the nucleated erythroid cell and for production of the exogenous stimulatory polypeptide comprising an IL-12 p40/IL-12 p35 fusion.

In another aspect, the disclosure features an engineered enucleated erythroid cell, comprising at least one exogenous stimulatory polypeptide comprising either IL-12 p40/IL-12 p35 fusion, IL-15/IL-15RA fusion, 4-1BBL, at the surface of the engineered enucleated cell, produced by a process comprising introducing an exogenous nucleic acid encoding the at least one exogenous stimulatory polypeptide into a nucleated erythroid cell; and culturing the nucleated erythroid cell under conditions suitable for enucleation of the nucleated erythroid cell and for production of the at least one exogenous stimulatory polypeptide.

In some embodiments, the engineered enucleated erythroid cells comprise more than one (e.g., two, three or more) exogenous stimulatory polypeptides at the surface of the engineered enucleated cell, and the cells are produced by introducing at least one (e.g., one, two, three, or ore) exogenous nucleic acids encoding the more than one exogenous stimulatory polypeptides into a nucleated erythroid cell; and culturing the nucleated erythroid cell under conditions suitable for enucleation of the nucleated erythroid cell and for production of the more than one exogenous stimulatory polypeptides.

Physical Characteristics of Engineered Erythroid Cells

In some embodiments, the erythroid cells described herein have one or more (e.g., 2, 3, 4, or more) physical characteristics described herein, e.g., osmotic fragility, cell size, hemoglobin concentration, or phosphatidylserine content. In some embodiments, the engineered erythroid cell is an enucleated cell. In some embodiments, the engineered erythroid cell is a nucleated cell. While not wishing to be bound by theory, in some embodiments an engineered erythroid cell, e.g. an enucleated cell, that expresses an exogenous protein has physical characteristics that resemble a wild-type, untreated erythroid cell. In contrast, a hypotonically loaded erythroid cell sometimes displays aberrant physical characteristics such as increased osmotic fragility, altered cell size, reduced hemoglobin concentration, or increased phosphatidylserine levels on the outer leaflet of the cell membrane.

In some embodiments, the engineered erythroid cell comprises an exogenous protein that was encoded by an exogenous nucleic acid that was not retained by the cell, has not been purified, or has not existed fully outside an erythroid cell. In some embodiments, the erythroid cell is in a composition that lacks a stabilizer.

Osmotic Fragility

In some embodiments, the engineered erythroid cell exhibits substantially the same osmotic membrane fragility as an isolated, uncultured erythroid cell that does not comprise an exogenous polypeptide. In some embodiments, the population of engineered erythroid cells has an osmotic fragility of less than 50% cell lysis at 0.3%, 0.35%, 0.4%, 0.45%, or 0.5% NaCl. Osmotic fragility can be assayed using the method of Example 59 of WO2015/073587, which is herein incorporated by reference in its entirety.

Cell Size

In some embodiments, the engineered erythroid cell, e.g. enucleated cell, has approximately the diameter or volume as a wild-type, untreated erythroid cell. In some embodiments, the population of erythroid cells has an average diameter of about 4, 5, 6, 7, or 8 microns, and optionally the standard deviation of the population is less than 1, 2, or 3 microns. In some embodiments, the one or more erythroid cell has a diameter of about 4-8, 5-7, or about 6 microns. In some embodiments, the diameter of the erythroid cell is less than about 1 micron, larger than about 20 microns, between about 1 micron and about 20 microns, between about 2 microns and about 20 microns, between about 3 microns and about 20 microns, between about 4 microns and about 20 microns, between about 5 microns and about 20 microns, between about 6 microns and about 20 microns, between about 5 microns and about 15 microns or between about 10 microns and about 30 microns. Cell diameter is measured, in some embodiments, using an Advia 120 hematology system.

In some embodiment the volume of the mean corpuscular volume of the erythroid cells is greater than 10 fL, 20 fL, 30 fL, 40 fL, 50 fL, 60 fL, 70 fL, 80 fL, 90 fL, 100 fL, 110 fL, 120 fL, 130 fL, 140 fL, 150 fL, or greater than 150 fL. In some embodiments the mean corpuscular volume of the erythroid cells is less than 30 fL, 40 fL, 50 fL, 60 fL, 70 fL, 80 fL, 90 fL, 100 fL, 110 fL, 120 fL, 130 fL, 140 fL, 150 fL, 160 fL, 170 fL, 180 fL, 190 fL, 200 fL, or less than 200 fL. In some embodiments the mean corpuscular volume of the erythroid cells is between 80-100, 100-200, 200-300, 300-400, or 400-500 femtoliters (fL). In some embodiments, a population of erythroid cells has a mean corpuscular volume set out in this paragraph and the standard deviation of the population is less than 50, 40, 30, 20, 10, 5, or 2 fL. The mean corpuscular volume is measured, in some embodiments, using a hematological analysis instrument, e.g., a Coulter counter.

Hemoglobin Concentration

In some embodiments, the engineered erythroid cell, e.g. enucleated cell, has a hemoglobin content similar to a wild-type, untreated erythroid cell. In some embodiments, the erythroid cells comprise greater than 1%, 2%, 3%, 4%, 5%, 6%, 7%, 8%, 9% or greater than 10% fetal hemoglobin. In some embodiments, the erythroid cells comprise at least about 20, 22, 24, 26, 28, or 30 pg, and optionally up to about 30 pg, of total hemoglobin. Hemoglobin levels are determined, in some embodiments, using the Drabkin's reagent method of Example 33 of WO2015/073587, which is herein incorporated by reference in its entirety.

Phosphatidylserine Content

In some embodiments, the engineered erythroid cell, e.g. enucleated cell, has approximately the same phosphatidylserine content on the outer leaflet of its cell membrane as a wild-type, untreated erythroid cell. Phosphatidylserine is predominantly on the inner leaflet of the cell membrane of wild-type, untreated erythroid cells, and hypotonic loading can cause the phosphatidylserine to distribute to the outer leaflet where it can trigger an immune response. In some embodiments, the population of erythroid cells comprises less than about 30, 25, 20, 15, 10, 9, 8, 6, 5, 4, 3, 2, or 1% of cells that are positive for Annexin V staining. Phosphatidylserine exposure is assessed, in some embodiments, by staining for Annexin-V-FITC, which binds preferentially to PS, and measuring FITC fluorescence by flow cytometry, e.g., using the method of Example 54 of WO2015/073587, which is herein incorporated by reference in its entirety.

Other Characteristics

In some embodiments, the population of erythroid cells comprises at least about 50%, 60%, 70%, 80%, 90%, or 95% (and optionally up to 90 or 100%) of cells that are positive for GPA. The presence of GPA is detected, in some embodiments, using FACS.

In some embodiments, a population of cells comprising erythroid cells comprises less than about 10, 5, 4, 3, 2, or 1% echinocytes.

In some embodiments, an erythroid cell is enucleated, e.g., a population of cells comprising erythroid cells used as a therapeutic preparation described herein is greater than 50%, 60%, 70%, 80%, 90% enucleated. In some embodiments, a cell, e.g., an erythroid cell, contains a nucleus that is non-functional, e.g., has been inactivated.

Isolating Erythrocytes

Mature erythrocytes may be isolated using various methods such as, for example, a cell washer, a continuous flow cell separator, density gradient separation, fluorescence-activated cell sorting (FACS), Miltenyi immunomagnetic depletion (MACS), or a combination of these methods (See, e.g., van der Berg et al., Clin. Chem. 33:1081-1082 (1987); Bar-Zvi et al., J. Biol. Chem. 262:17719-17723 (1987); Goodman et al., Exp. Biol. Med. 232:1470-1476 (2007)).

Erythrocytes may be isolated from whole blood by simple centrifugation (See, e.g., van der Berg et al., Clin. Chem. 33:1081-1082 (1987)). For example, EDTA-anticoagulated whole blood may be centrifuged at 800×g for 10 min at 4° C. The platelet-rich plasma and buffy coat are removed and the red blood cells are washed three times with isotonic saline solution (NaCl, 9 g/L).

Alternatively, erythrocytes may be isolated using density gradient centrifugation with various separation mediums such as, for example, Ficoll, Hypaque, Histopaque, Percoll, Sigmacell, or combinations thereof. For example, a volume of Histopaque-1077 is layered on top of an equal volume of Histopaque-1119. EDTA-anticoagulated whole blood diluted 1:1 in an equal volume of isotonic saline solution (NaCl, 9 g/L) is layered on top of the Histopaque and the sample is centrifuged at 700×g for 30 min at room temperature. Under these conditions, granulocytes migrate to the 1077/1119 interface, lymphocytes, other mononuclear cells and platelets remain at the plasma/1077 interface, and the red blood cells are pelleted. The red blood cells are washed twice with isotonic saline solution.

Alternatively, erythrocytes may be isolated by centrifugation using a Percoll step gradient (See, e.g., Bar-Zvi et al., J. Biol. Chem. 262:17719-17723 (1987)). For example, fresh blood is mixed with an anticoagulant solution containing 75 mM sodium citrate and 38 mM citric acid and the cells washed briefly in Hepes-buffered saline. Leukocytes and platelets are removed by adsorption with a mixture of α-cellulose and Sigmacell (1:1). The erythrocytes are further isolated from reticulocytes and residual white blood cells by centrifugation through a 45/75% Percoll step gradient for 10 min at 2500 rpm in a Sorvall SS34 rotor. The erythrocytes are recovered in the pellet while reticulocytes band at the 45/75% interface and the remaining white blood cells band at the 0/45% interface. The Percoll is removed from the erythrocytes by several washes in Hepes-buffered saline. Other materials that may be used to generate density gradients for isolation of erythrocytes include OPTIPREP, a 60% solution of iodixanol in water (from Axis-Shield, Dundee, Scotland).

Erythrocytes may be separated from reticulocytes, for example, using flow cytometry (See, e.g., Goodman el al., Exp. Biol. Med. 232:1470-1476 (2007)). In this instance, whole blood is centrifuged (550×g, 20 min, 25° C.) to separate cells from plasma. The cell pellet is resuspended in phosphate buffered saline solution and further fractionated on Ficoll-Paque (1.077 density), for example, by centrifugation (400×g, 30 min, 25° C.) to separate the erythrocytes from the white blood cells. The resulting cell pellet is resuspended in RPMI supplemented with 10% fetal bovine serum and sorted on a FACS instrument such as, for example, a Becton Dickinson FACSCalibur (BD Biosciences, Franklin Lakes, N.J., USA) based on size and granularity.

Erythrocytes may be isolated by immunomagnetic depletion (See, e.g., Goodman, el al., (2007) Exp. Biol. Med. 232:1470-1476). In this instance, magnetic beads with cell-type specific antibodies are used to eliminate non-erythrocytes. For example, erythrocytes are isolated from the majority of other blood components using a density gradient as described herein followed by immunomagnetic depletion of any residual reticulocytes. The cells are pre-treated with human antibody serum for 20 min at 25° C. and then treated with antibodies against reticulocyte specific antigens such as, for example, CD71 and CD36. The antibodies may be directly attached to magnetic beads or conjugated to PE, for example, to which magnetic beads with anti-PE antibody will react. The antibody-magnetic bead complex is able to selectively extract residual reticulocytes, for example, from the erythrocyte population.

Erythrocytes may also be isolated using apheresis. The process of apheresis involves removal of whole blood from a patient or donor, separation of blood components using centrifugation or cell sorting, withdrawal of one or more of the separated portions, and transfusion of remaining components back into the patient or donor. A number of instruments are currently in use for this purpose such as for example the Amicus and Alyx instruments from Baxter (Deerfield, Ill., USA), the Trima Accel instrument from Gambro BCT (Lakewood, Colo., USA), and the MCS+9000 instrument from Haemonetics (Braintree, Mass., USA). Additional purification methods may be necessary to achieve the appropriate degree of cell purity.

Reticulocytes are immature red blood cells and compose approximately 1% of the red blood cells in the human body. Reticulocytes develop and mature in the bone marrow. Once released into circulation, reticulocytes rapidly undergo terminal differentiation to mature erythrocytes. Like mature erythrocytes, reticulocytes do not have a cell nucleus.

Reticulocytes of varying age may be isolated from peripheral blood based on the differences in cell density as the reticulocytes mature. Reticulocytes may be isolated from peripheral blood using differential centrifugation through various density gradients. For example, Percoll gradients may be used to isolate reticulocytes (See, e.g., Noble el al., Blood 74:475-481 (1989)). Sterile isotonic Percoll solutions of density 1.096 and 1.058 g/ml are made by diluting Percoll (Sigma-Aldrich, Saint Louis, Mo., USA) to a final concentration of 10 mM triethanolamine, 117 mM NaCl, 5 mM glucose, and 1.5 mg/ml bovine serum albumin (BSA). These solutions have an osmolarity between 295 and 310 mOsm. Five milliliters, for example, of the first Percoll solution (density 1.096) is added to a sterile 15 ml conical centrifuge tube. Two milliliters, for example, of the second Percoll solution (density 1.058) is layered over the higher density first Percoll solution. Two to four milliliters of whole blood are layered on top of the tube. The tube is centrifuged at 250×g for 30 min in a refrigerated centrifuge with swing-out tube holders. Reticulocytes and some white cells migrate to the interface between the two Percoll layers. The cells at the interface are transferred to a new tube and washed twice with phosphate buffered saline (PBS) with 5 mM glucose, 0.03 mM sodium azide and 1 mg/ml BSA. Residual white blood cells are removed by chromatography in PBS over a size exclusion column.

Alternatively, reticulocytes may be isolated by positive selection using an immunomagnetic separation approach (See, e.g., Brun et al., Blood 76:2397-2403 (1990)). This approach takes advantage of the large number of transferrin receptors that are expressed on the surface of reticulocytes relative to erythrocytes prior to maturation. Magnetic beads coated with an antibody to the transferrin receptor may be used to selectively isolate reticulocytes from a mixed blood cell population. Antibodies to the transferrin receptor of a variety of mammalian species, including human, are available from commercial sources (e.g., Affinity BioReagents, Golden, Colo., USA; Sigma-Aldrich, Saint Louis, Mo., USA). The transferrin antibody may be directly linked to the magnetic beads. Alternatively, the transferrin antibody may be indirectly linked to the magnetic beads via a secondary antibody. For example, mouse monoclonal antibody 10D2 (Affinity BioReagents, Golden, Colo., USA) against human transferrin may be mixed with immunomagnetic beads coated with a sheep anti-mouse immunoglobulin G (Dynal/Invitrogen, Carlsbad, Calif., USA). The immunomagnetic beads are then incubated with a leukocyte-depleted red blood cell fraction. The beads and red blood cells are incubated at 22° C. with gentle mixing for 60-90 min followed by isolation of the beads with attached reticulocytes using a magnetic field. The isolated reticulocytes may be removed from the magnetic beads using, for example, DETACHaBEAD solution (from Invitrogen, Carlsbad, Calif., USA). Alternatively, reticulocytes may be isolated from in vitro growth and maturation of CD34+ hematopoietic stem cells using the methods described herein.

Terminally-differentiated enucleated erythrocytes can be separated from other cells based on their DNA content. In a non-limiting example, cells are first labeled with a vital DNA dye, such as Hoechst 33342 (Invitrogen Corp.). Hoechst 33342 is a cell-permeant nuclear counterstain that emits blue fluorescence when bound to double-stranded DNA. Undifferentiated precursor cells, macrophages or other nucleated cells in the culture are stained by Hoechst 33342, while enucleated erythrocytes are Hoechst-negative. The Hoechst-positive cells can be separated from enucleated erythrocytes by using fluorescence activated cell sorters or other cell sorting techniques. The Hoechst dye can be removed from the isolated erythrocytes by dialysis or other suitable methods.

Vehicles for Polypeptides Described Herein

While in many embodiments herein, the one or more (e.g., two or more) exogenous polypeptides are situated on or in an enucleated erythroid cell, it is understood that any polypeptide or combination of exogenous polypeptides described herein can also be situated on or in another vehicle. The vehicle can comprise, e.g., a cell, an erythroid cell, a corpuscle, a nanoparticle, a micelle, a liposome, or an exosome. For instance, in some aspects, the present disclosure provides a vehicle (e.g., a cell, an erythroid cell, a corpuscle, a nanoparticle, a micelle, a liposome, or an exosome) comprising, e.g., on its surface, one or more agents described herein. In some embodiments, the one or more agents comprise an agent selected from a polypeptide of any of Tables 1 or 8-16, or a fragment or variant thereof, or an antibody molecule thereto. In some embodiments, the vehicle comprises two or more agents described herein, e.g., any pair of agents described herein.

In one aspect, one or more polypeptides described herein are loaded onto, attached (e.g., immobilized or conjugated) to the surface of, and/or enclosed in a non-cellular delivery vehicle. The non-cellular delivery vehicle can be, for example, a nanolipidgel, a polymeric particle, an agarose particle, a latex particle, a silica particle, a liposome, or a multilamellar vesicles. In some embodiments, the non-cellular delivery vehicle comprises or consists of a nanoparticle of from about 1 nm to about 900 nm in diameter. In some embodiments, the non-cellular delivery vehicle comprises an average diameter of from about 0.1 to about 20 microns (such as from about 0.5 microns to about 10 microns, e.g., about 5 microns or less (e.g., about 2.5 to about 5 microns)). In some embodiments, the non-cellular delivery vehicle comprises an average diameter of from about 1 μm to about 10 μm. In some embodiments, the non-cellular delivery vehicle comprises a biodegradable polymer. In some embodiments, the non-cellular delivery vehicle comprises a natural polymer. In some embodiments, the non-cellular delivery vehicle comprises a synthetic polymer. Representative polymers include, but are not limited to, a poly(hydroxy acid), a polyhydroxyalkanoate, a polycaprolactone, a polycarbonate, a polyamide, a polyesteramide, poly(acrylamide), poly(ester), poly(alkylcyanoacrylates), poly(lactic acid) (PLA), poly(glycolic acids) (PGA), and poly(D,L-lactic-co-glycolic acid) (PLGA), and combinations thereof. In some embodiments, the non-cellular delivery vehicle comprises agarose, latex, or polystyrene. One or more of the polypeptides described herein can be conjugated to a non-cellular delivery vehicle using standard methods known in the art (see, e.g., Ulbrich et al. (2016) *Chem Rev.* 116(9): 5338-431). Conjugation can be either covalent or non-covalent. For example, in embodiments in which the non-cellular delivery vehicle is a liposome, a polypeptide described herein may be attached to the liposome via a polyethylene glycol (PEG) chain. Conjugation of a polypeptide to a liposome can also involve thioester bonds, for example by reaction of thiols and maleimide groups. Cross-linking agents can be used to create sulfhydryl groups for attachment of polypeptides to non-cellular delivery vehicles (see, e.g., Paszko and Senge (2012) *Curr. Med. Chem.* 19(31): 5239-77). In some embodiments, the non-cellular delivery vehicles comprising one or more of the polypeptides described herein may be used in any of therapeutic methods provided herein.

Heterogeneous Populations of Cells

While in many embodiments herein, the one or more (e.g., two or more) exogenous polypeptides are situated on or in a single cell, it is understood that any polypeptide or combination of polypeptides described herein can also be situated on a plurality of cells. For instance, in some aspects, the disclosure provides a plurality of erythroid cells, wherein a first cell of the plurality comprises a first exogenous polypeptide and a second cell of the plurality comprises a second exogenous polypeptide. In some embodiments, the plurality of cells comprises two or more polypeptides described herein, e.g., any pair of polypeptides described herein. In some embodiments, less than 90%, 80%, 70%, 60%, 50%, 40%, 30%, 20%, 10%, 5%, 2%, or 1% of the cells in the population comprise both the first exogenous polypeptide and the second exogenous polypeptide.

Cells Encapsulated in a Membrane

In some embodiments, enucleated erythroid cells or other vehicles described herein are encapsulated in a membrane, e.g., semi-permeable membrane. In some embodiments, the membrane comprises a polysaccharide, e.g., an anionic polysaccharide alginate. In some embodiments, the semi-permeable membrane does not allow cells to pass through, but allows passage of small molecules or macromolecules, e.g., metabolites, proteins, or DNA. In some embodiments, the membrane is one described in Lienert et al., "Synthetic biology in mammalian cells: next generation research tools and therapeutics" Nature Reviews Molecular Cell Biology 15, 95-107 (2014), incorporated herein by reference in its entirety. While not wishing to be bound by theory, in some embodiments, the membrane shields the cells from the immune system and/or keeps a plurality of cells in proximity, facilitating interaction with each other or each other's products.

Erythroid Precursor Cells

Provided herein are engineered erythroid precursor cells, and methods of making the engineered erythroid precursor cells, reticulocytes and erythrocytes.

Pluripotent stem cells give rise to erythrocytes by the process of erythropoiesis. The stem cell looks like a small lymphocyte and lacks the functional capabilities of the erythrocyte. The stem cells have the capacity of infinite division, something the mature cells lack. Some of the daughter cells arising from the stem cell acquire erythroid characters over generations and time. Most of the erythroid cells in the bone marrow have a distinct morphology but commitment to erythroid maturation is seen even in cells that have not acquired morphological features distinctive of the erythroid lineage. These cells are recognized by the type of colonies they form in vitro. Two such cells are recognized. Burst-forming unit erythroid (BFU-E) arise from the stem cell and gives rise to colony-forming unit erythroid (CFU-E). CFU-E gives rise to pronormoblast, the most immature of erythroid cells with a distinct morphology. BFU-E and CFU-E form a very small fraction of bone marrow cells. Morphologically five erythroid precursors are identifiable in the bone marrow stained with Romanovsky stains. The five stages from the most immature to the most mature are the proerythroblast, the basophilic normoblast (early erythroblast), polychromatophilic normoblast (intermediate erythroblast), orthochromatophilic normoblast (late erythroblast) and reticulocyte. BFU-E (burst forming unit-erythroid), CFU-E (erythroid colony-forming unit), pronormoblast (proerythroblast), basophilic normoblast, polychromatophilic normoblast and orthochromatophilic normoblast are lineage restricted.

Table 6 below summarizes the morphological features of erythroid precursor cells and erythrocytes.

TABLE 6

| Cell | Nucleus |
|---|---|
| Hematopoietic stem cell (HSC) | Yes |
| CMP (Common myeloid progenitor) | Yes |
| CFU-S (spleen colony forming cell; myeloid precursor cell) | Yes; Can differentiate into erythrocytes, platelets, macrophages. |
| BFU-E (burst forming unit-erythroid) | Yes |
| CFU-E (erythroid colony-forming unit) | Yes |
| Pronormoblast (proerythroblast) | Yes; fine chromatin, many nucleoli |
| Basophilic Normoblast | Yes; granular chromatin, no nucleoli |
| Polychromatophilic Normoblast | Yes; chromatin is visibly clumped with dark staining areas |
| Orthochromatophilic normoblast | Yes; featureless nucleus with dense chromatin |
| Reticulocyte | No Nucleus |
| Erythrocyte (fully matured RBC) | No Nucleus |

Normal human erythrocytes express CD36, an adhesion molecule of monocytes, platelets, and endothelial cells (van Schravendijk M R et al., Blood. 1992 Oct. 15; 80(8):2105-14). Accordingly, in some embodiments, an anti-CD36 antibody can be used to identify human erythrocytes.

Any type of cell known in the art that is capable of differentiating into an erythrocyte, i.e., any erythroid precursor cell, can be modified in accordance with the methods described herein to produce engineered erythroid precursor cells. In certain embodiments, the erythroid precursor cells modified in accordance with the methods described herein are cells that are in the process of differentiating into an erythrocyte, i.e., the cells are of a type known to exist during mammalian erythropoiesis. For example, the cells may be pluripotent hematopoietic stem cells (HSCs) or CD34+ cells, multipotent myeloid progenitor cells, CFU-S cells, BFU-E cells, CFU-E cells, pronormoblasts (proerythroblast), basophilic normoblasts, polychromatophilic normoblasts and orthochromatophilic normoblasts. The modified erythroid precursor cells provided herein can be differentiated into engineered reticulocytes or erythrocytes in vitro using methods known in the art, i.e., using molecules known to promote erythropoiesis, e.g., SCF, Erythropoietin, IL-3, and/or GM-CSF, described herein below. Alternatively, the modified erythroid precursor cells are provided in a composition of the invention, and are capable of differentiating into erythrocytes upon administration to a subject in vivo.

In some embodiments, the erythroid precursor cells, e.g., hematopoietic stem cells, are from an O-negative donor. In some embodiments, the erythroid precursor cells lack (e.g., do not express or encode) A and/or B antigen.

Culturing

Sources for generating engineered erythroid cells described herein include circulating erythroid cells. A suitable cell source may be isolated from a subject as described herein from patient-derived hematopoietic or erythroid progenitor cells, derived from immortalized erythroid cell lines, or derived from induced pluripotent stem cells, optionally cultured and differentiated. Methods for generating erythrocytes using cell culture techniques are well known in the art, e.g., Giarratana et al., Blood 2011, 118:5071, Huang et al., Mol Ther 2013, epub ahead of print September 3, or Kurita et al., PLOS One 2013, 8:e59890. Protocols vary according to growth factors, starting cell lines, culture period, and morphological traits by which the resulting cells are characterized. Culture systems have also been established for blood production that may substitute for donor transfusions (Fibach et al. 1989 Blood 73:100). Recently, CD34+ cells were differentiated to the reticulocyte stage, followed by successful transfusion into a human subject (Giarratana et al., Blood 2011, 118:5071).

Provided herein are culturing methods for erythroid cells and engineered erythroid cell. Erythroid cells can be cultured from hematopoietic progenitor cells, including, for example, CD34+ hematopoietic progenitor cells (Giarratana et al., Blood 2011, 118:5071), induced pluripotent stem cells (Kurita et al., PLOS One 2013, 8:e59890), and embryonic stem cells (Hirose et al. 2013 Stem Cell Reports 1:499). Cocktails of growth and differentiation factors that are suitable to expand and differentiate progenitor cells are known in the art. Examples of suitable expansion and differentiation factors include, but are not limited to, stem cell factor (SCF), an interleukin (IL) such as IL-1, IL-2, IL-3, IL-4, IL-5, IL-6, IL-7, IL-8, IL-9, IL-11, IL-12, CSF, G-CSF, thrombopoietin (TPO), GM-CSF, erythropoietin (EPO), Flt3, Flt2, PIXY 321, and leukemia inhibitory factor (LIF).

Erythroid cells can be cultured from hematopoietic progenitors, such as CD34+ cells, by contacting the progenitor cells with defined factors in a multi-step culture process. For example, erythroid cells can be cultured from hematopoietic progenitors in a three-step process.

The first step may comprise contacting the cells in culture with stem cell factor (SCF) at 1-1000 ng/mL, erythropoietin (EPO) at 1-100 U/mL, and interleukin-3 (IL-3) at 0.1-100 ng/mL. The first step optionally comprises contacting the cells in culture with a ligand that binds and activates a nuclear hormone receptor, such as e.g., the glucocorticoid receptor, the estrogen receptor, the progesterone receptor, the androgen receptor, or the pregnane x receptor. The ligands for these receptors include, for example, a corticosteroid, such as, e.g., dexamethasone at 10 nM-100 μM or hydrocortisone at 10 nM-100 μM; an estrogen, such as, e.g., beta-estradiol at 10 nM-100 μM; a progestogen, such as, e.g., progesterone at 10 nM-100 μM, hydroxyprogesterone at 10 nM-100 μM, 5a-dihydroprogesterone at 10 nM-100 μM, 11-deoxycorticosterone at 10 nM-100 μM, or a synthetic progestin, such as, e.g., chlormadinone acetate at 10 nM-100 μM; an androgen, such as, e.g., testosterone at 10 nM-100 μM, dihydrotestosterone at 10 nM-100 μM or androstenedione at 10 nM-100 μM; or a pregnane x receptor ligand, such as, e.g., rifampicin at 10 nM-100 μM, hyperforin at 10 nM-100 St. John's Wort (hypericin) at 10 nM-100 μM, or vitamin E-like molecules, such as, e.g., tocopherol at 10 nM-100 The first step may also optionally comprise contacting the cells in culture with an insulin-like molecule, such as, e.g., insulin at 1-50 μ.g/mL, insulin-like growth factor 1 (IGF-1) at 1-50 μg/mL, insulin-like growth factor 2

(IGF-2) at 1-50 μg/mL, or mechano-growth factor at 1-50 μg/mL. The first step further may optionally comprise contacting the cells in culture with transferrin at 0.1-5 mg/mL.

The first step may optionally comprise contacting the cells in culture with one or more interleukins (IL) or growth factors such as, e.g., IL-1, IL-2, IL-4, IL-5, IL-6, IL-7, IL-8, IL-9, IL-11, IL-12, granulocyte colony-stimulating factor (G-CSF), macrophage colony-stimulating factor (M-CSF), granulocyte-macrophage colony-stimulating factor (GM-CSF), thrombopoietin, fibroblast growth factor (FGF), platelet-derived growth factor (PDGF), transforming growth factor beta (TGF-B), tumor necrosis factor alpha (TNF-A), megakaryocyte growth and development factor (MGDF), leukemia inhibitory factor (LIF), and Flt3 ligand. Each interleukin or growth factor may typically be supplied at a concentration of 0.1-100 ng/mL. The first step may also optionally comprise contacting the cells in culture with serum proteins or non-protein molecules such as, e.g., fetal bovine serum (1-20%), human plasma (1-20%), plasmanate (1-20%), human serum (1-20%), albumin (0.1-100 mg/mL), or heparin (0.1-10 U/mL).

The second step may comprise contacting the cells in culture with stem cell factor (SCF) at 1-1000 ng/mL and erythropoietin (EPO) at 1-100 U/mL. The second step may also optionally comprise contacting the cells in culture with an insulin-like molecule, such as e.g., insulin at 1-50 μg/mL, insulin-like growth factor 1 (IGF-1) at 1-50 μg/mL, insulin-like growth factor 2 (IGF-2) at 1-50 μg/mL, or mechano-growth factor at 1-50 μg/mL. The second step may further optionally comprise contacting the cells in culture with transferrin at 0.1-5 mg/mL. The second may also optionally comprise contacting the cells in culture with serum proteins or non-protein molecules such as, e.g., fetal bovine serum (1-20%), human plasma (1-20%), plasmanate (1-20%), human serum (1-20%), albumin (0.1-100 mg/mL), or heparin (0.1-10 U/mL).

The third step may comprise contacting the cells in culture with erythropoietin (EPO) at 1-100 U/mL. The third step may optionally comprise contacting the cells in culture with stem cell factor (SCF) at 1-1000 ng/mL. The third step may further optionally comprise contacting the cells in culture with an insulin-like molecule, such as e.g., insulin at 1-50 μg/mL, insulin-like growth factor 1 (IGF-1) at 1-50 μg/mL, insulin-like growth factor 2 (IGF-2) at 1-50 μg/mL, or mechano-growth factor at 1-50 μg/mL. The third step may also optionally comprise contacting the cells in culture with transferrin at 0.1-5 mg/mL. The third step may also optionally comprise contacting the cells in culture with serum proteins or non-protein molecules such as, e.g., fetal bovine serum (1-20%), human plasma (1-20%), plasmanate (1-20%), human serum (1-20%), albumin (0.1-100 mg/mL), or heparin (0.1-10 U/mL).

In some embodiments, methods of expansion and differentiation of the engineered erythroid cells comprising an enucleated cell presenting one or more exogenous polypeptides, do not include culturing the engineered erythroid cells in a medium comprising a myeloproliferative receptor (mpl) ligand.

The culture process may optionally comprise contacting cells by a method known in the art with a molecule, e.g., a DNA molecule, an RNA molecule, a mRNA, an siRNA, a microRNA, a lncRNA, a shRNA, a hormone, or a small molecule, that activates or knocks down one or more genes. Target genes can include, for example, genes that encode a transcription factor, a growth factor, or a growth factor receptor, including but not limited to, e.g., GATA1, GATA2, CMyc, hTERT, p53, EPO, SCF, insulin, EPO-R, SCF-R, transferrin-R, insulin-R.

In some embodiments, CD34+ cells are placed in a culture containing varying amounts of IMDM, FBS, glutamine, BSA, holotransferrin, insulin, dexamethasone, β-estradiol, IL-3, SCF, and erythropoietin, in three separate differentiation stages for a total of 22 days.

In some embodiments, CD34+ cells are placed in a culture containing varying amounts of IMDM, FBS, glutamine, BSA, holotransferrin, insulin, dexamethasone, .beta.-estradiol, IL-3, SCF, and thrombopoietin, in three separate differentiation stages for a total of 14 days.

In some embodiments, CD34+ cells are placed in a culture containing varying amounts of IMDM, FBS, glutamine, BSA, holotransferrin, insulin, dexamethasone, .beta.-estradiol, IL-3, SCF, and GCSF, in three separate differentiation stages for a total of 15 days.

In some embodiments, the erythroid cells are expanded at least 100, 1000, 2000, 5000, 10,000, 20,000, 50,000, or 100,000 fold (and optionally up to 100,000, 200,000, or 500,000 fold). Number of cells is measured, in some embodiments, using an automated cell counter.

In some embodiments, the population of erythroid cells comprises at least 30, 35, 40, 45, 50, 55, 60, 65, 70, 75, 80, 85, 90, 95, or 98% (and optionally up to about 80, 90, or 100%) engineered erythroid cells. Enucleation is measured, in some embodiments, by FACS using a nuclear stain. In some embodiments, at least 30, 35, 40, 45, 50, 55, 60, 65, 70, 75, or 80% (and optionally up to about 70, 80, 90, or 100%) of erythroid cells in the population comprise one or more (e.g., 2, 3, 4 or more) of the exogenous polypeptides. Expression of the polypeptides is measured, in some embodiments, by erythroid cells using labeled antibodies against the polypeptides. In some embodiments, at least 30, 35, 40, 45, 50, 55, 60, 65, 70, 75, or 80% (and optionally up to about 70, 80, 90, or 100%) of erythroid cells in the population are enucleated and comprise one or more (e.g., 2, 3, 4, or more) of the exogenous polypeptides. In some embodiments, the population of erythroid cells comprises about $1\times10^9$-$2\times10^9$, $2\times10^9$-$5\times10^9$, $5\times10^9$-$1\times10^{10}$, $1\times10^{10}$-$2\times10^{10}$, $2\times10^{10}$-$5\times10^{10}$, $5\times10^{10}$-$1\times10^{11}$, $1\times10^{11}$-$2\times10^{11}$, $2\times10^{11}$-$5\times10^{11}$, $5\times10^{11}$-$1\times10^{12}$, $1\times10^{12}$-$2\times10^{12}$, $2\times10^{12}$-$5\times10^{12}$, or $5\times10^{12}$-$1\times10^{13}$ cells.

In some embodiments, it may be desirable during culturing to only partially differentiate the erythroid progenitor cells, e.g., hematopoietic stem cells, in vitro, allowing further differentiation, e.g., differentiation into reticulocytes or fully mature erythrocytes, to occur upon introduction to a subject in vivo (See, e.g., Neildez-Nguyen et al., Nature Biotech. 20:467-472 (2002)). It will be understood that, in various embodiments of the invention, maturation and/or differentiation in vitro may be arrested at any stage desired. For example, isolated CD34+ hematopoietic stem cells may be expanded in vitro as described elsewhere herein, e.g., in medium containing various factors, including, for example, interleukin 3, Flt3 ligand, stem cell factor, thrombopoietin, erythropoietin, transferrin, and insulin growth factor, to reach a desired stage of differentiation. The resulting engineered erythroid cells may be characterized by the surface expression of CD36 and GPA, and other characteristics specific to the particular desired cell type, and may be transfused into a subject where terminal differentiation to mature erythrocytes is allowed to occur.

In some embodiments, engineered erythroid cells are partially expanded from erythroid progenitor cells to any stage of maturation prior to but not including enucleation, and thus remain nucleated cells, e.g., erythroid precursor cells. In certain embodiments, the resulting cells are nucleated and erythroid lineage restricted. In certain embodiments, the resulting cells are selected from multipotent myeloid progenitor cells, CFU-S cells, BFU-E cells, CFU-E cells, pronormoblasts (proerythroblast), basophilic normoblasts, polychromatophilic normoblasts and orthochromatophilic normoblasts. The final differentiation steps, including enucleation, occur only after administration of the engineered erythroid cell to a subject, that is, in such embodiments, the enucleation step occurs in vivo. In another embodiment, engineered erythroid cells are expanded and differentiated in vitro through the stage of enucleation to become, e.g., reticulocytes. In such embodiments where the engineered erythroid cells are differentiated to the stage of reticuloyctes, the final differentiation step to become erythrocytes occurs only after administration of the engineered erythroid cell to a subject, that is, the terminal differentiation step occurs in vivo. In another embodiment, engineered erythroid cells are expanded and differentiated in vitro through the terminal differentiation stage to become erythrocytes. It will be further recognized that in some embodiments, the engineered erythroid cells may be expanded and differentiated from erythroid progenitor cells, e.g., hematopoietic stem cells, to become hematopoietic cells of different lineage, such as, for example, to become platelets. Methods for maturing and differentiating hematopoietic cells of various lineages, such as platelets, are well known in the art to the skilled artisan. Such engineered platelets expressing exogenous polypeptides as described herein are considered to be encompassed by the present invention.

In some embodiments of the above aspects and embodiments, the engineered erythroid cell is an enucleated cell. In some embodiments of the above aspects and embodiments, the engineered erythroid cell is a nucleated cell.

It will be further recognized that in some embodiments, the engineered erythroid cells may be expanded and differentiated from erythroid progenitor cells, e.g., hematopoietic stem cells, to become hematopoietic cells of different lineage, such as, for example, to become platelets. Methods for maturing and differentiating hematopoietic cells of various lineages, such as platelets, are well known in the art to the skilled artisan. In some embodiments, such engineered platelets expressing exogenous polypeptides as described herein are considered to be encompassed by the present invention.

In some embodiments of the above aspects and embodiments, the engineered erythroid cell is an enucleated cell. In some embodiments of the above aspects and embodiments, the engineered erythroid cell is a nucleated cell.

In some embodiments, an enucleated cell provided herein is a platelet. Methods of manufacturing platelets in vitro are known in the art (see, e.g., Wang and Zheng (2016) *Springerplus* 5(1): 787, and U.S. Pat. No. 9,574,178). Methods of manufacturing platelets including an exogenous polypeptide are described, e.g., in International Patent Application Publication Nos. WO2015/073587 and WO2015/153102, each of which is incorporated by reference in its entirety. Platelet production is in part regulated by signaling mechanisms induced by interaction between thrombopoietin (TPO) and its cellular receptor TPOR/MPUc-MPL. In addition, multiple cytokines (e.g., stem cell factor (SCF), IL-1, IL-3, IL-6, IL-11, leukemia inhibiting factor (LIF), G-CSF, GM-CSF, M-CSF, erythropoietin (EPO), kit ligand, and interferon) have been shown to possess thrombocytopoietic activity.

In some embodiments, platelets are generated from hematopoietic progenitor cells, such as $CD34^+$ hematopoietic stem cells, induced pluripotent stem cells or embryonic stem cells. In some embodiments, platelets are produced by contacting the progenitor cells with defined factors in a multi-step culture process. In some embodiments, the multi-step culture process comprises: culturing a population of hematopoietic progenitor cells under conditions suitable to produce a population of megakaryocyte progenitor cells, and culturing the population of megakaryocyte progenitor cells under conditions suitable to produce platelets. Cocktails of growth and differentiation factors that are suitable to expand and differentiate progenitor cells and produce platelets are known in the art. Examples of suitable expansion and differentiation factors include, but are not limited to, stem cell factor (SCF), Flt-3/Flk-2 ligand (FL), TPO, IL-11, IL-3, IL-6, and IL-9. For instance, in some embodiments, platelets may be produced by seeding $CD34^+$ HSCs in a serum-free medium at $2\text{-}4\times10^4$ cells/mL, and refreshing the medium on culture day 4 by adding an equal volume of media. On culture day 6, cells are counted and analyzed: $1.5\times10^5$ cells are washed and placed in 1 mL of the same medium supplemented with a cytokine cocktail comprising TPO (30 ng/mL), SCF (1 ng/mL), IL-6 (7.5 ng/mL), and IL-9 (13.5 ng/mL) to induce megakaryocyte differentiation. At culture day 10, from about one quarter to about half of the suspension culture is replaced with fresh media. The cells are cultured in a humidified atmosphere (10% $CO_2$) at 39° C. for the first 6 culture days, and at 37° C. for the last 8 culture days. Viable nucleated cells are counted with a hemocytometer following trypan blue staining. The differentiation state of platelets in culture can be assessed by flow cytometry or quantitative PCR as described in Examples 44 and 45 of in International Patent Application Publication No. WO2015/073587, incorporated herein by reference.

Other Characteristics

In some embodiments, an engineered erythroid cell (e.g., engineered enucleated erythroid cell) or an engineered enucleated cell, or a population of engineered erythroid cells or engineered enucleated cells comprises one or more of (e.g., all of) endogenous GPA (C235a), transferrin receptor (CD71), Band 3 (CD233), or integrin alpha4 (C49d). These proteins can be measured, e.g., as described in Example 10 of International Application Publication No. WO2018/009838, which is herein incorporated by reference in its entirety. The percentage of GPA-positive cells and Band 3-positive cells typically increases during maturation of an erythroid cell, and the percentage of integrin alpha4-positive typically remains high throughout maturation.

In some embodiments, the population of erythroid cells comprises at least about 50%, 60%, 70%, 80%, 90%, or 95% (and optionally up to 90 or 100%) of cells that are positive for GPA. The presence of GPA is detected, in some embodiments, using FACS.

In some embodiments, the population of engineered erythroid cells (engineered enucleated erythroid cells) or engineered enucleated cells comprises at least about 50%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% $GPA^+$ (i.e., $CD235a^+$) cells. In some embodiments, the population of engineered erythroid cells (engineered enucleated erythroid cells) or engineered enucleated cells comprises between about 50% and about 100% (e.g., from about 60% and about 100%, from about 65% and about 100%, from about 70% and about 100%, from about 75% to about 100%, from about 80% to about 100%, from about 85% to about 100%, from about 90% to about 100%, from about 95% to about 100%, from about 75% to about 99%, from about 80% to about 99%, from about 85% to about 99%, from about 90% to about 99%, from about 95% to about 99%, from about 75% to about 95%, from about 80% to about 95%, from about 85% to about 95%, from about 90% to about 95%, from about 95% to about 98%) $GPA^+$ cells. The presence of GPA is detected, in some embodiments, using FACS.

In some embodiments, the population of engineered erythroid cells (engineered enucleated erythroid cells) or engineered enucleated cells comprises at least about 50%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% $CD71^+$ cells. In some embodiments, the population of engineered erythroid cells (engineered enucleated erythroid cells) or engineered enucleated cells comprises between about 70% and about 100% (e.g., from about 75% to about 100%, from about 80% to about 100%, from about 85% to about 100%, from about 90% to about 100%, from about 95% to about 100%, from about 75% to about 99%, from about 80% to about 99%, from about 85% to about 99%, from about 90% to about 99%, from about 95% to about 99%, from about 75% to about 95%, from about 80% to about 95%, from about 85% to about 95%, from about 90% to about 95%, from about 95% to about 98%) $CD71^+$ cells. The presence of CD71 (transferrin receptor) is detected, in some embodiments, using FACS.

In some embodiments, the population of engineered erythroid cells (engineered enucleated erythroid cells) or engineered enucleated cells comprises at least about 50%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% $CD233^+$ cells. In some embodiments, the population of engineered erythroid cells (engineered enucleated erythroid cells) or engineered enucleated cells comprises between about 70% and about 100% (e.g., from about 75% to about 100%, from about 80% to about 100%, from about 85% to about 100%, from about 90% to about 100%, from about 95% to about 100%, from about 75% to about 99%, from about 80% to about 99%, from about 85% to about 99%, from about 90% to about 99%, from about 95% to about 99%, from about 75% to about 95%, from about 80% to about 95%, from about 85% to about 95%, from about 90% to about 95%, from about 95% to about 98%) $CD233^+$ cells. The presence of CD233 (Band 3) is detected, in some embodiments, using FACS.

In some embodiments, the population of engineered erythroid cells (engineered enucleated erythroid cells) or engineered enucleated cells comprises at least about 50%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% $CD47^+$ cells. In some embodiments, the population of engineered erythroid cells (engineered enucleated erythroid cells) or engineered enucleated cells comprises between about 70% and about 100% (e.g., from about 75% to about 100%, from about 80% to about 100%, from about 85% to about 100%, from about 90% to about 100%, from about 95% to about 100%, from about 75% to about 99%, from about 80% to about 99%, from about 85% to about 99%, from about 90% to about 99%, from about 95% to about 99%, from about 75% to about 95%, from about 80% to about 95%, from about 85% to about 95%, from about 90% to about 95%, from about 95% to about 98%) $CD47^+$ cells. The presence of CD47 (integrin associate protein) is detected, in some embodiments, using FACS.

In some embodiments, the population of engineered erythroid cells (engineered enucleated erythroid cells) or engineered enucleated cells comprises at least about 50%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% $CD36^-$ (CD36-negative) cells. In some embodiments, the population of engineered erythroid cells (engineered enucleated erythroid cells) or engineered enucleated cells comprises between about 70% and about 100% (e.g., from about 75% to about 100%, from about 80% to about 100%, from about 85% to about 100%, from about 90% to about 100%, from about 95% to about 100%, from about 75% to about 99%, from about 80% to about 99%, from about 85% to about 99%, from about 90% to about 99%, from about 95% to about 99%, from about 75% to about 95%, from about 80% to about 95%, from about 85% to about 95%, from about 90% to about 95%, from about 95% to about 98%) $CD36^-$ (CD36-negative) cells. The presence of CD36 is detected, in some embodiments, using FACS.

In some embodiments, the population of engineered erythroid cells (engineered enucleated erythroid cells) or engineered enucleated cells comprises at least about 50%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% $CD34^-$ (CD34-negative) cells. In some embodiments, the population of engineered erythroid cells (engineered enucleated erythroid cells) or engineered enucleated cells comprises between about 70% and about 100% (e.g., from about 75% to about 100%, from about 80% to about 100%, from about 85% to about 100%, from about 90% to about 100%, from about 95% to about 100%, from about 75% to about 99%, from about 80% to about 99%, from about 85% to about 99%, from about 90% to about 99%, from about 95% to about 99%, from about 75% to about 95%, from about 80% to about 95%, from about 85% to about 95%, from about 90% to about 95%, from about 95% to about 98%) $CD34^-$ (CD34-negative) cells. The presence of CD34 is detected, in some embodiments, using FACS.

In some embodiments, the population of engineered erythroid cells (engineered enucleated erythroid cells) or engineered enucleated cells comprises at least about 50%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% $CD235a^+/CD47^+/CD233^+$ cells. In some embodiments, the population of engineered erythroid cells (engineered enucleated erythroid cells) or engineered enucleated cells comprises between about 70% and about 100% (e.g., from about 75% to about 100%, from about 80% to about 100%, from about 85% to about 100%, from about 90% to about 100%, from about 95% to about 100%, from about 75% to about 99%, from about 80% to about 99%, from about 85% to about 99%, from about 90% to about 99%, from about 95% to about 99%, from about 75% to about 95%, from about 80% to about 95%, from about 85% to about 95%, from about 90% to about 95%, from about 95% to about 98%) $CD235a^+/CD47^+/CD233^+$ cells.

In some embodiments, the population of engineered erythroid cells (engineered enucleated erythroid cells) or engineered enucleated cells comprises at least about 50%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% $CD235a^+/CD47^+/CD233^+/CD34^-/CD36^-$ cells. In some embodiments, the population of engineered erythroid cells (engineered enucleated erythroid cells) or engineered enucleated cells comprises between about 70% and about 100% (e.g., from about 75% to about 100%, from about 80% to about 100%, from about 85% to about 100%, from about 90% to about 100%, from about 95% to about 100%, from about 75% to about 99%, from about 80% to about 99%, from about 85% to about 99%, from about 90% to about 99%, from about 95% to about 99%, from about 75% to about 95%, from about 80% to about 95%, from about 85% to about 95%, from about 90% to about 95%, from about 95% to about 98%) $CD235a^+/CD47^+/CD233^+/CD34^-/CD36^-$ cells.

In some embodiments, a population of engineered erythroid cells (engineered enucleated erythroid cells) or engineered enucleated cells comprising erythroid cells comprises less than about 10%, 9%, 8%, 7%, 6%, 5%, 4%, 3%, 2%, or 1% echinocytes.

In some embodiments, a population of engineered erythroid cells (e.g. artificial antigen presenting cells as described herein) comprising erythroid cells comprises less than about 10%, 9%, 8%, 7%, 6%, 5%, 4%, 3%, 2%, or 1% echinocytes.

In some embodiments, a population of engineered erythroid cells (engineered enucleated erythroid cells) or engineered enucleated cells comprises less than about 10%, 9%, 8%, 7%, 6%, 5%, 4%, 3%, 2%, or 1% pyrenocytes.

In some embodiments, an erythroid cell is enucleated, e.g., a population of cells comprising erythroid cells used as a therapeutic preparation described herein is greater than 50%, 60%, 70%, 80%, 90% enucleated. In some embodiments, a cell, e.g., an erythroid cell, contains a nucleus that is non-functional, e.g., has been inactivated. In some embodiments, the engineered erythroid cell is an enucleated cell. In some embodiments, the engineered erythroid cell is a nucleated cell.

Expression of Exogenous Stimulatory Polypeptides

In some embodiments, the engineered erythroid cells, e.g. enucleated cell, described herein are generated by contacting a suitable isolated cell, e.g., an erythroid cell, a reticulocyte, an erythroid precursor cell, a platelet, or a platelet precursor, with an exogenous nucleic acid encoding a stimulatory polypeptide of the disclosure (e.g. IL-1, IL-2, IL-12, IL-15, IL-15/IL-15RA fusion, IL-18, IL-21, IFNα, 4-1BBL, MICA, MICB, PVR/CD155, CD48, HLA-A, HLA-C, HLA-G, HS, HLA-E, CpG, IgG, ULBP, MIC, B7-H6, NkP44L, Nectin2, NTBA, AICL and IGF-1). In some embodiments, the engineered erythroid cell is an enucleated cell. In some embodiments, the engineered erythroid cell is a nucleated cell.

In some embodiments, the exogenous stimulatory polypeptide is encoded by a DNA, which is contacted with a nucleated erythroid precursor cell or a nucleated platelet precursor cell. In some embodiments, the exogenous polypeptide is encoded by an RNA, which is contacted with a platelet, a nucleate erythroid cell, a nucleated platelet precursor cell, or a reticulocyte. In some embodiments, the exogenous polypeptide is contacted with a primary platelet, a nucleated erythroid cell, a nucleated platelet precursor cell, a reticulocyte, or an erythrocyte.

An exogenous stimulatory polypeptide may be expressed from a transgene introduced into an erythroid cell by electroporation, chemical or polymeric transfection, viral transduction, mechanical membrane disruption, or other method; an exogenous polypeptide that is expressed from mRNA that is introduced into a cell by electroporation, chemical or polymeric transfection, viral transduction, mechanical membrane disruption, or other method; an exogenous polypeptide that is over-expressed from the native locus by the introduction of an external factor, e.g., a transcriptional activator, transcriptional repressor, or secretory pathway enhancer; and/or a polypeptide that is synthesized, extracted, or produced from a production cell or other external system and incorporated into the erythroid cell.

Exogenous stimulatory polypeptides (e.g. IL-1, IL-2, IL-12, IL-15, IL-15/IL-15RA fusion, IL-18, IL-21, IFNα, 4-1BBL, MICA, MICB, PVR/CD155, CD48, HLA-A, HLA-C, HLA-G, HS, HLA-E, CpG, IgG, ULBP, MIC, B7-H6, NkP44L, Nectin2, NTBA, AICL and IGF-1) can be introduced by transfection of single or multiple copies of genes, transduction with a virus, or electroporation in the presence of DNA or RNA. Methods for expression of exogenous proteins in mammalian cells are well known in the art. For example, expression of exogenous factor IX in hematopoietic cells is induced by viral transduction of CD34+ progenitor cells, see Chang et al., Nat Biotechnol 2006, 24:1017.

In some embodiments, when there are more than one stimulatory polypeptides (e.g. two or more) the stimulatory polypeptides are encoded in a single nucleic acid, e.g. a single vector. In embodiments, the single vector has a separate promoter for each gene, has two proteins that are initially transcribed into a single polypeptide having a protease cleavage site in the middle, so that subsequent proteolytic processing yields two proteins, or any other suitable configuration. In some embodiments, the two or more polypeptides are encoded in two or more nucleic acids, e.g., each vector encodes one of the polypeptides.

Nucleic acids such as DNA expression vectors or mRNA for producing the exogenous polypeptides may be introduced into progenitor cells (e.g., an erythroid cell progenitor or a platelet progenitor and the like) that are suitable to produce the exogenous polypeptides described herein. The progenitor cells can be isolated from an original source or obtained from expanded progenitor cell population via routine recombinant technology as provided herein. In some instances, the expression vectors can be designed such that they can incorporate into the genome of cells by homologous or non-homologous recombination by methods known in the art.

In some embodiments, hematopoietic progenitor cells, e.g., CD34+ hematopoietic progenitor cells, are contacted with a nucleic acid or nucleic acids encoding one or more exogenous polypeptides, and the cells are allowed to expand and differentiate in culture.

According to some embodiments, one or more exogenous stimulatory polypeptides may be cloned into plasmid constructs for transfection. Methods for transferring expression vectors into cells that are suitable to produce the engineered erythroid cells described herein include, but are not limited to, viral mediated gene transfer, liposome mediated transfer, transformation, gene guns, transfection and transduction, e.g., viral mediated gene transfer such as the use of vectors based on DNA viruses such as adenovirus, adenoassociated virus and herpes virus, as well as retroviral based vectors.

Examples of modes of gene transfer include e.g., naked DNA, $CaPO_4$ precipitation, DEAE dextran, electroporation, protoplast fusion, lipofection, and cell microinjection.

According to some embodiments, recombinant DNA encoding each exogenous stimulatory polypeptide may be cloned into a lentiviral vector plasmid for integration into erythroid cells. In some embodiments, the lentiviral vector comprises DNA encoding a single exogenous stimulatory polypeptide for integration into erythroid cells. In other embodiments, the lentiviral vector comprises two, three, four or more exogenous stimulatory polypeptides as described herein for integration into erythroid cells. According to some embodiments, recombinant DNA encoding the one or more exogenous stimulatory polypeptides may be cloned into a plasmid DNA construct encoding a selectable trait, such as an antibiotic resistance gene. According to some embodiments, recombinant DNA encoding the exogenous stimulatory polypeptides may be cloned into a plasmid construct that is adapted to stably express each recombinant protein in the erythroid cells.

According to some embodiments, the lentiviral system may be employed where the transfer vector with exogenous stimulatory polypeptides sequences (e.g., one, two, three, four or more exogenous polypeptide sequences), an envelope vector, and a packaging vector are each transfected into host cells for virus production. According to some embodiments, the lentiviral vectors may be transfected into host cells by any of calcium phosphate precipitation transfection, lipid based transfection, or electroporation, and incubated overnight. For embodiments where the exogenous stimulatory polypeptide sequence may be accompanied by a fluorescence reporter, inspection of the host cells for florescence may be checked after overnight incubation. The culture medium of the host cells comprising virus particles may be harvested 2 or 3 times every 8-12 hours and centrifuged to sediment detached cells and debris. The culture medium may then be used directly, frozen or concentrated as needed.

A progenitor cell subject to transfer of an exogenous nucleic acid that encodes an exogenous stimulatory polypeptide can be cultured under suitable conditions allowing for differentiation into mature red blood cells, e.g., the in vitro culturing process described herein. The resulting red blood cells display proteins associated with mature erythrocytes, e.g., hemoglobin, glycophorin A, and exogenous stimulatory polypeptides which can be validated and quantified by standard methods (e.g., Western blotting or FACS analysis). Isolated mature red blood cells comprising a plurality of exogenous stimulatory polypeptides, isolated mature red blood cells comprising an IL-15 polypeptide, or a fragment thereof, and an extracellular portion of an IL-15RA polypeptide, or a fragment thereof, and isolated mature enucleated red blood cells comprising at least one exogenous stimulatory polypeptide selected from the group consisting of MICA, MICB, and IGF-1, are non-limiting examples of engineered erythroid cells of the disclosure.

In some embodiments, the engineered erythroid cell is generated by contacting a erythroid precursor cell with an exogenous nucleic acid encoding an exogenous stimulatory polypeptide. In some embodiments, the exogenous stimulatory polypeptide is encoded by an RNA which is contacted with an erythroid precursor cell.

Isolated erythroid precursor cells may be transfected with mRNA encoding one or more exogenous stimulatory polypeptides to generate an engineered erythroid cell. Messenger RNA may be derived from in vitro transcription of a cDNA plasmid construct containing the coding sequence corresponding to the one or more exogenous stimulatory polypeptides. For example, the cDNA sequence corresponding to the exogenous stimulatory polypeptide may be inserted into a cloning vector containing a promoter sequence compatible with specific RNA polymerases. For example, the cloning vector ZAP EXPRESS pBK-CMV (Stratagene, La Jolla, Calif., USA) contains T3 and T7 promoter sequence compatible with T3 and T7 RNA polymerase, respectively. For in vitro transcription of sense mRNA, the plasmid is linearized at a restriction site downstream of the stop codon(s) corresponding to the end of the coding sequence of the exogenous polypeptide. The mRNA is transcribed from the linear DNA template using a commercially available kit such as, for example, the RNAMAXX High Yield Transcription Kit (from Stratagene, La Jolla, Calif., USA). In some instances, it may be desirable to generate 5'-m7GpppG-capped mRNA. As such, transcription of a linearized cDNA template may be carried out using, for example, the mMESSAGE mMACHINE High Yield Capped RNA Transcription Kit from Ambion (Austin, Tex., USA). Transcription may be carried out in a reaction volume of 20-100 μl at 37° C. for 30 min to 4 h. The transcribed mRNA is purified from the reaction mix by a brief treatment with DNase I to eliminate the linearized DNA template followed by precipitation in 70% ethanol in the presence of lithium chloride, sodium acetate or ammonium acetate. The integrity of the transcribed mRNA may be assessed using electrophoresis with an agarose-formaldehyde gel or commercially available Novex pre-cast TBE gels (e.g., Novex, Invitrogen, Carlsbad, Calif., USA).

Messenger RNA encoding the one or more exogenous stimulatory polypeptides may be introduced into reticulocytes using a variety of approaches including, for example, lipofection and electroporation (van Tandeloo et al., Blood 98:49-56 (2001)). For lipofection, for example, 5 μg of in vitro transcribed mRNA in Opti-MEM (Invitrogen, Carlsbad, Calif., USA) is incubated for 5-15 min at a 1:4 ratio with the cationic lipid DMRIE-C (Invitrogen). Alternatively, a variety of other cationic lipids or cationic polymers may be used to transfect cells with mRNA including, for example, DOTAP, various forms of polyethylenimine, and polyL-lysine (Sigma-Aldrich, Saint Louis, Mo., USA), and Superfect (Qiagen, Inc., Valencia, Calif., USA; See, e.g., Bettinger et al., Nucleic Acids Res. 29:3882-3891 (2001)). The resulting mRNA/lipid complexes are incubated with cells ($1\text{-}2\times10^6$ cells/ml) for 2 h at 37° C., washed and returned to culture. For electroporation, for example, about 5 to $20\times10^6$ cells in 500 μl of Opti-MEM (Invitrogen, Carlsbad, Calif., USA) are mixed with about 20 μg of in vitro transcribed mRNA and electroporated in a 0.4-cm cuvette using, for example, and Easyject Plus device (EquiBio, Kent, United Kingdom). In some instances, it may be necessary to test various voltages, capacitances and electroporation volumes to determine the useful conditions for transfection of a particular mRNA into a reticulocyte. In general, the electroporation parameters required to efficiently transfect cells with mRNA appear to be less detrimental to cells than those required for electroporation of DNA (van Tandeloo et al., Blood 98:49-56 (2001)).

Alternatively, mRNA may be transfected into an erythroid precursor cellusing a peptide-mediated RNA delivery strategy (see, e.g., Bettinger et al., Nucleic Acids Res. 29:3882-3891 (2001)). For example, the cationic lipid polyethylenimine 2 kDA (Sigma-Aldrich, Saint Louis, Mo., USA) may be combined with the melittin peptide (Alta Biosciences, Birmingham, UK) to increase the efficiency of mRNA transfection, particularly in post-mitotic primary cells. The mellitin peptide may be conjugated to the PEI using a disulfide cross-linker such as, for example, the hetero-bifunctional cross-linker succinimidyl 3-(2-pyridyldithio) propionate. In vitro transcribed mRNA is preincubated for 5 to 15 min with the mellitin-PEI to form an RNA/peptide/lipid complex. This complex is then added to cells in serum-free culture medium for 2 to 4 h at 37° C. in a 5% $CO_2$ humidified environment and then removed and the transfected cells allowed to continue growing in culture.

In some embodiments, the engineered erythroid cell is generated by contacting a suitable isolated erythroid precursor cell or a platelet precursor cell with an exogenous nucleic acid encoding one or more exogenous stimulatory polypeptides. In some embodiments, the exogenous stimulatory polypeptide is encoded by a DNA, which is contacted with a nucleated erythroid precursor cell or a nucleated platelet precursor cell. In some embodiments, the exogenous stimulatory polypeptide is encoded by an RNA, which is contacted with a platelet, a nucleate erythroid cell, or a nucleated platelet precursor cell.

The one or more exogenous stimulatory polypeptides may be genetically introduced into erythroid precursors cell, platelet precursor, or nucleated erythroid cells prior to terminal differentiation using a variety of DNA techniques, including transient or stable transfections and gene therapy approaches. The exogenous stimulatory polypeptides may be expressed on the surface and/or in the cytoplasm of mature red blood cell or platelet.

Viral gene transfer may be used to transfect the cells with DNA encoding one or more exogenous stimulatory polypeptides. A number of viruses may be used as gene transfer vehicles including Moloney murine leukemia virus (MMLV), adenovirus, adeno-associated virus (AAV), herpes simplex virus (HSV), lentiviruses such as human immunodeficiency virus 1 (HIV 1), and spumaviruses such as foamy viruses, for example (See, e.g., Osten et al., HEP 178:177-202 (2007)). Retroviruses, for example, efficiently transduce mammalian cells including human cells and integrate into chromosomes, conferring stable gene transfer.

One or more exogenous stimulatory polypeptides may be transfected into an erythroid precursor cell, a platelet precursor cell, or a nucleated erythroid cell, expressed and subsequently retained and exhibited in a mature red blood cell or platelet. A suitable vector is the Moloney murine leukemia virus (MMLV) vector backbone (Malik et al., Blood 91:2664-2671 (1998)). Vectors based on MMLV, an oncogenic retrovirus, are currently used in gene therapy clinical trials (Hossle et al., News Physiol. Sci. 17:87-92 (2002)). For example, a DNA construct containing the cDNA encoding an exogenous stimulatory polypeptide can be generated in the MMLV vector backbone using standard molecular biology techniques. The construct is transfected into a packaging cell line such as, for example, PA317 cells and the viral supernatant is used to transfect producer cells such as, for example, PG13 cells. The PG13 viral supernatant is incubated with an erythroid precursor cell, a platelet precursor, or a nucleated erythroid cell that has been isolated and cultured or has been freshly isolated as described herein. The expression of the exogenous polypeptide may be monitored using FACS analysis (fluorescence-activated cell sorting), for example, with a fluorescently labeled antibody directed against the exogenous stimulatory polypeptide, if it is located on the surface of the engineered erythroid cell. Similar methods may be used to express an exogenous polypeptide that is located in the inside of the engineered erythroid cell.

Optionally, a fluorescent tracking molecule such as, for example, green fluorescent protein (GFP) may be transfected using a viral-based approach (Tao et al., Stem Cells 25:670-678 (2007)). Ecotopic retroviral vectors containing DNA encoding the enhanced green fluorescent protein (EGFP) or a red fluorescent protein (e.g., DsRed-Express) are packaged using a packaging cell such as, for example, the Phoenix-Eco cell line (distributed by Orbigen, San Diego, Calif.). Packaging cell lines stably express viral proteins needed for proper viral packaging including, for example, gag, pol, and env. Supernatants from the Phoenix-Eco cells into which viral particles have been shed are used to transduce e.g., erythroid precursor cell, platelet precursors, or a nucleated erythroid cells. In some instances, transduction may be performed on a specially coated surface such as, for example, fragments of recombinant fibronectin to improve the efficiency of retroviral mediated gene transfer (e.g., RetroNectin, Takara Bio USA, Madison, Wis.). Cells are incubated in RetroNectin-coated plates with retroviral Phoenix-Eco supernatants plus suitable co-factors. Transduction may be repeated the next day. In this instance, the percentage of cells expressing EGFP or DsRed-Express may be assessed by FACS. Other reporter genes that may be used to assess transduction efficiency include, for example, beta-galactosidase, chloramphenicol acetyltransferase, and luciferase as well as low-affinity nerve growth factor receptor (LNGFR), and the human cell surface CD24 antigen (Bierhuizen et al., Leukemia 13:605-613 (1999)).

Nonviral vectors may be used to introduce genetic material into suitable erythroid cells, platelets or precursors thereof to generate engineered erythroid cells described herein. Nonviral-mediated gene transfer differs from viral-mediated gene transfer in that the plasmid vectors contain no proteins, are less toxic and easier to scale up, and have no host cell preferences. The "naked DNA" of plasmid vectors is by itself inefficient in delivering genetic material encoding a polypeptide to a cell and therefore is combined with a gene delivery method that enables entry into cells. A number of delivery methods may be used to transfer nonviral vectors into suitable erythroid cells, platelets or precursors thereof including chemical and physical methods.

A nonviral vector encoding one or more exogenous stimulatory polypeptides may be introduced into suitable erythroid cells, platelets or precursors thereof using synthetic macromolecules such as cationic lipids and polymers (Papapetrou et al., Gene Therapy 12:S118-S130 (2005)). Cationic liposomes, for example form complexes with DNA through charge interactions. The positively charged DNA/lipid complexes bind to the negative cell surface and are taken up by the cell by endocytosis. This approach may be used, for example, to transfect hematopoietic cells (See, e.g., Keller et al., Gene Therapy 6:931-938 (1999)). For erythroid cells, platelets or precursors thereof the plasmid DNA (approximately 0.5 μg in 25-100 μL of a serum free medium, such as, for example, OptiMEM (Invitrogen, Carlsbad, Calif.)) is mixed with a cationic liposome (approximately 4μ.g in 25 μ.L of serum free medium) such as the commercially available transfection reagent Lipofectamine™ (Invitrogen, Carlsbad, Calif.) and allowed to incubate for at least 20 min to form complexes. The DNA/liposome complex is added to suitable erythroid cells, platelets or precursors thereof and allowed to incubate for 5-24 hours, after which time transgene expression of the polypeptide may be assayed. Alternatively, other commercially available liposome transfection agents may be used (e.g., In vivo GeneSHUTTLE., Qbiogene, Carlsbad, Calif.).

Optionally, a cationic polymer such as, for example, polyethylenimine (PEI) may be used to efficiently transfect erythroid cell progenitor cells, for example hematopoietic and umbilical cord blood-derived CD34+ cells (See, e.g., Shin et al., Biochim. Biophys. Acta 1725:377-384 (2005)). Human CD34+ cells are isolated from human umbilical cord blood and cultured in Iscove's modified Dulbecco's medium supplemented with 200 ng/ml stem cell factor and 20% heat-inactivated fetal bovine serum. Plasmid DNA encoding the exogenous stimulatory polypeptide is incubated with branched or linear PEIs varying in size from 0.8 K to 750 K (Sigma Aldrich, Saint Louis, Mo., USA; Fermetas, Hanover, Md., USA). PEI is prepared as a stock solution at 4.2 mg/ml distilled water and slightly acidified to pH 5.0 using HCl. The DNA may be combined with the PEI for 30 min at room temperature at various nitrogen/phosphate ratios based on the calculation that 1 µg of DNA contains 3 nmol phosphate and 1 µl of PEI stock solution contains 10 nmol amine nitrogen. The isolated CD34+ cells are seeded with the DNA/cationic complex, centrifuged at 280×g for 5 min and incubated in culture medium for 4 or more h until gene expression of the polypeptide is assessed.

A plasmid vector may be introduced into suitable erythroid cells, platelets or precursors thereof using a physical method such as particle-mediated transfection, "gene gun", biolistics, or particle bombardment technology (Papapetrou, et al., (2005) Gene Therapy 12:S118-S130). In this instance, DNA encoding the polypeptide is absorbed onto gold particles and administered to cells by a particle gun. This approach may be used, for example, to transfect erythroid progenitor cells, e.g., hematopoietic stem cells derived from umbilical cord blood (See, e.g., Verma et al., Gene Therapy 5:692-699 (1998)). As such, umbilical cord blood is isolated and diluted three fold in phosphate buffered saline. CD34+ cells are purified using an anti-CD34 monoclonal antibody in combination with magnetic microbeads coated with a secondary antibody and a magnetic isolation system (e.g., Miltenyi MiniMac System, Auburn, Calif., USA). The CD34+ enriched cells may be cultured as described herein. For transfection, plasmid DNA encoding the polypeptide is precipitated onto a particle, for example gold beads, by treatment with calcium chloride and spermidine. Following washing of the DNA-coated beads with ethanol, the beads may be delivered into the cultured cells using, for example, a Biolistic PDS-1000/He System (Bio-Rad, Hercules, Calif., USA). A reporter gene such as, for example, beta-galactosidase, chloramphenicol acetyltransferase, luciferase, or green fluorescent protein may be used to assess efficiency of transfection.

Optionally, electroporation methods may be used to introduce a plasmid vector into suitable erythroid cells, platelets or precursors thereof. Electroporation creates transient pores in the cell membrane, allowing for the introduction of various molecules into the cells including, for example, DNA and RNA as well as antibodies and drugs. As such, CD34+ cells are isolated and cultured as described herein. Immediately prior to electroporation, the cells are isolated by centrifugation for 10 min at 250×g at room temperature and resuspended at 0.2-10×10$^6$ viable cells/ml in an electroporation buffer such as, for example, X-VIVO 10 supplemented with 1.0% human serum albumin (HSA). The plasmid DNA (1-50 µg) is added to an appropriate electroporation cuvette along with 500 µl of cell suspension. Electroporation may be done using, for example, an ECM 600 electroporator (Genetronics, San Diego, Calif., USA) with voltages ranging from 200 V to 280 V and pulse lengths ranging from 25 to 70 milliseconds. A number of alternative electroporation instruments are commercially available and may be used for this purpose (e.g., Gene Pulser XCELL, BioRad, Hercules, Calif.; Cellject Duo, Thermo Science, Milford, Mass.). Alternatively, efficient electroporation of isolated CD34+ cells may be performed using the following parameters: 4 mm cuvette, 1600 µF, 550 V/cm, and 10 µg of DNA per 500 µl of cells at 1×10$^5$ cells/ml (Oldak et al., Acta Biochimica Polonica 49:625-632 (2002)).

Nucleofection, a form of electroporation, may also be used to transfect suitable erythroid cells, platelets or precursors thereof. In this instance, transfection is performed using electrical parameters in cell-type specific solutions that enable DNA (or other reagents) to be directly transported to the nucleus thus reducing the risk of possible degradation in the cytoplasm. For example, a Human CD34 CELL NYCLEOFECTOR Kit (from Amaxa Inc.) may be used to transfect suitable erythroid cells, platelets or precursors thereof. In this instance, 1-5×10$^6$ cells in Human CD34 Cell NUCLEOFECTOR Solution are mixed with 1-5 µg of DNA and transfected in the NUCLEOFECTOR instrument using preprogrammed settings as determined by the manufacturer.

Erythroid cells, platelets or precursors thereof may be non-virally transfected with a conventional expression vector which is unable to self-replicate in mammalian cells unless it is integrated in the genome. Alternatively, erythroid cells, platelets or precursors thereof may be transfected with an episomal vector which may persist in the host nucleus as autonomously replicating genetic units without integration into chromosomes (Papapetrou et al., Gene Therapy 12:S118-S130 (2005)). These vectors exploit genetic elements derived from viruses that are normally extrachromosomally replicating in cells upon latent infection such as, for example, EBV, human polyomavirus BK, bovine papilloma virus-1 (BPV-1), herpes simplex virus-1 (HSV) and Simian virus 40 (SV40). Mammalian artificial chromosomes may also be used for nonviral gene transfer (Vanderbyl et al., Exp. Hematol. 33:1470-1476 (2005)).

Exogenous nucleic acids encoding one or more exogenous stimulatory polypeptides may be assembled into expression vectors by standard molecular biology methods known in the art, e.g., restriction digestion, overlap-extension PCR, and Gibson assembly.

Exogenous nucleic acids may comprise a gene encoding one or more exogenous stimulatory polypeptides that are not normally expressed on the cell surface, e.g., of an erythroid cell, fused to a gene that encodes an endogenous or native membrane protein, such that the exogenous stimulatory polypeptide is expressed on the cell surface. For example, a exogenous gene encoding an exogenous stimulatory polypeptide can be cloned at the N terminus following the leader sequence of a type 1 membrane protein, at the C terminus of a type 2 membrane protein, or upstream of the GPI attachment site of a GPI-linked membrane protein.

Standard cloning methods can be used to introduce flexible amino acid linkers between two fused genes. For example, the flexible linker is a poly-glycine poly-serine linker such as [Gly4Ser]3 commonly used in generating single-chain antibody fragments from full-length antibodies (Antibody Engineering: Methods & Protocols, Lo 2004), or ala-gly-ser-thr polypeptides such as those used to generate single-chain Arc repressors (Robinson & Sauer, PNAS 1998). In some embodiments, the flexible linker provides the polypeptide with more flexibility and steric freedom than the equivalent construct without the flexible linker.

An epitope tag may be placed between two fused genes, such as, e.g., a nucleic acid sequence encoding an HA epitope tag—amino acids YPYDVPDYA (SEQ ID NO: 78), a CMyc tag—amino acids EQKLISEEDL (SEQ ID NO: 79), or a Flag tag—amino acids DYKDDDDK (SEQ ID NO: 80). The epitope tag may be used for the facile detection and quantification of expression using antibodies against the epitope tag by flow cytometry, western blot, or immunoprecipitation.

In some embodiments, the engineered erythroid cell comprises one or more exogenous stimulatory polypeptides and at least one other heterologous polypeptide. The at least one other heterologous polypeptide can be a fluorescent protein. The fluorescent protein can be used as a reporter to assess transduction efficiency. In some embodiments, the fluorescent protein is used as a reporter to assess expression levels of the exogenous stimulatory polypeptide if both are made from the same transcript. In some embodiments, the at least one other polypeptide is heterologous and provides a function, such as, e.g., multiple antigens, multiple capture targets, enzyme cascade. In some embodiments, the recombinant nucleic acid comprises a gene encoding an exogenous stimulatory polypeptide and a second gene, wherein the second gene is separated from the gene encoding the exogenous stimulatory polypeptide by a viral-derived T2A sequence (gagggcagaggaagtcttctaacatgcggtgacgtggaggsgsstcccggccct (SEQ ID NO: 81)) that is post-translationally cleaved into two mature proteins.

In some embodiments, a population of erythroid cells is incubated with lentiviral vectors comprising exogenous nucleic acid encoding one or more exogenous stimulatory polypeptides, specific plasmids of which may include; pLKO.1 puro, PLKO.1—TRC cloning vector, pSico, FUGW, pLVTHM, pLJM1, pLion11, pMD2.G, pCMV-VSV-G, pCI-VSVG, pCMV-dR8.2 dvpr, psPAX2, pRSV-Rev, and pMDLg/pRRE to generate an engineered erythroid cell. The vectors may be administered at 10, 100, 1,000, 10,000 pfu and incubated for 12 hrs.

In certain embodiments, the engineered erythroid cell is an enucleated cell that presents a first exogenous stimulatory polypeptide that is conjugated with a second exogenous stimulatory polypeptide. Conjugation may be achieved chemically or enzymatically. Chemical conjugation may be accomplished by covalent bonding of the exogenous antigen-presenting polypeptide to one or more exogenous stimulatory polypeptides, with or without the use of a linker. Chemical conjugation may be accomplished by the covalent bonding of a costimulatory polypeptide and a binding pair member, with or without the use of a linker. Chemical conjugation may be accomplished by the covalent bonding of a coinhibitory polypeptide and a binding pair member, with or without the use of a linker. The formation of such conjugates is within the skill of artisans and various techniques are known for accomplishing the conjugation, with the choice of the particular technique being guided by the materials to be conjugated. The addition of amino acids to the polypeptide (C- or N-terminal) which contain ionizable side chains, e.g., aspartic acid, glutamic acid, lysine, arginine, cysteine, histidine, or tyrosine, and are not contained in the active portion of the polypeptide sequence, serve in their unprotonated state as a potent nucleophile to engage in various bioconjugation reactions with reactive groups attached to polymers, e.g., homo- or hetero-bi-functional PEG (e.g., Lutolf and Hubbell, Biomacromolecules 2003; 4:713-22, Hermanson, Bioconjugate Techniques, London. Academic Press Ltd; 1996).

Other molecular fusions may be formed between exogenous stimulatory polypeptides and include direct or indirect conjugation. The exogenous polypeptides may be directly conjugated to each other or indirectly through a linker. The linker may be a peptide, a polymer, an aptamer, or a nucleic acid. The polymer may be, e.g., natural, synthetic, linear, or branched. Exogenous stimulatory polypeptides can comprise a heterologous fusion protein that comprises a first polypeptide and a second polypeptide with the fusion protein comprising the polypeptides directly joined to each other or with intervening linker sequences and/or further sequences at one or both ends. The conjugation to the linker may be through covalent bonds or ionic bonds.

In certain embodiments, the engineered erythroid cell is an enucleated cell that presents a first exogenous stimulatory polypeptide that is in a complex with a second exogenous stimulatory polypeptide. In other embodiments, the first exogenous stimulatory polypeptide comprises an IL-15 polypeptide, or a fragment thereof, and an extracellular portion of an IL-15RA polypeptide, or a fragment thereof. In further embodiments, the IL-15 polypeptide and the extracellular portion of an IL-15RA polypeptide are present as a complex. In other further embodiments, the IL-15 polypeptide and the extracellular portion of an IL-15RA polypeptide are present as a fusion polypeptide. In some embodiments, the IL-15 polypeptide is linked to the extracellular portion of the IL-15RA polypeptide by a linker, for example a GGGGS linker (SEQ ID NO: 11), in particular a $(GGGGS)_3$ linker (SEQ ID NO: 12).

Erythroid cells described herein can also be produced using coupling reagents to link an exogenous stimulatory polypeptide to a cell. For instance, click chemistry can be used. Coupling reagents can be used to couple an exogenous polypeptide to a cell, for example, when the exogenous polypeptide is a complex or difficult to express polypeptide, e.g., a polypeptide, e.g., a multimeric polypeptide; large polypeptide; polypeptide derivatized in vitro; an exogenous polypeptide that may have toxicity to, or which is not expressed efficiently in, the erythroid cells. Click chemistry and other conjugation methods for functionalizing erythroid cells is described in International Application No. PCT/US2018/000042, which claims priority to U.S. Provisional Application No. 62/460,589, filed Feb. 17, 2017 and U.S. Provisional Application No. 62/542,142, filed Jul. 8, 2017, incorporated by reference in their entireties herein.

Thus, in some embodiments, an erythroid cell described herein comprises many as, at least, more than, or about 5,000, 10,000, 50,000, 100,000, 200,000, 300,000, 400,000, 500,000 coupling reagents per cell. In some embodiments, the erythroid cells are made by a method comprising a) coupling a first coupling reagent to an erythroid cell, thereby making a pharmaceutical preparation, product, or intermediate. In an embodiment, the method further comprises: b) contacting the cell with an exogenous stimulatory polypeptide coupled to a second coupling reagent e.g., under conditions suitable for reaction of the first coupling reagent with the second coupling reagent. In embodiments, two or more exogenous stimulatory polypeptides are coupled to the cell (e.g., using click chemistry). In embodiments, a first exogenous stimulatory polypeptide is coupled to the cell (e.g., using click chemistry) and a second exogenous stimulatory polypeptide comprises a polypeptide expressed from an exogenous nucleic acid.

In some embodiments, the coupling reagent comprises an azide coupling reagent. In some embodiments, the azide coupling reagent comprises an azidoalkyl moiety, azidoaryl moiety, or an azidoheteroaryl moiety. Exemplary azide coupling reagents include 3-azidopropionic acid sulfo-NHS ester, azidoacetic acid NHS ester, azido-PEG-NHS ester, azidopropylamine, azido-PEG-amine, azido-PEG-maleimide, bis-sulfone-PEG-azide, or a derivative thereof. Coupling reagents may also comprise an alkene moiety, e.g., a transcycloalkene moiety, an oxanorbornadiene moiety, or a tetrazine moiety. Additional coupling reagents can be found in Click Chemistry Tools (https://clickchemistrytools.com/) or Lahann, J (ed) (2009) *Click Chemistry for Biotechnology and Materials Science*, each of which is incorporated herein by reference in its entirety.

In another embodiment, the exogenous stimulatory polypeptide is attached to an erythroid cell via a covalent attachment to generate an engineered erythroid cell comprising an erytrhroid cell presenting one or more exogenous stimulatory polypeptides (e.g. a first exogenous stimulatory polypeptide and a second exogenous stimulatory polypeptide). For example, the exogenous stimulatory polypeptide may be derivatized and bound to the erythroid cell or platelet using a coupling compound containing an electrophilic group that will react with nucleophiles on the erythroid cell or platelet to form the interbonded relationship. Representative of these electrophilic groups are αβ unsaturated carbonyls, alkyl halides and thiol reagents such as substituted maleimides. In addition, the coupling compound can be coupled to an exogenous stimulatory polypeptide via one or more of the functional groups in the polypeptide such as amino, carboxyl and tryosine groups. For this purpose, coupling compounds should contain free carboxyl groups, free amino groups, aromatic amino groups, and other groups capable of reaction with enzyme functional groups. Highly charged exogenous stimulatory polypeptides can also be prepared for immobilization on, e.g., erythroid cells or platelets through electrostatic bonding to generate an engineered erythroid cell. Examples of these derivatives would include polylysyl and polyglutamyl enzymes.

The choice of the reactive group embodied in the derivative depends on the reactive conditions employed to couple the electrophile with the nucleophilic groups on the erythroid cell or platelet for immobilization. A controlling factor is the desire not to inactivate the coupling agent prior to coupling of the exogenous stimulatory polypeptide immobilized by the attachment to the erythroid cell or platelet. Such coupling immobilization reactions can proceed in a number of ways. Typically, a coupling agent can be used to form a bridge between the exogenous polypeptide and the erythroid cell or platelet. In this case, the coupling agent should possess a functional group such as a carboxyl group which can be caused to react with the exogenous polypeptide. One way of preparing the exogenous stimulatory polypeptide for conjugation includes the utilization of carboxyl groups in the coupling agent to form mixed anhydrides which react with the exogenous polypeptide, in which use is made of an activator which is capable of forming the mixed anhydride. Representative of such activators are isobutylchloroformate or other chloroformates which give a mixed anhydride with coupling agents such as 5,5'-(dithiobis(2-nitrobenzoic acid) (DTNB), p-chloromercuribenzoate (CMB), or m-maleimidobenzoic acid (MBA). The mixed anhydride of the coupling agent reacts with the exogenous polypeptide to yield the reactive derivative which in turn can react with nucleophilic groups on the erythroid cell or platelet to immobilize the exogenous stimulatory polypeptide.

Functional groups on an exogenous stimulatory polypeptide, such as carboxyl groups can be activated with carbodiimides and the like activators. Subsequently, functional groups on the bridging reagent, such as amino groups, will react with the activated group on the exogenous stimulatory polypeptide to form the reactive derivative. In addition, the coupling agent should possess a second reactive group which will react with appropriate nucleophilic groups on the erythroid cell or platelet to form the bridge. Typical of such reactive groups are alkylating agents such as iodoacetic acid, αβ unsaturated carbonyl compounds, such as acrylic acid and the like, thiol reagents, such as mercurials, substituted maleimides and the like.

Alternatively, functional groups on the exogenous stimulatory polypeptide can be activated so as to react directly with nucleophiles on, e.g., erythroid cells or platelets to obviate the need for a bridge-forming compound. For this purpose, use is made of an activator such as Woodward's Reagent K or the like reagent which brings about the formation of carboxyl groups in the exogenous polypeptide into enol esters, as distinguished from mixed anhydrides. The enol ester derivatives of exogenous polypeptides subsequently react with nucleophilic groups on, e.g., an erythroid cell or platelet to effect immobilization of the exogenous stimulatory polypeptide, thereby creating an engineered erythroid cell.

In some embodiments, the engineered erythroid cell comprising a plurality of exogenous stimulatory polypeptides is generated by contacting an erythroid cell with an exogenous stimulatory polypeptide and optionally a payload, wherein contacting does not include conjugating the exogenous stimulatory polypeptide to the erythroid cell using an attachment site comprising Band 3 (CD233), aquaporin-1, Glut-1, Kidd antigen, RhAg/R1i50 (CD241), Rli (CD240), Rh30CE (CD240CE), Rh30D (CD240D), Kx, glycophorin B (CD235b), glycophorin C (CD235c), glycophorin D (CD235d), Kell (CD238), Duffy/DARCi (CD234), CR1 (CD35), DAF (CD55), Globoside, CD44, ICAM-4 (CD242), Lu/B-CAM (CD239), XG1/XG2 (CD99), EMMPRIN/neurothelin (CD147), JMH, Glycosyltransferase, Cartwright, Dombrock, C4A/CAB, Scianna, MER2, stomatin, BA-1 (CD24), GPIV (CD36), CD108, CD139, or H antigen (CD173).

In some embodiments, the engineered erythroid cell comprises an erythroid cell presenting one or more exogenous stimulatory polypeptides, wherein the one or more exogenous stimulatory polypeptides are enzymatically conjugated onto the cell.

In specific embodiments, the exogenous stimulatory polypeptide can be conjugated to the surface of, e.g., an erythroid cell or platelet by various chemical and enzymatic means, including but not limited to chemical conjugation with bifunctional cross-linking agents such as, e.g., an NHS ester-maleimide heterobifunctional crosslinker to connect a primary amine group with a reduced thiol group. These methods also include enzymatic strategies such as, e.g., transpeptidase reaction mediated by a sortase enzyme to connect one polypeptide containing the acceptor sequence LPXTG (SEQ ID NO: 82) or LPXTA (SEQ ID NO: 83) with a polypeptide containing the N-terminal donor sequence GGG, see e.g., Swee et al., PNAS 2013. The methods also include combination methods, such as e.g., sortase-mediated conjugation of Click Chemistry handles (an azide and an alkyne) on the antigen and the cell, respectively, followed by a cyclo-addition reaction to chemically bond the antigen to the cell, see e.g., Neves et al., Bioconjugate Chemistry, 2013. Sortase-mediated modification of proteins is described in International Application No. PCT/US2014/037545 and International Application No. PCT/US2014/037554, both of which are incorporated by reference in their entireties herein.

In some embodiments, a protein is modified by the conjugation of a sortase substrate comprising an amino acid, a peptide, a protein, a polynucleotide, a carbohydrate, a tag, a metal atom, a contrast agent, a catalyst, a non-polypeptide polymer, a recognition element, a small molecule, a lipid, a linker, a label, an epitope, an antigen, a therapeutic agent, a toxin, a radioisotope, a particle, or moiety comprising a reactive chemical group, e.g., a click chemistry handle.

If desired, a catalytic bond-forming polypeptide domain can be expressed on or in e.g., an erythroid cell or platelet, either intracellularly or extracellularly. Many catalytic bond-forming polypeptides exist, including transpeptidases, sortases, and isopeptidases, including those derived from Spy0128, a protein isolated from *Streptococcus pyogenes*.

In some embodiments, any of the polypeptides described herein are not conjugated to the cell using a sortase.

It has been demonstrated that splitting the autocatalytic isopeptide bond-forming subunit (CnaB2 domain) of Spy0128 results in two distinct polypeptides that retain catalytic activity with specificity for each other. The polypeptides in this system are termed SpyTag and SpyCatcher. Upon mixing, SpyTag and SpyCatcher undergo isopeptide bond formation between Asp117 on SpyTag and Lys31 on SpyCatcher (Zakeri and Howarth, JACS 2010, 132:4526). The reaction is compatible with the cellular environment and highly specific for protein/peptide conjugation (Zakeri, B.; Fierer, J. O.; Celik, E.; Chittock, E. C.; Schwarz-Linek, U.; Moy, V. T.; Howarth, M. Proc. Natl. Acad. Sci. U.S.A. 2012, 109, E690-E697). SpyTag and SpyCatcher has been shown to direct post-translational topological modification in elastin-like protein. For example, placement of SpyTag at the N-terminus and SpyCatcher at the C-terminus directs formation of circular elastin-like proteins (Zhang et al, Journal of the American Chemical Society, 2013).

The components SpyTag and SpyCatcher can be interchanged such that a system in which molecule A is fused to SpyTag and molecule B is fused to SpyCatcher is functionally equivalent to a system in which molecule A is fused to SpyCatcher and molecule B is fused to SpyTag. For the purposes of this document, when SpyTag and SpyCatcher are used, it is to be understood that the complementary molecule could be substituted in its place.

A catalytic bond-forming polypeptide, such as a SpyTag/SpyCatcher system, can be used to attach the exogenous stimulatory polypeptide to the surface of, e.g., an erythroid cell, to generate an engineered erythroid cell. The SpyTag polypeptide sequence can be expressed on the extracellular surface of the erythroid cell. The SpyTag polypeptide can be, for example, fused to the N terminus of a type-1 or type-3 transmembrane protein, e.g., glycophorin A, fused to the C terminus of a type-2 transmembrane protein, e.g., Kell, inserted in-frame at the extracellular terminus or in an extracellular loop of a multi-pass transmembrane protein, e.g., Band 3, fused to a GPI-acceptor polypeptide, e.g., CD55 or CD59, fused to a lipid-chain-anchored polypeptide, or fused to a peripheral membrane protein. The nucleic acid sequence encoding the SpyTag fusion can be expressed within an engineered erythroid cell. An exogenous stimulatory polypeptide can be fused to SpyCatcher. The nucleic acid sequence encoding the SpyCatcher fusion can be expressed and secreted from the same erythroid cell that expresses the SpyTag fusion. Alternatively, the nucleic acid sequence encoding the SpyCatcher fusion can be produced exogenously, for example in a bacterial, fungal, insect, mammalian, or cell-free production system. Upon reaction of the SpyTag and SpyCatcher polypeptides, a covalent bond will be formed that attaches the exogenous stimulatory polypeptide to the surface of the erythroid cell to form an engineered erythroid cell.

In some embodiments, the SpyTag polypeptide may be expressed as a fusion to the N terminus of glycophorin A under the control of the Gatal promoter in an erythroid cell. An exogenous stimulatory polypeptide, fused to the SpyCatcher polypeptide sequence can be expressed under the control of the Gatal promoter in the same erythroid cell. Upon expression of both fusion polypeptides, an isopeptide bond will be formed between the SpyTag and SpyCatcher polypeptides, forming a covalent bond between the erythroid cell surface and the exogenous stimulatory polypeptide.

In another embodiment, the SpyTag polypeptide may be expressed as a fusion to the N terminus of glycophorin A under the control of the Gatal promoter in an erythroid cell. An exogenous stimulatory polypeptide fused to the SpyCatcher polypeptide sequence can be expressed in a suitable mammalian cell expression system, for example HEK293 cells. Upon expression of the SpyTag fusion polypeptide on the erythroid cell, the SpyCatcher fusion polypeptide can be brought in contact with the cell. Under suitable reaction conditions, an isopeptide bond will be formed between the SpyTag and SpyCatcher polypeptides, forming a covalent bond between the erythroid cell surface and the exogenous stimulatory polypeptide.

In certain embodiments, the exogenous stimulatory polypeptide is loaded into the engineered erythroid cell. In some embodiments, engineered erythroid cells are generated by loading, e.g., erythroid cells or platelets with one or more exogenous stimulatory polypeptides, such that the one or more exogenous stimulatory polypeptides are internalized within the erythroid cells or platelets. Optionally, the erythroid cells or platelets may additionally be loaded with a payload, such as, e.g., a therapeutic agent.

A number of methods may be used to load, e.g., erythroid cells or platelets with an exogenous stimulatory polypeptide. Suitable methods include, for example, hypotonic lysis, hypotonic dialysis, osmosis, osmotic pulsing, osmotic shock, ionophoresis, electroporation, sonication, microinjection, calcium precipitation, membrane intercalation, lipid mediated transfection, detergent treatment, viral infection, diffusion, receptor mediated endocytosis, use of protein transduction domains, particle firing, membrane fusion, freeze-thawing, mechanical disruption, and filtration. Any one such method or a combination thereof may be used to generate the engineered erythroid cells described herein.

For hypotonic lysis, e.g., erythroid cell are exposed to low ionic strength buffer causing them to burst. The exogenous stimulatory polypeptide distributes within the cells. Erythroid cell, specifically red blood cells may be hypotonically lysed by adding 30-50 fold volume excess of 5 mM phosphate buffer (pH 8) to a pellet of isolated red blood cells. The resulting lysed cell membranes are isolated by centrifugation. The pellet of lysed red blood cell membranes is resuspended and incubated in the presence of the exogenous polypeptide in a low ionic strength buffer, e.g., for 30 min. Alternatively, the lysed red blood cell membranes may be incubated with the exogenous polypeptide for as little as one minute or as long as several days, depending upon the best conditions determined to efficiently load the erythroid cells.

Alternatively, erythroid cells, specifically red blood cells may be loaded with an exogenous stimulatory polypeptide using controlled dialysis against a hypotonic solution to swell the cells and create pores in the cell membrane (See, e.g., U.S. Pat. Nos. 4,327,710; 5,753,221; and 6,495,351). For example, a pellet of isolated red blood cells is resuspended in 10 mM HEPES, 140 mM NaCl, 5 mM glucose pH 7.4 and dialyzed against a low ionic strength buffer containing 10 mM $NaH_2PO_4$, 10 mM $NaHCO_3$, 20 mM glucose, and 4 mM $MgCl_2$, pH 7.4. After 30-60 min, the red blood cells are further dialyzed against 16 mM $NaH_2PO_4$, pH 7.4 solution containing the exogenous polypeptide for an additional 30-60 min. All of these procedures may be advantageously performed at a temperature of 4° C. In some instances, it may be beneficial to load a large quantity of erythroid cells, specifically red blood cells by a dialysis approach and a specific apparatus designed for this purpose may be used (See, e.g., U.S. Pat. Nos. 4,327,710, 6,139,836 and 6,495,351).

The loaded erythroid cells, specifically red blood cells can be resealed by gentle heating in the presence of a physiological solution such as, for example, 0.9% saline, phosphate buffered saline, Ringer's solution, cell culture medium, blood plasma or lymphatic fluid. For example, well-sealed membranes may be generated by treating the disrupted erythroid cells, specifically red blood cells for 1-2 min in 150 mM salt solution of, for example, 100 mM phosphate (pH 8.0) and 150 mM sodium chloride at a temperature of 60° C. Alternatively, the cells may be incubated at a temperature of 25-50° C. for 30 min to 4 h (See, e.g., U.S. Patent Application 2007/0243137 A1). Alternatively, the disrupted red blood cells may be resealed by incubation in 5 mM adenine, 100 mM inosine, 2 mM ATP, 100 mM glucose, 100 mM Na-pyruvate, 4 mM MgCl2, 194 mM NaCl, 1.6 M KCl, and 35 mM $NaH_2PO_4$, pH 7.4 at a temperature of 37° C. for 20-30 min (See, e.g., U.S. Pat. No. 5,753,221).

For electroporation, e.g., erythroid cells or platelets are exposed to an electrical field which causes transient holes in the cell membrane, allowing the one or more exogenous stimulatory polypeptides to diffuse into the cell (See, e.g., U.S. Pat. No. 4,935,223). Erythroid cells, specifically red blood cells, for example, are suspended in a physiological and electrically conductive media such as platelet-free plasma to which the one or more exogenous stimulatory polypeptides are added. The mixture in a volume ranging from 0.2 to 1.0 ml is placed in an electroporation cuvette and cooled on ice for 10 min. The cuvette is placed in an electroporation apparatus such as, for example, an ECM 830 (from BTX Instrument Division, Harvard Apparatus, Holliston, Mass.). The cells are electroporated with a single pulse of approximately 2.4 milliseconds in length and a field strength of approximately 2.0 kV/cm. Alternatively, electroporation of erythroid cells, specifically red blood cells may be carried out using double pulses of 2.2 kV delivered at 0.25.mu.F using a Bio-Rad Gene Pulsar apparatus (Bio-Rad, Hercules, Calif., USA) to achieve a loading capacity of over 60% (Flynn et al., Cancer Lett. 82:225-229 (1994)). The cuvette is returned to the ice bath for 10-60 min and then placed in a 37° C. water bath to induce resealing of the cell membrane. Any suitable electroporation method may be used to generate the engineered erythroid cells described herein.

For sonication, erythroid cells are, for example, exposed to high intensity sound waves, causing transient disruption of the cell membrane allowing the one or more exogenous stimulatory polypeptides to diffuse into the cell. Any suitable sonication method may be used to generate the engineered erythroid cells described herein.

For detergent treatment, erythroid cells, for example, are treated with a mild detergent which transiently compromises the cell membrane by creating holes through which the one or more exogenous stimulatory polypeptides may diffuse. After cells are loaded, the detergent is washed from the cells. For example, the detergent may be saponin. Any suitable detergent treatment method may be used to generate the engineered erythroid cells described herein.

For receptor mediated endocytosis, erythroid cells, for example, may have a surface receptor which upon binding of the one or more exogenous stimulatory polypeptides induces internalization of the receptor and the associated exogenous stimulatory polypeptides. Any suitable endocytosis method may be used to generate the engineered erythroid cells described herein.

For mechanical firing, erythroid cells, for example, may be bombarded with the one or more exogenous stimulatory polypeptides attached to a heavy or charged particle such as, for example, gold microcarriers and are mechanically or electrically accelerated such that they traverse the cell membrane. Microparticle bombardment may be achieved using, for example, the Helios Gene Gun (from, e.g., Bio-Rad, Hercules, Calif., USA). Any suitable microparticle bombardment method may be used to generate the engineered erythroid cells described herein.

For filtration, erythroid cells or platelets and the exogenous stimulatory polypeptides may be forced through a filter of pore size smaller than the cell causing transient disruption of the cell membrane and allowing the exogenous stimulatory polypeptides to enter the cell. Any suitable filtration method may be used to generate the engineered erythroid cells as described herein.

For freeze thawing, erythroid cells are subjected to several freeze thaw cycles, resulting in cell membrane disruption (See, e.g., U.S. Patent Application 2007/0243137 A1). In this instance, a pellet of packed red blood cells (0.1-1.0 ml) is mixed with an equal volume (0.1-1.0 ml) of an isotonic solution (e.g., phosphate buffered saline) containing the one or more exogenous stimulatory polypeptides. The red blood cells are frozen by immersing the tube containing the cells and one or more exogenous stimulatory polypeptides into liquid nitrogen. Alternatively, the cells may be frozen by placing the tube in a freezer at −20° C. or −80° C. The cells are then thawed in, e.g., a 23° C. water bath and the cycle repeated if necessary to increase loading. Any suitable freeze-thaw method may be used to generate the engineered erythroid cells as described herein.

Exogenous stimulatory polypeptides can be detected on the engineered erythroid cells. The presence of the exogenous stimulatory polypeptide can be validated and quantified using standard molecular biology methods, e.g., Western blotting or FACS analysis. Exogenous stimulatory polypeptides present in the intracellular environment may be quantified upon cell lysis or using fluorescent detection.

In some embodiments of the above aspects and embodiments, the engineered erythroid cell is an enucleated cell. In some embodiments of the above aspects and embodiments, the engineered erythroid cell is a nucleated cell.

III. Methods of Use

As described herein, the present invention provides methods of simulating immune cells, for example cytolytic T cells (CD8+ cells), memory CD8+ T cells, T helper cells (CD4+ cells) and NK cells. The stimulation of the immune cells may enhance normal cellular functions, or initiate normal cell functions in an abnormal cell. The methods involve contacting the immune cell to be activated with an engineered erythroid cell of any one of the aspects and embodiments herein, in an amount effective to stimulate the immune cell. In some embodiments, the engineered erythroid cell is an enucleated cell. In some embodiments, the engineered erythroid cell is a nucleated cell. Stimulating an immune cell refers to a process (e.g., that involves the provision of a signal or stimulus) which results in a cellular response, such as activation and/or expansion, of an immune cell, e.g. a killer immune cell such as an NK cell and/or a CD8+ T cell. In some embodiments, methods of stimulating an immune cell, e.g., a killer immune cell such as an NK cell and/or a CD8+ T cell, refer to providing a stimulus or signal, such as a stimulating polypeptide, that results in the activation and/or expansion of the immune cell.

In a preferred embodiment, the invention provides methods of simulating immune killer cells, for example cytolytic T cells (CD8+ cells), memory CD8+ T cells, and NK cells, comprising contacting the immune killer cell with an engineered erythroid cell (e.g., engineered enucleated cell) of any one of the aspects and embodiments herein, in an amount effective to stimulate the immune killer cell. Immune killer cells that may be stimulated by the methods of the invention include, for example, cytolytic T cells (CD8+ cells), memory CD8+ T cells, and NK cells. In some embodiments, the killer immune cells are Natural Killer (NK) cells. In some embodiments, the NK cells are memory-like NK cells. In some embodiments, the killer immune cells are CD8+ T-cells. In some embodiments, the CD8+ T-cells are memory T cells. Accordingly, the present invention also provides populations of cells resulting from the methods of stimulation with the engineered erythroid cells described herein.

In certain embodiments, the engineered erythroid cells are used in a method of stimulating more than one type of killer immune cell at the same time, for example, more than one of cytolytic T cells (CD8+ cells), memory CD8+ T cells, and NK cells. In exemplary embodiments, the engineered erythroid cells are capable of stimulating both CD8+ T cells and NK cells at the same.

In some embodiments, contacting the immune killer cell with an engineered erythroid cell is performed in vivo. It is an advantage of the present invention that, when contacting is performed in vivo, more than one population of immune killer cells can be activated. For example, when contacting is performed in vivo, both NK cells and CD8+ T cells can be activated and/or expanded.

In another embodiment, contacting the immune killer cell with an engineered erythroid cell is performed ex vivo. Thus, In some embodiments, one or more natural killer cells is contacted with the engineered erythroid cell(s) of the invention ex vivo.

NK cells can be obtained from any conventional source and are preferably derived from peripheral blood, bone marrow, cord blood, cell lines or cytokine stimulated peripheral blood. NK cells can, for example, be expanded from a sample of peripheral blood mononuclear cells (PBMCs). PBMCs are a mixture of monocytes and lymphocytes; blood leucocytes from which granulocytes have been separated and removed. Before culturing the cells (e.g. PBMCs), they are purified and separated according to methods well known for the skilled person. The culture conditions for the expansion of cytotoxic cells have previously been optimized on PBMCs from healthy individuals (Carlens et al., Hum. Immunol. 2001; 62:1092-1098). In certain embodiments, NK cells are expanded to between about 100 and about 1,000,000 fold, or between about 1,000 and about 1,000,000 fold, e.g., between 1,000 and about 100,000 fold.

Subsequently, the expanded NK cells may be administered to a subject in need thereof, e.g. a subject in need of immune cell stimulation. Administration may be performed once or repeated several times.

In another embodiment, one or more CD8+ T cells re contacted with the engineered erythroid cell(s) of the invention ex vivo.

Ex vivo T cell activation and expansion can be performed by isolation of T cells and subsequent stimulation followed by further expansion. Prior to expansion, a source of T cells is obtained from a subject. T cells can be obtained from a number of sources, including peripheral blood mononuclear cells, bone marrow, lymph node tissue, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as ficoll separation. In some embodiments, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments of the invention, the cells are washed with phosphate buffered saline (PBS). As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL gradient. A specific subpopulation of T cells, such as CD28+, CD4.+, CD8+, CD45RA+, and CD45RO+T cells, can be further isolated by positive or negative selection techniques. Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For isolation of a desired population of cells by positive or negative selection, the concentration of cells and surface (e.g. particles such as beads) can be varied. In certain embodiments, it may be desirable to significantly decrease the volume in which beads and cells are mixed together (i.e., increase the concentration of cells), to ensure maximum contact of cells and beads. For example, In some embodiments, a concentration of 2 billion cells/ml is used. In some embodiments, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In certain embodiments, T cells are expanded to between about 100 and about 1,000,000 fold, or between about 1,000 and about 1,000,000 fold, e.g., between 1,000 and about 100,000 fold.

The fitness of T cells after ex vivo expansion is an excellent predicator of their ability to function in vivo. Thus, in certain embodiments, the ability of the engineered erythroid cells to induce the key cell survival gene Bcl-xL is also measured. The percentage of apoptotic cells in a culture during the expansion process is used to determine whether any of the engineered erythroid cells confer a particular survival advantage to the expanded T cells. Additionally, the telomere length of cells after ex vivo expansion can be measured to determine if a particular engineered erythroid cell is more effective in preserving the replicative potential of the cells it expands.

The present disclosure contemplates various methods of using the engineered erythroid cells described herein. As would be understood by one skilled in the art, based upon the disclosure provided herein, the dose and timing of administration of the engineered erythroid cells can be specifically tailored for each application described herein.

Advantageously, administration of the engineered erythroid cells of the present invention does not result in liver toxicity. In some embodiments, administration of the engineered erythroid cells presenting an exogenous polypeptide of the present invention results in less toxicity compared to administration of the corresponding recombinant protein(s) alone, or compared to administration of a recombinant binding protein alone, such as an antibody, that binds to the target (e.g., receptor) of the exogenous polypeptide (e.g. administration of engineered erythroid cells comprising a first exogenous stimulatory polypeptide comprising 4-1BBL and a second exogenous stimulatory polypeptide comprising IL-15/IL-15RA, results in less liver toxicity as compared to administration of recombinant 4-1BBL alone, recombinant IL-15/IL-15RA alone, a combination thereof, or an anti-4-1BB antibody; administration of engineered erythroid cells comprising a first exogenous stimulatory polypeptide comprising -IL-12 and a second exogenous stimulatory polypeptide comprising IL-15/IL-15RA, results in less liver toxicity as compared to administration of recombinant IL-12 alone, recombinant IL-15/IL-15RA alone, or a combination thereof; or administration of engineered erythroid cells comprising a first exogenous stimulatory polypeptide comprising IL-12 and a second exogenous stimulatory polypeptide comprising 4-1BBL results in less liver toxicity as compared to administration of recombinant IL-12 alone, recombinant 4-1BBL alone, a combination thereof, or 4-1BB antibody).

In some embodiments, administration of the engineered erythroid cells of the present invention results in less liver toxicity and greater therapeutic efficacy as compared to administration of the corresponding recombinant protein(s) alone, or compared to administration of a recombinant binding protein alone, such as an antibody, that binds to the target (e.g., receptor) of the exogenous polypeptide (e.g. administration of engineered erythroid cells comprising a first exogenous stimulatory polypeptide comprising 4-1BBL and a second exogenous stimulatory polypeptide comprising IL-15/IL-15RA, results in less liver toxicity and greater therapeutic efficacy compared to administration of recombinant 4-1BBL alone, recombinant IL-15/IL-15RA alone, a combination thereof, or an anti-4-1BB antibody;

administration of engineered erythroid cells comprising a first exogenous stimulatory polypeptide comprising IL-12 and a second exogenous stimulatory polypeptide comprising IL-15/IL-15RA, results in less liver toxicity and greater therapeutic efficacy as compared to administration of recombinant IL-12 alone, recombinant IL-15/IL-15RA alone, or a combination thereof; or administration engineered erythroid cells comprising a first exogenous stimulatory polypeptide comprising IL-12 and a second exogenous stimulatory polypeptide comprising 4-1BBL results in less liver toxicity and greater therapeutic efficiacy as compared to administration of recombinant IL-12 alone, recombinant 4-1BBL alone, a combination thereof, or anti-4-1BB antibody).

The therapeutic index (TI, or therapeutic ratio) is a comparison of the amount of a therapeutic agent that causes the therapeutic effect to the amount that causes toxicity (Trevor A et al. (2013). "Chapter 2: Pharmacodynamics". Pharmacology Examination & Board Review (10th ed.). New York: McGraw-Hill Medical. p. 17, incorporated by reference in its entirety herein). The Therapeutic Index (TI) is used to compare the therapeutically effective dose to the toxic dose of a pharmaceutical agent. The TI is a statement of relative safety of a drug. It is the ratio of the dose that produces toxicity to the dose needed to produce the desired therapeutic response. The common method used to derive the TI is to use the 50% dose-response points, including TD50 (toxic dose) and ED50 (effective dose).

$$TI = \frac{\text{toxic dose}}{\text{dose needed for therapeutic response}} = \frac{TD50}{ED50}$$

Thus, a drug that has a higher TI would be considered safer than a drug with a lower TI (e.g. a drug with a TI of 10 would be considered safer than a drug with a TI of 3).

In some embodiments, administration of the engineered erythroid cells of the present invention results in a higher therapeutic index (TI) compared to administration of the corresponding recombinant protein(s) alone, or compared to administration of a recombinant binding protein alone, such as an antibody, that binds to the target (e.g., receptor) of the exogenous polypeptide (e.g. administration of engineered erythroid cells comprising a first exogenous stimulatory polypeptide comprising 4-1BBL and a second exogenous stimulatory polypeptide comprising IL-15/IL-15RA has a higher TI as compared to administration of recombinant 4-1BBL alone, recombinant IL-15/IL-15RA alone, a combination thereof, or an anti-4-1BB antibody; administration of engineered erythroid cells comprising a first exogenous stimulatory polypeptide comprising IL-12 and a second exogenous stimulatory polypeptide comprising IL-15/IL-15RA has a higher TI as compared to administration of recombinant IL-12 alone, recombinant IL-15/IL-15RA alone, or a combination thereof; or administration of engineered erythroid cells comprising a first exogenous stimulatory polypeptide comprising IL-12 and a second exogenous stimulatory polypeptide comprising 4-1BBL has a higher TI compared to administration of recombinant IL-12 alone, recombinant 4-1BBL alone, a combination thereof, or an anti-4-1BB antibody). In some embodiments, the therapeutic response is tumor burden reduction.

In some embodiments, administration of the engineered erythroid cells of the present invention results in less toxicity as compared to administration of the corresponding recombinant protein(s) alone, or compared to administration of a recombinant binding protein alone, such as an antibody, that binds to the target (e.g., receptor) of the exogenous polypeptide, as determined by a mouse model of liver toxicity (Niu et al J Immunology 2007 178:4194-4213, the entire content of which is incorporated herein by reference) (e.g. administration of engineered erythroid cells comprising a first exogenous stimulatory polypeptide comprising 4-1BBL and a second exogenous stimulatory polypeptide comprising IL-15/IL-15RA results in less liver toxicity as compared to administration of recombinant 4-1BBL, recombinant IL-15/IL-15RA alone, a combination thereof, or an anti-4-1BB antibody; administration of engineered erythroid cells comprising a first exogenous stimulatory polypeptide comprising IL-12 and a second exogenous stimulatory polypeptide comprising IL-15/IL-15RA results in less liver toxicity as compared to administration of recombinant IL-12 alone, recombinant IL-15/IL-15RA alone, or a combination thereof; or administration of engineered erythroid cells comprising a first exogenous stimulatory polypeptide comprising IL-12 and a second exogenous stimulatory polypeptide comprising 4-1BBL results in less liver toxicity as compared to administration of recombinant IL-12 alone, recombinant 4-1BBL alone, a combination thereof, or an anti-41BB antibody).

In some embodiments, administration of the engineered erythroid cells of the present invention results in less liver toxicity and greater therapeutic efficacy compared to administration of the corresponding recombinant protein(s) alone, or compared to administration of a recombinant binding protein alone, such as an antibody, that binds to the target (e.g., receptor) of the exogenous polypeptide, (e.g. administration of engineered erythroid cells comprising a first exogenous stimulatory polypeptide comprising 4-1BBL and a second exogenous stimulatory polypeptide comprising IL-15/IL-15RA results in less liver toxicity and greater therapeutic efficacy as compared to administration of recombinant 4-1BBL alone, recombinant IL-15/IL-15RA alone, a combination thereof, or an anti-41BB antibody; administration of engineered erythroid cells comprising a first exogenous stimulatory polypeptide comprising IL-12 and a second exogenous stimulatory polypeptide comprising IL-15/IL-15RA results in less liver toxicity and greater therapeutic efficacy as compared to administration of recombinant IL-12 alone, recombinant IL-15/IL-15RA alone, or a combination thereof; or administration of engineered erythroid cells comprising a first exogenous stimulatory polypeptide comprising IL-12 and a second exogenous stimulatory polypeptide comprising 4-1BBL results in less liver toxicity and greater therapeutic efficiacy as compared to administration of recombinant IL-12 alone, recombinant 4-1BBL alone, a combination thereof, or an anti-41BB antibody).

In some embodiments, administration of the engineered erythroid cells of the present invention results in a lesser effect or no effect (i.e. no significant effect compared to levels before administration of the engineered erythroid cells) on the levels of the alanine transaminase (ALT) liver enzyme as compared to administration of the corresponding recombinant protein(s) alone, or compared to administration of a recombinant binding protein alone, such as an antibody, that binds to the target (e.g., receptor) of the exogenous polypeptide, where the levels of ALT are elevated by administration of the recombinant protein(s) as compared to levels before administration of the recombinant protein(s) (e.g. administration of engineered erythroid cells comprising a first exogenous stimulatory polypeptide comprising 4-1BBL and a second exogenous stimulatory polypeptide comprising IL-15/IL-15RA results in a lesser effect or no effect on the levels of ALT compared to administration of recombinant 4-1BBL alone, recombinant IL-15/IL-15RA alone, a combination thereof, or an anti-4-1BB antibody, where levels of ALT are elevated by administration of the recombinant protein(s) compared to levels before administration; administration of engineered erythroid cells comprising a first exogenous stimulatory polypeptide comprising IL-12 and a second exogenous stimulatory polypeptide comprising IL-15/IL-15RA results in a lesser effect or no effect on the levels of ALT compared to administration of recombinant IL-12 alone, recombinant IL-15/IL-15RA alone, or a combination thereof, where levels of ALT are elevated by administration of the recombinant protein(s) as compared to levels before administration; administration of engineered erythroid cells comprising a first exogenous stimulatory polypeptide comprising -IL-12 and a second exogenous stimulatory polypeptide comprising 4-1BBL results in a lesser effect or no effect on the levels of ALT as compared to administration of recombinant IL-12 alone, recombinant 4-1BBL alone, a combination thereof, or an anti-4-1BB antibody, where levels of ALT are elevated by administration of the recombinant protein(s) as compared to levels before administration).

In some embodiments, administration of the engineered erythroid cells of the present invention results in a lesser effect or no effect (i.e. no significant effect compared to levels before administration of the engineered erythroid cells) on the levels of interferon gamma (IFNg) compared to administration of the corresponding recombinant protein(s) alone, or compared to administration of a recombinant binding protein alone, such as an antibody, that binds to the target (e.g., receptor) of the exogenous polypeptide, where the levels of IFNg are elevated by administration of the recombinant protein(s) as compared to levels before administration of the recombinant protein(s) (e.g. administration of engineered erythroid cells comprising a first exogenous stimulatory polypeptide comprising 4-1BBL and a second exogenous stimulatory polypeptide comprising IL-15/IL-15RA results in a lesser effect or no effect on the levels of IFNg compared to administration of recombinant 4-1BBL alone, recombinant IL-15/IL-15RA alone, a combination thereof, or an anti-4-1BB antibody, where levels of IFNg are elevated by administration of the recombinant protein(s) as compared to levels before administration; administration of engineered erythroid cells comprising a first exogenous stimulatory polypeptide comprising -IL-12 and a second exogenous stimulatory polypeptide comprising IL-15/IL-15RA results in a lesser effect or no effect on the levels of IFNg as compared to administration of recombinant IL-12 alone, recombinant IL-15/IL-15RA alone, or a combination thereof, where levels of IFNg are elevated by administration of the recombinant protein(s) as compared to levels before administration; administration engineered erythroid cells comprising a first exogenous stimulatory polypeptide comprising -IL-12 and a second exogenous stimulatory polypeptide comprising 4-1BBL results in a lesser effect or no effect on the levels of IFNg compared to administration of recombinant IL-12 alone, recombinant 4-1BBL alone, or a combination thereof, or an anti-4-1BB antibody, where levels of IFNg are elevated, by administration of the recombinant protein(s) as compared to levels before administration).

Liver infiltration of macrophages, CD8+ T cells, and/or CD8+/Eomes+/KLGR1+ T cells are thought to be important factors in liver toxicity. In some embodiments, administration of the engineered erythroid cells of the present invention results in a lesser effect or no effect (i.e. no significant effect compared to levels before administration of the engineered erythroid cells) on the number of infiltrating macrophages, CD8+ T cells, and/or CD8+/Eomes+/KLGR1+ T cells compared to administration of the corresponding recombinant protein(s) alone, or compared to administration of a recombinant binding protein alone, such as an antibody, that binds to the target (e.g., receptor) of the exogenous polypeptide, where the number of infiltrating macrophages, CD8+ T cells, and/or CD8+/Eomes+/KLGR1+ T cells are increased by administration of the recombinant protein(s) as compared to levels before administration of the recombinant protein(s) (e.g. administration of engineered erythroid cells comprising a first exogenous stimulatory polypeptide comprising 4-1BBL and a second exogenous stimulatory polypeptide comprising IL-15/IL-15RA results in a lesser effect or no effect on the number of infiltrating macrophages, CD8+ T cells, and/or CD8+/Eomes+/KLGR1+ T cells compared to administration of recombinant 4-1BBL alone, recombinant IL-15/IL-15RA alone, a combination thereof, or an anti-41BB antibody, where the number of infiltrating macrophages, CD8+ T cells, and/or CD8+/Eomes+/KLGR1+ T cells are increased by administration of the recombinant protein(s) as compared to levels before administration; administration of engineered erythroid cells comprising a first exogenous stimulatory polypeptide comprising IL-12 and a second exogenous stimulatory polypeptide comprising IL-15/IL-15RA results in a lesser effect or no effect on the number of infiltrating macrophages, CD8+ T cells, and/or CD8+/Eomes+/KLGR1+ T cells compared to administration of recombinant IL-12 alone, recombinant IL-15/IL-15RA alone, or a combination thereof, where the number of infiltrating macrophages, CD8+ T cells, and/or CD8+/Eomes+/KLGR1+ T cells are increased by administration of the recombinant protein(s) as compared to levels before administration; administration of engineered erythroid cells comprising a first exogenous stimulatory polypeptide comprising -IL-12 and a second exogenous stimulatory polypeptide comprising 4-1BBL results in a lesser effect or no effect on the number of infiltrating macrophages, CD8+ T cells, and/or CD8+/Eomes+/KLGR1+ T cells compared to administration of recombinant IL-12 alone, recombinant 4-1BBL alone, a combination thereof, or an anti-4-1BB antibody, where the number of infiltrating macrophages, CD8+ T cells, and/or CD8+/Eomes+/KLGR1+ T cells are increased by administration of the recombinant protein(s) as compared to levels before administration). While not wishing to be bound by theory, it is believed that the engineered erythroid cells (e.g., enucleated engineered erythroid cells) are sequestered in the blood vessels, unlike recombinant proteins (e.g. antibodies), which are believed to cause liver toxicity by diffusing from blood vessels to the bone marrow where they activate and expand myeloid cells, which in turn traffic to the liver to become Kupfer cells, and activate CD8 cells.

In certain embodiments, inflammation can be measure by ALT and Ishak score (Ishak K, Baptista A, Bianchi L, et al. Histological grading and staging of chronic hepatitis. J Hepatol 1995; 22:696, incorporated by reference in its entirety herein). In some embodiments, administration of the engineered erythroid cells of the present invention results in a lesser effect or no effect (i.e. no significant effect compared to the score before administration of the engineered erythroid cells) on the liver inflammation score compared to administration of the recombinant protein(s) alone, or compared to administration of a recombinant binding protein alone, such as an antibody, that binds to the target (e.g., receptor) of the exogenous polypeptide, where the liver inflammation score is increased by administration of the recombinant protein(s) as compared to levels before administration of the recombinant protein(s) (e.g. administration of engineered erythroid cells comprising a first exogenous stimulatory polypeptide comprising 4-1BBL and a second exogenous stimulatory polypeptide comprising IL-15/IL-15RA results in a lesser effect or no effect on the liver inflammation score relative to the score before administration, as compared to administration of recombinant 4-1BBL alone, recombinant IL-15/IL-15RA alone, a combination thereof, or an anti-4-1BB antibody, that results in an increased liver inflammation score relative to the score before administration; administration of engineered erythroid cells comprising a first exogenous stimulatory polypeptide comprising IL-12 and a second exogenous stimulatory polypeptide comprising IL-15/IL-15RA results in a lesser effect or no effect on the liver inflammation score relative to the score before administration, as compared to administration of recombinant IL-12 alone, recombinant IL-15/IL-15RA alone, or a combination thereof, that results in increased liver inflammation score relative to the score before administration; or administration of engineered erythroid cells comprising a first exogenous stimulatory polypeptide comprising IL-12 and a second exogenous stimulatory polypeptide comprising 4-1BBL results in lesser or no effect on the liver inflammation score relative to the score before administration, as compared to administration of recombinant IL-12 alone, recombinant 4-1BBL alone, a combination thereof, or an anti-4-1BB antibody, that results in an increased liver inflammation score relative to the score before administration).

In some embodiments of any of the above aspects and embodiments, the engineered erythroid cell is an enucleated cell. In some embodiments of any of the above aspects and embodiments, the engineered erythroid cell is a nucleated cell.

In some aspects, the disclosure provides a method of stimulating an immune killer cell in a subject, comprising administering to the subject a plurality of engineered erythroid cells, wherein the engineered erythroid cells comprise a first exogenous stimulatory polypeptide comprising a 4-1BBL polypeptide, in an amount effective to stimulate the immune killer cell, and wherein the effective amount does not cause toxicity in the subject.

In some aspects, the disclosure provides a method of treating a cancer in a subject, comprising administering to the subject a plurality of engineered erythroid cells, wherein the engineered erythroid cells comprise a first exogenous stimulatory polypeptide comprising a 4-1BBL polypeptide, in an amount effective to treat the cancer, and wherein the effective amount does not cause toxicity in the subject.

In some aspects, the disclosure provides a method of treating an infectious disease in a subject, comprising administering to the subject a plurality of engineered erythroid cells, wherein the engineered erythroid cells comprise a first exogenous stimulatory polypeptide comprising a 4-1BBL polypeptide, in an amount effective to treat the infection disease, and wherein the effective amount does not cause toxicity in the subject.

In some embodiments of the methods disclosed herein, administration of the effective amount results in less toxicity in the subject than administration of an isolated 4-1BB agonist antibody. In some embodiments of the methods disclosed herein, administration of the effective amount results in less toxicity in the subject than administration of an equivalent amount of isolated 4-1BB agonist antibody.

In some embodiments of the methods disclosed herein, the equivalent amount of isolated 4-1BB agonist antibody is an amount of isolated 4-1BB agonist antibody equivalent (e.g., in copy number, weight or molarity) to the amount of 4-1BBL polypeptide comprised in the effective amount of engineered erythroid cells. In some embodiments of the methods disclosed herein, the equivalent amount of isolated 4-1BB agonist antibody is an amount of isolated 4-1BB agonist antibody having the same agonist activity as the amount of 4-1BBL polypeptide comprised in the effective amount of engineered erythroid cells. In some embodiments of the methods disclosed herein, the equivalent amount of isolated 4-1BB agonist antibody is an amount of isolated 4-1BB agonist antibody having the same agonist activity as the effective amount of engineered erythroid cells comprising the 4-1BBL polypeptide. In some embodiments of the methods disclosed herein, the equivalent amount of isolated 4-1BB agonist antibody is an amount of isolated 4-1BB agonist antibody having the same biological effect as the amount of 4-1BBL polypeptide comprised in the effective amount of engineered erythroid cells. In some embodiments of the methods disclosed herein, the equivalent amount of isolated 4-1BB agonist antibody is an amount of isolated 4-1BB agonist antibody having the same biological effect as the effective mount of engineered erythroid cells comprising the 4-1BBL polypeptide. In some embodiments of the methods disclosed herein, the equivalent amount of isolated 4-1BB agonist antibody is an amount of isolated 4-1BB agonist antibody having the same therapeutic potency as the amount of 4-1BBL polypeptide comprised in the effective amount of engineered erythroid cells. In some embodiments of the methods disclosed herein, the equivalent amount of isolated 4-1BB agonist antibody is an amount of isolated 4-1BB agonist antibody having the same therapeutic potency as the effective amount of engineered erythroid cells comprising the 4-1BBL polypeptide.

In some aspects, the disclosure provides a method of stimulating an immune killer cell in a subject, comprising administering to the subject a plurality of engineered erythroid cells, wherein the engineered erythroid cells comprise a first exogenous stimulatory polypeptide comprising an IL-15 polypeptide, in an amount effective to stimulate the immune killer cell, and wherein the effective amount does not cause toxicity in the subject.

In some aspects, the disclosure provides a method of treating a cancer in a subject, comprising administering to the subject a plurality of engineered erythroid cells, wherein the engineered erythroid cells comprise a first exogenous stimulatory polypeptide comprising an IL-15 polypeptide, in an amount effective to treat the cancer, and wherein the effective amount does not cause toxicity in the subject.

In some aspects, the disclosure provides a method of treating an infectious disease in a subject, comprising administering to the subject a plurality of engineered erythroid cells, wherein the engineered erythroid cells comprise a first exogenous stimulatory polypeptide comprising an IL-15 polypeptide, in an amount effective to treat the infection disease, and wherein the effective amount does not cause toxicity in the subject.

In some embodiments, said administration results in less toxicity in the subject than administration of an amount of an isolated IL-15 polypeptide that is equivalent to the amount of IL-15 polypeptide comprised in the plurality of the engineered erythroid cells.

In some embodiments of the methods disclosed herein, administration of the effective amount results in less toxicity in the subject than administration of an isolated IL-15 polypeptide.

In some embodiments of the methods disclosed herein, administration of the effective amount results in less toxicity in the subject than administration of an equivalent amount of isolated IL-15 polypeptide.

In some embodiments of the methods disclosed herein, the equivalent amount of an isolated IL-15 polypeptide is the quantitatively same amount (e.g., in copy number or molarity) as the amount of IL-15 polypeptide comprised in the effective amount of engineered erythroid cells. In some embodiments of the methods disclosed herein, the equivalent amount of isolated IL-15 polypeptide is an amount of isolated IL-15 polypeptide having the same biological activity as the amount of IL-15 polypeptide comprised in the effective amount of engineered erythroid cells. In some embodiments of the methods disclosed herein, the equivalent amount of isolated IL-15 polypeptide is an amount of isolated IL-15 polypeptide having the same biological activity as the effective amount of engineered erythroid cells comprising the IL-15 polypeptide. In some embodiments of the methods disclosed herein, the equivalent amount of isolated IL-15 polypeptide is an amount of isolated IL-15 polypeptide having the same therapeutic potency as the amount of IL-15 polypeptide comprised in the effective amount of engineered erythroid cells. In some embodiments of the methods disclosed herein, the equivalent amount of isolated IL-15 polypeptide is an amount of isolated IL-15 polypeptide having the same therapeutic potency as the effective amount of engineered erythroid cells comprising the IL-15 polypeptide.

In some embodiments, the first exogenous polypeptide comprises an IL-15 polypeptide, or a fragment thereof, and an extracellular portion of an IL-15RA polypeptide, or a fragment thereof. In some embodiments, the IL-15 polypeptide and the extracellular portion of an IL-15RA polypeptide are present as a complex. In some embodiments, the IL-15 polypeptide and the extracellular portion of an IL-15RA polypeptide are a fusion polypeptide. In some embodiments, the IL-15 polypeptide, or a fragment thereof, is linked to the extracellular portion of the IL-15RA polypeptide, or a fragment thereof, by a linker. In some embodiments, the linker comprises GGGGS (SEQ ID NO: 11). In some embodiments, the linker comprises a $(GGGGS)_3$ linker (SEQ ID NO: 12). In some embodiments, the fusion polypeptide comprises an amino acid sequence that is at least 95% identical to SEQ ID NO: 1.

In some embodiments, the first exogenous stimulatory polypeptide comprises an IL-15 polypeptide, or a fragment thereof, and a IL-15 receptor alpha sushi-binding domain. In some embodiments, the IL-15 polypeptide, or a fragment thereof, and the IL-15 receptor alpha sushi-binding domain are present as a complex. In some embodiments, the IL-15 polypeptide, or a fragment thereof, and the IL-15 receptor alpha sushi-binding domain are present as a fusion polypeptide. In some embodiments, the IL-15 polypeptide, or a fragment thereof, is linked to the IL-15 receptor alpha sushi-binding domain by a linker. In some embodiments, the linker comprises GGGGS (SEQ ID NO: 11), optionally wherein the linker comprises a (GGGGS)3 linker (SEQ ID NO: 12). In some embodiments, the fusion polypeptide comprises an amino acid sequence that is at least 95% identical to SEQ ID NO: 2.

In some aspects, the disclosure provides a method of stimulating an immune killer cell in a subject, comprising administering to the subject a plurality of engineered erythroid cells, wherein the engineered erythroid cells comprise a first exogenous stimulatory polypeptide comprising an IL-12 polypeptide, in an amount effective to stimulate the immune killer cell, and wherein the effective amount does not cause toxicity in the subject.

In some aspects, the disclosure provides a method of treating a cancer in a subject, comprising administering to the subject a plurality of engineered erythroid cells, wherein the engineered erythroid cells comprise a first exogenous stimulatory polypeptide comprising an IL-12 polypeptide, in an amount effective to treat the cancer, and wherein the effective amount does not cause toxicity in the subject.

In some aspects, the disclosure provides a method of treating an infectious disease in a subject, comprising administering to the subject a plurality of engineered erythroid cells, wherein the engineered erythroid cells comprise a first exogenous stimulatory polypeptide comprising an IL-12 polypeptide, in an amount effective to treat the infection disease, and wherein the effective amount does not cause toxicity in the subject.

In some embodiments of the methods disclosed herein, administration of the effective amount results in less toxicity in the subject than administration of an isolated IL-12 polypeptide. In some embodiments of the methods disclosed herein, administration of the effective amount results in less toxicity in the subject than administration of an equivalent amount of isolated IL-12 polypeptide.

In some embodiments of the methods disclosed herein, the equivalent amount of an isolated IL-12 polypeptide is the quantitatively same amount (e.g., in copy number or molarity) as the amount of IL-12 polypeptide comprised in the effective amount of engineered erythroid cells. In some embodiments of the methods disclosed herein, the equivalent amount of isolated IL-12 polypeptide is an amount of isolated IL-12 polypeptide having the same biological activity as the amount of IL-12 polypeptide comprised in the effective amount of engineered erythroid cells. In some embodiments of the methods disclosed herein, the equivalent amount of isolated IL-12 polypeptide is an amount of isolated IL-12 polypeptide having the same biological activity as the effective amount of engineered erythroid cells comprising the IL-12 polypeptide. In some embodiments of the methods disclosed herein, the equivalent amount of isolated IL-12 polypeptide is an amount of isolated IL-12 polypeptide having the same therapeutic potency as the amount of IL-12 polypeptide comprised in the effective amount of engineered erythroid cells. In some embodiments of the methods disclosed herein, the equivalent amount of isolated IL-12 polypeptide is an amount of isolated IL-12 polypeptide having the same therapeutic potency as the effective amount of engineered erythroid cells comprising the IL-12 polypeptide. In some aspects, the disclosure provides a method of stimulating an immune killer cell in a subject, comprising administering to the subject a plurality of engineered erythroid cells, wherein the engineered erythroid cells comprise a first exogenous stimulatory polypeptide comprising a 4-1BBL polypeptide and a second exogenous stimulatory polypeptide comprising an IL-15 polypeptide, in an amount effective to stimulate the immune killer cell, and wherein the effective amount does not cause toxicity in the subject.

In some aspects, the disclosure provides a method of treating cancer in a subject, comprising administering to the subject a plurality of engineered erythroid cells, wherein the engineered erythroid cells comprise a first exogenous stimulatory polypeptide comprising a 4-1BBL polypeptide and a second exogenous stimulatory polypeptide comprising an IL-15 polypeptide, in an amount effective to treat the cancer, and wherein the effective amount does not cause toxicity in the subject.

In some aspects, the disclosure provides a method of treating an infectious disease in a subject, comprising administering to the subject a plurality of engineered erythroid cells, wherein the engineered erythroid cells comprise a first exogenous stimulatory polypeptide comprising a 4-1BBL polypeptide and a second exogenous stimulatory polypeptide comprising an IL-15 polypeptide, in an amount effective to treat the infectious disease, and wherein the effective amount does not cause toxicity in the subject.

In some embodiments of the methods disclosed herein, administration of the effective amount results in less toxicity in the subject than administration of an isolated 4-1BB agonist antibody, an isolated IL-15 polypeptide, or a combination thereof. In some embodiments of the methods disclosed herein, administration of the effective amount results in less toxicity in the subject than administration of an equivalent amount of an isolated 4-1BB agonist antibody, an equivalent amount of an isolated IL-15 polypeptide, or a combination thereof.

In some embodiments of the methods disclosed herein, the equivalent amount of an isolated IL-15 polypeptide is the quantitatively same amount (e.g., in copy number or molarity) as the amount of IL-15 polypeptide comprised in the effective amount of engineered erythroid cells. In some embodiments of the methods disclosed herein, the equivalent amount of isolated IL-15 polypeptide is an amount of isolated IL-15 polypeptide having the same biological activity as the amount of IL-15 polypeptide comprised in the effective amount of engineered erythroid cells. In some embodiments of the methods disclosed herein, the equivalent amount of isolated IL-15 polypeptide is an amount of isolated IL-15 polypeptide having the same therapeutic potency as the amount of IL-15 polypeptide comprised in the effective amount of engineered erythroid cells. In some embodiments of the methods disclosed herein, the equivalent amount of isolated 4-1BB agonist antibody is an amount of isolated 4-1BB agonist antibody having the same agonist activity as the amount of 4-1BBL polypeptide comprised in the effective amount of engineered erythroid cells. In some embodiments of the methods disclosed herein, the equivalent amount of isolated 4-1BB agonist antibody is an amount of isolated 4-1BB agonist antibody having the same biological effect as the amount of 4-1BBL polypeptide comprised in the effective amount of engineered erythroid cells. In some embodiments of the methods disclosed herein, the equivalent amount of isolated 4-1BB agonist antibody is an amount of isolated 4-1BB agonist antibody having the same therapeutic potency as the amount of 4-1BBL polypeptide comprised in the effective amount of engineered erythroid cells.

In some embodiments, the first exogenous polypeptide comprises an IL-15 polypeptide, or a fragment thereof, and an extracellular portion of an IL-15RA polypeptide, or a fragment thereof. In some embodiments, the IL-15 polypeptide and the extracellular portion of an IL-15RA polypeptide are present as a complex. In some embodiments, the IL-15 polypeptide and the extracellular portion of an IL-15RA polypeptide are a fusion polypeptide. In some embodiments, the IL-15 polypeptide, or a fragment thereof, is linked to the extracellular portion of the IL-15RA polypeptide, or a fragment thereof, by a linker. In some embodiments, the linker comprises GGGGS (SEQ ID NO: 11). In some embodiments, the linker comprises a (GGGGS)3 linker (SEQ ID NO: 12). In some embodiments, the fusion polypeptide comprises an amino acid sequence that is at least 95% identical to SEQ ID NO: 1.

In some embodiments, the first exogenous stimulatory polypeptide comprises an IL-15 polypeptide, or a fragment thereof, and a IL-15 receptor alpha sushi-binding domain. In some embodiments, the IL-15 polypeptide, or a fragment thereof, and the IL-15 receptor alpha sushi-binding domain are present as a complex. In some embodiments, the IL-15 polypeptide, or a fragment thereof, and the IL-15 receptor alpha sushi-binding domain are present as a fusion polypeptide. In some embodiments, the IL-15 polypeptide, or a fragment thereof, is linked to the IL-15 receptor alpha sushi-binding domain by a linker. In some embodiments, the linker comprises GGGGS (SEQ ID NO: 11), optionally wherein the linker comprises a (GGGGS)3 linker (SEQ ID NO: 12). In some embodiments, the fusion polypeptide comprises an amino acid sequence that is at least 95% identical to SEQ ID NO: 2.

In some aspects, the disclosure provides a method of stimulating an immune killer cell in a subject, comprising administering to the subject a plurality of engineered erythroid cells, wherein the engineered erythroid cells comprise a first exogenous stimulatory polypeptide comprising a 4-1BBL polypeptide and a second exogenous stimulatory polypeptide comprising an IL-12 polypeptide, in an amount effective to stimulate the immune killer cell, and wherein the effective amount does not cause toxicity in the subject.

In some aspects, the disclosure provides a method of treating cancer in a subject, comprising administering to the subject a plurality of engineered erythroid cells, wherein the engineered erythroid cells comprise a first exogenous stimulatory polypeptide comprising a 4-1BBL polypeptide and a second exogenous stimulatory polypeptide comprising an IL-12 polypeptide, in an amount effective to treat the cancer, and wherein the effective amount does not cause toxicity in the subject.

In some aspects, the disclosure provides a method of treating an infectious disease in a subject, comprising administering to the subject a plurality of engineered erythroid cells, wherein the engineered erythroid cells comprise a first exogenous stimulatory polypeptide comprising a 4-1BBL polypeptide and a second exogenous stimulatory polypeptide comprising an IL-12 polypeptide, in an amount effective to treat the infectious disease, and wherein the effective amount does not cause toxicity in the subject.

In some embodiments of the methods disclosed herein, administration of the effective amount results in less toxicity in the subject than administration of an isolated 4-1BB agonist antibody, an isolated IL-12 polypeptide, or a combination thereof. In some embodiments of the methods disclosed herein, administration of the effective amount results in less toxicity in the subject than administration of an equivalent amount of an isolated 4-1BB agonist antibody, an equivalent amount of an isolated IL-12 polypeptide, or a combination thereof.

In some embodiments of the methods disclosed herein, the equivalent amount of an isolated IL-12 polypeptide is the quantitatively same amount (e.g., in copy number or molarity) as the amount of IL-12 polypeptide comprised in the effective amount of engineered erythroid cells. In some embodiments of the methods disclosed herein, the equivalent amount of isolated IL-12 polypeptide is an amount of isolated IL-12 polypeptide having the same biological activity as the amount of IL-12 polypeptide comprised in the effective amount of engineered erythroid cells. In some embodiments of the methods disclosed herein, the equivalent amount of isolated IL-12 polypeptide is an amount of isolated IL-12 polypeptide having the same therapeutic potency as the amount of IL-12 polypeptide comprised in the effective amount of engineered erythroid cells. In some embodiments of the methods disclosed herein, the equivalent amount of isolated 4-1BB agonist antibody is an amount of isolated 4-1BB agonist antibody having the same agonist activity as the amount of 4-1BBL polypeptide comprised in the effective amount of engineered erythroid cells. In some embodiments of the methods disclosed herein, the equivalent amount of isolated 4-1BB agonist antibody is an amount of isolated 4-1BB agonist antibody having the same biological effect as the amount of 4-1BBL polypeptide comprised in the effective amount of engineered erythroid cells. In some embodiments of the methods disclosed herein, the equivalent amount of isolated 4-1BB agonist antibody is an amount of isolated 4-1BB agonist antibody having the same therapeutic potency as the amount of 4-1BBL polypeptide comprised in the effective amount of engineered erythroid cells.

In some aspects, the disclosure provides a method of stimulating an immune killer cell in a subject, comprising administering to the subject a plurality of engineered erythroid cells, wherein the engineered erythroid cells comprise a first exogenous stimulatory polypeptide comprising an IL-15 polypeptide and a second exogenous stimulatory polypeptide comprising an IL-12 polypeptide, in an amount effective to stimulate the immune killer cell, and wherein the effective amount does not cause toxicity in the subject.

In some aspects, the disclosure provides a method of treating cancer in a subject, comprising administering to the subject a plurality of engineered erythroid cells, wherein the engineered erythroid cells comprise a first exogenous stimulatory polypeptide comprising a IL-15 polypeptide and a second exogenous stimulatory polypeptide comprising an IL-12 polypeptide, in an amount effective to treat the cancer, and wherein the effective amount does not cause toxicity in the subject.

In some aspects, the disclosure provides a method of treating an infectious disease in a subject, comprising administering to the subject a plurality of engineered erythroid cells, wherein the engineered erythroid cells comprise a first exogenous stimulatory polypeptide comprising a IL-15 polypeptide and a second exogenous stimulatory polypeptide comprising an IL-12 polypeptide, in an amount effective to treat the infectious disease, and wherein the effective amount does not cause toxicity in the subject.

In some embodiments of the methods disclosed herein, administration of the effective amount results in less toxicity in the subject than administration of an isolated IL-15 polypeptide, an isolated IL-12 polypeptide, or a combination thereof. In some embodiments of the methods disclosed herein, administration of the effective amount results in less toxicity in the subject than administration of an equivalent amount of an isolated IL-15 polypeptide, an equivalent amount of an isolated IL-12 polypeptide, or a combination thereof.

In some embodiments of the methods disclosed herein, the equivalent amount of an isolated IL-12 polypeptide is the quantitatively same amount (e.g., in copy number or molarity) as the amount of IL-12 polypeptide comprised in the effective amount of engineered erythroid cells. In some embodiments of the methods disclosed herein, the equivalent amount of isolated IL-12 polypeptide is an amount of isolated IL-12 polypeptide having the same biological activity as the amount of IL-12 polypeptide comprised in the effective amount of engineered erythroid cells. In some embodiments of the methods disclosed herein, the equivalent amount of isolated IL-12 polypeptide is an amount of isolated IL-12 polypeptide having the same therapeutic potency as the amount of IL-12 polypeptide comprised in the effective amount of engineered erythroid cells. In some embodiments of the methods disclosed herein, the equivalent amount of isolated IL-15 polypeptide is an amount of isolated IL-15 polypeptide having the same amount (e.g., in copy number or molarity) as the amount of IL-15 polypeptide comprised in the effective amount of engineered erythroid cells. In some embodiments of the methods disclosed herein, the equivalent amount of isolated IL-15 polypeptide is an amount of isolated IL-15 polypeptide having the same biological activity as the amount of IL-15 polypeptide comprised in the effective amount of engineered erythroid cells. In some embodiments of the methods disclosed herein, the equivalent amount of isolated IL-15 polypeptide is an amount of isolated IL-15 polypeptide having the same therapeutic potency as the amount of IL-15 polypeptide comprised in the effective amount of engineered erythroid cells.

In some embodiments, the first exogenous polypeptide comprises an IL-15 polypeptide, or a fragment thereof, and an extracellular portion of an IL-15RA polypeptide, or a fragment thereof. In some embodiments, the IL-15 polypeptide and the extracellular portion of an IL-15RA polypeptide are present as a complex. In some embodiments, the IL-15 polypeptide and the extracellular portion of an IL-15RA polypeptide are a fusion polypeptide. In some embodiments, the IL-15 polypeptide, or a fragment thereof, is linked to the extracellular portion of the IL-15RA polypeptide, or a fragment thereof, by a linker. In some embodiments, the linker comprises GGGGS (SEQ ID NO: 11). In some embodiments, the linker comprises a (GGGGS)3 linker (SEQ ID NO: 12). In some embodiments, the fusion polypeptide comprises an amino acid sequence that is at least 95% identical to SEQ ID NO: 1.

In some embodiments, the first exogenous stimulatory polypeptide comprises an IL-15 polypeptide, or a fragment thereof, and a IL-15 receptor alpha sushi-binding domain. In some embodiments, the IL-15 polypeptide, or a fragment thereof, and the IL-15 receptor alpha sushi-binding domain are present as a complex. In some embodiments, the IL-15 polypeptide, or a fragment thereof, and the IL-15 receptor alpha sushi-binding domain are present as a fusion polypeptide. In some embodiments, the IL-15 polypeptide, or a fragment thereof, is linked to the IL-15 receptor alpha sushi-binding domain by a linker. In some embodiments, the linker comprises GGGGS (SEQ ID NO: 11), optionally wherein the linker comprises a (GGGGS)3 linker (SEQ ID NO: 12). In some embodiments, the fusion polypeptide comprises an amino acid sequence that is at least 95% identical to SEQ ID NO: 2.

Treatment of Conditions that would Benefit from Immune Killer Cell Activation

Methods of administering engineered erythroid cells comprising (e.g., presenting) exogenous agent (e.g., polypeptides) are described, e.g., in WO2015/073587 and WO2015/153102, each of which is incorporated by reference in its entirety.

In embodiments, the engineered erythroid cells described herein are administered to a subject, e.g., a mammal, e.g., a human. Exemplary mammals that can be treated include without limitation, humans, domestic animals (e.g., dogs, cats and the like), farm animals (e.g., cows, sheep, pigs, horses and the like) and laboratory animals (e.g., monkey, rats, mice, rabbits, guinea pigs and the like). The methods described herein are applicable to both human therapy and veterinary applications. In some embodiments, the engineered erythroid cell is an enucleated cell. In some embodiments, the engineered erythroid cell is a nucleated cell.

In some embodiments, the engineered erythroid cells are administered to a patient every 1, 2, 3, 4, 5, or 6 months.

In some embodiments, a dose of engineered erythroid cells comprises about $1\times10^9$-$2\times10^9$, $2\times10^9$-$5\times10^9$, $5\times10^9$-$1\times10^{10}$, $1\times10^{10}$-$2\times10^{10}$, $2\times10^{10}$-$5\times10^{10}$, $5\times10^{10}$-$1\times10^{11}$, $1\times10^{11}$-$2\times10^{11}$, $2\times10^{11}$-$5\times10^{11}$, $5\times10^{11}$-$1\times10^{12}$, $1\times10^{12}$-$2\times10^{12}$, $2\times10^{12}$-$5\times10^{12}$, or $5\times10^{12}$-$1\times10^{13}$ cells.

In some embodiments, the engineered erythroid cells are administered to a patient in a dosing regimen (dose and periodicity of administration) sufficient to maintain function of the administered erythroid cells in the bloodstream of the patient over a period of 2 weeks to a year, e.g., one month to one year or longer, e.g., at least 2 weeks, 4 weeks, 6 weeks, 8 weeks, 3 months, 6 months, a year, 2 years.

In some aspects, the present disclosure provides method of stimulating an immune killer cell, comprising contacting the immune killer cell with an engineered erythroid cell described herein, in an amount effective to stimulate the immune cell, to a subject in need of immune killer cell activation.

In some embodiments, the subject has been diagnosed with cancer.

In some embodiments, the subject has an infectious disease.

In some aspects, the disclosure provides a use of an engineered erythroid cell described herein for treating a disease or condition described herein, e.g., cancer or an infectious disease. In some aspects, the disclosure provides a use of an engineered erythroid cell described herein for manufacture of a medicament for treating a disease or condition described herein, e.g., cancer or an infectious disease.

Cancer

In some aspects, the invention provides a method of treating a cancer in a subject comprising administering to the subject an erythroid cell engineered to stimulate an immune cell, in particular a killer immune cell such as an NK cell or CD8+ T cell, as described herein. The engineered erythroid cell is administered in an amount effective to treat the cancer in the subject. In embodiments, the subject has cancer and/or has been diagnosed with a cancer, and is therefore in need of treatment.

The present disclosure is not limited to a certain type of cancer, but rather any cancer is contemplated as being treated by the engineered erythroid cells described herein. In certain embodiments, the cancer includes, but is not limited to, a cancer selected from acute lymphoblastic leukemia (ALL), acute myeloid leukemia (AML), anal cancer, bile duct cancer, bladder cancer, bone cancer, bowel cancer, brain tumors, breast cancer, cancer of unknown primary, cancer spread to bone, cancer spread to brain, cancer spread to liver, cancer spread to lung, carcinoid, cervical cancer, choriocarcinoma, chronic lymphocytic leukemia (CLL), chronic myeloid leukemia (CML), colon cancer, colorectal cancer, endometrial cancer, eye cancer, gallbladder cancer, gastric cancer, gestational trophoblastic tumors (GTT), hairy cell leukaemia, head and neck cancer, hodgkin lymphoma, kidney cancer, laryngeal cancer, leukaemia, liver cancer, lung cancer, lymphoma, melanoma skin cancer, mesothelioma, molar pregnancy, mouth and oropharyngeal cancer, myeloma, nasal and sinus cancers, nasopharyngeal cancer, non hodgkin lymphoma (NHL), oesophageal cancer, ovarian cancer, pancreatic cancer, penile cancer, prostate cancer, rare cancers, rectal cancer, salivary gland cancer, secondary cancers, skin cancer (non melanoma), soft tissue sarcoma, stomach cancer, testicular cancer, thyroid cancer, unknown primary cancer, uterine cancer, vaginal cancer, and vulval cancer.

In certain embodiments, the cancer to be treated is selected from lung cancer, hepatocellular cancer, melanoma, and lymphoma. In further embodiments, the lymphoma is selected from Hodgkin's Lymphoma or non-Hodgkin's lymphoma. In some embodiments, the cancer to be treated is lung cancer. In some embodiments, the cancer is hepatocellular cancer. In some embodiments, the cancer is melanoma. In some embodiments, the cancer is lymphoma. In some embodiments, the cancer is Hodgkin's lymphoma. In some embodiments, the cancer is non-Hodgkin's lymphoma.

In some embodiments, the cancer to be treated is a solid tumor. Solid tumors include, but are not limited to, breast cancer, bladder cancer, colon and rectal cancer, endometrial cancer, kidney (renal cell) cancer, lung cancer, melanoma, pancreatic cancer, prostate cancer, thyroid cancer, skin cancer, bone cancer, brain cancer, cervical cancer, liver cancer, stomach cancer, mouth and oral cancers, neuroblastoma, testicular cancer, uterine cancer, thyroid cancer, head and neck, kidney, lung, non-small cell lung, melanoma, mesothelioma, ovary, sarcoma, stomach, uterus and medulloblastoma, and vulvar cancer. In certain embodiments, the solid tumor to be treated is lung cancer, hepatocellular cancer or melanoma. In some embodiments, the solid tumor is lung cancer. In some embodiments, the solid tumor is hepatocellular cancer. In some embodiments, the solid tumor is melanoma.

In certain embodiments, the cancer to be treated is a hematologic cancer. Hematologic cancer is a cancer that affects the blood, bone marrow or lymphatic system. Hematologic cancers represent the fifth most commonly occurring cancers and the second leading cause of cancer death. The most common forms of hematologic cancers include leukemia, lymphoma and myeloma. Leukemia occurs when the bone marrow overproduces abnormal white blood cells, and is classified by the type of white blood cell affected: myeloid or lymphocytic. Lymphoma is a cancer of the lymphatic system that results in uncontrolled growth of malignant white blood cells, forming tumors in the lymph nodes. Lymphoma is classified into two main types: Hodgkin's and Non-Hodgkin's lymphoma (HL and NHL). Myeloma occurs when abnormal plasma cells (a type of white blood cell that produces antibodies) accumulate in the bone marrow.

Leukemias can be classified into 4 main types based on whether they are acute or chronic, and myeloid or lymphocytic: Acute myeloid (or myelogenous) leukemia (AML); Chronic myeloid (or myelogenous) leukemia (CML); Acute lymphocytic (or lymphoblastic) leukemia (ALL); Chronic lymphocytic leukemia (CLL). While many patients achieve a remission (an absence of signs and symptoms) after initial treatment for AML, some patients have residual leukemic cells in their marrow even after intensive treatment. This is referred to as "refractory leukemia." Some patients reach remission and then have a return of leukemia cells in the marrow and a decrease in normal blood cells. This is called "relapsed leukemia."

Acute myeloid leukemia, or AML, is characterized by proliferation of myeloid blasts. Myeloid blasts replace the bone marrow so that there is minimal production of platelets, red cells and neutrophils. It is primarily a disease of the elderly with a median age of diagnosis is 68. In 2017, there were more than 20,000 new cases of AML and more than 10,000 deaths caused by AML in the United States.

Standard front-line AML treatment has been unchanged for over 40 years: a regimen of intensive induction and consolidation therapy. Although most patients respond, the majority relapse over time. Therefore, many younger patients with AML undergo hematopoietic stem cell transplant, or HSCT, which can be curative if the transplant is successful. In 2016, more than 3,500 AML patients underwent allo-HSCT in the United States and over, 200 underwent the procedure in Europe.

Patients with AML that respond to therapy and survive will often bridge to hematopoietic stem cell transplant, which can be curative for two-thirds of patients. For the one third of patients who relapse following allogeneic transplant (3,235 allogeneic transplants were performed in the US in 2015 for AML patients), treatment options are limited and nearly all patients die within the span of a year. In these cases, patients lose the benefit of the graft v. tumor effect, principally due to immune checkpoint engagement (CTLA4-B7 and PD-1-PDL-1) which inhibits T-cell function and anti-tumor immunity.

Recently, additional therapies have been approved for treatment of AML, such as gemtuzamab ozogamicin, an anti-CD33 antibody drug conjugate, CPX-351, a combination chemotherapy, and, for patients with specific mutations, midostaurin and enasidenib. Although these therapies improve response rates and enable more patients to bridge to transplant, overall survival rates remain low.

NK cells and the engagement of the innate immune system are considered central to the effective immunological treatment of AML, and potentially other related hematological malignancies post-hematopoietic stem cell transplantation (HSCT). After bone marrow ablation and allogeneic transplantation, NK cells are the first lymphocyte population to recover, but their killing and cytokine-secreting functions are limited when compared to the NK cells of healthy donors. The rate of return and function of NK cells are correlated with treatment outcome post-HSCT, so increasing the number and function of NK cells post-HSCT to stimulate the graft versus leukemia effect has the potential to increase survival in patients receiving HSCT for treatment of AML.

Accordingly, in some embodiments, the engineered erythroid cells described herein are used in the treatment of AML, particularly in patients receiving or who are scheduled to receive allogeneic HSCT, with the intention of activating NK cell, CD8+ T cell, or NK and CD8+ T cell populations, in order to improve transplant response and/or overall survival. In some embodiments, engineered erythroid cells comprising an IL-15 polypeptide, or a fragment thereof, and an extracellular portion of an IL-15RA polypeptide, or a fragment thereof, as described herein, are used in the treatment of AML in a patient receiving or who is scheduled to receive allogeneic HSCT. In some embodiments, engineered erythroid cells comprising an IL-15 polypeptide, or a fragment thereof, and an extracellular portion of an IL-15RA polypeptide, or a fragment thereof, and a 4-1BBL polypeptide, or a fragment thereof, as described herein, are used in the treatment of AML in a patient receiving or scheduled to receive allogeneic HSCT. In some embodiments, engineered erythroid cells comprising an exogenous stimulatory polypeptide comprising an IL-15 polypeptide, or a fragment thereof, and an extracellular portion of an IL-15RA polypeptide, or a fragment thereof, and an exogenous polypeptide comprising an IL-12 polypeptide, or a fragment thereof, as described herein, are used in the treatment of AML in a patient receiving or scheduled to receive allogeneic HSCT. In some embodiments, engineered erythroid cells comprising an exogenous stimulatory polypeptide comprising an IL-15 polypeptide, or a fragment thereof, and an extracellular portion of an IL-15RA polypeptide, or a fragment thereof, and an exogenous stimulatory polypeptide comprising an IL-12 polypeptide, as described herein, are used in the treatment of AML in a patient receiving or scheduled to receive allogeneic HSCT. In some embodiments, engineered erythroid cells comprising an exogenous stimulatory polypeptide comprising an IL-12 polypeptide, or a fragment thereof, and an exogenous stimulatory polypeptide comprising a 4-1BBL polypeptide, or a fragment thereof, as described herein, are used in the treatment of AML in a patient receiving or scheduled to receive allogeneic HSCT.

In another embodiment, the engineered erythroid cells described herein are used in the treatment of relapsing or refractory AML. In an embodiment, the engineered erythroid cells are used in the treatment of relapsing or refractory AML in patients receiving or scheduled to receive allogeneic HSCT, with the intention of activating NK cell, CD8+ T cell, or NK and CD8+ T cell populations, in order to improve transplant response and overall survival. In certain embodiments, engineered erythroid cells comprising exogenous stimulatory polypeptide comprising an IL-15 polypeptide, or a fragment thereof, and an extracellular portion of an IL-15RA polypeptide, or a fragment thereof, as described herein, are used in the treatment of relapsing or refractory AML. In certain embodiments, engineered erythroid cells comprising an exogenous stimulatory polypeptide comprising an IL-15 polypeptide, or a fragment thereof, and an extracellular portion of an IL-15RA polypeptide, or a fragment thereof, and a 4-1BBL polypeptide, or a fragment thereof, as described herein, are used in the treatment of relapsing or refractory AML. In certain embodiments, engineered erythroid cells comprising an exogenous stimulatory polypeptide comprising an IL-15 polypeptide, or a fragment thereof, and an extracellular portion of an IL-15RA polypeptide, or a fragment thereof, and an exogenous stimulatory polypeptide comprising a 4-1BBL polypeptide, or fragment thereof, as described herein, are used in the treatment of relapsing or refractory AML. In certain embodiments, engineered erythroid cells comprising an exogenous stimulatory polypeptide comprising an IL-12 polypeptide, or a fragment thereof, and an exogenous stimulatory polypeptide comprising a 4-1BBL polypeptide, or fragment thereof, as described herein, are used in the treatment of relapsing or refractory AML.

In embodiments, the patients to be treated are receiving or are scheduled to receive allogeneic HSCT, with the intention of activating both NK and CD8+ T cell populations in order to improve transplant response and overall survival.

Recent analyses of The Cancer Genome Atlas (TCGA) datasets have linked the genomic landscape of tumors with tumor immunity, implicating neoantigen load in driving T cell responses (Brown et al., Genome Res. 2014 May; 24(5):743-50, 2014) and identifying somatic mutations associated with immune infiltrates (Rutledge et al., Clin Cancer Res. 2013 Sep. 15; 19(18):4951-60, 2013). Rooney et al. (2015 Jan. 15; 160(1-2):48-61) suggest that neoantigens and viruses are likely to drive cytolytic activity, and reveal known and novel mutations that enable tumors to resist immune attack. Thus, in certain embodiments, the cancer to be treated is a cancer associated with an oncogenic virus. Non-limiting examples of an oncogenic virus include, for example, Epstein Barr virus (EBV), hepatitis B and C (HBV and HCV), human papilloma virus (HPV), Kaposi sarcoma virus (KSV), and polyoma viruses. In other certain embodiments, the cancer is a cancer where retrovirus epitopes are identified. Cancers which are associated with a virus and which may be treated using the methods of the invention include, but are not limited to, cervical cancer, head and neck cancer, lymphomas, and kidney clear cell carcinoma.

Cancers with Low MHC Class I Expression

MHC I expression on cancer cells is required for detection and destruction by T-cells. Cytotoxic T lymphocytes (CTLs, CD8+) require tumor antigen presentation on the target cell by MHC Class I molecules to delineate self from non-self. One of the most common means by which tumors evade the host immune response is by down-regulation of MHC Class I molecule expression, such that the tumor has low MHCI expression, thereby rendering any endogenous or therapeutic anti-tumor T cell responses ineffective (Haworth et al., Pediatr Blood Cancer. 2015 April; 62(4): 571-576). Most often, the loss of MHC expression on tumor cells is mediated by epigenetic events and transcriptional down-regulation of the MHC locus and/or the antigen processing machinery. Lack of a processed peptide leads to decreased MHC expression since empty MHC molecules are not stable on the cell surface.

MHC Class I expression in various adult tumors is shown below in Table 7. MHC Class I expression in various pediatric cancers is shown below in Table 8. The most extensively studied pediatric tumor with respect to MHC expression is neuroblastoma, which has particularly low MHC Class I expression, especially in high-risk patients.

TABLE 7

| Adult Tumor Type | MHC Class I Expression | Prognostic Indications |
|---|---|---|
| Colorectal Carcinoma | Down-regulated | Strong expression correlated with improved survival; |
| Breast Adenocarcinoma | Down-regulated | Inversely correlated with HER2 expression; |
| Endometrial Carcinoma | Down-regulated | Down-regulation predictor of worse survival |
| Cervical Carcinoma | Down-regulated | |
| Head and Neck Carcinomas | Down-regulated | |
| Prostate Carcinoma | Down-regulated | |
| Melanoma | Down-regulated | Predicts immunotherapy response in vitro |
| Renal Cortical Adenocarcinoma | Low | Predicts immunotherapy response in vitro |
| Lung Carcinoma | | Down-regulated Down-regulation unfavorable prognostic factor in tumors with cancer testis antigen expression; |

TABLE 8

| Pediatric Tumor Type | MHC Class I Expression | Prognostic Indications |
|---|---|---|
| Neuroblastoma | Low | Lower stage associated with higher expression |
| Ewing Sarcoma/PNET | Low | Decreased expression associated with disease progression |

NK cells are a subset of lymphocytes that contribute to innate immunity, capable of lysing tumor cells without prior sensitization using the same killing mechanisms as CTLs. Natural killer reactivity, including cytokine secretion and cytotoxicity, is controlled by a balance of several germ-line encoded inhibitory and activating receptors such as killer immunoglobulin-like receptors (KIRs) and natural cytotoxicity receptors (NCRs). The presence of the MHC Class I molecule on target cells serves as one such inhibitory ligand for MHC Class I-specific receptors, the Killer cell Immunoglobulin-like Receptor (KIR), on NK cells. Engagement of MR receptors blocks NK activation and, paradoxically, preserves their ability to respond to successive encounters by triggering inactivating signals. Therefore, if a MR is able to sufficiently bind to MHC Class I, this engagement may override the signal for killing and allows the target cell to live. In contrast, if the NK cell is unable to sufficiently bind to MHC Class I on the target cell, killing of the target cell may proceed. Consequently, those tumors which express low MHC Class I and which are thought to be capable of evading a T-cell-mediated attack may actually be susceptible to an NK cell-mediated immune response instead.

Thus, in certain embodiments, the engineered erythroid cells of the invention are used to treat a cancer that is characterized by low MHC I presentation. For example, the engineered erythroid cells of the invention are used to treat a cancer that is characterized by low MHC I presentation as set forth in Tables 7 and 8. In some embodiments, the engineered erythroid cells of the invention are used to treat a cancer that is characterized by low MHC I presentation as set forth in Table 7. In another embodiment, the engineered erythroid cells of the invention are used to treat a cancer that is characterized by low MHC I presentation as set forth in Table 85. In some embodiments, the cancer with low MHC I presentation is a colorectal carcinoma. In some embodiments, the cancer with low MHC I presentation is breast adenocarcinoma. In some embodiments, the cancer with low MHC I presentation is a endometrial carcinoma. In some embodiments, the cancer with low MHC I presentation is a cervical carcinoma. In some embodiments, the cancer with low MHC I presentation is a head and neck carcinoma. In some embodiments, the cancer with low MHC I presentation is a prostate carcinoma. In some embodiments, the cancer with low MHC I presentation is a melanoma. In some embodiments, the cancer with low MHC I presentation is a lung carcinoma. In some embodiments, the cancer with low MHC I presentation is a neuroblastoma. In some embodiments, the cancer with low MHC I presentation is a Ewing sarcoma/PNET.

Cancers with Modulation of Stress Ligands

In other embodiments, the cancer to be treated with the engineered erythroid cells of the invention is characterized by tumors which exhibit effects of cellular stress that alter NK receptor engagement (either activating or suppressing). For example, cancer cells generally exist in a constant state of cellular stress due to hypoxia, chronic proliferative signals (i.e., due to constitutively activating Ras mutations), and ongoing genomic instability. Many cancer cells therefore upregulate killer activating receptor (KAR) ligands on their surface, rendering them susceptible to NK cell killing. However, modulation of stress ligands is an important escape mechanism used by cancer cells to diminish NK cell recognition. For example, the stress ligand ULBP2 can be suppressed by an RNA-binding protein that is frequently overexpressed in tumor cells. By binding of this oncogenic protein to ULBP2 mRNA the stability of the mRNA is reduced and ULBP2 levels on the cell surface are downregulated. In consequence, the tumor cells are protected from NK cell recognition (Schmiedel D, et al. Elife (2016) 5:e13426). Inhibition of NK cells can also occur by blocking of NKG2D via soluble forms of the stress ligand MICA as shown for neuroblastoma as well as head and neck carcinoma. Thus, In some embodiments, the invention provides methods of treating a cancer in which the level of one or more stress ligands or KAR ligands is upregulated. Without wishing to be bound by theory, it is expected that such cancers, which are susceptible to NK cell killing, would be particularly responsive to an increase in the number and/or activity of NK cells. In another embodiment, the invention provides methods of treating a cancer in which the level or activity of a stress ligand is downmodulated or inhibited, for example, a cancer in which a suppressor of a stress ligand or KAR ligand is expressed. Without wishing to be bound by theory, it is expected that such cancers, which are less susceptible to NK cell killing due to the presence of the suppressor, would benefit from an increase in the number and/or activity of NK cells.

Cancers Characterized by Non-Responsiveness to 4-1BB Agonists

In other embodiments, the cancer to be treated with the engineered erythroid cells of the invention, e.g. an engineered erythroid cell described herein, is characterized by non-responsiveness to 4-1BB agonists. In some embodiments, the non-responsiveness of the cancer to 4-1BB agonists is due to toxicity, e.g. liver toxicity, at higher doses. Accordingly, the present disclosure includes methods of treating a subject with a cancer that is non-responsive to one or more 4-1BB agonists due to, e.g. toxicity of the 4-1BB agonist, by administration of an engineered erythroid cell described herein.

In some embodiments, the 4-1BB agonistic antibody may be any 4-1BB agonistic antibody as known in the art. In some embodiments the 4-1BB agonistic antibody is utomilumab (see e.g., International Patent Application Publication No. WO2012/032433; incorporated in its entirety herein by reference). In some embodiments the 4-1BB agonistic antibody is INBRX-105 (see e.g., International Patent Application Publication No. WO2017/123650; incorporated in its entirety herein by reference). In some embodiments the 4-1BB agonistic antibody is ADG106 (see e.g., International Patent Application Publication No. WO2019/036855; incorporated in its entirety herein by reference). In some embodiments the 4-1BB agonistic antibody is urelumab (see e.g., International Patent Application Publication No. WO2005/035584; incorporated in its entirety herein by reference)

In some embodiments, the engineered erythroid cell comprises an exogenous stimulatory polypeptide comprising a 4-1BB polypeptide, or a fragment thereof. In some embodiments, the engineered erythroid cell comprises an exogenous stimulatory polypeptide comprising an IL-15 polypeptide, or a fragment thereof, and an extracellular portion of an IL-15RA polypeptide, or a fragment thereof, and an exogenous stimulatory polypeptide comprising a 4-1BBL polypeptide, or a fragment thereof. In some embodiments, the engineered erythroid cell comprises an exogenous stimulatory polypeptide comprising an IL-12 polypeptide, or a fragment thereof, and an exogenous stimulatory polypeptide comprising a 4-1BBL polypeptide, or a fragment thereof.

Tumors Characterized by Response to Checkpoint Inhibition

While checkpoint inhibitors have revolutionized cancer treatment, their limitations are becoming increasingly evident. Responses are confined to certain tumor types and only few patients are cured. Currently, the challenge in immunotherapy is to extend the efficacy of checkpoint inhibitors across more tumor types as well as increase the rate, depth and duration of response. By stimulating both arms of the immune system, the engineered erythroid cells described herein are used in combination with checkpoint inhibitors to both improve and extend responses. In some embodiments, the engineered erythroid cell comprises an exogenous stimulatory polypeptide comprising ab IL-15 polypeptide, or a fragment thereof, and an extracellular portion of an IL-15RA polypeptide, or a fragment thereof, and an exogenous stimulatory polypeptide comprising a 4-1BBL polypeptide, or a fragment thereof. In some embodiments, the engineered erythroid cell comprises an exogenous stimulatory polypeptide comprising an IL-12 polypeptide, or a fragment thereof, and an exogenous stimulatory polypeptide comprising a 4-1BBL polypeptide, or a fragment thereof. In some embodiments, the engineered erythroid cell comprises an exogenous stimulatory polypeptide comprising an IL-15 polypeptide, or a fragment thereof, and an extracellular portion of an IL-15RA polypeptide, or a fragment thereof, and an exogenous stimulatory polypeptide comprising an IL-12 polypeptide, or a fragment thereof.

In certain embodiments, the engineered erythroid cells described herein are used to treat cancers that are characterized by their responsiveness, e.g., responsive or nonresponsive, to a checkpoint inhibitor.

Immune checkpoint molecules such as PD-1, PD-L1, PD-L2, CTLA4, TIM3, LAGS, CCR4, OX40, OX40L, IDO, and A2AR are cell surface signaling receptors that play an important role in modulating the T-cell response in the tumor microenvironment. Tumor cells have been shown to utilize these checkpoints to their benefit by up regulating their expression and activity, thereby evading an anti-tumor immune response.

Some human tumors, however, can be eliminated by a patient's immune system. For example, immune checkpoint inhibitors targeting checkpoint molecules, such as CTLA-4 and the PD-1/PD-L1 axis, have shown clinical activity in several types of cancer and can lead to complete response and tumor remission. Immune checkpoint inhibitors reinvigorate anti-tumour immune responses by disrupting co-inhibitory T-cell signalling. In particular, the mode of action of anti-CTLA-4 and anti-PD-1 antibodies is through inhibition of CTLA-4 and PD-1, respectively, which the tumors have co-opted as protection from an anti-tumor immune response. By inhibiting these checkpoint molecules (e.g., with an antagonistic antibody), a patient's CD8+ T cells may be allowed to proliferate and destroy tumor cells. However, the majority of cancer patients receiving treatment with checkpoint inhibitors will progress within 12 months depending on the cancer and the therapeutic intervention. The MHC complex is an important nexus in the immune system; it is the way T cells recognize and kill cancer cells, but it also blocks the killing function of NK cells. A common means of resistance to checkpoint inhibitors is loss of MHC expression making the cancer invisible to T cells, but as a result it becomes susceptible to NK cell dependent killing. Downregulation of MHC presentation on tumor cells and T-cell exhaustion in the surrounding area contribute to this immunotherapy resistance.

Accordingly, in some embodiments, the engineered erythroid cells as described herein are used in the treatment of a cancer (e.g., a solid tumor or a hematologic cancer) that has responded, is responsive or is known to be responsive to a checkpoint inhibitor. For example, a number of immunomodulatory agents that target immune system checkpoints such as the cytotoxic T-lymphocyte antigen 4 (CTLA-4), the programmed death-1 (PD-1) or its ligand (PD-L1), have received regulatory approval for the treatment of multiple cancers including malignant melanoma, non-small cell lung cancer, renal cell carcinoma, classical Hodgkin lymphoma, and recurrent or metastatic head and neck squamous cell carcinoma. Thus, in some embodiments, the engineered erythroid cells are used to treat a cancer that is characterized by PD-1 responsive tumors. In embodiments, the engineered erythroid cells are administered or used for treatment in combination with a checkpoint inhibitor for the treatment of such cancers. Checkpoint inhibitors suitable in such methods are described herein.

In other embodiments, the engineered erythroid cells as described herein, are used to treat solid tumors in patients that no longer respond to checkpoint inhibitors. In some embodiments, the engineered erythroid cells are used alone as a monotherapy to treat solid tumors in patients that no longer respond to checkpoint inhibitors. In some embodiments, the engineered erythroid cells are used in combination with a checkpoint inhibitor to treat solid tumors in patients that no longer respond to checkpoint inhibitors. In some embodiments, the solid tumor is selected from melanoma, non-small cell lung cancer, renal cell carcinoma, bladder cancer, and head and neck cancer.

As discussed above, the MHC complex is an important nexus in the immune system; it is the way T cells recognize and kill cancer cells, but it also blocks the killing function of NK cells. A common means of resistance to checkpoint inhibitors is loss of MHC expression making the cancer invisible to T cells, but as a result it becomes susceptible to NK cell dependent killing. In some embodiments, the engineered erythroid cells as described herein, are used to treat a patient population who has progressed on checkpoint inhibitor therapy due to loss of MHC expression.

For example, in some embodiments, the engineered erythroid cells as described herein may be used in combination with an agent that blocks, reduces and/or inhibits PD-1 and either PD-L1 or PD-L2, and/or blocks, reduces and/or inhibits the binding of PD-1 with PD-L1 or PD-L2 (by way of non-limiting example, one or more of nivolumab (ONO-4538/BMS-936558, MDX1106, OPDIVO, BRISTOL MYERS SQUIBB), pembrolizumab (KEYTRUDA, Merck), pidilizumab (CT-011, CURE TECH), MK-3475 (MERCK), BMS 936559 (BRISTOL MYERS SQUIBB), and MPDL328OA (ROCHE)). In some embodiments, the engineered erythroid cells as described herein may be used in combination with an agent that blocks, reduces and/or inhibits the activity of CTLA-4 and/or the binding of CTLA-4 with one or more of its receptors (e.g. CD80, CD86, AP2M1, SHP-2, and PPP2R5A). For example, in some embodiments, the agent that inhibits the activity of CTLA-4 is an antibody such as, by way of non-limitation, ipilimumab (MDX-010, MDX-101, Yervoy, BMS) and/or tremelimumab (Pfizer). Further, engineered erythroid cells provided herein can be used in combination with one or more blocking antibodies targeted to an immune checkpoint molecule such as, for example, BTLA, HVEM, TIM3, GALS, LAG3, VISTA, KIR, 2B4, CD160 (also referred to as BY55), CGEN-15049, CHK 1 and CHK2 kinases, A2aR, CEACAM (e.g., CEACAM-1, CEACAM-3 and/or CEACAM-5), GITR, GITRL, galectin-9, CD244, CD160, TIGIT, SIRPα, ICOS, CD172a, TMIGD2 and various B-7 family ligands (including, but are not limited to, B7-1, B7-2, B7-DC, B7-H1, B7-H2, B7-H3, B7-H4, B7-H5, B7-H6 and B7-H7).

In some embodiments, the engineered erythroid cells described herein are administered in combination with an anti-PD-1 antibody.

Treatment with the engineered erythroid cells as described herein, can function to boost the activation of not only T-cells but also NK cells and thereby reactivate the local adaptive immune response, re-sensitize the cancer to checkpoint inhibition, and enhance tumor killing either additively or synergistically via activation of the innate immune response.

In particular embodiments of the foregoing methods of treatment, the engineered erythroid cell comprises an exogenous stimulatory polypeptide comprising an IL-15 polypeptide, or a fragment thereof, and an extracellular portion of an IL-15RA polypeptide, or a fragment thereof. In particular embodiments, the engineered erythroid cell comprises an exogenous stimulatory polypeptide comprising IL-15 polypeptide, or a fragment thereof, and an extracellular portion of an IL-15RA polypeptide, or a fragment thereof, and exogenous stimulatory polypeptide comprising a 4-1BBL polypeptide.

In particular embodiments of the foregoing methods of treatment, the engineered erythroid cell comprises an exogenous stimulatory polypeptide comprising an interleukin-12 p40 (IL-12 p40) polypeptide, or a fragment thereof, and an interleukin-12 p35 (IL-12 p35) polypeptide, or a fragment thereof. In particular embodiments, the engineered erythroid cell comprises an exogenous stimulatory polypeptide comprising an interleukin-12 p40 (IL-12 p40) polypeptide, or a fragment thereof, and an interleukin-12 p35 (IL-12 p35) polypeptide, or a fragment thereof, and an exogenous stimulatory polypeptide comprising an IL-15 polypeptide, or a fragment thereof, and an extracellular portion of an IL-15RA polypeptide, or a fragment thereof.

In particular embodiments of the foregoing methods of treatment, the engineered erythroid cell comprises an exogenous stimulatory polypeptide comprising an interleukin-12 p40 (IL-12 p40) polypeptide, or a fragment thereof, and an interleukin-12 p35 (IL-12 p35) polypeptide, or a fragment thereof. In particular embodiments, the engineered erythroid cell comprises an exogenous stimulatory polypeptide comprising an interleukin-12 p40 (IL-12 p40) polypeptide, or a fragment thereof, and an interleukin-12 p35 (IL-12 p35) polypeptide, or a fragment thereof, and an exogenous stimulatory polypeptide comprising a 4-1BBL polypeptide.

Cancers with High Tumor Mutational Burden

Tumors may accumulate mutations in their genetic material as they grow. These somatic mutations can be passed along to new cancer cells during cell division. Acquired mutations in tumor cells may alter the expression of proteins, resulting in the formation of neoantigens. Tumor mutation burden (TMB) is a measurement of the mutations carried by tumor cells. TMB is a new clinical marker that predicts responses to immunotherapy in a range of advanced cancers. Unlike protein-based biomarkers, TMB is a quantitative measure of the total number of mutations per coding area of a tumor genome. Tumors that have higher levels of TMB are believed to express more neoantigens, that may allow for a more robust immune response and therefore a more durable response to immunotherapy. Thus, in some embodiments, the engineered erythroid cells are used to treat a cancer that is characterized by tumors with a high mutational burden.

Vascularized Tumors/Tumors with Leaky Vasculature

In other embodiments, the engineered erythroid cells of the disclosure are used to treat highly vascularized tumors. Without being bound by theory, greater vascularization renders the tumors more accessible to the engineered erythroid cells of the present disclosure. Tumor vascularity can be measured, for example, by intercapillary distance (thought to reflect tumor oxygenation) and microvessel density (provides a histological assessment of tumor angiogenesis). A highly vascular tumor can be any tumor of vascular origin, for example a hemangioma, a lymphangioma, a hemangioendothelioma, Kaposi sarcoma, an angiosarcoma, a hemangioblastoma.

In other embodiments, the engineered erythroid cells of the disclosure are used to treat tumors with leaky vasculature. There is general agreement that blood vessels in tumors are abnormal. One manifestation of this abnormality is a defective and leaky endothelium. Blood vessel leakiness not only influences the internal environment of tumors and perhaps the rate of angiogenesis, but it also governs access of therapeutics. Without being bound by theory, a leaky blood vessel would provide more access to the engineered erythroid cells of the present disclosure.

Infectious Diseases

In some aspects, the invention provides a method of treating an infectious disease in a subject, comprising administering to the subject an erythroid cell engineered to stimulate an immune cell, e.g, an immune killer cell. The engineered erythroid cell is administered in an amount effective to treat the infectious disease in the subject.

In certain embodiments, the infectious disease is caused by a viral infection.

Viral infections to be treated with an engineered erythroid cell of the invention include adenovirus, coxsackievirus, hepatitis A virus, poliovirus, Epstein-Barr virus, herpes simplex type 1, herpes simplex type 2, human cytomegalovirus, human herpesvirus type 8, varicella-zoster virus, hepatitis B virus, hepatitis C viruses, human immunodeficiency virus (HIV), influenza virus, measles virus, mumps virus, parainfluenza virus, respiratory syncytial virus, papillomavirus, rabies virus, and Rubella virus. Other viral targets include Paramyxoviridae (e.g., pneumovirus, morbillivirus, metapneumovirus, respirovirus or rubulavirus), Adenoviridae (e.g., adenovirus), Arenaviridae (e.g., arenavirus such as lymphocytic choriomeningitis virus), Arteriviridae (e.g., porcine respiratory and reproductive syndrome virus or equine arteritis virus), Bunyaviridae (e.g., phlebovirus or hantavirus), Caliciviridae (e.g., Norwalk virus), Coronaviridae (e.g., coronavirus or torovirus), Filoviridae (e.g., Ebola-like viruses), Flaviviridae (e.g., hepacivirus or flavivirus), Herpesviridae (e.g., simplexvirus, varicellovirus, cytomegalovirus, roseolovirus, or lymphocryptovirus), Orthomyxoviridae (e.g., influenza virus or thogotovirus), Parvoviridae (e.g., parvovirus), Picomaviridae (e.g., enterovirus or hepatovirus), Poxviridae (e.g., orthopoxvirus, avipoxvirus, or leporipoxvirus), Retroviridae (e.g., lentivirus or spumavirus), Reoviridae (e.g., rotavirus), Rhabdoviridae (e.g., lyssavirus, novirhabdovirus, or vesiculovirus), and Togaviridae (e.g., alphavirus or rubivirus). Specific examples of these viruses include human respiratory coronavirus, influenza viruses A-C, hepatitis viruses A to G, and herpes simplex viruses 1-9.

In certain embodiments, the viral infection is caused by a virus selected from adenovirus, Epstein barr virus (EBV), hetpatitis B virus (HBV), tuberculosis, human immunodeficientcy virus (HIV), herpes simplex virus (HSV), papilloma virus and cytomegalovirus.

In other embodiments, the viral infection is characterized by down-regulation of MHC I presentation. Human viruses employ diverse mechanisms to inhibit the MHC class I pathway in order to escape CTL lysis. Examples of proteins that interfere with the MHC class I pathway are encoded by adenoviruses and retroviruses (Tortorella et al., Annu Rev Immunol. 2000; 180:861-926). These include the adenovirus E3/19K and the human immunodeficiency virus-1 (HIV-1) Nef gene products. Herpes viruses establish persistent lifelong infections in immunocompetent hosts, and most if not all, herpes viruses encode proteins that inhibit MHC class I antigen presentation, and these proteins play an important role in allowing the virus to evade detection by CTLs. This is exemplified by the human cytomegalovirus (HCMV), where the unique short region of the viral genome encodes at least five proteins (US2, US3, US6, US10 and US11) that inhibit the MHC class I pathway.

MICB is a stress-induced ligand of the natural killer (NK) cell activating receptor NKG2D and is critical for the NK cell killing of virus-infected cells and tumor cells. In another example of evasion of NK cell killing, MICB expression is down-regulated during viral infection, leading to decreased binding of NKG2D and reduced killing by NK cells. Therefore, In some embodiments, the invention provides methods of treating a viral disease associated with downregulated MICB, wherein the killing by NK cells of the virally infected cells is increased.

In certain embodiments, the infectious disease is caused by a bacterial infection.

Bacterial infections to be treated with an engineered erythroid cell of the invention include, but are not limited to, Mycobacteria, *Rickettsia, Mycoplasma, Neisseria meningitides, Neisseria gonorrheoeae, Legionella, Vibrio cholerae*, Streptococci, *Staphylococcus aureus, Staphylococcus epidermidis, Pseudomonas aeruginosa, Corynobacteria diphtheriae, Clostridium* spp., enterotoxigenic *Eschericia coli, Bacillus anthracis, Rickettsia, Bartonella henselae, Bartonella quintana, Coxiella burnetii, Chlamydia trachomatis, Mycobacterium leprae, Salmonella; Shigella; Yersinia enterocolitica; Yersinia pseudotuberculosis; Legionella pneumophila; Mycobacterium tuberculosis; Listeria monocytogenes; Mycoplasma* spp.; *Pseudomonas fluorescens; Vibrio cholerae; Haemophilus influenzae; Bacillus anthracis; Treponema pallidum; Leptospira; Borrelia; Corynebacterium diphtheriae; Francisella; Brucella melitensis; Campylobacter jejuni; Enterobacter; Proteus mirabilis; Proteus*; and *Klebsiella pneumoniae.*

Subjects

The methods described herein are intended for use with any subject that may experience the benefits of these methods. Thus, "subjects," "patients," and "individuals" (used interchangeably) include humans as well as non-human subjects, particularly domesticated animals.

In some embodiments, the subject and/or animal is a mammal, e g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal. In some embodiments, the subject and/or animal is a human. In some embodiments, the human is a pediatric human In other embodiments, the human is an adult human. In other embodiments, the human is a geriatric human. In other embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In other embodiments, the subject is a non-human animal, and therefore the disclosure pertains to veterinary use. In a specific embodiment, the non-human animal is a household pet. In another specific embodiment, the non-human animal is a livestock animal In certain embodiments, the subject is a human cancer patient that cannot receive chemotherapy, e.g. the patient is unresponsive to chemotherapy or too ill to have a suitable therapeutic window for chemotherapy (e.g. experiencing too many dose- or regimen-limiting side effects). In certain embodiments, the subject is a human cancer patient having advanced and/or metastatic disease.

In some embodiments, the subject is selected for treatment with an erythroid cell engineered to stimulate an immune killer cell, comprising a plurality of exogenous stimulatory polypeptides sufficient to stimulate the immune killer cell, of the present disclosure. In some embodiments, the subject is selected for treatment of cancer with an erythroidcell engineered to stimulate an immune killer cell, comprising a plurality of exogenous stimulatory polypeptides sufficient to stimulate the immune killer cell, of the present disclosure. In some embodiments, the subject is selected for treatment of an infectious disease with an erythroid cell engineered to stimulate an immune killer cell, comprising a plurality of exogenous stimulatory polypeptides sufficient to stimulate the immune killer cell, of the present disclosure.

In some embodiments, the subject is selected for treatment with an engineered erythroid cell comprising a first exogenous stimulatory polypeptide, wherein the first exogenous stimulatory polypeptide comprises IL-15 polypeptide, or a fragment thereof, and an extracellular portion of an IL-15RA polypeptide, or a fragment thereof, of the present disclosure. In some embodiments, the engineered erythroid cell further comprises a second exogenous stimulatory polypeptide, e.g., comprising 4-1BBL. In some embodiments, the subject is selected for treatment of cancer with an engineered erythroid cell comprising a first exogenous stimulatory polypeptide, wherein the first exogenous stimulatory polypeptide comprises an IL-15 polypeptide, or a fragment thereof, and an extracellular portion of an IL-15RA polypeptide, or a fragment thereof, of the present disclosure. In some embodiments, the engineered erythroid cell further comprises a second exogenous stimulatory polypeptide, e.g., comprising 4-1BBL. In some embodiments, the subject is selected for treatment of an infectious disease with an engineered erythroid cell comprising a first exogenous stimulatory polypeptide, wherein the first exogenous stimulatory polypeptide comprises an IL-15 polypeptide, or a fragment thereof, and an extracellular portion of an IL-15RA polypeptide, or a fragment thereof, of the present disclosure. In some embodiments, the engineered erythroid cell further comprises a second exogenous stimulatory polypeptide, e.g., comprising 4-1BBL.

In some embodiments, the subject is selected for treatment with an engineered erythroid cell comprising at least one exogenous stimulatory polypeptide selected from the group consisting of MICA, MICB and IGF-1, of the present disclosure.

In some embodiments of the above aspects and embodiments, the engineered erythroid cell is an enucleated cell. In some embodiments of the above aspects and embodiments, the engineered erythroid cell is a nucleated cell.

IV. Pharmaceutical Compositions

The present disclosure encompasses the preparation and use of pharmaceutical compositions comprising an engineered erythroid cell of the disclosure as an active ingredient. In some embodiments, the engineered erythroid cell is an enucleated cell. In some embodiments, the engineered erythroid cell is a nucleated cell. Such a pharmaceutical composition may consist of the active ingredient alone, as a combination of at least one active ingredient (e.g., an effective dose of an engineered erythroid cell) in a form suitable for administration to a subject, or the pharmaceutical composition may comprise the active ingredient and one or more pharmaceutically acceptable carriers, one or more additional (active and/or inactive) ingredients, or some combination of these.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

The administration of the pharmaceutical compositions may be carried out in any convenient manner, including by aerosol inhalation, injection, ingestion, transfusion, implantation or transplantation. The compositions of the present disclosure may be administered to a patient subcutaneously, intradermally, intramuscularly, by intravenous (i.v.) injection, or intraperitoneally. The pharmaceutical compositions may be injected directly into a tumor or lymph node.

As used herein, the term "pharmaceutically acceptable carrier" means a chemical composition with which the active ingredient may be combined and which, following the combination, can be used to administer the active ingredient to a subject.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the disclosure is contemplated include, but are not limited to, humans and other primates, mammals including commercially relevant mammals such as non-human primates, cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical compositions that are useful in the methods of the disclosure may be prepared, packaged, or sold in formulations suitable for oral, rectal, vaginal, parenteral, topical, pulmonary, intranasal, intra-lesional, buccal, ophthalmic, intravenous, intra-organ or another route of administration. Other contemplated formulations include projected nanoparticles, liposomal preparations, resealed erythrocytes containing the active ingredient, and immunologically-based formulations.

A pharmaceutical composition of the disclosure may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the disclosure may further comprise one or more additional pharmaceutically active agents. Particularly contemplated additional agents include anti-emetics and scavengers such as cyanide and cyanate scavengers and AZT, protease inhibitors, reverse transcriptase inhibitors, interleukin-2, interferons, cytokines, and the like.

Controlled- or sustained-release formulations of a pharmaceutical composition of the disclosure may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

The engineered erythroid cell of the disclosure can be administered to an animal, preferably a human. Where the engineered erythroid cell are administered, either with or without T cells or NK cells expanded thereby, they can be administered in an amount ranging from about 100,000 to about one billion cells wherein the cells are infused into the animal, preferably, a human patient in need thereof. While the precise dosage administered will vary depending upon any number of factors, including but not limited to, the type of animal and type of disease state being treated, the age of the animal and the route of administration.

The engineered erythroid cell may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

An engineered erythroid cell (or T cells or NK cells expanded thereby) may be co-administered with the various other compounds (cytokines, chemotherapeutic drugs, checkpoint inhibitors and/or antiviral drugs, among many others). Alternatively, the compound(s) may be administered an hour, a day, a week, a month, or even more, in advance of the engineered erythroid cell (or T cells or NK cells expanded thereby), or any permutation thereof. Further, the compound(s) may be administered an hour, a day, a week, or even more, after administration of the engineered erythroid cell (or T cells or NK cells expanded thereby), or any permutation thereof. The frequency and administration regimen will be readily apparent to the skilled artisan and will depend upon any number of factors such as, but not limited to, the type and severity of the disease being treated, the age and health status of the animal, the identity of the compound or compounds being administered, the route of administration of the various compounds and the engineered erythroid cell (or T cells or NK cells expanded thereby), and the like.

Further, it would be appreciated by one skilled in the art, based upon the disclosure provided herein, that where the engineered erythroid cell is to be administered to a mammal, the cells are treated so that they are in a "state of no growth"; that is, the cells are incapable of dividing when administered to a mammal. As disclosed elsewhere herein, the cells can be irradiated to render them incapable of growth or division once administered into a mammal. Other methods, including haptenization (e.g., using dinitrophenyl and other compounds), are known in the art for rendering cells to be administered, especially to a human, incapable of growth, and these methods are not discussed further herein. Moreover, the safety of administration of engineered erythroid cells that have been rendered incapable of dividing in vivo has been established in Phase I clinical trials using engineered erythroid cell transfected with plasmid vectors encoding some of the molecules discussed herein.

In some embodiments of the above aspects and embodiments, the engineered erythroid cell is an enucleated cell. In some embodiments of the above aspects and embodiments, the engineered erythroid cell is a nucleated cell.

In some embodiments, the disclosure features a pharmaceutical composition comprising a plurality of the engineered erythroid cells described herein, and a pharmaceutical carrier. In other embodiments, the disclosure features a pharmaceutical composition comprising a population of engineered erythroid cells as described herein, and a pharmaceutical carrier. It will be understood that any single engineered erythroid cell, plurality of engineered erythroid cells, or population of engineered erythroid cells as described elsewhere herein may be present in a pharmaceutical composition of the invention.

In some embodiments, the pharmaceutical compositions provided herein comprise engineered (i.e. modified) erythroid cells and unmodified erythroid cells. For example, a single unit dose of erythroid cells (e.g., modified and unmodified erythroid cells) can comprise, in various embodiments, about, at least, or no more than 10%, 20%, 30%, 40%, 50%, 60%, 70%, 75%, 80%), 85%, 90%, 95%, or 99% engineered erythroid cells, wherein the remaining erythroid cells in the composition are not engineered.

In some embodiments, the pharmaceutical compositions provided herein comprise engineered enucleated erythroid cells and nucleated erythroid cells. For example, a single unit dose of engineered erythroid cells (e.g., enucleated and nucleated erythroid cells) can comprise, in various embodiments, about, or at least 10%, 20%, 30%, 40%, 50%, 60%, 70%, 75%, 80%, 85%, 90%, 91%, 92%, 93%, 94%, 95%, 96%, 97%, 98%, or 99% enucleated erythroid cells, wherein the remaining erythroid cells in the composition are nucleated.

Combination Therapies

According to some embodiments, the disclosure provides methods that further comprise administering an additional agent to a subject. In some embodiments, the disclosure pertains to co-administration and/or co-formulation.

In some embodiments, the engineered erythroid cells described herein are used in combination with monoclonal antibodies that kill tumors via antibody dependent cellular cytotoxicity (ADCC). In some embodiments, the engineered erythroid cells comprising an IL-15 polypeptide, or a fragment thereof, and an extracellular portion of an IL-15RA polypeptide, or a fragment thereof, as described herein, are used in combination with monoclonal antibodies that kill tumors via antibody dependent cellular cytotoxicity (ADCC). In some embodiments, the engineered erythroid cells comprising an IL-15 polypeptide, or a fragment thereof, and an extracellular portion of an IL-15RA polypeptide, or a fragment thereof, and 4-1BBL, as described herein, are used in combination with monoclonal antibodies that kill tumors via antibody dependent cellular cytotoxicity (ADCC).

Tumor-specific mAbs that recognize tumor-selective antigens on the surface of tumor cells target and attack tumor cells through various mechanisms, including directing toxic molecules to target cells, inhibiting target cell proliferation, blocking inhibitory signals for immune cells, and directing immune cells to kill targets through ADCC. Examples of tumor-antigen targeting monoclonal antibodies functioning through ADCC include, but are not limited to, rituximab, obinutuzumab, dinituximab, trastuzumab and cetuximab. For example, traztuzumab (Roche) binds to the HER-2 antigen expressed on the surface of breast cancer cells. Local NK cells recognize the Fc portion of the antibody, and once bound release cytotoxins that drive a programmed cell death (apoptotic) signal into the target. Combination therapies including such tumor-specific mAbs are encompassed by the methods of the invention.

In some embodiments, administration of the engineered erythroid cell acts synergistically when co-administered with another agent and is administered at doses that are lower than the doses commonly employed when such agents are used as monotherapy.

In some embodiments, inclusive of, without limitation, cancer applications, the present disclosure pertains to chemotherapeutic agents as additional agents. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall; dynemicin, including dynemicin A; bisphosphonates, such as clodronate; an esperamicin; as well as neocarzinostatin chromophore and related chromoprotein enediyne antibiotic chromophores), aclacinomy sins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel, and TAXOTERE doxetaxel; chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation.

Some human tumors can be eliminated by a patient's immune system. For example, administration of a monoclonal antibody targeted to an immune "checkpoint" molecule can lead to complete response and tumor remission. A mode of action of such antibodies is through inhibition of an immune regulatory molecule that the tumors have co-opted as protection from an anti-tumor immune response. By inhibiting these "checkpoint" molecules (e.g., with an antagonistic antibody), a patient's CD8+ T cells may be allowed to proliferate and destroy tumor cells.

For example, administration of a monoclonal antibody targeted to, by way of example and without limitation, CTLA-4 or PD-1 can lead to complete response and tumor remission. The mode of action of such antibodies is through inhibition of CTLA-4 or PD-1, which the tumors have co-opted as protection from an anti-tumor immune response. By inhibiting these "checkpoint" molecules (e.g., with an antagonistic antibody), a patient's CD8+ T cells may be allowed to proliferate and destroy tumor cells.

Thus, the engineered erythroid cell described herein can be used in combination with one or more blocking antibodies targeted to an immune "checkpoint" molecule. For instance, in some embodiments, the compositions provided herein can be used in combination with one or more blocking antibodies targeted to a molecule such as CTLA-4 or PD-1. For example, the compositions provided herein may be used in combination with an agent that blocks, reduces and/or inhibits PD-1 and PD-L1 or PD-L2 and/or the binding of PD-1 with PD-L1 or PD-L2 (by way of non-limiting example, one or more of nivolumab (ONO-4538/BMS-936558, MDX1106, OPDIVO, BRISTOL MYERS SQUIBB), pembrolizumab (KEYTRUDA, Merck), pidilizumab (CT-011, CURE TECH), MK-3475 (MERCK), BMS 936559 (BRISTOL MYERS SQUIBB), MPDL328OA (ROCHE)). In an embodiment, the compositions provided herein may be used in combination with an agent that blocks, reduces and/or inhibits the activity of CTLA-4 and/or the binding of CTLA-4 with one or more receptors (e.g. CD80, CD86, AP2M1, SHP-2, and PPP2R5A). For instance, in some embodiments, the immune-modulating agent is an antibody such as, by way of non-limitation, ipilimumab (MDX-010, MDX-101, Yervoy, BMS) and/or tremelimumab (Pfizer). Blocking antibodies against these molecules can be obtained from, for example, Bristol Myers Squibb (New York, N.Y.), Merck (Kenilworth, N.J.), MedImmune (Gaithersburg, Md.), and Pfizer (New York, N.Y.).

Further, the engineered erythroid cell compositions provided herein can be used in combination with one or more blocking antibodies targeted to an immune checkpoint molecule such as for example, BTLA, HVEM, TIM3, GALS, LAGS, VISTA, KIR, 2B4, CD160 (also referred to as BY55), CGEN-15049, CHK 1 and CHK2 kinases, A2aR, CEACAM (e.g., CEACAM-1, CEACAM-3 and/or CEACAM-5), GITR, GITRL, galectin-9, CD244, CD160, TIGIT, SIRPα, ICOS, CD172a, and TMIGD2 and various B-7 family ligands (including, but are not limited to, B7-1, B7-2, B7-DC, B7-H1, B7-H2, B7-H3, B7-H4, B7-H5, B7-H6 and B7-H7).

V. Kits

The disclosure includes various kits which comprise an engineered erythroid cell of the disclosure, and optionally further include nucleic acids encoding the exogenous stimulatory polypeptides. In some embodiments, the engineered erythroid cell is an enucleated cell. In some embodiments, the engineered erythroid cell is a nucleated cell.

Although exemplary kits are described below, the contents of other useful kits will be apparent to the skilled artisan in light of the present disclosure. Each of these kits is included within the disclosure.

In some embodiments, the kit further comprises an applicator useful for administering the engineered erythroid cells to the NK cells or the T cells. The particular applicator included in the kit will depend on, e.g., the method used to administer the engineered erythroid cell, and such applicators are well-known in the art and may include, among other things, a pipette, a syringe, a dropper, and the like. Moreover, in embodiments the kit further comprises an instructional material which describe the use of the kit to perform the methods described herein. These instructions simply embody the disclosure provided herein.

In some embodiments, the kit includes a pharmaceutically-acceptable carrier. The composition is provided in an appropriate amount as set forth elsewhere herein. Further, the route of administration and the frequency of administration are as previously set forth elsewhere herein.

The kit encompasses an engineered erythroid cell comprising a wide plethora of molecules, such as, but not limited to, the exogenous stimulatory polypeptides set forth herein. However, the skilled artisan armed with the teachings provided herein, would readily appreciate that the disclosure is in no way limited to these, or any other, combination of molecules. Rather, the combinations set forth herein are for illustrative purposes and they in no way limit the combinations encompassed by the present disclosure. Further, the kit comprises a kit where each molecule to be transduced into the engineered erythroid cell is provided as an isolated nucleic acid encoding a molecule, a vector comprising a nucleic acid encoding a molecule, and any combination thereof, including where at least two molecules are encoded by a contiguous nucleic acid and/or are encoded by the same vector.

All publications and patent applications cited in this specification are herein incorporated by reference in their entirety for all purposes as if each individual publication or patent application were specifically and individually indicated to be incorporated by reference for all purposes. The publications discussed herein are provided solely for their disclosure prior to the filing date of the present application. Nothing herein is to be construed as an admission that the inventors described herein are not entitled to antedate such disclosure by virtue of prior disclosure or for any other reason.

TABLE 9

Sequences

| SEQ ID NO: | Description |
|---|---|
| 1 | mature human IL-15 (SEQ ID NO: 4) + $(G4S)_3$ linker (SEQ ID NO: 12) + mature extracellular soluble human IL-15 receptor α (SEQ ID NO: 8) |
| 2 | mature human IL-15 (SEQ ID NO: 4) + $(G4S)_3$ linker (SEQ ID NO: 12) + IL-15 receptor α sushi domain + 13 additional amino acids of IL-15 receptor α (SEQ ID NO: 10) |
| 3 | immature human IL-15 |
| 4 | mature human IL-15 |
| 5 | immature full-length human IL-15 receptor α |
| 6 | mature full-length human IL-15 receptor α |
| 7 | immature extracellular human IL-15 receptor α |
| 8 | mature extracellular human IL-15 receptor α |
| 9 | human IL-15 receptor sushi domain |
| 10 | human IL-15 receptor sushi domain + 13 additional amino acids of IL-15 receptor α |
| 11 | G4S linker |
| 12 | $(G4S)_3$ linker (flexible linker) |
| 13 | encodes SEQ ID NO: 4 (mature human IL-15) |
| 14 | encodes SEQ ID NO: 4 (mature human IL-15) |
| 15 | encodes SEQ ID NO: 8 (mature extracellular human IL-15 receptor α) |
| 16 | encodes SEQ ID NO: 10 (human IL-15 receptor sushi domain + 13 additional amino acids of IL-15 receptor α) |
| 17 | encodes SEQ ID NO: 12 ($(G4S)_3$ linker) |
| 18 | encodes SEQ ID NO: 12 ($(G4S)_3$ linker) |
| 19 | encodes SEQ ID NO: 1 |
| 20 | encodes SEQ ID NO: 2 |
| 21 | GPA signal peptide |
| 22 | encodes SEQ ID NO: 21 |
| 23 | Linker-HA-linker |
| 24 | encodes SEQ ID NO: 23 |
| 25 | GPA |
| 26 | encodes SEQ ID NO: 25 |
| 27 | IL-15 V3 construct (GPA signal peptide (SEQ ID NO: 21)-mature human IL-15 (SEQ ID NO: 4)-linker-HA-linker (SEQ ID NO: 23)-GPA (SEQ ID NO: 25)) |
| 28 | encodes SEQ ID NO: 27 |
| 29 | IL-15/IL-15Ra V4 construct GPA signal peptide (SEQ ID NO: 21)-mature human IL-15 (SEQ ID NO: 4)-flexible linker (SEQ ID NO: 12)-mature human extra-cellular IL-15RA (SEQ ID NO: 8)-linker-HA-linker (SEQ ID NO: 23)-GPA (SEQ ID NO: 25) |
| 30 | encodes SEQ ID NO: 29 |
| 31 | IL-15/IL-15Ra (sushi domain + 13aa) V5 construct GPA signal peptide (SEQ ID NO: 21)-mature human IL-15 (SEQ ID NO: 4)-flexible linker (SEQ ID NO: 12)-mature human IL-15RA (sushi domain + 13aa) (SEQ ID NO: 10)-linker-HA-linker (SEQ ID NO: 23)-GPA (SEQ ID NO: 25) |
| 32 | encodes SEQ ID NO: 31 |
| 33 | alternate IL-15 linker (between GPA and IL-15/IL-15RA) |
| 34 | encodes SEQ ID NO: 33 |
| 35 | IL-15 V3.1 construct (alternate linker) GPA signal peptide (SEQ ID NO: 21)-mature human IL-15 (SEQ ID NO: 4)-linker (SEQ ID NO: 33)-GPA (SEQ ID NO: 25) |
| 36 | encodes SEQ ID NO: 35 |
| 37 | IL-15/IL-15Ra V4.1 construct (alternate linker) GPA signal peptide (SEQ ID NO: 21)-mature human IL-15 (SEQ ID NO: 4)-flexible linker (SEQ ID NO: 12)-mature human extra-cellular IL-15RA (SEQ ID NO: 8)-linker (SEQ ID NO: 33)-GPA (SEQ ID NO: 25) |

TABLE 9-continued

| Sequences | |
|---|---|
| SEQ ID NO: | Description |
| 38 | encodes SEQ ID NO: 37 |
| 39 | 4-1BBL linker (between GPA and 4-1BBL) |
| 40 | encodes SEQ ID NO: 39 |
| 41 | human 4-1BBL |
| 42 | encodes SEQ ID NO: 41 |
| 43 | 4-1BBL construct GPA signal peptide (SEQ ID NO: 21)-human extracellular 4-1BBL (SEQ ID NO: 41) – 4-1BBL linker (SEQ ID NO: 39)-GPA (SEQ ID NO: 25) |
| 44 | encodes SEQ ID NO: 43 |
| 45 | Human IL-12 p40 |
| 46 | encodes SEQ ID NO: 45 |
| 47 | Human IL-12 p35 |
| 48 | encodes SEQ ID NO: 47 |
| 49 | SMIM1 |
| 50 | encodes SEQ ID NO: 49 |
| 51 | IL-12 linker (between GPA and IL-12) |
| 52 | encodes SEQ ID NO: 51 |
| 53 | IL-12 V1 construct (comprising GPA) GPA signal peptide (SEQ ID NO: 21)-IL-12 p40 (SEQ ID NO: 45) – flexible linker (SEQ ID NO: 12)-IL-12 p35 (SEQ ID NO: 47)-IL-12 linker (SEQ ID NO: 51)-GPA (SEQ ID NO: 25) |
| 54 | encodes SEQ ID NO: 53 |
| 55 | IL-12 V2 construct (comprising SMIM1) SMIM1 (SEQ ID NO: 49) – flexible linker (SEQ ID NO: 12)-IL12 p40 (SEQ ID NO: 45) – flexible linker (SEQ ID NO: 12) – IL-12 p35 (SEQ ID NO: 47) |
| 56 | encodes SEQ ID NO: 55 |
| 57 | IL-12 p40/IL-12 p35 fusion IL-12 p40 (SEQ ID NO: 45) – flexible linker (SEQ ID NO: 12)-IL-12 p35 (SEQ ID NO: 47) |
| 58 | encodes SEQ ID NO: 57 |
| 62 | 41BBL-T2A-IL-12 construct GPA signal peptide(SEQ ID NO: 21)-41BBL (SEQ ID NO: 41)-4-1BBL linker (SEQ ID NO: 39)-GPA (SEQ ID NO: 25)-(T2A skip peptide)-SMIM1 SEQ ID NO: 49)-linker (SEQ ID NO: 12)-IL12 p40 (SEQ ID NO: 45) – flexible linker (SEQ ID NO: 12) – IL-12 p35 (SEQ ID NO: 47) |
| 63 | encodes SEQ ID NO: 62 |
| 64 | T2A skip peptide |
| 65 | encodes SEQ ID NO: 64 |

TABLE 10

| Protein Construct Sequences for Mouse Studies | |
|---|---|
| 59 | Ig heavy chain V region 3 signal sequence (aa 1-19) + His6 (aa 20-25) + TEV cleavage site (zz 26-32) + murine 4-1BBL extracellular domain (aa 33-238) |
| 60 | Human light chain leader (aa 1-20) + mouse hinge – CH2 – CH3 (aa 21-258) + TEV cleavage site (aa 259-265) + human IL-15Ra Sushi domain* (aa 266-333) + Linker (aa 334-361) + human IL15** (aa 362-475) *Sushi domain is from PDB:4GS7 Chain D; Sushi domain is aa 31-95, and sequence used is aa 30-97. **human IL15 is from PDB:4GS7 Chain D, aa 49-162. |

TABLE 10-continued

| Protein Construct Sequences for Mouse Studies | |
|---|---|
| 61 | Human light chain leader (aa 1-20) + mouse hinge – CH2 – CH3 – (aa 21-258) + Linker (aa 259-273) + murine IL-12 subunit beta (p40) (aa 274-586) + Linker (aa 587-601) + human IL-12 subunit alpha (p35) (aa 602-794) |

EXAMPLES

Example 1. Generation of Erythroid Cells Genetically Engineered to Express an IL-15/IL-15-RA Fusion Protein

IL-15 and IL-15/IL-15RA Fusion Constructs

Various DNA constructs encoding fusion polypeptides were prepared for expression in erythroid cells as shown in Table 11 below:

TABLE 11

IL-15 and IL-15/IL-15RA fusion constructs and polypeptides. SEQ ID NOs. refer to amino acid sequences.

| Construct/ Polypeptide | Description | SEQ ID NO: |
|---|---|---|
| V3 IL-15 | GPA signal peptide (SEQ ID NO: 21)-mature human IL-15 (SEQ ID NO: 4)-linker-HA-linker (SEQ ID NO: 23)-GPA (SEQ ID NO: 25) | 27 |
| V4 IL-15 + IL-15RA (extracellular) | GPA signal peptide (SEQ ID NO: 21)-mature human IL-15 (SEQ ID NO: 4)-flexible linker (SEQ ID NO: 12)-mature human extra-cellular IL-15RA (SEQ ID NO: 8)-linker-HA-linker (SEQ ID NO: 23)-GPA (SEQ ID NO: 25) | 29 |
| V5 IL-15 + IL-15RA (sushi domain + 13 aa) | GPA signal peptide (SEQ ID NO: 21)-mature human IL-15 (SEQ ID NO: 4)-flexible linker (SEQ ID NO: 12)-mature human IL-15RA (sushi domain + 13aa) (SEQ ID NO: 10)-linker-HA-linker (SEQ ID NO: 23)-GPA (SEQ ID NO: 25) | 31 |
| V3.1 | GPA signal peptide (SEQ ID NO: 21)-mature human IL-15 (SEQ ID NO: 4)-linker (SEQ ID NO: 33)-GPA (SEQ ID NO: 25) | 35 |
| V4.1 | GPA signal peptide (SEQ ID NO: 21)-mature human IL-15 (SEQ ID NO: 4)-flexible linker (SEQ ID NO: 12)-mature human extra-cellular IL-15RA (SEQ ID NO: 8)-linker (SEQ ID NO: 33)-GPA (SEQ ID NO: 25) | 37 |
| IL-15/IL-15RA fusion polypeptide | mature human IL-15 (SEQ ID NO: 4)-flexible linker (SEQ ID NO: 12)-mature human extra-cellular IL-15RA (SEQ ID NO: 8) | 1 |
| IL-15/IL-15RA (sushi domain + 13aa) fusion polypeptide | mature human IL-15 (SEQ ID NO: 4)-flexible linker (SEQ ID NO: 12)-mature human IL-15RA (sushi domain + 13aa) (SEQ ID NO: 10) | 2 |

The DNA constructs (V3, V4, V5, V3.1 or V4.1) were cloned into the multiple cloning site of lentivirus vector pCDH with the MSCV promoter sequence from System Biosciences for expression in erythroid cells, as described below.

Production of Lentiviral Vector

IL-15/IL-15-RA fusion protein genes were cloned into the multiple cloning site of lentivirus vector pCDH with the MSCV promoter sequence from System Biosciences. Lentivirus is produced in 293T cells by transfecting the cells with pPACKH1 (System Biosciences) and pCDH lentivirus vector containing IL-15/IL-15-RA fusion genes. Cells were placed in fresh culturing medium. The virus supernatant was collected 48 hours post-medium change by centrifugation at 1,500 rpm for 5 minutes. The supernatant was collected, filtered, and frozen in aliquots at −80° C.

The IL-15/IL-15RA fusion protein is also referred to as IL-15TP herein.

Expansion and Differentiation of Erythroid Cells

Human CD34+ cells derived from mobilized peripheral blood cells from normal human donors were purchased frozen from AllCells Inc. The expansion/differentiation procedure comprises 3 stages. In the first stage, thawed CD34+ erythroid precursors were cultured in Iscove's MDM medium comprising recombinant human insulin, human transferrin, recombinant human recombinant human stem cell factor, and recombinant human interleukin 3. In the second stage, erythroid cells were cultured in Iscove's MDM medium supplemented with recombinant human insulin, human transferrin, human recombinant stem cell factor, human recombinant erythropoietin, and L-glutamine. In the third stage, erythroid cells were cultured in Iscove's MDM medium supplemented with human transferrin, recombinant human insulin, human recombinant erythropoietin, and heparin. The cultures were maintained at 37° C. in 5% CO2 incubator.

Transduction of Erythroid Precursor Cells

Erythroid precursor cells were transduced during step 1 of the culture process described above. Erythroid cells in culturing medium were combined with lentiviral supernatant and polybrene. Infection was achieved by spinoculation, spinning the plate at 2000 rpm for 90 minutes at room temperature. After spinoculation, the cells were incubated at 37° C. overnight.

Antibody Binding

Binding of a PE-labelled anti-IL-15-RA antibody (e.g., anti-IL-15RA antibody (JM7A4) (ab91270), AbCam) was used to validate expression of the IL-15/IL-15-RA in the engineered erythroid cells. Binding of the antibody was measured by flow cytometry for APC fluorescence or PE fluorescence. A gate was set based on stained untransduced cells.

Example 2. Erythroid Cells Genetically Engineered to Express IL-15/IL-15RA Induce an Increase in Total CD8+ Cells In Vitro Erythroid cells comprising the IL-15/IL-15RA variants IL-15v3 (SEQ ID NO: 27), IL-15v4 (SEQ ID NO: 29) and IL-15v5 (SEQ ID NO: 31) were prepared generally as described in Example 1.

100,000 peripheral blood mononuclear cells (PBMCs) from 3 donors were cultured with 300,000 engineered erythroid cells. PBMCs cultured without engineered erythroid cells (no RBC) and PBMCs cultured with erythroid cells which express on their surface just the HA epitope tag were used as negative controls. FIG. 1A is a graph showing that erythroid cells engineered to express IL-15/IL-15RA variants v3, v4 and v5, when cultured with peripheral blood mononuclear cells (PBMCs) and unstimulated, induce an increase in total number of CD8+ cells. PBMCs cultured with recombinant human IL-15 (rh IL-15) were used as a comparison to soluble IL-15. The total number of CD8+ cells was counted on day 5. The results shown in FIG. 1A are representative of 4 independent experiments with 2-3 PBMC donors each (total of 6 different PBMC donors tested).

Figure 1B:
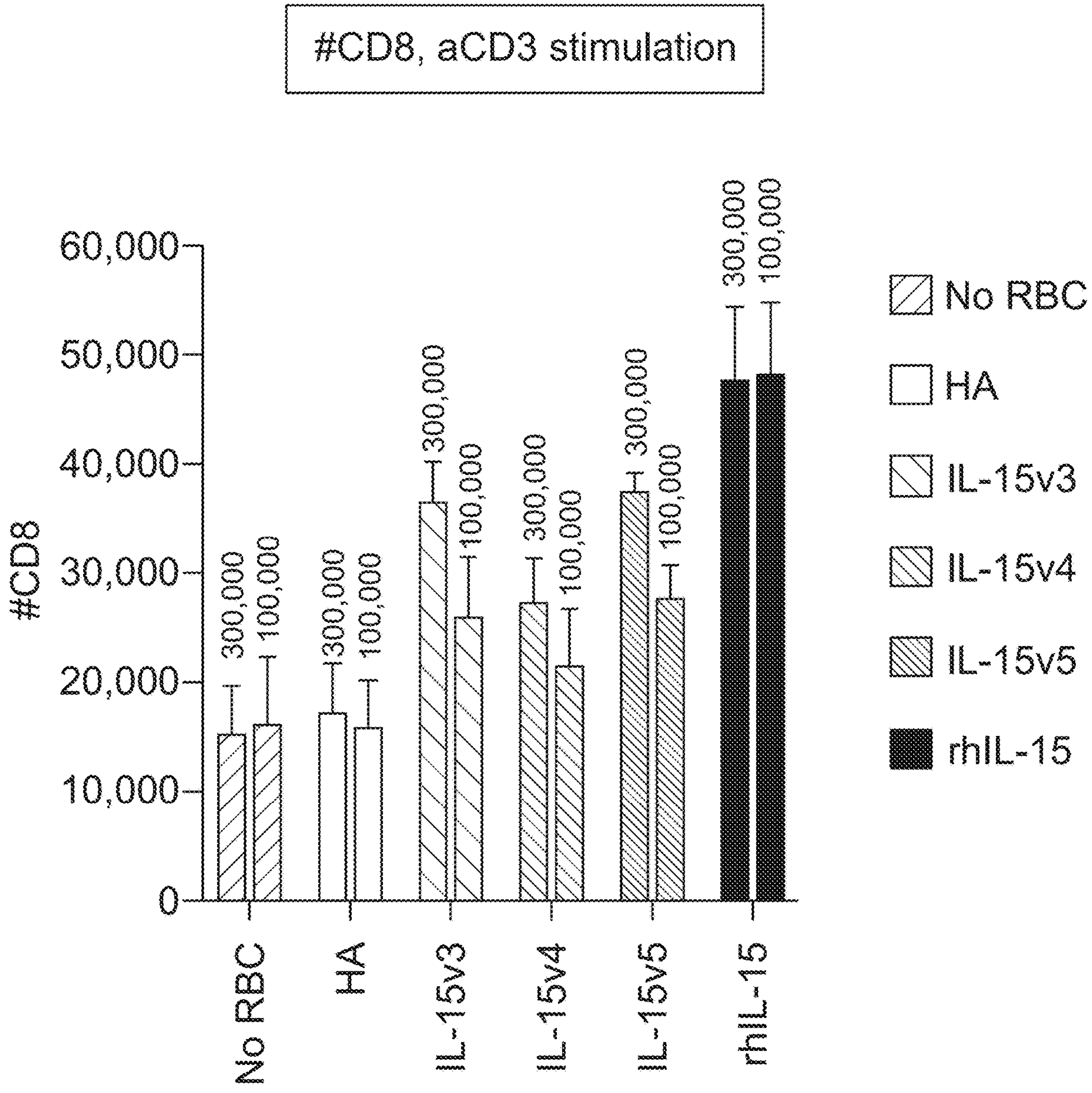
FIG. 1B is a graph showing that erythroid cells engineered to express IL-15/IL-15RA variants v3, v4 and v5, when cultured with peripheral blood mononuclear cells (PBMCs) and stimulated with anti-CD3 antibody (aCD3), induce an increase in total number of CD8+ cells. 100,000 PBMCs from 3 donors were cultured with 0.5 μg/mL aCD3 plus 300,000 or 100,000 engineered erythroid cells. The two bars in the graph shown in FIG. 1B represent the 300,000 (left) or 100,000 (right) engineered erythroid cells that were used. PBMCs cultured without engineered erythroid cells (no RBC) and PBMCs cultured with erythroid cells which express on their surface just the HA epitope tag were used as negative controls. PBMCs cultured with recombinant human IL-15 (rh IL-15) were used as a positive control. The total number of CD8+ cells was counted on day 5. The results shown in FIG. 1B are representative of 4 independent experiments with 2-3 PBMC donors each (total of 6 different PBMC donors tested).

In a next set of experiments, the engineered erythroid cells that express IL-15/IL-15-RA variants v3, v4 and v5 were cultured with PBMCs and stimulated with anti-CD3 antibody (aCD3). 100,000 PBMCs from 3 donors were cultured with 0.5 μg/mL aCD3 plus 300,000 or 100,000 erythroid cells. PBMCs cultured without engineered erythroid cells (no RBC) and PBMCs cultured with erythroid cells which express on their surface just the HA epitope tag were used as negative controls. PBMCs cultured with recombinant human IL-15 (rh IL-15) were used as a positive control. FIG. 1B is a graph showing that when erythroid cells engineered to express IL-15/IL-15RA variants v3, v4 and v5 are cultured with PBMCs and stimulated with aCD3, an increase in total number of CD8+ cells is induced. The two bars in the graph shown in FIG. 1B represent the 300,000 (left) or 100,000 (right) engineered erythroid cells that were used. The total number of CD8+ cells was counted on day 5. The results shown in FIG. 1B are representative of 4 independent experiments with 2-3 PBMC donors each (total of 6 different PBMC donors tested).

The results from this example show that erythroid cells genetically engineered to express IL-15/IL-15RA induce an increase in total CD8+ cells in the presence or absence of stimulation. The erythroid cells comprising IL-15/IL-15RA lead to a higher induction of CD8+ cells compared to a HA-comprising control erythrocyte, both in the presence and absence of stimulation.

Example 3. Erythroid Cells Genetically Engineered to Express IL-15/IL-15RA Variants Expand NK Cells In Vitro Erythroid cells comprising the IL-15/IL-15RA variants IL-15v3, IL-15v4 and IL-15v5 were prepared generally as described in Example 1.

Figure 2A:
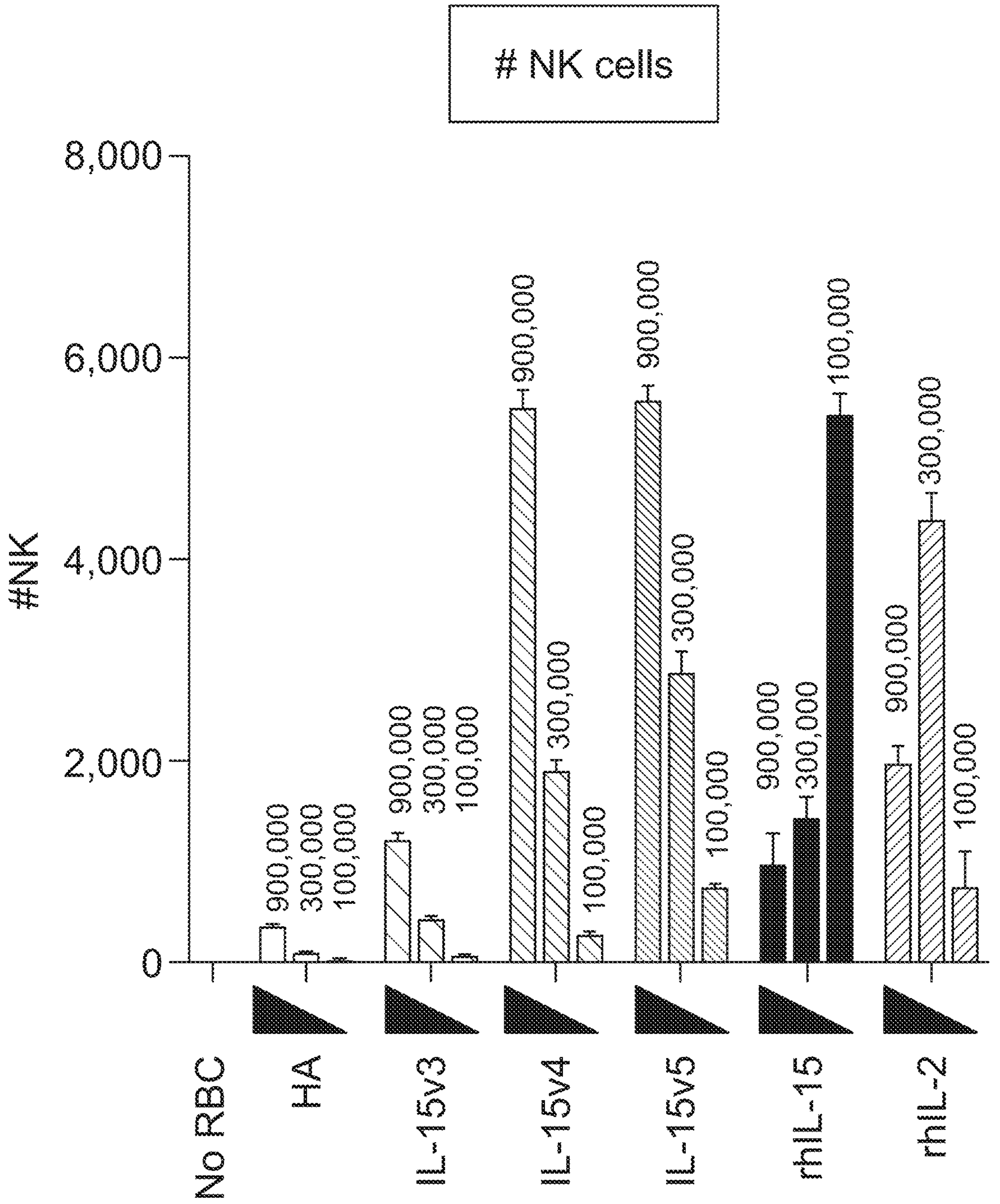
FIG. 2A, FIG. 2B and FIG. 2C are showing that erythroid cells engineered to express IL-15/IL-15RA variants v3, v4 and v5, can expand NK cells when cultured with purified NK cells.

The effects of the IL-15/IL-15RA variants on NK cell expansion were examined. FIG. 2A is a panel of graphs (i, ii and iii) showing that erythroid cells engineered to express IL-15/IL-15RA variants v3, v4 and v5, can expand NK cells when cultured with purified NK cells. In FIG. 2A (i) NK cells were cultured without engineered erythroid cells (no RBC). NK cells cultured with erythroid cells which express on their surface just the HA epitope tag were used as a control. 40,000 purified NK cells from one donor were plated in duplicate and cultured for 7 days with a titration of: engineered erythroid cells (900,000, 300,000, 100,000), rhIL-2 (1000, 100, 10 U/mL), rhIL-15 (10, 1, 0.1 ng/mL). Analysis was carried out on day 7. In FIG. 2A (ii) NK cells were cultured with 900,000 engineered erythrocytes, and the copy number that was expressed on these cells was taken into account to calculate the total IL-15 copy number that was presented to the cells (shown on the X axis). In FIG. 2A (iii) NK cells were cultured with 300,000 engineered erythrocytes, and the copy number that was expressed on these cells was taken into account to calculate the total IL-15 copy number that was presented to the cells (shown on the X axis).

Figure 2B:
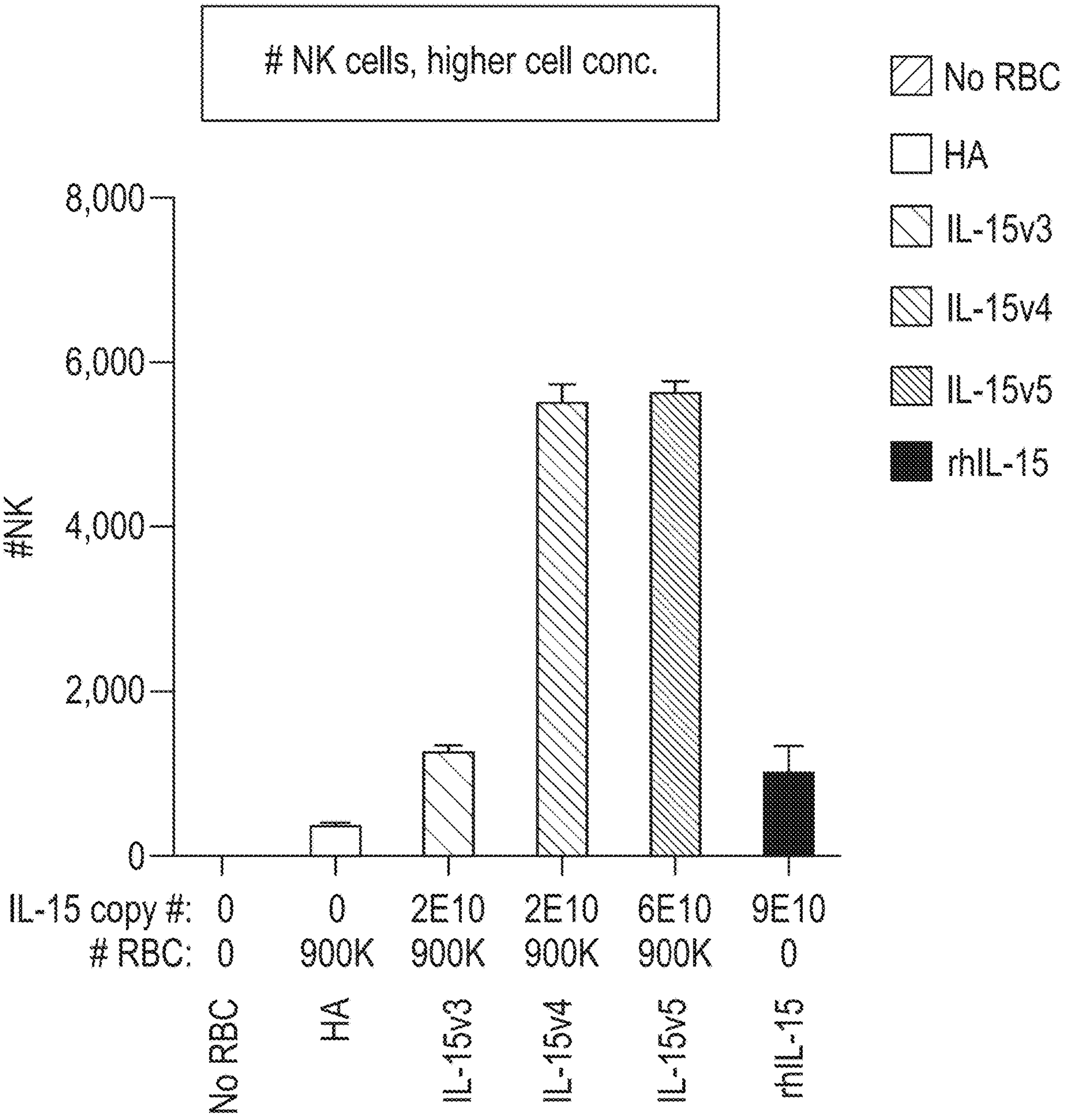
Figure 2C:
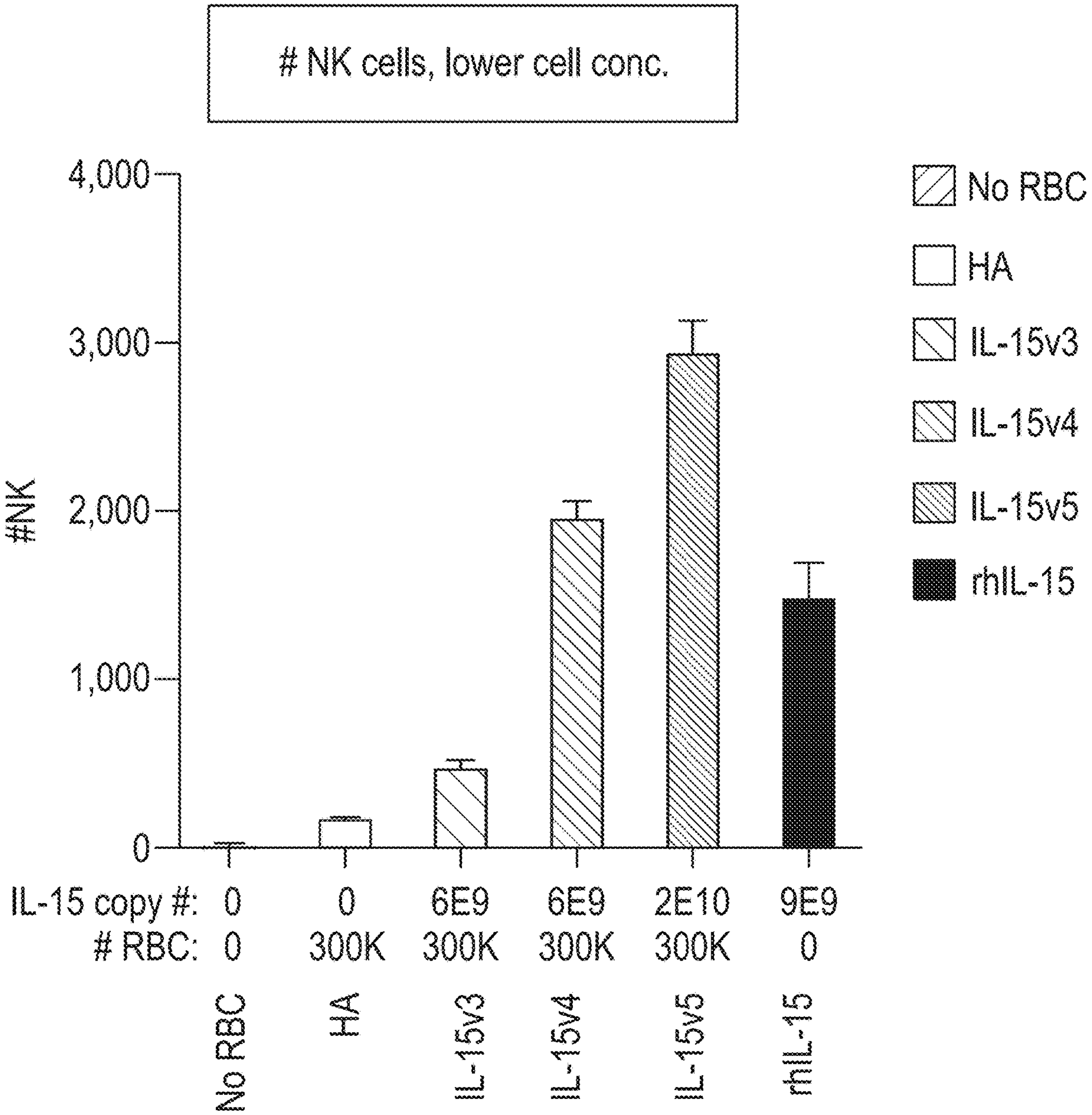
Figure 2D:
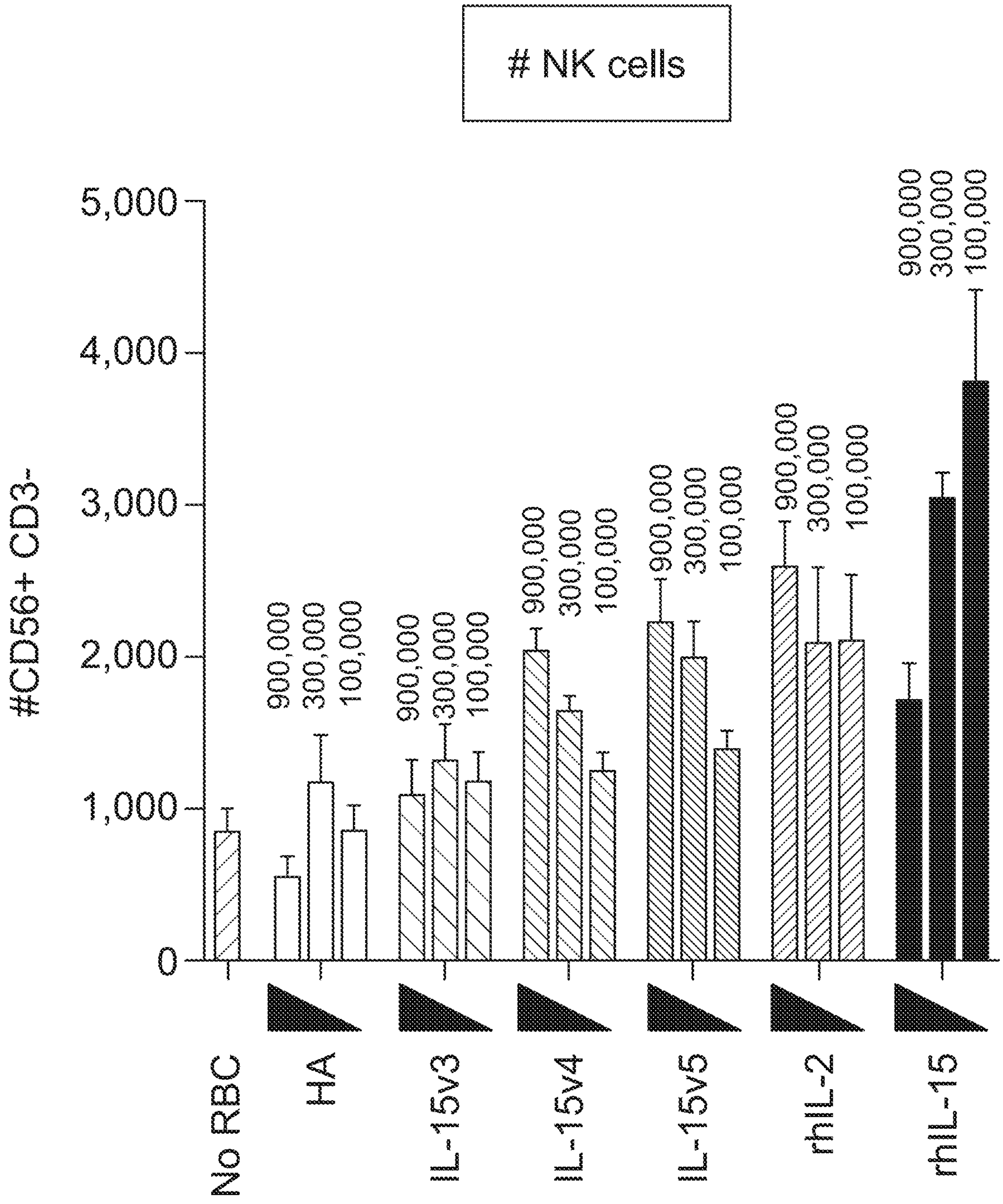
FIG. 2D, FIG. 2E and FIG. 2F are graphs showing that erythroid cells engineered to express IL-15/IL-15RA variants v3, v4 and v5, can expand NK cells when cultured with PBMCs.
Figure 2E:
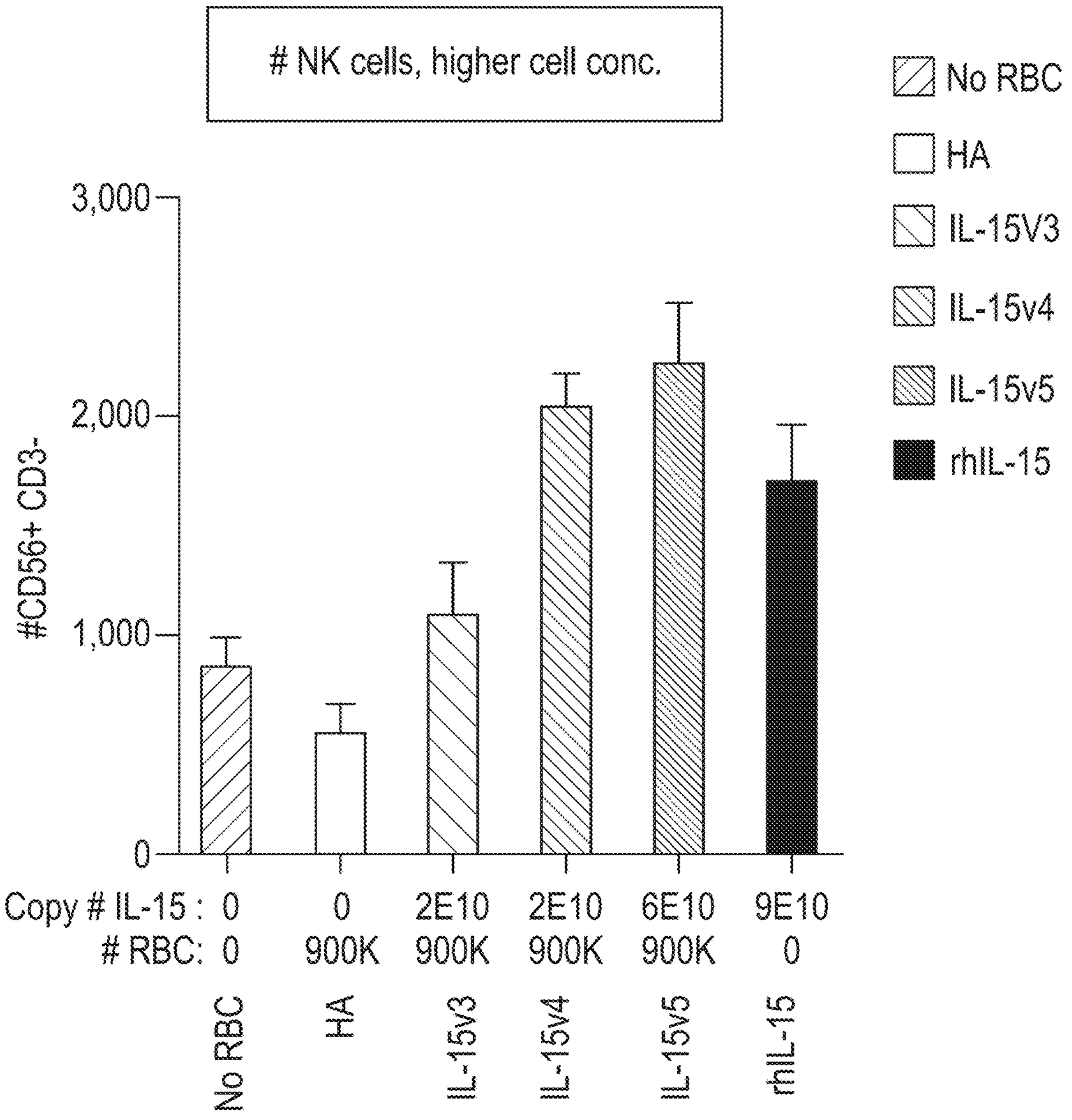
Figure 2F:
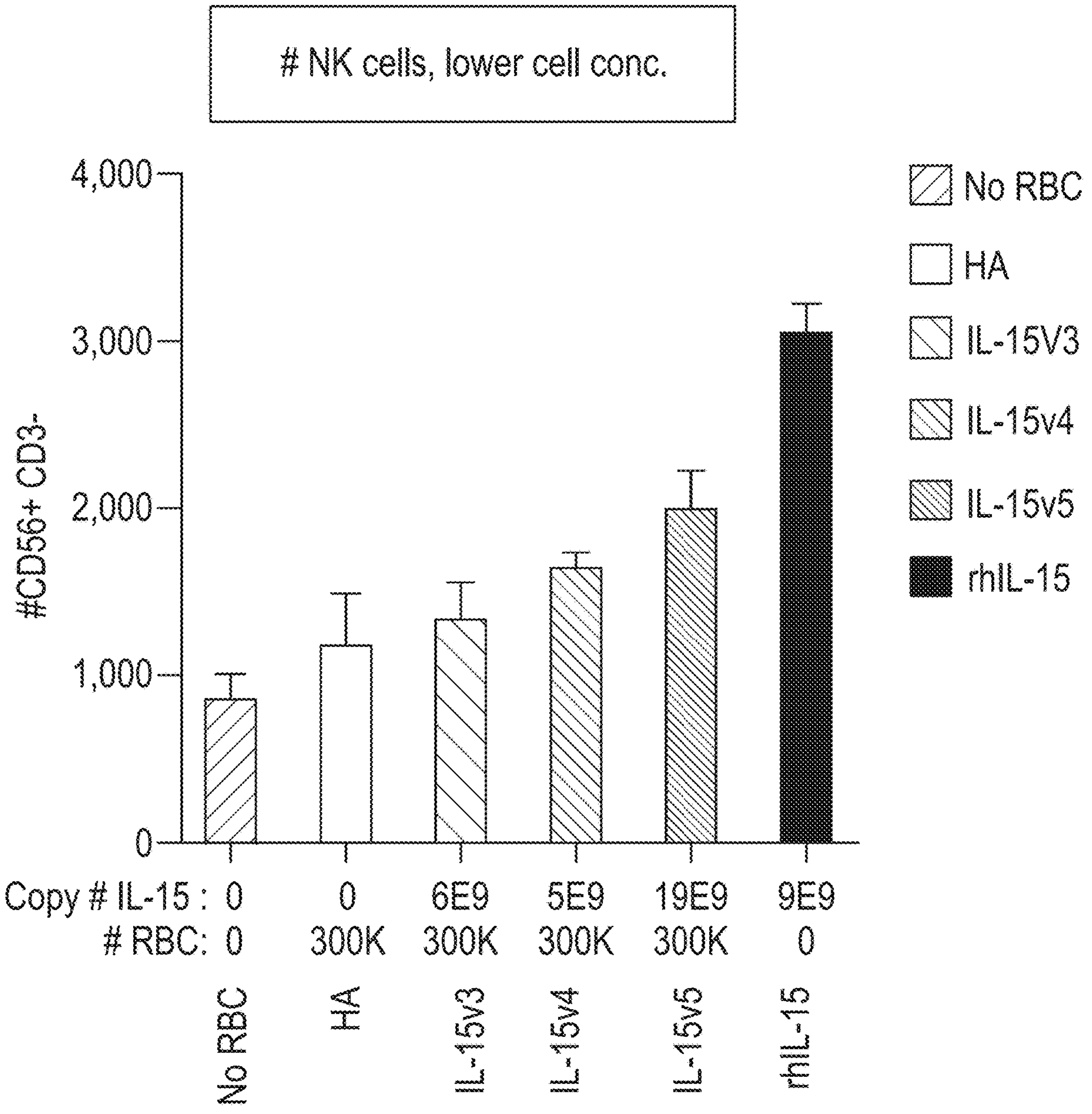

FIG. 2B is a panel of graphs (i, ii and iii), showing that engineered erythroid cells that express IL-15/IL-15RA variants v3, v4 and v5, can expand NK cells when cultured with PBMCs. In FIG. 2B (i) 100,000 PBMCs from two donors were obtained and plated in duplicate. Cells were cultured without engineered erythroid cells (no RBC) or with erythroid cells which express on their surface just the HA epitope tag as negative controls. 100,000 PBMCs from two donors were obtained and plated in duplicate. Cells were cultured with 900,000, 300,000 or 100,000 engineered erythroid cells. Flow cytometry analysis was carried out on day 7, applying a gate on live/dead, CD56+CD3− cells. In FIG. 2B (ii) PBMCs were cultured with 900,000 engineered erythrocytes, and the copy number that was expressed on these cells was taken into account to calculate the total IL-15 copy number that was presented to the cells (shown on the X axis). In FIG. 2B (iii) PBMCs cells were cultured with 300,000 engineered erythrocytes, and the copy number that was expressed on these cells was taken into account to calculate the total IL-15 copy number that was presented to the cells (shown on the X axis).

The results from this example show that erythroid cells genetically engineered to express IL-15/IL-15RA variants can expand NK cells from a purified NK cell population or from PBMC. Comparing the activities of v3 and v4, it was shown that v3 and v4, at the same copy number, show different activities. The erythroid cells comprising IL-15/IL-15RA lead to a higher NK cell expansion, at both high and low concentration, compared to a HA-comprising control erythrocyte. Further, a dose response is seen for variants v4 and v5.

Example 4. Erythroid Cells Prepared to Express IL-15/IL-15RA Activate NK Cells In Vivo The effect of murine erythroid cells prepared to present on the cell surface human IL-15/IL-15RA on NK cell expansion ex vivo was examined. Murine erythroid cells were conjugated with IL-15-RA-Fc using the click methodology (click chemistry for functionalizing erythroid cells is described in International Application No. PCT/US2018/000042, which claims priority to U.S. Provisional Application No. 62/460,589, filed Feb. 17, 2017 and U.S. Provisional Application No. 62/542,142, filed Jul. 8, 2017, incorporated by reference in their entireties herein). The IL-15/IL-15RA fusion protein includes the sushi domain of the receptor fused to the IL-15 chain (see protein construct presented in Table 10 herein).

Figure 3A:
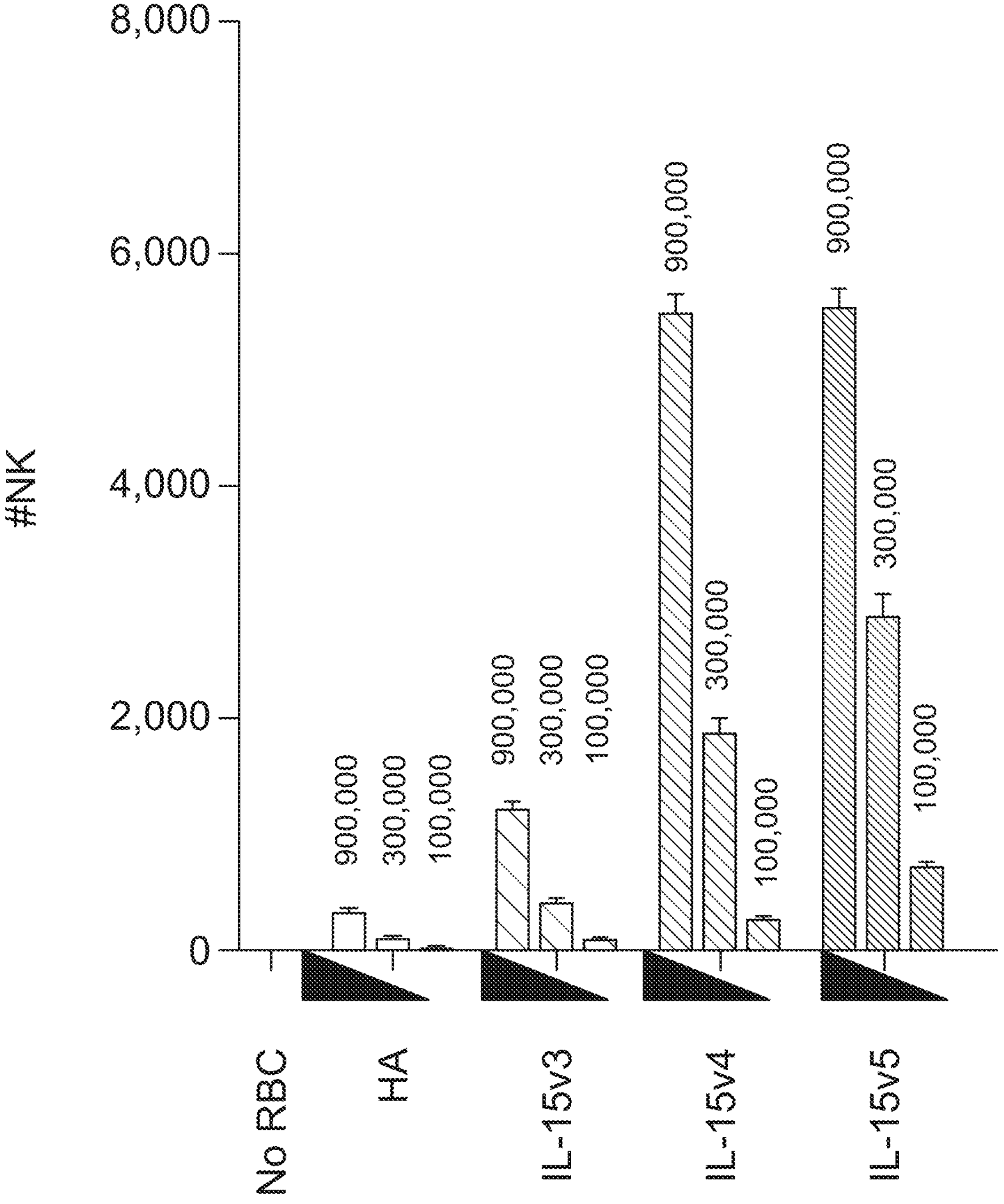
FIG. 3A is a graph showing the results of ex vivo experiments, where potent NK cell expansion was observed ex vivo.

First, 40,000 purified NK cells from one donor (Astsrte Biologics) were plated in duplicate and cultured for 7 days with a titration of RBCs (900 000, 300 000, 100 000). After 7 days samples were analyzed with flow cytometry to estimate relative amount of NK cells in the culture by looking at live cells that are CD56+/CD3−. As shown in FIG. 3A, erythroid cells prepared to present IL-15/IL-15R at their surface promote potent NK cell expansion ex vivo.

Next, the effect of murine erythroid cells prepared to present IL-15/IL-15RA at their surface on NK cell activation in vivo was examined. IL-15-RA-Fc erythroid cells and control erythroid cells were injected intravenously to C57/B6 mice. Spleens were collected 3 days post injection, processed for single cell suspension and stained for Ki67 and Granzyme B using flow cytometry.

Figure 3C:
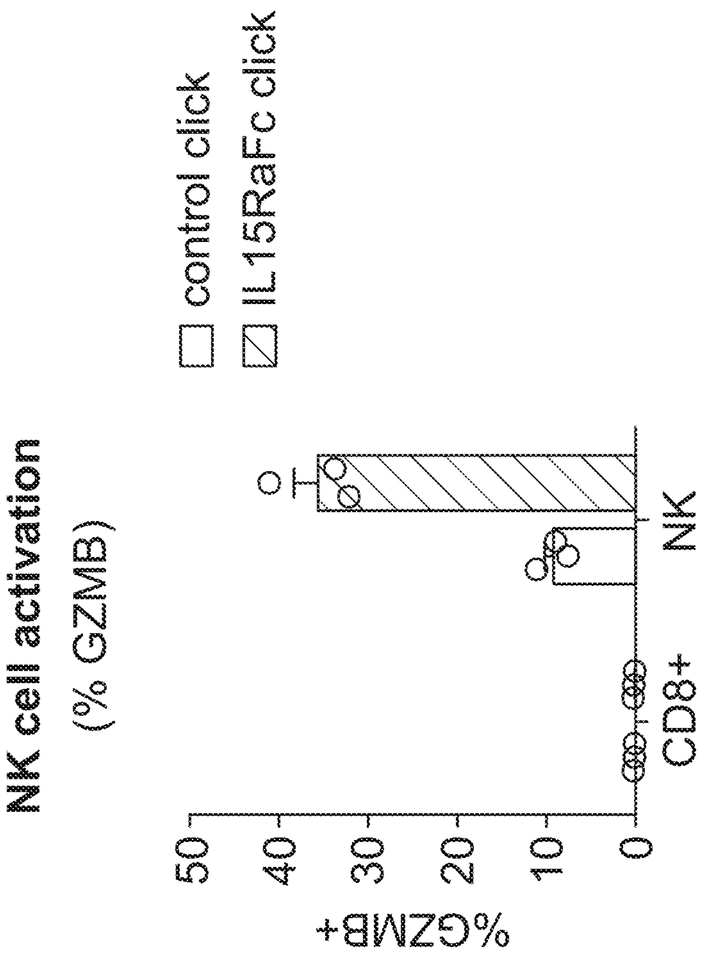
FIG. 3C is a graph showing the results of in vivo experiments, where potent lymphocyte activation was observed in mice treated with erythroid cells (mRBC) conjugated with IL-15/IL-15RA recombinant proteins. NK cell activation as determined by percent granzyme B expression as a marker of activated cells is shown.
Figure 3B:
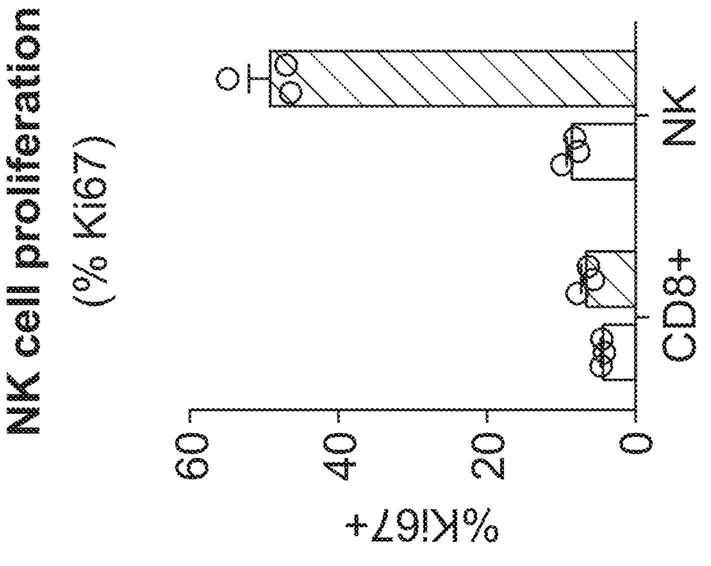
FIG. 3B is a graph showing the results of in vivo experiments, where potent lymphocyte proliferation was observed in mice treated with erythroid cells (mRBC) conjugated with IL-15/IL-15RA recombinant proteins. NK cell proliferation as determined by percent Ki67 staining as a marker of proliferating cells is shown.

As shown in FIG. 3B, potent lymphocyte proliferation was observed in mice treated with erythroid cells (mRBC) prepared to express IL-15/IL-15RA. NK cell proliferation as determined by percent Ki67 staining as a marker of proliferating cells is shown. Further, as shown in FIG. 3C, potent lymphocyte activation was found in mice treated with erythroid cells (mRBC) prepared to present IL-15/IL-15RA. NK cell activation as determined by percent granzyme B expression as a marker of activated cells is shown.

The results presented in this example show that murine erythroid cells prepared to present IL-15/IL-15RA induce proliferation and activation of NK cells in vivo.

Example 5. Erythroid Cells Comprising IL-15/IL-15RA Slow Tumor Growth In Vivo A B16F10 mouse model system for melanoma is used to test the effects of murine erythroid cells comprising human IL-15/IL-15RA (IL-15 RBC) on tumor growth. Upon subcutaneous injection, B16 will form a palpable tumor in 5 to 10 days and grow to a 1×1×1 cm tumor in 14 to 21 days. The B16 mouse model system is described by Overwijk and Restifo (Curr Protoc Immunol. 2001 May; CHAPTER: Unit-20.1, expressly incorporated by reference in its entirety herein).

Murine erythroid cells are conjugated with human IL-15/IL-15RA using the click methodology (click chemistry for functionalizing erythroid cells is described in International Application No. PCT/US2018/000042, which claims priority to U.S. Provisional Application No. 62/460,589, filed Feb. 17, 2017 and U.S. Provisional Application No. 62/542,142, filed Jul. 8, 2017, incorporated by reference in their entireties herein). The IL-15/IL-15RA fusion protein is expressed as the sushi domain of the receptor fused to the IL-15 chain in the construct presented in Table 10 herein. IL-15/IL-15RA is quantitated using flow cytometry.

Initially, 6 to 12-week old female C57BL/6 mice are inoculated subcutaneously with $1\times10^5$ B16 cells/mouse. When the tumors reach volume of approximately 100 $mm^3$, the animals are dosed with erythroid cells presenting IL-15/IL-15RA, or with erythroid cells without the IL-15/IL-15RA, or with saline, as controls. For dosing animals, an average of 1e9 IL-15 RBCs are administered per dose with an average of 50,000 IL-15/RA molecules per cell corresponding to 2 ug or 0.1 mg/kg IL-15/IL-15RA per dose.

Animals' weights and condition are recorded daily, and tumors are measured 3 times per week. Tumors are measured three times a week by measuring each tumor in 2 dimensions. Tumor volumes are calculated using the standard formula: $(L\times W^2)/2$. The mean tumor weight and standard error of the mean are calculated for each group at each time point.

Further, body weight is recorded daily. Changes in body weight are calculated for each mouse relative to the body weight recorded on day 1.

The anti-tumor activity of prepared erythroid cells comprising IL-15/IL-15RA compared to saline and untreated controls is determined by assessing the change in tumor volume and/or tumor weight over time.

Example 6. Generation of Erythroid Cells Genetically Engineered to Express 4-1BBL

4-1BBL Constructs

DNA constructs were prepared for expression in erythroid cells as shown in Table 12 below:

TABLE 12

4-1BBL construct. SEQ ID NOs. refer to amino acid sequences.

| Construct | Description | SEQ ID NO: |
|---|---|---|
| 4-1BBL | GPA signal peptide (SEQ ID NO: 21)-human extracellular 4-1BBL (SEQ ID NO: 41) − 4-1BBL linker (SEQ ID NO: 39)-GPA (SEQ ID NO: 25) | 43 |

Production of Lentiviral Vector 4-1BBL gene constructs were constructed as shown in Table 12. Genes were cloned into the multiple cloning site of lentivirus vector pCDH with the MSCV promoter sequence from System Biosciences. Lentivirus was produced in 293T cells by transfecting the cells with pPACKH1 (System Biosciences) and pCDH lentivirus vector containing 4-1BBL genes. Cells were placed in fresh culturing medium. The virus supernatant was collected 48 hours post-medium change by centrifugation at 1,500 rpm for 5 minutes. The supernatant was collected, filtered, and frozen in aliquots at −80° C.

Expansion and Differentiation of Erythroid Cells

Human CD34+ cells derived from mobilized peripheral blood cells from normal human donors were purchased frozen from AllCells Inc. The expansion/differentiation procedure comprises 3 stages. In the first stage, thawed CD34+ erythroid precursors were cultured in Iscove's MDM medium comprising recombinant human insulin, human transferrin, recombinant human recombinant human stem cell factor, and recombinant human interleukin 3. In the second stage, erythroid cells were cultured in Iscove's MDM medium supplemented with recombinant human insulin, human transferrin, human recombinant stem cell factor, human recombinant erythropoietin, and L-glutamine. In the third stage, erythroid cells were cultured in Iscove's MDM medium supplemented with human transferrin, recombinant human insulin, human recombinant erythropoietin, and heparin. The cultures were maintained at 37° C. in 5% CO2 incubator.

Transduction of Erythroid Precursor Cells

Erythroid precursor cells were transduced during step 1 of the culture process described above. Erythroid cells in culturing medium were combined with lentiviral supernatant and polybrene. Infection was achieved by spinoculation, spinning the plate at 2000 rpm for 90 minutes at room temperature. After spinoculation, the cells were incubated at 37° C. overnight.

Antibody Binding

Binding of a PE-labelled anti-4-1BBL antibody (e.g., purified anti-human 4-1BB Ligand (CD137L) antibody, BioLegend) was used to validate expression of 4-1BBL in the engineered erythroid cells. Binding of the antibody was measured by flow cytometry for PE fluorescence. A gate was set based on stained untransduced cells.

Example 7. Expression of 4-1BBL on the Surface of Engineered Erythroid Cells Drives T-Cell Activation In Vitro Erythroid cells comprising 4-1BBL were prepared as described in Example 6.

Figure 4A:
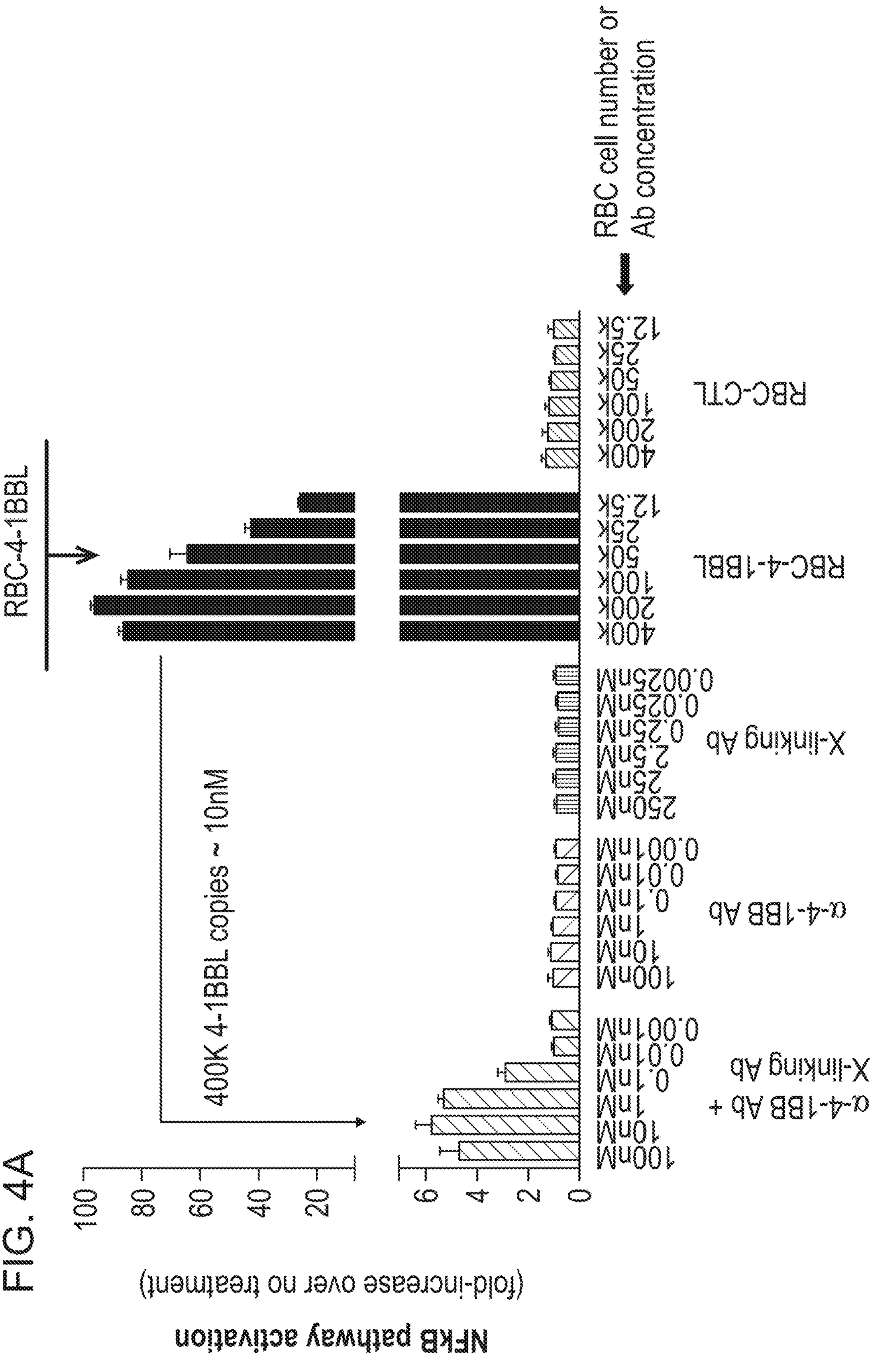
FIG. 4A is a graph showing that expression of 4-1BBL in its natural trimeric conformation on the surface of engineered erythroid cells drives highly potent T-cell activation as measured by NFκB activation in Jurkat cells that express high levels of 4-1BB receptor as well as NFκB/Luc.

The effect of 4-1BBL expression on the surface of engineered erythroid cells on T-cell activation was examined in a standard in vitro assay in which intracellular NFκB signaling is measured using Jurkat cells, a human T cell line. Untransduced RBCs (UTR RBC) represent control RBCs as these have not been engineered to express an active protein. As shown in FIG. 4A, RBC-4-1BBL drives potent T-cell activation, stimulating an 80-100 fold activation of the NFκB pathway as measured by luciferase activity of Jurkat cells that over express 4-1BB/NFκB/Luc. In contrast, the 4-1BB agonistic mAb (α-4-1BB Ab), when cross linked with a secondary antibody, stimulates limited 6-fold NFκB activation. When α-4-1BB Ab alone or when the secondary antibody alone were incubated with Jurkat cells, there was no induction of NFκB activation. Similar results were obtained when control RBC were incubated with the Jurkat cells. This experiment shows that engineered erythroid cells comprising 4-1BB-L induces >15 fold higher NFκB activation compared to an agonistic 4-1BB monoclonal antibody, α-4-1BB Ab, and untreated control.

Figure 4B:
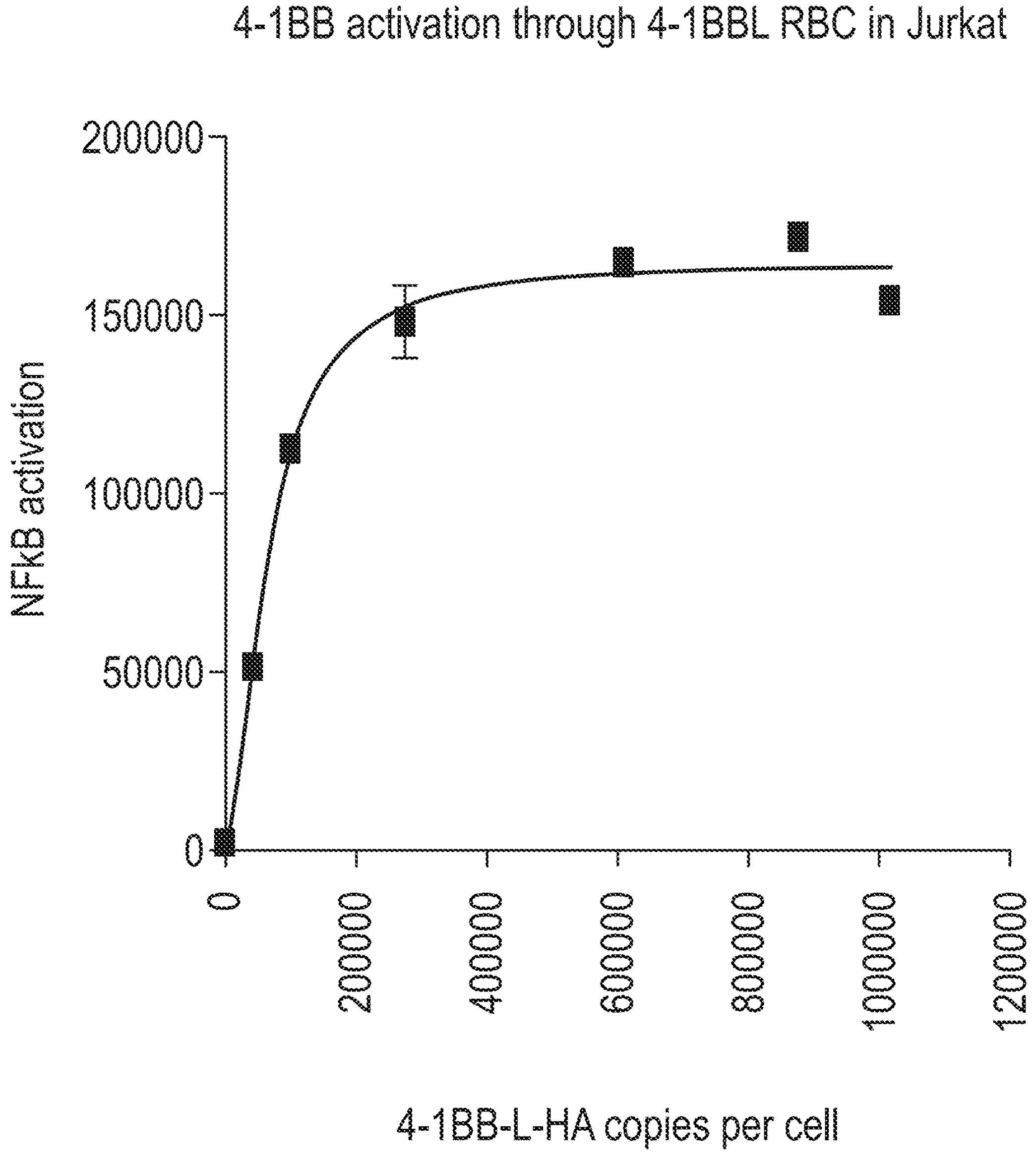
FIG. 4B is a graph showing that activation of NFκB by engineered erythroid cells expressing 4-1BBL is tunable.

In another experiment, erythroid cells were transfected with increasing amounts of 4-1BB-L mRNA and 4-1BB-L expression was measured (FIG. 4B). The number of 4-1BBL molecule copies per cell is shown on the x-axis. 50,000 engineered erythroid cells comprising 4-1BBL were cocultured with Jurkat cells. Cells were collected after 6 hrs, and luciferase activity was determined. FIG. 4B shows that activation of NFκB by engineered erythroid cells comprising 4-1BBL is tunable.

Thus, as shown in FIG. 4A and FIG. 4B, increasing the copy number of the 4-1BBL protein on engineered erythroid cells engineered to express 4-1BBL on the surface, results in a dose-response for activation. Accordingly, erythroid cells can be engineered to express 4-1BBL to ensure maximal T-cell activation.

Figure 5A:
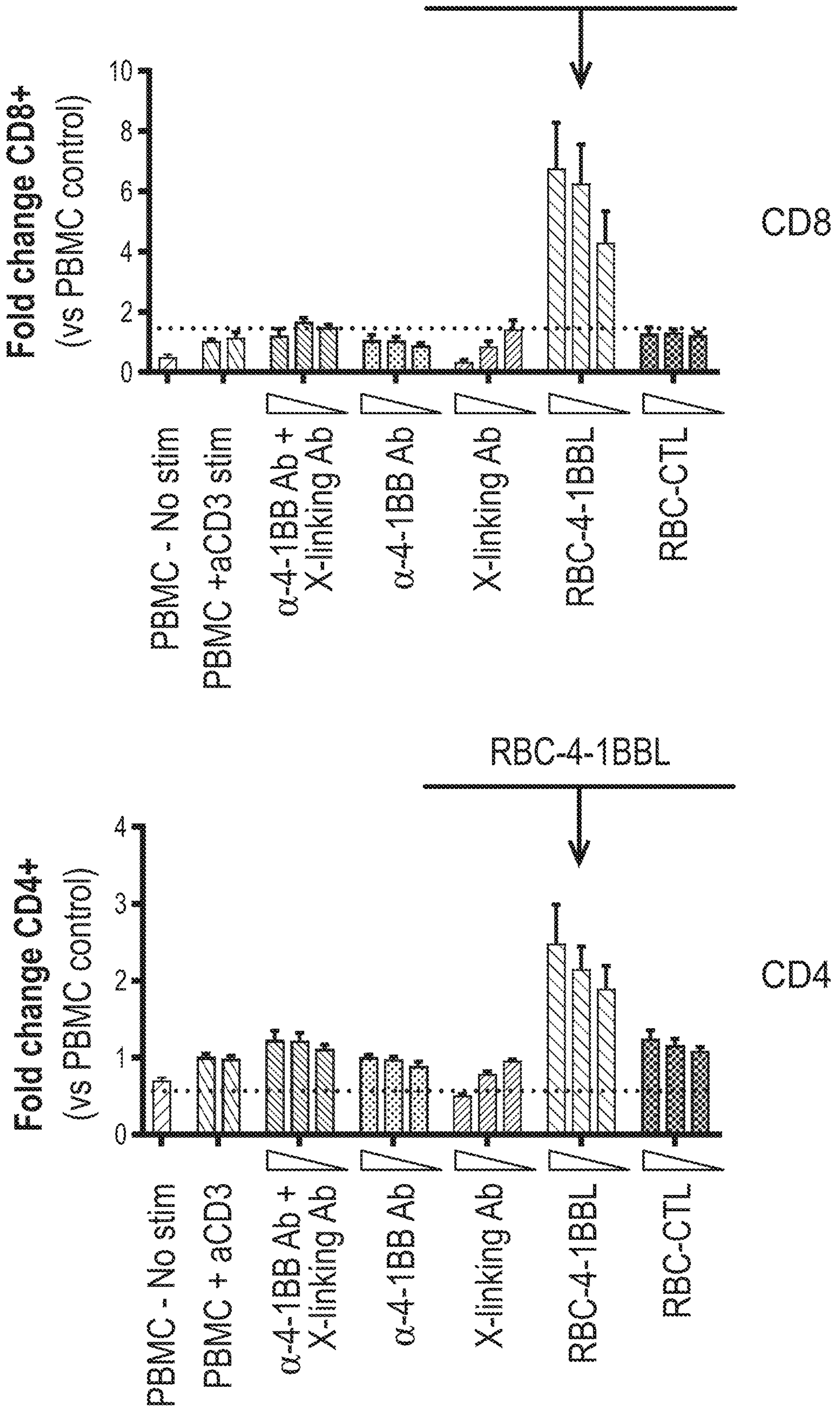
FIG. 5A is a graph showing that expression of 41BBL in its natural trimeric conformation on the surface of engineered erythroid cells drives highly potent T-cell activation as measured by proliferation and activation of primary CD4+ and CD8+ T cells.
Figure 5B:
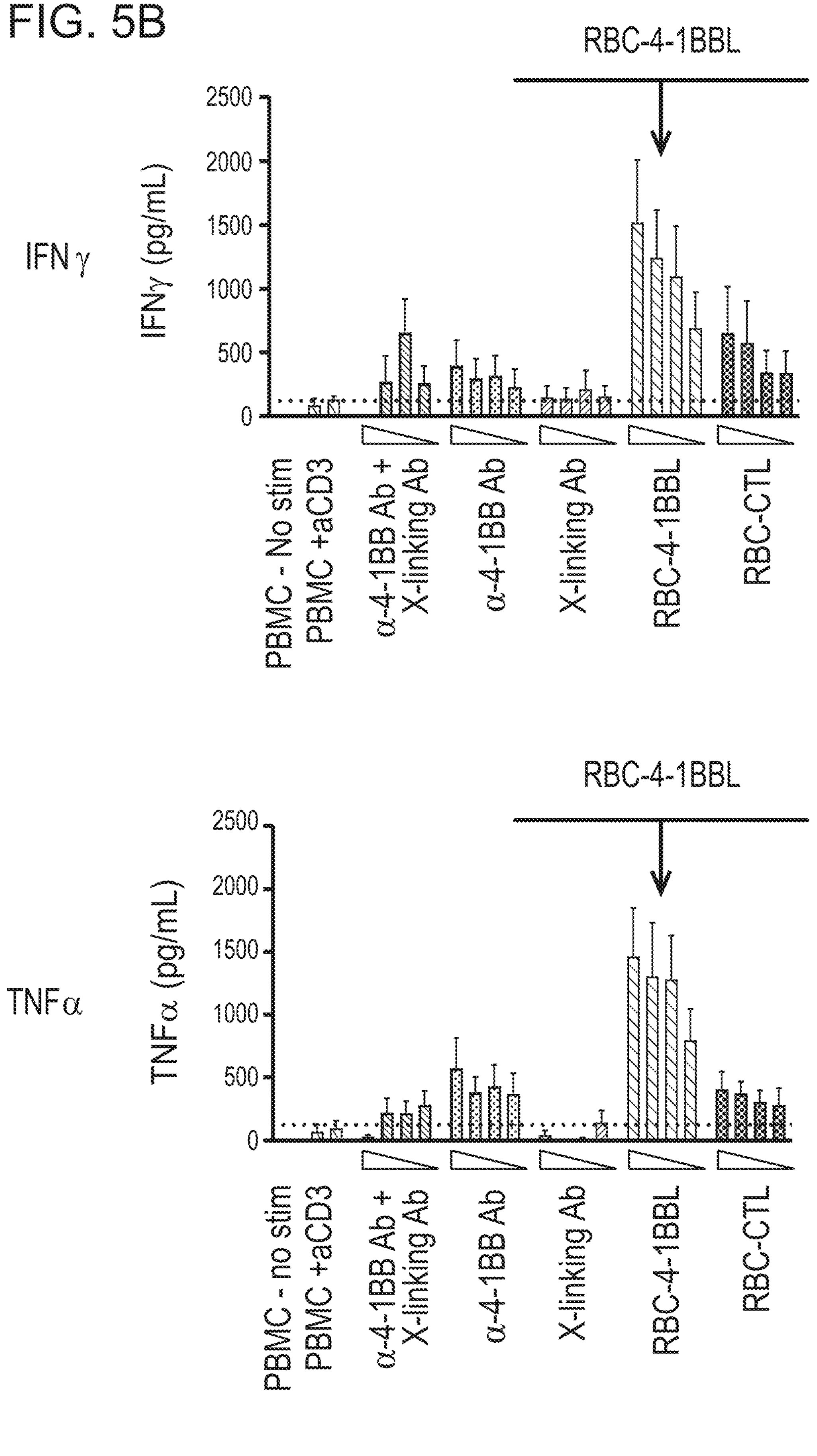
FIG. 5B is a graph showing that expression of 41BBL in its natural trimeric conformation on the surface of engineered erythroid cells drives highly potent T-cell activation as measured by IFNγ and TNFα secretion, measured by ELISA.

Next, proliferation and activation of primary CD4+ and CD8+ T cells were measured. 100,000 PBMCs from 3 donors were labelled with CTFR and incubated with engineered erythroid cells comprising 4-1BB-L ("RBC-4-1BBL"), control RBC ("RBC-CTL"), α-4-1BB Ab alone or with a secondary antibody. RBC were present at 50,000, 25,000 or 12,500 cells. α-4-1BB Ab concentration ranged from 100 nM, 10 nM, 1 nM. On day 5, relative amounts of CD8+ and CD4+ T cells were evaluated using CTFR dilution. Supernatant was collected and amounts of IFNγ and TNFα were evaluated using ELISA. As shown in FIGS. 5A and 5B, RBC-4-1BBL stimulated primary CD4+ and CD8+ T cells to potently proliferate as well as become activated as measured by the production of IFNγ and TNFα, two cytokines released by activated T cells that are central to human immune response. RBC-41BBL stimulates a 4-6 fold and 2-3-fold increase in CD8+ and CD4+ T-cells, respectively, as well as significant T-cell activation as measured by up to a 3-fold increase in IFNγ and TNFα production. In contrast, the 4-1BB agonistic mAb (α-4-1BB Ab) did not stimulate any measurable proliferation and only minimal activation of T cells. Without being bound by theory, it is considered that the potent T cell stimulating activity of RBC-4-1BBL is due to high expression of 4-1BBL on the cell surface in its natural, trimeric conformation, simulating the immune synapse that is formed between antigen presenting cells and T cells.

Taken together, the results presented in this example show that expression of 4-1BBL in its natural trimeric conformation on the surface of RBCs drives highly potent T-cell activation, as measured by NFκB activation in 4-1BB/NKfB/Luc Jurkat cells as well as potent proliferation and activation of primary CD4+ and CD8+ T cells.

Example 8. Erythroid Cells Comprising 4-1BBL Stimulate CD8+ T Cells in a Metastatic Melanoma Mouse Model The B16F10 lung metastases mouse model was used to test the effects of murine erythroid cells comprising murine 4-1BBL on the stimulation of CD8+ T cells, and CD8+ T cell subpopulations, such as proliferating CD8+ memory T cells, CD8+ effector T cells and Granzyme B+ CD8+ T cells, which are important for improved and sustained clinical response rates in cancer patients.

Murine erythroid cells were conjugated with murine 4-1BBL using the click methodology (click chemistry for functionalizing erythroid cells is described in International Application No. PCT/US2018/000042, which claims priority to U.S. Provisional Application No. 62/460,589, filed Feb. 17, 2017 and U.S. Provisional Application No. 62/542,142, filed Jul. 8, 2017, incorporated by reference in their entireties herein). The murine 4-1BBL protein was expressed in the construct presented in Table 10 herein.

Figure 9:
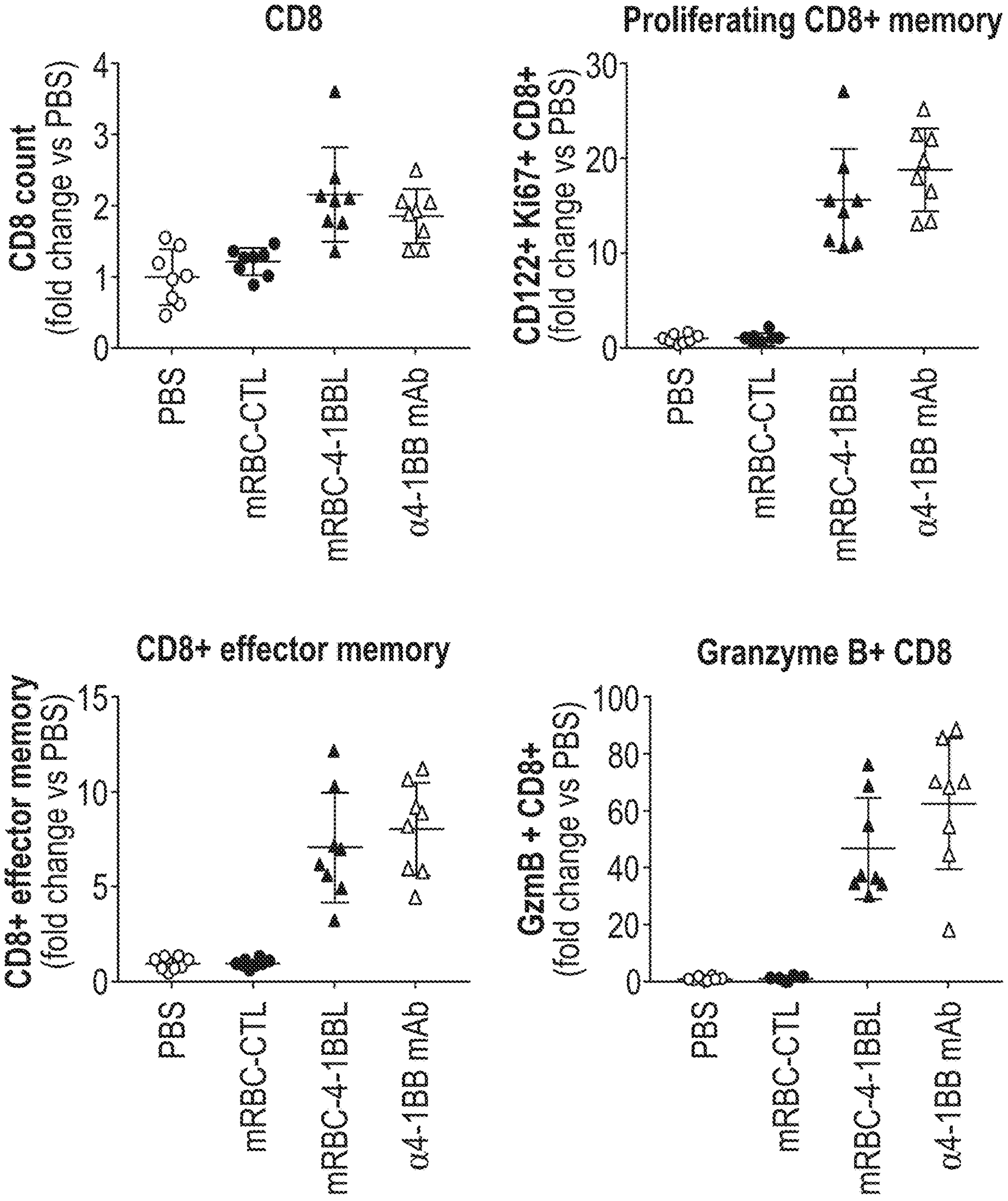
FIG. 9 is a graph showing in vivo proliferation of CD8+ T cells and subsets (proliferating CD8+ memory cells; CD8+ effector memory cells, granzyme B+ CD8 cells) by murine erythroid cells prepared to express 4-1BBL.

Murine erythroid cells conjugated to 4-1BBL (RBC-4-1BBL) in its natural trimeric conformation contain approximately 150,000 copies of 4-1BBL on their cell surface, which is 2-fold lower than human erythroid cells prepared to express 4-1BBL, but is sufficient to stimulate strong T cell activation and proliferation. The results, which are shown in FIG. 9, indicate that mRBC-4-1BBL is sufficient to stimulate potent T cell activation and proliferation because the mRBC-4-1BBL drove similar levels of activation and proliferation of CD8+ T cells in vivo as a 15-fold higher dose of 3H3, an anti-mouse 4-1BB agonistic monoclonal antibody (a4-1BB mAb), indicating that the cellular presentation of the trimeric 4-1BBL is more potent. The negative controls phosphate buffered saline (PBS), and a murine control RBC that does not express an active protein (mRBC-CTRL), did not stimulate in vivo proliferation of CD8+ T cells.

Example 9. Erythroid Cells Comprising 4-1BBL Slow Tumor Growth In Vivo

The MC38 syngeneic mouse model system for colon carcinoma was used to test the effects of murine erythroid cells comprising murine 4-1BBL on tumor growth. MC38 is a commercially available colon carcinoma mouse model (see, e.g., Selby et al. (2016) PLoS ONE 11(9): e0161779; Altogen Labs; Charles River Laboratories).

Murine erythroid cells were conjugated with recombinant murine 4-1BBL protein using the click methodology (click chemistry for functionalizing erythroid cells is described in International Application No. PCT/US2018/000042, which claims priority to U.S. Provisional Application No. 62/460,589, filed Feb. 17, 2017 and U.S. Provisional Application No. 62/542,142, filed Jul. 8, 2017, incorporated by reference in their entireties herein). The murine 4-1BBL protein was expressed in the construct presented in Table 10 herein.

When the tumors reached volume of approximately 100 $mm^3$, the animals were dosed with erythroid cells presenting 4-1BBL, or with erythroid cells without 4-1BBL, or with saline, as controls. For dosing animals, an average of 1e9 4-1BBL RBCs were administered per dose with an average of 20,000-65,000 4-1BBL molecules per cell corresponding to 1-3 μg of 4-1BB-L, or approximately 0.05-0.15 mg/kg per dose per mouse.

The weight and condition of the animals were recorded daily, and tumors were measured 3 times per week by measuring each tumor in 2 dimensions. Tumor volumes were calculated using the standard formula: $(L\times W^2)/2$. The mean tumor weight and standard error of the mean were calculated for each group at each time point.

Further, body weight was recorded daily. Changes in body weight were calculated for each mouse relative to the body weight recorded on day 1.

Figure 6:
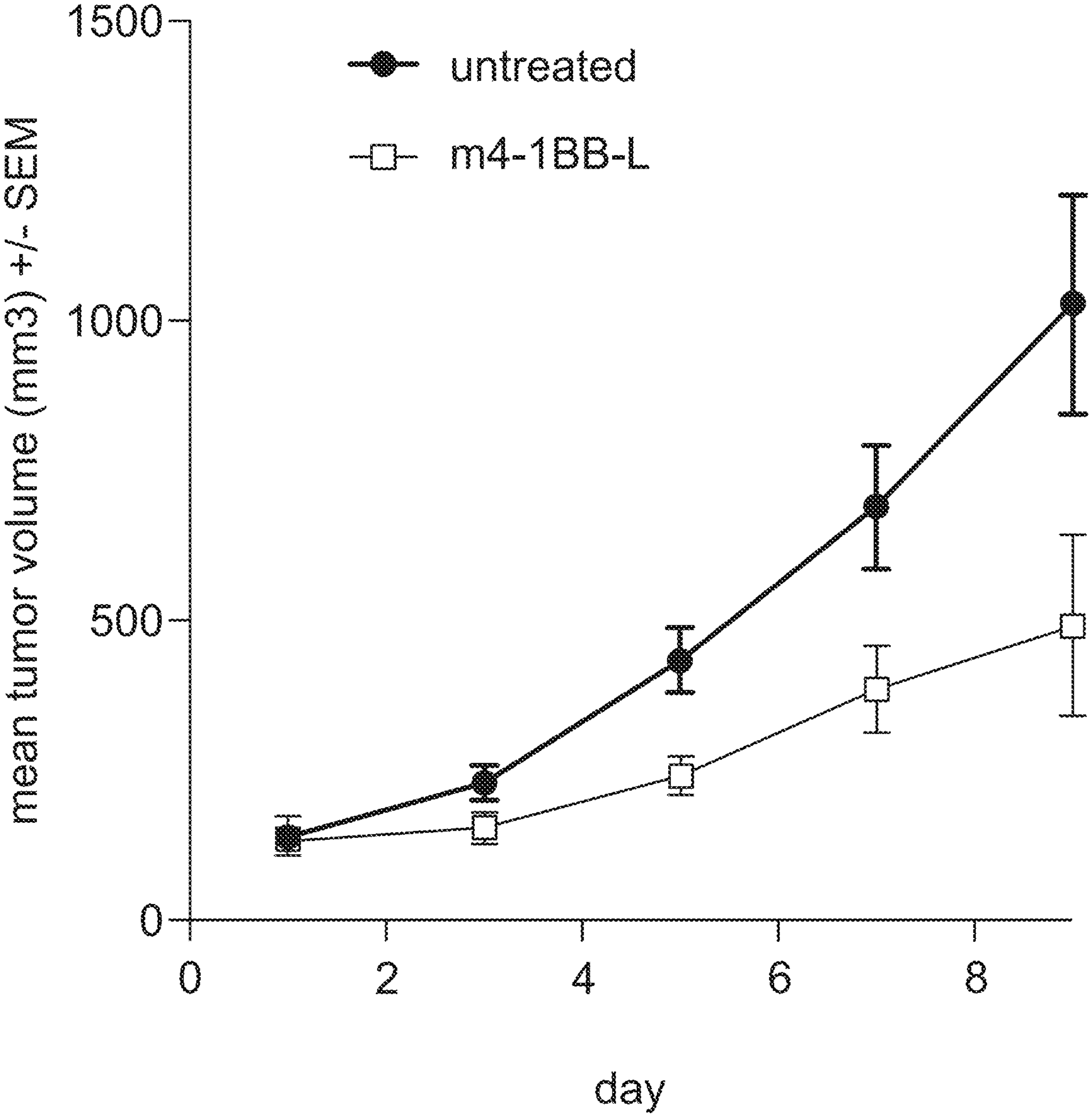
FIG. 6 is a graph showing that erythroid cells expressing 4-1BBL inhibits tumor growth in a MC38 tumor model.

The anti-tumor activity of prepared erythroid cells comprising 4-1BBL as compared to untreated controls was determined by assessing the change in tumor volume and/or tumor weight over time. The results are shown in FIG. 6, and demonstrate that prepared erythroid cells comprising 4-1BBL reduced the increase in tumor volume over time as compared to untreated control.

Example 10. Lack of Toxicity of Murine RBC-4-1BBL

Figure 10:
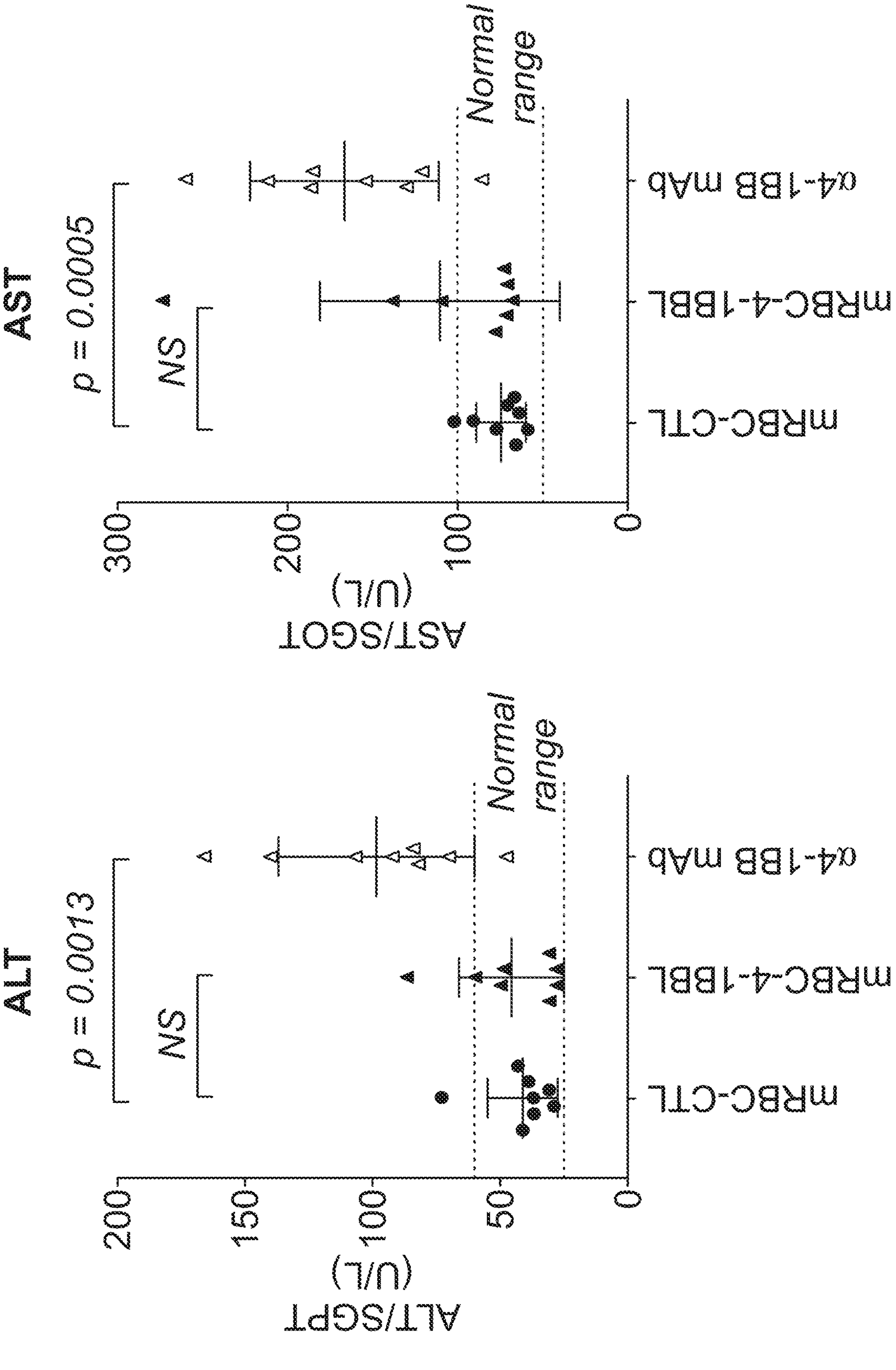
FIG. 10 is a graph showing murine erythroid cells prepared to express 4-1BBL do not cause liver toxicity in mice in contrast to anti-4-1BB mAb, 3H3. Levels of alanine transaminase (ALT; SGPT) and aspartate transaminase (AST; SGOT) were measured.

A mouse model of liver toxicity was used to assess the lack of toxicity or tolerability of murine RBC-4-1-BBL (see, e.g., Niu et al (2007) J. Immunology 178:4194-4213). As shown in FIG. 10, favorable tolerability of murine RBC-4-1BBL was observed, following the same dosing schedule that was used in the preclinical study described in Example 8. Levels of alanine transaminase (ALT) and aspartate transaminase (AST) liver enzymes were not significantly elevated following administration of murine RBC-4-1BBL. In contrast, significant elevations of these liver enzymes were observed after administration of the 4-1BB agonist monoclonal antibody, 3H3. This indicates that the potent stimulation of CD8 positive T cells that was observed in vivo with murine RBC-4-1BBL is not accompanied by the liver toxicities that have been associated with administration of other 4-1BB agonists.

Example 11. Generation of Erythroid Cells Genetically Engineered to Express an IL-15/IL-15-RA Fusion Protein and 4-1BBL Production of Lentiviral Vectors IL-15/IL-15-RA fusion protein and 4-1BBL genes were constructed. Each gene was cloned into the multiple cloning site of lentivirus vector pCDH under the control of the MSCV promoter sequence (System Biosciences), such that one vector comprised the gene for IL-15/IL-15RA and another vector comprised the gene for 4-1BBL. Lentivirus was produced in 293T cells by co-transfecting the cells with pPACKH1 (System Biosciences) and pCDH lentivirus vector containing IL-15/IL-15-RA gene and pCDH lentivirus vector containing 4-1BBL gene. Cells were placed in fresh culturing medium. The virus supernatant was collected 48 hours post-medium change by centrifugation at 1,500 rpm for 5 minutes. The supernatant was collected, filtered, and frozen in aliquots at −80° C.

Alternatively, IL-15/IL-15-RA fusion protein and 4-1BBL genes were constructed and cloned into the multiple cloning site of lentivirus vector pCDH, under the control of the MSCV promoter sequence (System Biosciences), such that a single vector comprised the genes for IL-15/IL-15RA and the gene for 4-1BBL. Lentivirus was produced in 293T cells by co-transfecting the cells with pPACKH1 (System Biosciences) and pCDH lentivirus vector containing both IL-15/IL-15-RA gene and 4-1BBL gene. Cells were placed in fresh culturing medium. The virus supernatant was collected 48 hours post-medium change by centrifugation at 1,500 rpm for 5 minutes. The supernatant was collected, filtered, and frozen in aliquots at −80° C.

Expansion and Differentiation of Erythroid Cells

Human CD34+ cells derived from mobilized peripheral blood cells from normal human donors were purchased frozen from AllCells Inc. The expansion/differentiation procedure comprises 3 stages. In the first stage, thawed CD34+ erythroid precursors were cultured in Iscove's MDM medium comprising recombinant human insulin, human transferrin, recombinant human recombinant human stem cell factor, and recombinant human interleukin 3. In the second stage, erythroid cells were cultured in Iscove's MDM medium supplemented with recombinant human insulin, human transferrin, human recombinant stem cell factor, human recombinant erythropoietin, and L-glutamine. In the third stage, erythroid cells were cultured in Iscove's MDM medium supplemented with human transferrin, recombinant human insulin, human recombinant erythropoietin, and heparin. The cultures were maintained at 37° C. in 5% CO2 incubator.

Transduction of Erythroid Precursor Cells

Erythroid precursor cells were transduced during step 1 of the culture process described above. Erythroid cells in culturing medium were combined with lentiviral supernatant and polybrene. Infection was achieved by spinoculation, spinning the plate at 2000 rpm for 90 minutes at room temperature. After spinoculation, the cells were incubated at 37° C. overnight.

Antibody Binding

Binding of a PE-labelled anti-IL-15-RA antibody (e.g., anti-IL-15RA antibody (JM7A4) (ab91270), AbCam) was used to validate expression of the IL-15/IL-15-RA in the engineered erythroid cells. Binding of a PE-labelled anti-4-1BBL antibody (e.g., purified anti-human 4-1BB Ligand (CD137L) antibody, BioLegend) was used to validate expression of 4-1BBL in the engineered erythroid cells. Binding of the antibody was measured by flow cytometry for PE fluorescence. A gate was set based on stained untransduced cells.

Example 12. Expression of IL-15/IL-15RA and 4-1BBL on the Surface of Engineered Erythroid Cells Drives T-Cell Activation In Vitro Human erythroid cells comprising IL-15/IL-15RA and 4-1BBL were prepared as described in Example 11.

Figure 11:
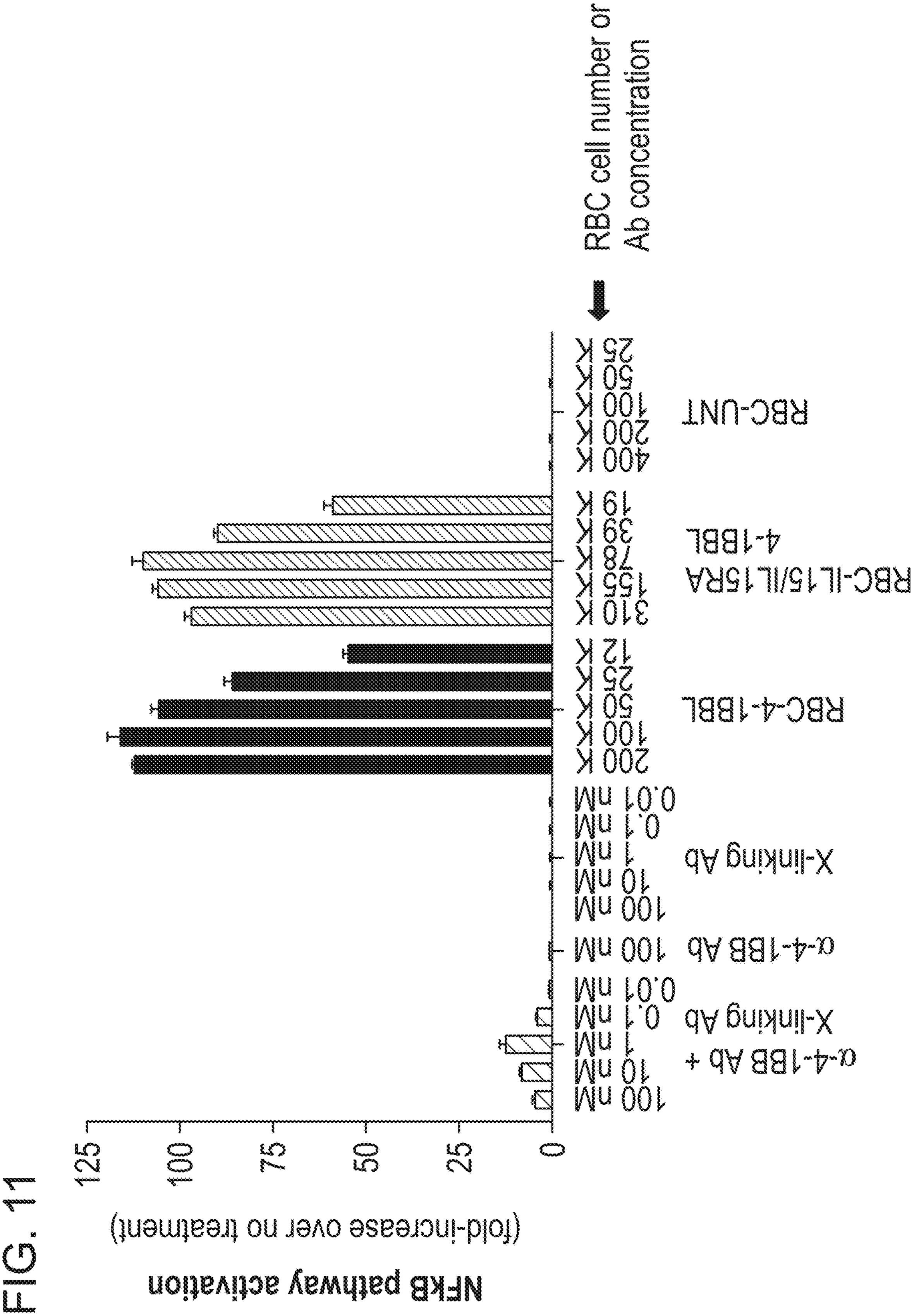
FIG. 11 is a graph showing that expression of IL-15/IL-15RA and 4-1BBL together on the surface of engineered erythroid cells, and expression of 4-1BBL alone on the surface of engineered erythroid cells, resulted in highly potent T-cell activation as measured by NFκB activation in Jurkat cells.

The effect of expression of IL-15/IL-15RA and 4-1BBL on the surface of engineered erythroid cells on T-cell activation was examined in a standard in vitro assay in which intracellular NFκB signaling is measured using Jurkat cells, a human T cell line. Untransduced RBCs (UTR RBC) represent control RBCs as these have not been engineered to express an active protein. As shown in FIG. 11, RBC-IL-15/IL-15RA-4-1BBL drives potent T-cell activation, similar to the level of T cell activation that was observed for RBC-4-1BBL (FIG. 4A). When the 4-1BB agonistic mAb (α-4-1BB Ab) was cross linked with a secondary antibody, limited NFκB activation was seen. When α-4-1BB Ab alone or when the secondary antibody alone were incubated with Jurkat cells, there was no induction of NFκB activation. This experiment shows that engineered erythroid cells comprising IL-15/IL-15RA and 4-1BB-L induced potent NFκB activation compared to an agonistic 4-1BB monoclonal antibody, α-4-1BB Ab, and untreated control. As also shown in FIG. 11, erythroid cells were transfected with increasing amounts of IL-15/IL-15RA and 4-1BB-L, and IL-15/IL-15RA and 4-1BBL expression was measured. The number of IL-15/IL-15RA and 4-1BB-L copies per cell is shown on the x-axis. FIG. 11 shows that activation of NFκB by engineered erythroid cells comprising IL-15/IL-15RA and 4-1BBL is tunable.

Example 13. Erythroid Cells Engineered to Express an IL-15/IL-15-RA Fusion Protein and 4-1BBL Potently Activate Splenocytes with or without CD3 Stimulation Murine erythroid cells were conjugated with IL-15/IL-15-RA fusion protein and with 4-1BBL using the click methodology (click chemistry for functionalizing erythroid cells is described in International Application No. PCT/US2018/000042, which claims priority to U.S. Provisional Application No. 62/460,589, filed Feb. 17, 2017 and U.S. Provisional Application No. 62/542,142, filed Jul. 8, 2017, incorporated by reference in their entireties herein).

Splenocytes consist of a variety of cell populations with immune functions, including CD8+ T-cells and NK cells. Splenocytes were isolated from 3 naïve mice. 150,000 splenocytes were co-incubated with either $1e^7$ clicked cells comprising either 4-1BBL alone, IL-15/IL-15RA alone, both IL-15/IL-15RA and 41BBL, or no protein; mouse 4-1BB agonist antibody 3H3 (1 ug/mL) or recombinant human IL-15 (10 ng/mL) for 2 days at 37 degrees. Splenocytes were treated with or without anti CD3 (aCD3). aCD3 was used to stimulate splenocyte T-cell populations. In the absence of aCD3 stimulation, activity may be attributed to NK cell activation. IFNγ produced in the supernatant was measured by ELISA. Interferon gamma (IFNγ) cytokine secretion was used as a measure of splenocyte activation.

Figure 7:
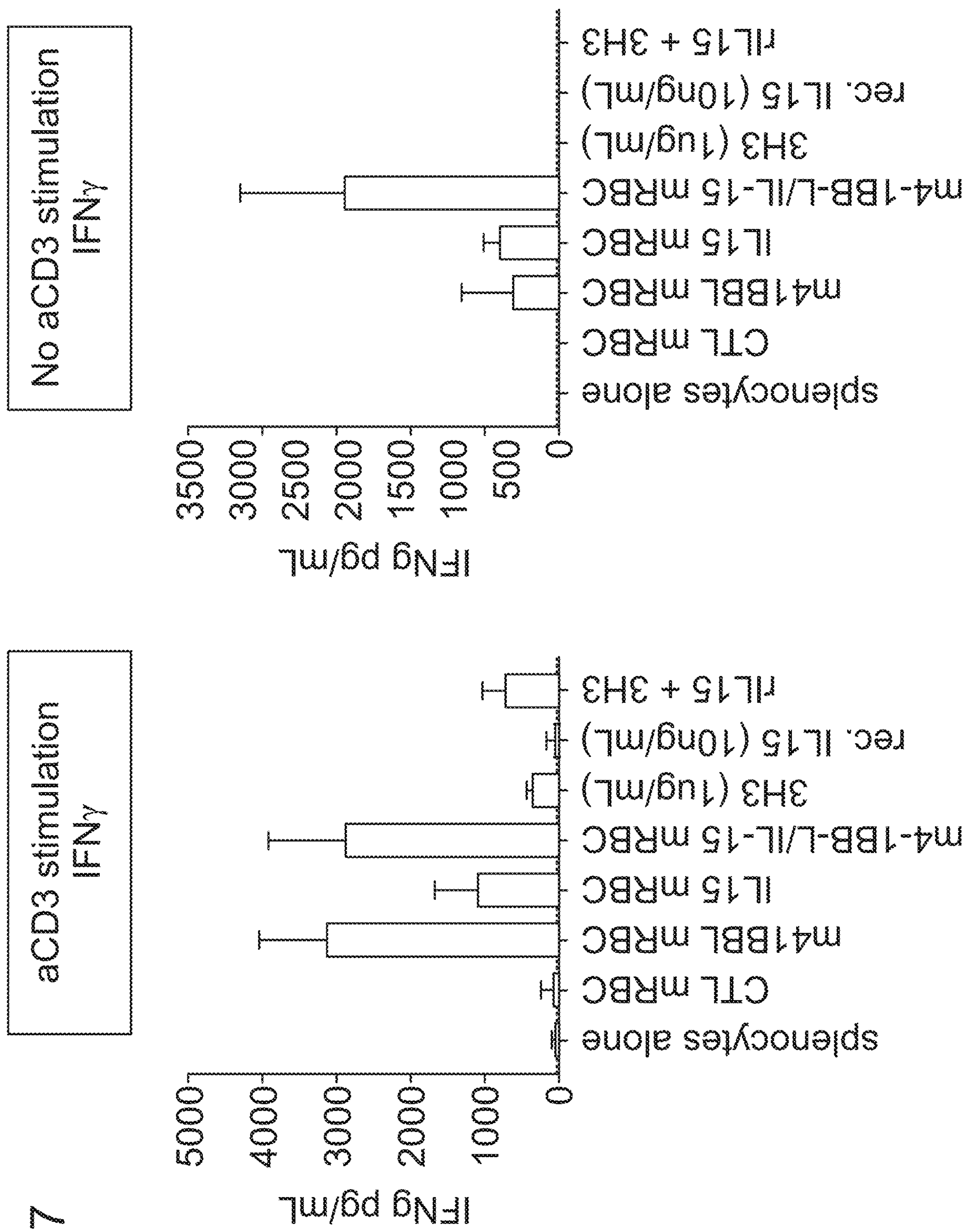
FIG. 7 is a graph showing that engineered erythroid cells expressing both 4-1BBL and IL-15/IL-15RA potently activate splenocytes with or without CD3 stimulation.

As shown in FIG. 7, when stimulated with aCD3, the erythroid cells engineered to present an IL-15/IL-15-RA fusion protein and 4-1BBL showed a superior response as compared to recombinant human IL-15 or mouse 4-1BB agonist antibody 3H3, alone or combined. Also as shown in FIG. 7, when aCD3 stimulation was not used, there is a high synergy between IL-15/IL-15RA and 4-1BBL, and erythroid cells engineered to present an IL-15/IL-15-RA fusion protein and 4-1BBL show a superior response as compared to recombinant human IL-15. In the absence of CD3 stimulation, it can be concluded that the observed effects were a result of NK cell activation.

To confirm the presence of activated NK cells, IFNγ staining was carried out. Splenocytes were isolated and stimulated with PMA/ionomycin (2 ug/mL) in the presence of brefeldin A for 4 hours at 37° C. After the incubation, cells were spun down and washed in PBS before performing cell surface staining for 15 minutes at room temperature (RT). Cells were then washed, fixed for 15 minutes and stained for IFNγ in the permeabilization buffer for 30 minutes at RT. The presence of IFNγ confirmed the activation of NK cells.

Example 14. Erythroid Cells Genetically Engineered to Express IL-15/IL-15RA and 4-1BBL Induce an Increase in Total CD8+ Cells Human erythroid cells comprising IL-15/IL-15RA and 4-1BBL were prepared generally as described in Example 11.

Figure 12:
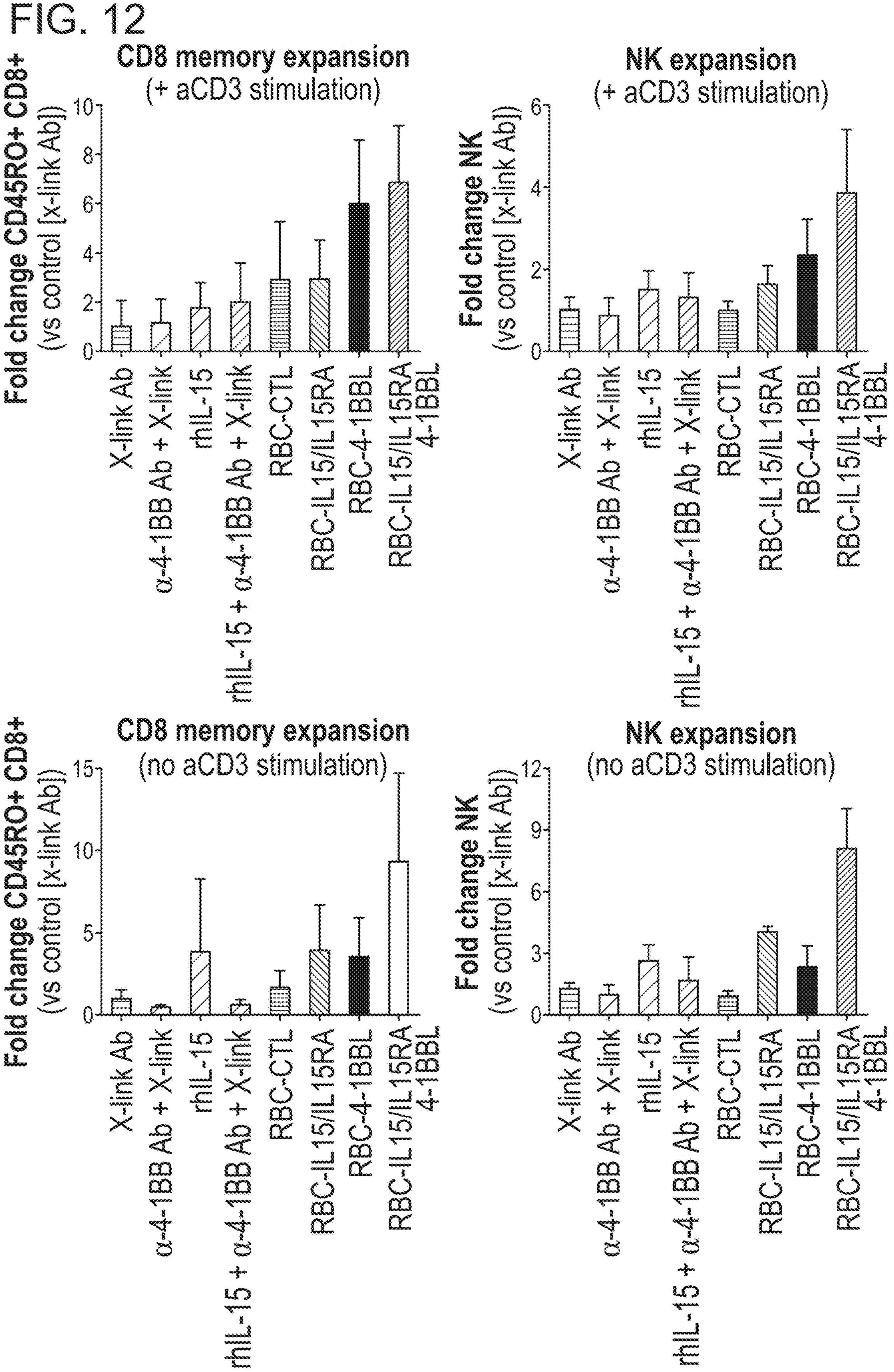
FIG. 12 is a graph showing that expression of IL-15/IL-15RA and 4-1BBL on the surface of engineered erythroid cells potently expands both CD8+ T cells, NK cells and subsets of these cells as compared to engineered erythroid cells expressing 4-1BBL or IL-15/IL-15RA alone.

The effect of engineered enucleated cells comprising IL-15/IL-15RA and 4-1BBL on the cell surface on the expansion of CD8+ T cells, NK cells, and key subsets of these cells, was determined. In particular, the effect of the engineered erythroid cells comprising both IL-15/IL-15RA and 4-1BBL on the cell surface on cell expansion was compared to that of engineered erythroid cells comprising a single agonist, either 4-1BBL (RBC-4-1-BBL) or IL-15/IL-15RA fusion protein (RBC-IL-15/IL-15RA), was examined. As shown in FIG. 12, in the presence of T cell receptor stimulation (+aCD3 stimulation), a greater than 6-fold expansion of CD8+ memory T cells was observed following 5 days of co-culture, which compared favorably to α-4-1BB Ab, recombinant human IL-15 (rhIL-15), a combination of α-4-1BB Ab and rh1L-15, and RBC-CTRL. In the absence of T cell stimulation with an anti-CD3 antibody (no aCD3 stimulation), there was a synergistic effect of the combination of the 4-1BBL and IL-15/IL-15RA in expanding both CD8+ memory T cells and NK cells by approximately 9-fold after 8 days of culture, which was significantly higher than α-4-1BB Ab, rhIL-15, a combination of α-4-1BB Ab and rhIL-15, RBC-IL-15/IL-15RA and RBC-4-1BB.

Taken together, the results presented in this example show that engineered enucleated cells comprising IL-15/IL-15RA and 4-1BBL on the surface drive highly potent T-cell activation, as measured by NFκB activation, as well as expansion of CD8+ memory T cells and NK cells. Further, as compared to engineered erythroid cells comprising either 4-1-BBL alone or IL-15/IL-15RA fusion protein alone, the combination of IL-15/IL-15RA and 4-1BBL led to a synergistic effect in expanding CD8+ memory T cells and NK cells.

Example 15. Erythroid Cells Comprising IL-15/IL-15RA and 4-1BBL Reduce Lung Metastases In Vivo A B16F10 metastatic mouse model system for melanoma (Kubo et al. (2017) Cancer Immunology Research 5(9): 1-9, incorporated by reference in its entirety herein) was used to test the effects of murine erythroid cells comprising human IL-15/IL-15RA and murine 4-1BBL (IL-15/RA 4-1BBL RBC) on metastatic growth. In this model, tumor cells were injected intravenously to establish metastases in the lung and then mice were treated with murine erythroid cells prepared to present IL-15/IL-15RA and 4-1BBL alone or in combination with an anti-PD1 antibody. Upon subcutaneous injection, B16 formed a palpable tumor in 5 to 10 days and grew to a 1×1×1 cm tumor in 14 to 21 days.

Murine erythroid cells were conjugated with human IL-15/IL-15RA, murine 4-1BBL, or co-conjugated with both human IL-15/IL-15RA and murine 4-1BBL using the click methodology (click chemistry for functionalizing erythroid cells is described in International Application No. PCT/US2018/000042, which claims priority to U.S. Provisional Application No. 62/460,589, filed Feb. 17, 2017 and U.S. Provisional Application No. 62/542,142, filed Jul. 8, 2017, incorporated by reference in their entireties herein). IL-15/IL-15RA and 4-1BBL were quantitated using flow cytometry. The IL-15/IL-15RA fusion protein was expressed as the sushi domain of the receptor fused to the IL-15 chain in the construct presented in Table 10 herein. The murine 4-1BBL protein was expressed in the construct presented in Table 10 herein.

Initially, 7 week old female C57BL/6 mice were inoculated intravenously with $1\times10^5$ B16F10 cells/mouse. In various experiments, the animals were then dosed intravenously (IV) with the following: erythroid cells presenting 4-1BBL, IL-15/IL-15RA, or presenting both 4-1BBL and IL-15/IL-15RA; with anti-PD1 monoclonal antibody alone (αPD-1 mAb); with erythroid cells presenting 4-1BBL and IL-15/IL-15RA administered IV in combination with αPD-1 (IP); with erythroid cells presenting 4-1BBL and IL-15/IL-15RA administered intraperitoneally (IP); with a mouse 4-1BB agonist antibody (3H3); or with erythroid cells without 4-1BBL and IL-15/IL-15RA (mRBC-CTL) as control. For dosing animals, an average of 1e9 erythroid cells were administered per dose with an average of 100,000 molecules per cell of 41BBL alone, corresponding to 0.2 mg/kg 4-1BBL, and 60,000 molecules per cell of IL-15-RA alone, corresponding to 0.12 mg/kg IL-15/IL-15RA per dose, or for erythroid cells comprising 4-1BBL and IL-15/IL-15RA, 50,000-60,000 molecules of 41BBL and 30,000-40,000 molecules of IL-15-RA, corresponding to 0.1-0.12 mg/kg and 0.06-0.08 mg/kg respectively. Agonistic 41BB antibody (3H3) was dosed at 2.5 mg/kg. Animals were dosed with mRBC or 3H3 on days 1, 5 and 8 post inoculation.

Animals' weights and condition were recorded daily. On day 14 post inoculation animals were sacrificed and lungs were collected. Lung metastases was assessed using a stereoscope. The number of metastases was determined after 2 weeks. Further, body weight was recorded daily. Changes in body weight was calculated for each mouse relative to the body weight recorded on day 1. Immune infiltrates within perfused lungs of treated mice were measured by flow cytometry. NK cell (NK1.1+) infiltration was reported as a percent of total cells within CD45+ immune cells.

Figure 13A:
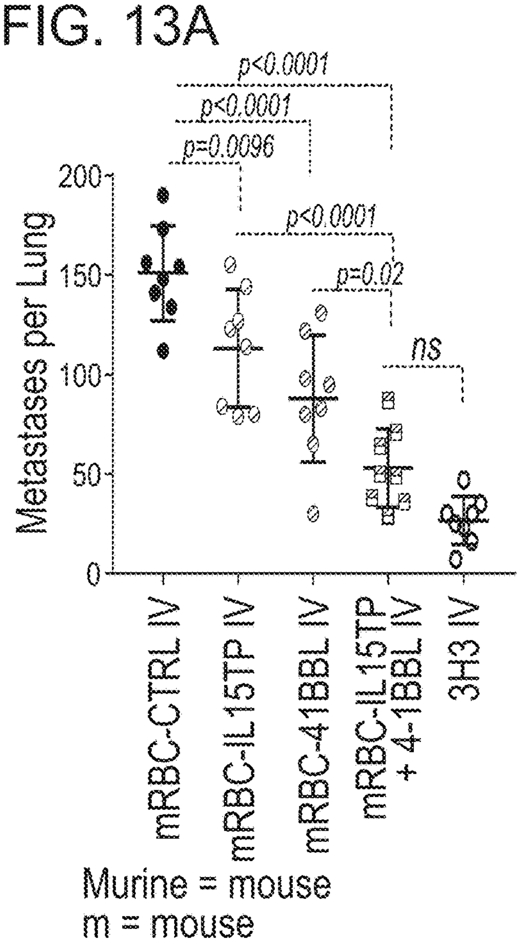
FIG. 13A and FIG. 13C are graphs showing the efficacy of murine erythroid cells prepared to present IL-15/IL-15RA and 4-1BBL together on the surface of the erythroid cells in the murine B16F10 lung metastasis model.

As shown in FIG. 13A, murine erythroid cells prepared to present both IL-15/IL-15RA+ 4-1BBL on their surface administered i.v. as a monotherapy reduced tumor burden in mice as compared to those treated individually with mRBC CTRL, mRBC 4-1BBL, and mRBC IL-15/IL-15RA, thereby indicating the potential synergy that may be achieved by comprising both 4-1BBL and IL-15/IL-15RA on the cell surface of the erythroid cell. The reduction in tumor burden achieved with mRBC-4-1BBL+IL-15/IL-15RA was not significantly different than that achieved with the 41BB agonist monoclonal antibody 3H3. Furthermore, this decrease in the number of lung metastases was also associated with a significant increase in NK cell infiltration into the lungs (p=0.02), as shown in FIG. 13B.

Figure 13C:
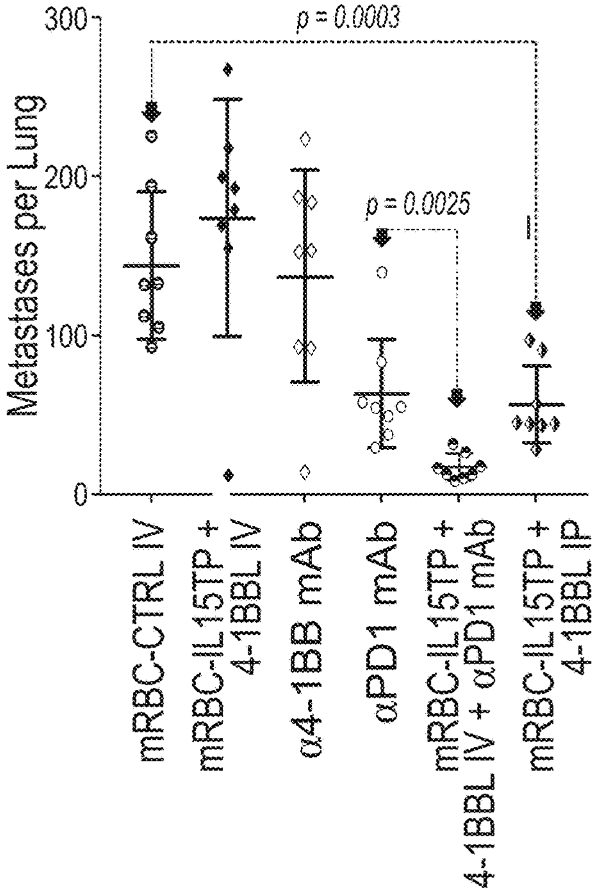
Figure 13B:
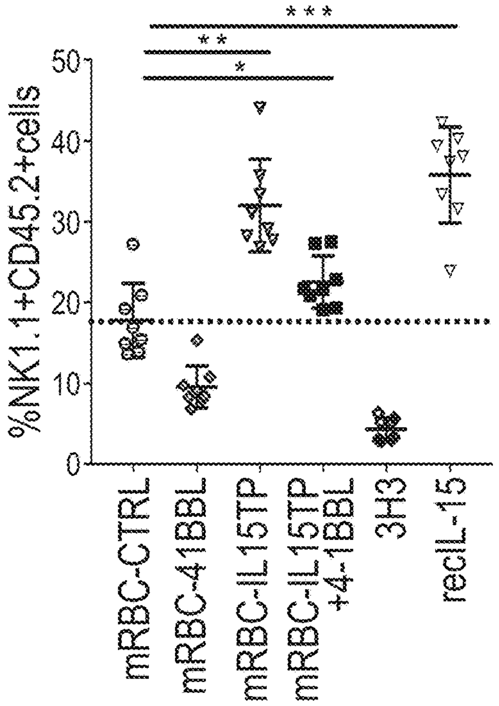
FIG. 13B is a graph showing the infiltration of NK cells in the lungs of the mice treated with murine erythroid cells prepared to present IL-15/IL-15RA and 4-1BBL together on the surface of the erythroid cells, in the murine B16F10 lung metastasis model.

The results of a separate, similar study are shown in FIG. 13C. This study was carried out as described above, except that for dosing animals, an average of 1e9 erythroid cells were administered per dose with an average of 25,000 molecules per cell of 4-1BBL, and an average of 45,000 molecules per cell of IL-15/IL-15RA. As can be seen in FIG. 13C, the murine erythoid cells prepared to present IL-15/IL-15RA+4-1BBL, when administered i.v. in combination with the anti-PD1 antibody, significantly reduced tumor burden in mice compared to those treated with the negative controls PBS and mRBC CTRL, as well as the anti-PD1 antibody alone. A mouse 4-1BB agonist antibody, 3H3, was not active as a monotherapy. In this study, the murine erythoid cells prepared to present IL-15/IL-15RA+4-1BBL were not active as a monotherapy, as the exposure of the murine erythroid cell presenting IL-15/IL-15RA+4-1BBL administered i.v. was approximately threefold lower than in the previous monotherapy study (described above and FIG. 13A). However, the murine erythoid cells prepared to present IL-15/IL-15RA+4-1BBL were highly effective in this study as a monotherapy in reducing lung metastases when administered intraperitoneally, or i.p., presumably because greater exposure in the blood and/or distribution into other organs (e.g., lymph node) was obtained.

In an additional experiment, the pharmacodynamic effect of erythoid cells prepared to present IL-15/IL-15RA+4-1BBL was evaluated in the B16F10 model by quantification of NK cell infiltration into the tumor. C57BL/6 mice were inoculated subcutaneously with B16F10 cells. When the tumors reached a volume of approximately 50 cubic millimeter, the animals were randomized and dosed on Days 1, 4 and 8 intravenously with $1\times10^9$ mRBC-m4-1BBL, mRBC-IL-15/IL-15RA or mRBC IL-15/IL-15RA+4-1BBL. An additional group received 200 μL of phosphate-buffered saline (PBS) which served as a negative control. Here, as described above in this Example, the IL-15/IL-15RA fusion protein was expressed as the sushi domain of the receptor fused to the IL-15 chain (in the construct presented in Table 10).

Evaluation of molecules per cell showed that mRBC-m4-1BBL expressed 150,000 molecules per cell, IL-15/IL-15RA expressed 90,000 molecules per cell and mRBC IL-15/IL-15RA+4-1BBL expressed 70,000 molecules of m4-1BBL and 50,000 molecules of IL-15/IL-15RA per cell. On day 11, tumors were collected, digested, and tumor cell suspensions were analyzed for amounts of NK cells, as well as NK maturation and differentiation markers by flow cytometry.

Figure 13D:
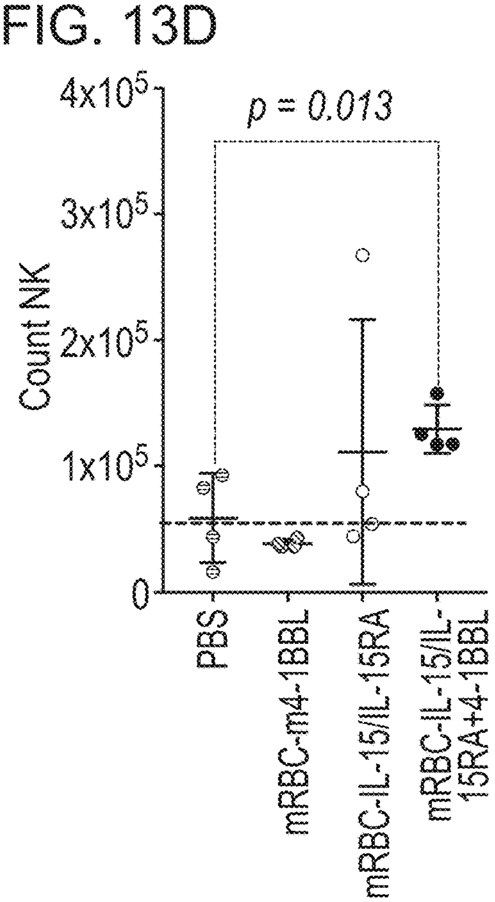
FIG. 13D is a graph showing an increase in total NK cell count in the tumor of the mice treated with murine erythroid cells prepared to present IL-15/IL-15RA and 4-1BBL together on the surface of the erythroid cells, in the murine B16F10 lung metastasis model.
Figure 13E:
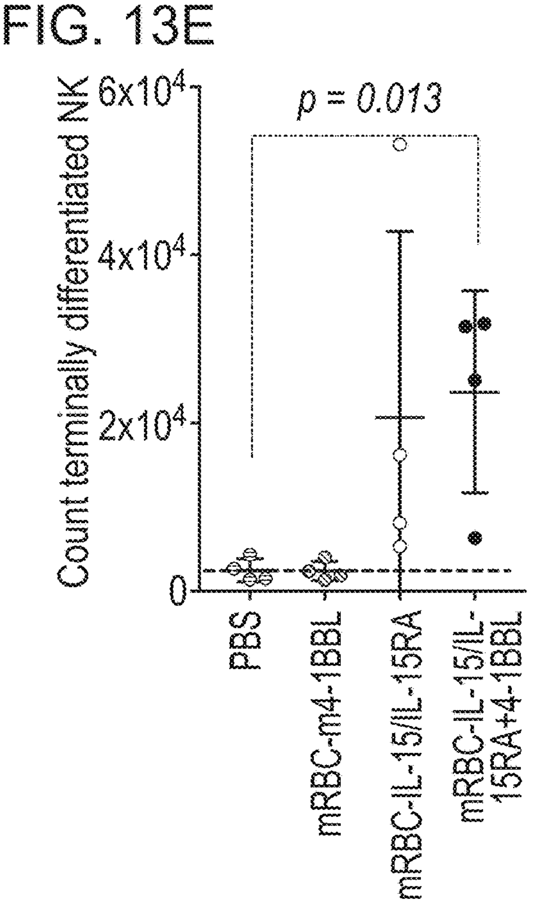
FIG. 13E is a graph showing an increase in mature NK cell count in the tumor of the mice treated with murine erythroid cells prepared to present IL-15/IL-15RA and 4-1BBL together on the surface of the erythroid cells, in the murine B16F10 lung metastasis model.
Figure 13F:
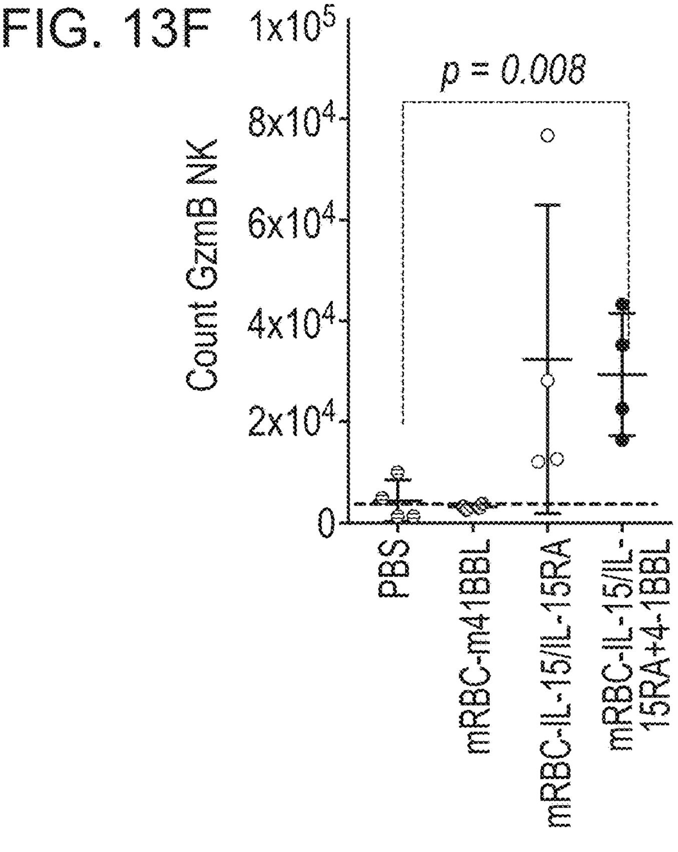
FIG. 13F is a graph showing an increase in functional NK cell count in the tumor of the mice treated with murine erythroid cells prepared to present IL-15/IL-15RA and 4-1BBL together on the surface of the erythroid cells, in the murine B16F10 lung metastasis model.

As shown in FIG. 13D-F, mRBC IL-15/IL-15RA+4-1BBL led to an increase in total NK cell count in the tumor compared to PBS-treated control mice (p=0.013, FIG. 13D). Further analysis demonstrated that NK cells in mRBC IL-15/IL-15RA+4-1BBL treated mice were more mature (p=0.013; FIG. 13E) and highly functional (p=0.008; FIG. 13F), as demonstrated by an increase in total number of terminally differentiated and granzyme B+ NK cells when compared to control mice. The effect of mRBC IL-15/IL-15RA+4-1BBL was more pronounced than the effect of mRBC-m41BBL and mRBC-IL-15/IL-15RA. These findings indicate that the murine surrogate product comprising m4-1BBL and IL-15/IL-15RA is highly functional in mice and can lead to NK cell infiltration into tumors

Example 16. Erythroid Cells Comprising IL-15/IL-15RA, 4-1BBL or Comprising IL-15/IL-15RA and 4-1BBL Modulate Phenotypic Markers Indicative of NK Cell Expansion and Activation In Vitro Erythroid cells comprising IL-15/IL-15RA (v4, comprising mature extracellular IL-15RA) were prepared generally as described in Example 1. Erythroid cells comprising 4-1BBL were prepared generally as described in Example 6.

Frozen peripheral blood mononuclear cells (PBMCs; Astarte) were thawed, resuspended in RPMI with 10% FBS, and plated at 100,000 cells per well in 96-well round-bottom plates. Erythroid cells comprising IL-15/IL-15RA (v4; which expresses mature extracellular IL-15RA), 4-1BBL or comprising IL-15/IL-15RA and 4-1BBL were added in varying amounts (250,000 or 500,000 cells for IL-15/IL-15RA, and 500,000 cells for 4-1BBL). Cultures were incubated for 8 days (long term priming) and then stained for analysis by flow cytometry using the following antibodies: CD69 (FN50), TRAIL(RIK-2), 41BB (4B4-1), NKp44 (P44-8), and KLRG1 (14C2A07) from BioLegend, and Aqua Dye from Invitrogen to label dead cells. For intracellular staining, cells were fixed and permeabilized with the Foxp3/Transcription Factor Fixation/Permeabilization kit (eBioscience), and stained for Ki67 (B56, BD Biosciences) and GZMB (GB11 BioLegend). Cells were analyzed by flow cytometry (Novocyte).

Figure 14:
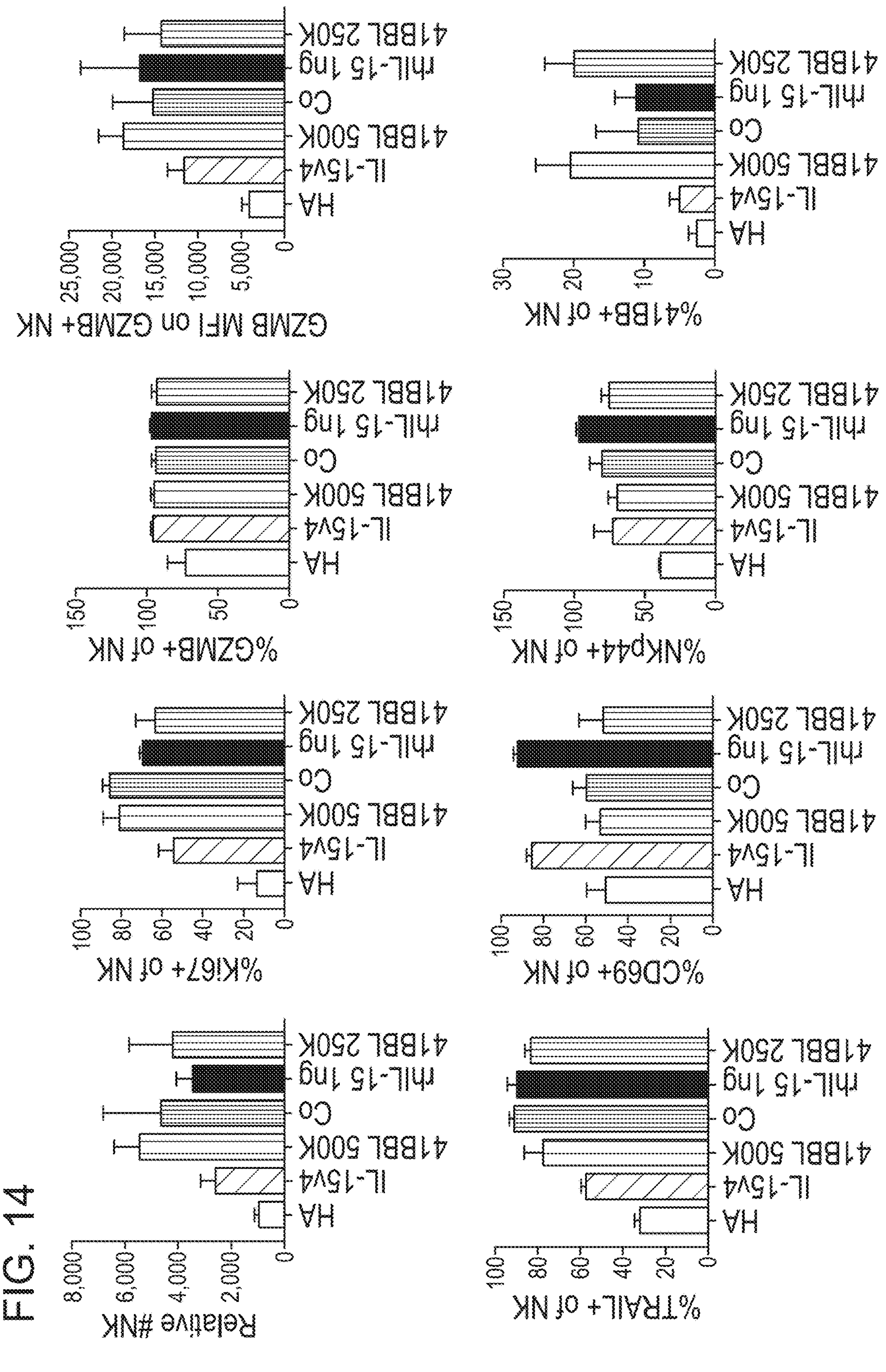
FIG. 14 is a panel of graphs that show a phenotypic analysis of PBMCs after long term priming (8 days) with erythroid cells expressing IL-15/IL-15RA (v4), 4-1BBL or co-expressing IL-15/IL-15RA and 4-1BBL ("co"). The markers Ki67, Granzyme B, TRAIL, CD69, NKp44 and 41BB were used as phenotypic readouts to show enhanced NK cell survival, expansion and activation.

The results of this experiment are shown in FIG. 14. After long term (8 day) priming of NK cells, it was found that erythroid cells comprising IL-15/IL-15RA (v4), 41BBL or comprising IL-15/IL-15RA and 41BBL ("co") enhance NK cell recovery after the 8 days in culture, as compared to NK cells cultured with control erythroid cells comprising HA. Also shown in FIG. 14 are the results from analysis of the panel of markers used as phenotypic readouts for NK cell survival, expansion and activation. The results obtained for each marker are described below.

Ki67: Erythroid cells comprising IL-15/IL-15RA, 4-1BBL or comprising IL-15/IL-15RA and 41BBL enhanced NK cell proliferation, as measured by Ki67 staining, as compared to NK cells cultured with control erythroid cells comprising HA.

Granzyme B: Erythroid cells comprising IL-15/IL-15RA, 4-1BBL or comprising IL-15/IL-15RA and 41BBL led to increased proportions and levels of granzyme B expression in NK cells, a marker of NK cytotoxicity, as compared to that observed with control HA (see top right most panel, which shows the relative intensity of flow cytometric staining for GZMB in NK cells positive for GZMB.

TRAIL: Erythroid cells comprising IL-15/IL-15RA, 4-1BBL or comprising IL-15/IL-15RA and 41BBL led to increased proportions of TRAIL-comprising NK cells, a marker of NK cell activation and a death-inducing ligand for TRAIL-ligand-comprising cells, as compared to that observed with control HA. TRAIL expression is reported to increase with IL-15 stimulation, suggesting that these engineered erythroid cells recapitulate the effects of IL-15 transpresentation.

CD69: Erythroid cells comprising IL-15/IL-15RA led to increased proportions of CD69-comprising NK cells as compared to that observed with control HA. CD69 is a marker of early activation in lymphocytes.

NKp44: Erythroid cells comprising IL-15/IL-15RA, 4-1BBL or comprising IL-15/IL-15RA and 41BBL IL-15/IL-15RA led to increased proportions of NKp44-comprising cells as compared to that observed with control HA. NKp44 is expressed exclusively on activated NK cells, and can promote killing of some virally infected cells and tumor cells.

41BB: Erythroid cells comprising 4-1BBL or comprising IL-15/IL-15RA and 41BBL led to increased 41BB expression on NK cells as compared to that observed with control HA. 41BB is an activation marker on NK and T cells.

In summary, the results from analysis of a panel of phenotypic markers demonstrated that erythroid cells comprising IL-15/IL-15RA, 4-1BBL or both IL-15/IL-15RA and 4-1BBL enhanced NK cell survival, expansion and activation in vitro.

Example 17. Erythroid Cells Genetically Engineered to Express 4-1BBL and IL-15/IL-15RA Induce Tumor Cell Killing In Vitro Erythroid Cells Comprising IL-15/IL-15RA (v5, IL-15RA Sushi Domain)

Figure 8:
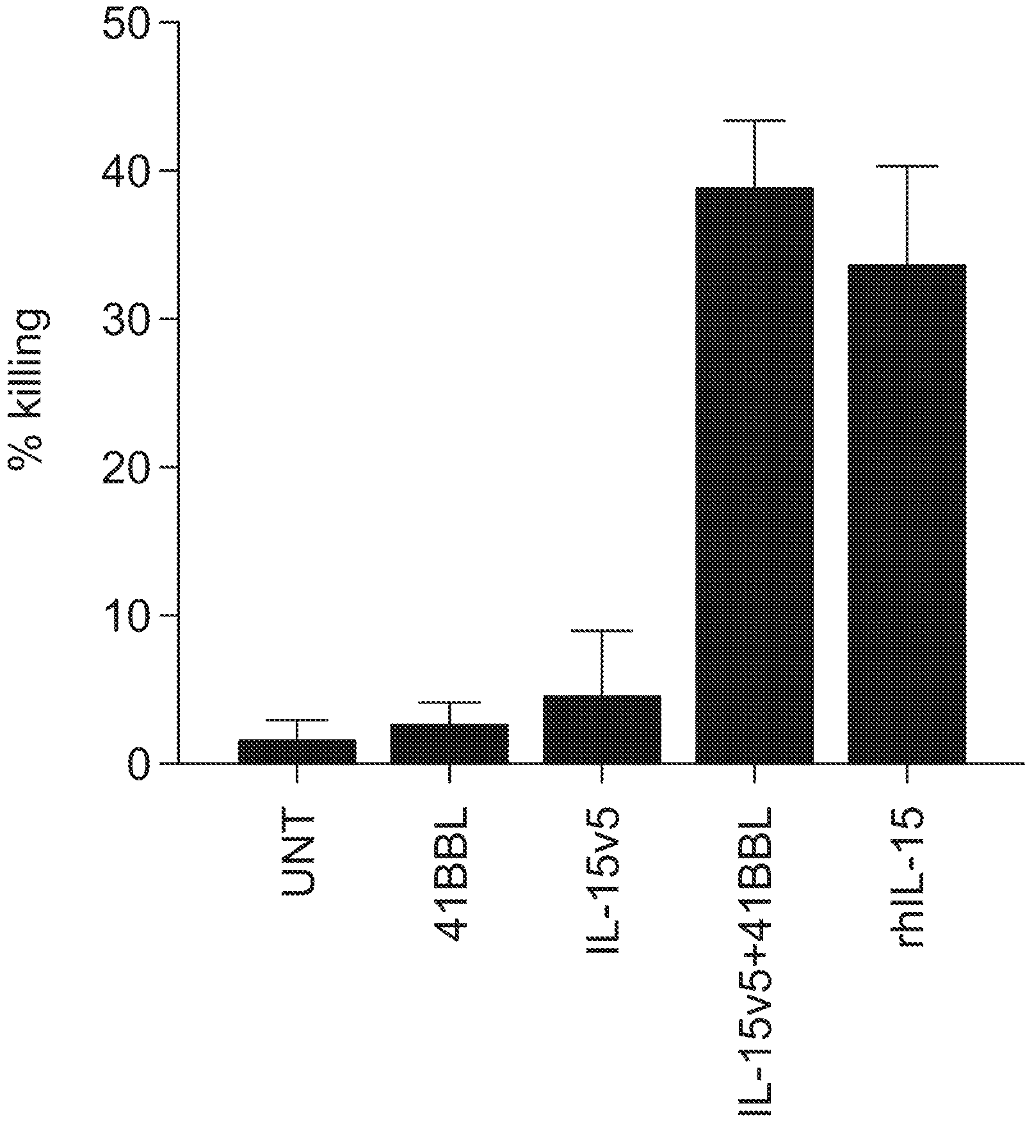
FIG. 8 is a graph showing in vitro killing of K562 human chronic myelogenous leukemia (CML) cells by NK cells incubated with 200,000 engineered erythroid cells expressing 4-1BB-L, IL-15/IL-15RA or a mixture of both 4-1BBL and IL-15/IL-15RA at 200,000 cells each.

Erythroid cells comprising IL-15/IL-15RA (v5, comprising the IL-15RA sushi domain) were prepared generally as described in Example 1. Erythroid cells comprising 4-1BBL were prepared generally as described in Example 6. The in vitro killing of K562 human chronic myelogenous leukemia (CML) by NK cells was examined for each of (i) the 4-1BBL comprising erythroid cells, (ii) the IL-15/IL-15RA comprising erythroid cells; and (iii) a mixture of the IL-15/IL-15RA comprising erythroid cells and 4-1BBL comprising erythroid cells. Briefly, 20,000 purified NK cells (Astarte Biologics) were incubated for 16 hours with 200,000 RBC comprising 4-1BBL or IL-15/IL-15RA or a mixture of both 4-1BBL and IL-15/IL-15RA at 200 000 each. Additionally, in one treatment group, 20,000 NK cells were incubated with 5 ng/mL of recombinant IL-15. After 16 hours of incubation, 20,000 K562 cells were added to the culture for 4 hours. These cells served as a target cell population for NK cells. A count of live K562 cells was measured by flow cytometry. Percent killing was calculated based on the percent alive compared to control. The results are shown in FIG. 8. As shown in FIG. 8, erythroid cells comprising IL-15/IL-15RA+4-1BBL showed the highest percent killing by NK cells.

Erythroid Cells Comprising IL-15/IL-15RA (v4, Mature Extracellular IL-15RA) and 4-1BBL Additional studies were carried out to those described above, but in which (i) a different IL-15/IL-15RA fusion, specifically IL-15/IL-15RA v4 comprising mature extracellular IL-15RA rather than the sushi domain, was used, and (ii) erythroid cells were engineered to co-express IL-15/IL-15RA and 4-1BBL. The effect of both long term (8 hours) priming and short term (overnight) priming of NK cells with erythroid cells comprising IL-15/IL-15RA (v4), 4-1BBL or comprising IL-15/IL-15RA on in vitro killing of K562 human CML cells was examined. For these experiments, erythroid cells comprising IL-15/IL-15RA (v4), 4-1BBL and comprising 4-1BBL and IL-15/IL-15RA (v4) were prepared generally as described in Example 1, Example 6, and Example 11, respectively.

(i) Long Term Priming

For long term priming, PBMCs were isolated from fresh blood using Ficoll, and NK cells were further enriched using the Human NK Negative Selection kit from Miltenyi. Then, 5e5 NK cells were cultured in 24-well plates with 3e6 erythroid cells comprising IL-15/IL-15RA (v4), 4-1BBL or comprising IL-15/IL-15-RA and 4-1BBL for 8 days. For controls, NK cells were cultured with rhIL-15 at 0.1, 1 or 10 ng/mL (Peprotech).

After 8 days, the cells were stained for analysis by flow cytometry using the following antibodies: CD56 (5.1H11), CD3 (UCHT1), CD8 (RPA-T8), CD69 (FN50), TRAIL (RIK-2), 41BB (4B4-1), and NKp44 (P44-8) from BioLegend, and Aqua Dye from Invitrogen to label dead cells. For intracellular staining, cells were fixed and permeabilized with the Foxp3/Transcription Factor Fixation/Permeabilization kit (eBioscience), and stained for Ki67 (B56, BD Biosciences) and GZMB (GB11 BioLegend). Cells were analyzed by flow cytometry (Novocyte). The results from analysis of the panel of markers used as phenotypic readouts for NK cell survival, expansion and activation were similar to those found in Example 16 (data not shown). Briefly, erythroid cells comprising 4-1BBL or comprising IL-15/IL-15RA and 41BBL enhanced NK cell proliferation, as measured by Ki67 staining, as compared to NK cells cultured with control erythroid cells comprising HA. Erythroid cells comprising IL-15/IL-15RA or comprising IL-15/IL-15RA and 41BBL led to increased proportions and levels of granzyme B expression in NK cells, a marker of NK cytotoxicity, as compared to that observed with control HA. Erythroid cells comprising IL-15/IL-15RA, 4-1BBL or comprising IL-15/IL-15RA and 41BBL led to increased proportions of TRAIL-comprising NK cells, a marker of NK cell activation and a death-inducing ligand for TRAIL-ligand-comprising cells, as compared to that observed with control HA. Erythroid cells comprising IL-15/IL-15RA, 4-1BBL or comprising IL-15/IL-15RA and 41BBL led to increased proportions of CD69-comprising NK cells as compared to that observed with control HA. CD69 is a marker of early activation in lymphocytes. Erythroid cells comprising IL-15/IL-15RA, 4-1BBL or comprising IL-15/IL-15RA and 41BBL led to increased proportions of NKp44-comprising cells as compared to that observed with control HA. NKp44 is expressed exclusively on activated NK cells, and can promote killing of some virally infected cells and tumor cells. Erythroid cells comprising 4-1BBL or comprising IL-15/IL-15RA and 41BBL led to increased 41BB expression on NK cells as compared to that observed with control HA. 41BB is an activation marker on NK and T cells. Thus, the results from analysis of the phenotypic markers demonstrated that erythroid cells comprising IL-15/IL-15RA, 4-1BBL or both IL-15/IL-15RA and 4-1BBL enhanced the NK cell survival, expansion and activation.

NK cells from co-cultures of NK and erythroid cells comprising IL-15/IL-15-RA, 4-1BBL or comprising IL-15/IL-15-RA and 4-1BBL were re-purified using the Human NK negative selection kit. For killing assays with K562 cells, the K562 target cells were labeled with CellTrace Far Red and 20,000 cells were plated with purified NK at varying ratios (Erythroid:Target of 1:1, or 5:1) and incubated for 4 hrs. Cells were then stained on ice with CD56 (clone), CD3 (clone), live/dead (Invitrogen), fixed with 2% paraformaldehyde, and analyzed by flow cytometry (Novocyte) to determine the number of live targets. Specific killing was calculated as (% dead K562 target cells in "K562+NK" condition)−(% dead K562 target cells in "K562 only" condition) to account for spontaneous target cell death.

Figure 15:
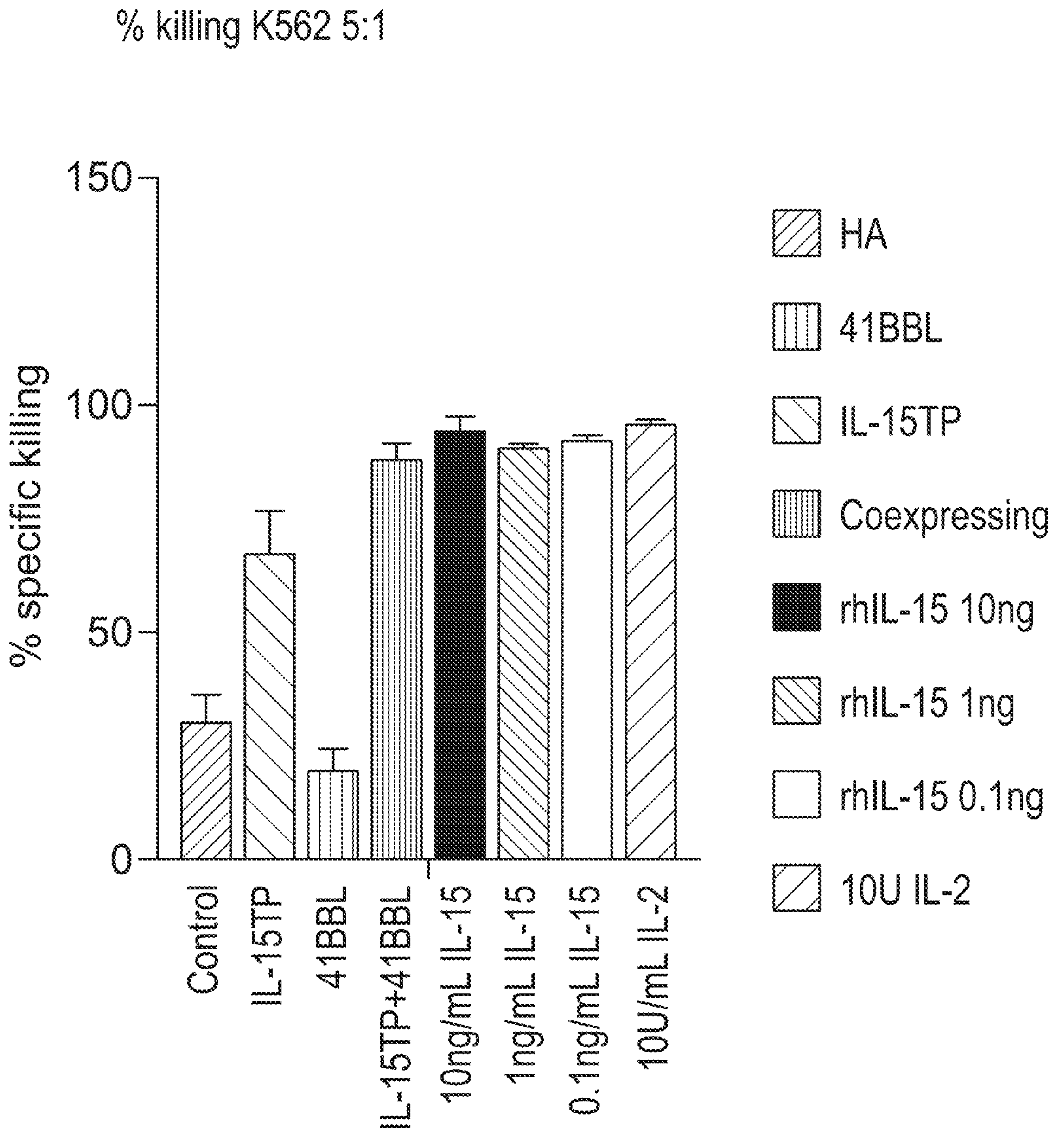
FIG. 15 is a graph showing that NK cells primed for 8 days with erythroid cells expressing IL-15/IL-15RA ("IL-15TP") or co-expressing IL-15/IL-15RA and 41BBL ("IL-15TP+41BBL") have enhanced cytotoxicity against K562 targets. The percent killing of K562 cells is shown.

The results are shown in FIG. 15. FIG. 15 shows the average percent killing for two PBMC donors, plotted as specific killing, and where the E:T (Effector (NK):Target (tumor)) cell ratio was 5:1. As shown in FIG. 15, NK cells primed with erythroid cells comprising IL-15/IL-15RA or comprising IL-15/IL-15RA and 4-1BBL have enhanced cytotoxicity against K562 target cells as compared to control HA. Similar to the results shown in FIG. 8, erythroid cells comprising IL-15/IL-15RA (v4)+4-1BBL showed the highest percent killing by NK cells, comparable to that observed with NK cells primed with soluble IL-15 or IL-2. Results obtained when the E:T cell ratio was 1:1 similarly showed that NK cells primed with erythroid cells comprising IL-15/IL-15RA or comprising IL-15/IL-15RA (v4) and 4-1BBL have increased cytotoxicity against K562 cells as compared to control HA, although less killing overall was observed and the target killing was not as great as that seen with NK cells primed with soluble IL-15 or IL-2 (data not shown).

(ii) Short Term Priming

For short term priming, frozen, purified NK cells (Astarte) were thawed resuspended in media (RPMI with 10% FBS, 1% Pen-Step) and plated in 96-well U-bottom plates at 2e4 or 1e5 per well, along with 2e5 erythroid cells comprising IL-15/IL-15RA (v4), 4-1BBL or comprising IL-15/IL-15-RA and 4-1BBL. For controls, NK cells were plated alone, or with rhIL-15 (0.1, 1 or 10 ng/mL depending on experiment; Peprotech). In addition, control wells were set up with the erythroid cells only. Cells were incubated overnight at 37 C in a humidified incubator (between 16-20 hrs).

For killing assays with K562 cells, K562 cells were labeled with CellTrace Far Red, and 20,000 target cells were added to wells containing the overnight culture of NK cells, NK and erythroid cells comprising IL-15/IL-15RA (v4), 4-1BBL or comprising IL-15/IL-15-RA and 4-1BBL, or the erythroid cells only as controls, at a 5:1 E:T ratio and were incubated for 4 hrs. Cells were then stained on ice with CD56 (clone), CD3 (clone), live/dead (Invitrogen), fixed with 2% paraformaldehyde, and analyzed by flow cytometry (Novocyte) to determine the number of live targets. Specific killing was calculated as (% dead K562 target cells in "K562+NK" condition)−(% dead K562 target cells in "K562 only" condition) to account for spontaneous target cell death. The results (data not shown) show that NK cells primed overnight with erythroid cells comprising IL-15/IL-15RA or comprising IL-15/IL-15RA and 4-1BBL have enhanced cytotoxicity (approximately 60% killing) against K562 targets as compared to control or erythroid cells comprising 4-1BBL (each approximately 40% killing), but less than NK cells primed with rhIL-15 (at least 90% killing).

Taken together, the results in this example demonstrate that erythroid cells comprising IL-15/IL-15RA, alone or together with 4-1BBL, enhance the cytotoxicity of NK cells on a per cell basis, which is to say that the NK cells are not only better expanded, but the resulting individual NK cells themselves are more active.

Example 18. Erythroid Cells Genetically Engineered to Express 4-1BBL and IL-15/IL-15RA v4) Induce ADCC Killing In Vitro Short term (overnight) priming of NK cells with erythroid cells comprising IL-15/IL-15RA (v4), 4-1BBL or comprising IL-15/IL-15RA (v4) and 4-1BBL was performed as described in Example 17 above.

For antibody-dependent cell-mediated cytotoxicity (ADCC) assays, Raji cells were labeled with CellTrace Far Red, and then incubated with 5 μg/mL anti-CD20 IgG1 (Invivogen) or IgG1 Isotype control antibody ("iso", BioLegend) for 15 minutes at 37 C. Raji cells were then washed and 20,000 cells were added to wells containing the overnight culture of NK cells, NK cells and erythroid cells comprising 4-1BBL, IL-15/IL-15RA, or comprising IL-15/IL-15RA and 41BBL, or the engineered erythroid cells only, and incubated for 4 hrs. Cells were then stained on ice with CD56 (clone), CD3 (clone), live/dead (Invitrogen), fixed with 2% paraformaldehyde, and analyzed by flow cytometry (Novocyte) to determine the number of live targets. Specific killing was calculated as (% dead Raji targets in "Raji+NK" condition)−(% dead Raji targets in "Raji only" condition) to account for spontaneous target cell death.

Figure 16:
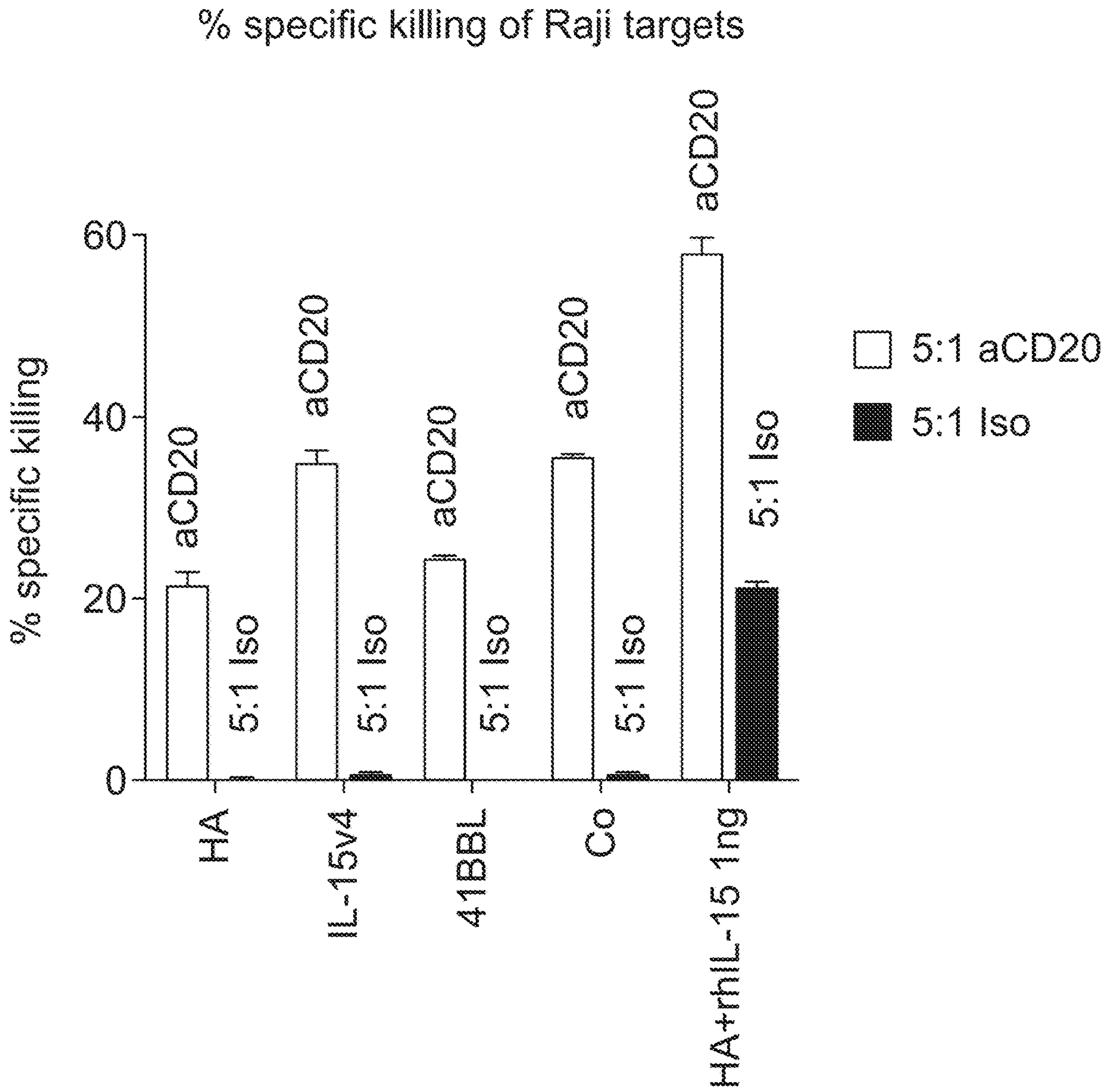
FIG. 16 is a graph showing that NK cells primed overnight with erythroid cells expressing IL-15/IL-15RA ("IL-15v4") or co-expressing IL-15/IL-15RA and 41BBL ("Co") have enhanced ADCC killing against Raji human B-lymphocyte target cells. The percent specific killing of Raji cells is shown.

As shown in FIG. 16, NK cells primed overnight with erythroid cells comprising IL-15/IL-15RA or comprising IL-15/IL-15RA and 41BBL demonstrated increased percent killing of Raji cells compared to NK cells primed overnight with erythroid cells comprising 4-1BBL or control. These results thus demonstrate that erythroid cells comprising IL-15/IL-15RA or comprising IL-15/IL-15RA and 41BBL lead to enhanced ADCC killing of Raji cell targets, indicating that these erythroid cells enhance the cytotoxicity of NK cells on a per cell basis, which is to say that the NK cells are not only better expanded, but the resulting individual NK cells themselves are more active.

Example 19. Erythroid Cells Comprising IL-15/IL-15RA and 4-1BBL Reduce Tumor Burden in Colon Cancer Mouse Model In Vivo A CT26 syngeneic mouse model system for colon cancer was used to test the effects of murine erythroid cells comprising human IL-15/IL-15RA and murine 4-1BBL on tumor burden. CT26 is a commercially available mouse colon carcinoma model (Zhang et al., Clin Exp Metastasis. 2013 October; 30(7): 10.1007/s10585-013-9591-8, incorporated by reference in its entirety herein).

Murine erythroid cells were co-conjugated with IL-15/IL-15RA ("IL-15TP") and 4-1BBL (i.e., both IL-15TP and 4-1BBL conjugated on same cell) using the click methodology (click chemistry for functionalizing erythroid cells is described in International Application No. PCT/US2018/000042, which claims priority to U.S. Provisional Application No. 62/460,589, filed Feb. 17, 2017 and U.S. Provisional Application No. 62/542,142, filed Jul. 8, 2017, incorporated by reference in their entireties herein). The IL-15/IL-15RA fusion protein was expressed as the sushi domain of the receptor fused to the IL-15 chain in the construct presented in Table 10 herein. The murine 4-1BBL protein was expressed in the construct presented in Table 10 herein.

When the tumors reached a volume of approximately 50 $mm^3$, the animals were dosed with murine erythroid cells presenting 4-1BBL and IL-15/IL-15RA ("IL-15TP") administered intravenously (IV), with anti-PD1 monoclonal antibody alone (αPD-1 mAb; 150 μg) administered intraperitoneally (IP), or with murine erythroid cells presenting 4-1BBL and IL-15/IL-15RA ("IL-15TP") administered IV in combination with αPD-1 administered IP. Murine erythroid cells without 4-1BBL and IL-15/IL-15RA were used as a control ("mRBC-CTRL"). For dosing animals, an average of 1e9 erythroid cells were administered per dose with an average of 30,000 molecules per cell of m4-1BBL, and with an average of 35,000 molecules per cell of IL-15TP.

Animal weight and condition was recorded daily, and tumors were measured 3 times per week by measuring each tumor in 2 dimensions. Tumor volumes were calculated using the standard formula: $(L\times W^2)/2$. The mean tumor weight and standard error of the mean were calculated for each group at each time point. Body weight was recorded daily. Changes in body weight were calculated for each mouse relative to the body weight recorded on day 1 (the indicated treatment days commence from the day in which the desired tumor volume was observed). Spleens and tumors from the tumor bearing mice were harvested and a cell suspension from both tissues was generated for analysis by flow cytometry on day 11. Total number of proliferative CD8 T cells (Ki67+) and functional CD8 T cells (Granzyme B+) were analyzed.

Figure 17A:
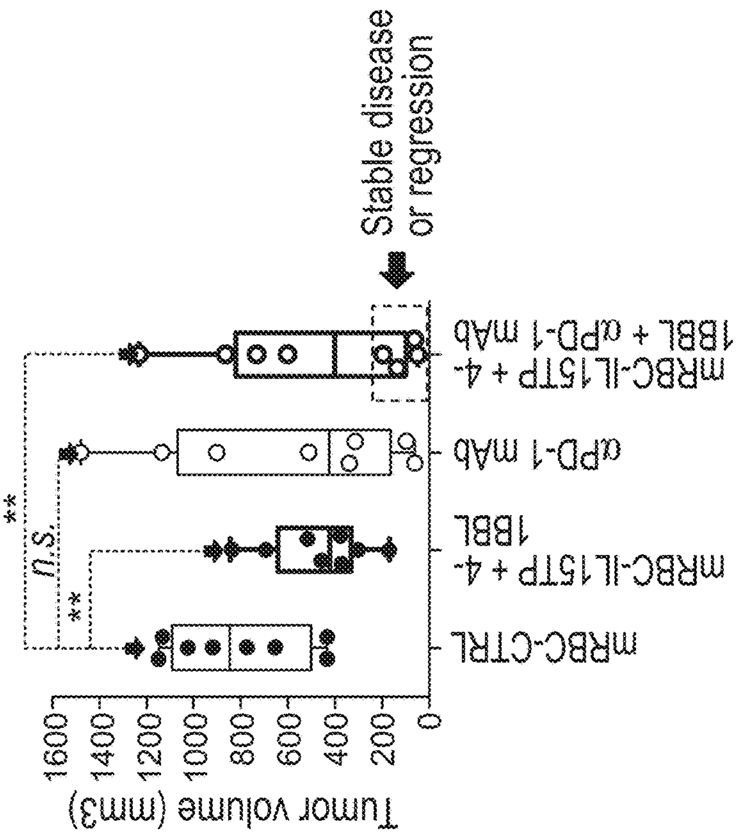
FIG. 17A is a graph showing the efficacy of murine erythroid cells prepared to present IL-15/IL-15RA and 4-1BBL together on the surface of the erythroid cells in the CT26 colon cancer murine model.
Figure 17B:
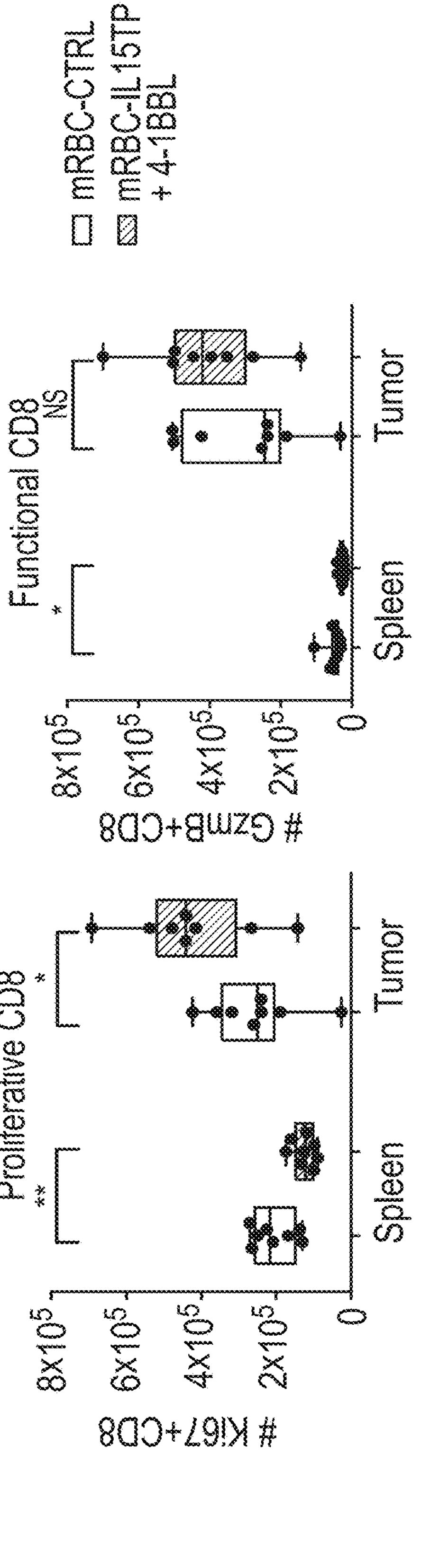
FIG. 17B is a panel of 2 graphs showing the infiltration of proliferating (left) and functional (right) cytotoxic CD8 T cells into the tumors of mice treated with murine erythroid cells prepared to present IL-15/IL-15RA and 4-1BBL together on the surface of the erythroid cells, in the CT26 colon cancer murine model.

The anti-tumor activity of prepared murine erythroid cells presenting 4-1BBL and IL-15/IL-15RA compared to controls was determined by assessing the change in tumor volume and/or tumor weight over time. As shown in FIG. 17A (data shown is at day 13, and each point represents a tumor in 1 mouse), murine erythroid cells prepared to present 4-1BBL and IL-15/IL-15RA administered i.v. as a monotherapy or in combination with an anti-PD1 antibody reduced tumor burden in the CT26 colon cancer mouse model. Treatment with the combination of murine erythroid cells presenting 4-1BBL and IL-15/IL-15RA and anti-PD1 antibody resulted in a higher number of mice with stable disease or tumor regression compared to either the prepared erythroid cells or the anti-PD1 antibody alone. Furthermore, the tumor growth inhibition by 4-1BBL and IL-15/IL-15RA was accompanied by a 1.7-fold increase in the tumor infiltration of proliferating and cytotoxic CD8 T cells (FIG. 17B).

Example 20. Lack of Toxicity of Murine Erythroid Cells Comprising IL-15/IL-15RA and 4-1BBL In Vivo A mouse model of liver toxicity was used to assess the lack of toxicity or tolerability of murine RBC-4-1-BBL and IL-15/IL-15RA (Niu et al J Immunology 2007 178:4194-4213, the entire content of which is incorporated herein by reference). Briefly, 6 to 12 week old female C57BL/6 mice were dosed with the following: murine erythroid cells presenting 4-1BBL and IL-15/IL-15RA (1E9 cells), murine erythroid cells without 4-1BBL and IL-15/IL-15RA, anti-PD1 antibody at 150 μg, murine erythroid cells presenting 4-1BBL and IL-15/IL-15RA (1E9 cells) and anti-PD1 antibody at 150 ug, or with 3H3 antibodies at 50 ug or 200 ug, or with saline, as controls. Animal weight and condition was recorded daily. Dosing was conducted on days 1, 4, 8 and 11, and final sacrifice was conducted on day 18. The livers and serum were collected, and analysis for macrophages and CD8 infiltration was conducted on the liver following liver digestion and processing to single cell suspension. Additionally, the levels of the liver transaminase ALT in the serum were quantified.

As shown in FIG. 18, favorable tolerability of murine RBC-4-1BBL+IL/15/IL-15RA was observed. Levels of the alanine transaminase (ALT) liver enzyme were not significantly elevated following administration of murine RBC-4-1BBL+IL-15/IL-15RA. In contrast, significant elevation of this liver enzyme was observed after administration of the 4-1BB agonist monoclonal antibody, 3H3. Liver infiltration of macrophages, CD8+ T cells, and in particular, CD8+/Eomes+/KLGR1+ T cells are thought to be critical to 4-1BBL induced liver toxicity. As expected, increased liver infiltration of all of these populations was observed following the treatment with the 4-1BB agonist antibody 3H3. Importantly, there was no increased liver infiltration of any of these populations following the administration of murine RBC-4-1BBL+IL-15/IL-15RA. These results indicate that the potent stimulation of CD8 positive T cells that was observed in vivo with murine RBC-4-1BBL+IL-15/IL-15RA is not accompanied by the liver toxicities that have been associated with administration of other 4-1BB agonists. While not wishing to be bound by theory, it is believed that the RBC-41BBL+IL-15/IL-15RA is sequestered in the blood vessels, unlike 4-1BB agonist antibodies, which are believed to cause liver toxicity by diffusing from blood vessels to the bone marrow where they activate and expand myeloid cells, which in turn traffic to the liver to become Kupfer cells, and activate CD8 cells. The data presented herein suggests that RBC-4-1BBL+IL-15/IL-15RA does not stimulate the bone marrow derived monocytes, consistent with the hypothesis that activation occurs in the bone marrow, which has limited exposure to RBC-4-1BBL+IL-15/IL-15RA. Thus, the RBCs presenting 4-1BBL provided herein provide a significant therapeutic advantage over other 4-1BB agonists.

For example, in Example 15, the tumor burden reduction that was achieved after administration of 4-1BB agonist monoclonal antibody at a dose level equivalent to that which generated hepatotoxicity in mice, was not significantly different from the tumor burden reduction achieved with murine RBC-4-1BBL+IL-15/IL-15RA. Similarly, in Example 19, the anti-tumor activity that was achieved after administration of 4-1BB agonist monoclonal antibody at a dose level equivalent to that which generated hepatotoxicity in mice was not significantly different from the tumor burden reduction achieved with murine RBC-4-1BBL+IL-15/IL-15RA. As murine RBC-4-1BBL+IL-15/IL-15RA did not generate liver toxicity in mice, this observation supports that RBC-4-1BBL+IL-15/IL-15RA may have an improved therapeutic index, or improved risk-benefit, over agonistic 4-1BB antibodies in cancer patients.

Figure 18A:
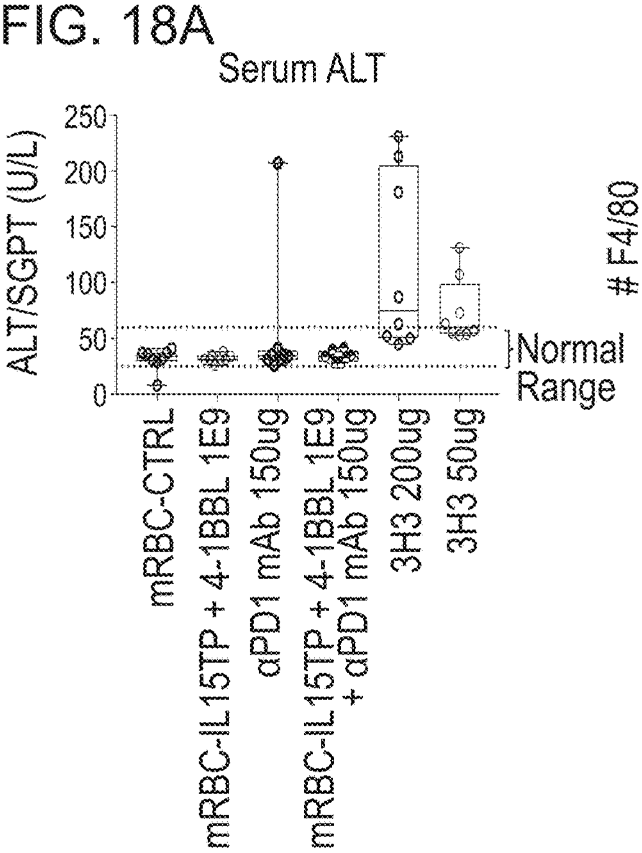
FIG. 18A-FIG. 18E are panels of graphs showing murine erythroid cells prepared to present 4-1BBL and IL-15/IL-15RA do not cause liver toxicity in mice in contrast to anti-4-1BB mAb, 3H3. Levels of the liver enzyme alanine transaminase in serum (ALT/SGPT) (FIG. 18A), liver macrophages (FIG. 18B), liver CD8+/Eomes+/KLRG1+ cells (FIG. 18C), and liver infiltrating T cells (CD8+ T cells) (FIG. 18D) were measured. Liver staining and the inflammation scores were also determined (FIG. 18E).
Figure 18B:
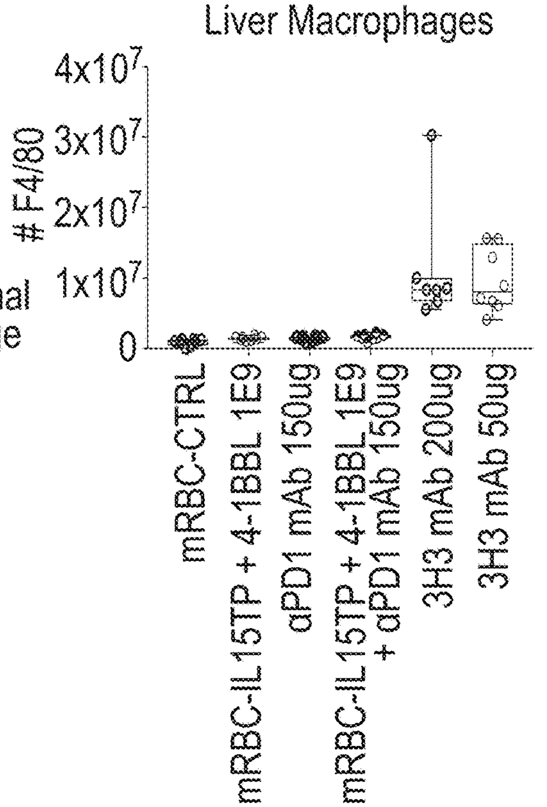
Figure 18C:
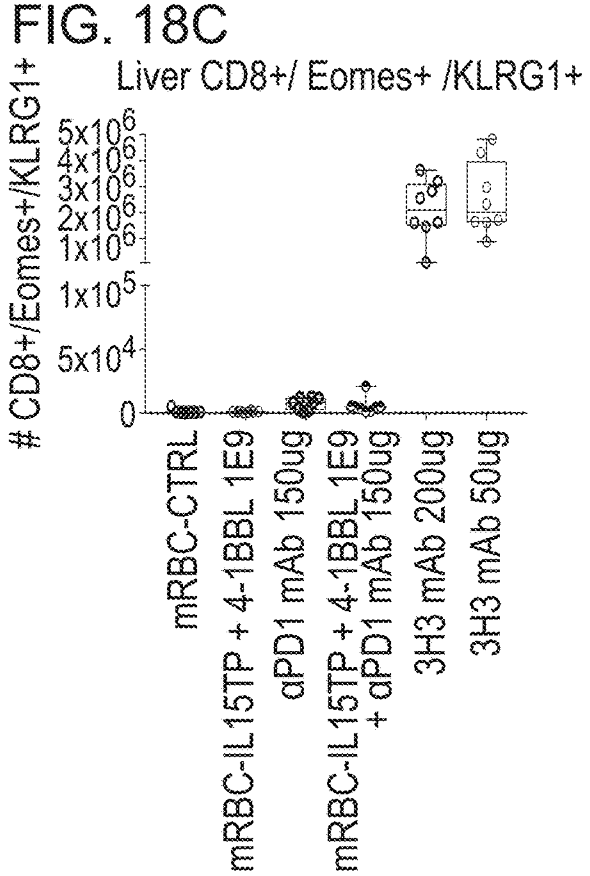
Figure 18D:
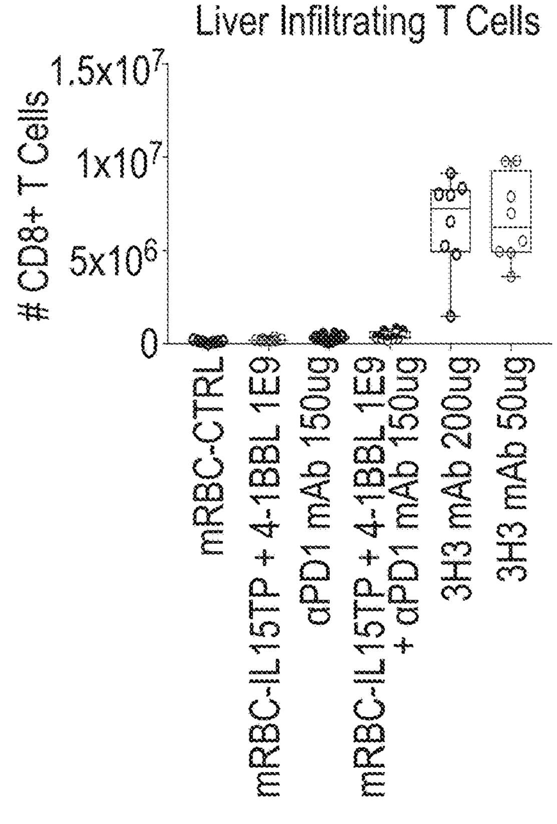
Figure 18E:
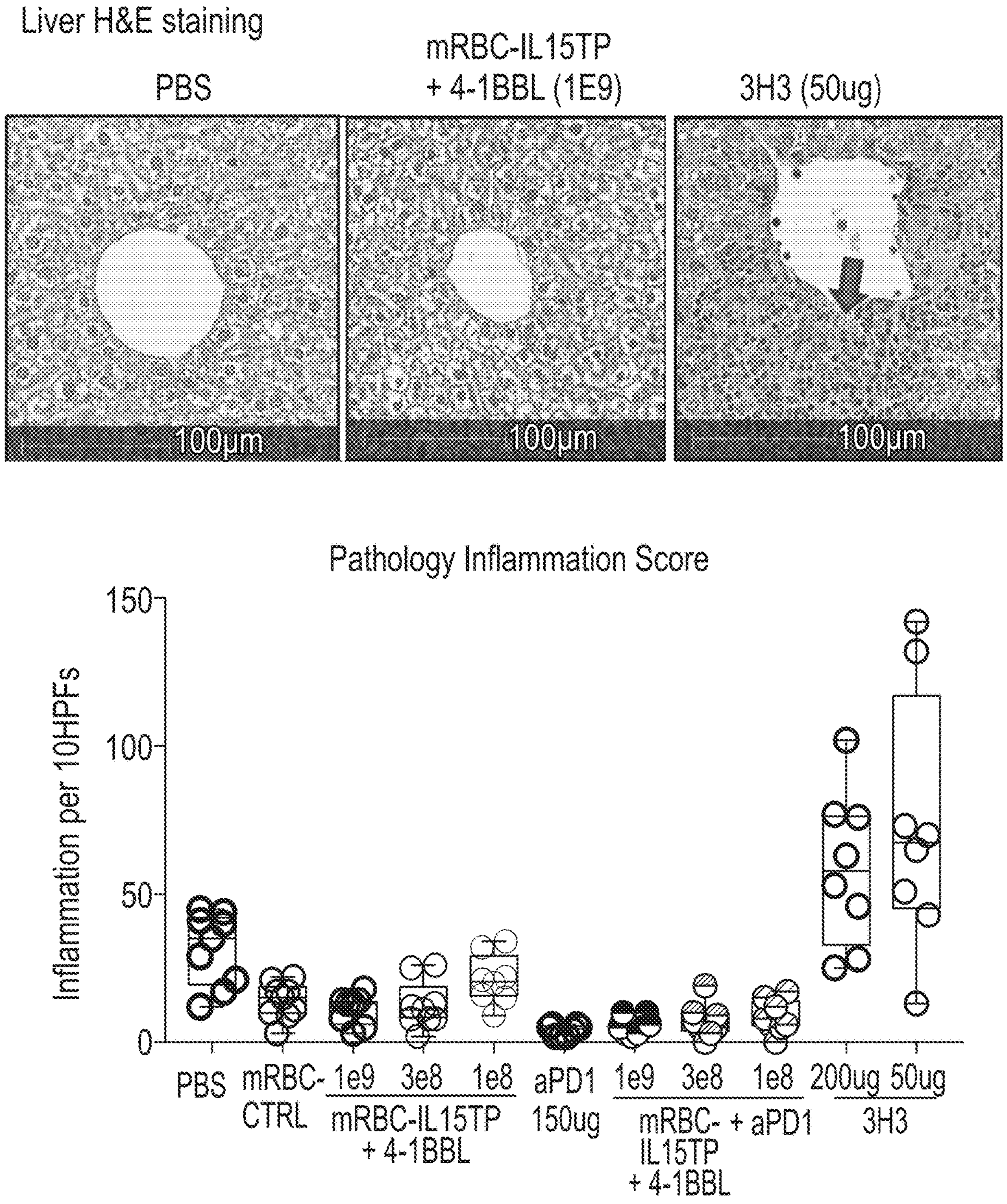
Figure 18F:
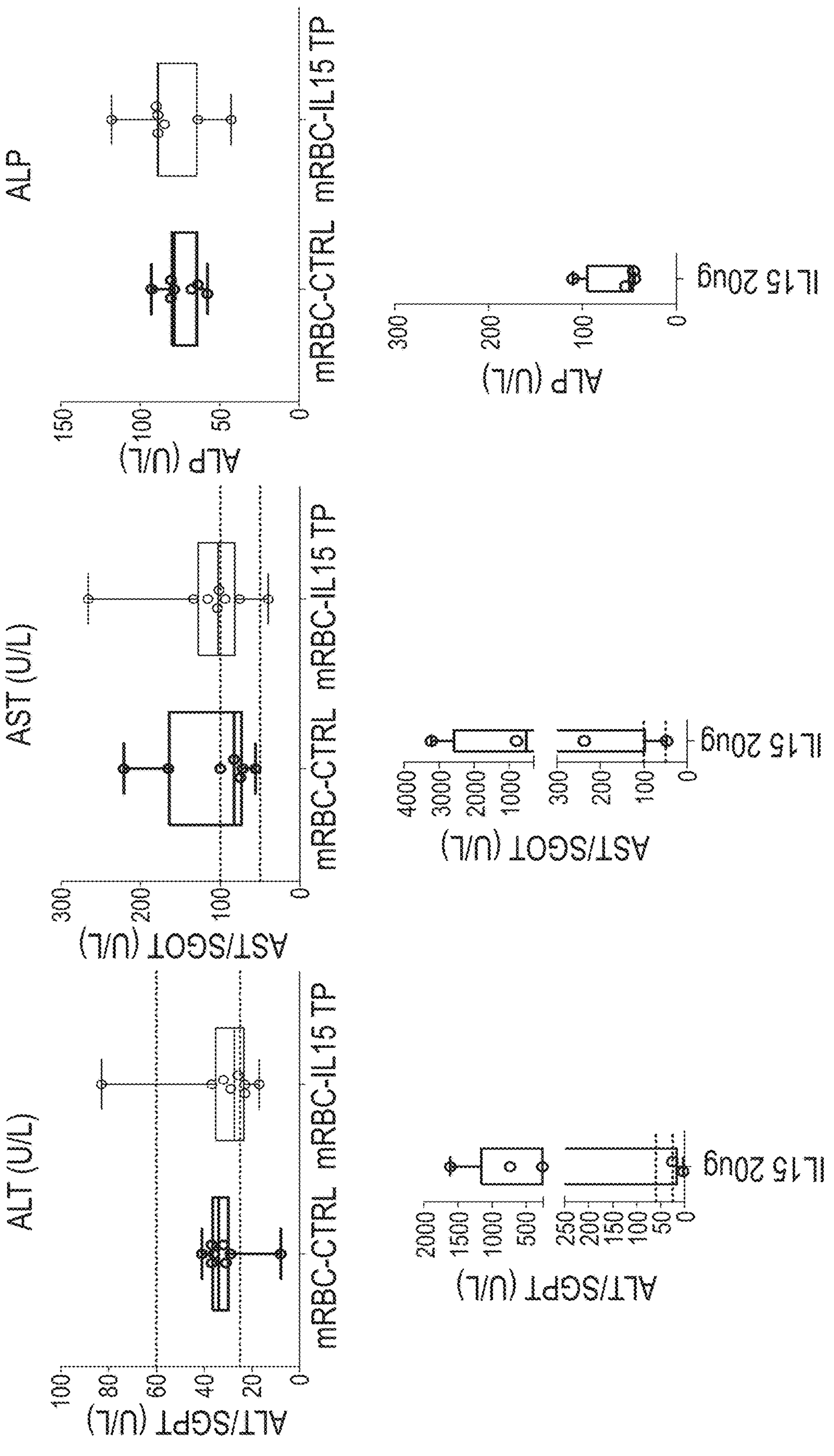
FIG. 18F is a panel of graphs showing murine erythroid cells prepared to present IL-15/IL-15RA do not cause liver toxicity in mice in contrast to soluble IL-15.
Figure 19A:
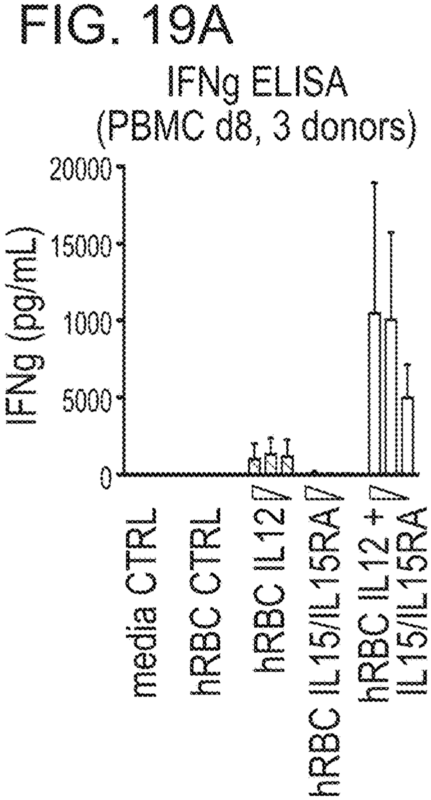
FIG. 19A-FIG. 19E are graphs showing that the expression of IL-12 and IL-15/IL-15RA on the surface of engineered erythroid cells synergistically induces INFg secretion, as measured by ELISA (FIG. 19A), and drives a highly potent immune-response via proliferation of CD8 (FIG. 19B), CD4 (FIG. 19C), NK (FIG. 19D) and NKT (FIG. 19E) cells.
Figure 19B:
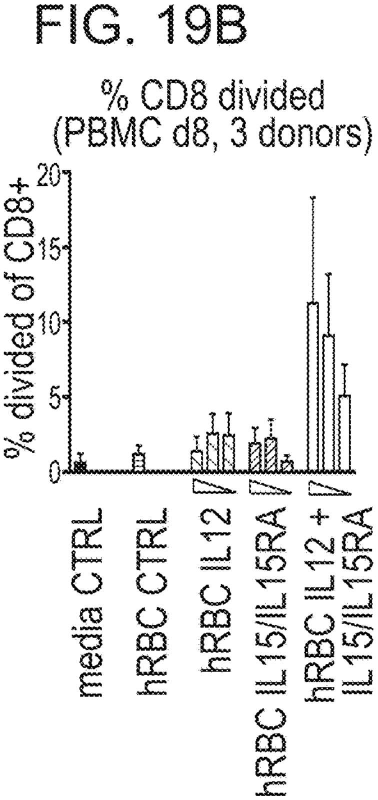
Figure 19C:
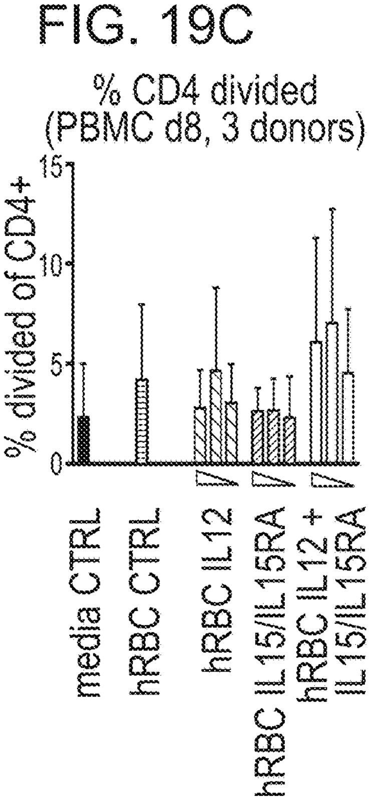
Figure 19D:
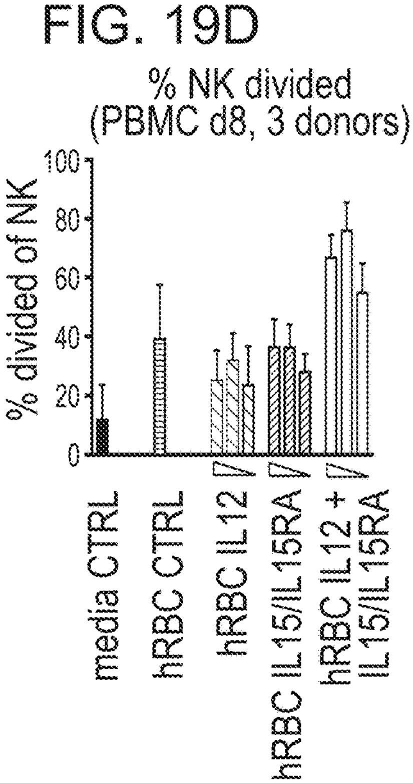
Figure 19E:
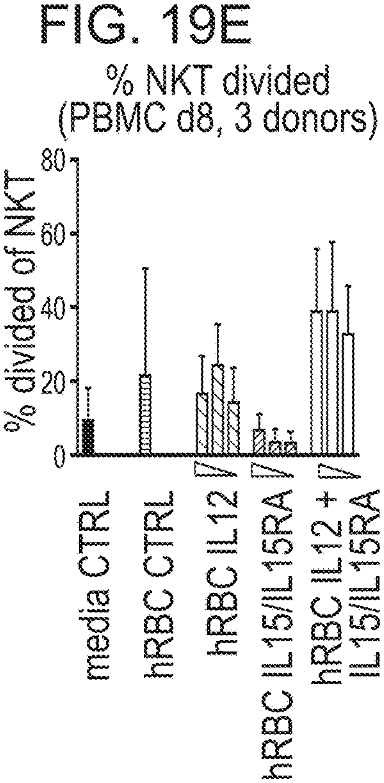

In addition to the analysis above, liver H&E staining sections were evaluated by a pathologist and assigned inflammation scores. These results revealed a significant increase in liver pathology for 3H3 groups as can be seen by increased inflammation score (FIG. 18E). Importantly, RBC-4-1BBL+IL-15/IL-15RA groups did not show signs of increased inflammation or toxicity compared with mRBC-CTRL or the PBS control group. For the 3H3 groups, the pathology report described a prominent perivascular infiltrate that appears to be primarily lymphocytic in nature.

Taken together the data presented show that RBC-4-1BBL+IL-15/IL-15RA was well tolerated and did not raise any safety concerns. The mechanism for lack of toxicity despite using 41BBL and IL-15TP could be the biodistribution of RBC-4-1BBL+IL-15/IL-15RA that is confined to the circulation, and so the cells can't interact with myeloid cells in the bone marrow, a process suggested to initiate the liver toxicity cascade, and offers a significant therapeutic advantage over other 4-1BB agonists.

Example 21. Generation of Erythroid Cells Genetically Engineered to Express IL-12. IL-12 Constructs DNA constructs were prepared for expression in erythroid cells as shown in Table 13 below:

TABLE 13

IL-12 constructs and polypeptides. SEQ ID NOs. refer to amino acid sequences.

| Construct/ Polypeptide | Description | SEQ ID NO: |
|---|---|---|
| IL-12 V1 | GPA signal peptide (SEQ ID NO: 21)-IL-12 p40 (SEQ ID NO: 45) – flexible linker (SEQ ID NO: 12)-IL-12 p35 (SEQ ID NO: 47)-IL-12 linker (SEQ ID NO: 51)-GPA (SEQ ID NO: 25) | 53 |
| IL-12 V2 | SMIM1 (SEQ ID NO: 49) – flexible linker (SEQ ID NO: 12)-IL12 p40 (SEQ ID NO: 45) – flexible linker (SEQ ID NO: 12) – IL-12 p35 (SEQ ID NO: 47) | 55 |
| IL-12 p40/IL-12 p35 fusion polypeptide | IL-12 p40 (SEQ ID NO: 45) – flexible linker (SEQ ID NO: 12)-IL-12 p35 (SEQ ID NO: 47) | 57 |

Production of Lentiviral Vector

IL-12 gene constructs were constructed (V1 or V2 as shown in Table 13). Genes were cloned into the multiple cloning site of lentivirus vector pCDH with the MSCV promoter sequence from System Biosciences. Lentivirus was produced in 293T cells by transfecting the cells with pPACKH1 (System Biosciences) and pCDH lentivirus vector containing IL-12 genes. Cells were placed in fresh culturing medium. The virus supernatant was collected 48 hours post-medium change by centrifugation at 1,500 rpm for 5 minutes. The supernatant was collected, filtered, and frozen in aliquots at −80° C.

Expansion and Differentiation of Erythroid Cells

Human CD34+ cells derived from mobilized peripheral blood cells from normal human donors were purchased frozen from AllCells Inc. The expansion/differentiation procedure comprises 3 stages. In the first stage, thawed CD34+ erythroid precursors were cultured in Iscove's MDM medium comprising recombinant human insulin, human transferrin, recombinant human recombinant human stem cell factor, and recombinant human interleukin 3. In the second stage, erythroid cells were cultured in Iscove's MDM medium supplemented with recombinant human insulin, human transferrin, human recombinant stem cell factor, human recombinant erythropoietin, and L-glutamine. In the third stage, erythroid cells were cultured in Iscove's MDM medium supplemented with human transferrin, recombinant human insulin, human recombinant erythropoietin, and heparin. The cultures were maintained at 37° C. in 5% CO2 incubator.

Transduction of Erythroid Precursor Cells

Erythroid precursor cells were transduced during step 1 of the culture process described above. Erythroid cells in culturing medium were combined with lentiviral supernatant and polybrene. Infection was achieved by spinoculation, spinning the plate at 2000 rpm for 90 minutes at room temperature. After spinoculation, the cells were incubated at 37° C. overnight.

Antibody Binding

Binding of a PE-labelled anti-IL-12 antibody (e.g., purified anti-human IL-12-p'70 (clone 20C2) was used to validate expression of IL-12 in the engineered erythroid cells. Binding of the antibody was measured by flow cytometry for PE fluorescence. A gate was set based on stained untransduced cells.

Example 22. Generation of Erythroid Cells Genetically Engineered to Express IL-12 and 4-1BBL Production of Lentiviral Vectors IL-12 (V1 or V2 as shown in Table 13) and 4-1BBL genes were constructed. Genes were cloned into the multiple cloning site of lentivirus vector pCDH with the MSCV promoter sequence from System Biosciences such that one vector comprises the gene for IL-12 and one vector comprises the gene for 4-1BBL. Lentivirus was produced in 293T cells by co-transfecting the cells with pPACKH1 (System Biosciences) and pCDH lentivirus vector containing the IL-12 gene and pCDH lentivirus vector containing the 4-1BBL gene. Cells were placed in fresh culturing medium. The virus supernatant was collected 48 hours post-medium change by centrifugation at 1,500 rpm for 5 minutes. The supernatant was collected, filtered, and frozen in aliquots at −80° C.

It will be recognized that, alternatively, IL-12 and 4-1BBL genes can be constructed and cloned into the multiple cloning site of lentivirus vector pCDH with the MSCV promoter sequence from System Biosciences such that one vector comprises the gene for IL-12 and the gene for 4-1BBL. In that case, lentivirus is produced in 293T cells by co-transfecting the cells with pPACKH1 (System Biosciences) and pCDH lentivirus vector containing both the IL-12 gene and 4-1BBL gene. Cells are placed in fresh culturing medium. The virus supernatant is collected 48 hours post-medium change by centrifugation at 1,500 rpm for 5 minutes. The supernatant is collected, filtered, and frozen in aliquots at −80° C.

Expansion and Differentiation of Erythroid Cells

Human CD34+ cells derived from mobilized peripheral blood cells from normal human donors were expanded and differentiated as described in Example 21.

Transduction of Erythroid Precursor Cells

Erythroid precursor cells were transduced during step 1 of the culture process described above. Erythroid cells in culturing medium were combined with lentiviral supernatant and polybrene. Infection was achieved by spinoculation, spinning the plate at 2000 rpm for 90 minutes at room temperature. After spinoculation, the cells were incubated at 37° C. overnight.

Antibody Binding

Binding of a PE-labelled anti-IL-12 antibody (e.g., anti-IL-12 antibody (IL-12-p'70 (clone 20C2) was used to validate expression of the IL-12 in the engineered erythroid cells. Binding of a PE-labelled anti-4-1BBL antibody (e.g., purified anti-human 4-1BB Ligand (CD137L) antibody, BioLegend) was used to validate expression of 4-1BBL in the engineered erythroid cells. Binding of the antibody was measured by flow cytometry for PE fluorescence. A gate was set based on stained untransduced cells.

Figure 30A:
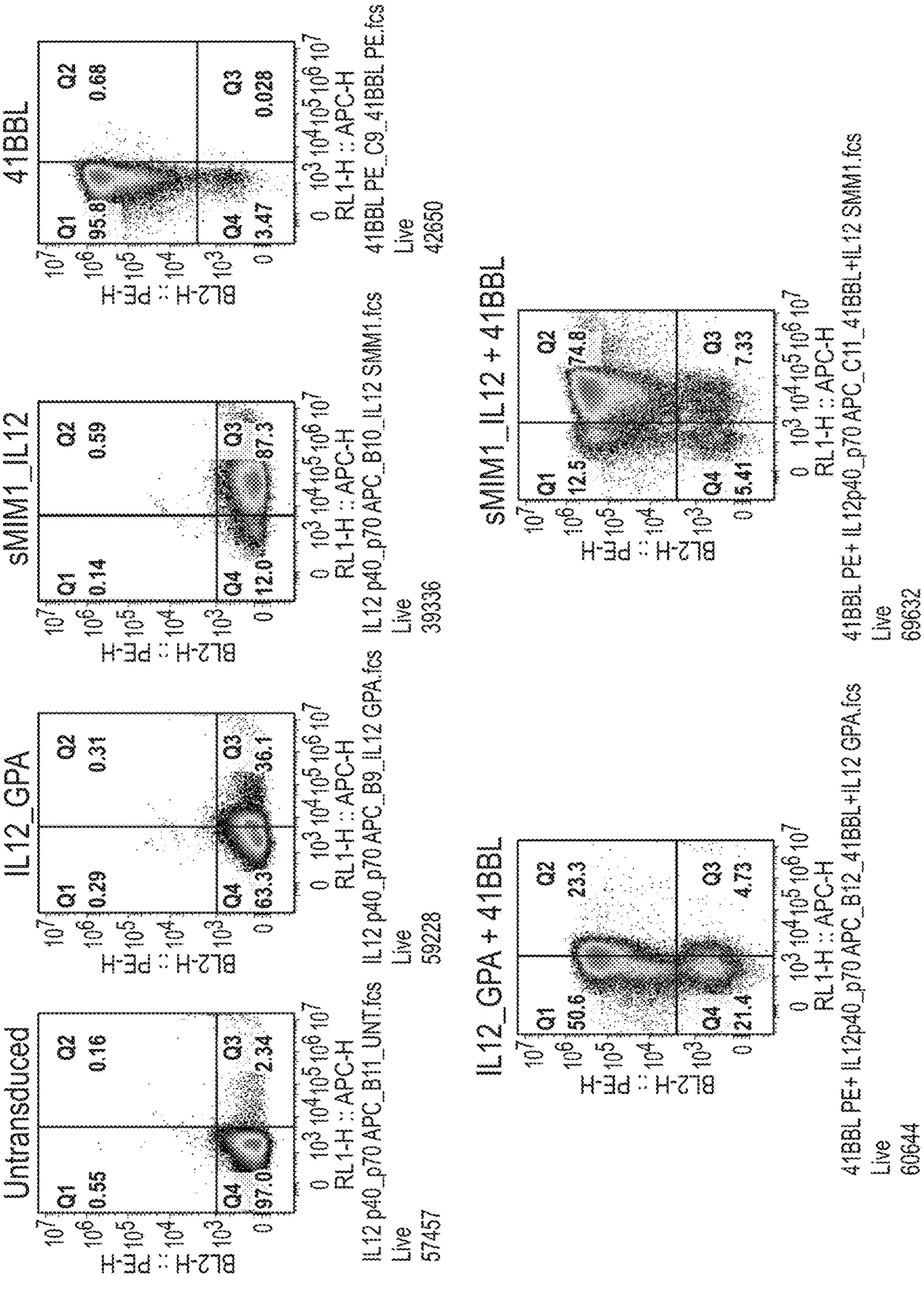
FIG. 30A is a graph showing that IL-12 V2 (IL-12 linked to SMIM1) was observed to exhibit significantly greater IL-12 at the cell surface relative to IL-12 V1 (IL-12 linked to GPA), alone or in combination with 4-1BBL.
Figure 30B:
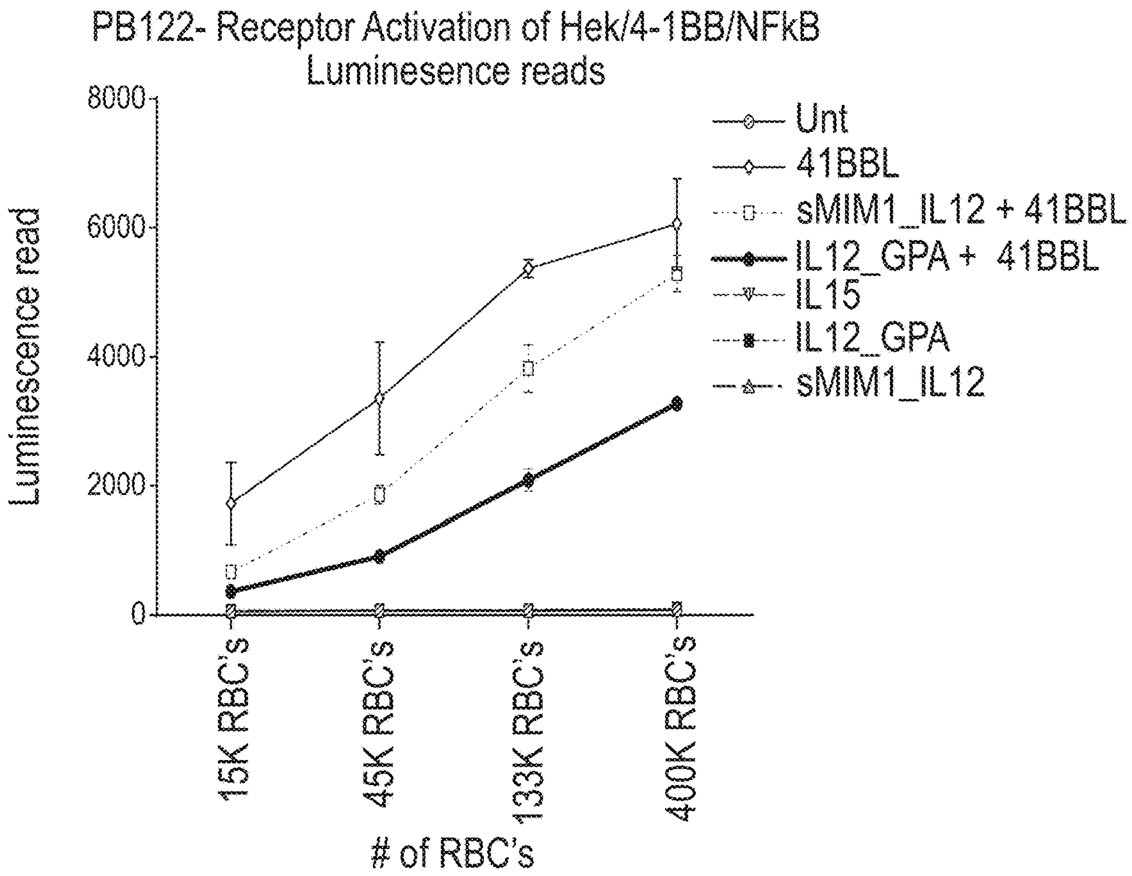
FIG. 30B is a graph showing that the increased level of IL-12 on the cell surface, when SMIM1 is used as the membrane domain, provides an enhanced activity of NFκB signaling.
Figure 30B:
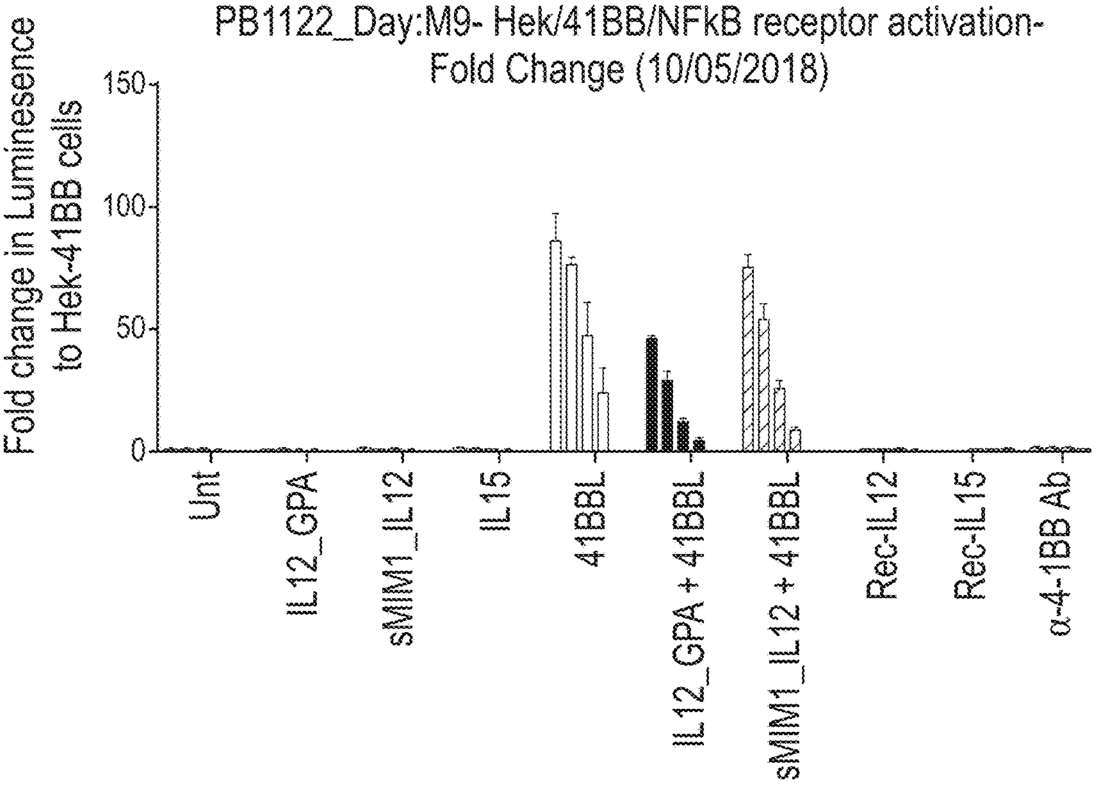

As shown in FIG. 30A, IL-12 V2 (IL-12 linked to SMIM1) was observed to exhibit significantly greater IL-12 at the cell surface relative to IL-12 V1 (IL-12 linked to GPA), alone or in combination with 4-1BBL. This increased level of IL-12 on the cell surface, when SMIM1 is used as the membrane domain, provides an unexpected advantage of increased copy number of 4-1BBL on the surface of erythroid cells, and thus, expected enhanced activity as well (FIG. 30B).

Example 23. Generation of Erythroid Cells Genetically Engineered to Express an IL-15/IL-15-RA Fusion Protein and IL-12

Production of Lentiviral Vectors

IL-15/IL-15-RA (V4.1) fusion protein and IL-12 genes were constructed. Genes were cloned into the multiple cloning site of lentivirus vector pCDH with the MSCV promoter sequence from System Biosciences such that one vector comprises the gene for IL-15/IL-15RA and one vector comprises the gene for IL-12. Lentivirus was produced in 293T cells by co-transfecting the cells with pPACKH1 (System Biosciences) and pCDH lentivirus vector containing IL-15/IL-15-RA gene and pCDH lentivirus vector containing IL-12 gene. Cells were placed in fresh culturing medium. The virus supernatant was collected 48 hours post-medium change by centrifugation at 1,500 rpm for 5 minutes. The supernatant was collected, filtered, and frozen in aliquots at −80° C.

It will be recognized that, alternatively, IL-15/IL-15-RA fusion protein and IL-12 genes can be constructed and cloned into the multiple cloning site of lentivirus vector pCDH with the MSCV promoter sequence from System Biosciences such that one vector comprises the gene for IL-15/IL-15RA and the gene for IL-12. In that case, lentivirus is produced in 293T cells by co-transfecting the cells with pPACKH1 (System Biosciences) and pCDH lentivirus vector containing both IL-15/IL-15-RA gene and IL-12 gene. Cells are placed in fresh culturing medium. The virus supernatant is collected 48 hours post-medium change by centrifugation at 1,500 rpm for 5 minutes. The supernatant is collected, filtered, and frozen in aliquots at −80° C.

Expansion and Differentiation of Erythroid Cells

Human CD34+ cells derived from mobilized peripheral blood cells from normal human donors were expanded and differentiated as described in Example 21.

Transduction of Erythroid Precursor Cells

Erythroid precursor cells were transduced during step 1 of the culture process described above. Erythroid cells in culturing medium were combined with lentiviral supernatant and polybrene. Infection was achieved by spinoculation, spinning the plate at 2000 rpm for 90 minutes at room temperature. After spinoculation, the cells were incubated at 37° C. overnight.

Antibody Binding

Binding of a PE-labelled anti-IL-15-RA antibody (e.g., anti-IL-15RA antibody (JM7A4) (ab91270), AbCam) was used to validate expression of the IL-15/IL-15-RA in the engineered erythroid cells. Binding of a PE-labelled anti-IL-12 antibody (e.g., purified anti-human IL-12 antibody (IL-12-p'70 (clone 20C2)) was used to validate expression of IL-12 in the engineered erythroid cells. Binding of the antibody was measured by flow cytometry for PE fluorescence. A gate was set based on stained untransduced cells.

Example 24. Engineered Erythroid Cells Comprising a Combination of IL-12 and IL-15/IL-15RA Causes Synergistic Induction of IFNγ Response and Proliferation of CD4, CD8, NK and NKT Cells Erythroid cells comprising IL-12, IL-15/IL-15RA (V4.1), and IL-12+IL-15/IL-15RA (V4.1) were prepared as described in Examples 21, 1 and 23, respectively.

The proliferation and activation of primary CD4+, CD8+, NK and NKT cells were measured. 100,000 PBMCs from 3 donors were labelled with CTFR and incubated with engineered erythroid cells comprising IL-12 ("RBC-IL-12"), IL-15/IL-15RA ("RBC-IL-15/IL-15RA"), and IL-12+IL-15/IL-15RA ("RBC-IL-12+IL-15/IL-15RA"), control RBC ("RBC-CTRL"), and media control ("media CTRL"). RBC were present at 400,000, 200,000 or 100,000 cells. On day 8, the percentage of CD8, CD4, NK and NKT that were actively dividing was evaluated using CTFR dilution. Supernatant was collected and the amount of IFNγ was evaluated using ELISA. As shown in FIG. 19A-E, RBC-IL-12+IL-15/IL-15RA stimulated primary CD4+, CD8+, NK and NKT cells to potently proliferate as well as become activated, as measured by the production of the IFNγ cytokine released by activated cells. RBC-IL-12 and RBC-IL-15/IL-15RA stimulated some measurable proliferation and activation of these cells. However, RBC-IL-12+IL-15/IL-15RA exhibited substantially greater, and in some instances a synergistic, stimulation of proliferation of CD8+, CD4+, NK and NKT cells, as well as a dramatic increase in IFNγ production. Taken together, the results presented in this example show that expression of RBC-IL-12+IL-15/IL-15RA on the surface of RBCs drove a highly synergistic and potent activation of primary CD4+, CD8+, NK and NKT cells.

Example 25. Erythroid Cells Comprising IL-12, IL-15/IL-15RA, 4-1BBL and Combinations Thereof Reduce Lung Metastases In Vivo The B16F10 metastatic mouse model system for melanoma (see, e.g., Kubo et al. (2017)) was used to test the effects of murine erythroid cells presenting on the cell surface murine IL-12, human IL-15/IL-15RA fusion protein and murine 4-1BBL, either alone or in combinations, on metastatic growth. In this model, tumor cells were injected intravenously to establish metastases in the lung and then mice were treated with murine erythroid cells prepared to present either IL-12, IL-15/IL-15RA, or 4-1BBL alone, or to present the following combinations: IL-12 and IL-15/IL-15RA (IL-12/IL-15 RBC), IL-12 and 4-1BBL (IL-12/4-1BBL RBC), and IL-15/IL-15RA and 4-1BBL (IL-15/4-1BBL RBC).

Figure 20A:
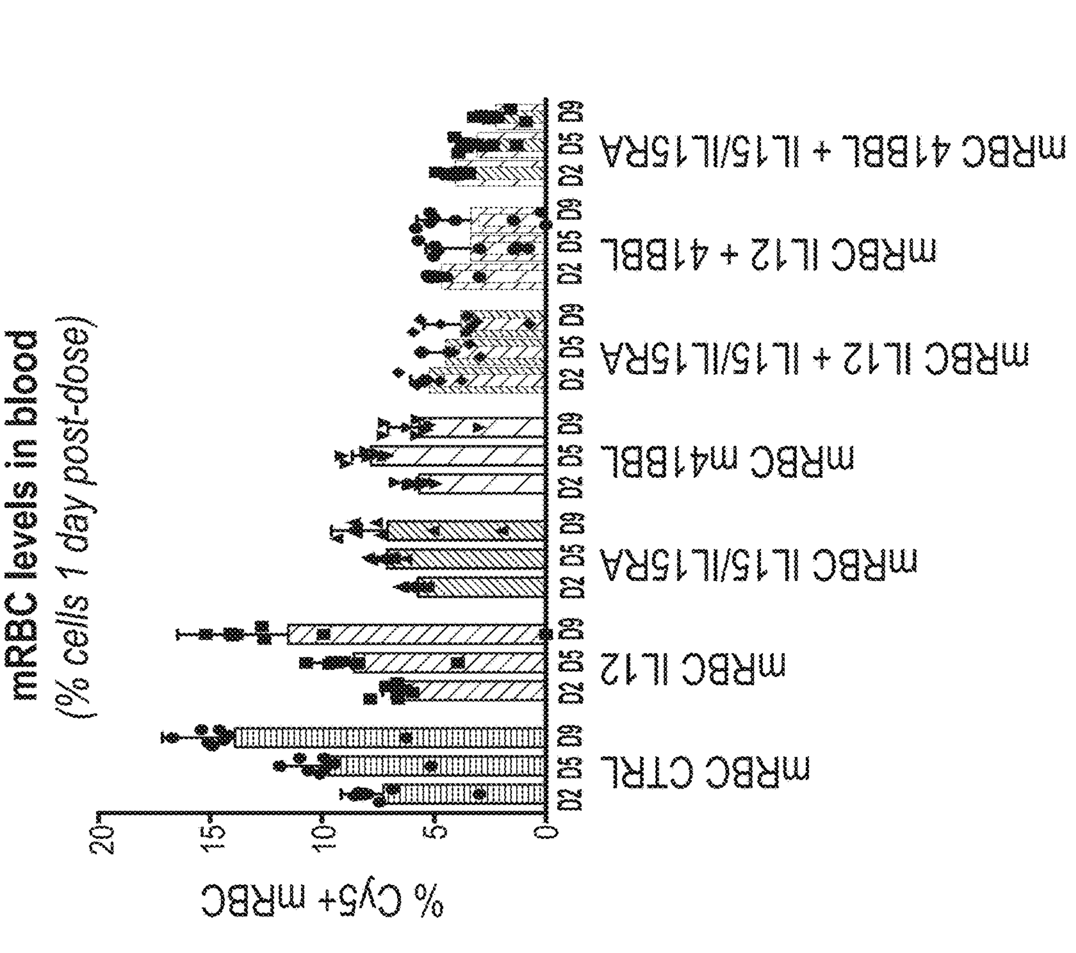
FIG. 20A is a graph showing the percentage of murine erythroid cells conjugated with IL-12, IL-15/IL-15RA, 4-1BBL, or co-conjugated with both IL-12 and IL-15/IL-15RA, IL-12 and 4-1BBL, and IL-15/IL-15RA and 4-1BBL using the click methodology. These cells were quantified by flow cytometry for Cy5 fluorescence.

Murine erythroid cells were conjugated with IL-12, IL-15/IL-15RA, 4-1BBL, or co-conjugated with both IL-12 and IL-15/IL-15RA, IL-12 and 4-1BBL, and IL-15/IL-15RA and 4-1BBL using the click methodology. These cells were quantified by flow cytometry for Cy5 fluorescence (FIG. 20A). The amino acid sequences of the IL-15/IL-15RA fusion protein, murine 4-1BBL protein, and murine 11-12 protein are provided in Table 10 herein.

Initially, 7-week old female C57BL/6 mice were inoculated intravenously with $1\times10^5$ B16F10 cells/mouse. The animals were then dosed intravenously (IV) with the following: with erythroid cells presenting IL-12; with erythroid cells presenting IL-15/IL-15RA; with erythroid cells presenting 4-1BBL; with erythroid cells presenting both IL-12 and IL-15/IL-15RA; with erythroid cells presenting IL-12 and 4-1BBL; with erythroid cells presenting IL-15/IL-15RA and 4-1BBL; with recombinant IL-12 (rIL-12) administered intraperitoneally (IP); with recombinant IL-15/IL-15RA fusion protein administered intraperitoneally (IP); with a mouse 4-1BB agonist antibody (3H3) administered intraperitoneally (IP); or with erythroid cells without IL-12, IL-15/IL-15RA or 4-1BBL (mRBC-CTRL) as control. For dosing animals, an average of 1e9 erythroid cells were administered per dose with an average of 30,000 molecules per cell of IL-12 alone, corresponding to 0.14 mg/kg IL-12 per dose, 120,000 molecules per cell of 4-1BBL alone, corresponding to 0.22 mg/kg 4-1BBL per dose, and 60,000 molecules per cell of IL-15/IL-15RA alone, corresponding to 0.1 mg/kg IL-15/IL-15RA per dose; or for erythroid cells comprising IL-12 and IL-15/IL-15RA, 20,000 molecules of IL-12 and 20,000 molecules of IL-15-RA, corresponding to 0.1 mg/kg and 0.03 mg/kg respectively; for erythroid cells comprising IL-12 and 4-1BBL, 20,000 molecules of IL-12 and 40,000 molecules of 4-1BBL, corresponding to 0.1 mg/kg of both; or for erythroid cells comprising 4-1BBL and IL-15/IL-15RA, 60,000 molecules of 4-1BBL and 40,000 molecules of IL-15/IL-15RA, corresponding to 0.11 mg/kg and 0.07 mg/kg respectively. Agonistic 41BB antibody (3H3) was dosed at 2.5 mg/kg. Animals were dosed with erythroid cells or 3H3 on days 1, 4 and 8 post inoculation.

Animal weight and condition was recorded daily. Changes in body weight were calculated for each mouse relative to the body weight recorded on day 1. On day 14 post inoculation animals were sacrificed and lungs were collected. The number of lung metastases was assessed using a microscope. Additionally, lung tissue was processed to single cell suspensions and was stained for Ki67 and Granzyme B and examined using flow cytometry.

Figure 20B:
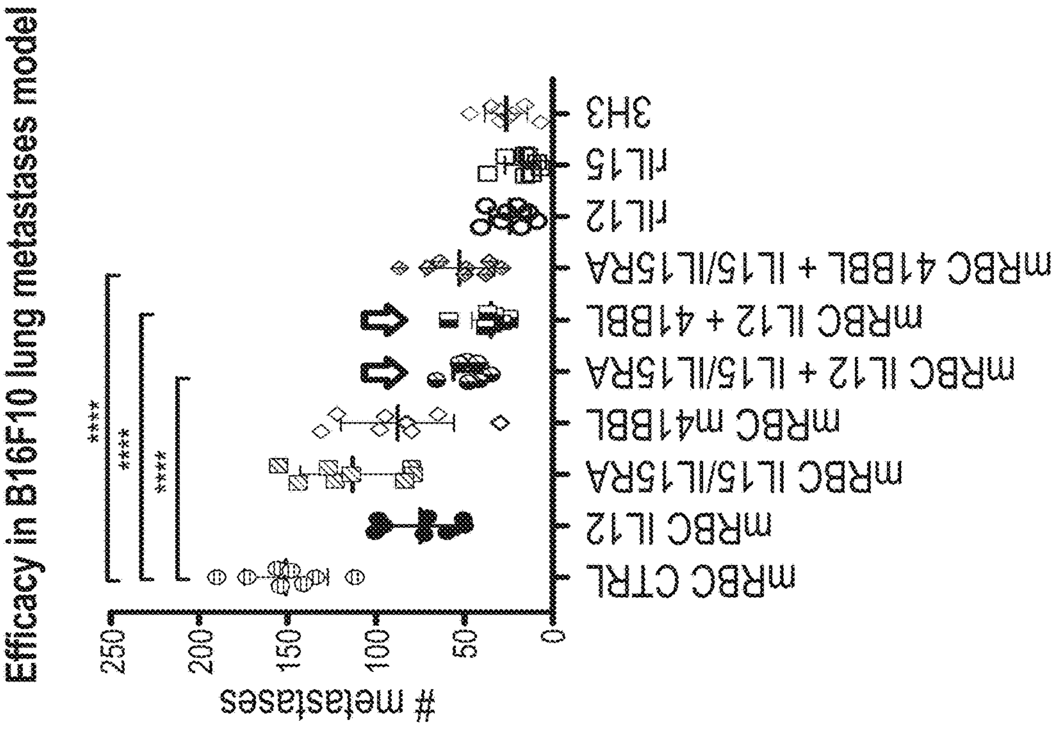
FIG. 20B is a graph showing the efficacy of murine erythroid cells prepared to present IL-12, IL-15/IL-15RA, 4-1BBL and combinations thereof, on the surface of the erythroid cells in the murine B16F10 lung metastasis model.

As shown in FIG. 20B, murine erythroid cells prepared to present a combination of IL-12 and IL-15/IL-15RA, or IL-12 and 4-1BBL, or IL-15/IL-15RA and 4-1BBL on their surface administered i.v. as monotherapy significantly reduced tumor burden in mice as compared to mRBC CTRL, and showed greater efficacy as compared to erythroid cells presenting the molecules individually, i.e., mRBC IL-12, mRBC IL-15/IL-15RA and mRBC 4-1BBL. This data showed that a therapeutic benefit that may be achieved by administering erythroid cells comprising these combinations of proteins on the cell surface. The reduction in tumor burden achieved with the combination of IL-12 and 4-1BBL was significantly better than that achieved with IL-12 or 4-1BBL alone, and the reduction in tumor burden achieved with the combination of 4-1BBL and IL-15/IL-15RA, was significantly better than that achieved with 4-1BBL or IL-15/IL-15RA alone.

Figure 20C:
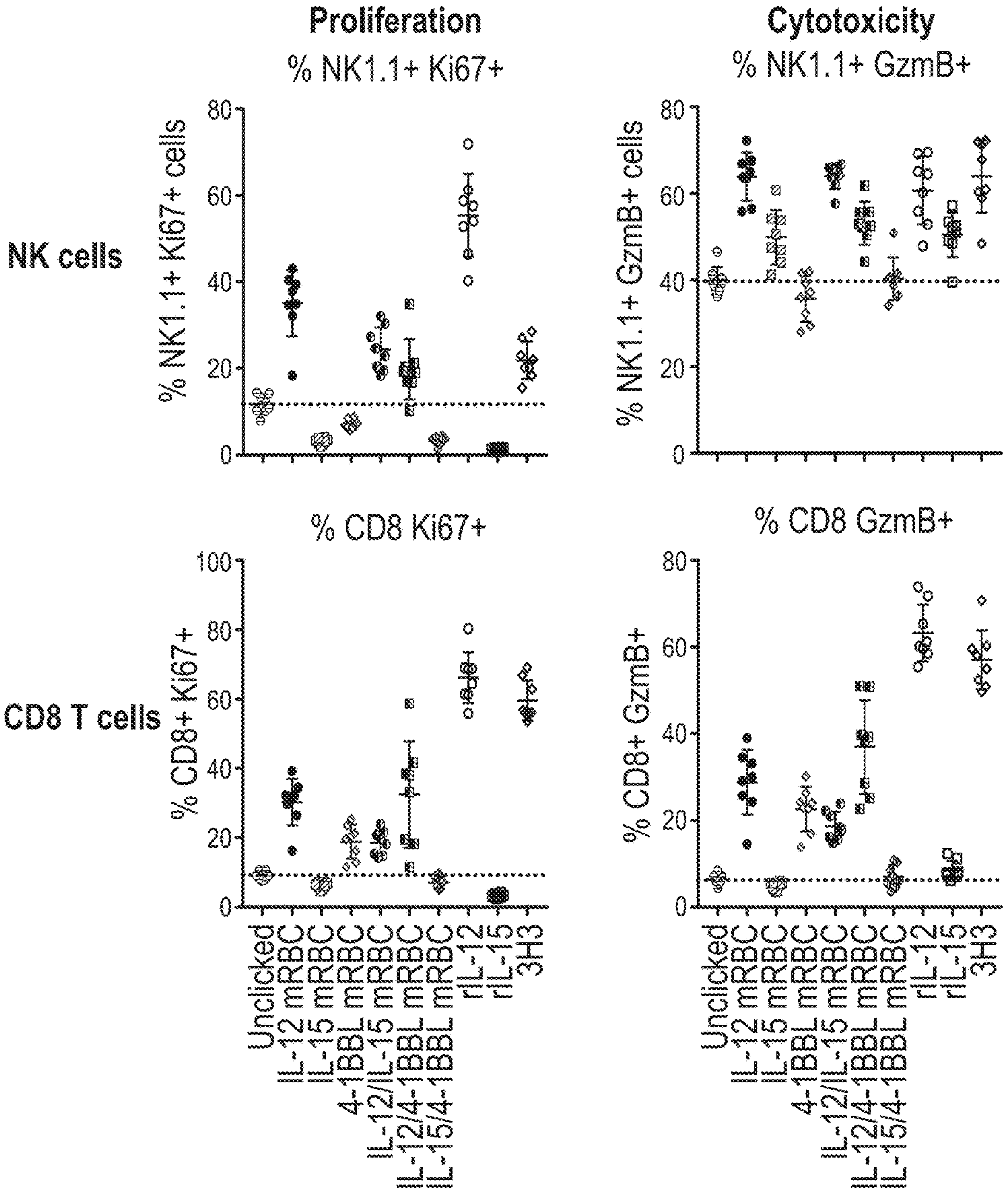
FIG. 20C is a panel of graphs showing that the decrease in the number of lung metastases was associated with infiltration of increased proliferating and cytotoxic CD8 T cells and NK cells in the lungs, in mice treated with murine erythroid cells prepared to present IL-12, IL-15/IL-15RA, 4-1BBL and combinations thereof.

Furthermore, as shown in FIG. 20C, the decrease in the number of lung metastases was associated with increased infiltration of proliferating cytotoxic CD8+ T cells and NK cells in the lungs (p=0.0002).

Example 26. Erythroid Cells Comprising IL-12 Slow Tumor Growth In Vivo

The MC38 syngeneic mouse model system for colon carcinoma as well as the B16F10 tumor model for melanoma were used to test the effects of murine erythroid cells presenting on the cell surface murine IL-12 on tumor growth (e.g., solid tumor growth). Murine erythroid cells were co-conjugated with either human IL-15/IL-15RA and murine 4-1BBL, murine IL-12 and murine 4-1BBL, or murine IL-12 and human IL-15/IL-15RA, using the click methodology. The the amino acid sequences of the IL-15/IL-15RA fusion protein, murine 4-1BBL protein, and murine 11-12 protein are provided in Table 10 herein.

When the tumors reached a volume of approximately 100 $mm^3$ (approximately 7-10 days), the animals were dosed with either erythroid cells presenting either IL-15/IL-15RA and 4-1BBL (mRBC IL-15/IL-15RA+4-1BBL), IL-12 and 4-1BBL (mRBC IL-12+4-1BBL), IL-12 and IL-15/IL-15RA (mRBC IL-12+IL-15/IL-15RA); with erythroid cells without these proteins (mRBC CTRL); or with the 4-1BB agonist monoclonal antibody 3H3, as controls. Dosing was conducted on days 1, 4 and 8 (the indicated treatment days commence from the day in which the desired tumor volume was observed). For dosing animals, an average of 1e9 RBCs were administered per dose with an average number of molecules per cell as follows: for erythroid cells comprising IL-12 and IL-15/IL-15RA, 20,000 molecules of IL-12 and 20,000 molecules of IL-15-RA, corresponding to 0.1 mg/kg and 0.03 mg/kg for each; for erythroid cells comprising IL-12 and 4-1BBL, 30,000 molecules of IL-12 and 80,000 molecules of 4-1BBL, corresponding to 0.14 mg/kg and 0.15 mg/kg respectively; and for erythroid cells comprising 4-1BBL and IL-15/IL-15RA, 80,000 molecules of 4-1BBL and 50,000 molecules of IL-15/IL-15RA, corresponding to 0.15 mg/kg 4-BBL and 0.09 mg/kg respectively, per dose per mouse.

The weight and condition of the animals were recorded daily. Changes in body weight were calculated for each mouse relative to the body weight recorded on day 1. Tumors were measured 3 times per week by measuring each tumor in 2 dimensions. Tumor volumes were calculated using the standard formula: $(L \times W^2)/2$. The mean tumor weight and standard error of the mean were calculated for each group at each time point.

Figure 21A:
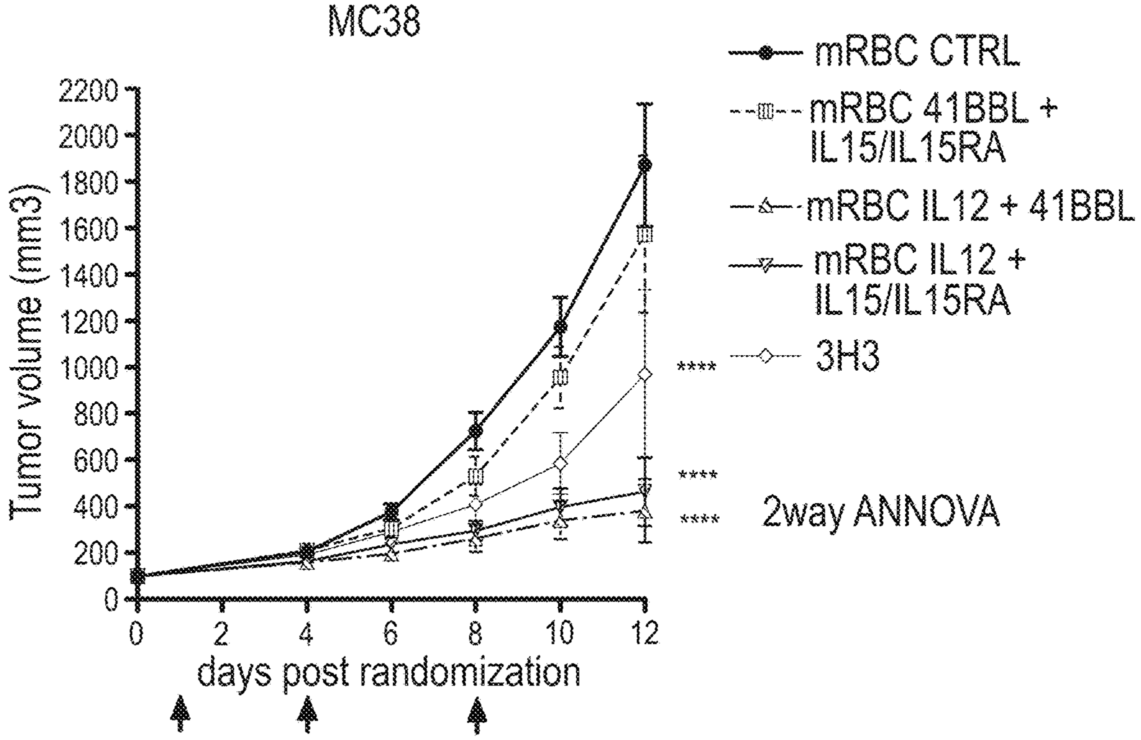
FIG. 21A and FIG. 21B are graphs showing that erythroid cells comprising IL-12 inhibit tumor growth in the MC38 (FIG. 21A) and B16F10 (FIG. 21B) mouse models.
Figure 21B:
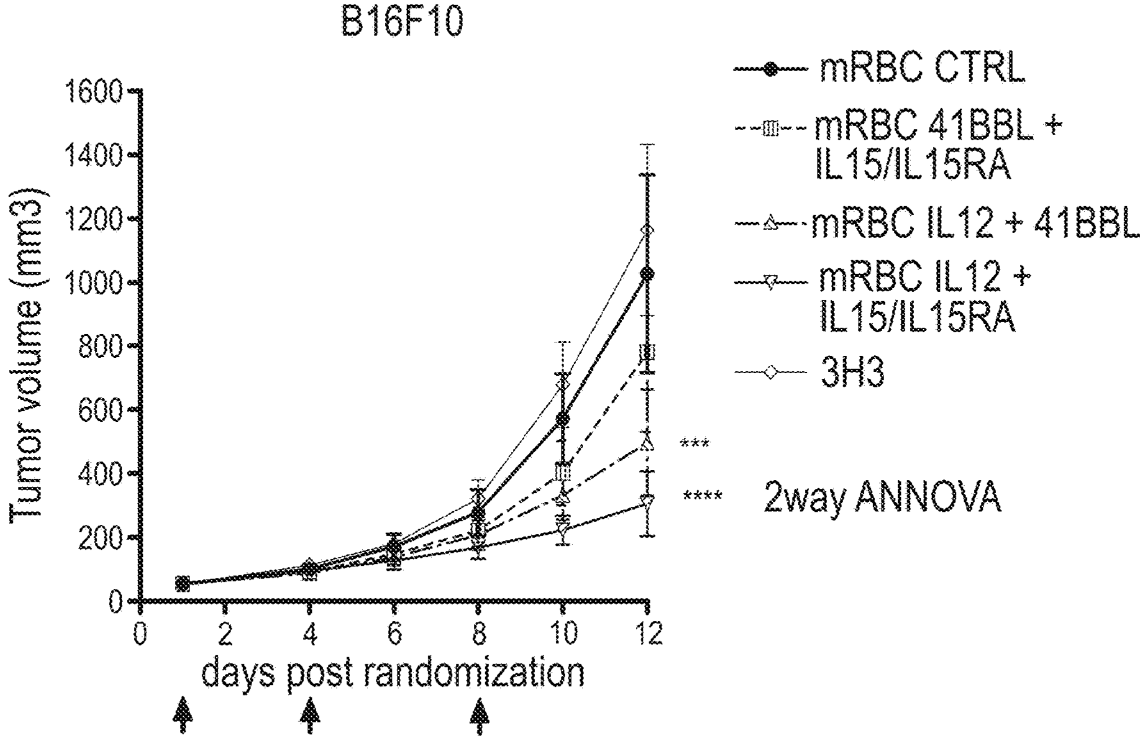
Figure 22A:
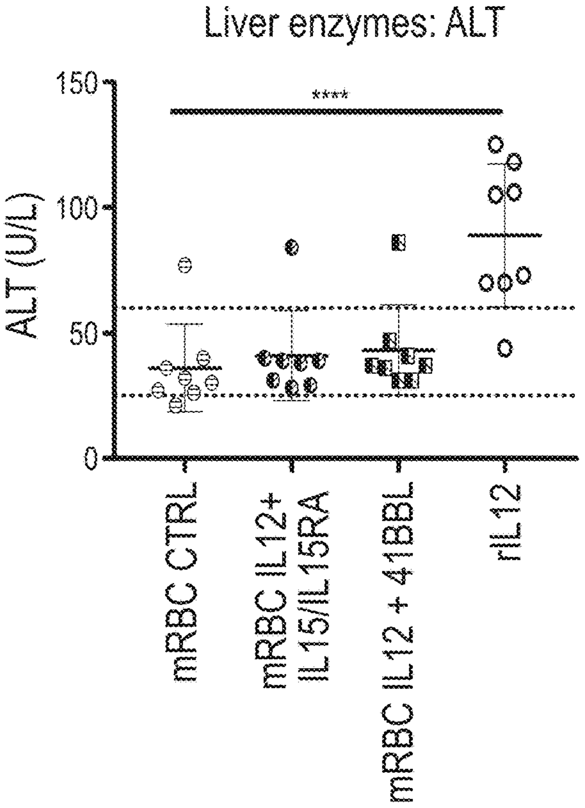
FIG. 22A-FIG. 22D are graphs showing murine erythroid cells prepared to present IL-12 and IL-15/IL-15RA, and IL-12 and 4-1BBL do not cause liver toxicity in mice in contrast to recombinant IL-12 (rIL-12). Levels of the liver enzyme alanine transaminase in serum (ALT) (FIG. 22A), interferon gamma (IFNg) in the serum (FIG. 22B), liver weights (FIG. 22C), and spleen weights (FIG. 22D) were measured.
Figure 22B:
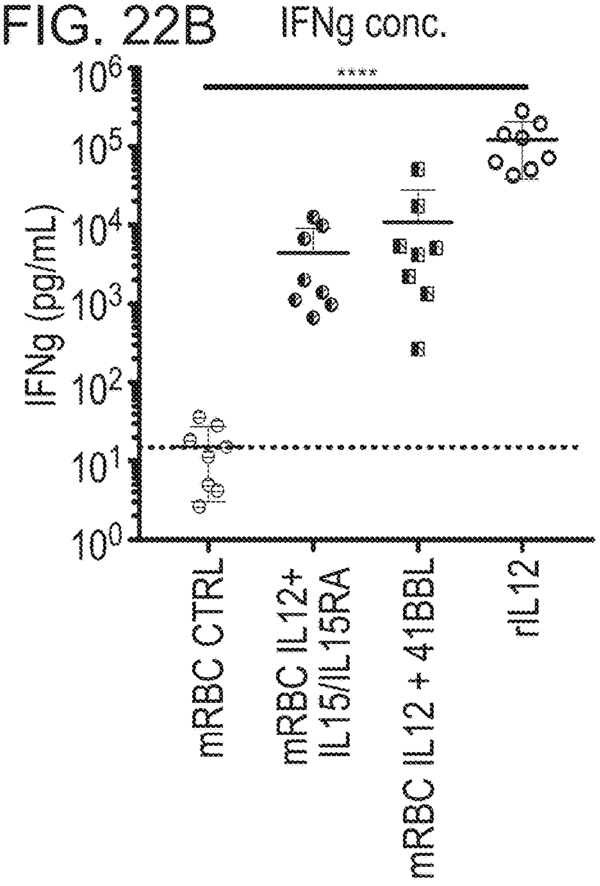
Figure 22C:
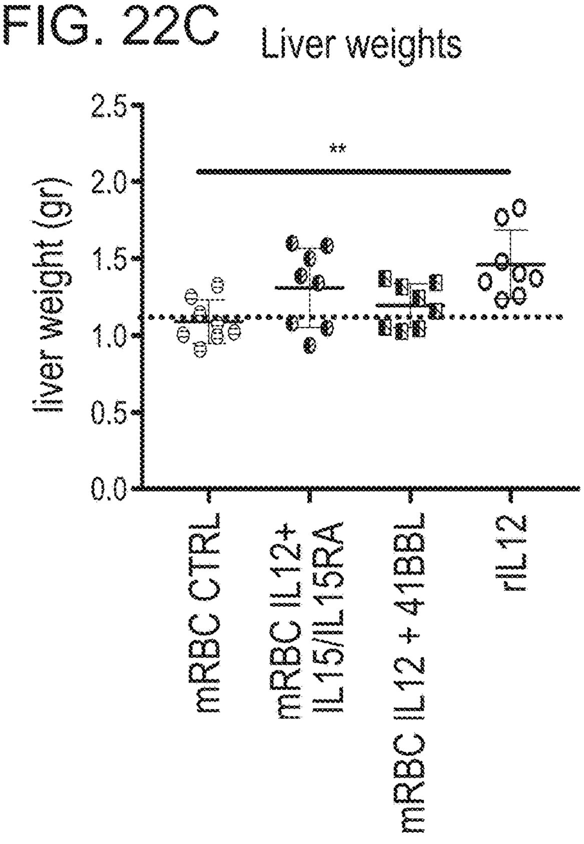
Figure 22D:
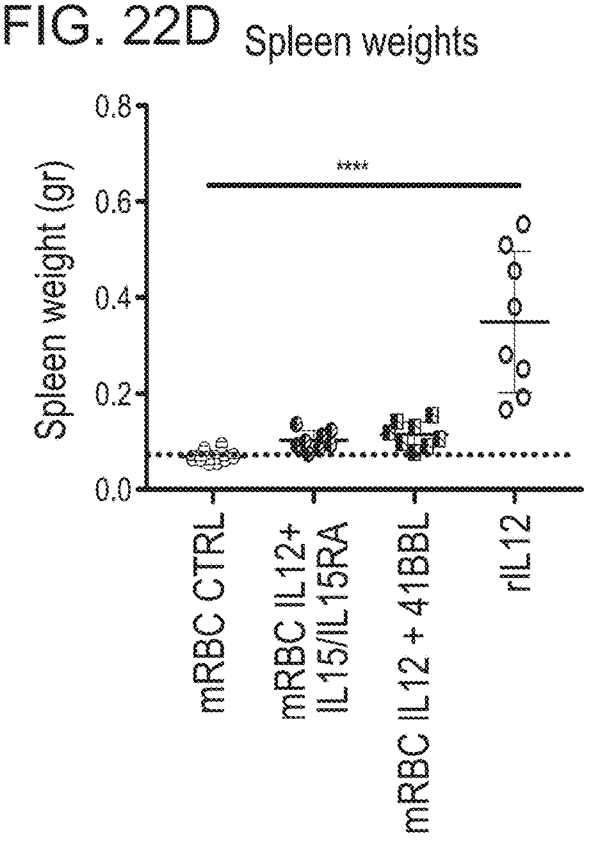

The anti-tumor activity of prepared erythroid cells comprising IL-12 (i.e., erythroid cells presenting the combination of either IL-12 and 4-1BBL, or IL-12 and IL-15/IL-15RA), as compared to untreated controls, was determined by assessing the change in tumor volume and/or tumor weight over time. The results, as shown in FIGS. 21A and 21B, demonstrate that prepared erythroid cells comprising IL-12 markedly reduced tumor progression over time as compared to untreated control. Moreover, the prepared erythroid cells comprising IL-12 and 4-1BBL significantly reduced the progression of tumor volume relative to that of 3H3, in the MC38 mouse model system.

Example 27. Lack of Toxicity of Murine Erythroid Cells Comprising IL-12 In Vivo A B16F10 metastatic mouse model system for melanoma (Kubo et al., 2017; the entire contents of which is incorporated herein by reference) was used to assess the lack of toxicity or tolerability of murine RBC-IL-12+IL-15/IL-15RA, and RBC-IL-12+4-1BBL. In this experiment to assess liver toxicity, the various RBCs, the mouse model and the RBC dosing schedule were as described in Example 25.

As described in Example 25, 6 to 12 week old female C57BL/6 mice were inoculated intravenously with B16F10 melanoma cells to establish metastases in the lung, and then mice were dosed with the following: murine erythroid cells presenting IL-12 and IL-15/IL-15RA (mRBC IL12+L-15/IL-15RA) (1E9 cells), murine erythroid cells presenting IL-12 and 4-1BBL (mRBC IL-12+4-1BBL) (1E9 cells), murine erythroid cells without IL-12, IL-15/IL-15RA and 4-1BBL (mRBC CTRL) (1E9 cells), or rIL-12 at 3 μg, as controls.

Animal weight and condition was recorded daily. Dosing was conducted on days 1, 4 and 8, and final sacrifice was conducted on day 10. Livers, spleens and serum were collected, and the level of alanine transaminase (ALT) liver enzyme and interferon gamma (IFNg) in the serum were quantified.

As shown in FIG. 22, favorable tolerability was observed for murine erythroid cells co-conjugated with IL-12 and IL-15/IL-15RA, or with IL-12 and 4-1BBL, as compared to recombinant IL12. Spleen and liver weights, and the level of ALT and IFNg, were not significantly elevated following administration of the prepared murine erythroid cells. In contrast, spleen and liver weights, and levels of ALT and IFNg, were significant elevated after the administration of rIL-12. Taken together with the results of Examples 25 and 26, the data indicate that murine erythroid cells comprising IL-12 are efficacious in reducing solid tumor growth and metastases, without the toxicity that is observed when rIL-12 is administered.

While not wishing to be bound by theory, it is postulated that the lack of toxicity of the erythroid cells comprising both IL-12 and IL-15/IL-15RA, or IL-12 and 4-1BBL is due to the sequestration of the cells in blood vessels, i.e., confined to the circulation. This confinement may render the cells unable to interact with myeloid cells in the bone marrow, a process which has been suggested to initiate liver toxicity cascades. The data presented herein suggests that the erythroid cells presenting IL-12 do not stimulate the bone marrow-derived monocytes and therefore the cells provide a significant therapeutic advantage over rIL-12.

Example 28. Erythroid Cells Comprising IL-12 or IL-12/IL-15, Either Alone or in Combination with Anti-PD1 Antibody, Inhibit Tumor Growth In Vivo The B16F10 tumor model system for melanoma was used to test the effect of murine erythroid cells comprising murine IL-12 either alone, or in combination with human IL-15/IL-15RA, on tumor growth. In this model, B16F10 cells were injected subcutaneously into mice to form a palpable tumor in about 7 days. and treated with murine erythroid cells prepared to present either IL-12, IL-15/IL-15RA, or IL-12 and IL-15/IL-15RA fusion (IL-12/IL-15/IL-15RA), without or in combination with an anti-PD1 antibody. Upon subcutaneous injection, the B16F10 cells formed a palpable tumor in 5 to 10 days and grew to a 1×1×1 cm tumor in 14 to 21 days.

Murine erythroid cells were conjugated with human IL-15/IL-15RA alone, murine IL-12 alone, or co-conjugated with both human IL-15/IL-15RA and murine IL-12, using the click methodology. The amount of IL-15/IL-15RA and IL-12 conjugated to the cells was quantitated using flow cytometry. The amino acid sequences of the IL-15/IL-15RA fusion protein, murine 4-1BBL protein, and murine 11-12 protein are provided in Table 10 herein.

When the tumors reached a volume of approximately 100 $mm^3$ (approximately 7-10 days), the animals were dosed with either erythroid cells presenting either IL-12 alone (mRBC IL-12), IL-15/IL-15RA fusion alone (mRBC IL-15), and both IL-12 and IL-15/IL-15RA (mRBC IL-12+IL-15/IL-15RA), with or without an anti-PD1 monoclonal antibody (αPD-1 mAb); or with either erythroid cells without these proteins (mRBC CTRL), with 4 μg of recombinant IL-12, 5 μg of recombinant IL-15/IL-15RA fusion, and with both recombinant IL-12 and recombinant IL-15/IL-15RA fusion, as controls. Dosing was conducted on days 1, 4 and 8 (the indicated treatment days commence from the day in which the desired tumor volume was observed). For dosing animals, an average of 3e8 or 1e9 erythroid cells were administered per dose comprising an average number of molecules per cell as follows: for erythroid cells comprising IL-12 and IL-15/IL-15RA, 70,000 molecules of IL-12 and 80,000 molecules of IL-15/IL-15-RA, corresponding to 0.3 mg/kg and 0.15 mg/kg respectively; for erythroid cells comprising IL-12, 35,000 molecules of IL-12 corresponding to 0.17 mg/kg; and for erythroid cells comprising IL-15/IL-15RA, 40,000 molecules of IL-15/IL-15RA, corresponding to 0.07 mg/kg, per dose per mouse.

The weight and condition of the animals were recorded daily. Changes in body weight were calculated for each mouse relative to the body weight recorded on day 1. Tumors were measured 3 times per week by measuring each tumor in 2 dimensions. Tumor volumes were calculated using the standard formula: $(L\times W^2)/2$. The mean tumor weight and standard error of the mean were calculated for each group at each time point. Tumors were collected on days 11-12 and tissues were enzymatically digested to obtain a homogenous cell suspension using a tissue dissociator. Cells were then stained and analyzed by flow cytometry using a range of different antibodies for immune profiling. M1 cells (activated macrophages) were defined as the live cells population that was CD45+, CD8−, CD11b+, Ly6C low/− and MHC class II+. M2 cells were defined as the live cell population that was Ly6C+, MHC class II negative. M1 cells are anti-tumor cells and M2 cells (immunosuppressive) are pro-tumor cells. Mouse survival was also monitored for up to 30 days post treatment.

Figure 23A:
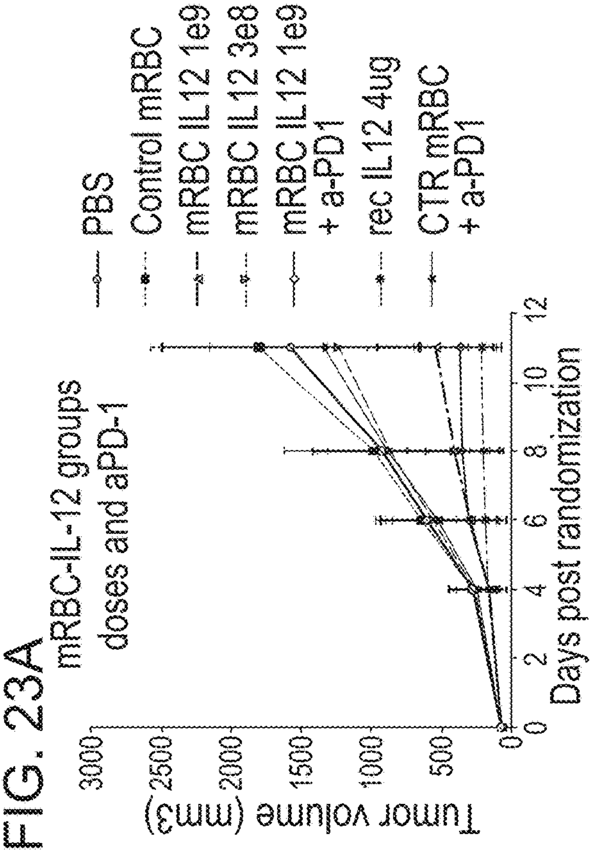
FIG. 23A is a graph showing murine erythroid cells prepared to present IL-12, alone or in combination with anti-PD1 antibody, inhibit tumor growth in the B16F10 mouse model.
Figure 23B:
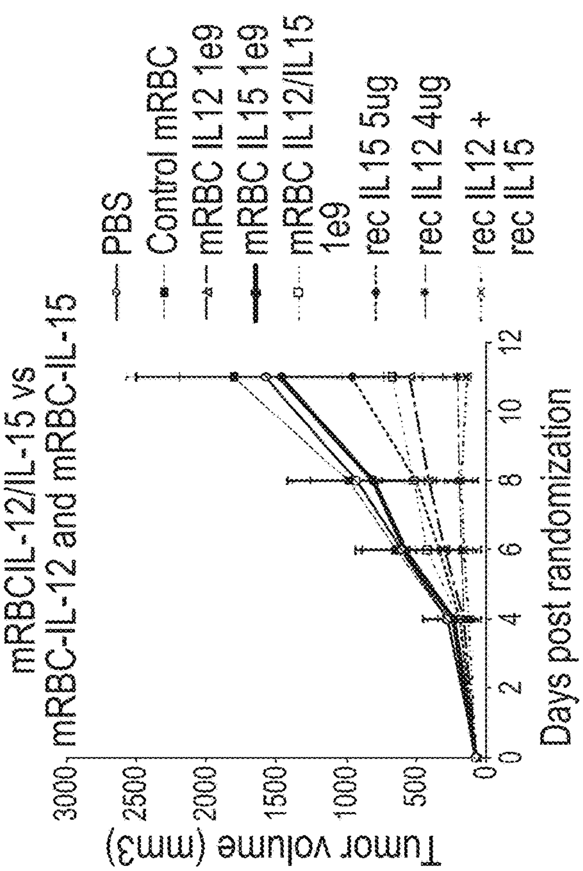
FIG. 23B is a graph showing murine erythroid cells prepared to present IL-12, IL-15/IL-15RA, or a combination, inhibit tumor growth in the B16F10 mouse model.
Figure 23C:
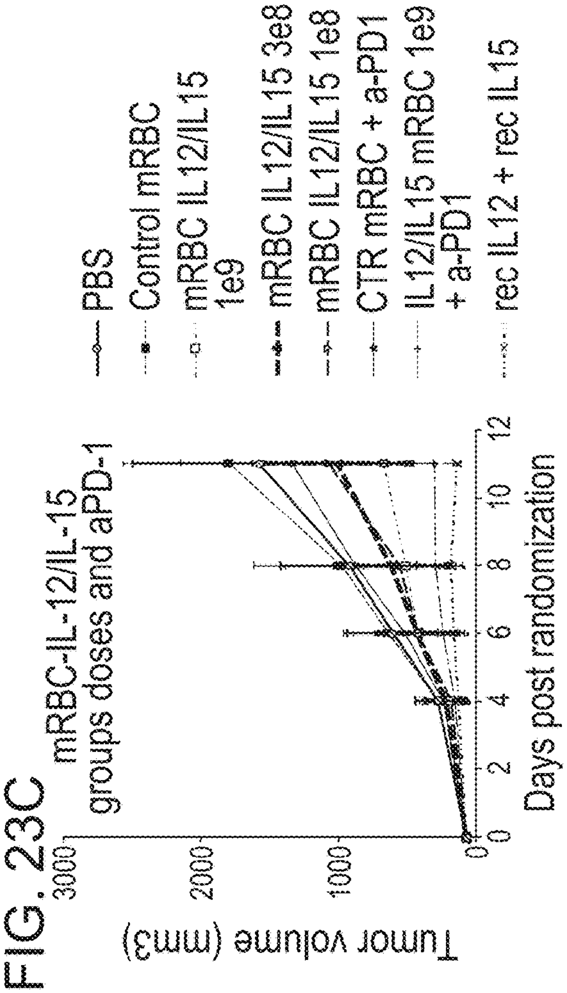
FIG. 23C is a graph showing murine erythroid cells prepared to present IL-12/IL-15/IL-15RA, alone or in combination with anti-PD1 antibody, inhibit tumor growth in the B16F10 mouse model.
Figure 23D:
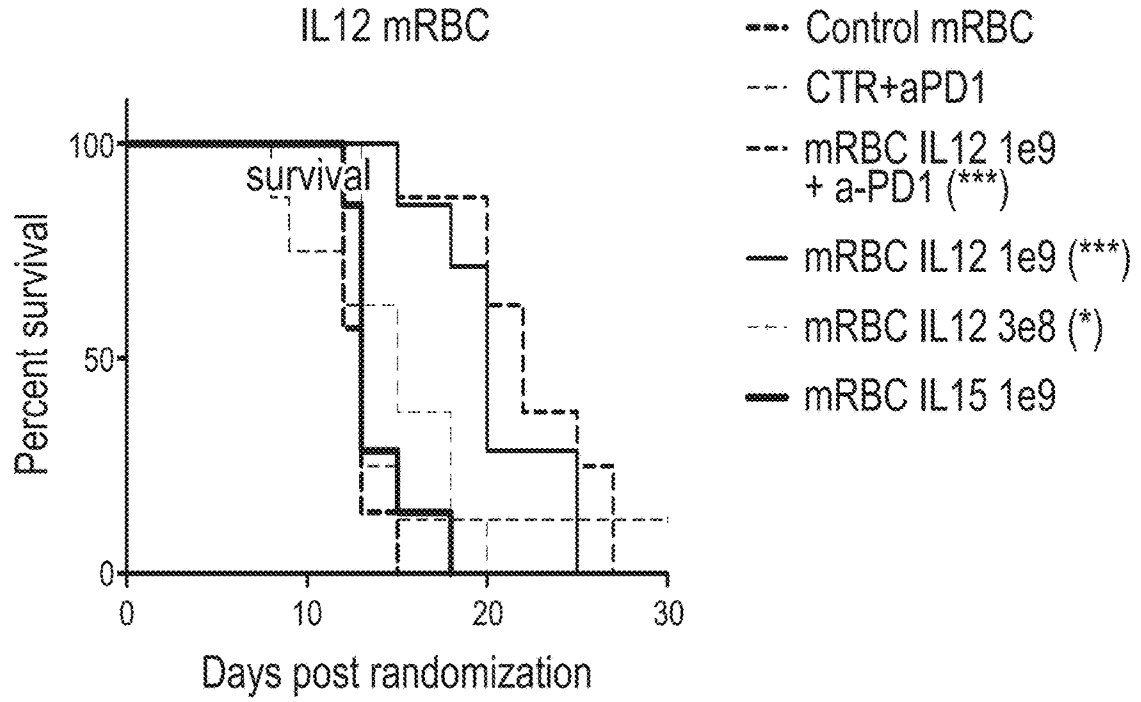
FIG. 23D is a graph showing murine erythroid cells prepared to present IL-12, alone or in combination with anti-PD1 antibody, improved survival of the treated mice, in the B16F10 mouse model.
Figure 23E:
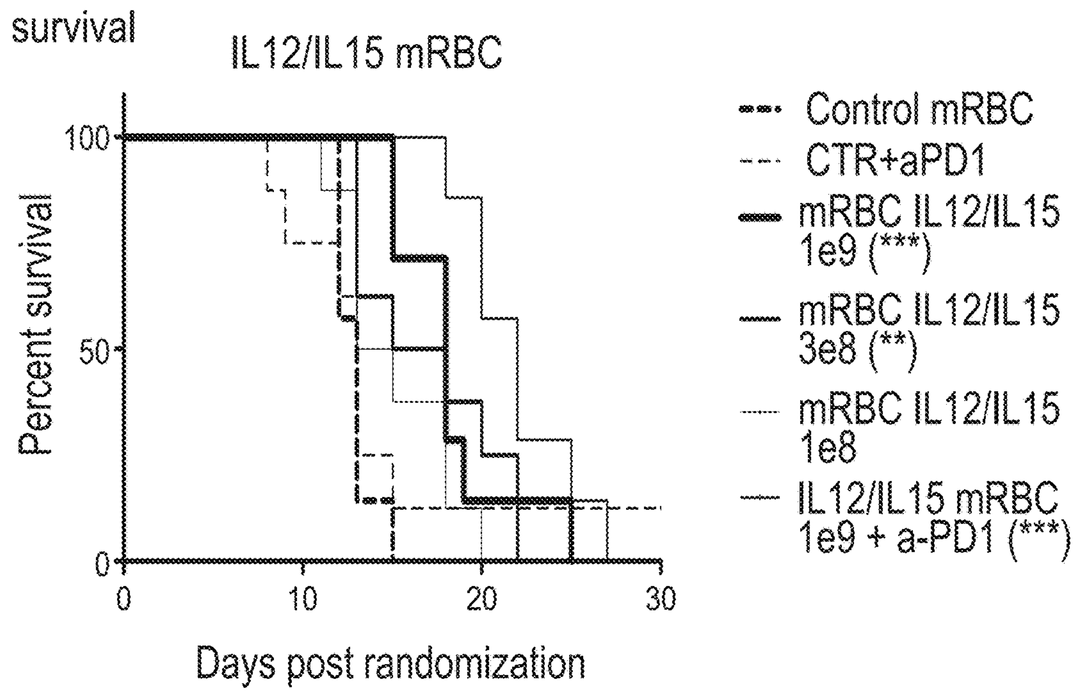
FIG. 23E is a graph showing murine erythroid cells prepared to present IL-12/IL-15/IL-15RA, alone or in combination with anti-PD1 antibody, improved survival of the treated mice, in the B16F10 mouse model.

The anti-tumor activity of prepared erythroid cells comprising IL-12 (i.e., erythroid cells presenting IL-12 or the combination of IL-12, and IL-15/IL-15RA) compared to untreated controls was determined by assessing the change in tumor volume and/or tumor weight over time. The results, as shown in FIG. 23A-C, demonstrate that prepared erythroid cells comprising IL-12 markedly reduced tumor progression over time as compared to untreated control. The prepared erythroid cells comprising IL-12 alone, or IL-12 with IL-15 significantly reduced the progression of tumor volume, which was further improved in combination with a-PD1. Treatment with 1e9 cells was observed to be more effective for tumor inhibition, than treatment with 3e8 cells. Furthermore, FIG. 23D-E, demonstrate that prepared erythroid cells comprising IL-12 alone, or IL-12 with IL-15, in combination with a-PD1 exhibit improved survival of the mice up to 30 days post treatment, compared to the untreated controls. In the absence of a-PD1 treatment an improved survival was observed compared to mice that received control mRBCs. Interestingly, the treatment with erythroid cells comprising IL-12 with IL-15, significantly improved survival of mice at doses of 3e8 cells. No changes in body weight were observed for any of the groups treated with the mRBCs, in contrast to the dramatic loss of body weight observed in the rIL-12, and r-IL-12+rIL-15 treated groups (data not shown).

Figure 23F:
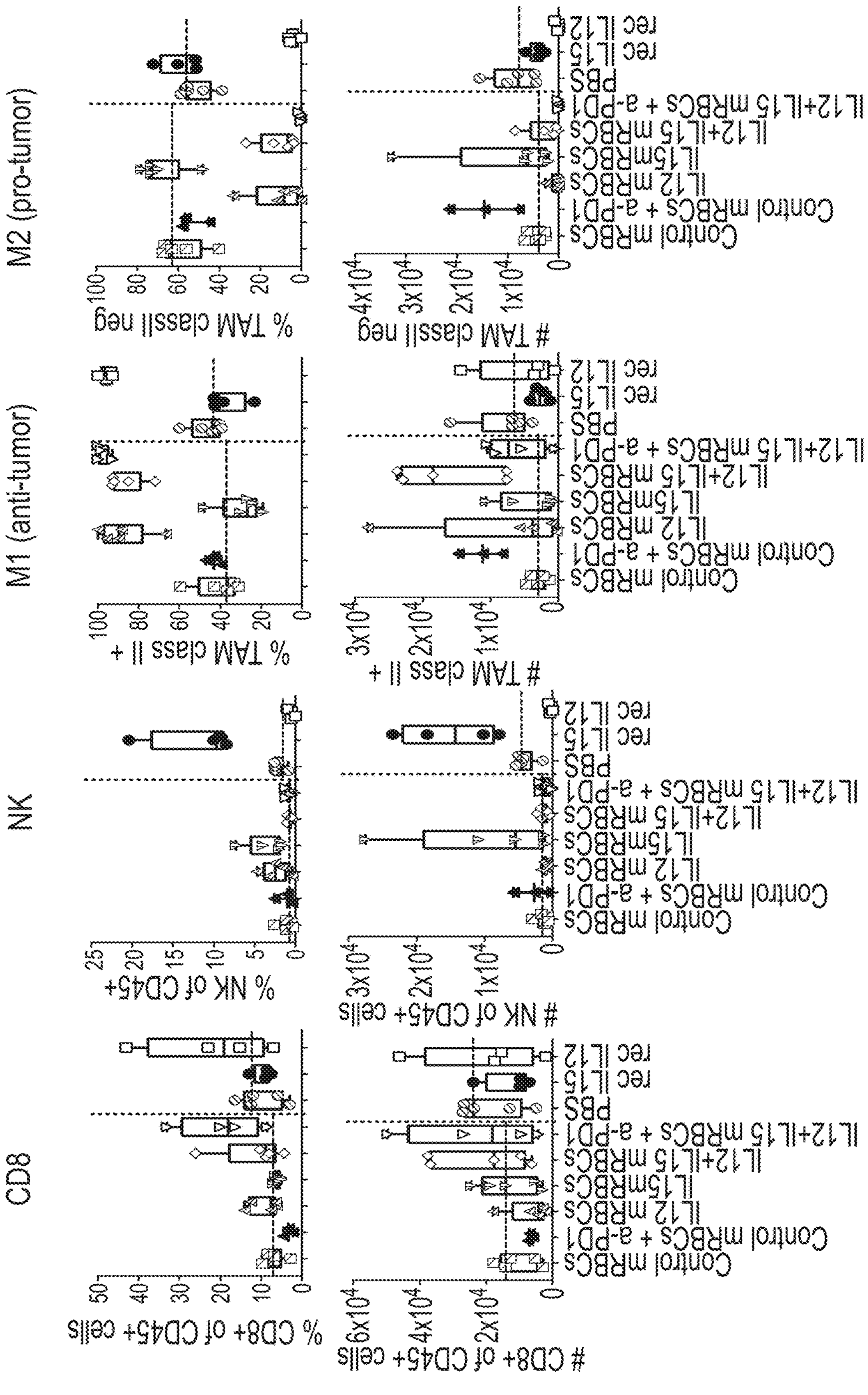
FIG. 23F is a graph showing an increased infiltration of CD8 T cells in tumors treated with IL-12/IL-15+a-PD1 groups, an increased infiltration of NK cells in the IL-15/IL-15RA mRBC groups, and an increased polarization of macrophages toward an M1 phenotype, i.e. anti-tumor phenotype of classically activated macrophages, in the IL-12 containing groups.

Furthermore, FIG. 23F demonstrates an increased infiltration of CD8 T cells in tumors treated with IL-12/IL-15+a-PD1 groups, and an increased infiltration of NK cells in the IL-15/IL-15RA mRBC groups. IL-12 containing groups were also observed to polarize macrophages toward an M1 phenotype, i.e. anti-tumor phenotype of classically activated macrophages. In contrast to rIL-12, IL-12 containing groups did not induce high levels of immunosuppressive IL-10 (data not shown).

Example 29. Erythroid Cells Comprising IL-12, or IL-12/4-1BBL, or IL-12/IL-15/IL-15RA Alone or in Combination with an Anti-PD1 Antibody, Inhibit Tumor Growth In Vivo The MC38 syngeneic mouse model system for colon carcinoma was used to test the effects on tumor growth of murine erythroid cells prepared to present IL-12, or IL-12/4-1BBL, alone or in combination with an anti-PD1 antibody.

Murine erythroid cells were conjugated with murine 4-1BBL, IL-12, or co-conjugated with both 4-1BBL and IL-12 using the click methodology. The amount of 4-1BBL and IL-12 conjugated to the cells was quantitated using flow cytometry. The amino acid sequences of the IL-15/IL-15RA fusion protein, murine 4-1BBL protein, and murine 11-12 protein are provided in Table 10 herein.

When the tumors reached a volume of approximately 100 $mm^3$ (approximately 7-10 days), the animals were dosed with erythroid cells presenting either IL-12 alone (mRBC IL-12), 4-1BBL alone (mRBC 4-1BBL), or both IL-12 and 4-1BBL (mRBC IL-12+4-1BBL), with or without an anti-PD1 monoclonal antibody (αPD-1 mAb); or with erythroid cells without these proteins (mRBC CTRL), or with 4 μg of recombinant IL-12, 50 μg of an agonist 41BB antibody (clone 3H3), or with both recombinant IL-12 and 41BB agonist antibody (3H3), as controls. Dosing was conducted on days 1, 4 and 8 (the indicated treatment days commence from the day in which the desired tumor volume was observed). For dosing animals, an average of 3e8 or 1e9 erythroid cells were administered per dose, with an average number of molecules per cell as follows: for erythroid cells comprising IL-12 and 4-1BBL, 100,000 molecules of IL-12 and 180,000 molecules of 4-1BBL, corresponding to 0.5 mg/kg and 0.3 mg/kg respectively; for erythroid cells comprising IL-12, 70,000 molecules of IL-12 corresponding to 0.3 mg/kg; and for erythroid cells comprising 4-1BBL, 70,000 molecules of 4-1BBL, corresponding to 0.13 mg/kg, per dose per mouse.

The weight and condition of the animals were recorded daily. Changes in body weight were calculated for each mouse relative to the body weight recorded on day 1. Tumors were measured 3 times per week by measuring each tumor in 2 dimensions. Tumor volumes were calculated using the standard formula: $(L\times W^2)/2$. The mean tumor weight and standard error of the mean were calculated for each group at each time point. Tumors were collected on days 11-12 and tissues were enzymatically digested to obtain an homogenous cell suspension using a tissue dissociator.

Cells were then stained and analyzed by flow cytometry using a range of different antibodies to look at immune profiling. M1 and M2 cells were defined as described in Example 28 above. Tumor regression was determined by calculating the percent change in tumor size relative to the tumor size at the starting point.

Figure 24A:
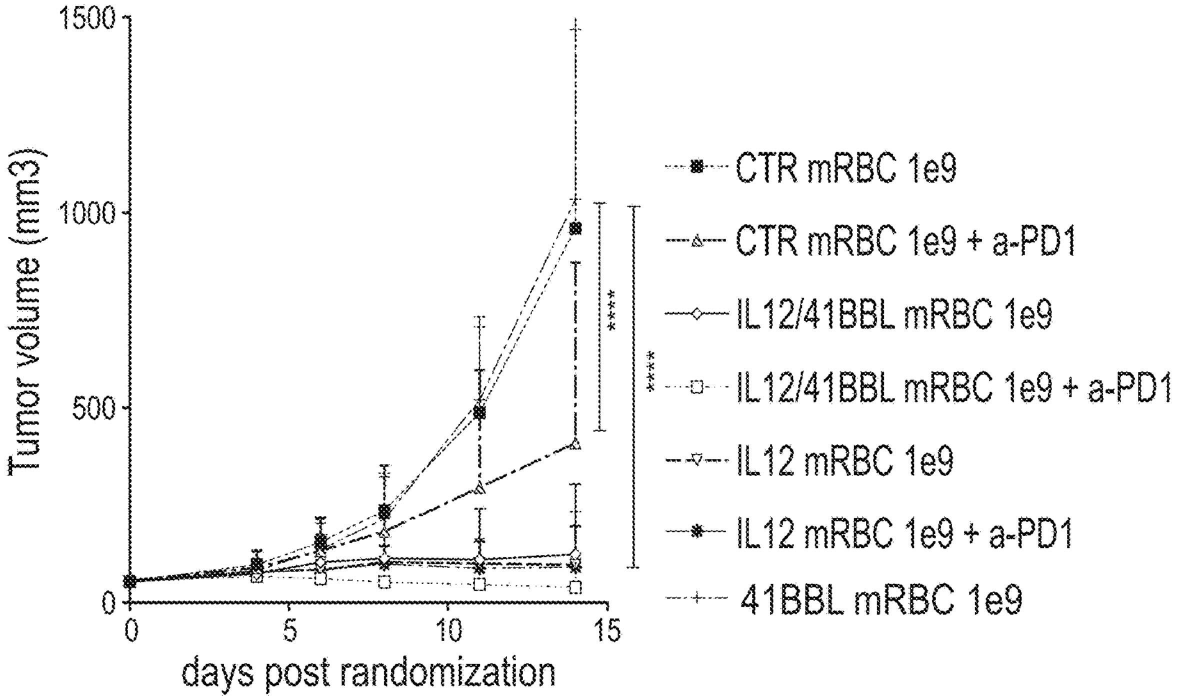
FIG. 24A is a graph showing treatment with 1e9 murine erythroid cells prepared to present IL-12 or IL-12/4-1BBL, alone or in combination with an anti-PD1 antibody, inhibits tumor growth in the MC38 mouse model.
Figure 24B:
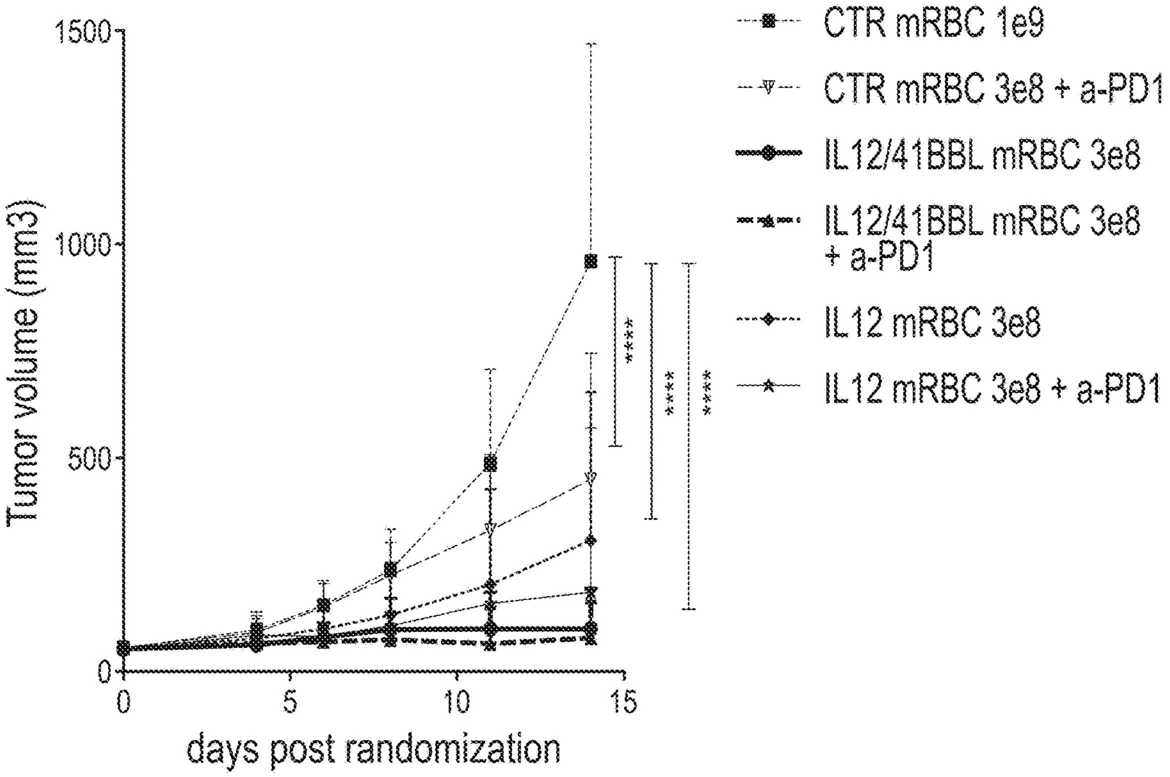
FIG. 24B is a graph showing treatment with 3e8 murine erythroid cells prepared to present IL-12 or IL-12/4-1BBL, alone or in combination with an anti-PD1 antibody, inhibits tumor growth in the MC38 mouse model.
Figure 24C:
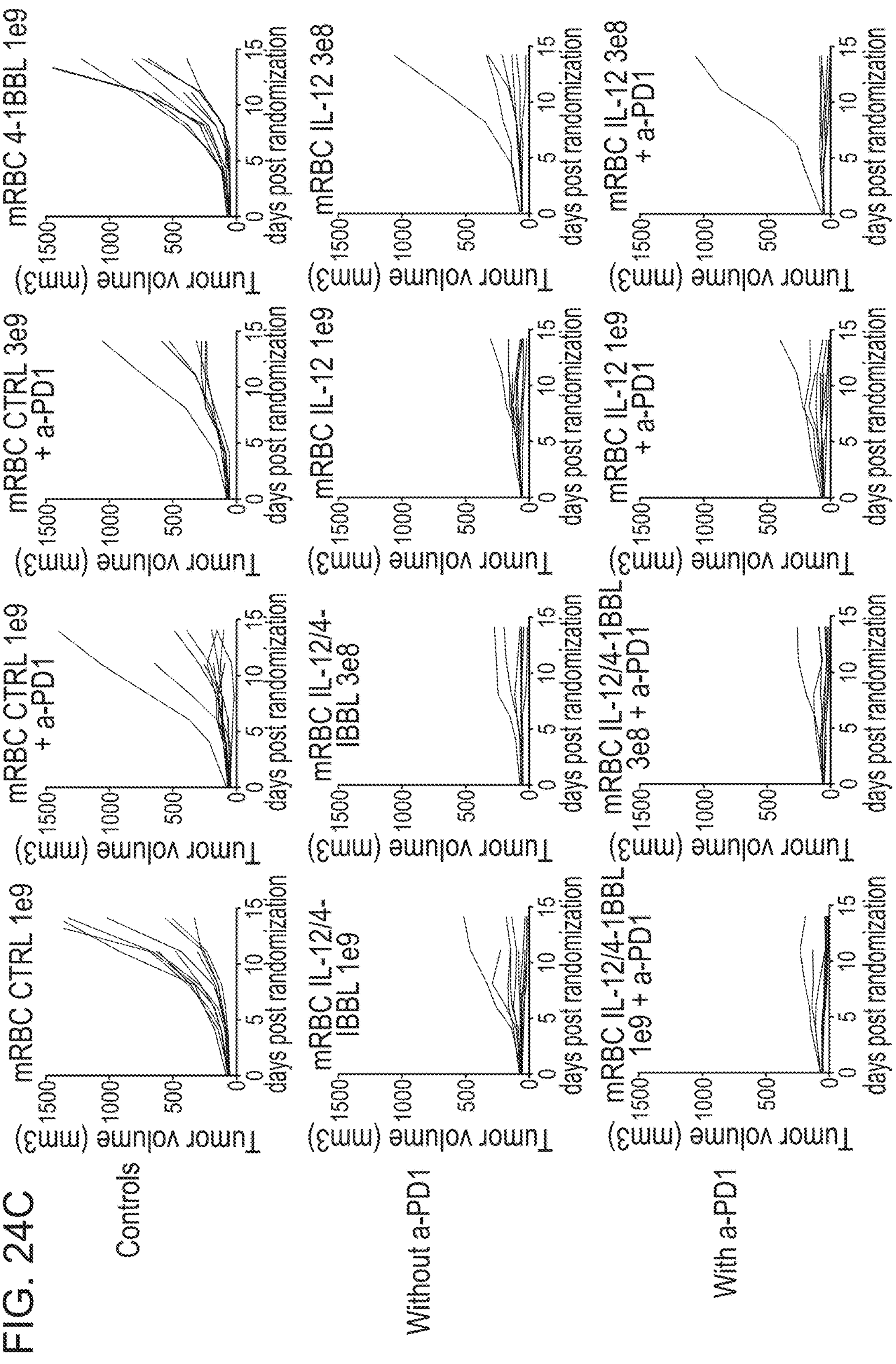
FIG. 24C is a graph showing murine erythroid cells prepared to present IL-12 or IL-12/4-1BBL, alone or in combination with an anti-PD1 antibody inhibit tumor growth in the MC38 mouse model. Data is represented for the individual mice used in the study.
Figure 24D:
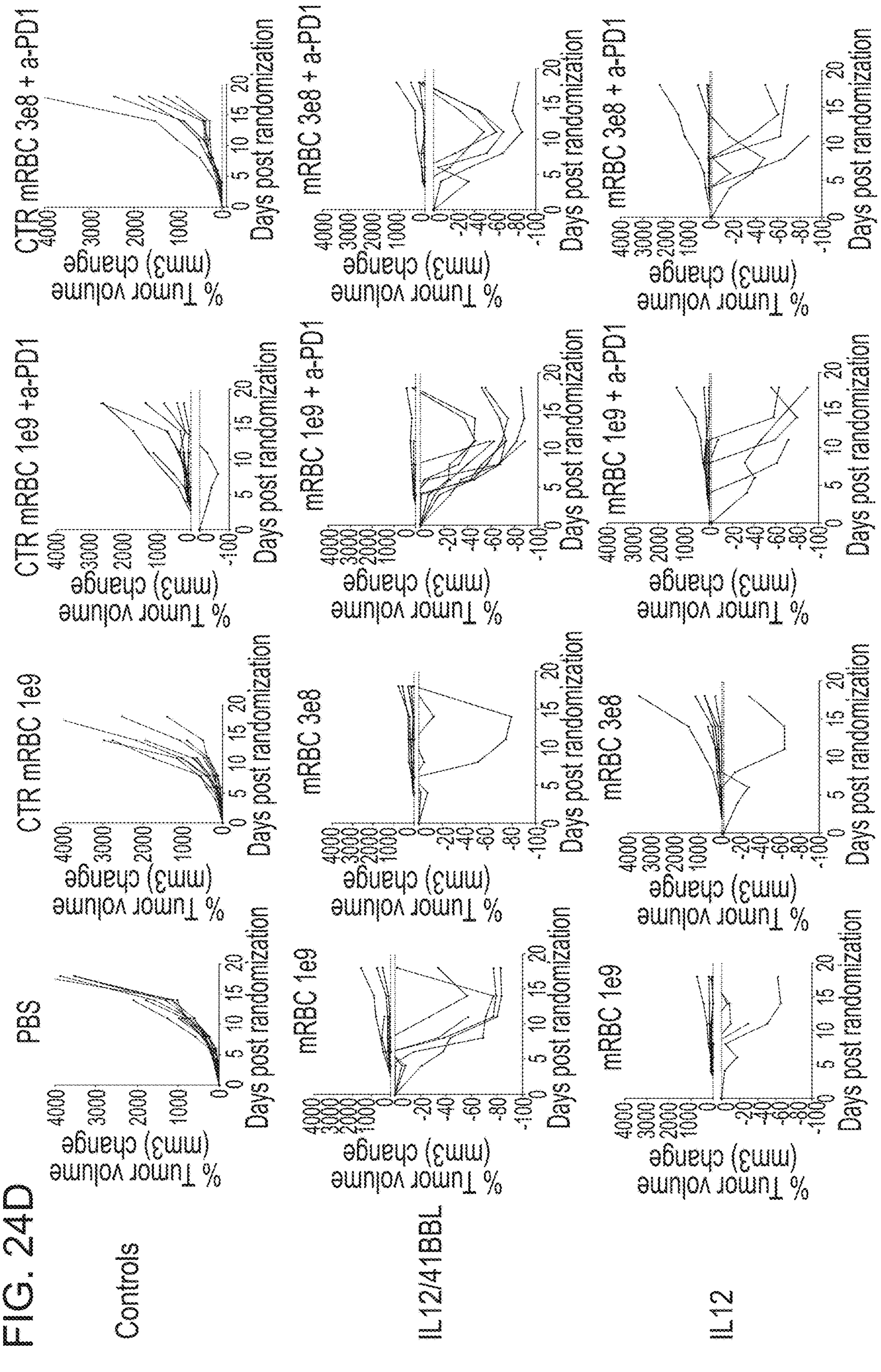
FIG. 24D is a graph showing murine erythroid cells prepared to present IL-12 or IL-12/4-1BBL, alone or in combination with an anti-PD1 antibody induce tumor shrinkage in the MC38 mouse model. Data is represented for the individual mice used in the study.

The anti-tumor activity of prepared erythroid cells comprising IL-12 (i.e., erythroid cells presenting IL-12 alone or the combination of IL-12 and 4-1BBL) compared to untreated controls was determined by assessing the change in tumor volume and/or tumor weight over time. The results, as shown in FIG. 24A-D, demonstrate that erythroid cells comprising IL-12 markedly reduced tumor progression over time as compared to untreated control. Moreover, the prepared erythroid cells comprising IL-12 and 4-1BBL significantly reduced the progression of tumor volume. FIG. 24D, further demonstrates that mice treated with erythroid cells comprising IL-12 alone, or both IL-12 and 4-1BBL, exhibited a shrinkage of the tumors as compared to the untreated controls. The reduction in tumor size was exacerbated when mice were also treated with αPD-1 mAb. Overall, the prepared erythroid cells comprising both IL-12 and 4-1BBL effectively inhibited tumors in this colon cancer mouse model, which was further exacerbated when administered in combination with αPD-1 mAb.

Figure 25A:
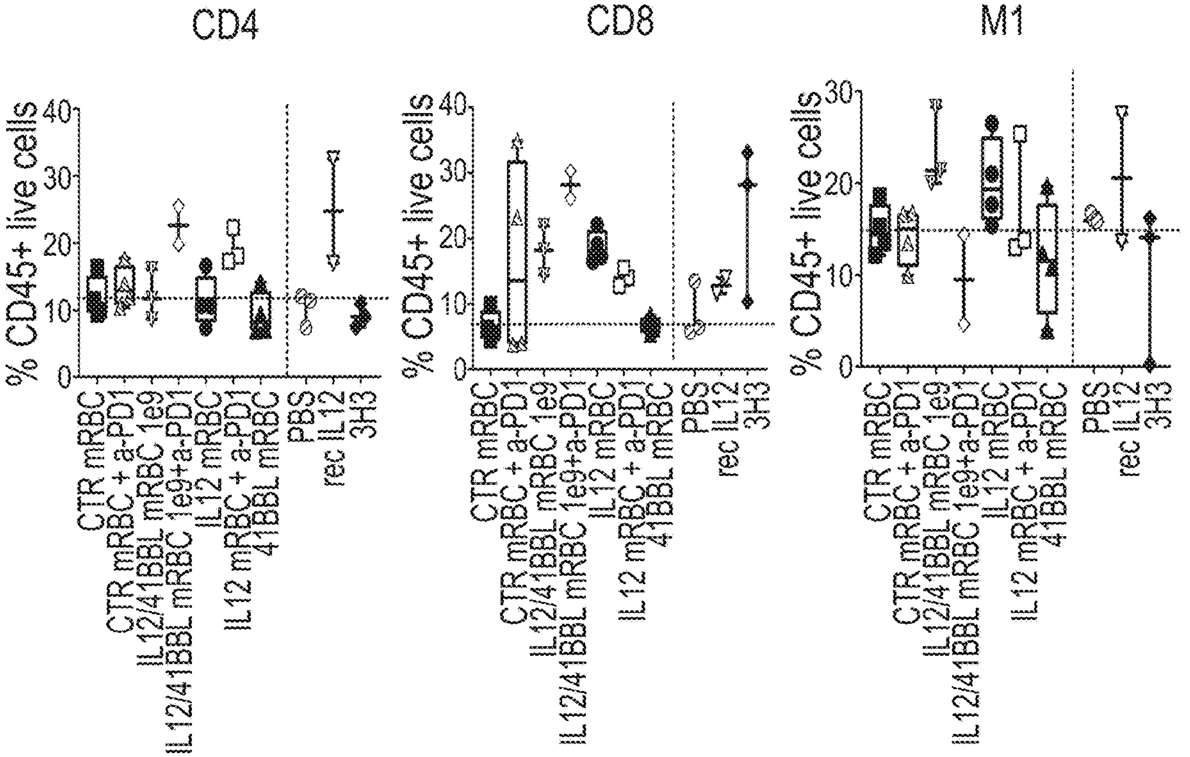
FIG. 25A is a graph showing an increased infiltration of CD4, CD8 T cells, and an increased polarization to the classically activated macrophages (M1 phenotype), in the tumors treated with murine erythroid cells prepared to present IL-12 or IL-12/4-1BBL, alone or in combination with an anti-PD1 antibody, in the MC38 mouse model.
Figure 25B:
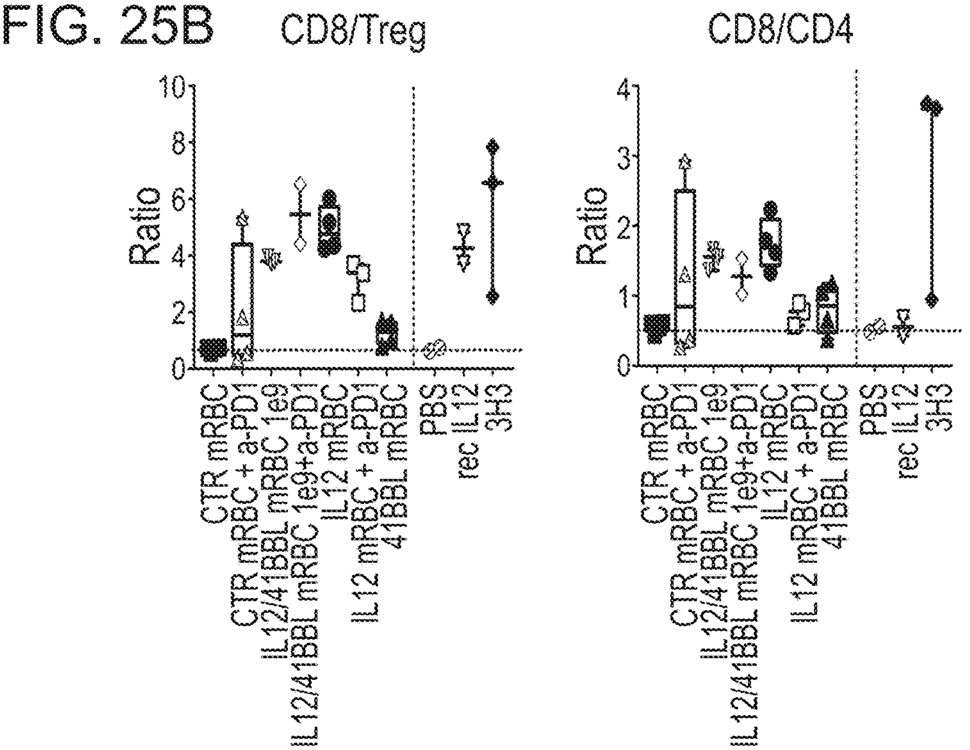
FIG. 25B is a graph showing a shift towards more CD8 over CD4 T cells, and a loss of regulatory T cells, in the tumors treated with murine erythroid cells prepared to present IL-12 or IL-12/4-1BBL, alone or in combination with an anti-PD1 antibody, in the MC38 mouse model.

Furthermore, the results of FIG. 25A demonstrate the infiltration of the different immune cells into the tumors. Infiltration of CD4+ T cells was observed in the tumors of mice treated with mRBC-IL12 and αPD-1 mAb, or with IL12 and 4-1BBL a-PD1. Infiltration of CD8+ cells was observed in the tumors of mice treated with all of the IL-12 groups (i.e., IL-12, or IL-12/4-1BBL, or IL-12/IL-15/IL-15RA), with an increased infiltration observed in the mRBC IL-12+4-1BBL and αPD-1 mAb. Polarization to the classically-activated macrophages (M1 phenotype) was observed in mice treated with the mRBC IL-12+4-1BBL and mice treated with mRBC-IL-12. Notably, administration of αPD-1 mAb dampened this M1 polarization. FIG. 25B further demonstrates a shift towards more CD8+ T cells over CD4+ T cells, and a loss of regulatory T cells in all of the mice groups treated with IL-12, over effector CD8+ T cells. The survival of mice treated with the mRBCs was observed to be directly correlated with the effectiveness of tumor inhibition, up to 20 days post treatment (data not shown).

Additional experiments were performed, using methods as described above in this Example, to determine the effect on tumor growth in vivo of erythroid cells comprising IL-12 alone, or both IL-12 and IL-15/IL-15RA, alone or in combination with an anti-PD1 antibody. The results demonstrated that administration of erythroid cells comprising IL-12 markedly reduced tumor progression over time as compared to administration of control erythroid cells lacking conjugated protein (i.e., mRBC CTRL). Moreover, the prepared erythroid cells comprising IL-12 and IL-15/IL-15RA significantly reduced the progression of tumor volume. The results further demonstrated that prepared erythroid cells comprising IL-12 alone, or IL-12 and IL-15/IL-15RA, exhibited tumor shrinkage as compared to the untreated controls, an effect that was further increased when mice were treated with the anti-PD1 antibody. Overall, the prepared erythroid cells comprising IL-12 and IL-15/IL-15RA exhibited effective tumor inhibition, which was further improved when administered in combination with αPD-1 mAb (data not shown).

Example 30. Lack of Toxicity of Murine Erythroid Cells Comprising IL-12+IL-15/IL-15RA, or IL-12+4-1BBL In Vivo A mouse model of toxicity was used to assess the lack of toxicity or tolerability of murine erythroid cells conjugated with IL-12 and IL-15/IL-15RA (mRBC-IL-12+IL-15/IL-15RA), or IL12 and 3-1BBL (mRBC-IL-12+4-1BBL). In this experiment to assess toxicity, the various mRBCs and the mRBC dosing schedule were as described in Example 20. The assessment of toxicity was carried out as generally described in Example 20.

Generally, as described in Example 20, 6 to 12 week old female C57BL/6 mice were dosed with the following: murine erythroid cells presenting IL-12 and IL-15/IL-15RA (mRBC IL12+L-15/IL-15RA) (1E9, 3e8 and 1e8 cells), murine erythroid cells presenting IL-12 and 4-1BBL (mRBC IL-12+4-1BBL) (1E9, 3e8 and 1e8 cells); or with murine erythroid cells without IL-12, IL-15/IL-15RA or 4-1BBL (mRBC CTRL) (1E9, 3e8 and 1e8 cells), with recombinant IL-12 (rIL-12), recombinant IL-15) (rIL-15), agonist 4-1BB antibody (3H3), or combination of rIL-12 and 3H3, as controls.

Animal weight and condition was recorded daily. Dosing was conducted on days 1, 4, 8 and 11 and final sacrifice was conducted on day 18. The livers, spleens, blood and serum were collected. The level of the alanine transaminase (ALT) liver enzyme was quantified in the serum. The level of cytokine interferon gamma (IFNg), TNFa, IL-2, IL-4, IL-5, IL-6, IL-10, and IL-13 in the serum were quantified using a cytokine bead assay (CBA). Beads were conjugated with analyte-specific antibodies (including IFNg, TNFa, IL-2, IL-4, IL-5, IL-6, IL-10, and IL-13) and were incubated with the sera. Detection antibody was added and fluorescence was quantified and analyzed by flow cytometry. Complete blood count was also performed.

Figure 26A:
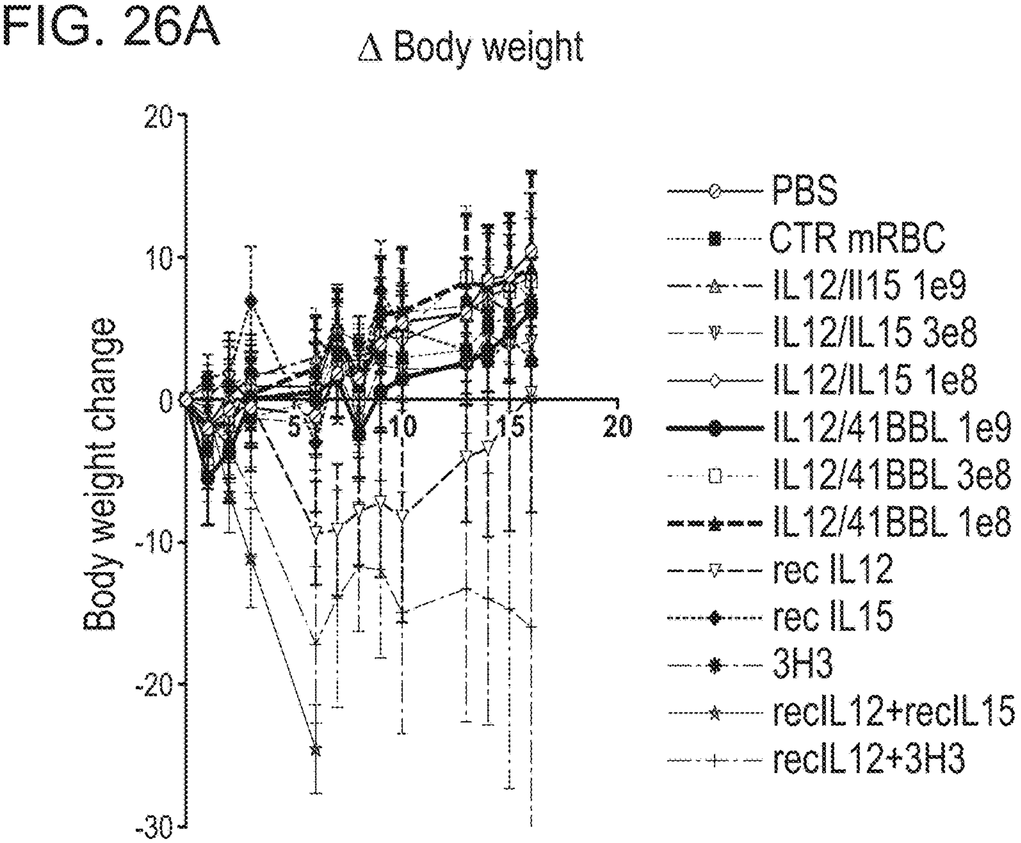
FIG. 26A-FIG. 26D are graphs showing murine erythroid cells prepared to present IL-12 and IL-15/IL-15RA, or IL-12 and 4-1BBL do not cause toxicity in mice in contrast to recombinant IL-12 (rIL-12). Changes in the body weight (FIG. 26A), liver weight (FIG. 26B), spleen weight (FIG. 26C), WBC counts and levels of hemoglobin (FIG. 26D) were measured.
Figure 26B:
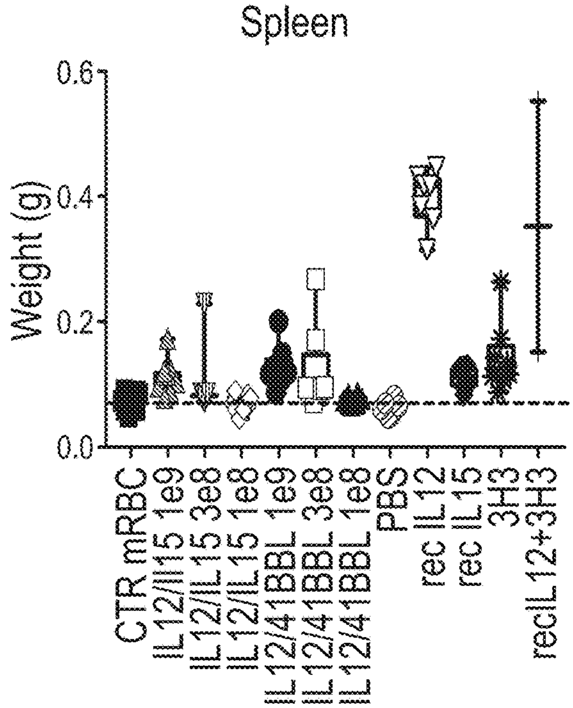
Figure 26C:
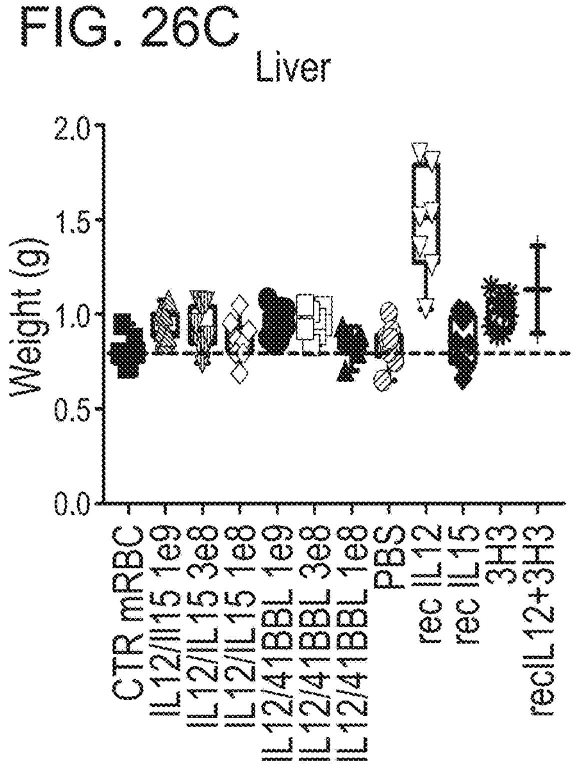
Figure 26D:
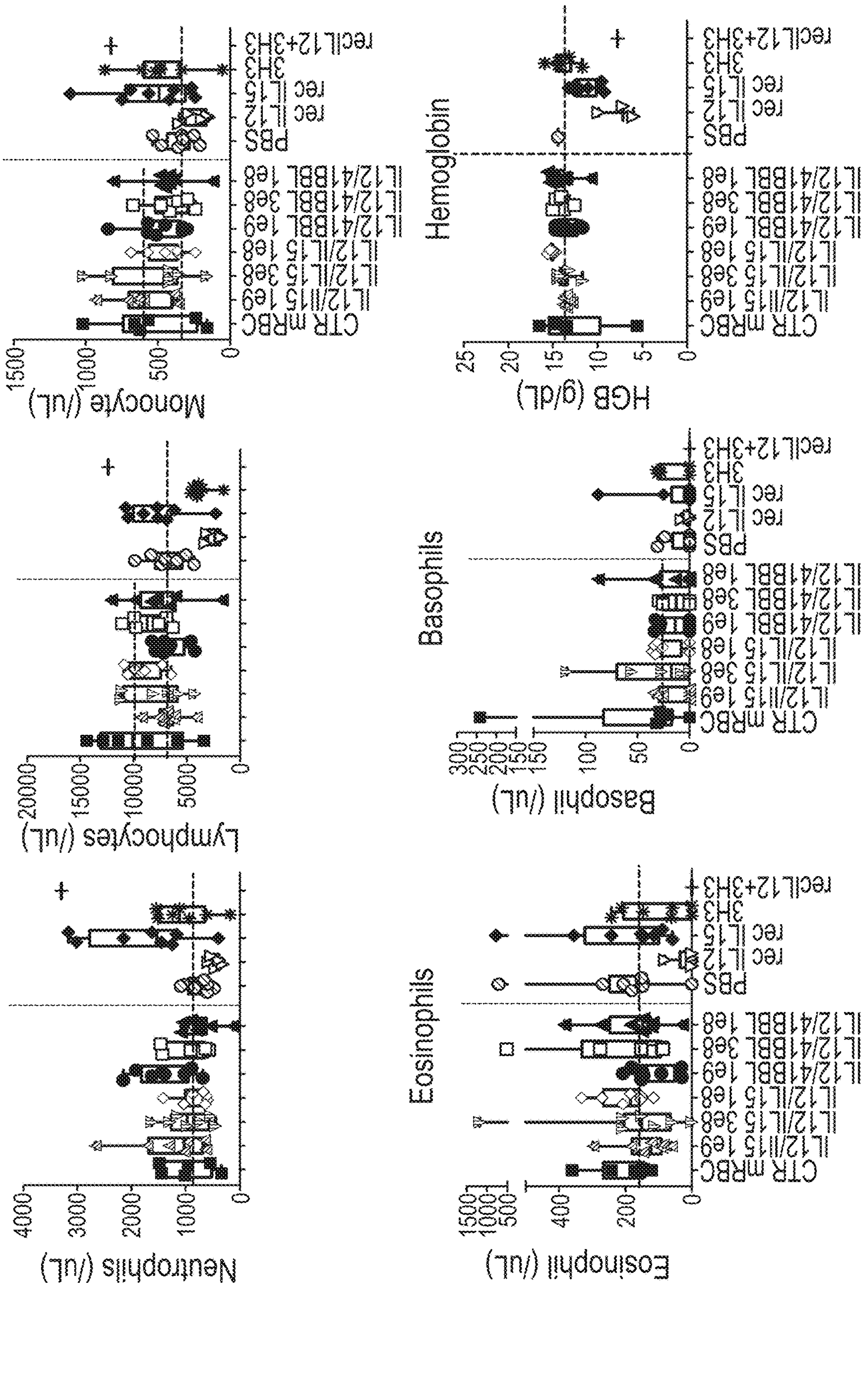

As shown in FIGS. 26A-26C, favorable tolerability was observed for murine erythroid cells co-conjugated with IL-12 and IL-15/IL-15RA, or with IL-12 and 4-1BBL, as compared to the controls. There was no change observed in the body, spleen or liver weights in any of the tested mRBC combinations. However, a loss in body weight was observed in all the groups that received rIL-12 Similarly, a dramatic increase in spleen and liver weights was observed in the rIL-12 treated groups. FIG. 26D demonstrates that the rIL-12-treated mice exhibited anemia with low levels of hemoglobin, loss of white blood cell (WBC) counts characterized by lymphopenia, neutropenia and loss of eosinophils. In contrast, no major changes in cell counts were observed in groups that received the mRBC treatment. Furthermore, rIL-12-treated mice exhibited low levels of lymphocytes and red blood cells, and high levels of ALT (as detected on day 14 and day 18), relative to the mice that were administered mRBCs comprising IL-12 (data not shown).

Figure 27A:
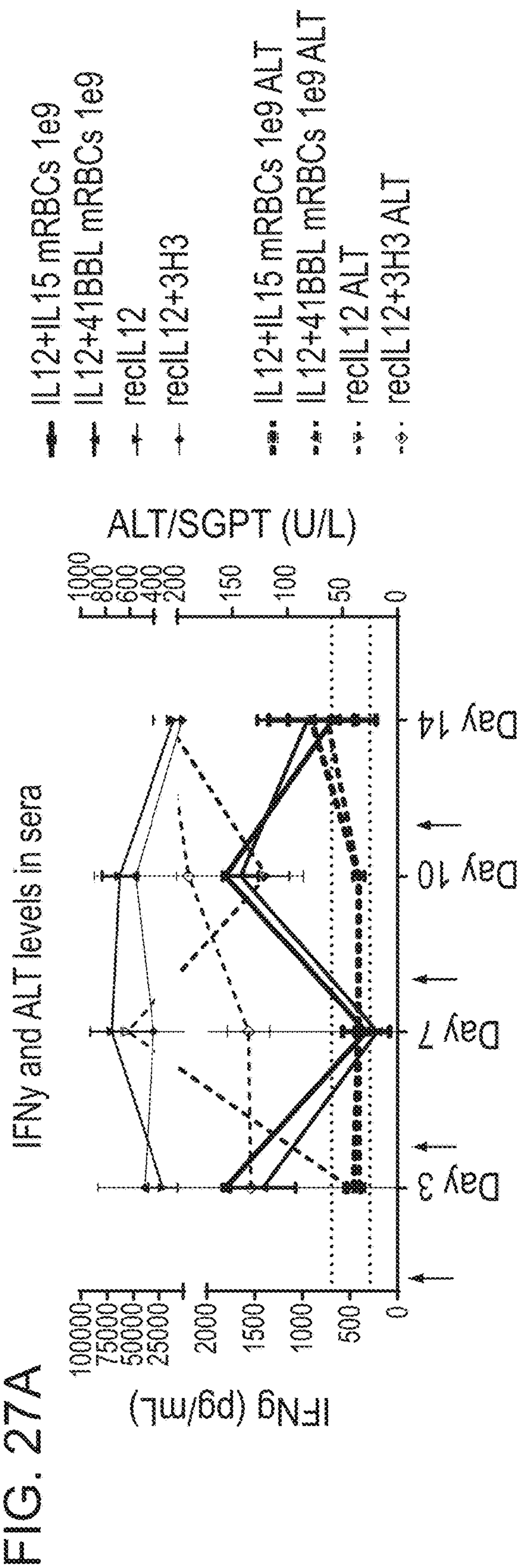
FIG. 27A and FIG. 27B are graphs showing murine erythroid cells prepared to present IL-12 and IL-15/IL-15RA, or IL-12 and 4-1BBL do not cause toxicity in mice in contrast to recombinant IL-12 (rIL-12). Changes in the levels of the enzymes IFNg (FIG. 27A), TNFa (FIG. 27B) were measured, and compared to the levels of the liver enzyme ALT.
Figure 27B:
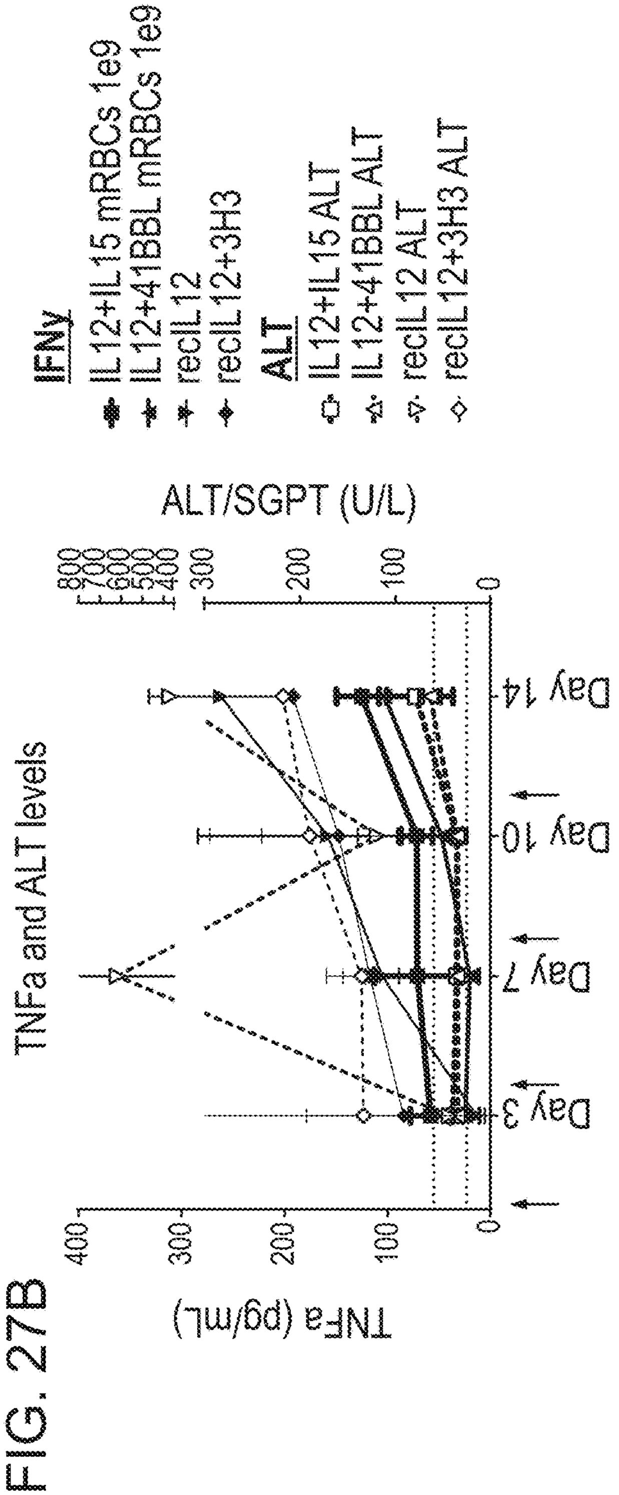

Furthermore, results in FIG. 27A demonstrate that the mice receiving mRBCs co-conjugated with both IL-12 and IL-15/IL-15RA, or with IL-12 and 4-1BBL, increased IFNg levels in serum at days 3 and 10 which was rapidly decreased 2 days after each dosing. Thus, the mRBC treatment induces a controlled IFNg response, which is capable of retracting post-treatment. In contrast, the mice treated with rIL-12 show dramatically higher ALT and IFNg levels, as early as day 3, which did not drop throughout the entirety of the study Similar levels of ALT and IFNg were observed on day 18 (data not shown). As shown in FIG. 27B, in contrast to IFNg levels, the TNFa levels continued to rise with each dose. However, mice treated with mRBCs had a lower increase of TNFa levels as compared to mice treated with rIL-12. Moreover, while no major impact was observed on the IL-10 production in mice treated with mRBCs, IL-10 was detected in the sera of animals treated with rIL-12 (data not shown).

Figure 26E:
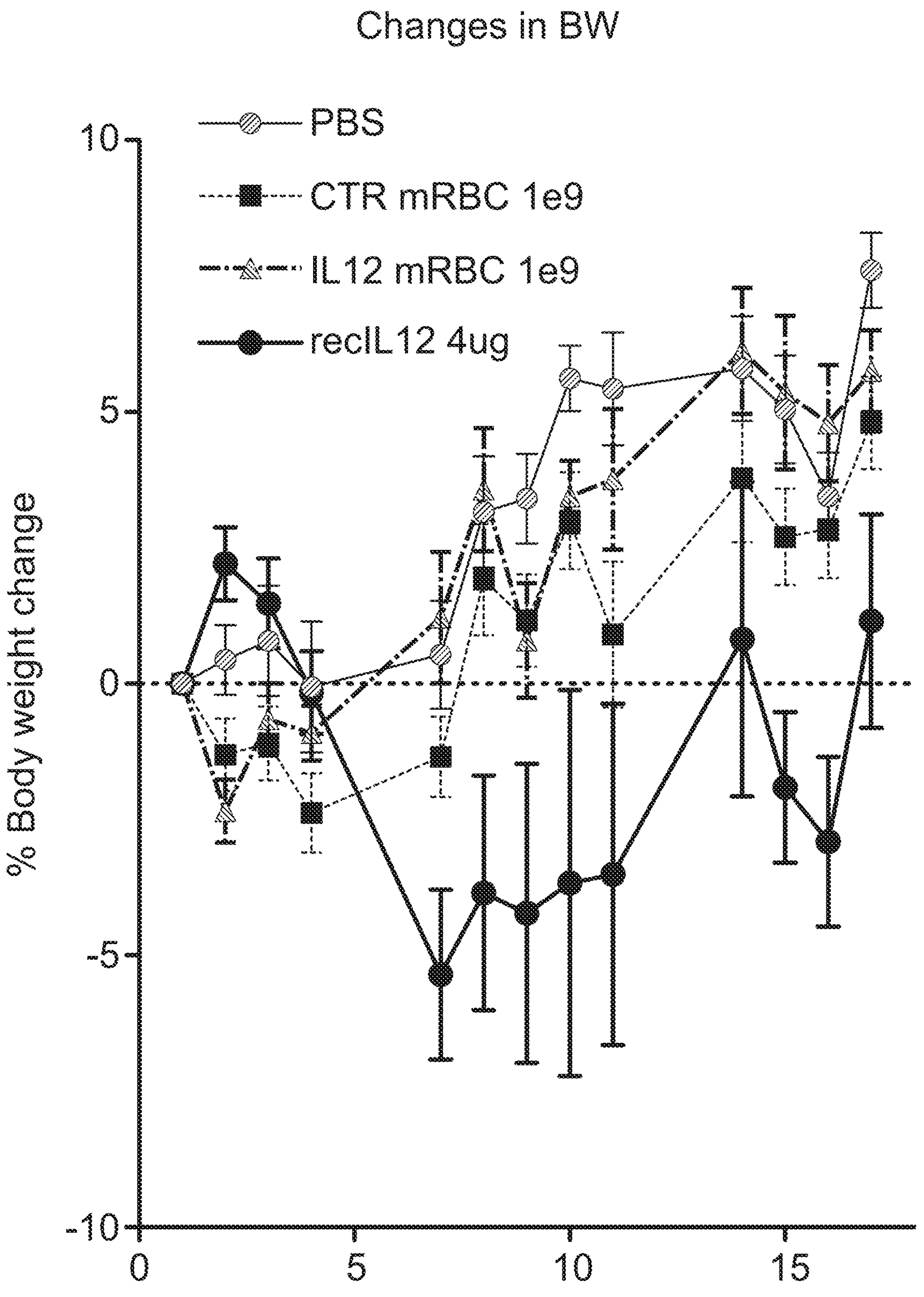
FIG. 26E-FIG. 26F are panels of graphs showing murine erythroid cells conjugated to present IL-12 do not cause toxicity in mice in contrast to recombinant IL-12 (rIL-12). Changes in the body weight (FIG. 26E), liver weight, spleen weight, WBC, RBC counts and levels of hemoglobin, ALT and IFNg (FIG. 26F) were measured.
Figure 26F:
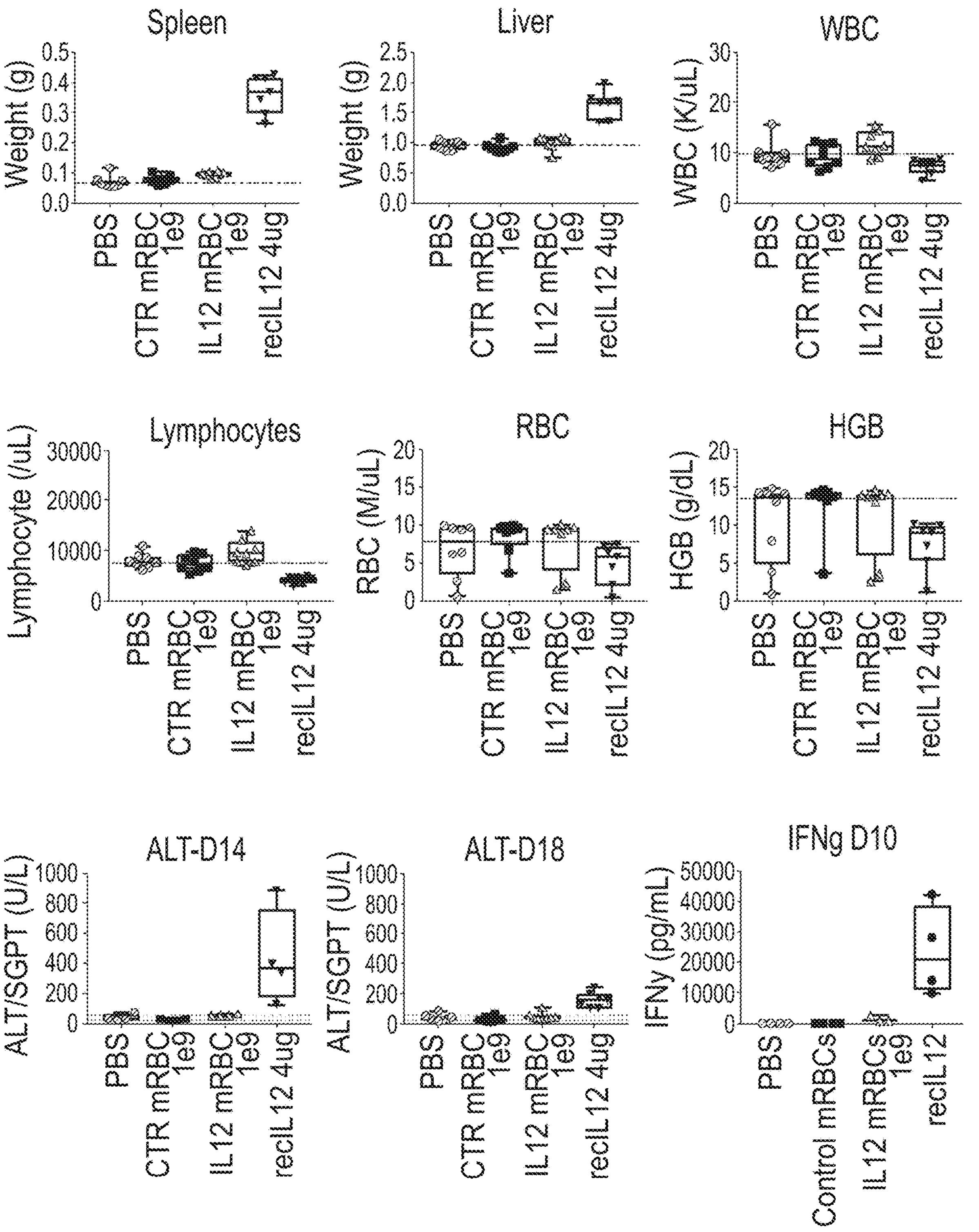

Additional experiments were conducted to examine and confirm the lack of toxicity of murine erythroid cells conjugated with IL12 alone. As shown in FIG. 26E-F, similar favorable tolerability was observed in mice treated with murine erythroid cells conjugated with IL-12 as compared to rIL-12. No change in body, spleen or liver weights was observed in any of the mice treated with erythroid cells conjugated with IL-12. However, a loss in body weight was observed in all the groups of mice that received rIL-12 Similarly, a dramatic increase in spleen and liver weights was observed in mice treated with rIL-12. FIG. 26F further demonstrates that the rIL-12-treated mice exhibited anemia with low levels of hemoglobin, loss of WBC counts, low levels of lymphocytes and red blood cells, high levels of ALT (as detected on day 14 and day 18), and high levels of IFNg (as detected on day 10), relative to the mice treated with murine erythroid cells conjugated with IL-12.

These results demonstrate that murine erythroid cells comprising IL-12, either alone or in combination with IL-15/IL-15RA or 4-1BBL, are efficacious in reducing solid tumor growth and metastases, in the absence of the toxicity associated with the administration of rIL-12, rIL-15, or 3H3.

Example 31. Genetically Engineered Enucleated Erythroid Cells Genetically Comprising IL-12, IL-15/IL-15RA, 4-1BBL, or Combinations Thereof, Induce NK Cell Cytotoxicity Short term (overnight) priming of human NK cells with human enucleated erythroid cells comprising IL-12 alone, IL-15/IL-15RA alone (V4.1), 4-1BBL alone, or a combination of IL-12 and IL-15/IL-15RA (V4.1), IL-12 and 4-1BBL, or IL-15/IL-15RA and 4-1BBL, was performed as previously described in Example 17. Briefly, frozen NK donors cells were incubated with the enucleated erythroid cells (RBCs) overnight at a 5:1 ratio (100,000 NK cells+500,000 RBC cells, 40,000 NK cells+200,000 RBC cells). The next day, 20,000 CTFR-labeled K562 target cells were contacted with the NK and RBC cells at E:T ratios of 5:1 and 2:1 for 4 hours. Staining was performed with GPA PE, CD56 PE-Cy7, fixable viability dye (AmCyan), CellTrace Far Red (targets), and samples were analyzed using flow cytometry. Additional phenotyping was performed using GzmB, PacBlue & CD69 BV605, at a 2:1 E:T ratio.

Antibody-dependent cell-mediated cytotoxicity (ADCC) assays were performed as described in Example 18. Briefly, 100,000 or 40,000 NK cells were contacted with Raji target cells at E:T ratios of 5:1 and 2:1. Raji cells were CTFR-labeled, and pre-treated with either anti-CD20 or isotype antibody, and incubated for 4 hours. Cells were then additionally stained for CD16.

Figure 28A:
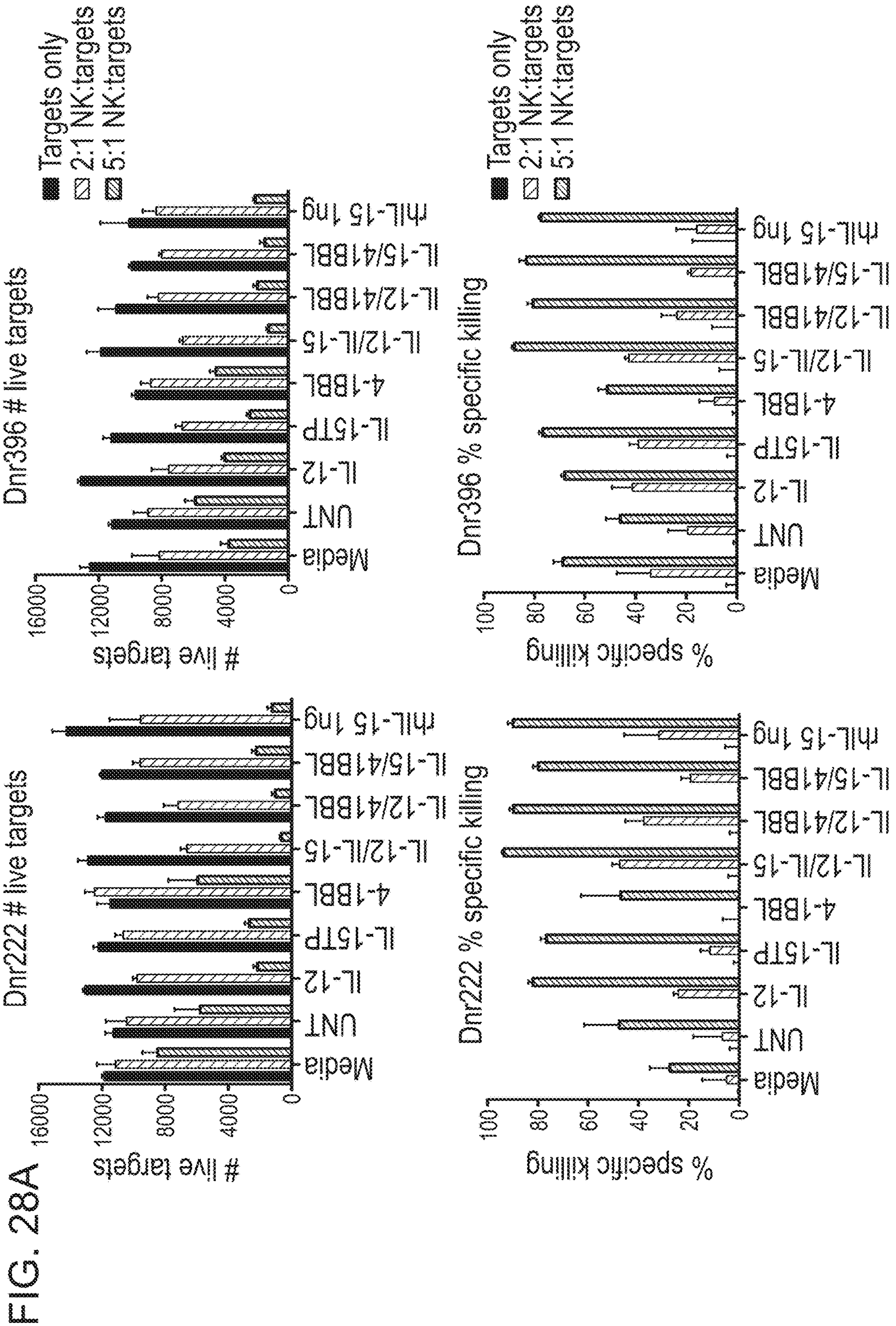
FIG. 28A and FIG. 28B are graphs showing human erythroid cells genetically engineered to express IL-12, IL-15/IL-15RA, 4-1BBL or combinations thereof, induce NK cell cytotoxicity, by enhanced killing against K562 targets (FIG. 28A), and enhanced antibody-dependent cell-mediated cytotoxicity (ADCC) killing of Raji cell targets (FIG. 28B).

The results as shown in FIG. 28A, demonstrate that NK cells primed overnight with human enucleated erythroid cells comprising IL-12alone, IL-15/IL-15RA alone, or a combination of IL-12 and IL-15/IL-15RA, IL-12 and 4-1BBL, or IL-15/IL-15RA and 4-1BBL exhibited enhanced cytotoxicity against K562 target cells (approximately 80%-90% killing), which was comparable to NK cells primed with rhIL-15 (at least 90% killing) at a 5:1 NK:target ratio. Thus, enucleated erythroid cells comprising these molecules enhanced the cytotoxicity of NK cells on a per cell basis, that is, the NK cells were not only better expanded, but the resulting individual NK cell population was more active (e.g., more cytotoxic).

Figure 28B:
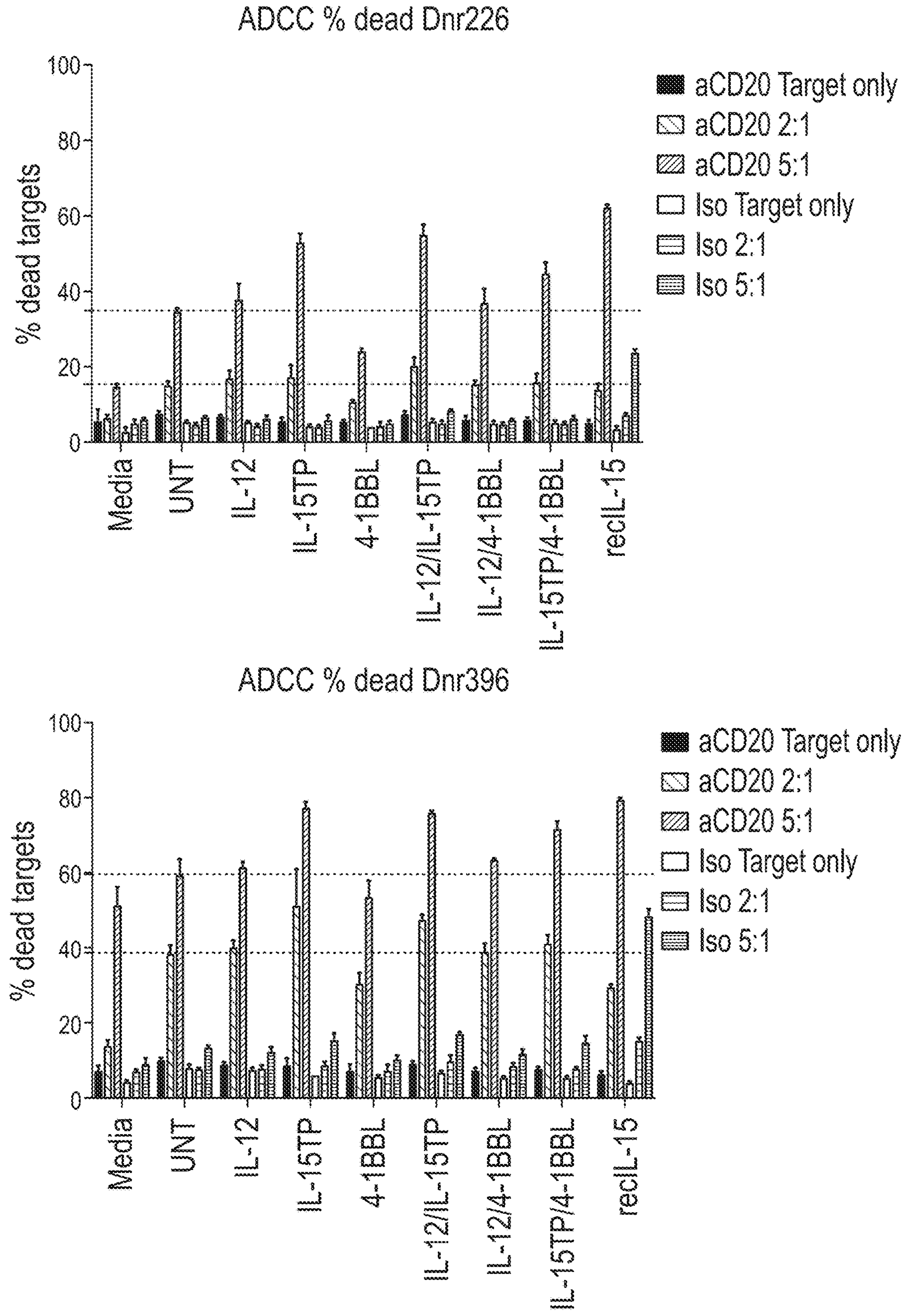

As shown in FIG. 28B, NK cells primed overnight with enucleated erythroid cells comprising IL-15/IL-15RA alone, or comprising both IL-12 and IL-15/IL-15RA, or IL-15/IL-15RA and 4-1BBL demonstrated increased cytotoxicity against Raji cells, as compared to NK cells primed overnight with enucleated erythroid cells comprising IL-12 alone, 4-1BBL alone, or no protein (control). Cytotoxocity was most prominent at a 5:1 E:T ratio, and the enucleated erythroid cells comprising combinations of IL-12 and IL-15/IL-15RA, or IL-15/IL-15RA and 4-1BBL, did not exhibit enhanced cytotoxicity as compared to cells comprising either 4-1BBL alone or IL-12 alone Therefore, the enhancement of ADCC appears to be driven by IL-15/IL-15RA. These results thus demonstrate that enucleated erythroid cells comprising IL-15/IL-15RA alone or both IL-12 and IL-15/IL-15RA, or IL-15/IL-15RA and 4-1BBL enhanced the ADCC activity of NK cells on a per cell basis of Raji cell targets.

Example 32. Engineered Human Erythroid Cells Comprising IL-12, IL-15/IL-15RA, 4-1BBL or Combinations Thereof, with or without Anti-CD3 Antibody Stimulation, Induce an IFNg Response and the Proliferation of CD4+ and CD8+ T Cells, NK and NKT Cells The effect of human enucleated erythroid cells comprising IL-12 alone, IL-15/IL-15RA (V4.1) alone, 4-1BBL alone, or both IL-12 and IL-15/IL-15RA (V4.1), IL-12 and 4-1BBL, or IL-15/IL-15RA and 4-1BBL on the proliferation and activation of primary CD4+ T cells, CD8+ T cells, NK cells, and NKT cells was assessed with or without anti-CD3 antibody stimulation. Briefly, 100,000 PBMCs from 3 donors were labelled with CTFR and incubated with either enucleated erythroid cells comprising IL-12 alone, IL-15/IL-15RA alone, 4-1BBL alone, or a combination of IL-12 and IL-15/IL-15RA, IL-12 and 4-1BBL, or IL-15/IL-15RA and 4-1BBL; or as controls, PBMC were incubated with enucleated erythroid cells lacking exogenous protein (UNT), or contacted with media (Media). Either 400,000, 200,000 or 100,000 enucleated erythroid cells were used. On day 5 or day 8, the percentage of CD8+ T cells, CD4+ T cells, NK cells, and NKT cells that were actively dividing was evaluated using CTFR dilution. Supernatants were collected and the amount of IFNγ was evaluated using ELISA. The experiments were performed as a 5 day assay with 0.5 ug/mL in combination with anti-CD3 treatment, or an 8-day assay, with no anti-CD3 antibody treatment.

Figure 29A:
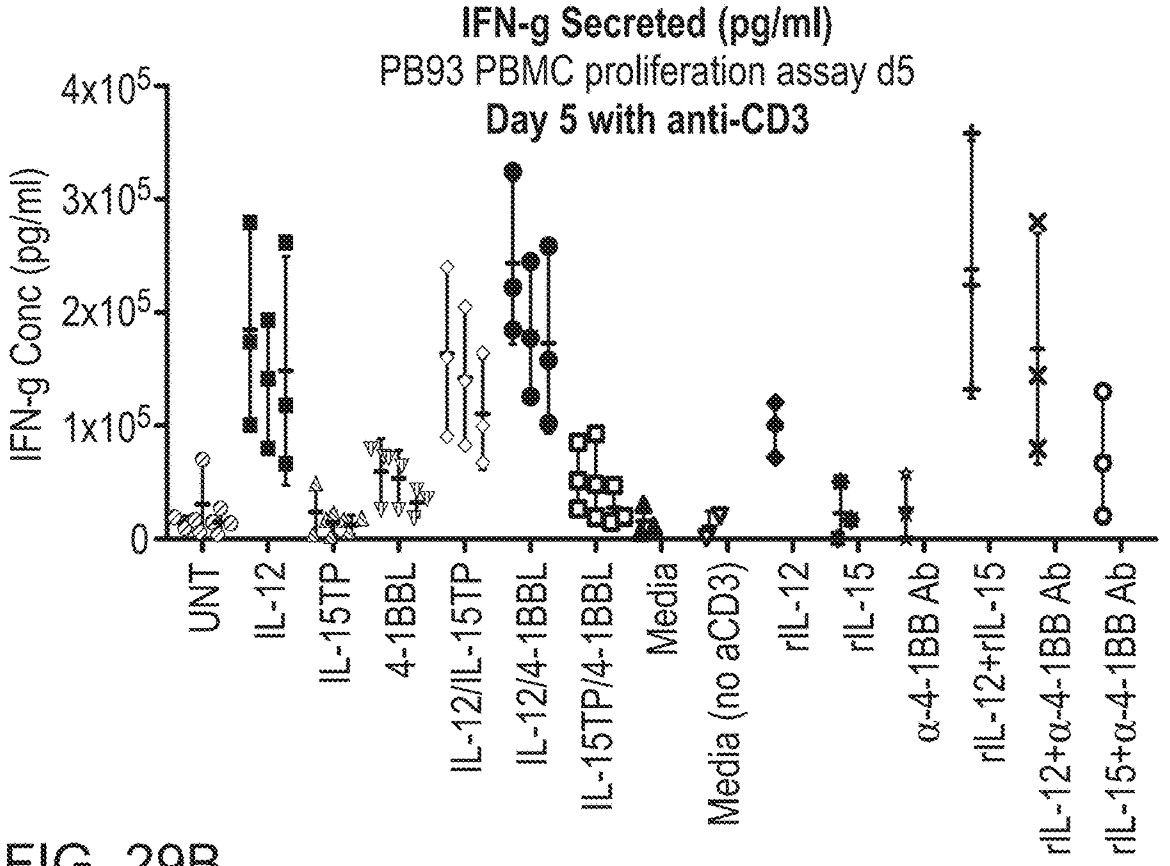
FIG. 29A is a graph showing that human enucleated engineered erythroid cells comprising IL-12, in combination with anti-CD3, induced a significant amount of IFNg production from PBMCs, and IL-12/4-1BBL induce the highest levels of IFNg.
Figure 29B:
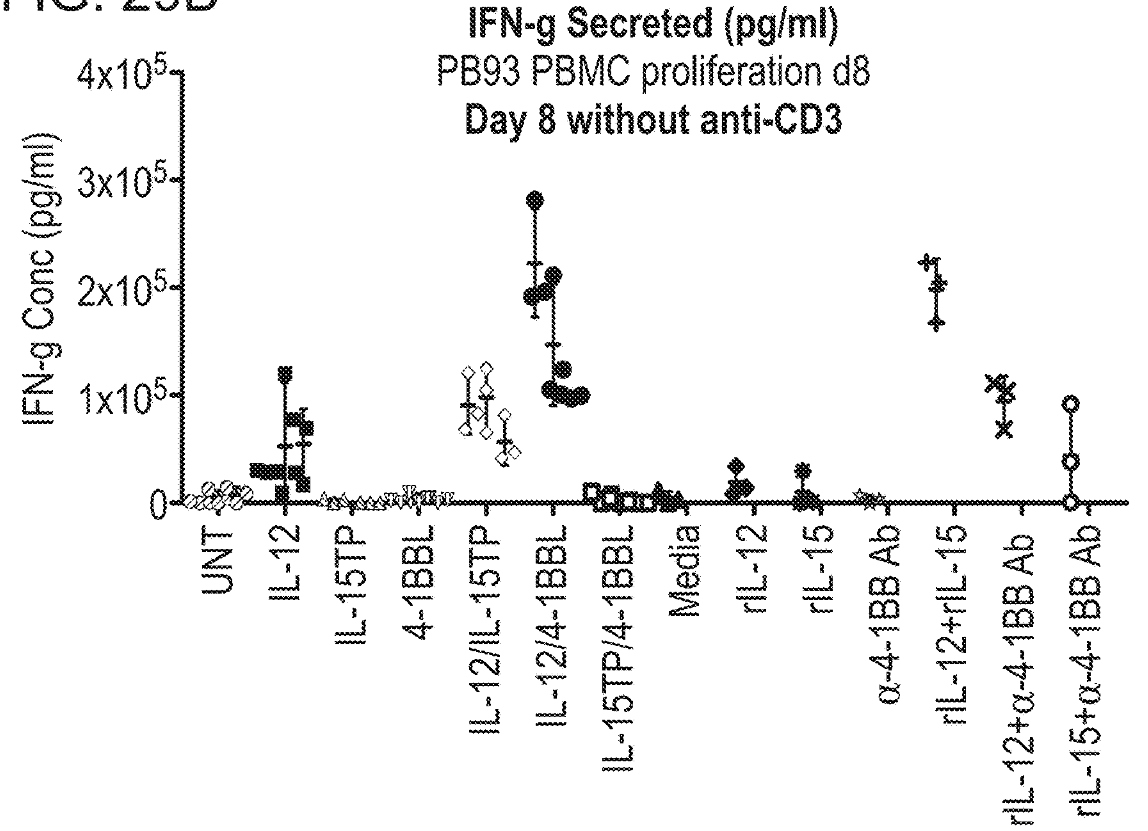
FIG. 29B is a graph showing that human enucleated engineered erythroid cells comprising IL-12, without anti-CD3, induced IFNg production from the PBMCs.
Figure 29C:
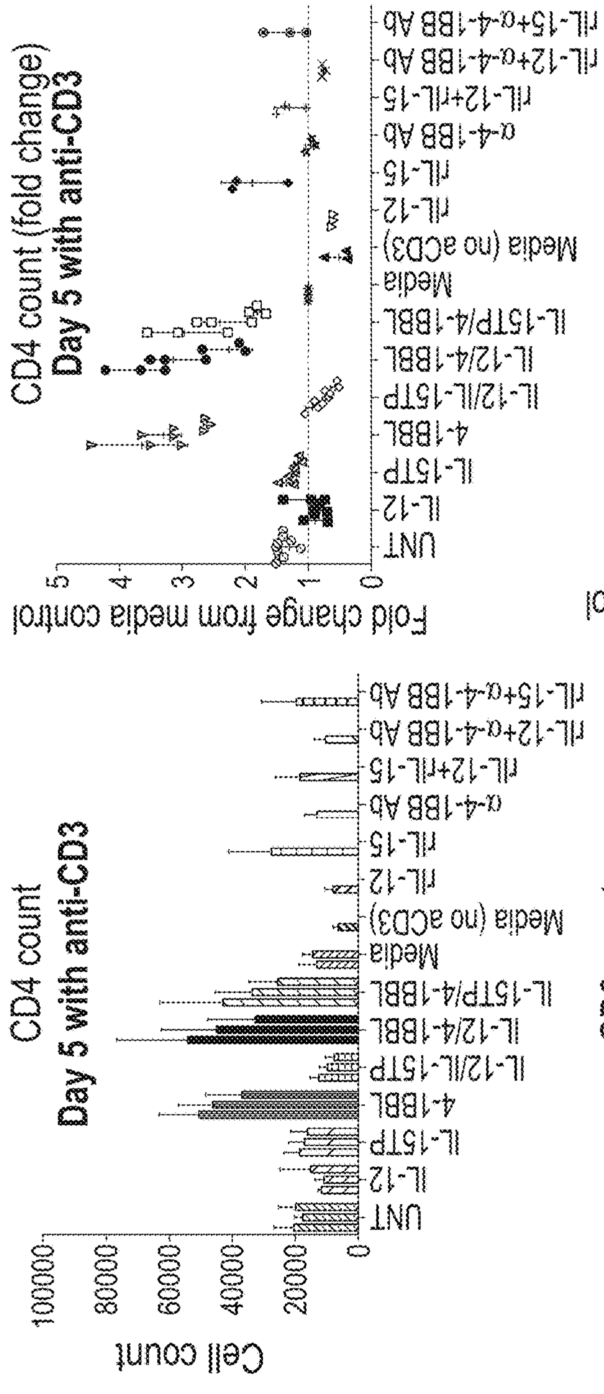
FIG. 29C is a graph showing human engineered erythroid cells expressing 41BBL, IL-12/4-1BBL or IL-15/IL-15RA/4-1BBL, in combination with anti-CD3, induced proliferation of CD4 cells.

As shown in FIG. 29A, treatment with enucleated erythroid cells comprising IL-12, in combination with anti-CD3 antibody stimulation, induced a significant amount of IFNg production by PBMCs, while treatment with enucleated erythroid cells comprising both IL-12 and 4-1BBL, in combination with anti-CD3 antibody stimulation, induced the highest levels of IFNg production by PBMCs. In the absence of anti-CD3 antibody stimulation, only the enucleated erythroid cells comprising IL-12 induced IFNg production by PBMCs (see FIG. 29B). Further, in PBMCs stimulated with anti-CD3 antibody, treatment with enucleated erythroid cells comprising either 41BBL alone, both IL-12 and 4-1BBL, or both IL-15/IL-15RA and 4-1BBL, induced proliferation of CD4+ T cells (see FIG. 29C). Thus, CD4+ T cell proliferation appears to be driven by 4-1BBL.

Figure 29D:
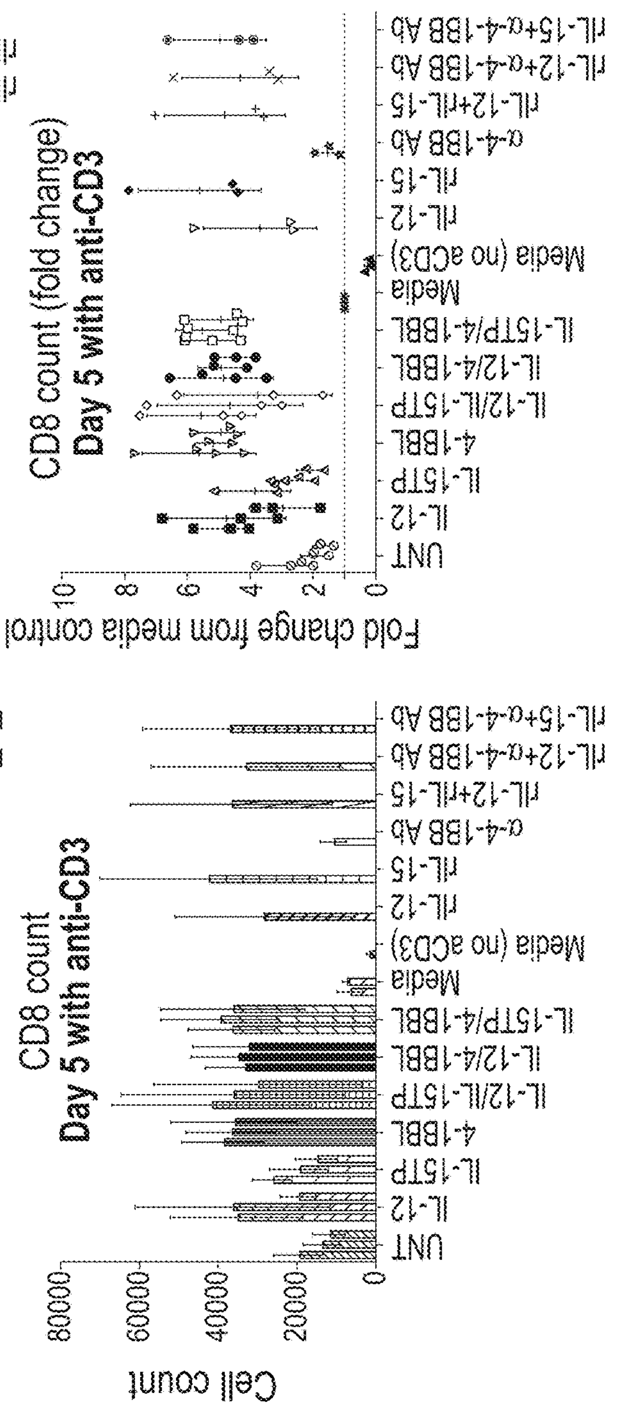
FIG. 29D is a graph showing human engineered erythroid cells expressing IL-12/IL-15/IL-15RA, IL-12/4-1BBL or IL-15/IL-15RA/4-1BBL, in combination with anti-CD3, moderately enhanced CD8 cell proliferation.
Figure 29E:
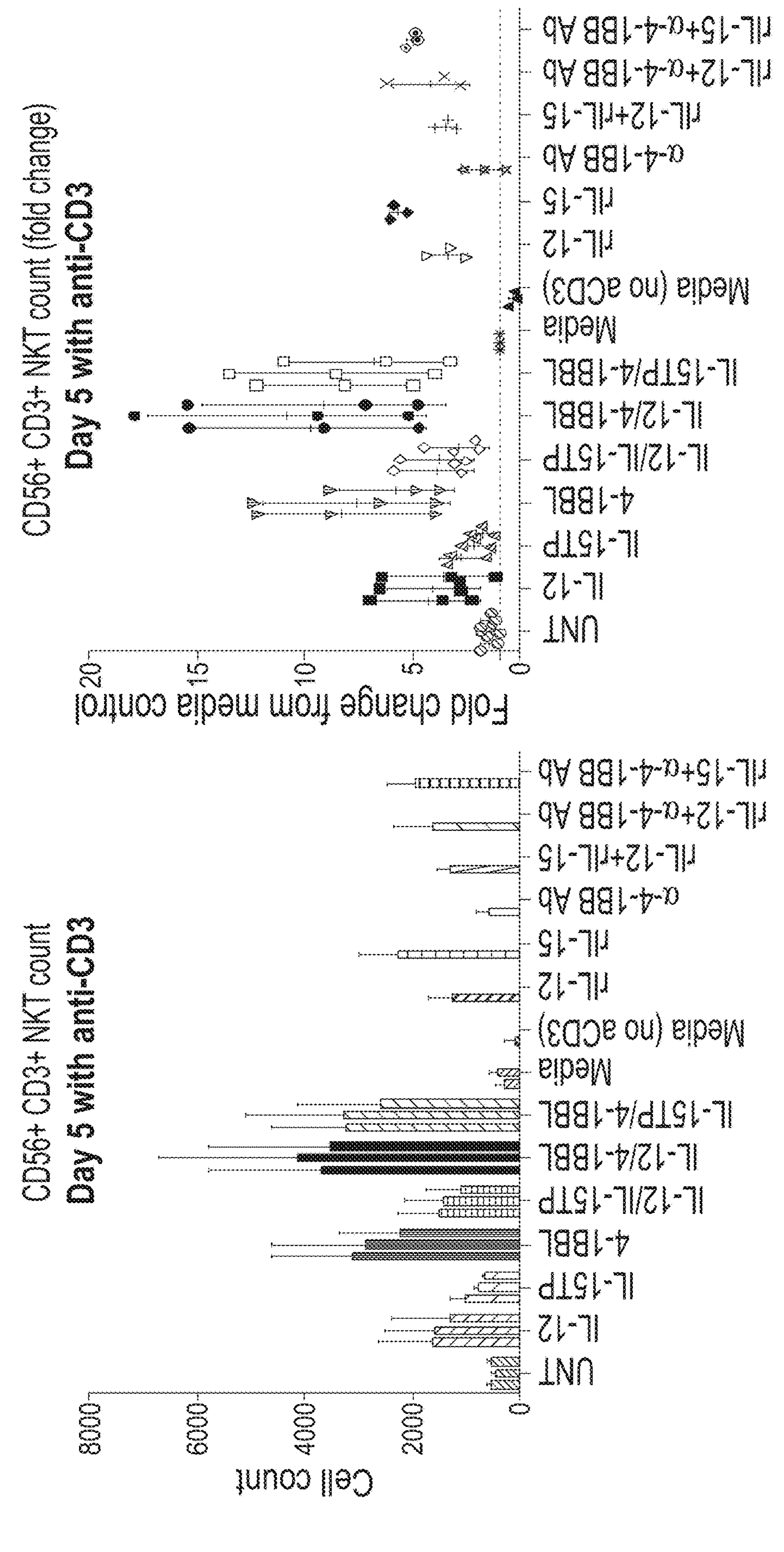
FIG. 29E is a graph showing human engineered erythroid cells expressing IL-12/4-1BBL or IL-15/IL-15RA/4-1BBL, in combination with anti-CD3, induced significant NKT cell proliferation.

FIG. 29D shows that PBMCs treated with a combination of anti-CD3 antibody and enucleated erythroid cells comprising either IL-12 and IL-15/IL-15RA, IL-12 and 4-1BBL, or IL-15/IL-15RA and 4-1BBL, exhibited moderately enhanced CD8+ T cell proliferation (approximately 5-fold increase in cell count). This CD8+ T cell fold change was more variable in PBMCs treated with enucleated erythroid cells comprising IL-12 and IL-15/IL-15RA than PBMCs treated with the other enucleated erythroid cells. Moreover, PBMCs treated with a combination of anti-CD3 antibody, and enucleated erythroid cells comprising either IL-12 and 4-1BBL or IL-15/IL-15RA and 4-1BBL, exhibited significant NKT cell proliferation, that is also likely driven by 4-1BBL (see FIG. 29E). Treatment of PBMCs with enucleated erythroid cells comprising IL-12 and IL-15/IL-15RA induced moderate NKT cell proliferation which did not surpass the NKT cell proliferation observed when PBMCs were treated with enucleated erythroid cells comprising IL-12 alone.

Figure 29F:
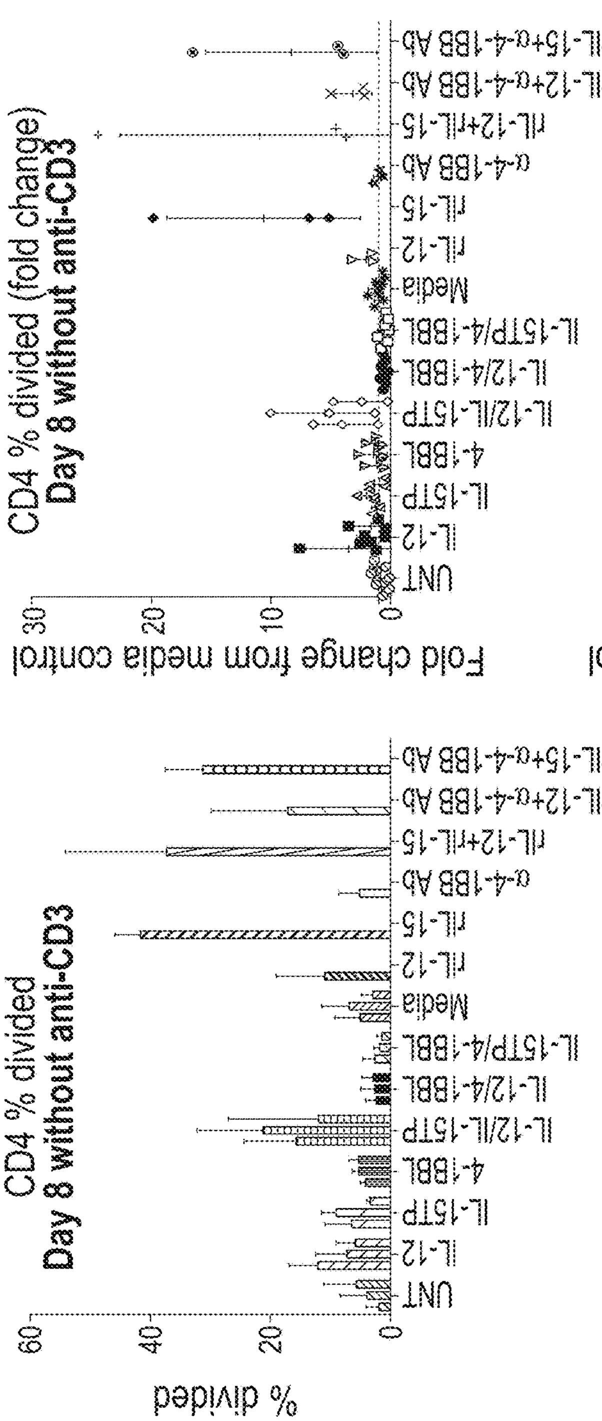
FIG. 29F is a graph showing human engineered erythroid cells expressing IL-12/IL-15/IL-15RA, without anti-CD3, induced limited CD4 cell proliferation.
Figure 29G:
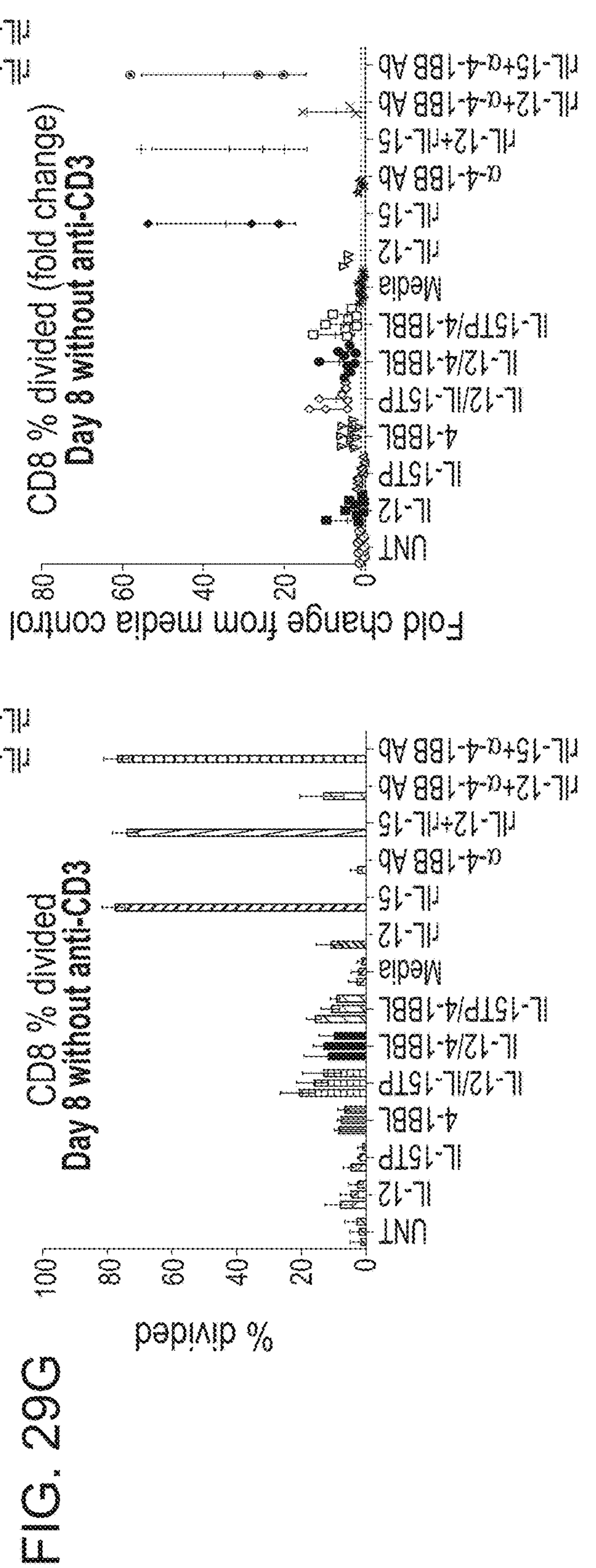
FIG. 29G is a graph showing human engineered erythroid cells expressing IL-12/IL-15/IL-15RA, IL-12/4-1BBL, or IL-15/IL-15RA/4-1BBL, without anti-CD3, moderately enhanced CD8 cell proliferation.
Figure 29H:
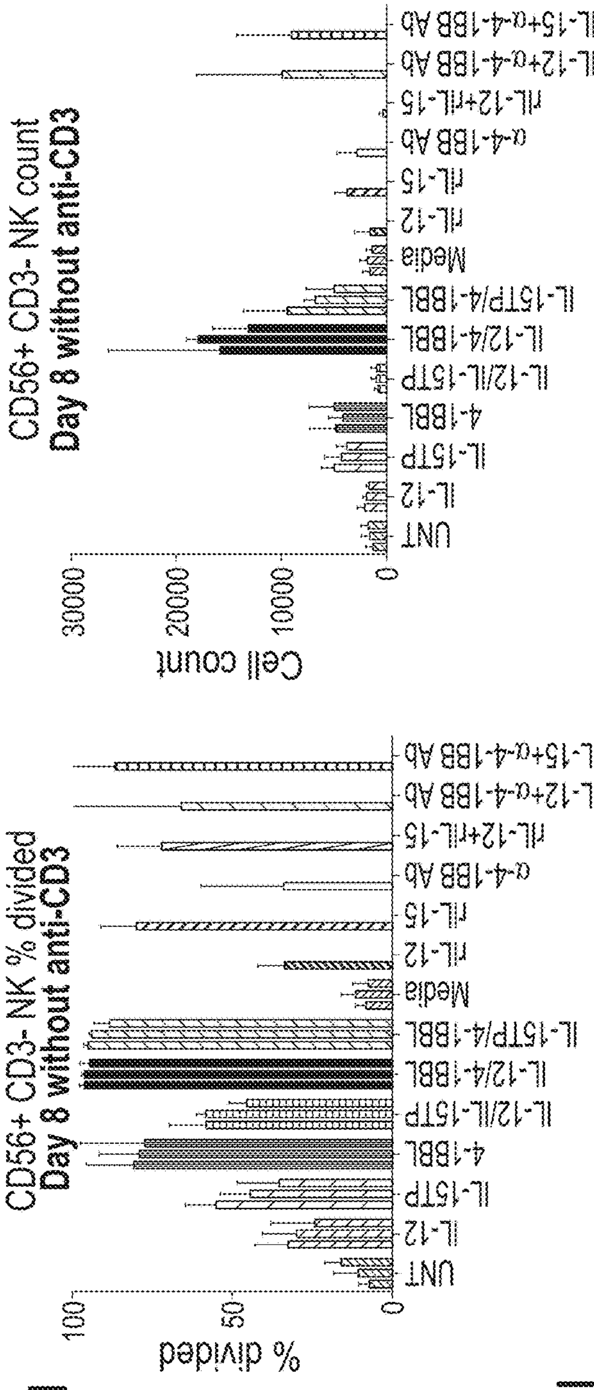
FIG. 29H is a graph showing human engineered erythroid cells expressing IL-12/IL-15/IL-15RA, without anti-CD3, enhanced division of NK cells but did not increase cell count, indicating only a modest proliferation of NK cells. IL-12/4-1BBL and IL-15/4-1BBL induced extensive NK cell proliferation, leading to greatly increased cell numbers with IL-12/4-1BBL, and surpassing the effects of IL-15/IL-15RA/4-1BBL.
Figure 29I:
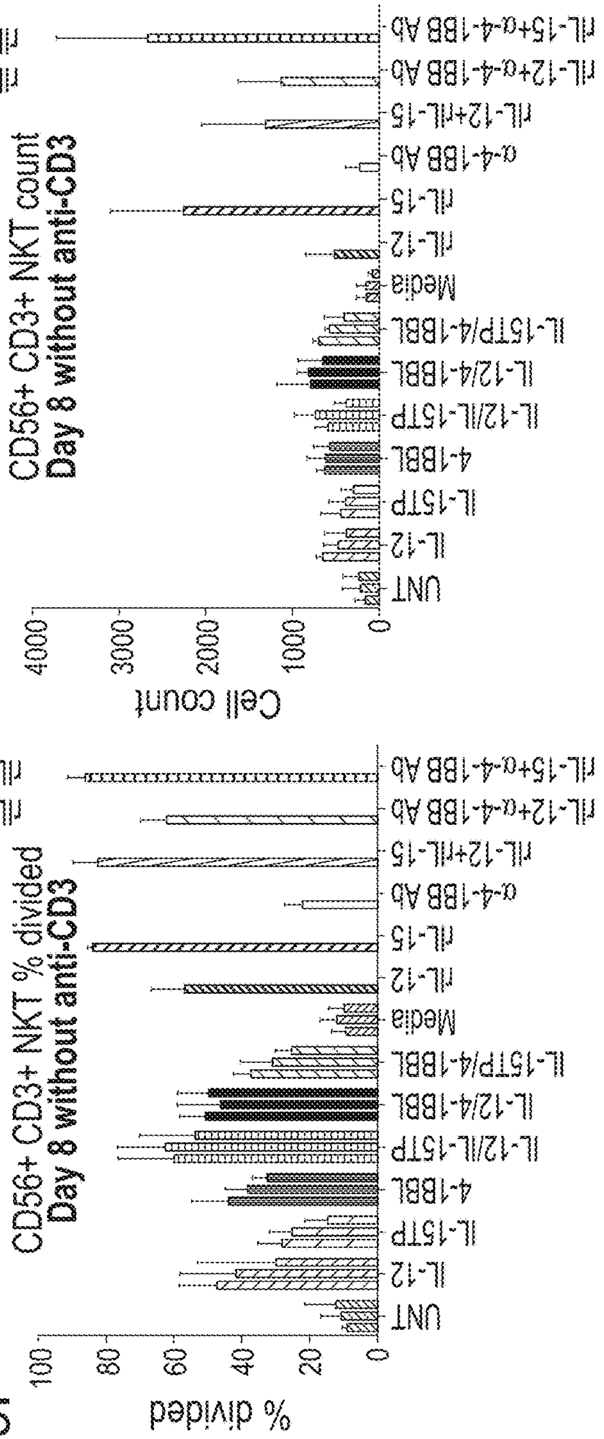
FIG. 29I is a graph showing human engineered erythroid cells expressing IL-12/IL-15/IL-15RA, IL-12/4-1BBL or IL-15/IL-15RA/4-1BBL, without anti-CD3, induced moderate proliferative effects on NKT cells.

As shown in FIG. 29F, in PBMCs that were not stimulated with anti-CD3 antibody, only enucleated erythroid cells comprising both IL-12 and IL-15/IL-15RA induced limited CD4+ T cell proliferation. Further, as shown in FIG. 29G, in PBMCs that were also not stimulated with anti-CD3 antibody, enucleated erythroid cells comprising IL-12 and IL-15/IL-15RA, IL-12 and 4-1BBL, or IL-15/IL-15RA and 4-1BBL, moderately enhanced CD8+ T cell proliferation (approximately 10-20% division). Treatment of PBMCs with enucleated erythroid cells comprising both IL-12 and IL-15/IL-15RA enhanced division of NK cells (approximately 50-60%) but did not increase cell count, indicating only a modest proliferation of NK cells (see FIG. 29H). However, treatment of PBMCs with enucleated erythroid cells comprising either IL-12 and 4-1BBL or IL-15/IL-15RA and 4-1BBL, induced extensive NK cell proliferation. Finally, in PBMCs that were not stimulated with anti-CD3 antibody, enucleated erythroid cells comprising IL-12 and IL-15/IL-15RA, IL-12 and 4-1BBL, or IL-15/IL-15RA and 4-1BBL, induced moderate proliferative effects on NKT cells.

Taken together, the results presented in this example demonstrated that enucleated erythroid cells comprising either IL-12 and IL-15/IL-15RA, IL-12 and 4-1BBL, or and IL-15/IL-15RA and 4-1BBL induced potent activation of primary CD4+ T cells, CD8+ T cells, NK cells, and NKT cells. The activation of CD4+ T cells, CD8+ T cells and NKT cells was further enhanced when PBMCs were stimulated with anti-CD3 antibody.

Figure 29J:
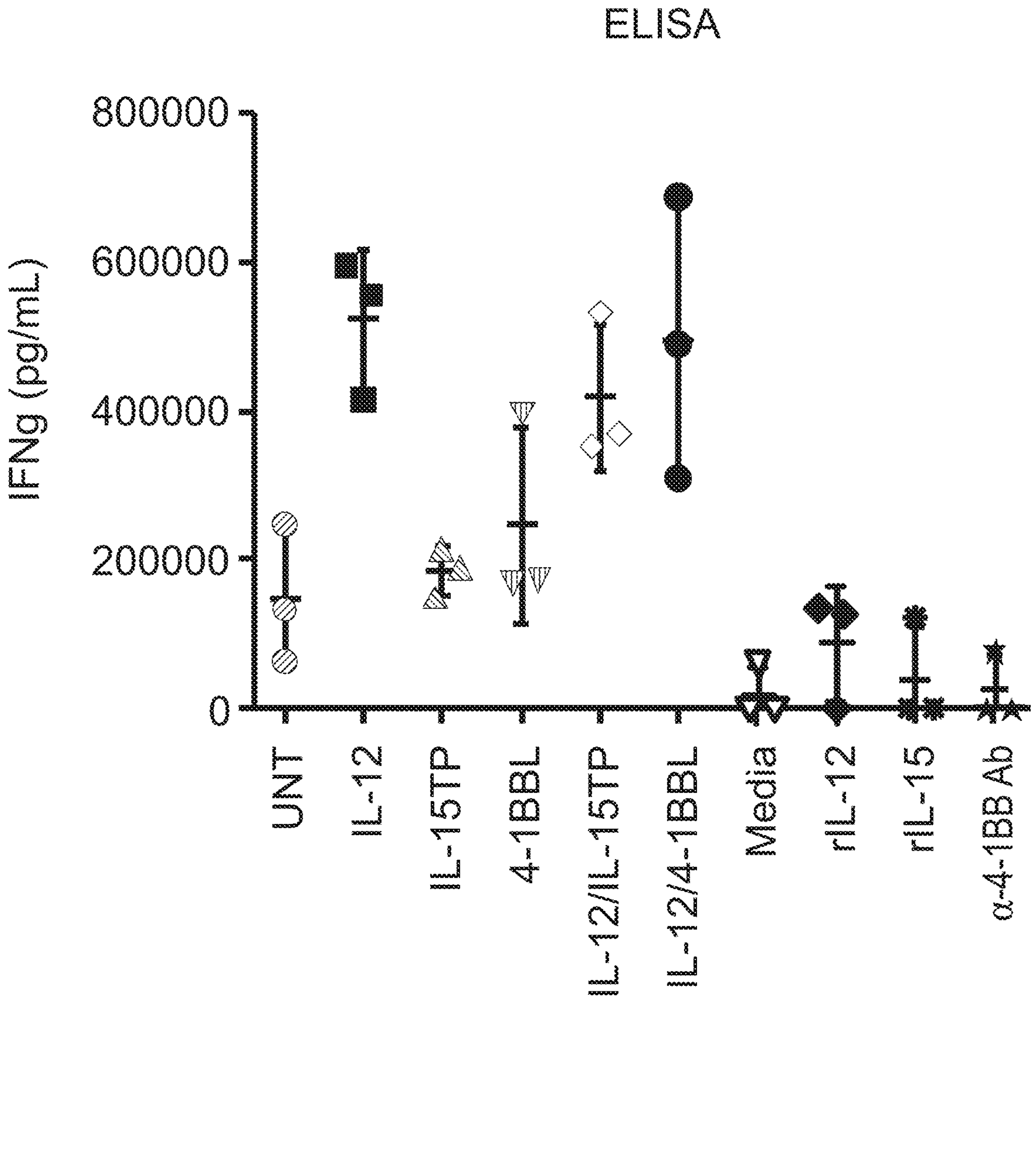
FIG. 29J is a graph showing that RBCs expressing IL-12, IL-15/IL-15RA, 4-1BBL or co-expressing IL-12/IL-15/IL-15RA, IL-12/4-1BBL and IL-15/IL-15RA/4-1BBL, are able to drive Th1 differentiation of human naïve CD4 cells.

In additional experiments, human naïve CD4+ T cells were isolated from PBMCs using negative selection using Miltenyi microbeads according to the manufacturer's protocol. The purified naïve CD4+ T cells were incubated with enucleated erythroid cells comprising either IL-12 alone, IL-15/IL-15RA alone, 4-1BBL alone, or both IL-12 and IL-15/IL-15RA, IL-12 and 4-1BBL, or IL-15/IL-15RA and 4-1BBL; or as controls, CD4+ T cells were contacted with (UNT), or contacted with media (Media). The CD4+ T cells were also stimulated with anti-CD3 antibody and anti-CD28 antibody, and the contacting was performed at a ratio of 1:5 (CD4+ T cells:engineered erythroid cells) for 5 days. IFNg levels were analyzed in the media supernatant using ELISA. The data, presented as the average from 3 different PBMC donors in FIG. 29J, demonstrates that enucleated erythroid cells comprising IL-12 alone, IL-15/IL-15RA alone, 4-1BBL alone, or both IL-12 and IL-15/IL-15RA, IL-12 and 4-1BBL, or IL-15/IL-15RA and 4-1BBL, were able to induce Th1 differentiation of human naïve CD4+ T cells.

Sequences:

SEQ ID NO: 1, IL-15/1L-15 receptor α fusion
NWVNVISDLKKIEDLIQSMHIDATLYTESDVHPSCKVTAMKCFLLELQVISLESGDASIHDTVE
NLIILANNSLSSNGNVTESGCKECEELEEKNIKEFLQSFVHIVQMFINTSGGGGSGGGGSGGGG
SITCPPPMSVEHADIWVKSYSLYSRERYICNSGFKRKAGTSSLTECVLNKATNVAHWTTPSLKC
IRDPALVHQRPAPPSTVTTAGVTPQPESLSPSGKEPAASSPSSNNTAATTAAIVPGSQLMPSKS
PSTGTTEISSHESSHGTPSQTTAKNWELTASASHQPPGVYPQGHSDTT SEQ ID NO: 2, IL-15/IL-15 receptor α sushi domain + 13 aa
NWVNVISDLKKIEDLIQSMHIDATLYTESDVHPSCKVTAMKCFLLELQVISLESGDASIHDTVE
NLIILANNSLSSNGNVTESGCKECEELEEKNIKEFLQSFVHIVQMFINTSGGGGSGGGGSGGGG
SITCPPPMSVEHADIWVKSYSLYSRERYICNSGFKRKAGTSSLTECVLNKATNVAHWTTPSLKC
IRDPALVHQRPAPPS SEQ ID NO: 3, immature human IL-15
MRISKPHLRSISIQCYLCLLLNSHFLTEAGIHVFILGCFSAGLPKTEANWVNVISDLKKI
EDLIQSMHIDATLYTESDVHPSCKVTAMKCFLLELQVISLESGDASIHDTVENLIILANN
SLSSNGNVTESGCKECEELEEKNIKEFLQSFVHIVQMFINTS SEQ ID NO: 4, mature human IL-15
NWVNVISDLKKIEDLIQSMHIDATLYTESDVHPSCKVTAMKCFLLELQVISLESGDASIHDTVE
NLIILANNSLSSNGNVTESGCKECEELEEKNIKEFLQSFVHIVQMFINTS SEQ ID NO: 5, immature full-length human IL-15 receptor α
MAPRRARGCRTLGLPALLLLLLLRPPATRGITCPPPMSVEHADIWVKSYSLYSRERYICNSGFK
RKAGTSSLTECVLNKATNVAHWTTPSLKCIRDPALVHQRPAPPSTVTTAGVTPQPESLSPSGKE
PAASSPSSNNTAATTAAIVPGSQLMPSKSPSTGTTEISSHESSHGTPSQTTAKNWELTASASHQ
PPGVYPQGHSDTTVAISTSTVLLCGLSAVSLLACYLKSRQTPPLASVEMEAMEALPVTWGTSSR
DEDLENCSHHL SEQ ID NO: 6, mature full-length human IL-15 receptor α
ITCPPPMSVEHADIWVKSYSLYSRERYICNSGFKRKAGTSSLTECVLNKATNVAHWTTPSLKCI
RDPALVHQRPAPPSTVTTAGVTPQPESLSPSGKEPAASSPSSNNTAATTAAIVPGSQLMPSKSP
STGTTEISSHESSHGTPSQTTAKNWELTASASHQPPGVYPQGHSDTTVAISTSTVLLCGLSAVS
LLACYLKSRQTPPLASVEMEAMEALPVTWGTSSRDEDLENCSHHL -continued

| Sequences: |
|---|

SEQ ID NO: 7, immature extracellular human IL-15 receptor α
MAPRRARGCRTLGLPALLLLLLLRPPATRGITCPPPMSVEHADIWVKSYSLYSRERYICNSGFK
RKAGTSSLTECVLNKATNVAHWTTPSLKCIRDPALVHQRPAPPSTVTTAGVTPQPESLSPSGKE
PAASSPSSNNTAATTAAIVPGSQLMPSKSPSTGTTEISSHESSHGTPSQTTAKNWELTASASHQ
PPGVYPQGHSDTT SEQ ID NO: 8, mature extracellular human IL-15 receptor α
ITCPPPMSVEHADIWVKSYSLYSRERYICNSGFKRKAGTSSLTECVLNKATNVAHWTTPSLKCI
RDPALVHQRPAPPSTVTTAGVTPQPESLSPSGKEPAASSPSSNNTAATTAAIVPGSQLMPSKSP
STGTTEISSHESSHGTPSQTTAKNWELTASASHQPPGVYPQGHSDTT SEQ ID NO: 9, human IL-15 receptor α sushi domain
ITCPPPMSVEHADIWVKSYSLYSRERYICNSGFKRKAGTSSLTECVLNKATNVAHWTTPSLKCI
R SEQ ID NO: 10, human IL-15 receptor αsushi domain + 13
additional amino acids of IL-15 receptor α
ITCPPPMSVEHADIWVKSYSLYSRERYICNSGFKRKAGTSSLTECVLNKATNVAHWTTPSLKCI
RDPALVHQRPAPPS SEQ ID NO: 11, G4S linker
GGGGS SEQ ID NO: 12, (G4S)3 linker
GGGGSGGGGSGGGGS SEQ ID NO: 13 (encodes SEQ ID NO: 4, mature human IL-15)
AACTGGGTGAACGTTATTAGTGACCTTAAAAAGATCGAAGATTTGATACAGTCAATGCACATAG
ACGCGACGCTTTATACAGAATCTGATGTACATCCTTCATGCAAGGTTACTGCTATGAAGTGTTT
TCTTCTCGAACTCCAAGTAATAAGTCTTGAGAGCGGAGATGCGAGCATTCATGACACCGTTGAG
AATCTTATTATATTGGCTAACAACTCTCTGTCCAGCAATGGTAATGTGACAGAAAGCGGGTGTA
AGGAGTGCGAGGAACTCGAGGAGAAGAACATCAAAGAGTTCTTGCAGTCTTTCGTCCATATTGT
CCAGATGTTCATAAATACTAGC SEQ ID NO: 14 (encodes SEQ ID NO: 4, mature human IL-15)
AACTGGGTAAACGTCATAAGCGACCTCAAAAAGATCGAGGACCTTATACAGTCTATGCACATAG
ATGCGACACTTTACACGGAATCAGACGTGCACCCGTCCTGCAAAGTCACAGCCATGAAGTGCTT
TCTTCTCGAACTGCAGGTAATTTCTCTCGAATCAGGTGACGCATCTATCCACGACACAGTTGAA
AATCTTATTATCCTGGCTAATAACTCCCTTAGCTCAAACGGCAATGTCACCGAGAGTGGATGTA
AAGAATGTGAGGAACTTGAAGAGAAAAACATAAAGGAATTCTTGCAGAGTTTCGTTCATATTGT
GCAAATGTTCATCAATACTAGT SEQ ID NO: 15 (encodes SEQ ID NO: 8, mature extracellular human
IL-15 receptor α)
ATCACATGCCCACCGCCCATGTCTGTTGAACACGCAGACATTTGGGTTAAAAGTTACTCACTTT
ACTCACGCGAGAGATATATATGCAACAGCGGCTTCAAGCGCAAAGCAGGCACTAGTAGTCTTAC
AGAGTGCGTGCTCAATAAAGCTACAAATGTAGCTCATTGGACTACTCCTAGTCTCAAATGCATT
CGGGACCCCGCGCTTGTGCACCAGAGACCTGCGCCGCCGTCCACAGTGACGACAGCTGGTGTAA
CCCCCCAACCTGAATCCCTTAGTCCGTCTGGTAAAGAACCGGCGGCGTCTTCACCTTCCAGCAA
TAATACTGCGGCGACAACAGCCGCGATAGTTCCTGGATCCCAACTCATGCCGTCAAAGTCTCCT
TCAACGGGAACGACAGAGATCTCTTCACATGAAAGTTCTCATGGAACACCGAGCCAAACTACGG
CAAAGAACTGGGAACTGACTGCCTCAGCAAGCCACCAGCCGCCAGGGGTGTACCCGCAAGGGCA
CTCAGATACTACT SEQ ID NO: 16 (encodes SEQ ID NO: 10, human IL-15 receptor α
sushi domain + 13 additional amino acids of IL-15 receptor α)
ATCACCTGCCCGCCTCCCATGAGCGTGGAACACGCGGACATTTGGGTTAAGAGCTACAGTCTTT
ACAGCCGGGAGCGCTATATCTGCAACTCAGGGTTTAAGCGGAAAGCAGGGACATCAAGTTTGAC
AGAATGTGTGTTGAACAAGGCTACAAATGTTGCTCACTGGACCACGCCATCTTTGAAGTGTATC
CGAGATCCCGCGCTTGTCCATCAGCGCCCAGCGCCTCCCTCC SEQ ID NO: 17 (encodes SEQ ID NO: 12, $(G4S)_3$ linker)
GGGGGAGGTGGCTCTGGTGGAGGCGGGAGTGGCGGGGGCGGCTCA SEQ ID NO: 18 (encodes SEQ ID NO: 12, $(G4S)_3$ linker)
GGCGGGGGGGGAAGCGGTGGTGGAGGGAGCGGGGGTGGTGGATCC SEQ ID NO: 19 (encodes SEQ ID NO: 1, IL-15/IL-15 receptor α
fusion)
AACTGGGTGAACGTTATTAGTGACCTTAAAAAGATCGAAGATTTGATACAGTCAATGCACATAG
ACGCGACGCTTTATACAGAATCTGATGTACATCCTTCATGCAAGGTTACTGCTATGAAGTGTTT
TCTTCTCGAACTCCAAGTAATAAGTCTTGAGAGCGGAGATGCGAGCATTCATGACACCGTTGAG
AATCTTATTATATTGGCTAACAACTCTCTGTCCAGCAATGGTAATGTGACAGAAAGCGGGTGTA
AGGAGTGCGAGGAACTCGAGGAGAAGAACATCAAAGAGTTCTTGCAGTCTTTCGTCCATATTGT
CCAGATGTTCATAAATACTAGCGGGGGAGGTGGCTCTGGTGGAGGCGGGAGTGGCGGGGGCGGC
TCAATCACATGCCCACCGCCCATGTCTGTTGAACACGCAGACATTTGGGTTAAAAGTTACTCAC -continued

| Sequences: |
|---|

TTTACTCACGCGAGAGATATATATGCAACAGCGGCTTCAAGCGCAAAGCAGGCACTAGTAGTCT
TACAGAGTGCGTGCTCAATAAAGCTACAAATGTAGCTCATTGGACTACTCCTAGTCTCAAATGC
ATTCGGGACCCCGCGCTTGTGCACCAGAGACCTGCGCCGCCGTCCACAGTGACGACAGCTGGTG
TAACCCCCCAACCTGAATCCCTTAGTCCGTCTGGTAAAGAACCGGCGGCGTCTTCACCTTCCAG
CAATAATACTGCGGCGACAACAGCCGCGATAGTTCCTGGATCCCAACTCATGCCGTCAAAGTCT
CCTTCAACGGGAACGACAGAGATCTCTTCACATGAAAGTTCTCATGGAACACCGAGCCAAACTA
CGGCAAAGAACTGGGAACTGACTGCCTCAGCAAGCCACCAGCCGCCAGGGGTGTACCCGCAAGG
GCACTCAGATACTACT

SEQ ID NO: 20 (encodes SEQ ID NO: 2, IL-15/1L-15 receptor α sushi domain + 13 aa)
AACTGGGTAAACGTCATAAGCGACCTCAAAAAGATCGAGGACCTTATACAGTCTATGCACATAG
ATGCGACACTTTACACGGAATCAGACGTGCACCCGTCCTGCAAAGTCACAGCCATGAAGTGCTT
TCTTCTCGAACTGCAGGTAATTTCTCTCGAATCAGGTGACGCATCTATCCACGACACAGTTGAA
AATCTTATTATCCTGGCTAATAACTCCCTTAGCTCAAACGGCAATGTCACCGAGAGTGGATGTA
AAGAATGTGAGGAACTTGAAGAGAAAAACATAAAGGAATTCTTGCAGAGTTTCGTTCATATTGT
GCAAATGTTCATCAATACTAGTGGCGGGGGGGGAAGCGGTGGTGGAGGGAGCGGGGGTGGTGGA
TCCATCACCTGCCCGCCTCCCATGAGCGTGGAACACGCGGACATTTGGGTTAAGAGCTACAGTC
TTTACAGCCGGGAGCGCTATATCTGCAACTCAGGGTTTAAGCGGAAAGCAGGGACATCAAGTTT
GACAGAATGTGTGTTGAACAAGGCTACAAATGTTGCTCACTGGACCACGCCATCTTTGAAGTGT
ATCCGAGATCCCGCGCTTGTCCATCAGCGCCCAGCGCCTCCCTCC SEQ ID NO: 21, GPA signal peptide:
MYGKIIFVLLLSEIVSISA SEQ ID NO: 22, encodes GPA signal peptide:
ATGTATGGAAAAATAATCTTTGTATTACTATTGTCAGAAATTGTGAGCATATCAGCA SEQ ID NO: 23, Linker-HA-linker:
GGSGGSGGYPYDVPDYAGGGSGGGS SEQ ID NO: 24, encodes Linker-HA-linker:
GGAGGATCTGGCGGGTCTGGAGGCTACCCCTATGACGTGCCCGACTATGCCGGCGGAGGGTCTG
GAGGCGGTTCC SEQ ID NO: 25, GPA:
LSTTEVAMHTSTSSSVTKSYISSQTNDTHKRDTYAATPRAHEVSEISVRTVYPPEEETGE
RVQLAHHFSEPEITLIIFGVMAGVIGTILLISYGIRRLIKKSPSDVKPLPSPDTDVPLSS
VEIENPETSDQ SEQ ID NO: 26, encodes GPA:
TTAAGTACCACTGAGGTGGCAATGCACACTTCAACCTCTTCTTCAGTCACAAAGAGTTACATCT
CATCACAGACAAATGATACGCACAAACGGGACACATATGCAGCCACTCCTAGAGCTCATGAAGT
TTCAGAAATTTCTGTTAGAACTGTTTACCCTCCAGAAGAGGAAACCGGAGAAAGGGTACAACTT
GCCCATCATTTCTCTGAACCAGAGATAACACTCATTATTTTTGGGGTGATGGCTGGTGTTATTG
GAACGATCCTCTTAATTTCTTACGGTATTCGCCGACTGATAAAGAAAAGCCCATCTGATGTAAA
ACCTCTCCCCTCACCTGACACAGACGTGCCTTTAAGTTCTGTTGAAATAGAAAATCCAGAGACA
AGTGATCAA SEQ ID NO: 27, IL-15 V3:
MYGKIIFVLLLSEIVSISANWVNVISDLKKIEDLIQSMHIDATLYTESDVHPSCKVTAMKCFLL
ELQVISLESGDASIHDTVENLIILANNSLSSNGNVTESGCKECEELEEKNIKEFLQSFVHIVQM
FINTSGGSGGSGGYPYDVPDYAGGGSGGGSLSTTEVAMHTSTSSSVTKSYISSQTNDTHKRDTY
AATPRAHEVSEISVRTVYPPEEETGERVQLAHHFSEPEITLIIFGVMAGVIGTILLISYGIRRL
IKKSPSDVKPLPSPDTDVPLSSVEIENPETSDQ SEQ ID NO: 28, encodes SEQ ID NO: 27, IL-15 V3:
ATGTATGGAAAAATAATCTTTGTATTACTATTGTCAGAAATTGTGAGCATATCAGCA
AACTGGGTAAATGTGATTTCAGACCTGAAAAAAATCGAAGACCTTATTCAATCCATGCACATCG
ACGCGACACTTTATACTGAATCAGACGTACACCCGTCCTGTAAGGTTACTGCGATGAAGTGCTT
TCTGTTGGAATTGCAAGTGATCTCCCTCGAATCAGGGGATGCATCCATTCATGATACCGTCGAG
AATTTGATCATTCTGGCAAATAACTCCCTCAGTAGTAACGGGAATGTGACCGAGTCTGGGTGTA
AGGAGTGCGAAGAGTTGGAGGAAAAGAATATCAAAGAATTCCTTCAGTCCTTTGTTCACATCGT
GCAAATGTTTATTAATACATCTGGAGGATCTGGCGGGTCTGGAGGCTACCCCTATGACGTGCCC
GACTATGCCGGCGGAGGGTCTGGAGGCGGTTCCTTAAGTACCACTGAGGTGGCAATGCACACTT
CAACCTCTTCTTCAGTCACAAAGAGTTACATCTCATCACAGACAAATGATACGCACAAACGGGA
CACATATGCAGCCACTCCTAGAGCTCATGAAGTTTCAGAAATTTCTGTTAGAACTGTTTACCCT
CCAGAAGAGGAAACCGGAGAAAGGGTACAACTTGCCCATCATTTCTCTGAACCAGAGATAACAC
TCATTATTTTTGGGGTGATGGCTGGTGTTATTGGAACGATCCTCTTAATTTCTTACGGTATTCG
CCGACTGATAAAGAAAAGCCCATCTGATGTAAAACCTCTCCCCTCACCTGACACAGACGTGCCT
TTAAGTTCTGTTGAAATAGAAAATCCAGAGACAAGTGATCAA SEQ ID NO: 29, IL-15-V4:
MYGKIIFVLLLSEIVSISANWVNVISDLKKIEDLIQSMHIDATLYTESDVHPSCKVTAMKCFLL
ELQVISLESGDASIHDTVENLIILANNSLSSNGNVTESGCKECEELEEKNIKEFLQSFVHIVQM
FINTSGGGGSGGGGSGGGGSITCPPPMSVEHADIWVKSYSLYSRERYICNSGFKRKAGTSSLTE
CVLNKATNVAHWTTPSLKCIRDPALVHQRPAPPSTVTTAGVTPQPESLSPSGKEPAASSPSSNN -continued

| Sequences: |
|---|

TAATTAAIVPGSQLMPSKSPSTGTTEISSHESSHGTPSQTTAKNWELTASASHQPPGVYPQGH
SDTTGGSGGSGGYPYDVPDYAGGGSGGGSLSTTEVAMHTSTSSSVTKSYISSQTNDTHKRDTYA
ATPRAHEVSEISVRTVYPPEEETGERVQLAHHFSEPEITLIIFGVMAGVIGTILLISYGIRRLI
KKSPSDVKPLPSPDTDVPLSSVEIENPETSDQ

SEQ ID NO: 30, encodes SEQ ID NO: 29, IL-15-V4:
ATGTATGGAAAAATAATCTTTGTATTACTATTGTCAGAAATTGTGAGCATATCAGCA
AACTGGGTGAACGTTATTAGTGACCTTAAAAAGATCGAAGATTTGATACAGTCAATGCACATAG
ACGCGACGCTTTATACAGAATCTGATGTACATCCTTCATGCAAGGTTACTGCTATGAAGTGTTT
TCTTCTCGAACTCCAAGTAATAAGTCTTGAGAGCGGAGATGCGAGCATTCATGACACCGTTGAG
AATCTTATTATATTGGCTAACAACTCTCTGTCCAGCAATGGTAATGTGACAGAAAGCGGGTGTA
AGGAGTGCGAGGAACTCGAGGAGAAGAACATCAAAGAGTTCTTGCAGTCTTTCGTCCATATTGT
CCAGATGTTCATAAATACTAGCGGGGGAGGTGGCTCTGGTGGAGGCGGGAGTGGCGGGGGCGGC
TCAATCACATGCCCACCGCCCATGTCTGTTGAACACGCAGACATTTGGGTTAAAAGTTACTCAC
TTTACTCACGCGAGAGATATATATGCAACAGCGGCTTCAAGCGCAAAGCAGGCACTAGTAGTCT
TACAGAGTGCGTGCTCAATAAAGCTACAAATGTAGCTCATTGGACTACTCCTAGTCTCAAATGC
ATTCGGGACCCCGCGCTTGTGCACCAGAGACCTGCGCCGCCGTCCACAGTGACGACAGCTGGTG
TAACCCCCCAACCTGAATCCCTTAGTCCGTCTGGTAAAGAACCGGCGGCGTCTTCACCTTCCAG
CAATAATACTGCGGCGACAACAGCCGCGATAGTTCCTGGATCCCAACTCATGCCGTCAAAGTCT
CCTTCAACGGGAACGACAGAGATCTCTTCACATGAAAGTTCTCATGGAACACCGAGCCAAACTA
CGGCAAAGAACTGGGAACTGACTGCCTCAGCAAGCCACCAGCCGCCAGGGGTGTACCCGCAAGG
GCACTCAGATACTACTGGAGGATCTGGCGGGTCTGGAGGCTACCCCTATGACGTGCCCGACTAT
GCCGGCGGAGGGTCTGGAGGCGGTTCCTTAAGTACCACTGAGGTGGCAATGCACACTTCAACCT
CTTCTTCAGTCACAAAGAGTTACATCTCATCACAGACAAATGATACGCACAAACGGGACACATA
TGCAGCCACTCCTAGAGCTCATGAAGTTTCAGAAATTTCTGTTAGAACTGTTTACCCTCCAGAA
GAGGAAACCGGAGAAAGGGTACAACTTGCCCATCATTTCTCTGAACCAGAGATAACACTCATTA
TTTTTGGGGTGATGGCTGGTGTTATTGGAACGATCCTCTTAATTTCTTACGGTATTCGCCGACT
GATAAAGAAAAGCCCATCTGATGTAAAACCTCTCCCCTCACCTGACACAGACGTGCCTTTAAGT
TCTGTTGAAATAGAAAATCCAGAGACAAGTGATCAA SEQ ID NO: 31, IL-15-V5:
MYGKIIFVLLLSEIVSISANWVNVISDLKKIEDLIQSMHIDATLYTESDVHPSCKVTAMKCFLL
ELQVISLESGDASIHDTVENLIILANNSLSSNGNVTESGCKECEELEEKNIKEFLQSFVHIVQM
FINTSGGGGSGGGGSGGGGSITCPPPMSVEHADIWVKSYSLYSRERYICNSGFKRKAGTSSLTE
CVLNKATNVAHWTTPSLKCIRDPALVHQRPAPPSGGSGGSGGYPYDVPDYAGGGSGGGSLSTTEVAMHT
STSSSVTKSYISSQTNDTHKRDTYAATPRAHEVSEISVRTVYPPEEETGERVQLAHHFSEPEIT
LIIFGVMAGVIGTILLISYGIRRLIKKSPSDVKPLPSPDTDVPLSSVEIENPETSDQ SEQ ID NO: 32, encodes SEQ ID NO: 31, IL-15 V5:
ATGTATGGAAAAATAATCTTTGTATTACTATTGTCAGAAATTGTGAGCATATCAGCA
AACTGGGTAAACGTCATAAGCGACCTCAAAAAGATCGAGGACCTTATACAGTCTATGCACATAG
ATGCGACACTTTACACGGAATCAGACGTGCACCCGTCCTGCAAAGTCACAGCCATGAAGTGCTT
TCTTCTCGAACTGCAGGTAATTTCTCTCGAATCAGGTGACGCATCTATCCACGACACAGTTGAA
AATCTTATTATCCTGGCTAATAACTCCCTTAGCTCAAACGGCAATGTCACCGAGAGTGGATGTA
AAGAATGTGAGGAACTTGAAGAGAAAAACATAAAGGAATTCTTGCAGAGTTTCGTTCATATTGT
GCAAATGTTCATCAATACTAGTGGCGGGGGGGGAAGCGGTGGTGGAGGGAGCGGGGGTGGTGGA
TCCATCACCTGCCCGCCTCCCATGAGCGTGGAACACGCGGACATTTGGGTTAAGAGCTACAGTC
TTTACAGCCGGGAGCGCTATATCTGCAACTCAGGGTTTAAGCGGAAAGCAGGGACATCAAGTTT
GACAGAATGTGTGTTGAACAAGGCTACAAATGTTGCTCACTGGACCACGCCATCTTTGAAGTGT
ATCCGAGATCCCGCGCTTGTCCATCAGCGCCCAGCGCCTCCCTCCGGAGGATCTGGCGGGTCTG
GAGGCTACCCCTATGACGTGCCCGACTATGCCGGCGGAGGGTCTGGAGGCGGTTCCTTAAGTAC
CACTGAGGTGGCAATGCACACTTCAACCTCTTCTTCAGTCACAAAGAGTTACATCTCATCACAG
ACAAATGATACGCACAAACGGGACACATATGCAGCCACTCCTAGAGCTCATGAAGTTTCAGAAA
TTTCTGTTAGAACTGTTTACCCTCCAGAAGAGGAAACCGGAGAAAGGGTACAACTTGCCCATCA
TTTCTCTGAACCAGAGATAACACTCATTATTTTTGGGGTGATGGCTGGTGTTATTGGAACGATC
CTCTTAATTTCTTACGGTATTCGCCGACTGATAAAGAAAAGCCCATCTGATGTAAAACCTCTCC
CCTCACCTGACACAGACGTGCCTTTAAGTTCTGTTGAAATAGAAAATCCAGAGACAAGTGATCA
A SEQ ID NO: 33, IL-15 linker (between GPA and IL-15/IL-15RA):
GGSGGSGGGGGSGGGSGGGSGGGS SEQ ID NO: 34, encodes IL-15 linker (between GPA and IL-15/IL-15RA):
GGAGGATCTGGCGGGTCTGGAGGCGGCGGCGGCAGCGGCGGCGGCAGCGGCGGAGGGTCTGGAG
GCGGTTCC SEQ ID NO: 35, IL-15 V3.1:
MYGKIIFVLLLSEIVSISANWVNVISDLKKIEDLIQSMHIDATLYTESDVHPSCKVTAMKCFLL
ELQVISLESGDASIHDTVENLIILANNSLSSNGNVTESGCKECEELEEKNIKEFLQSFVHIVQM
FINTSGGSGGSGGGGGSGGGSGGGSGGGSLSTTEVAMHTSTSSSVTKSYISSQTNDTHKRDTYA
ATPRAHEVSEISVRTVYPPEEETGERVQLAHHFSEPEITLIIFGVMAGVIGTILLISYGIRRLI
KKSPSDVKPLPSPDTDVPLSSVEIENPETSDQ SEQ ID NO: 36, encodes SEQ ID NO: 35, IL-15 V3.1:
ATGTATGGAAAAATAATCTTTGTATTACTATTGTCAGAAATTGTGAGCATATCAGCA
AACTGGGTAAATGTGATTTCAGACCTGAAAAAAATCGAAGACCTTATTCAATCCATGCACATCG -continued

| Sequences: |
|---|

ACGCGACACTTTATACTGAATCAGACGTACACCCGTCCTGTAAGGTTACTGCGATGAAGTGCTT
TCTGTTGGAATTGCAAGTGATCTCCCTCGAATCAGGGGATGCATCCATTCATGATACCGTCGAG
AATTTGATCATTCTGGCAAATAACTCCCTCAGTAGTAACGGGAATGTGACCGAGTCTGGGTGTA
AGGAGTGCGAAGAGTTGGAGGAAAAGAATATCAAAGAATTCCTTCAGTCCTTTGTTCACATCGT
GCAAATGTTTATTAATACATCTGGAGGATCTGGCGGGTCTGGAGGCGGCGGCGGCAGCGGCGGC
GGCAGCGGCGGAGGGTCTGGAGGCGGTTCCTTAAGTACCACTGAGGTGGCAATGCACACTTCAA
CCTCTTCTTCAGTCACAAAGAGTTACATCTCATCACAGACAAATGATACGCACAAACGGGACAC
ATATGCAGCCACTCCTAGAGCTCATGAAGTTTCAGAAATTTCTGTTAGAACTGTTTACCCTCCA
GAAGAGGAAACCGGAGAAAGGGTACAACTTGCCCATCATTTCTCTGAACCAGAGATAACACTCA
TTATTTTTGGGGTGATGGCTGGTGTTATTGGAACGATCCTCTTAATTTCTTACGGTATTCGCCG
ACTGATAAAGAAAAGCCCATCTGATGTAAAACCTCTCCCCTCACCTGACACAGACGTGCCTTTA
AGTTCTGTTGAAATAGAAAATCCAGAGACAAGTGATCAA

SEQ ID NO: 37, IL-15-V4.1:
MYGKIIFVLLLSEIVSISANWVNVISDLKKIEDLIQSMHIDATLYTESDVHPSCKVTAMKCFLL
ELQVISLESGDASIHDTVENLIILANNSLSSNGNVTESGCKECEELEEKNIKEFLQSFVHIVQM
FINTSGGGGSGGGGSGGGGSITCPPPMSVEHADIWVKSYSLYSRERYICNSGFKRKAGTSSLTE
CVLNKATNVAHWTTPSLKCIRDPALVHQRPAPPSTVTTAGVTPQPESLSPSGKEPAASSPSSNN
TAATTAAIVPGSQLMPSKSPSTGTTEISSHESSHGTPSQTTAKNWELTASASHQPPGVYPQGHS
DTTGGSGGSGGGGGSGGGSGGGSGGGSLSTTEVAMHTSTSSSVTKSYISSQTNDTHKRDTYAAT
PRAHEVSEISVRTVYPPEEETGERVQLAHHFSEPEITLIIFGVMAGVIGTILLISYGIRRLIKK
SPSDVKPLPSPDTDVPLSSVEIENPETSDQ

SEQ ID NO: 38, encodes SEQ ID NO: 37, IL-15-V4.1:
ATGTATGGAAAAATAATCTTTGTATTACTATTGTCAGAAATTGTGAGCATATCAGCA
AACTGGGTGAACGTTATTAGTGACCTTAAAAAGATCGAAGATTTGATACAGTCAATGCACATAG
ACGCGACGCTTTATACAGAATCTGATGTACATCCTTCATGCAAGGTTACTGCTATGAAGTGTTT
TCTTCTCGAACTCCAAGTAATAAGTCTTGAGAGCGGAGATGCGAGCATTCATGACACCGTTGAG
AATCTTATTATATTGGCTAACAACTCTCTGTCCAGCAATGGTAATGTGACAGAAAGCGGGTGTA
AGGAGTGCGAGGAACTCGAGGAGAAGAACATCAAAGAGTTCTTGCAGTCTTTCGTCCATATTGT
CCAGATGTTCATAAATACTAGCGGGGGAGGTGGCTCTGGTGGAGGCGGGAGTGGCGGGGGCGGC
TCAATCACATGCCCACCGCCCATGTCTGTTGAACACGCAGACATTTGGGTTAAAAGTTACTCAC
TTTACTCACGCGAGAGATATATATGCAACAGCGGCTTCAAGCGCAAAGCAGGCACTAGTAGTCT
TACAGAGTGCGTGCTCAATAAAGCTACAAATGTAGCTCATTGGACTACTCCTAGTCTCAAATGC
ATTCGGGACCCCGCGCTTGTGCACCAGAGACCTGCGCCGCCGTCCACAGTGACGACAGCTGGTG
TAACCCCCCAACCTGAATCCCTTAGTCCGTCTGGTAAAGAACCGGCGGCGTCTTCACCTTCCAG
CAATAATACTGCGGCGACAACAGCCGCGATAGTTCCTGGATCCCAACTCATGCCGTCAAAGTCT
CCTTCAACGGGAACGACAGAGATCTCTTCACATGAAAGTTCTCATGGAACACCGAGCCAAACTA
CGGCAAAGAACTGGGAACTGACTGCCTCAGCAAGCCACCAGCCGCCAGGGGTGTACCCGCAAGG
GCACTCAGATACTACTGGAGGATCTGGCGGGTCTGGAGGCGGCGGCGGCAGCGGCGGCGGCAGC
GGCGGAGGGTCTGGAGGCGGTTCCTTAAGTACCACTGAGGTGGCAATGCACACTTCAACCTCTT
CTTCAGTCACAAAGAGTTACATCTCATCACAGACAAATGATACGCACAAACGGGACACATATGC
AGCCACTCCTAGAGCTCATGAAGTTTCAGAAATTTCTGTTAGAACTGTTTACCCTCCAGAAGAG
GAAACCGGAGAAAGGGTACAACTTGCCCATCATTTCTCTGAACCAGAGATAACACTCATTATTT
TTGGGGTGATGGCTGGTGTTATTGGAACGATCCTCTTAATTTCTTACGGTATTCGCCGACTGAT
AAAGAAAAGCCCATCTGATGTAAAACCTCTCCCCTCACCTGACACAGACGTGCCTTTAAGTTCT
GTTGAAATAGAAAATCCAGAGACAAGTGATCAA SEQ ID NO: 39, 4-1BBL linker (between GPA and 4-1BBL):
GGSGGSGGGPEDEPGSGSGGGSGGGS SEQ ID NO: 40, encodes SEQ ID NO: 39 4-1BBL linker (between GPA and 4-1BBL):
GGAGGATCTGGCGGGTCTGGAGGCGGCCCCGAGGACGAGCCCGGCAGCGGCAGCGGCGGAGGGT
CTGGAGGCGGTTCC SEQ ID NO: 41, Extracellular 4-1BBL:
ACPWAVSGARASPGSAASPRLREGPELSPDDPAGLLDLRQGMFAQLVAQNVLLIDGPLSW
YSDPGLAGVSLTGGLSYKEDTKELVVAKAGVYYVFFQLELRRVVAGEGSGSVSLALHLQP
LRSAAGAAALALTVDLPPASSEARNSAFGFQGRLLHLSAGQRLGVHLHTEARARHAWQLT
QGATVLGLFRVTPEIPAGLPSPRSE SEQ ID NO: 42, encodes SEQ ID NO: 41 Extracellular 4-1BBL:
GCCTGCCCCTGGGCCGTGTCCGGGGCTCGCGCCTCGCCCGGCTCCGCGGCCAGCCCGAGACTCC
GCGAGGGTCCCGAGCTTTCGCCCGACGATCCCGCCGGCCTCTTGGACCTGCGGCAGGGCATGTT
TGCGCAGCTGGTGGCCCAAAATGTTCTGCTGATCGATGGGCCCCTGAGCTGGTACAGTGACCCA
GGCCTGGCAGGCGTGTCCCTGACGGGGGGCCTGAGCTACAAAGAGGACACGAAGGAGCTGGTGG
TGGCCAAGGCTGGAGTCTACTATGTCTTCTTTCAACTAGAGCTGCGGCGCGTGGTGGCCGGCGA
GGGCTCAGGCTCCGTTTCACTTGCGCTGCACCTGCAGCCACTGCGCTCTGCTGCTGGGGCCGCC
GCCCTGGCTTTGACCGTGGACCTGCCACCCGCCTCCTCCGAGGCTCGGAACTCGGCCTTCGGTT
TCCAGGGCCGCTTGCTGCACCTGAGTGCCGGCCAGCGCCTGGGCGTCCATCTTCACACTGAGGC
CAGGGCACGCCATGCCTGGCAGCTTACCCAGGGCGCCACAGTCTTGGGACTCTTCCGGGTGACC
CCCGAAATCCCAGCCGGACTCCCTTCACCGAGGTCGGAA SEQ ID NO: 43, 4-1BBL construct:
MYGKIIFVLLLSEIVSISAACPWAVSGARASPGSAASPRLREGPELSPDDPAGLLDLRQGMFAQ
LVAQNVLLIDGPLSWYSDPGLAGVSLTGGLSYKEDTKELVVAKAGVYYVFFQLELRRVVAGEGS -continued

| Sequences: |
|---|

GSVSLALHLQPLRSAAGAAALALTVDLPPASSEARNSAFGFQGRLLHLSAGQRLGVHLHTEARA
RHAWQLTQGATVLGLFRVTPEIPAGLPSPRSEGGSGGSGGGPEDEPGSGSGGGSGGGSLSTTEV
AMHTSTSSSVTKSYISSQTNDTHKRDTYAATPRAHEVSEISVRTVYPPEEETGERVQLAHHFSE
PEITLIIFGVMAGVIGTILLISYGIRRLIKKSPSDVKPLPSPDTDVPLSSVEIENPETSDQ

SEQ ID NO: 44, encodes SEQ ID NO: 43, 4-1BBL construct:
ATGTATGGAAAAATAATCTTTGTATTACTATTGTCAGAAATTGTGAGCATATCAGCAGCCTGCC
CCTGGGCCGTGTCCGGGGCTCGCGCCTCGCCCGGCTCCGCGGCCAGCCCGAGACTCCGCGAGGG
TCCCGAGCTTTCGCCCGACGATCCCGCCGGCCTCTTGGACCTGCGGCAGGGCATGTTTGCGCAG
CTGGTGGCCCAAAATGTTCTGCTGATCGATGGGCCCCTGAGCTGGTACAGTGACCCAGGCCTGG
CAGGCGTGTCCCTGACGGGGGGCCTGAGCTACAAAGAGGACACGAAGGAGCTGGTGGTGGCCAA
GGCTGGAGTCTACTATGTCTTCTTTCAACTAGAGCTGCGGCGCGTGGTGGCCGGCGAGGGCTCA
GGCTCCGTTTCACTTGCGCTGCACCTGCAGCCACTGCGCTCTGCTGCTGGGGCCGCCGCCCTGG
CTTTGACCGTGGACCTGCCACCCGCCTCCTCCGAGGCTCGGAACTCGGCCTTCGGTTTCCAGGG
CCGCTTGCTGCACCTGAGTGCCGGCCAGCGCCTGGGCGTCCATCTTCACACTGAGGCCAGGGCA
CGCCATGCCTGGCAGCTTACCCAGGGCGCCACAGTCTTGGGACTCTTCCGGGTGACCCCCGAAA
TCCCAGCCGGACTCCCTTCACCGAGGTCGGAAGGAGGATCTGGCGGGTCTGGAGGCGGCCCCGA
GGACGAGCCCGGCAGCGGCAGCGGCGGAGGGTCTGGAGGCGGTTCCTTAAGTACCACTGAGGTG
GCAATGCACACTTCAACCTCTTCTTCAGTCACAAAGAGTTACATCTCATCACAGACAAATGATA
CGCACAAACGGGACACATATGCAGCCACTCCTAGAGCTCATGAAGTTTCAGAAATTTCTGTTAG
AACTGTTTACCCTCCAGAAGAGGAAACCGGAGAAAGGGTACAACTTGCCCATCATTTCTCTGAA
CCAGAGATAACACTCATTATTTTTGGGGTGATGGCTGGTGTTATTGGAACGATCCTCTTAATTT
CTTACGGTATTCGCCGACTGATAAAGAAAAGCCCATCTGATGTAAAACCTCTCCCCTCACCTGA
CACAGACGTGCCTTTAAGTTCTGTTGAAATAGAAAATCCAGAGACAAGTGATCAA SEQ ID NO: 45, IL-12 p40:
IWELKKDVYVVELDWYPDAPGEMVVLTCDTPEEDGITWTLDQSSEVLGSGKTLTIQVKEFGDAG
QYTCHKGGEVLSHSLLLLHKKEDGIWSTDILKDQKEPKNKTFLRCEAKNYSGRFTCWWLTTIST
DLTFSVKSSRGSSDPQGVTCGAATLSAERVRGDNKEYEYSVECQEDSACPAAEESLPIEVMVDA
VHKLKYENYTSSFFIRDIIKPDPPKNLQLKPLKNSRQVEVSWEYPDTWSTPHSYFSLTFCVQVQ
GKSKREKKDRVFTDKTSATVICRKNASISVRAQDRYYSSSWSEWASVPCS SEQ ID NO: 46, encodes SEQ ID NO: 45 IL-12 p40:
ATCTGGGAGCTGAAGAAGGACGTGTACGTGGTGGAGCTGGACTGGTATCCTGATGCCCCAGGCG
AGATGGTGGTGCTGACCTGCGACACACCTGAGGAGGATGGCATCACCTGGACACTGGATCAGAG
CAGCGAGGTGCTGGGCTCCGGCAAGACCCTGACAATCCAGGTGAAGGAGTTCGGCGACGCCGGC
CAGTACACATGTCACAAGGGAGGAGAGGTGCTGAGCCACTCCCTGCTGCTGCTGCACAAGAAGG
AGGACGGCATCTGGTCTACAGACATCCTGAAGGATCAGAAGGAGCCCAAGAACAAGACCTTCCT
GCGGTGCGAGGCCAAGAATTATAGCGGCCGGTTCACCTGTTGGTGGCTGACCACAATCTCTACC
GACCTGACCTTCAGCGTGAAGTCTAGCCGGGGCTCCTCTGACCCTCAGGGAGTGACATGCGGAG
CAGCCACCCTGTCCGCCGAGCGGGTGAGAGGCGATAACAAGGAGTACGAGTATAGCGTGGAGTG
CCAGGAGGACTCCGCCTGTCCAGCAGCAGAGGAGAGCCTGCCAATCGAAGTGATGGTGGATGCC
GTGCACAAGCTGAAGTACGAGAATTATACAAGCTCCTTCTTTATCAGGGACATCATCAAGCCCG
ATCCCCCTAAGAACCTGCAGCTGAAGCCCCTGAAGAACAGCCGGCAGGTGGAGGTGTCTTGGGA
GTACCCCGACACCTGGAGCACACCTCACTCCTATTTCTCTCTGACCTTTTGCGTGCAGGTGCAG
GGCAAGTCCAAGAGGGAGAAGAAGGACCGCGTGTTCACCGATAAGACATCTGCCACCGTGATCT
GTCGGAAGAACGCCTCTATCAGCGTGCGGGCCCAGGATAGATACTATTCTAGCTCCTGGAGCGA
GTGGGCCTCCGTGCCATGTTCT SEQ ID NO: 47, IL-12 p35:
RNLPVATPDPGMFPCLHHSQNLLRAVSNMLQKARQTLEFYPCTSEEIDHEDITKDKTSTVEACL
PLELTKNESCLNSRETSFITNGSCLASRKTSFMMALCLSSIYEDLKMYQVEFKTMNAKLLMDPK
RQIFLDQNMLAVIDELMQALNFNSETVPQKSSLEEPDFYKTKIKLCILLHAFRIRAVTIDRVMS
YLNAS SEQ ID NO: 48, encodes SEQ ID NO: 47 IL-12 p35:
CGGAATCTGCCAGTGGCAACCCCAGACCCCGGAATGTTCCCATGCCTGCACCACTCTCAGAACC
TGCTGAGGGCCGTGAGCAATATGCTGCAGAAGGCCCGCCAGACACTGGAGTTTTACCCTTGTAC
CAGCGAGGAGATCGACCACGAGGACATCACAAAGGATAAGACCTCCACAGTGGAGGCCTGCCTG
CCACTGGAGCTGACCAAGAACGAGAGCTGTCTGAACAGCCGGGAGACCAGCTTCATCACCAACG
GCAGCTGCCTGGCCTCCAGAAAGACATCTTTTATGATGGCCCTGTGCCTGTCTAGCATCTACGA
GGACCTGAAGATGTATCAGGTGGAGTTCAAGACCATGAACGCCAAGCTGCTGATGGACCCCAAG
AGGCAGATTTTCCTGGACCAGAATATGCTGGCCGTGATCGACGAGCTGATGCAGGCCCTGAACT
TTAATTCCGAGACAGTGCCTCAGAAGTCCTCTCTGGAGGAGCCAGATTTCTACAAGACCAAGAT
CAAGCTGTGCATCCTGCTGCACGCCTTCCGGATCAGAGCCGTGACCATCGACCGCGTGATGAGC
TATCTGAATGCCTCC SEQ ID NO: 49, SMIM1:
MQPQESHVHYSRWEDGSRDGVSLGAVSSTEEASRCRRISQRLCTGKLGIAMKVLGGVALFWIIF
ILGYLTGYYVHKCK SEQ ID NO: 50, encodes SMIM1:
ATGCAACCGCAAGAGAGTCACGTACATTATTCAAGATGGGAAGATGGAAGTCGGGACGGTGTGT
CTCTCGGCGCTGTTAGTTCAACGGAGGAAGCGTCTCGCTGTCGCCGGATAAGTCAACGCCTTTG
TACGGGAAAACTGGGTATAGCTATGAAGGTCCTCGGCGGGGTGGCGTTGTTTTGGATTATCTTT
ATACTTGGGTATCTGACCGGTTACTATGTTCACAAGTGTAAA -continued

| Sequences: |
|---|
| SEQ ID NO: 51, IL-12 linker (between IL-12 p35 and GPA):<br>GGSGGSGGGGGSGGGSGGGSGGGS |
| SEQ ID NO: 52, encodes IL-12 linker (between IL-12 p35 and GPA):<br>GGAGGATCTGGCGGGTCTGGAGGCGGCGGCGGCAGCGGCGGCGGCAGCGGCGGAGGGTCTGGAG<br>GCGGTTCC |
| SEQ ID NO: 53, IL-12 V1 construct:<br>MYGKIIFVLLLSEIVSISAIWELKKDVYVVELDWYPDAPGEMVVLTCDTPEEDGITWTLDQSSE<br>VLGSGKTLTIQVKEFGDAGQYTCHKGGEVLSHSLLLLHKKEDGIWSTDILKDQKEPKNKTFLRC<br>EAKNYSGRFTCWWLTTISTDLTFSVKSSRGSSDPQGVTCGAATLSAERVRGDNKEYEYSVECQE<br>DSACPAAEESLPIEVMVDAVHKLKYENYTSSFFIRDIIKPDPPKNLQLKPLKNSRQVEVSWEYP<br>DTWSTPHSYFSLTFCVQVQGKSKREKKDRVFTDKTSATVICRKNASISVRAQDRYYSSSWSEWA<br>SVPCSGGGGSGGGGSGGGGSRNLPVATPDPGMFPCLHHSQNLLRAVSNMLQKARQTLEFYPCTS<br>EEIDHEDITKDKTSTVEACLPLELTKNESCLNSRETSFITNGSCLASRKTSFMMALCLSSIYED<br>LKMYQVEFKTMNAKLLMDPKRQIFLDQNMLAVIDELMQALNFNSETVPQKSSLEEPDFYKTKIK<br>LCILLHAFRIRAVTIDRVMSYLNASGGSGGSGGGGGSGGGSGGGSGGGSLSTTEVAMHTSTSSS<br>VTKSYISSQTNDTHKRDTYAATPRAHEVSEISVRTVYPPEEETGERVQLAHHFSEPEITLIIFG<br>VMAGVIGTILLISYGIRRLIKKSPSDVKPLPSPDTDVPLSSVEIENPETSDQ |
| SEQ ID NO: 54, encodes SEQ ID NO: 53 IL-12 V1 construct:<br>ATGTATGGAAAAATAATCTTTGTATTACTATTGTCAGAAATTGTGAGCATATCAGCAATCTGGG<br>AGCTGAAGAAGGACGTGTACGTGGTGGAGCTGGACTGGTATCCTGATGCCCCAGGCGAGATGGT<br>GGTGCTGACCTGCGACACACCTGAGGAGGATGGCATCACCTGGACACTGGATCAGAGCAGCGAG<br>GTGCTGGGCTCCGGCAAGACCCTGACAATCCAGGTGAAGGAGTTCGGCGACGCCGGCCAGTACA<br>CATGTCACAAGGGAGGAGAGGTGCTGAGCCACTCCCTGCTGCTGCTGCACAAGAAGGAGGACGG<br>CATCTGGTCTACAGACATCCTGAAGGATCAGAAGGAGCCCAAGAACAAGACCTTCCTGCGGTGC<br>GAGGCCAAGAATTATAGCGGCCGGTTCACCTGTTGGTGGCTGACCACAATCTCTACCGACCTGA<br>CCTTCAGCGTGAAGTCTAGCCGGGGCTCCTCTGACCCTCAGGGAGTGACATGCGGAGCAGCCAC<br>CCTGTCCGCCGAGCGGGTGAGAGGCGATAACAAGGAGTACGAGTATAGCGTGGAGTGCCAGGAG<br>GACTCCGCCTGTCCAGCAGCAGAGGAGAGCCTGCCAATCGAAGTGATGGTGGATGCCGTGCACA<br>AGCTGAAGTACGAGAATTATACAAGCTCCTTCTTTATCAGGGACATCATCAAGCCCGATCCCCC<br>TAAGAACCTGCAGCTGAAGCCCCTGAAGAACAGCCGGCAGGTGGAGGTGTCTTGGGAGTACCCC<br>GACACCTGGAGCACACCTCACTCCTATTTCTCTCTGACCTTTTGCGTGCAGGTGCAGGGCAAGT<br>CCAAGAGGGAGAAGAAGGACCGCGTGTTCACCGATAAGACATCTGCCACCGTGATCTGTCGGAA<br>GAACGCCTCTATCAGCGTGCGGGCCCAGGATAGATACTATTCTAGCTCCTGGAGCGAGTGGGCC<br>TCCGTGCCATGTTCTGGAGGAGGAGGCAGCGGCGGAGGAGGCTCCGGCGGCGGCGGCAGCCGGA<br>ATCTGCCAGTGGCAACCCCAGACCCCGGAATGTTCCCATGCCTGCACCACTCTCAGAACCTGCT<br>GAGGGCCGTGAGCAATATGCTGCAGAAGGCCCGCCAGACACTGGAGTTTTACCCTTGTACCAGC<br>GAGGAGATCGACCACGAGGACATCACAAAGGATAAGACCTCCACAGTGGAGGCCTGCCTGCCAC<br>TGGAGCTGACCAAGAACGAGAGCTGTCTGAACAGCCGGGAGACCAGCTTCATCACCAACGGCAG<br>CTGCCTGGCCTCCAGAAAGACATCTTTTATGATGGCCCTGTGCCTGTCTAGCATCTACGAGGAC<br>CTGAAGATGTATCAGGTGGAGTTCAAGACCATGAACGCCAAGCTGCTGATGGACCCCAAGAGGC<br>AGATTTTCCTGGACCAGAATATGCTGGCCGTGATCGACGAGCTGATGCAGGCCCTGAACTTTAA<br>TTCCGAGACAGTGCCTCAGAAGTCCTCTCTGGAGGAGCCAGATTTCTACAAGACCAAGATCAAG<br>CTGTGCATCCTGCTGCACGCCTTCCGGATCAGAGCCGTGACCATCGACCGCGTGATGAGCTATC<br>TGAATGCCTCCGGAGGATCTGGCGGGTCTGGAGGCGGCGGCGGCAGCGGCGGCGGCAGCGGCGG<br>AGGGTCTGGAGGCGGTTCCTTAAGTACCACTGAGGTGGCAATGCACACTTCAACCTCTTCTTCA<br>GTCACAAAGAGTTACATCTCATCACAGACAAATGATACGCACAAACGGGACACATATGCAGCCA<br>CTCCTAGAGCTCATGAAGTTTCAGAAATTTCTGTTAGAACTGTTTACCCTCCAGAAGAGGAAAC<br>CGGAGAAAGGGTACAACTTGCCCATCATTTCTCTGAACCAGAGATAACACTCATTATTTTTGGG<br>GTGATGGCTGGTGTTATTGGAACGATCCTCTTAATTTCTTACGGTATTCGCCGACTGATAAAGA<br>AAAGCCCATCTGATGTAAAACCTCTCCCCTCACCTGACACAGACGTGCCTTTAAGTTGTGTTGA<br>AATAGAAAATCCAGAGACAAGTGATCAA |
| SEQ ID NO: 55, IL-12 V2 construct:<br>MQPQESHVHYSRWEDGSRDGVSLGAVSSTEEASRCRRISQRLCTGKLGIAMKVLGGVALFWIIF<br>ILGYLTGYYVHKCKGGGGSGGGGSGGGGSIWELKKDVYVVELDWYPDAPGEMVVLTCDTPEEDG<br>ITWTLDQSSEVLGSGKTLTIQVKEFGDAGQYTCHKGGEVLSHSLLLLHKKEDGIWSTDILKDQK<br>EPKNKTFLRCEAKNYSGRFTCWWLTTISTDLTFSVKSSRGSSDPQGVTCGAATLSAERVRGDNK<br>EYEYSVECQEDSACPAAEESLPIEVMVDAVHKLKYENYTSSFFIRDIIKPDPPKNLQLKPLKNS<br>RQVEVSWEYPDTWSTPHSYFSLTFCVQVQGKSKREKKDRVFTDKTSATVICRKNASISVRAQDR<br>YYSSSWSEWASVPCSGGGGSGGGGSGGGGSRNLPVATPDPGMFPCLHHSQNLLRAVSNMLQKAR<br>QTLEFYPCTSEEIDHEDITKDKTSTVEACLPLELTKNESCLNSRETSFITNGSCLASRKTSFMM<br>ALCLSSIYEDLKMYQVEFKTMNAKLLMDPKRQIFLDQNMLAVIDELMQALNFNSETVPQKSSLE<br>EPDFYKTKIKLCILLHAFRIRAVTIDRVMSYLNAS |
| SEQ ID NO: 56, encodes SEQ ID NO: 55 IL-12 V2 construct:<br>ATGCAACCGCAAGAGAGTCACGTACATTATTCAAGATGGGAAGATGGAAGTCGGGACGGTGTGT<br>CTCTCGGCGCTGTTAGTTCAACGGAGGAAGCGTCTCGCTGTCGCCGGATAAGTCAACGCCTTTG<br>TACGGGAAAACTGGGTATAGCTATGAAGGTCCTCGGCGGGGTGGCGTTGTTTTGGATTATCTTT<br>ATACTTGGGTATCTGACCGGTTACTATGTTCACAAGTGTAAAGGAGGTGGAGGATCAGGTGGAG<br>GTGGTTCAGGTGGAGGAGGTAGCATCTGGGAGCTGAAGAAGGACGTGTACGTGGTGGAGCTGGA<br>CTGGTATCCTGATGCCCCAGGCGAGATGGTGGTGCTGACCTGCGACACACCTGAGGAGGATGGC<br>ATCACCTGGACACTGGATCAGAGCAGCGAGGTGCTGGGCTCCGGCAAGACCCTGACAATCCAGG<br>TGAAGGAGTTCGGCGACGCCGGCCAGTACACATGTCACAAGGGAGGAGAGGTGCTGAGCCACTC<br>CCTGCTGCTGCTGCACAAGAAGGAGGACGGCATCTGGTCTACAGACATCCTGAAGGATCAGAAG |

-continued

| Sequences: |
|---|

GAGCCCAAGAACAAGACCTTCCTGCGGTGCGAGGCCAAGAATTATAGCGGCCGGTTCACCTGTT
GGTGGCTGACCACAATCTCTACCGACCTGACCTTCAGCGTGAAGTCTAGCCGGGGCTCCTCTGA
CCCTCAGGGAGTGACATGCGGAGCAGCCACCCTGTCCGCCGAGCGGGTGAGAGGCGATAACAAG
GAGTACGAGTATAGCGTGGAGTGCCAGGAGGACTCCGCCTGTCCAGCAGCAGAGGAGAGCCTGC
CAATCGAAGTGATGGTGGATGCCGTGCACAAGCTGAAGTACGAGAATTATACAAGCTCCTTCTT
TATCAGGGACATCATCAAGCCCGATCCCCCTAAGAACCTGCAGCTGAAGCCCCTGAAGAACAGC
CGGCAGGTGGAGGTGTCTTGGGAGTACCCCGACACCTGGAGCACACCTCACTCCTATTTCTCTC
TGACCTTTTGCGTGCAGGTGCAGGGCAAGTCCAAGAGGGAGAAGAAGGACCGCGTGTTCACCGA
TAAGACATCTGCCACCGTGATCTGTCGGAAGAACGCCTCTATCAGCGTGCGGGCCCAGGATAGA
TACTATTCTAGCTCCTGGAGCGAGTGGGCCTCCGTGCCATGTTCTGGAGGAGGAGGCAGCGGCG
GAGGAGGCTCCGGCGGCGGCGGCAGCCGGAATCTGCCAGTGGCAACCCCAGACCCCGGAATGTT
CCCATGCCTGCACCACTCTCAGAACCTGCTGAGGGCCGTGAGCAATATGCTGCAGAAGGCCCGC
CAGACACTGGAGTTTTACCCTTGTACCAGCGAGGAGATCGACCACGAGGACATCACAAAGGATA
AGACCTCCACAGTGGAGGCCTGCCTGCCACTGGAGCTGACCAAGAACGAGAGCTGTCTGAACAG
CCGGGAGACCAGCTTCATCACCAACGGCAGCTGCCTGGCCTCCAGAAAGACATCTTTTATGATG
GCCCTGTGCCTGTCTAGCATCTACGAGGACCTGAAGATGTATCAGGTGGAGTTCAAGACCATGA
ACGCCAAGCTGCTGATGGACCCCAAGAGGCAGATTTTCCTGGACCAGAATATGCTGGCCGTGAT
CGACGAGCTGATGCAGGCCCTGAACTTTAATTCCGAGACAGTGCCTCAGAAGTCCTCTCTGGAG
GAGCCAGATTTCTACAAGACCAAGATCAAGCTGTGCATCCTGCTGCACGCCTTCCGGATCAGAG
CCGTGACCATCGACCGCGTGATGAGCTATCTGAATGCCTCC

SEQ ID NO: 57, IL-12 p40/IL-12 p35 fusion:
IWELKKDVYVVELDWYPDAPGEMVVLTCDTPEEDGITWTLDQSSEVLGSGKTLTIQVKEFGDAG
QYTCHKGGEVLSHSLLLLHKKEDGIWSTDILKDQKEPKNKTFLRCEAKNYSGRFTCWWLTTIST
DLTFSVKSSRGSSDPQGVTCGAATLSAERVRGDNKEYEYSVECQEDSACPAAEESLPIEVMVDA
VHKLKYENYTSSFFIRDIIKPDPPKNLQLKPLKNSRQVEVSWEYPDTWSTPHSYFSLTFCVQVQ
GKSKREKKDRVFTDKTSATVICRKNASISVRAQDRYYSSSWSEWASVPCSGGGGSGGGGSGGGG
SRNLPVATPDPGMFPCLHHSQNLLRAVSNMLQKARQTLEFYPCTSEEIDHEDITKDKTSTVEAC
LPLELTKNESCLNSRETSFITNGSCLASRKTSFMMALCLSSIYEDLKMYQVEFKTMNAKLLMDP
KRQIFLDQNMLAVIDELMQALNFNSETVPQKSSLEEPDFYKTKIKLCILLHAFRIRAVTIDRVM
SYLNAS SEQ ID NO: 58, encodes SEQ ID NO: 57, IL-12 p40/IL-12 p35 fusion:
ATCTGGGAGCTGAAGAAGGACGTGTACGTGGTGGAGCTGGACTGGTATCCTGATGCCCCAGGCG
AGATGGTGGTGCTGACCTGCGACACACCTGAGGAGGATGGCATCACCTGGACACTGGATCAGAG
CAGCGAGGTGCTGGGCTCCGGCAAGACCCTGACAATCCAGGTGAAGGAGTTCGGCGACGCCGGC
CAGTACACATGTCACAAGGGAGGAGAGGTGCTGAGCCACTCCCTGCTGCTGCTGCACAAGAAGG
AGGACGGCATCTGGTCTACAGACATCCTGAAGGATCAGAAGGAGCCCAAGAACAAGACCTTCCT
GCGGTGCGAGGCCAAGAATTATAGCGGCCGGTTCACCTGTTGGTGGCTGACCACAATCTCTACC
GACCTGACCTTCAGCGTGAAGTCTAGCCGGGGCTCCTCTGACCCTCAGGGAGTGACATGCGGAG
CAGCCACCCTGTCCGCCGAGCGGGTGAGAGGCGATAACAAGGAGTACGAGTATAGCGTGGAGTG
CCAGGAGGACTCCGCCTGTCCAGCAGCAGAGGAGAGCCTGCCAATCGAAGTGATGGTGGATGCC
GTGCACAAGCTGAAGTACGAGAATTATACAAGCTCCTTCTTTATCAGGGACATCATCAAGCCCG
ATCCCCCTAAGAACCTGCAGCTGAAGCCCCTGAAGAACAGCCGGCAGGTGGAGGTGTCTTGGGA
GTACCCCGACACCTGGAGCACACCTCACTCCTATTTCTCTCTGACCTTTTGCGTGCAGGTGCAG
GGCAAGTCCAAGAGGGAGAAGAAGGACCGCGTGTTCACCGATAAGACATCTGCCACCGTGATCT
GTCGGAAGAACGCCTCTATCAGCGTGCGGGCCCAGGATAGATACTATTCTAGCTCCTGGAGCGA
GTGGGCCTCCGTGCCATGTTCTGGAGGAGGAGGCAGCGGCGGAGGAGGCTCCGGCGGCGGCGGC
AGCCGGAATCTGCCAGTGGCAACCCCAGACCCCGGAATGTTCCCATGCCTGCACCACTCTCAGA
ACCTGCTGAGGGCCGTGAGCAATATGCTGCAGAAGGCCCGCCAGACACTGGAGTTTTACCCTTG
TACCAGCGAGGAGATCGACCACGAGGACATCACAAAGGATAAGACCTCCACAGTGGAGGCCTGC
CTGCCACTGGAGCTGACCAAGAACGAGAGCTGTCTGAACAGCCGGGAGACCAGCTTCATCACCA
ACGGCAGCTGCCTGGCCTCCAGAAAGACATCTTTTATGATGGCCCTGTGCCTGTCTAGCATCTA
CGAGGACCTGAAGATGTATCAGGTGGAGTTCAAGACCATGAACGCCAAGCTGCTGATGGACCCC
AAGAGGCAGATTTTCCTGGACCAGAATATGCTGGCCGTGATCGACGAGCTGATGCAGGCCCTGA
ACTTTAATTCCGAGACAGTGCCTCAGAAGTCCTCTCTGGAGGAGCCAGATTTCTACAAGACCAA
GATCAAGCTGTGCATCCTGCTGCACGCCTTCCGGATCAGAGCCGTGACCATCGACCGCGTGATG
AGCTATCTGAATGCCTCC SEQ ID NO: 59, Ig heavy chain V region 3 signal sequence (aa 1-19) + His6 (aa 20-25) + TEV cleavage site (zz 26-32) + murine 4-1BBL extracellular domain (aa 33-238)
MGWSCIILFLVATATGVHSHHHHHHENLYFQGRTEPRPALTITTSPNLGTRENNADQVTPVSHI
GCPNTTQQGSPVFAKLLAKNQASLCNTTLNWHSQDGAGSSYLSQGLRYEEDKKELVVDSPGLYY
VFLELKLSPTFTNTGHKVQGWVSLVLQAKPQVDDFDNLALTVELFPCSMENKLVDRSWSQLLLL
KAGHRLSVGLRAYLHGAQDAYRDWELSYPNTTSFGLFLVKPDNPWE SEQ ID NO: 60, Human light chain leader (aa 1-20) + mouse hinge - CH2 – CH3 (aa 21-258) + TEV cleavage site (aa 259-265) + human IL-15Ra Sushi domain* (aa 266-333) + Linker (aa 334-361) + human IL15** (aa 362-475)
*Sushi domain from PDB: 4GS7 Chain D; Sushi domain is aa 31-95, sequence used is aa 30-97.
**human IL15 from PDB: 4GS7 Chain D, aa 49-162.
MRVPAQLLGLLLLWLPGARCEPRVPITQNPCPPLKECPPCAAPDLLGGPSVFIFPPKIKDVLMI
SLSPMVTCVVVAVSEDDPDVQISWFVNNVEVHTAQTQTHREDYNSTLRVVSALPIQHQDWMSGK
EFKCKVNNRALPSPIEKTISKPRGPVRAPQVYVLPPPAEEMTKKEFSLTCMITGFLPAEIAVDW -continued

| Sequences: |
|---|
| TSNGRTEQNYKNTATVLDSDGSYFMYSKLRVQKSTWERGSLFACSVVHEGLHNHLTTKTISRSL<br>GKENLYFQGGITCPPPMSVEHADIWVKSYSLYSRERYICNSGFKRKAGTSSLTECVLNKATNVA<br>HWTTPSLKCIRDPGSGSGSGSGSEDEDEDEDGSGSGSGSGSNWVNVISDLKKIEDLIQSMHIDA<br>TLYTESDVHPSCKVTAMKCFLLELQVISLESGDASIHDTVENLIILANNSLSSNGNVTESGCKE<br>CEELEEKNIKEFLQSFVHIVQMFINTS |
| SEQ ID NO: 61, Human light chain leader (aa 1-20) + mouse hinge - CH2 — CH3 - (aa 21-258) + Linker (aa 259-273) + murine IL-12 subunit beta (p40) (274-586) + Linker (aa 587-601) + human IL-12 subunit alpha (p35) (aa 602-794)<br>MRVPAQLLGLLLLWLPGARCEPRVPITQNPCPPLKECPPCAAPDLLGGPSVFIFPPKIKDVLMI<br>SLSPMVTCVVVAVSEDDPDVQISWFVNNVEVHTAQTQTHREDYNSTLRVVSALPIQHQDWMSGK<br>EFKCKVNNRALPSPIEKTISKPRGPVRAPQVYVLPPPAEEMTKKEFSLTCMITGFLPAEIAVDW<br>TSNGRTEQNYKNTATVLDSDGSYFMYSKLRVQKSTWERGSLFACSVVHEGLHNHLTTKTISRSL<br>GKGGGGSGGGGSGGGGSMWELEKDVYVVEVDWTPDAPGETVNLTCDTPEEDDITWTSDQRHGVI<br>GSGKTLTITVKEFLDAGQYTCHKGGETLSHSHLLLHKKENGIWSTEILKNFKNKTFLKCEAPNY<br>SGRFTCSWLVQRNMDLKFNIKSSSSSPDSRAVTCGMASLSAEKVTLDQRDYEKYSVSCQEDVTC<br>PTAEETLPIELALEARQQNKYENYSTSFFIRDIIKPDPPKNLQMKPLKNSQVEVSWEYPDSWST<br>PHSYFSLKFFVRIQRKKEKMKETEEGCNQKGAFLVEKTSTEVQCKGGNVCVQAQDRYYNSSCSK<br>WACVPCRVRSGGGGSGGGGSGGGGSRVIPVSGPARCLSQSRNLLKTTDDMVKTAREKLKHYSCT<br>AEDIDHEDITRDQTSTLKTCLPLELHKNESCLATRETSSTTRGSCLPPQKTSLMMTLCLGSIYE<br>DLKMYQTEFQAINAALQNHNHQQIILDKGMLVAIDELMQSLNHNGETLRQKPPVGEADPYRVKM<br>KLCILLHAFSTRVVTINRVMGYLSSA |
| SEQ ID NO: 62, 41BBL-T2A-IL-12 construct, GPA signal peptide (SEQ ID NO: 21)-41BBL (SEQ ID NO: 41)-4-1BBL linker (SEQ ID NO: 39)-GPA (SEQ ID NO: 25) -(T2A skip peptide)-SMIM1 SEQ ID NO: 49)-linker (SEQ ID NO: 12) -IL12 p40 (SEQ ID NO: 45) - flexible linker (SEQ ID NO: 12) - IL-12 p35 (SEQ ID NO: 47)<br>MYGKIIFVLLLSEIVSISAACPWAVSGARASPGSAASPRLREGPELSPDDPAGLLDLRQGMFAQ<br>LVAQNVLLIDGPLSWYSDPGLAGVSLTGGLSYKEDTKELVVAKAGVYYVFFQLELRRVVAGEGS<br>GSVSLALHLQPLRSAAGAAALALTVDLPPASSEARNSAFGFQGRLLHLSAGQRLGVHLHTEARA<br>RHAWQLTQGATVLGLFRVTPEIPAGLPSPRSEGGSGGSGGGPEDEPGSGSGGGSGGGSLSTTEV<br>AMHTSTSSSVTKSYISSQTNDTHKRDTYAATPRAHEVSEISVRTVYPPEEETGERVQLAHHFSE<br>PEITLIIFGVMAGVIGTILLISYGIRRLIKKSPSDVKPLPSPDTDVPLSSVEIENPETSDQAAA<br>EGRGSLLTCGDVEENPGPSGMQPQESHVHYSRWEDGSRDGVSLGAVSSTEEASRCRRISQRLCT<br>GKLGIAMKVLGGVALFWIIFILGYLTGYYVHKCKGGGGSGGGGSGGGGSIWELKKDVYVVELDW<br>YPDAPGEMVVLTCDTPEEDGITWTLDQSSEVLGSGKTLTIQVKEFGDAGQYTCHKGGEVLSHSL<br>LLLHKKEDGIWSTDILKDQKEPKNKTFLRCEAKNYSGRFTCWWLTTISTDLTFSVKSSRGSSDP<br>QGVTCGAATLSAERVRGDNKEYEYSVECQEDSACPAAEESLPIEVMVDAVHKLKYENYTSSFFI<br>RDIIKPDPPKNLQLKPLKNSRQVEVSWEYPDTWSTPHSYFSLTFCVQVQGKSKREKKDRVFTDK<br>TSATVICRKNASISVRAQDRYYSSSWSEWASVPCSGGGGSGGGGSGGGGSRNLPVATPDPGMFP<br>CLHHSQNLLRAVSNMLQKARQTLEFYPCTSEEIDHEDITKDKTSTVEACLPLELTKNESCLNSR<br>ETSFITNGSCLASRKTSFMMALCLSSIYEDLKMYQVEFKTMNAKLLMDPKRQIFLDQNMLAVID<br>ELMQALNFNSETVPQKSSLEEPDFYKTKIKLCILLHAFRIRAVTIDRVMSYLNAS* |
| SEQ ID NO: 63, encodes SEQ ID NO: 59, 41BBL-T2A-IL-12 construct<br>ATGTATGGAAAAATAATCTTTGTATTACTATTGTCAGAAATTGTGAGCATATCAGCAGCCTGCC<br>CCTGGGCCGTGTCCGGGGCTCGCGCCTCGCCCGGCTCCGCGGCCAGCCCGAGACTCCGCGAGGG<br>TCCCGAGCTTTCGCCCGACGATCCCGCCGGCCTCTTGGACCTGCGGCAGGGCATGTTTGCGCAG<br>CTGGTGGCCCAAAATGTTCTGCTGATCGATGGGCCCCTGAGCTGGTACAGTGACCCAGGCCTGG<br>CAGGCGTGTCCCTGACGGGGGGCCTGAGCTACAAAGAGGACACGAAGGAGCTGGTGGTGGCCAA<br>GGCTGGAGTCTACTATGTCTTCTTTCAACTAGAGCTGCGGCGCGTGGTGGCCGGCGAGGGCTCA<br>GGCTCCGTTTCACTTGCGCTGCACCTGCAGCCACTGCGCTCTGCTGCTGGGGCCGCCGCCCTGG<br>CTTTGACCGTGGACCTGCCACCCGCCTCCTCCGAGGCTCGGAACTCGGCCTTCGGTTTCCAGGG<br>CCGCTTGCTGCACCTGAGTGCCGGCCAGCGCCTGGGCGTCCATCTTCACACTGAGGCCAGGGCA<br>CGCCATGCCTGGCAGCTTACCCAGGGCGCCACAGTCTTGGGACTCTTCCGGGTGACCCCCGAAA<br>TCCCAGCCGGACTCCCTTCACCGAGGTCGGAAGGAGGATCTGGCGGGTCTGGAGGCGGCCCCGA<br>GGACGAGCCCGGCAGCGGCAGCGGCGGAGGGTCTGGAGGCGGTTCCTTAAGTACCACTGAGGTG<br>GCAATGCACACTTCAACCTCTTCTTCAGTCACAAAGAGTTACATCTCATCACAGACAAATGATA<br>CGCACAAACGGGACACATATGCAGCCACTCCTAGAGCTCATGAAGTTTCAGAAATTTCTGTTAG<br>AACTGTTTACCCTCCAGAAGAGGAAACCGGAGAAAGGGTACAACTTGCCCATCATTTCTCTGAA<br>CCAGAGATAACACTCATTATTTTTGGGGTGATGGCTGGTGTTATTGGAACGATCCTCTTAATTT<br>CTTACGGTATTCGCCGACTGATAAAGAAAAGCCCATCTGATGTAAAACCTCTCCCCTCACCTGA<br>CACAGACGTGCCTTTAAGTTCTGTTGAAATAGAAAATCCAGAGACAAGTGATCAAGCGGCCGCT<br>GAGGGCAGAGGAAGTCTTCTAACATGCGGTGACGTGGAGGAGAATCCCGGCCCTTCCGGAATGC<br>AACCGCAAGAGAGTCACGTACATTATTCAAGATGGGAAGATGGAAGTCGGGACGGTGTGTCTCT<br>CGGCGCTGTTAGTTCAACGGAGGAAGCGTCTCGCTGTCGCCGGATAAGTCAACGCCTTTGTACG<br>GGAAAACTGGGTATAGCTATGAAGGTCCTCGGCGGGGTGGCGTTGTTTTGGATTATCTTTATAC<br>TTGGGTATCTGACCGGTTACTATGTTCACAAGTGTAAAGGAGGTGGAGGATCAGGTGGAGGTGG<br>TTCAGGTGGAGGAGGTAGCATCTGGGAGCTGAAGAAGGACGTGTACGTGGTGGAGCTGGACTGG<br>TATCCTGATGCCCCAGGCGAGATGGTGGTGCTGACCTGCGACACACCTGAGGAGGATGGCATCA<br>CCTGGACACTGGATCAGAGCAGCGAGGTGCTGGGCTCCGGCAAGACCCTGACAATCCAGGTGAA<br>GGAGTTCGGCGACGCCGGCCAGTACACATGTCACAAGGGAGGAGAGGTGCTGAGCCACTCCCTG<br>CTGCTGCTGCACAAGAAGGAGGACGGCATCTGGTCTACAGACATCCTGAAGGATCAGAAGGAGC<br>CCAAGAACAAGACCTTCCTGCGGTGCGAGGCCAAGAATTATAGCGGCCGGTTCACCTGTTGGTG<br>GCTGACCACAATCTCTACCGACCTGACCTTCAGCGTGAAGTCTAGCCGGGGCTCCTCTGACCCT |

-continued

Sequences:

CAGGGAGTGACATGCGGAGCAGCCACCCTGTCCGCCGAGCGGGTGAGAGGCGATAACAAGGAGT
ACGAGTATAGCGTGGAGTGCCAGGAGGACTCCGCCTGTCCAGCAGCAGAGGAGAGCCTGCCAAT
CGAAGTGATGGTGGATGCCGTGCACAAGCTGAAGTACGAGAATTATACAAGCTCCTTCTTTATC
AGGGACATCATCAAGCCCGATCCCCCTAAGAACCTGCAGCTGAAGCCCCTGAAGAACAGCCGGC
AGGTGGAGGTGTCTTGGGAGTACCCCGACACCTGGAGCACACCTCACTCCTATTTCTCTCTGAC
CTTTTGCGTGCAGGTGCAGGGCAAGTCCAAGAGGGAGAAGAAGGACCGCGTGTTCACCGATAAG
ACATCTGCCACCGTGATCTGTCGGAAGAACGCCTCTATCAGCGTGCGGGCCCAGGATAGATACT
ATTCTAGCTCCTGGAGCGAGTGGGCCTCCGTGCCATGTTCTGGAGGAGGAGGCAGCGGCGGAGG
AGGCTCCGGCGGCGGCGGCAGCCGGAATCTGCCAGTGGCAACCCCAGACCCCGGAATGTTCCCA
TGCCTGCACCACTCTCAGAACCTGCTGAGGGCCGTGAGCAATATGCTGCAGAAGGCCCGCCAGA
CACTGGAGTTTTACCCTTGTACCAGCGAGGAGATCGACCACGAGGACATCACAAAGGATAAGAC
CTCCACAGTGGAGGCCTGCCTGCCACTGGAGCTGACCAAGAACGAGAGCTGTCTGAACAGCCGG
GAGACCAGCTTCATCACCAACGGCAGCTGCCTGGCCTCCAGAAAGACATCTTTTATGATGGCCC
TGTGCCTGTCTAGCATCTACGAGGACCTGAAGATGTATCAGGTGGAGTTCAAGACCATGAACGC
CAAGCTGCTGATGGACCCCAAGAGGCAGATTTTCCTGGACCAGAATATGCTGGCCGTGATCGAC
GAGCTGATGCAGGCCCTGAACTTTAATTCCGAGACAGTGCCTCAGAAGTCCTCTCTGGAGGAGC
CAGATTTCTACAAGACCAAGATCAAGCTGTGCATCCTGCTGCACGCCTTCCGGATCAGAGCCGT
GACCATCGACCGCGTGATGAGCTATCTGAATGCCTCCTAG

SEQ ID NO: 64, T2A skip peptide
AAAEGRGSLLTCGDVEENPGPSG

SEQ ID NO: 65, encodes SEQ ID NO: 64, T2A skip peptide
GCGGCCGCTGAGGGCAGAGGAAGTCTTCTAACATGCGGTGACGTGGAGGAGAATCCCGGCCCTT
CCGGA

The invention claimed is:

1. An enucleated erythroid cell engineered to stimulate an immune killer cell, wherein the enucleated erythroid cell comprises:

a first exogenous stimulatory polypeptide, wherein the first exogenous stimulatory polypeptide is a fusion polypeptide comprising a heterologous transmembrane domain from a polypeptide selected from the group consisting of: glycophorin A, glycophorin B, cluster of differentiation (CD) 147, CD44, CD58, intercellular adhesion molecule 4, basal cell adhesion molecule, complement receptor 1, CD99, erythroblast membrane-associated protein (ERMAP), junctional adhesion molecule A, neuroplastin, amphoterin-induced protein 2, Down Syndrome cell adhesion molecule-like 1, small integral membrane protein 1, transferrin receptor, Fas ligand, and Kell; and a second exogenous stimulatory polypeptide, wherein the first and second exogenous stimulatory polypeptides are sufficient to stimulate the immune killer cell.

2. The enucleated erythroid cell of claim 1, wherein the immune killer cell is a natural killer (NK) cell or a CD8+T cell.

3. The enucleated erythroid cell of claim 1, wherein the enucleated erythroid cell further comprises a third exogenous stimulatory polypeptide.

4. The enucleated erythroid cell of claim 1, wherein one or both of the first and second exogenous stimulatory polypeptides comprises a polypeptide selected from the group consisting of: interleukin (IL)-1 (IL-1), IL-2, IL-12, IL-15, IL-15/IL-15 receptor alpha (IL-15/IL-15RA) fusion, IL-18, IL-21, interferon alpha (IFNα), 4-1BBL, polovirus receptor (PVR), CD48, human leukocyte antigen (HLA)-A, HLA-C, HLA-G, heparan sulfate, HLA-E, immunoglobulin G (IgG), a MHC class I chain-related (MIC) protein, B7-H6, NK cell activating receptor 44 ligand, Nectin2, NK-T-B antigen, activation-induced C-type lectin (AICL), and insulin-like growth factor 1 .

5. The enucleated erythroid cell of claim 4, wherein the MIC protein is selected from the group consisting of: MICA, MICB, and UL16-binding proteins (ULBP).

6. The enucleated erythroid cell of claim 1, wherein the first exogenous stimulatory polypeptide comprises IL-15/

IL-15RA fusion and the second exogenous stimulatory polypeptide comprises a polypeptide selected from the group consisting of: IL-1, IL-2, IL-12, IL-18, IL-21, 4-1BBL, IFNα, MICA, MICB, PVR, and CD48.

7. The enucleated erythroid cell of claim 1, wherein the first exogenous stimulatory polypeptide and the second exogenous stimulatory polypeptide are selected from the group consisting of: IL-18 and IL-12, IL-18 and IL-21, IL-12 and 4-1BBL, IL-12 and IL-15/IL-15RA fusion, and 4-1BBL and IL-15/IL-15RA fusion.

8. The enucleated erythroid cell of claim 1, wherein the the second exogenous stimulatory polypeptide is a fusion polypeptide.

9. The enucleated erythroid cell of claim 3, wherein the second and the third exogenous stimulatory polypeptides are present as fusion polypeptides.

10. An engineered enucleated erythroid cell comprising a first exogenous stimulatory polypeptide, wherein the first exogenous stimulatory polypeptide is a fusion polypeptide comprising (i) an interleukin-15 (IL-15) polypeptide, or a fragment thereof, (ii) an extracellular portion of an interleukin-15 receptor alpha (IL-15RA) polypeptide, or a fragment thereof, and (iii) a heterologous transmembrane domain from a polypeptide selected from the group consisting of: glycophorin A, glycophorin B, CD147, CD44, CD58, intercellular adhesion molecule 4, basal cell adhesion molecule, complement receptor 1, CD99, ERMAP, junctional adhesion molecule A, neuroplastin, amphoterin-induced protein 2, Down Syndrome cell adhesion molecule-like 1, small integral membrane protein 1, transferrin receptor, Fas ligand, and Kell.

11. The engineered enucleated erythroid cell of claim 10, wherein the IL-15 polypeptide and the extracellular portion of an IL-15RA polypeptide are present as a complex.

12. The engineered enucleated erythroid cell of claim 10, wherein the fusion polypeptide comprises an amino acid sequence that is at least 95% identical to SEQ ID NO: 1.

13. The engineered enucleated erythroid cell of claim 10, wherein the fusion polypeptide comprises an amino acid sequence that is at least 95% identical to SEQ ID NO: 29 or SEQ ID NO: 37.

14. The engineered enucleated erythroid cell of claim 10, wherein the fusion polypeptide comprises an IL-15 polypeptide, or a fragment thereof, and an IL-15 receptor alpha sushi domain.

15. The engineered enucleated erythroid cell of claim 14, wherein the fusion polypeptide comprises an amino acid sequence that is at least 95% identical to SEQ ID NO: 2 or SEQ ID NO: 31.

16. The engineered enucleated erythroid cell of claim 10, further comprising a second exogenous stimulatory polypeptide, wherein the second exogenous stimulatory polypeptide comprises 4-1BBL.

17. The engineered enucleated erythroid cell of claim 16, wherein the second exogenous stimulatory polypeptide comprises an amino acid sequence that is at least 95% identical to SEQ ID NO: 41 or SEQ ID NO: 43.

18. The engineered enucleated erythroid cell of claim 10, further comprising a second exogenous stimulatory polypeptide, wherein the second exogenous stimulatory polypeptide comprises IL-12.

19. The engineered enucleated erythroid cell of claim 18, wherein the second exogenous stimulatory polypeptide comprises an amino acid sequence that is at least 95% identical to SEQ ID NO: 37 or SEQ ID NO: 55.

20. An engineered enucleated erythroid cell comprising at least a first exogenous stimulatory polypeptide comprising a fusion polypeptide comprising (i) a polypeptide selected from the group consisting of: MICA, MICB, and IGF-1, and (ii) a heterologous transmembrane domain from a polypeptide selected from the group consisting of: glycophorin A, glycophorin B, CD147, CD44, CD58, intercellular adhesion molecule 4, basal cell adhesion molecule, complement receptor 1, CD99, ERMAP, junctional adhesion molecule A, neuroplastin, amphoterin-induced protein 2, Down Syndrome cell adhesion molecule-like 1, small integral membrane protein 1, transferrin receptor, Fas ligand, and Kell.

21. A method of stimulating an immune killer cell, comprising contacting the immune killer cell with the enucleated erythroid cell of claim 1 or the engineered enucleated erythroid cell of claim 10, in an amount effective to stimulate the immune killer cell.

22. The method of claim 21, wherein the method further comprises administering the enucleated erythroid cell or the engineered enucleated erythroid cell to a subject in need of immune killer cell activation.

23. The method of claim 22, wherein the subject has cancer or an infectious disease.

24. The method of claim 23, wherein the cancer is selected from the group consisting of: acute lymphoblastic leukemia (ALL), acute myeloid leukemia (AML), anal cancer, bile duct cancer, bladder cancer, bone cancer, bowel cancer, brain tumor, breast cancer, cancer of unknown primary, cancer spread to bone, cancer spread to brain, cancer spread to liver, cancer spread to lung, carcinoid, cervical cancer, choriocarcinoma, chronic lymphocytic leukemia (CLL), chronic myeloid leukemia (CIVIL), colon cancer, colorectal cancer, endometrial cancer, eye cancer, gallbladder cancer, gastric cancer, gestational trophoblastic tumor (GTT), hairy cell leukemia, head and neck cancer, Hodgkin's lymphoma, kidney cancer, laryngeal cancer, leukemia, liver cancer, lung cancer, lymphoma, melanoma skin cancer, mesothelioma, men's cancer, molar pregnancy, mouth and oropharyngeal cancer, myeloma, nasal and sinus cancers, nasopharyngeal cancer, non-Hodgkin's lymphoma (NHL), oesophageal cancer, ovarian cancer, pancreatic cancer, penile cancer, prostate cancer, rare cancers, rectal cancer, salivary gland cancer, secondary cancers, skin cancer (non-melanoma), soft tissue sarcoma, stomach cancer, testicular cancer, thyroid cancer, unknown primary cancer, uterine cancer, vaginal cancer, and vulval cancer.

25. A method of treating a cancer in a subject, comprising administering to the subject the enucleated erythroid cell of claim 1 or the engineered enucleated erythroid cell of claim 10, in an amount effective to treat the cancer in the subject.

26. The method of claim 25, wherein the cancer is selected from the group consisting of: acute lymphoblastic leukemia (ALL), acute myeloid leukemia (AML), anal cancer, bile duct cancer, bladder cancer, bone cancer, bowel cancer, brain tumor, breast cancer, cancer of unknown primary, cancer spread to bone, cancer spread to brain, cancer spread to liver, cancer spread to lung, carcinoid, cervical cancer, choriocarcinoma, chronic lymphocytic leukemia (CLL), chronic myeloid leukemia (CML), colon cancer, colorectal cancer, endometrial cancer, eye cancer, gallbladder cancer, gastric cancer, gestational trophoblastic tumor (GTT), hairy cell leukemia, head and neck cancer, Hodgkin's lymphoma, kidney cancer, laryngeal cancer, leukemia, liver cancer, lung cancer, lymphoma, melanoma skin cancer, mesothelioma, men's cancer, molar pregnancy, mouth and oropharyngeal cancer, myeloma, nasal and sinus cancers, nasopharyngeal cancer, non-Hodgkin's lymphoma (NHL), oesophageal cancer, ovarian cancer, pancreatic cancer, penile cancer, prostate cancer, rare cancers, rectal cancer, salivary gland cancer, secondary cancers, skin cancer (non-melanoma), soft tissue sarcoma, stomach cancer, testicular cancer, thyroid cancer, unknown primary cancer, uterine cancer, vaginal cancer, and vulval cancer.

27. A method of treating an infectious disease in a subject, comprising administering to the subject the enucleated erythroid cell of claim 1 or the engineered enucleated erythroid cell of claim 10, in an amount effective to treat the infectious disease in the subject.

28. A method of making the enucleated erythroid cell of claim 1, the method comprising:

introducing at least one exogenous nucleic acid into a nucleated erythroid cell precursor, wherein the at least one exogenous nucleic acid encodes the first and second exogenous stimulatory polypeptides; and culturing the nucleated erythroid cell precursor under conditions suitable for enucleation of the nucleated erythroid cell precursor and for production of the first and second exogenous stimulatory polypeptides, thereby making the enucleated erythroid cell.

29. An engineered enucleated erythroid cell, comprising:

i. a first exogenous stimulatory polypeptide, wherein the first exogenous stimulatory polypeptide is a fusion polypeptide comprising an IL-15/IL15RA fusion comprising an IL-15 polypeptide, or a fragment thereof, linked to the extracellular portion of an IL-15RA polypeptide, or a fragment thereof, by a linker; and ii. a second exogenous stimulatory polypeptide, wherein the second exogenous stimulatory polypeptide comprises 4-1BBL, or a functional fragment thereof;

wherein one or both of the first exogenous stimulatory polypeptide and the second exogenous stimulatory polypeptide comprise a heterologous transmembrane domain from a polypeptide selected from the group consisting of: glycophorin A, glycophorin B, CD147, CD44, CD58, intercellular adhesion molecule 4, basal cell adhesion molecule, complement receptor 1, CD99, ERMAP, junctional adhesion molecule A, neuroplastin, amphoterin-induced protein 2, Down Syndrome cell adhesion molecule-like 1, small integral membrane protein 1, transferrin receptor, Fas ligand, and Kell.

30. An engineered enucleated erythroid cell, comprising:

i. a first exogenous stimulatory polypeptide, wherein the first exogenous stimulatory polypeptide comprises 4-1BBL, or a fragment thereof; and ii. a second exogenous stimulatory polypeptide, wherein the second exogenous stimulatory polypeptide comprises IL-12, or a fragment thereof, wherein one or both of the first exogenous stimulatory polypeptide and the second exogenous stimulatory polypeptide is a fusion polypeptide further comprising a heterologous transmembrane domain from a polypeptide selected from the group consisting of: glycophorin A, glycophorin B, CD147, CD44, CD58, intercellular adhesion molecule 4, basal cell adhesion molecule, complement receptor 1, CD99, ERMAP, junctional adhesion molecule A, neuroplastin, amphoterin-induced protein 2, Down Syndrome cell adhesion molecule-like 1, small integral membrane protein 1, transferrin receptor, Fas ligand, and Kell.

* * * * *

UNITED STATES PATENT AND TRADEMARK OFFICE

CERTIFICATE OF CORRECTION

PATENT NO. : 11,141,433 B2
APPLICATION NO. : 16/297540
DATED : October 12, 2021
INVENTOR(S) : Thomas Joseph Wickham and Sivan Elloul It is certified that error appears in the above-identified patent and that said Letters Patent is hereby corrected as shown below:

In the Claims

Column 312, Line 47, Claim 2, delete "CD8+T cell" and insert --$CD8^+$ T cell--.

Column 312, Line 56, Claim 4, delete "polovirus" and insert --poliovirus--.

Column 313, Lines 11-12, Claim 8, delete "the the" and insert --the--.

Column 314, Line 30, Claim 24, delete "(CIVIL)" and insert --(CML)--.

Column 314, Line 44, Claim 24, delete "vulval" and insert --vulvar--.

Column 315, Line 4, Claim 26, delete "vulval" and insert --vulvar--.

Column 315, Line 25, Claim 29, delete "IL-15/IL15RA" and insert --IL-15/IL-15RA--.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*